(12) United States Patent
Kuduk et al.

(10) Patent No.: US 11,753,393 B2
(45) Date of Patent: *Sep. 12, 2023

(54) DIHYDROOROTATE DEHYDROGENASE INHIBITORS

(71) Applicant: Janssen Biotech, Inc., Horsham, PA (US)

(72) Inventors: Scott Kuduk, Harleysville, PA (US); Zhuming Zhang, Hillsborough, NJ (US); Lindsey DeRatt, North Wales, PA (US); Aihua Wang, Jamison, PA (US)

(73) Assignee: Janssen Biotech, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 17/742,606

(22) Filed: May 12, 2022

(65) Prior Publication Data

US 2022/0298137 A1    Sep. 22, 2022

Related U.S. Application Data

(63) Continuation of application No. 16/850,171, filed on Apr. 16, 2020, now Pat. No. 11,505,536.

(60) Provisional application No. 62/835,113, filed on Apr. 17, 2019.

(51) Int. Cl.
| | | |
|---|---|---|
| *C07D 401/04* | (2006.01) | |
| *C07D 401/14* | (2006.01) | |
| *C07D 403/04* | (2006.01) | |
| *C07D 417/14* | (2006.01) | |
| *C07D 471/04* | (2006.01) | |

(52) U.S. Cl.
CPC ......... *C07D 401/04* (2013.01); *C07D 401/14* (2013.01); *C07D 403/04* (2013.01); *C07D 417/14* (2013.01); *C07D 471/04* (2013.01)

(58) Field of Classification Search
CPC .......................... C07D 401/04; A61K 31/4725
See application file for complete search history.

(56) References Cited

U.S. PATENT DOCUMENTS

| | | |
|---|---|---|
| 2007/0173507 A1 | 7/2007 | Hirata |
| 2016/0176869 A1 | 6/2016 | Chen et al. |
| 2019/0375747 A1 | 12/2019 | Gradl et al. |
| 2020/0123129 A1 | 4/2020 | Gradl et al. |

FOREIGN PATENT DOCUMENTS

| | | |
|---|---|---|
| JP | 2007 015952 A | 1/2007 |
| WO | WO 2005/085214 A1 | 9/2005 |
| WO | WO 2018/077923 A1 | 5/2018 |
| WO | WO 2018/077944 A2 | 5/2018 |
| WO | WO 2018/154088 A1 | 8/2018 |
| WO | WO 2019/191030 A1 | 10/2019 |
| WO | WO 2020/144638 A1 | 7/2020 |
| WO | WO 2020/161663 A1 | 8/2020 |

OTHER PUBLICATIONS

Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-110 O, 1995.*
Johnson et al., Relationships between drug activity in NCI preclinical in vitro and in vivo models and early clinical trials, British Journal of Cancer, 84(10):1424-1431, 2001.*
Gura et al., Systems for identifying new drugs are often faulty, Science, 278:1041-1042, 1997.*
Acute Leukemia, Merck Manual (Online Edition) 6 pages, pp. 1-6 (2013).*
Berge et al., "Pharmaceutical Salts", J. Pharm. Sci., 1977, pp. 1-19, vol. 66.
Christian et al., "The novel dihydroorotate dehydrogenase (DHODH) inhibitor BAY 2402234 triggers differentiation and is effective in the treatment of myeloid malignancies.", Leukemia, Apr. 2, 2019, pp. 2403-2415 vol. 33.
Lolli et al., "Use of human Dihydroorotate Dehydrogenase (hDHODH) Inhibitors in Autoimmune Diseases and New Perspectives in Cancer Therapy.", Recent patents on Anti-Cancer Drug Discovery, 2018, pp. 86-105, vol. 13(1).
Marchal et al., "Cycloisomerization of γ- and σ-acetylenic acids catalyzed by gold(I) chloride.", *Tetrahedron*, 2007, pp. 9979-9990, vol. 63.
Mathur et al., "PTEN Regulates Glutamine Flux to Pyrimidine Synthesis and Sensitivity to Dihydroorotate Dehydrogenase Inhibition.", Cancer Discovery, Apr. 2017, pp. 380-390, vol. 7(4).
McCulloch et al., "Retinoic acid and arsenic trioxide in the treatment of acute promyelocytic leukemia: current perspectives.", Onco Targets Ther. 2017, pp. 1585-1601, vol. 10.
Nowak et al., Differentiation therapy of leukemia: 3 decades of development.:, Blood, Apr. 16, 2009, pp. 3655-3665, vol. 113(16).
Reis et al., "The dihydroorotate dehydrogenases: Past and present.", Archives Biochem Biophysics, 2017, pp. 175-191, vol. 632.

(Continued)

*Primary Examiner* — Deepak R Rao

(57) ABSTRACT

Disclosed are compounds, compositions and methods for treating diseases, disorders, or medical conditions that are affected by the modulation of DHODH. Such compounds are represented by Formula (I) as follows:

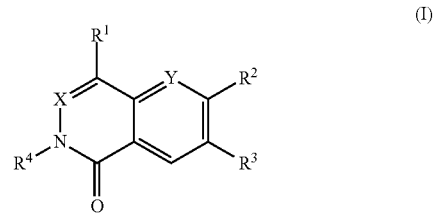

(I)

wherein $R^1$, $R^2$, $R^3$, $R^4$, X, and Y are defined herein.

8 Claims, No Drawings

(56) References Cited

OTHER PUBLICATIONS

Sainas et al., "Targeting Myeloid Differentiation Using Potent 2-Hydroxypyrazolo[1,5-a]pyridine Scaffold-Based Human Dihydroorotate Dehydrogenase Inhibitors.", J Med Chem, 2018, pp. 6034-3055, vol. 61.
Stein et al., "Assessing utility values for treatmentrelated health states of acute myeloid leukemia in the United States.", Health Qual Life Outcomes, 2018, 16:193.
Suchand et al., "Palladium-Catalyzed Environmentally Benign Acylation.", *J. Org. Chem.*, 2016, pp. 6409-6423, vol. 81.
Sykes et al., "Inhibition of Dihydroorotate Dehydrogenase Overcomes Differentiation Blockade in Acute Myeloid Leukemia.", Cell, 2016, pp. 171-186, vol. 167.
Vyas et al., "Recent Developments in the Medicinal Chemistry and Therapeutic Potential of Dihydroorotate Dehydrogenase (DHODH) Inhibitors.", Mini Rev Med Chem, 2011, pp. 1039-1055, vol. 11.
Wu et al., "Pharmacological inhibition of dihydroorotate dehydrogenase induces apoptosis and differentiation in acute myeloid leukemia cells.", Haematologica, 2018, pp. 1472-1483, vol. 103(9).
Pimlott, S.L, "Radiotracer development in psychiatry.", Nucl. Med. Commun., Mar. 2005, pp. 183-188, vol. 26(3).
Hulikal, V., "L15 Deuterium Labeled Compounds in Drug Discovery Process.", Abstract, 2010.
International Search Report relating to corresponding PCT Patent Application No. PCT/IB2020/053601, filed Apr. 16, 2020. Mailing Date of International Search Report: dated Jun. 17, 2020.
Written Opinion relating to corresponding PCT Patent Application No. PCT/IB2020/053601, filed Apr. 16, 2020. Mailing Date of Written Opinion: dated Jun. 17, 2020.

\* cited by examiner

DIHYDROOROTATE DEHYDROGENASE INHIBITORS

CROSS-REFERENCE TO RELATED APPLICATIONS

This application is a continuation of U.S. patent application Ser. No. 16/850,171, filed on Apr. 16, 2020, which claims the benefit of priority of U.S. Provisional Patent Application No. 62/835,113, filed Apr. 17, 2019, which is are incorporated by reference herein, in its entirety their entireties and for all purposes.

FIELD OF THE INVENTION

The present invention relates to novel compounds that are dihydroorotate dehydrogenase (DHODH) inhibitors. These compounds may be useful for the treatment of a disease, disorder, or medical condition where there is an advantage in inhibiting DHODH. The invention also relates to pharmaceutical compositions comprising one or more of such compounds, to processes to prepare such compounds and compositions, and to the use of such compounds or pharmaceutical compositions for the method of treatment of cancer, and autoimmune and inflammatory diseases, syndromes, and disorders.

BACKGROUND OF THE INVENTION

Acute myelogenous leukemia (AML) is a clonal disease of the blood and bone marrow resulting from mutations that occur in normal hematopoietic stem cells. AML is a heterogenous disease in that it presents with a range of cytogenetic, morphological and immunophenotypic features, and is characterized by an accumulation of clonal, abnormal myeloid progenitor cells, known as myeloblasts. These cells demonstrate disruption of normal myeloid differentiation and excessive proliferation, resulting in the decreased formation of hematopoietic cells. Disease remission can be achieved with standard induction chemotherapy, but refractory and relapsed disease remains a challenge due to persistence of leukemic stem cells. Therefore, AML represents an unmet medical need with >20,000 new cases per year in the US with 5-year overall survival below 30% (Stein E T et al., Health Qual Life Outcomes 16: 193, 2018).

Differentiation therapy is considered an attractive approach to AML treatment based on the knowledge that differentiation and loss of stem cell self-renewal are coupled in normal cells. Treatment of acute promyelocytic leukemia, which represents 10-15% of all AML, with all-trans retinoic acid is the paradigm for differentiation therapy. Retinoic acid targets the promyelocytic leukemia protein (PML)-retinoic acid receptor-α (RAR-α) fusion protein encoded by a t(15, 17) chromosomal translocation. Targeting PML-RAR specifically lifts the transcriptionally mediated differentiation block induced by the fusion protein and early clinical trials with single agent ATRA demonstrated complete hematologic remission in all treated patients (McCulloch D et al. Onco Targets Ther 2017; 10: 1585-1601; Nowak D et al. Blood 113: 3655, 2009).

Although differentiation therapy is successful, it is only applicable to a small population of AML patients. Research efforts have aimed at identifying additional differentiation inducing agents, but with limited success. Recently dihydroorotate dehydrogenase (DHODH) emerged as a potentially more broadly applicable differentiation target in a phenotypic screen aimed at identifying small molecules that overcome blockade of the maturation of primary murine bone marrow cells expressing the homeobox protein HoxA9. This protein is a key transcription factor involved in balancing stem cell maintenance/differentiation and is normally expressed in hematopoietic progenitor cells and downregulated upon induction of differentiation and has been found to be widely overexpressed in AML (Sykes et al., Cell 167: 171, 2016).

DHODH is a flavin mononucleotide (FMN) flavoprotein located in the inner mitochondrial membrane that catalyzes the oxidation of dihydroorotate to orotate, the fourth step in the de novo pyrimidine biosynthesis pathway. Inhibition of DHODH leads to decreased pyrimidine synthesis important precursors for nucleotide synthesis, but also glycoprotein and phospholipid biosynthesis (Reis RAG et al., Archives Biochem Biophysics 632: 175, 2017; Vyas V K et al., Mini Rev Med Chem 11: 1039, 2011). DHODH is a validated target for the treatment of autoimmune diseases with the FDA approved small molecule DHODH inhibitors leflunomide and teriflunomide for rheumatoid arthritis and multiple sclerosis, respectively (Lolli M L et al., Recent patents on Anti-Cancer Drug Discovery 13: 86, 2018).

Since the first observation by Sykes et al. demonstrating that DHODH inhibition drives AML differentiation in vitro, as evidenced by upregulation of the differentiation markers CD11b and CD14, and results in dose dependent anti-leukemic effects, decreased leukemic stem cells and prolonged survival in vivo, additional evidence emerged demonstrating that small molecule DHODH inhibitors mediate antiproliferative activity against AML cells with concomitant cell cycle arrest, upregulation of CD11b and CD14, and induction of apoptosis (Wu D et al. Haematologica 103: 1472, 2018; Sainas S et al., J Med Chem 61: 6034, 2018; Cao L et al., Mol Cancer Ther, October 23rd Epub ahead of print). Moreover, preclinical solid tumor in vitro and in vivo models demonstrated effectiveness of DHODH inhibition and DHODH was identified as a synthetic lethality in PTEN and KRAS mutant solid tumors (Pharmacology and Therapeutics, Epub Oct. 19, 2018; Mathur D et al., Cancer Discovery 7: 1, 2017; Cell Chemical Biology 25: 1, 2018).

Thus, there remains a need for DHODH inhibitors that provide a therapeutic benefit to patients suffering from cancer and/or inflammatory and immunological diseases.

SUMMARY OF THE INVENTION

Embodiments of the present invention relate to compounds, pharmaceutical compositions containing them, methods of making and purifying them, methods of using them as inhibitors of DHODH enzymatic activity and methods for using them in the treatment of a subject suffering from or diagnosed with a disease, disorder, or medical condition such as autoimmune or inflammatory disorders, or diseases such as cancer. DHODH inhibitors of the present invention may provide a therapeutic benefit to patients suffering from cancer and/or inflammatory and immunological diseases.

Embodiments of this invention are compounds of Formula (I),

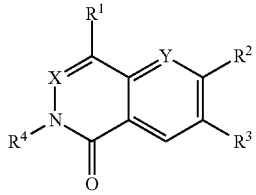
(I)

wherein
X is CH or N;
Y is CH or N;
R¹ is selected from the group consisting of: $C_{1-6}$alkyl; $C_{1-6}$alkyl substituted with OH, or $OCH_3$; $C_{2-6}$alkenyl; $C_{1-6}$haloalkyl; $C_{1-6}$haloalkyl substituted with OH, or $OCH_3$; $C_{2-6}$haloalkenyl; $N(CH_3)_2$; $C_{3-6}$cycloalkyl; $C_{3-6}$cycloalkyl substituted with $C_{1-6}$alkyl; and phenyl;
R² is

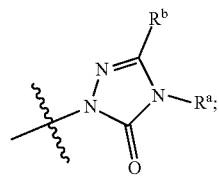

wherein
$R^a$ is selected from the group consisting of: $C_{1-6}$alkyl, $C_{1-6}$haloalkyl, and $C_{3-6}$cycloalkyl;
$R^b$ is $C_{1-6}$alkyl or $C_{1-6}$alkyl substituted with a member selected from the group consisting of: OH, halo, CN, $OC_{1-6}$alkyl, $OC_{1-6}$haloalkyl and $OC_{3-6}$cycloalkyl;
R³ is selected from the group consisting of: H, halo, $CH_3$, and $OCH_3$;
R⁴ is selected from the group consisting of:
(a) $C_{1-6}$alkyl; $C_{1-6}$alkyl substituted with one or two $OCH_3$; $C_{3-6}$cycloalkyl; $C_{3-6}$cycloalkyl substituted with $CH_3$, or $OCH_3$; $CH_2$—$C_{3-6}$cycloalkyl; and (b)

(c)
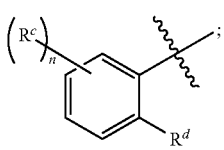

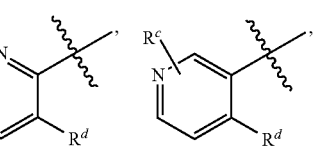

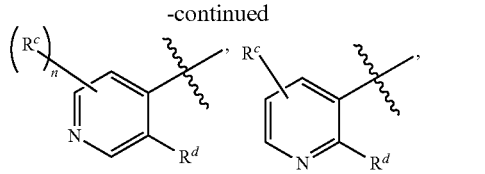

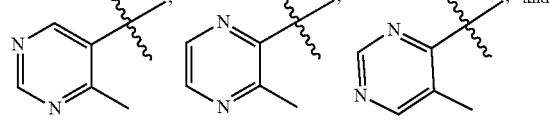

(d)
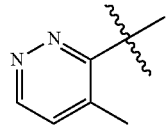

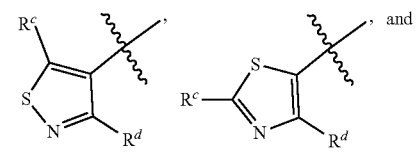

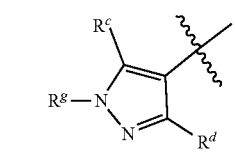

wherein
each $R^c$ is independently selected from the group consisting of: H; halo; $C_{1-6}$alkyl; $C_{1-6}$alkyl substituted with a member selected from the group consisting of: OH, $OCH_3$, $SCH_3$, and $OCF_3$; $C_{1-6}$haloalkyl; $C_{1-6}$haloalkyl substituted with a member selected from the group consisting of: OH, and $OCH_3$; $NO_2$; OH; O—$CH_2CH_2OH$; and $OC_{1-6}$alkyl;
$R^d$ is selected from the group consisting of: H; halo; $C_{1-6}$alkyl; $C_{1-6}$alkyl substituted with a member selected from the group consisting of: OH, $OCH_3$, $SCH_3$, and $OCF_3$; $C_{1-6}$haloalkyl; $C_{1-6}$haloalkyl substituted with a member selected from the group consisting of: OH, and $OCH_3$; CN; and $OC_{1-6}$alkyl;
$R^g$ is selected from the group consisting of: H; $C_{1-6}$alkyl; $C_{1-6}$alkyl substituted with a member selected from the group consisting of: OH, $OCH_3$, $SCH_3$, and $OCF_3$; $C_{1-6}$haloalkyl; and $C_{1-6}$haloalkyl substituted with a member selected from the group consisting of: OH, and $OCH_3$; and
n is 1, or 2;
or a pharmaceutically acceptable salt, isotope, N-oxide, solvate, or stereoisomer thereof.

The present invention further provides methods for treating or ameliorating a disease, syndrome, condition, or disorder in a subject, including a mammal and/or human in which the disease, syndrome, condition, or disorder is affected by the inhibition of DHODH enzymatic activity, including but not limited to, cancer and/or inflammatory or immunological diseases, using a compound of Formula (I) or a pharmaceutically acceptable salt, isotope, N-oxide, solvate, or stereoisomer thereof.

Additional embodiments, features, and advantages of the invention will be apparent from the following detailed description and through practice of the invention.

DETAILED DESCRIPTION OF THE INVENTION

Unless defined otherwise, all technical and scientific terms used herein have the same meaning as is commonly understood by one of ordinary skill in art. As used in the specification and the appended claims, unless specified to the contrary, the following terms have the meaning indicated in order to facilitate the understanding of the present invention.

The singular forms "a", "an" and "the" encompass plural references unless the context clearly indicates otherwise.

With reference to substituents, the term "independently" refers to the situation where when more than one substituent is possible, the substituents may be the same or different from each other.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Unless qualified specifically in particular instances of use, the term "alkyl" refers to a straight- or branched-chain alkyl group having from 1 to 8 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. "$C_{1-6}$alkyl" refers to straight- or branched-chain alkyl group having from 1 to 6 carbon atoms in the chain. "$C_{1-4}$alkyl" refers to straight- or branched-chain alkyl group having from 1 to 4 carbon atoms in the chain.

The term "alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl, etc.). The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_{2-6}$ for straight chain, $C_{3-6}$ for branched chain).

The term "cycloalkyl" refers to a saturated or partially saturated, monocyclic, fused polycyclic, or spiro polycyclic carbocycle having from 3 to 12 ring atoms per carbocycle. "$C_{3-6}$ cycloalkyl" refers to a carbocycle having from 3 to 6 ring atoms per carbocycle. Illustrative examples of cycloalkyl groups include the following entities, in the form of properly bonded moieties.

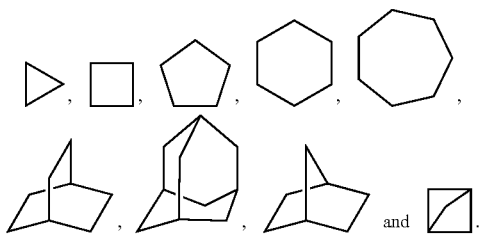

The term "halogen" or "halo" represents chlorine, fluorine, bromine, or iodine.

The term "cyano" refers to the group CN.

The term "haloalkyl" refers to a straight- or branched-chain alkyl group having from 1 to 6 carbon atoms in the chain optionally substituting hydrogens with halogens. The term "$C_{1-6}$ haloalkyl" as used here refers to a straight- or branched-chain alkyl group having from 1 to 6 carbon atoms in the chain, optionally substituting hydrogens with halogens. The term "$C_{1-4}$ haloalkyl" as used here refers to a straight- or branched-chain alkyl group having from 1 to 4 carbon atoms in the chain, optionally substituting hydrogens with halogens. Examples of "haloalkyl" groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), monofluoroethyl ($CH_2CH_2F$), trifluoroethyl ($CH_2CF_3$), tetrafluorotrifluoromethylethyl ($CF(CF_3)_2$), and groups that in light of the ordinary skill in the art and the teachings provided herein would be considered equivalent to any one of the foregoing examples.

The term "haloalkenyl" includes unsaturated aliphatic groups analogous in length and possible substitution to the alkyls described above, but that contain at least one double bond and having from 1 to 6 carbon atoms in the chain optionally substituting hydrogens with halogens.

The term "aryl" refers to a monocyclic, aromatic carbocycle (ring structure having ring atoms that are all carbon) having 6 atoms per ring. (Carbon atoms in the aryl groups are sp2 hybridized.)

The term "phenyl" represents the following moiety:

The term "heteroaryl" refers to a monocyclic or fused bicyclic heterocycle (ring structure having ring atoms selected from carbon atoms and up to four heteroatoms selected from nitrogen, oxygen, and sulfur) having from 3 to 9 ring atoms per heterocycle. Illustrative examples of heteroaryl groups include the following entities, in the form of properly bonded moieties:

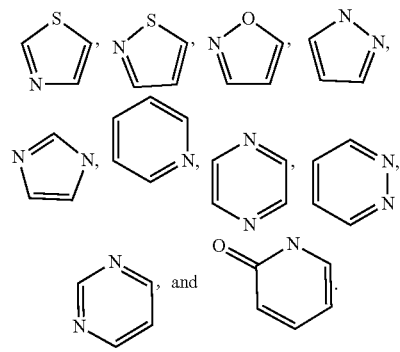

The term "phenyl" represents the following moiety:

Those skilled in the art will recognize that the species of cycloalkyl, heteroaryl and aryl groups listed or illustrated above are not exhaustive, and that additional species within the scope of these defined terms may also be selected.

The term "variable point of attachment" means that a group is allowed to be attached at more than one alternative position in a structure. The attachment will always replace a hydrogen atom on one of the ring atoms. In other words, all permutations of bonding are represented by the single diagram, as shown in the illustrations below.

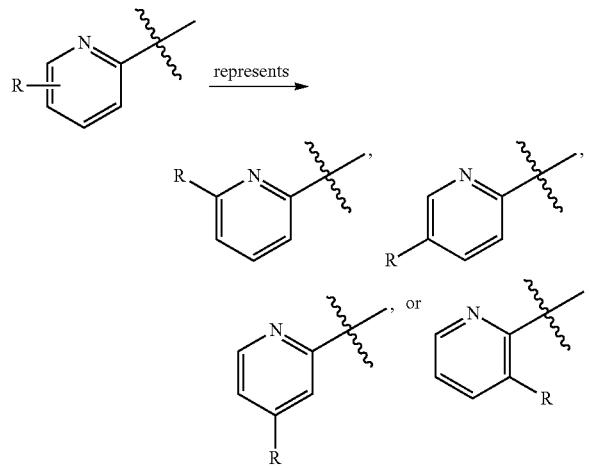

Those skilled in the art will recognize that that if more than one such substituent is present for a given ring, the bonding of each substituent is independent of all of the others. The groups listed or illustrated above are not exhaustive.

As used herein, the term "or" means "and/or" unless stated otherwise.

As used herein, the terms "including", "containing" and "comprising" are used in their open, non-limiting sense.

As used herein, the term "composition" is intended to encompass a product comprising the specified ingredients in the specified amounts, as well as any product which results, directly or indirectly, from combination of the specified ingredients in the specified amounts.

As used herein, the term "treat", "treating", or "treatment" of any disease, condition, syndrome or disorder refers, in one embodiment, to ameliorating the disease, condition, syndrome or disorder (i.e. slowing or arresting or reducing the development of the disease or at least one of the clinical symptoms thereof). In another embodiment, "treat", "treating", or "treatment" refers to alleviating or ameliorating at least one physiological or biochemical parameter associated with or causative of the disease, condition, syndrome or disorder, including those which may not be discernible by the patient. In a further embodiment, "treat", "treating", or "treatment" refers to modulating the disease, condition, syndrome or disorder either physically (e.g. stabilization of a discernible symptom), physiologically, (e.g. stabilization of a physical parameter), or both. In yet another embodiment, "treat", "treating", or "treatment" refers to preventing or delaying the onset or development or progression of the disease, condition, syndrome or disorder.

The terms "subject" and "patient" are used interchangeably herein and may refer to an animal, preferably a mammal, most preferably a human.

As used herein, the terms active compound, pharmaceutical agent and active ingredient are used interchangeably to refer to a pharmaceutically active compound. Other ingredients in a drug composition, such as carriers, diluents or excipients, may be substantially or completely pharmaceutically inert. A pharmaceutical composition (also referred to herein as a composition or formulation) may comprise the active ingredient in combination with one or more carriers and/or one or more excipients and/or one or more diluents.

The term "therapeutically effective amount" (used interchangeably herein with "effective amount") refers to an amount (e.g., of an active compound or pharmaceutical agent, such as a compound of the present invention), which elicits the biological or medicinal response in a tissue system, animal or human that is being sought by a researcher, veterinarian, medical doctor or other clinician, including reduction or inhibition of an enzyme or a protein activity, or ameliorating symptoms, alleviating conditions, slowing or delaying disease progression, or preventing a disease. Stated another way, the term therapeutically effective amount may refer to an amount that, when administered to a particular subject, achieves a therapeutic effect by inhibiting, alleviating or curing a disease, condition, syndrome or disorder in the subject or by prophylactically inhibiting, preventing or delaying the onset of a disease, condition, syndrome or disorder, or symptom(s) thereof. A therapeutically effective amount may be an amount which relieves to some extent one or more symptoms of a disease, condition, syndrome or disorder in a subject; and/or returns to normal either partially or completely one or more physiological or biochemical parameters associated with or causative of the disease, condition, syndrome or disorder; and/or reduces the likelihood of the onset of the disease, condition, syndrome or disorder, or symptom(s) thereof.

"Pharmaceutically acceptable" means that, which is useful in preparing a pharmaceutical composition that is generally safe, non-toxic and neither biologically nor otherwise undesirable and includes that which is acceptable for veterinary as well as human pharmaceutical use.

A "pharmaceutically acceptable salt" is intended to mean a salt of an acid or base of a compound represented by Formula (I) (as well as compounds of Formula (IA), (IB), and (IC)) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response.

Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

The term solvate comprises the solvent addition forms as well as the salts thereof, which the compounds of Formula (I) are able to form. Examples of such solvent addition forms are, e.g., hydrates, alcoholates and the like.

A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt.

Compounds of Formula (I) may contain at least one nitrogen of basic character, so desired pharmaceutically acceptable salts may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents.

Compounds of Formula (I) may contain a carboxylic acid moiety, a desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, piperazine, N-methyl-glucamine and tromethamine and inorganic salts derived from sodium, calcium, potassium, magnesium, manganese, iron, copper, zinc, aluminum, and lithium.

Each compound used herein may be discussed interchangeably with respect to its chemical formula, chemical name, abbreviation, etc.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of such formula. The compounds of this invention may possess one or more asymmetric centers; such compounds can therefore be produced as individual (R)- or (S)-stereoisomers or as mixtures thereof. Thus, any formula given herein is intended to represent a racemate, one or more of its enantiomeric forms, one or more of its diastereomeric forms, and mixtures thereof. Additionally, any formula given herein is intended to refer also to any one of hydrates, solvates, polymorphs and of such compounds, and mixtures thereof, even if such forms are not listed explicitly.

The term "R" at a stereocenter designates that the stereocenter is purely of the R-configuration as defined in the art; likewise, the term "S" means that the stereocenter is purely of the S-configuration. As used herein, the term "RS" refers to a stereocenter that exists as a mixture of the R- and S-configurations.

Compounds containing one stereocenter drawn without a stereo bond designation are a mixture of 2 enantiomers. Compounds containing 2 stereocenters both drawn without stereo bond designations are a mixture of 4 diastereomers. Compounds with 2 stereocenters both labeled "RS" and drawn with stereo bond designations are a 2-component mixture with relative stereochemistry as drawn. Unlabeled stereocenters drawn without stereo bond designations are a mixture of the R- and S-configurations. For unlabeled stereocenters drawn with stereo bond designations, the absolute stereochemistry is as depicted.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Reference to a compound herein stands for a reference to any one of: (a) the recited form of such compound, and (b) any of the forms of such compound in the medium in which the compound is being considered when named. For example, reference herein to a compound such as R—COOH, encompasses reference to any one of: for example, R—COOH(s), R—COOH(sol), and R—COO-(sol). In this example, R—COOH(s) refers to the solid compound, as it could be for example in a tablet or some other solid pharmaceutical composition or preparation; R—COOH(sol) refers to the undissociated form of the compound in a solvent; and R—COO-(sol) refers to the dissociated form of the compound in a solvent, such as the dissociated form of the compound in an aqueous environment, whether such dissociated form derives from R—COOH, from a salt thereof, or from any other entity that yields R—COO— upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH(aq) and/or R—COO-(aq), where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number in an enriched form. Examples of isotopes that can be incorporated into compounds of the invention in a form that exceeds natural abundances include isotopes of hydrogen, carbon, nitrogen, oxygen, phosphorous, fluorine, chlorine, and iodine, such as $^2$H (or chemical symbol D), $^3$H (or chemical symbol T), $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{125}$I, respectively. Such isotopically labelled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an 18F or $^{11}$C labeled compound may be particularly preferred for PET or SPECT studies. Further, substitution with heavier isotopes such as deuterium (i.e., $^2$H, or D) may afford certain therapeutic advantages resulting from greater metabolic stability, for example increased in vivo half-life or reduced dosage requirements. Isotopically labeled compounds of this invention can generally be prepared by carrying out the procedures disclosed in the schemes or in the examples and preparations described below by substituting a readily available isotopically labeled reagent for a non-isotopically labeled reagent.

The term $C_{n-m}$ alkyl refers to an aliphatic chain, whether straight or branched, with a total number N of carbon members in the chain that satisfies n≤N≤m, with m>n.

When the same plurality of substituents is assigned to various groups, the specific individual substituent assignment to each of such groups is meant to be independently made with respect to the specific individual substituent assignments to the remaining groups. By way of illustration, but not as a limitation, if each of groups Q and R can be H or F, the choice of H or F for Q is made independently of the choice of H or F for R, so the choice of assignment for Q does not determine or condition the choice of assignment for R, or vice-versa, unless it is expressly indicated otherwise. Illustrative claim recitation in this regard would read as "each of Q and R is independently H or F", or "each of Q and R is independently selected from the group consisting of H and F".

In another example, a zwitterionic compound would be encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well-established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein.

The nomenclature "$C_i$-$C_j$" with j>i, when applied herein to a class of substituents, is meant to refer to embodiments of this invention for which each and every one of the number of carbon members, from i to j including i and j, is independently realized. By way of example, the term $C_1$-$C_3$ refers independently to embodiments that have one carbon member (C₁), embodiments that have two carbon members (C₂), and embodiments that have three carbon members (C₃).

A first embodiment of this invention (also referred to herein as Embodiment #1) includes compounds of Formula (I),

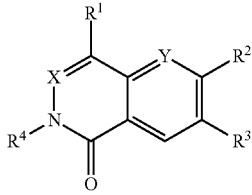

wherein
X is CH or N;
Y is CH or N;
R¹ is selected from the group consisting of: $C_{1-6}$alkyl; $C_{1-6}$alkyl substituted with one substituent selected from the group consisting of: OH, and $OCH_3$; $C_{2-6}$alkenyl; $C_{1-6}$haloalkyl; $C_{1-6}$ haloalkyl substituted with one substituent selected from the group consisting of OH, and $OCH_3$; $C_{2-6}$haloalkenyl; $N(CH_3)_2$; $C_{3-6}$cycloalkyl; $C_{3-6}$cycloalkyl substituted with one $C_{1-6}$ alkyl substituent; and phenyl;
R² is

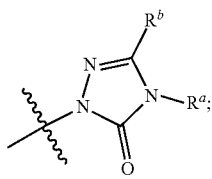

wherein
R$^a$ is selected from the group consisting of: $C_{1-6}$alkyl, $C_{1-6}$haloalkyl, and $C_{3-6}$cycloalkyl;
R$^b$ is $C_{1-6}$alkyl or $C_{1-6}$alkyl substituted with a member selected from the group consisting of: OH, halo, CN, $OC_{1-6}$alkyl, $OC_{1-6}$haloalkyl and $OC_{3-6}$cycloalkyl;
R³ is selected from the group consisting of: H, halo, $CH_3$ and $OCH_3$;
R⁴ is selected from the group consisting of:
(a) $C_{1-6}$alkyl; $C_{1-6}$alkyl substituted with one or two $OCH_3$; $C_{3-6}$cycloalkyl; $C_{3-6}$cycloalkyl substituted with $CH_3$, or $OCH_3$; $CH_2$—$C_{3-6}$cycloalkyl; and

(b)

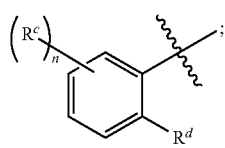

(c)

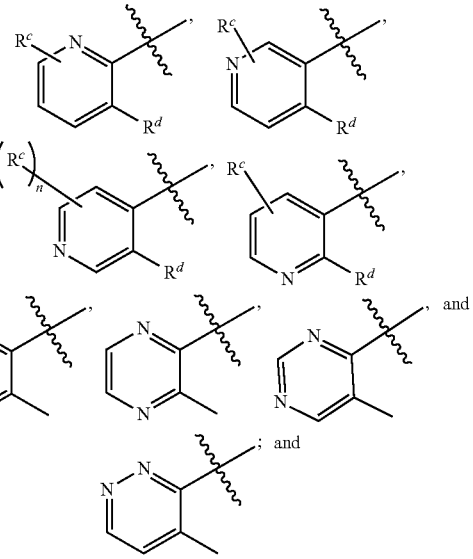

(d)

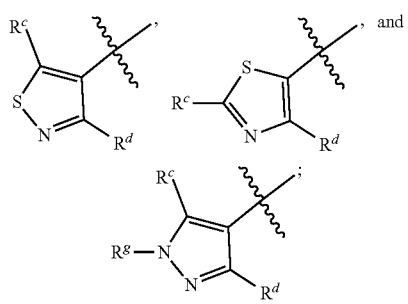

wherein
each R$^c$ is independently selected from the group consisting of: H; halo; $C_{1-6}$alkyl; $C_{1-6}$alkyl substituted with a member selected from the group consisting of: OH, $OCH_3$, $SCH_3$, and $OCF_3$; $C_{1-6}$haloalkyl; $C_{1-6}$haloalkyl substituted with a member selected from the group consisting of: OH, and $OCH_3$; $NO_2$; OH; O—$CH_2CH_2OH$; and $OC_{1-6}$alkyl;
R$^d$ is selected from the group consisting of: H; halo; $C_{1-6}$alkyl; $C_{1-6}$alkyl substituted with a member selected from the group consisting of: OH, $OCH_3$, $SCH_3$, and $OCF_3$; $C_{1-6}$haloalkyl; $C_{1-6}$haloalkyl substituted with a member selected from the group consisting of: OH, and $OCH_3$; CN; and $OC_{1-6}$alkyl;
R$^g$ is selected from the group consisting of: H; $C_{1-6}$alkyl; $C_{1-6}$alkyl substituted with a member selected from the group consisting of: OH, $OCH_3$, $SCH_3$, and $OCF_3$; $C_{1-6}$ haloalkyl; and $C_{1-6}$haloalkyl substituted with a member selected from the group consisting of: OH, and $OCH_3$; and
n is 1, or 2;
or a pharmaceutically acceptable salt, isotope, N-oxide, solvate, or stereoisomer thereof.

An additional embodiment of the invention is a compound of Formula (I) wherein X is CH.

An additional embodiment of the invention is a compound of Formula (I) wherein X is N.

An additional embodiment of the invention is a compound of Formula (I) wherein Y is CH.

An additional embodiment of the invention is a compound of Formula (I) wherein Y is N.

An additional embodiment of the invention is a compound of Formula (I) wherein $R^1$ is $C_{1-4}$alkyl; $C_{1-4}$alkyl substituted with OH, or $OCH_3$; $C_{2-4}$alkenyl; $C_{1-4}$haloalkyl; $C_{1-4}$haloalkyl substituted with OH, or $OCH_3$; $C_{2-4}$haloalkenyl; $N(CH_3)_2$; cyclopropyl; cyclopropyl substituted with $C_{1-4}$alkyl; or phenyl.

An additional embodiment of the invention is a compound of Formula (I) wherein R is $CH_3$, $CH_2CH_3$,

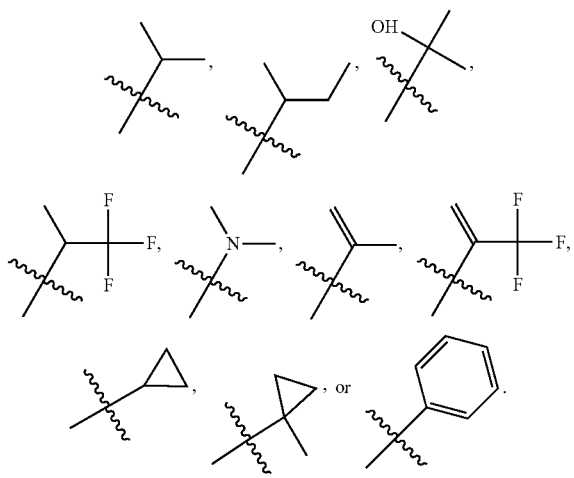

An additional embodiment of the invention is a compound of Formula (I) wherein $R^1$ is

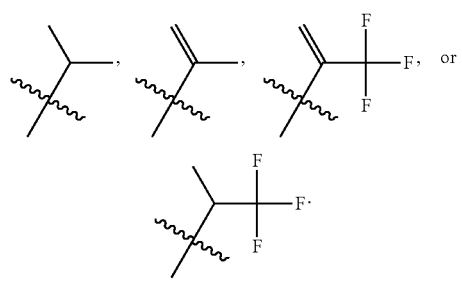

An additional embodiment of the invention is a compound of Formula (I) wherein $R^2$ is

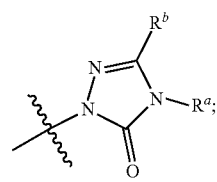

wherein $R^b$ is $C_{1-4}$alkyl substituted with OH, halo, CN, $OC_{1-4}$alkyl, $OC_{1-4}$haloalkyl or $OC_{3-6}$cycloalkyl; and $R^a$ is $C_{1-4}$alkyl, $C_{1-4}$haloalkyl, or $C_{3-6}$cycloalkyl.

An additional embodiment of the invention is a compound of Formula (I) wherein $R^2$ is

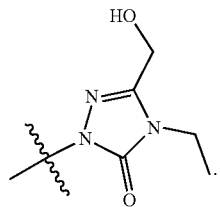 [SMILES: *n1nc(CO)n(CC)c1=O]

An additional embodiment of the invention is a compound of Formula (I) wherein $R^3$ is H.

An additional embodiment of the invention is a compound of Formula (I) wherein $R^3$ is F.

An additional embodiment of the invention is a compound of Formula (I) wherein $R^3$ is $CH_3$.

An additional embodiment of the invention is a compound of Formula (I) wherein $R^3$ is $OCH_3$.

An additional embodiment of the invention is a compound of Formula (I) wherein $R^4$ is

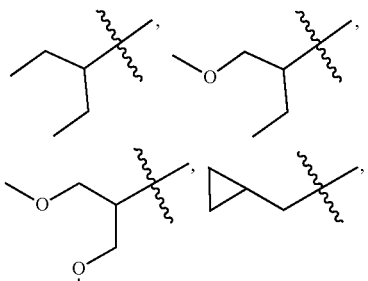

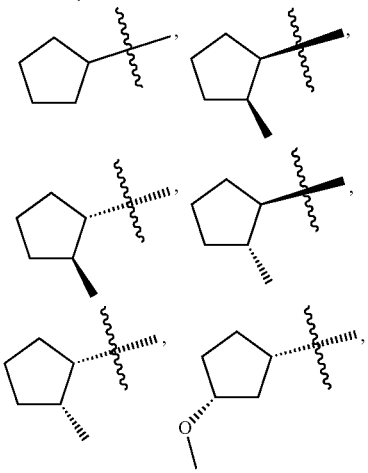

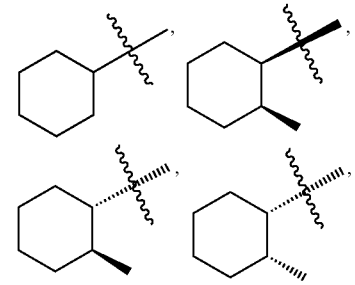

-continued

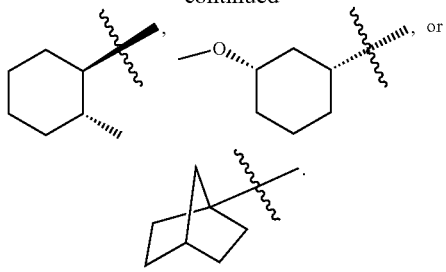

An additional embodiment of the invention is a compound of Formula (I) wherein
R⁴ is

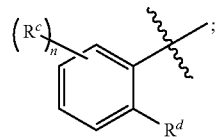

wherein
each $R^c$ is independently selected from the group consisting of: H; halo; $C_{1-4}$alkyl; $C_1$-alkyl substituted with a member selected from the group consisting of: OH, $OCH_3$, $SCH_3$, and $OCF_3$; $C_{1-4}$haloalkyl; $C_{1-4}$haloalkyl substituted with a member selected from the group consisting of: OH, and $OCH_3$; and $NO_2$;
$R^d$ is selected from the group consisting of: H; halo; $C_{1-4}$alkyl; $C_{1-4}$alkyl substituted with OH, $OCH_3$, $SCH_3$, or $OCF_3$; $C_{1-4}$haloalkyl; $C_{1-4}$haloalkyl substituted with OH, or $OCH_3$; or $OC_{1-4}$alkyl; CN; and $OC_{1-6}$alkyl; and
n is 1, or 2.

An additional embodiment of the invention is a compound of Formula (I) wherein
R⁴ is

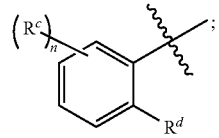

each $R^c$ is independently selected from the group consisting of: H, halo, $C_{1-4}$alkyl, $C_{1-4}$haloalkyl, $NO_2$, $O-CH_2CH_2OH$, and $OC_{1-4}$alkyl;
$R^d$ is selected from the group consisting of: H, halo, $C_{1-4}$alkyl, CN, and $OC_{1-6}$alkyl; and
n is 1, or 2.

An additional embodiment of the invention is a compound of Formula (I) wherein R⁴ is

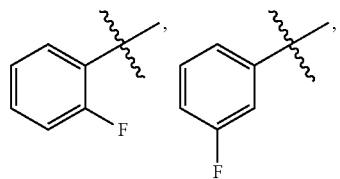

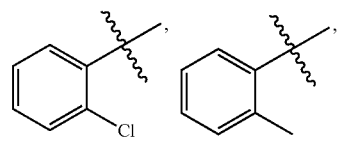
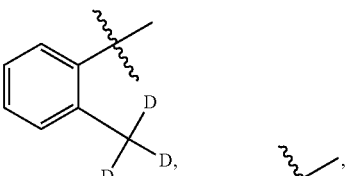
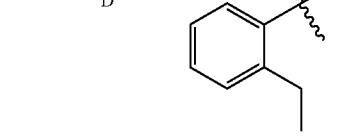
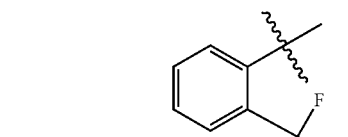
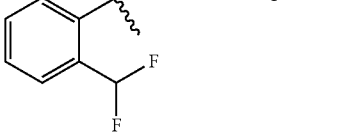
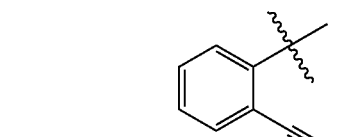
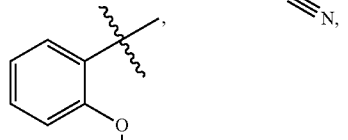
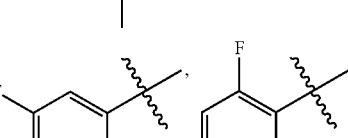
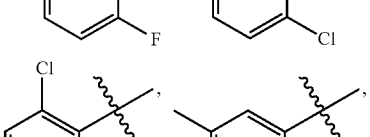
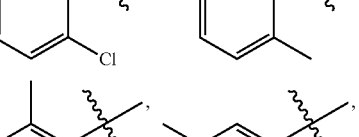
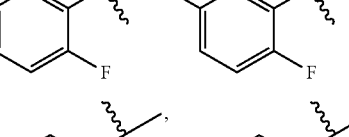
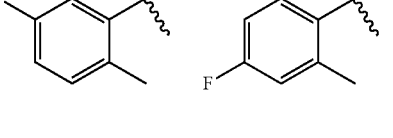

-continued

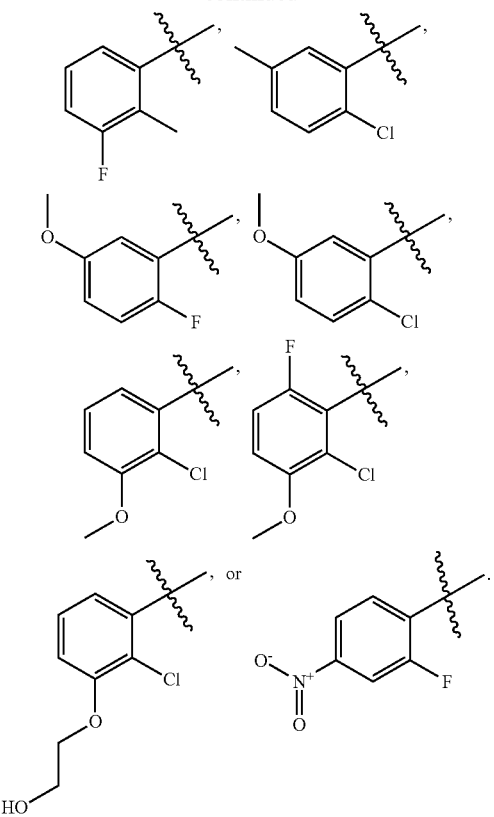

An additional embodiment of the invention is a compound of Formula (I) wherein $R^4$ is

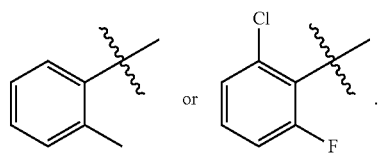

An additional embodiment of the invention is a compound of Formula (I) wherein $R^4$ is

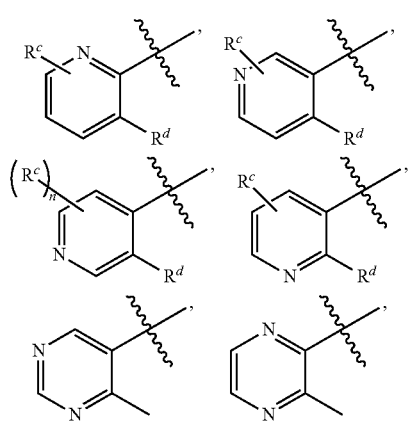

-continued

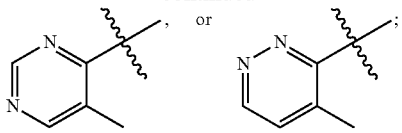

wherein
each $R^c$ is independently selected from the group consisting of: H; halo; $C_{1-4}$alkyl; $C_1$-alkyl substituted with a member selected from the group consisting of: OH, $OCH_3$, $SCH_3$, and $OCF_3$; $C_{1-4}$haloalkyl; $C_{1-4}$haloalkyl substituted with a member selected from the group consisting of: OH, and $OCH_3$; and $R^d$ is selected from the group consisting of: halo; $C_{1-4}$alkyl; $C_{1-4}$alkyl substituted with OH, $OCH_3$, $SCH_3$, or $OCF_3$; $C_{1-4}$haloalkyl; $C_{1-4}$haloalkyl substituted with OH, or $OCH_3$; or $OC_{1-4}$alkyl; CN; and $OC_{1-6}$alkyl.

An additional embodiment of the invention is a compound of Formula (I) wherein $R^4$ is

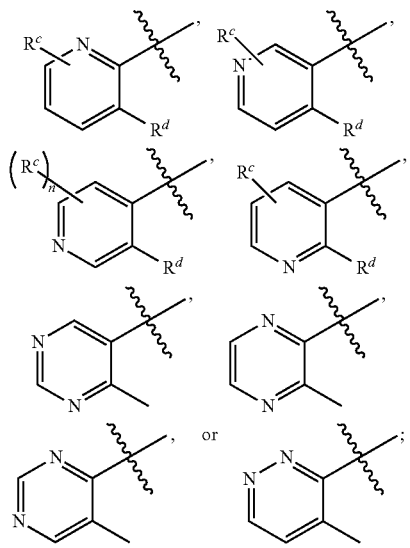

wherein
each $R^c$ is independently selected from the group consisting of: H, halo, $C_{1-4}$alkyl, $C_{1-4}$haloalkyl, $OC_{1-4}$alkyl, and OH;

$R^d$ is selected from the group consisting of: halo, $C_{1-4}$alkyl, and $OC_{1-4}$alkyl; and n is 1, or 2.

An additional embodiment of the invention is a compound of Formula (I) wherein $R^4$ is

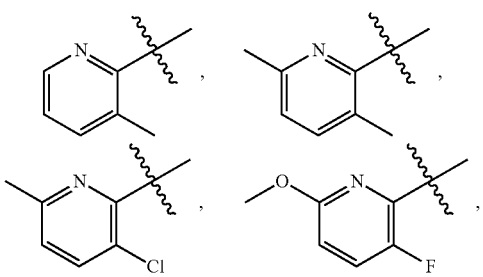

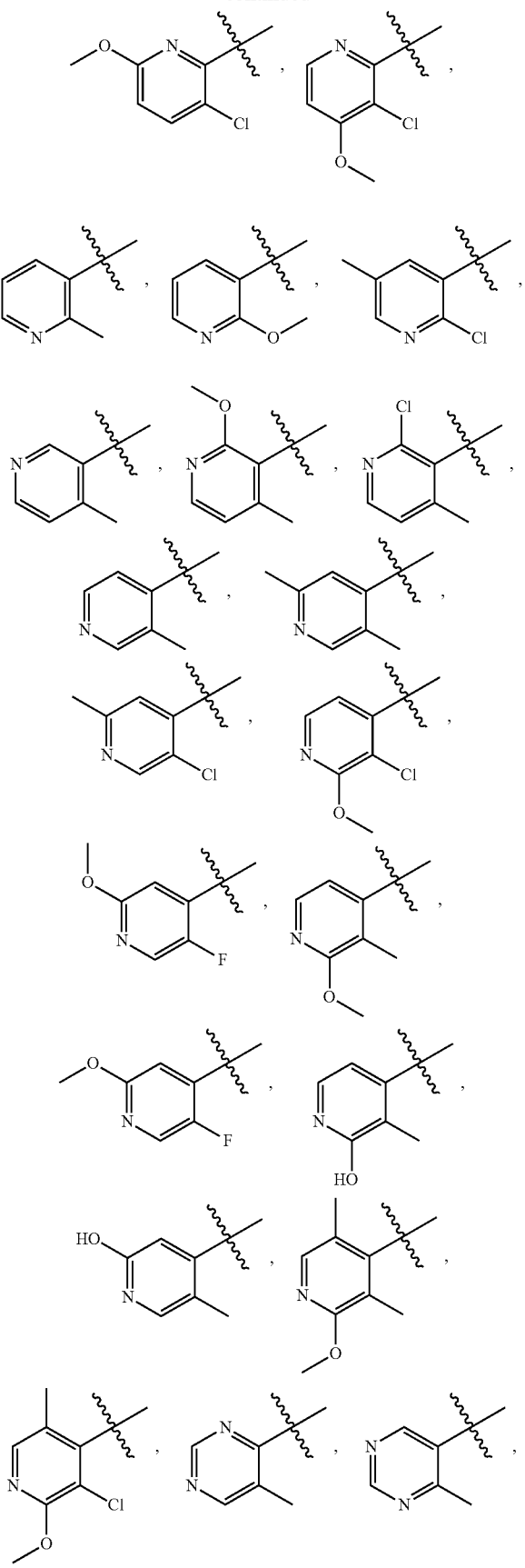

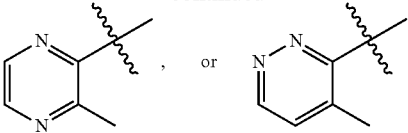

An additional embodiment of the invention is a compound of Formula (I) wherein $R^4$ is

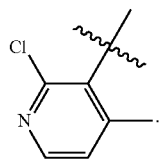

An additional embodiment of the invention is a compound of Formula (I) wherein $R^4$ is

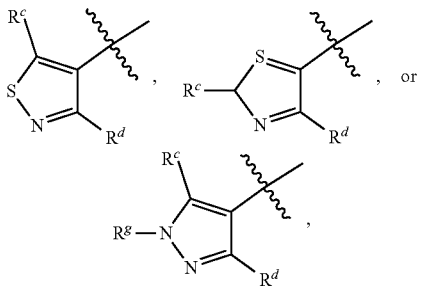

wherein
- $R^c$ is H; halo; $C_{1-4}$alkyl; $C_{1-4}$alkyl substituted with OH, $OCH_3$, $SCH_3$, or $OCF_3$; $C_{1-4}$haloalkyl; $C_{1-4}$haloalkyl substituted with OH, or $OCH_3$; or $OC_{1-4}$alkyl;
- $R^d$ is halo; $C_{1-4}$alkyl; $C_{1-4}$alkyl substituted with OH, $OCH_3$, $SCH_3$, or $OCF_3$; $C_{1-4}$haloalkyl; or $C_{1-4}$haloalkyl substituted with OH, or $OCH_3$; and
- $R^g$ is H; $C_{1-4}$alkyl; $C_{1-4}$alkyl substituted with OH, $OCH_3$, $SCH_3$, or $OCF_3$; $C_{1-4}$haloalkyl; or $C_{1-4}$haloalkyl substituted with OH, or $OCH_3$.

An additional embodiment of the invention is a compound of Formula (I) wherein $R^4$ is

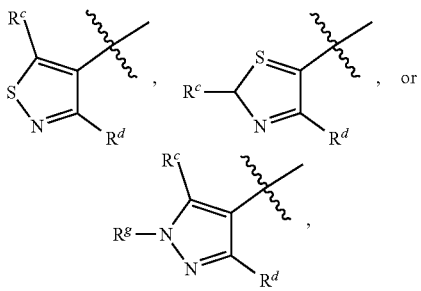

wherein
- $R^c$ is H or halo;
- $R^d$ is $C_{1-4}$alkyl; and
- $R^g$ is H.

An additional embodiment of the invention is a compound of Formula (I) wherein R⁴ is

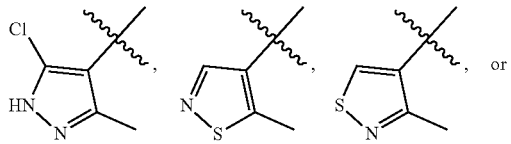, or 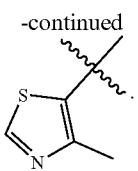.

An additional embodiment of the current invention is a compound selected from the compounds shown below in Table 1, and, optionally, one or more of pharmaceutically acceptable salts, isotopes, N-oxides, solvates, and stereoisomers thereof:

TABLE 1

| Example # | Compound Name |
|---|---|
| 1 | 6-(4-Ethyl-3-(hydroxymethyl)-5-oxo-4,5-dihydro-1H-1,2,4-triazol-1-yl)-2-(3-fluorophenyl)-4-(prop-1-en-2-yl)isoquinolin-1(2H)-one; |
| 2 | 6-(4-Ethyl-3-(hydroxymethyl)-5-oxo-4,5-dihydro-1H-1,2,4-triazol-1-yl)-2-(3-fluorophenyl)-4-isopropylisoquinolin-1(2H)-one; |
| 3 | 2-(2-Chloro-6-fluorophenyl)-6-(4-ethyl-3-(hydroxymethyl)-5-oxo-4,5-dihydro-1H-1,2,4-triazol-1-yl)-4-isopropylisoquinolin-1(2H)-one; |
| 4 | 6-(4-Ethyl-3-(hydroxymethyl)-5-oxo-4,5-dihydro-1H-1,2,4-triazol-1-yl)-2-(3-fluorophenyl)-4-phenylisoquinolin-1(2H)-one; |
| 5 | 2-(2-Chloro-6-fluorophenyl)-6-(4-ethyl-3-(hydroxymethyl)-5-oxo-4,5-dihydro-1H-1,2,4-triazol-1-yl)-4-(prop-1-en-2-yl)isoquinolin-1(2H)-one; |
| 6 | 2-(2-Chloro-6-fluorophenyl)-6-(4-ethyl-3-(hydroxymethyl)-5-oxo-4,5-dihydro-1H-1,2,4-triazol-1-yl)-4-(3,3,3-trifluoroprop-1-en-2-yl)isoquinolin-1(2H)-one; |
| 7 | 2-(2,6-Dichlorophenyl)-6-(4-ethyl-3-(hydroxymethyl)-5-oxo-4,5-dihydro-1H-1,2,4-triazol-1-yl)-4-(1-methylcyclopropyl)isoquinolin-1(2H)-one; |
| 8 | 2-(2,6-Dichlorophenyl)-6-(4-ethyl-3-(hydroxymethyl)-5-oxo-4,5-dihydro-1H-1,2,4-triazol-1-yl)-4-(prop-1-en-2-yl)isoquinolin-1(2H)-one; |
| 9 | 2-(2-Chloro-6-fluorophenyl)-4-cyclopropyl-6-(4-ethyl-3-(hydroxymethyl)-5-oxo-4,5-dihydro-1H-1,2,4-triazol-1-yl)isoquinolin-1(2H)-one; |
| 10 | 2-(2-Chloro-6-fluorophenyl)-6-(4-ethyl-3-(hydroxymethyl)-5-oxo-4,5-dihydro-1H-1,2,4-triazol-1-yl)isoquinolin-1(2H)-one; |
| 11 | 2-(2-Chloro-6-fluorophenyl)-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 12 | 6-(4-Ethyl-3-(hydroxymethyl)-5-oxo-4,5-dihydro-1H-1,2,4-triazol-1-yl)-4-(prop-1-en-2-yl)-2-(2-(trifluoromethyl)phenyl)isoquinolin-1(2H)-one; |
| 13 | 2-(6-(4-Ethyl-3-(hydroxymethyl)-5-oxo-4,5-dihydro-1H-1,2,4-triazol-1-yl)-1-oxo-4-(prop-1-en-2-yl)isoquinolin-2(1H)-yl)benzonitrile; |
| 14 | 2-(2-Chlorophenyl)-6-(4-ethyl-3-(hydroxymethyl)-5-oxo-4,5-dihydro-1H-1,2,4-triazol-1-yl)-4-(prop-1-en-2-yl)isoquinolin-1(2H)-one; |
| 15 | 6-(4-Ethyl-3-(hydroxymethyl)-5-oxo-4,5-dihydro-1H-1,2,4-triazol-1-yl)-4-(prop-1-en-2-yl)-2-(o-tolyl)isoquinolin-1(2H)-one; |
| 16 | 6-(4-Ethyl-3-(hydroxymethyl)-5-oxo-4,5-dihydro-1H-1,2,4-triazol-1-yl)-2-(2-fluoro-4-nitrophenyl)-4-iodoisoquinolin-1(2H)-one; |
| 17 | 2-(2-Chlorophenyl)-6-(4-ethyl-3-(hydroxymethyl)-5-oxo-4,5-dihydro-1H-1,2,4-triazol-1-yl)-4-isopropylphthalazin-1(2H)-one; |
| 18 | 6-(4-Ethyl-3-(hydroxymethyl)-5-oxo-4,5-dihydro-1H-1,2,4-triazol-1-yl)-2-(3-fluorophenyl)-4-isopropylphthalazin-1(2H)-one; |
| 19 | 2-(2-Chloro-6-fluorophenyl)-6-(4-ethyl-3-(hydroxymethyl)-5-oxo-4,5-dihydro-1H-1,2,4-triazol-1-yl)-4-isopropylphthalazin-1(2H)-one; |
| 20 | 4-Ethyl-6-(4-ethyl-3-(hydroxymethyl)-5-oxo-4,5-dihydro-1H-1,2,4-triazol-1-yl)-2-(3-fluorophenyl)phthalazin-1(2H)-one; |
| 21 | 4-Ethyl-6-(4-ethyl-3-(hydroxymethyl)-5-oxo-4,5-dihydro-1H-1,2,4-triazol-1-yl)-2-(o-tolyl)phthalazin-1(2H)-one; |
| 22 | 6-(4-Ethyl-3-(hydroxymethyl)-5-oxo-4,5-dihydro-1H-1,2,4-triazol-1-yl)-7-fluoro-4-isopropyl-2-(o-tolyl)isoquinolin-1(2H)-one; |
| 23 | 2-(2-Chloro-4-methylpyridin-3-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 24 | 2-(2-Chloro-6-fluorophenyl)-6-(4-ethyl-3-(hydroxymethyl)-5-oxo-4,5-dihydro-1H-1,2,4-triazol-1-yl)-4-(1-methylcyclopropyl)isoquinolin-1(2H)-one; |
| 25 | 6-(4-Ethyl-3-(hydroxymethyl)-5-oxo-4,5-dihydro-1H-1,2,4-triazol-1-yl)-2-(3-fluorophenyl)-4-(2-hydroxypropan-2-yl)isoquinolin-1(2H)-one; |
| 26 | 4-(Dimethylamino)-6-(4-ethyl-3-(hydroxymethyl)-5-oxo-4,5-dihydro-1H-1,2,4-triazol-1-yl)-2-(o-tolyl)isoquinolin-1(2H)-one; |
| 27 | 2-(2-Chloro-6-fluorophenyl)-6-(4-ethyl-3-(hydroxymethyl)-5-oxo-4,5-dihydro-1H-1,2,4-triazol-1-yl)-7-fluoro-4-(prop-1-en-2-yl)phthalazin-1(2H)-one; |
| 28 | 2-(2-Chloro-6-fluorophenyl)-7-(4-ethyl-3-(hydroxymethyl)-5-oxo-4,5-dihydro-1H-1,2,4-triazol-1-yl)-6-fluoro-4-(prop-1-en-2-yl)phthalazin-1(2H)-one; |
| 29 | 2-(2-Chloro-6-fluorophenyl)-6-(4-ethyl-3-(hydroxymethyl)-5-oxo-4,5-dihydro-1H-1,2,4-triazol-1-yl)-7-methoxy-4-(prop-1-en-2-yl)phthalazin-1(2H)-one; |
| 30 | 2-(2-Chloro-6-fluorophenyl)-7-(4-ethyl-3-(hydroxymethyl)-5-oxo-4,5-dihydro-1H-1,2,4-triazol-1-yl)-6-methoxy-4-(prop-1-en-2-yl)phthalazin-1(2H)-one; |

TABLE 1-continued

| Example # | Compound Name |
|---|---|
| 31 | 2-(5-Chloro-3-methyl-1H-pyrazol-4-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 32 | 2-(4-Ethyl-3-(hydroxymethyl)-5-oxo-4,5-dihydro-1H-1,2,4-triazol-1-yl)-3-fluoro-8-(prop-1-en-2-yl)-6-(o-tolyl)-1,6-naphthyridin-5(6H)-one; |
| 33 | 2-(4-Ethyl-3-(hydroxymethyl)-5-oxo-4,5-dihydro-1H-1,2,4-triazol-1-yl)-3-fluoro-8-methyl-6-(o-tolyl)pyrido[2,3-d]pyridazin-5(6H)-one; |
| 34 | 2-(4-Ethyl-3-(hydroxymethyl)-5-oxo-4,5-dihydro-1H-1,2,4-triazol-1-yl)-3-fluoro-8-isopropyl-6-(o-tolyl)pyrido[2,3-d]pyridazin-5(6H)-one; |
| 35 | 6-(2-Chloro-6-fluorophenyl)-2-(4-ethyl-3-(hydroxymethyl)-5-oxo-4,5-dihydro-1H-1,2,4-triazol-1-yl)-3-fluoro-8-(prop-1-en-2-yl)-1,6-naphthyridin-5(6H)-one; |
| 36 | 6-(2-Chloro-6-fluorophenyl)-2-(4-ethyl-3-(hydroxymethyl)-5-oxo-4,5-dihydro-1H-1,2,4-triazol-1-yl)-3-fluoro-8-isopropyl-1,6-naphthyridin-5(6H)-one; |
| 37 | (S)-2-(4-Ethyl-3-(hydroxymethyl)-5-oxo-4,5-dihydro-1H-1,2,4-triazol-1-yl)-3-fluoro-6-(o-tolyl)-8-(1,1,1-trifluoropropan-2-yl)-1,6-naphthyridin-5(6H)-one; |
| 38 | (R)-2-(4-Ethyl-3-(hydroxymethyl)-5-oxo-4,5-dihydro-1H-1,2,4-triazol-1-yl)-3-fluoro-6-(o-tolyl)-8-(1,1,1-trifluoropropan-2-yl)-1,6-naphthyridin-5(6H)-one; |
| 39 | 6-(4-Ethyl-3-(hydroxymethyl)-5-oxo-4,5-dihydro-1H-1,2,4-triazol-1-yl)-7-fluoro-4-isopropyl-2-(4-methylthiazol-5-yl)isoquinolin-1(2H)-one; |
| 40 | 2-(4-Ethyl-3-(hydroxymethyl)-5-oxo-4,5-dihydro-1H-1,2,4-triazol-1-yl)-3-fluoro-8-isopropyl-6-(o-tolyl)-1,6-naphthyridin-5(6H)-one; |
| 41 | 6-(4-Ethyl-3-(hydroxymethyl)-5-oxo-4,5-dihydro-1H-1,2,4-triazol-1-yl)-7-fluoro-2-(2-fluoro-5-methylphenyl)-4-isopropylisoquinolin-1(2H)-one; |
| 42 | 6-(4-Ethyl-3-(hydroxymethyl)-5-oxo-4,5-dihydro-1H-1,2,4-triazol-1-yl)-7-fluoro-2-(2-fluoro-5-methylphenyl)-4-(prop-1-en-2-yl)isoquinolin-1(2H)-one; |
| 43 | 2-(2-Chloro-5-methylphenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; |
| 44 | 6-(4-Ethyl-3-(hydroxymethyl)-5-oxo-4,5-dihydro-1H-1,2,4-triazol-1-yl)-7-fluoro-2-(2-fluoro-5-methoxyphenyl)-4-(prop-1-en-2-yl)isoquinolin-1(2H)-one; |
| 45 | 2-(2-Chlorophenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; |
| 46 | 6-(4-Ethyl-3-(hydroxymethyl)-5-oxo-4,5-dihydro-1H-1,2,4-triazol-1-yl)-7-fluoro-4-(prop-1-en-2-yl)-2-(o-tolyl)isoquinolin-1(2H)-one; |
| 47 | 2-(2-Chloro-5-methoxyphenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; |
| 48 | racemic-4-(sec-Butyl)-2-(2-chloro-6-fluorophenyl)-6-(4-ethyl-3-(hydroxymethyl)-5-oxo-4,5-dihydro-1H-1,2,4-triazol-1-yl)-7-fluoroisoquinolin-1(2H)-one; |
| 49 | 2-(3-Chloro-6-methoxypyridin-2-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 50 | 6-(4-Ethyl-3-(hydroxymethyl)-5-oxo-4,5-dihydro-1H-1,2,4-triazol-1-yl)-7-fluoro-4-isopropyl-2-(2-methoxy-4-methylpyridin-3-yl)isoquinolin-1(2H)-one; |
| 51 | 2-(2-Chloro-6-fluoro-3-methoxyphenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; |
| 52 | 2-(2-Chloro-6-fluorophenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; |
| 53 | 6-(4-Ethyl-3-(hydroxymethyl)-5-oxo-4,5-dihydro-1H-1,2,4-triazol-1-yl)-7-fluoro-4-isopropyl-2-(o-tolyl)phthalazin-1(2H)-one; |
| 54 | 2-(2-Chloro-6-fluorophenyl)-6-(4-ethyl-3-(hydroxymethyl)-5-oxo-4,5-dihydro-1H-1,2,4-triazol-1-yl)-7-fluoro-4-isopropylphthalazin-1(2H)-one; |
| 55 | Racemic 6-(4-Ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)phthalazin-1(2H)-one; |
| 56 | (S*)-6-(4-Ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)phthalazin-1(2H)-one; |
| 57 | (R*)-6-(4-Ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)phthalazin-1(2H)-one; |
| 58 | 2-(2-Chloro-6-fluorophenyl)-6-(4-ethyl-3-(hydroxymethyl)-5-oxo-4,5-dihydro-1H-1,2,4-triazol-1-yl)-7-fluoro-4-(1-methylcyclopropyl)isoquinolin-1(2H)-one; |
| 59 | 6-(4-Ethyl-3-(hydroxymethyl)-5-oxo-4,5-dihydro-1H-1,2,4-triazol-1-yl)-7-fluoro-2-(2-methoxy-4-methylpyridin-3-yl)-4-(prop-1-en-2-yl)isoquinolin-1(2H)-one; |
| 60 | 2-(5-Chloro-3-methyl-1H-pyrazol-4-yl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; |
| 61 | 2-(3-Chloro-2-methoxy-5-methylpyridin-4-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 62 | 2-(3-Chloro-2-methoxy-5-methylpyridin-4-yl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; |
| 63 | 6-(4-Ethyl-3-(hydroxymethyl)-5-oxo-4,5-dihydro-1H-1,2,4-triazol-1-yl)-7-fluoro-2-(2-fluoro-5-methoxyphenyl)-4-isopropylisoquinolin-1(2H)-one; |
| 64 | 6-(4-Ethyl-3-(hydroxymethyl)-5-oxo-4,5-dihydro-1H-1,2,4-triazol-1-yl)-7-fluoro-2-(4-fluoro-2-methylphenyl)-4-isopropylisoquinolin-1(2H)-one; |
| 65 | 2-(2-Chloro-3-(2-hydroxyethoxy)phenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; |
| 66 | 6-(4-Ethyl-3-(hydroxymethyl)-5-oxo-4,5-dihydro-1H-1,2,4-triazol-1-yl)-7-fluoro-2-(2-fluorophenyl)-4-(prop-1-en-2-yl)isoquinolin-1(2H)-one; |
| 67 | 6-(4-Ethyl-3-(hydroxymethyl)-5-oxo-4,5-dihydro-1H-1,2,4-triazol-1-yl)-7-fluoro-2-(5-fluoro-2-methylphenyl)-4-isopropylisoquinolin-1(2H)-one; |

TABLE 1-continued

| Example # | Compound Name |
|---|---|
| 68 | 2-(2,5-Difluorophenyl)-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 69 | 6-(4-Ethyl-3-(hydroxymethyl)-5-oxo-4,5-dihydro-1H-1,2,4-triazol-1-yl)-7-fluoro-2-(2-fluoro-6-methylphenyl)-4-isopropylisoquinolin-1(2H)-one; |
| 70 | 2-(2-Chloro-3-methoxyphenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; |
| 71 | 6-(4-Ethyl-3-(hydroxymethyl)-5-oxo-4,5-dihydro-1H-1,2,4-triazol-1-yl)-7-fluoro-2-(2-methoxy-3,5-dimethylpyridin-4-yl)-4-(prop-1-en-2-yl)isoquinolin-1(2H)-one; |
| 72 | 2-(2,5-Difluorophenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; |
| 73 | 6-(4-Ethyl-3-(hydroxymethyl)-5-oxo-4,5-dihydro-1H-1,2,4-triazol-1-yl)-7-fluoro-2-(2-fluoro-6-methylphenyl)-4-(prop-1-en-2-yl)isoquinolin-1(2H)-one; |
| 74 | 6-(4-Ethyl-3-(hydroxymethyl)-5-oxo-4,5-dihydro-1H-1,2,4-triazol-1-yl)-7-fluoro-2-(3-fluoro-2-methylphenyl)-4-isopropylisoquinolin-1(2H)-one; |
| 75 | 2-(2,5-Dimethylphenyl)-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 76 | 6-(4-Ethyl-3-(hydroxymethyl)-5-oxo-4,5-dihydro-1H-1,2,4-triazol-1-yl)-7-fluoro-2-(4-fluoro-2-methylphenyl)-4-(prop-1-en-2-yl)isoquinolin-1(2H)-one; |
| 77 | 6-(4-Ethyl-3-(hydroxymethyl)-5-oxo-4,5-dihydro-1H-1,2,4-triazol-1-yl)-7-fluoro-2-(2-fluorophenyl)-4-isopropylisoquinolin-1(2H)-one; |
| 78 | 6-(4-Ethyl-3-(hydroxymethyl)-5-oxo-4,5-dihydro-1H-1,2,4-triazol-1-yl)-7-fluoro-4-isopropyl-2-(2-methoxy-3,5-dimethylpyridin-4-yl)isoquinolin-1(2H)-one; |
| 79 | 6-(4-Ethyl-3-(hydroxymethyl)-5-oxo-4,5-dihydro-1H-1,2,4-triazol-1-yl)-7-methyl-4-(prop-1-en-2-yl)-2-(o-tolyl)isoquinolin-1(2H)-one; |
| 80 | 2-(2-Chloro-6-fluoro-3-methoxyphenyl)-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 81 | 6-(4-Ethyl-3-(hydroxymethyl)-5-oxo-4,5-dihydro-1H-1,2,4-triazol-1-yl)-7-fluoro-2-(o-tolyl)-4-(3,3,3-trifluoroprop-1-en-2-yl)isoquinolin-1(2H)-one; |
| 82 | 6-(4-Ethyl-3-(hydroxymethyl)-5-oxo-4,5-dihydro-1H-1,2,4-triazol-1-yl)-7-fluoro-2-(5-fluoro-2-methylphenyl)-4-(prop-1-en-2-yl)isoquinolin-1(2H)-one; |
| 83 | 6-(4-Ethyl-3-(hydroxymethyl)-5-oxo-4,5-dihydro-1H-1,2,4-triazol-1-yl)-7-fluoro-2-(2-methoxyphenyl)-4-(prop-1-en-2-yl)isoquinolin-1(2H)-one; |
| 84 | 2-(2-Chloro-5-methylpyridin-3-yl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; |
| 85 | 6-(4-Ethyl-3-(hydroxymethyl)-5-oxo-4,5-dihydro-1H-1,2,4-triazol-1-yl)-7-fluoro-2-(5-fluoro-2-methoxypyridin-4-yl)-4-(prop-1-en-2-yl)isoquinolin-1(2H)-one; |
| 86 | 6-(4-Ethyl-3-(hydroxymethyl)-5-oxo-4,5-dihydro-1H-1,2,4-triazol-1-yl)-7-fluoro-2-(3-fluoro-2-methylphenyl)-4-(prop-1-en-2-yl)isoquinolin-1(2H)-one; |
| 87 | 2-(2,5-Dimethylphenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; |
| 88 | Racemic-6-(4-Ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)isoquinolin-1(2H)-one; |
| 89 | 6-(4-Ethyl-3-(hydroxymethyl)-5-oxo-4,5-dihydro-1H-1,2,4-triazol-1-yl)-2-(2-ethylphenyl)-7-fluoro-4-isopropylisoquinolin-1(2H)-one; |
| 90 | 6-(4-Ethyl-3-(hydroxymethyl)-5-oxo-4,5-dihydro-1H-1,2,4-triazol-1-yl)-7-fluoro-4-isopropyl-2-(2-methoxypyridin-3-yl)isoquinolin-1(2H)-one; |
| 91 | 6-(4-Ethyl-3-(hydroxymethyl)-5-oxo-4,5-dihydro-1H-1,2,4-triazol-1-yl)-7-fluoro-2-(5-fluoro-2-methoxypyridin-4-yl)-4-isopropylisoquinolin-1(2H)-one; |
| 92 | 2-(2-Chloro-5-methylpyridin-3-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 93 | 6-(4-Ethyl-3-(hydroxymethyl)-5-oxo-4,5-dihydro-1H-1,2,4-triazol-1-yl)-7-fluoro-4-isopropyl-2-(2-(methyl-d$_3$)phenyl)isoquinolin-1(2H)-one; |
| 94 | 6-(4-Ethyl-3-(hydroxymethyl)-5-oxo-4,5-dihydro-1H-1,2,4-triazol-1-yl)-7-fluoro-4-isopropyl-2-(4-methylpyrimidin-5-yl)isoquinolin-1(2H)-one; |
| 95 | 6-(4-Ethyl-3-(hydroxymethyl)-5-oxo-4,5-dihydro-1H-1,2,4-triazol-1-yl)-7-fluoro-2-(2-methoxyphenyl)isoquinolin-1(2H)-one; |
| 96 | 6-(4-Ethyl-3-(hydroxymethyl)-5-oxo-4,5-dihydro-1H-1,2,4-triazol-1-yl)-7-fluoro-2-(3-fluoro-6-methoxypyridin-2-yl)-4-isopropylisoquinolin-1(2H)-one; |
| 97 | 6-(4-Ethyl-3-(hydroxymethyl)-5-oxo-4,5-dihydro-1H-1,2,4-triazol-1-yl)-7-fluoro-4-isopropyl-2-(3-methylpyrazin-2-yl)isoquinolin-1(2H)-one; |
| 98 | 2-(2-Chloro-5-methylpyridin-3-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 99 | 2-(4-Ethyl-3-(hydroxymethyl)-5-oxo-4,5-dihydro-1H-1,2,4-triazol-1-yl)-3-fluoro-6-(2-fluoro-5-methylphenyl)-8-isopropyl-1,6-naphthyridin-5(6H)-one; |
| 100 | 6-(4-Ethyl-3-(hydroxymethyl)-5-oxo-4,5-dihydro-1H-1,2,4-triazol-1-yl)-7-fluoro-4-isopropyl-2-(4-methylpyridazin-3-yl)isoquinolin-1(2H)-one; |
| 101 | (S)-6-(4-Ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)isoquinolin-1(2H)-one; |
| 102 | (R)-6-(4-Ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)isoquinolin-1(2H)-one; |
| 103 | 6-(4-Ethyl-3-(hydroxymethyl)-5-oxo-4,5-dihydro-1H-1,2,4-triazol-1-yl)-7-fluoro-4-isopropyl-2-(2-(trifluoromethyl)phenyl)isoquinolin-1(2H)-one; |
| 104 | 6-(4-Ethyl-3-(hydroxymethyl)-5-oxo-4,5-dihydro-1H-1,2,4-triazol-1-yl)-7-fluoro-4-isopropyl-2-(5-methylpyrimidin-4-yl)isoquinolin-1(2H)-one; |
| 105 | 2-(2-(Difluoromethyl)phenyl)-6-(4-ethyl-3-(hydroxymethyl)-5-oxo-4,5-dihydro-1H-1,2,4-triazol-1-yl)-7-fluoro-4-isopropylisoquinolin-1(2H)-one; |

TABLE 1-continued

| Example # | Compound Name |
|---|---|
| 106 | 2-(3-Chloro-2-methoxypyridin-4-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 107 | 2-Cyclohexyl-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 108 | 2-(3-Chloro-6-methylpyridin-2-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 109 | 2-Cyclopentyl-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 110 | 2-(3-Chloro-4-methoxypyridin-2-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 111 | 6-(4-Ethyl-3-(hydroxymethyl)-5-oxo-4,5-dihydro-1H-1,2,4-triazol-1-yl)-7-fluoro-4-isopropyl-2-((1R,2S)-2-methylcyclohexyl)isoquinolin-1(2H)-one; |
| 112 | 2-(1,3-Dimethoxypropan-2-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 113 | 6-(4-Ethyl-3-(hydroxymethyl)-5-oxo-4,5-dihydro-1H-1,2,4-triazol-1-yl)-7-fluoro-4-isopropyl-2-(2-methoxy-5-methylpyridin-4-yl)isoquinolin-1(2H)-one; |
| 114 | 6-(4-Ethyl-3-(hydroxymethyl)-5-oxo-4,5-dihydro-1H-1,2,4-triazol-1-yl)-7-fluoro-4-isopropyl-2-((1S,2R)-2-methylcyclohexyl)isoquinolin-1(2H)-one; |
| 115 | 2-(Cyclopropylmethyl)-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 116 | 6-(4-Ethyl-3-(hydroxymethyl)-5-oxo-4,5-dihydro-1H-1,2,4-triazol-1-yl)-7-fluoro-4-isopropyl-2-(1-methoxybutan-2-yl)isoquinolin-1(2H)-one; |
| 117 | 2-(2-Chlorophenyl)-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 118 | 6-(4-Ethyl-3-(hydroxymethyl)-5-oxo-4,5-dihydro-1H-1,2,4-triazol-1-yl)-7-fluoro-4-isopropyl-2-(3-methylpyridin-2-yl)isoquinolin-1(2H)-one; |
| 119 | Racemic 6-(4-Ethyl-3-(hydroxymethyl)-5-oxo-4,5-dihydro-1H-1,2,4-triazol-1-yl)-7-fluoro-4-isopropyl-2-((cis)-3-methoxycyclopentyl)isoquinolin-1(2H)-one; |
| 120 | 6-(4-Ethyl-3-(hydroxymethyl)-5-oxo-4,5-dihydro-1H-1,2,4-triazol-1-yl)-7-fluoro-4-isopropyl-2-((1R*,2R*)-2-methylcyclohexyl)isoquinolin-1(2H)-one; |
| 121 | 6-(4-Ethyl-3-(hydroxymethyl)-5-oxo-4,5-dihydro-1H-1,2,4-triazol-1-yl)-7-fluoro-4-isopropyl-2-((1S*,2S*)-2-methylcyclohexyl)isoquinolin-1(2H)-one; |
| 122 | 6-(4-Ethyl-3-(hydroxymethyl)-5-oxo-4,5-dihydro-1H-1,2,4-triazol-1-yl)-7-fluoro-4-isopropyl-2-(pentan-3-yl)isoquinolin-1(2H)-one; |
| 123 | 6-(4-Ethyl-3-(hydroxymethyl)-5-oxo-4,5-dihydro-1H-1,2,4-triazol-1-yl)-7-fluoro-4-isopropyl-2-((1R*,2R*)-2-methylcyclopentyl)isoquinolin-1(2H)-one; |
| 124 | 6-(4-Ethyl-3-(hydroxymethyl)-5-oxo-4,5-dihydro-1H-1,2,4-triazol-1-yl)-7-fluoro-4-isopropyl-2-((1S*,2S*)-2-methylcyclopentyl)isoquinolin-1(2H)-one; |
| 125 | 6-(4-Ethyl-3-(hydroxymethyl)-5-oxo-4,5-dihydro-1H-1,2,4-triazol-1-yl)-7-fluoro-4-isopropyl-2-((1R*,2S*)-2-methylcyclopentyl)isoquinolin-1(2H)-one; |
| 126 | 6-(4-Ethyl-3-(hydroxymethyl)-5-oxo-4,5-dihydro-1H-1,2,4-triazol-1-yl)-7-fluoro-4-isopropyl-2-((1S*,2R*)-2-methylcyclopentyl)isoquinolin-1(2H)-one; |
| 127 | Racemic 6-(4-Ethyl-3-(hydroxymethyl)-5-oxo-4,5-dihydro-1H-1,2,4-triazol-1-yl)-7-fluoro-4-isopropyl-2-((cis)-3-methoxycyclohexyl)isoquinolin-1(2H)-one; |
| 128 | 2-(Bicyclo[2.2.1]heptan-1-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 129 | 6-(4-Ethyl-3-(hydroxymethyl)-5-oxo-4,5-dihydro-1H-1,2,4-triazol-1-yl)-7-fluoro-4-isopropyl-2-(2-methoxy-3-methylpyridin-4-yl)isoquinolin-1(2H)-one; |
| 130 | 2-(4-Ethyl-3-(hydroxymethyl)-5-oxo-4,5-dihydro-1H-1,2,4-triazol-1-yl)-3-fluoro-8-isopropyl-6-(2-methoxyphenyl)-1,6-naphthyridin-5(6H)-one; |
| 131 | 6-(4-Ethyl-3-(hydroxymethyl)-5-oxo-4,5-dihydro-1H-1,2,4-triazol-1-yl)-7-fluoro-4-isopropyl-2-(3-methylisothiazol-4-yl)isoquinolin-1(2H)-one; |
| 132 | 6-(4-Ethyl-3-(hydroxymethyl)-5-oxo-4,5-dihydro-1H-1,2,4-triazol-1-yl)-7-fluoro-4-isopropyl-2-(5-methylisothiazol-4-yl)isoquinolin-1(2H)-one; |
| 133 | 2-(4-Ethyl-3-(hydroxymethyl)-5-oxo-4,5-dihydro-1H-1,2,4-triazol-1-yl)-3-fluoro-8-isopropyl-6-(2-(trifluoromethyl)phenyl)-1,6-naphthyridin-5(6H)-one; |
| 134 | 2-(3,6-Dimethylpyridin-2-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 135 | 2-(2,5-Dimethylpyridin-4-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; |
| 136 | 6-(4-Ethyl-3-(hydroxymethyl)-5-oxo-4,5-dihydro-1H-1,2,4-triazol-1-yl)-7-fluoro-4-isopropyl-2-(4-methylpyridin-3-yl)isoquinolin-1(2H)-one; |
| 137 | 6-(4-Ethyl-3-(hydroxymethyl)-5-oxo-4,5-dihydro-1H-1,2,4-triazol-1-yl)-7-fluoro-4-isopropyl-2-(3-methylpyridin-4-yl)isoquinolin-1(2H)-one; |
| 138 | 6-(4-Ethyl-3-(hydroxymethyl)-5-oxo-4,5-dihydro-1H-1,2,4-triazol-1-yl)-7-fluoro-4-isopropyl-2-(2-methylpyridin-3-yl)isoquinolin-1(2H)-one; |
| 139 | 6-(4-Ethyl-3-(hydroxymethyl)-5-oxo-4,5-dihydro-1H-1,2,4-triazol-1-yl)-7-fluoro-2-(2-hydroxy-5-methylpyridin-4-yl)-4-isopropylisoquinolin-1(2H)-one; |
| 140 | 6-(2-(Difluoromethyl)phenyl)-2-(4-ethyl-3-(hydroxymethyl)-5-oxo-4,5-dihydro-1H-1,2,4-triazol-1-yl)-3-fluoro-8-isopropyl-1,6-naphthyridin-5(6H)-one; |
| 141 | 6-(4-Ethyl-3-(hydroxymethyl)-5-oxo-4,5-dihydro-1H-1,2,4-triazol-1-yl)-7-fluoro-2-(2-hydroxy-3-methylpyridin-4-yl)-4-isopropylisoquinolin-1(2H)-one; and |
| 142 | 2-(4-Ethyl-3-(hydroxymethyl)-5-oxo-4,5-dihydro-1H-1,2,4-triazol-1-yl)-3-fluoro-8-isopropyl-6-(o-$D_3$-tolyl)-1,6-naphthyridin-5(6H)-one. |

A further embodiment of the current invention is a compound selected from the group consisting of:

- 2-(2-Chloro-6-fluorophenyl)-6-(4-ethyl-3-(hydroxymethyl)-5-oxo-4,5-dihydro-1H-1,2,4-triazol-1-yl)-7-fluoro-4-isopropylisoquinolin-1(2H)-one;
- 6-(4-Ethyl-3-(hydroxymethyl)-5-oxo-4,5-dihydro-1H-1,2,4-triazol-1-yl)-7-fluoro-4-isopropyl-2-(o-tolyl)isoquinolin-1(2H)-one;
- 2-(2-Chloro-4-methylpyridin-3-yl)-6-(4-ethyl-3-(hydroxymethyl)-5-oxo-4,5-dihydro-1H-1,2,4-triazol-1-yl)-7-fluoro-4-isopropylisoquinolin-1(2H)-one;
- 2-(2-Chloro-6-fluorophenyl)-6-(4-ethyl-3-(hydroxymethyl)-5-oxo-4,5-dihydro-1H-1,2,4-triazol-1-yl)-4-(1-methylcyclopropyl)isoquinolin-1(2H)-one;
- 2-(2-Chloro-6-fluorophenyl)-6-(4-ethyl-3-(hydroxymethyl)-5-oxo-4,5-dihydro-1H-1,2,4-triazol-1-yl)-7-fluoro-4-(prop-1-en-2-yl)phthalazin-1(2H)-one;
- 2-(4-Ethyl-3-(hydroxymethyl)-5-oxo-4,5-dihydro-1H-1,2,4-triazol-1-yl)-3-fluoro-8-isopropyl-6-(o-tolyl)-1,6-naphthyridin-5(6H)-one;
- 6-(4-Ethyl-3-(hydroxymethyl)-5-oxo-4,5-dihydro-1H-1,2,4-triazol-1-yl)-7-fluoro-4-isopropyl-2-(o-tolyl)phthalazin-1(2H)-one;
- 2-(2-Chloro-6-fluorophenyl)-6-(4-ethyl-3-(hydroxymethyl)-5-oxo-4,5-dihydro-1H-1,2,4-triazol-1-yl)-7-fluoro-4-isopropylphthalazin-1(2H)-one;
- 6-(4-Ethyl-3-(hydroxymethyl)-5-oxo-4,5-dihydro-1H-1,2,4-triazol-1-yl)-7-fluoro-4-isopropyl-2-(2-(methyl-d3)phenyl)isoquinolin-1(2H)-one;
- (R)-6-(4-Ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)isoquinolin-1(2H)-one;
- 6-(4-Ethyl-3-(hydroxymethyl)-5-oxo-4,5-dihydro-1H-1,2,4-triazol-1-yl)-7-fluoro-4-isopropyl-2-(2-(trifluoromethyl)phenyl)isoquinolin-1(2H)-one; and
- 2-(2-(Difluoromethyl)phenyl)-6-(4-ethyl-3-(hydroxymethyl)-5-oxo-4,5-dihydro-1H-1,2,4-triazol-1-yl)-7-fluoro-4-isopropylisoquinolin-1(2H)-one;

and, optionally, one or more of pharmaceutically acceptable salts, isotopes, N-oxides, solvates, and stereoisomers thereof.

An additional embodiment of the invention is a compound of Formula (I) having the Formula (IA):

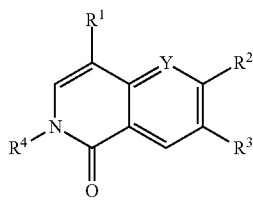

(IA)

wherein
Y is CH or N;
$R^1$ is selected from the group consisting of: $C_{1-6}$alkyl; $C_{1-6}$alkyl substituted with OH, or $OCH_3$; $C_{2-6}$alkenyl; $C_{1-6}$haloalkyl; $C_{1-6}$haloalkyl substituted with OH, or $OCH_3$; $C_{2-6}$haloalkenyl; $N(CH_3)_2$; $C_{3-6}$cycloalkyl; $C_{3-6}$cycloalkyl substituted with $C_{1-6}$alkyl; and phenyl;

$R^2$ is

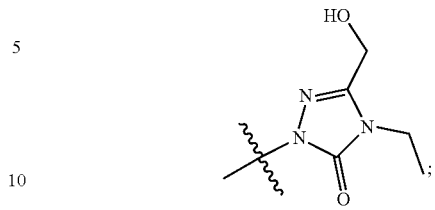

$R^3$ is selected from the group consisting of: H, halo, $CH_3$ and $OCH_3$;
$R^4$ is selected from the group consisting of:
(a) $C_{1-6}$alkyl; $C_{1-6}$alkyl substituted with one or two $OCH_3$; $C_{3-6}$cycloalkyl; $C_{3-6}$cycloalkyl substituted with $CH_3$, or $OCH_3$; $CH_2$—$C_{3-6}$cycloalkyl; and (b) 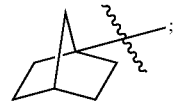

(c) 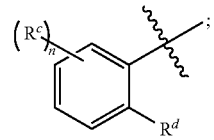

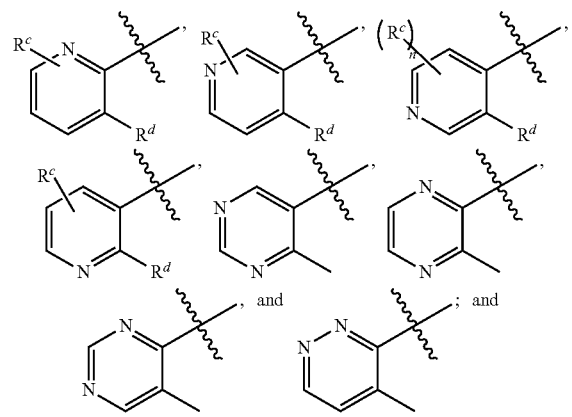

(d) 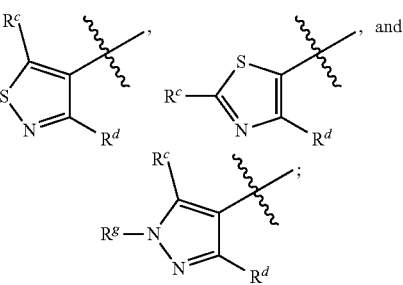

wherein
each $R^c$ is independently selected from the group consisting of: H; halo; $C_{1-6}$alkyl; $C_{1-6}$alkyl substituted with a member selected from the group consisting of: OH, $OCH_3$, $SCH_3$, and $OCF_3$; $C_{1-6}$haloalkyl; $C_{1-6}$haloalkyl substituted with a member selected from the group consisting of: OH, and $OCH_3$; $NO_2$; OH; O—$CH_2CH_2OH$; and $OC_{1-6}$alkyl;

R$^d$ is selected from the group consisting of: H; halo; C$_{1-6}$alkyl; C$_{1-6}$alkyl substituted with a member selected from the group consisting of: OH, OCH$_3$, SCH$_3$, and OCF$_3$; C$_{1-6}$haloalkyl; C$_{1-6}$haloalkyl substituted with a member selected from the group consisting of: OH, and OCH$_3$; CN; and OC$_{1-6}$alkyl;

R$^g$ is selected from the group consisting of: H; C$_{1-6}$alkyl; C$_{1-6}$alkyl substituted with a member selected from the group consisting of: OH, OCH$_3$, SCH$_3$, and OCF$_3$; C$_{1-6}$haloalkyl; and C$_{1-6}$haloalkyl substituted with a member selected from the group consisting of: OH, and OCH$_3$; and n is 1, or 2;

or a pharmaceutically acceptable salt, solvate, stereoisomer, isotopic variant, or N-oxide thereof.

An additional embodiment of the invention is a compound of Formula (I) having the Formula (IB):

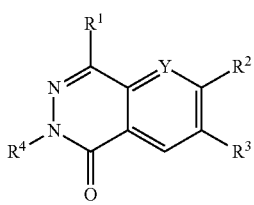

(IB)

wherein
Y is CH or N;
R$^1$ is selected from the group consisting of: C$_{1-6}$alkyl, C$_{1-6}$haloalkyl and C$_{2-6}$alkenyl;
R$^2$ is

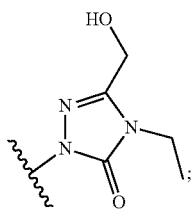 [SMILES: *n1nc(CO)n(CC)c1=O]

;

R$^3$ is selected from the group consisting of: H, halo and OCH$_3$;
R$^4$ is selected from the group consisting of:

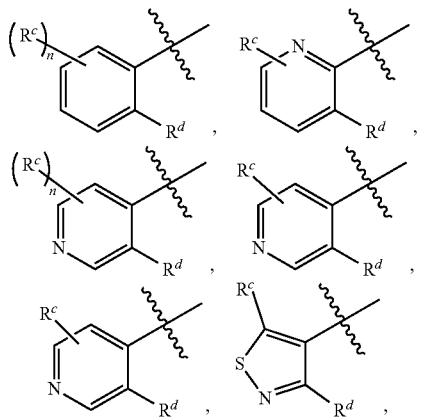

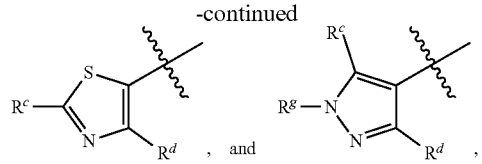

, and wherein
R$^c$ is selected from the group consisting of: H; halo; C$_{1-6}$alkyl; C$_{1-6}$alkyl substituted with a member selected from the group consisting of: OH, OCH$_3$, SCH$_3$, and OCF$_3$; C$_{1-6}$haloalkyl; C$_{1-6}$haloalkyl substituted with a member selected from the group consisting of: OH, and OCH$_3$; and NO$_2$;

R$^d$ is selected from the group consisting of: H; halo; C$_{1-6}$alkyl; C$_{1-6}$alkyl substituted with a member selected from the group consisting of: OH, OCH$_3$, SCH$_3$, and OCF$_3$; C$_{1-6}$haloalkyl; C$_{1-6}$haloalkyl substituted with a member selected from the group consisting of: OH, and OCH$_3$; CN; and OC$_{1-6}$alkyl;

R$^g$ is selected from the group consisting of: H; C$_{1-6}$alkyl; C$_{1-6}$alkyl substituted with a member selected from the group consisting of: OH, OCH$_3$, SCH$_3$, and OCF$_3$; C$_{1-6}$haloalkyl; and C$_{1-6}$haloalkyl substituted with a member selected from the group consisting of: OH, and OCH$_3$; and n is 1;

or a pharmaceutically acceptable salt, solvate, stereoisomer, isotopic variant, or N-oxide thereof.

Also within the scope of the invention are enantiomers and diastereomers of the compounds of Formula (I) (as well as Formulas (IA) and (IB)). Also within the scope of the invention are the pharmaceutically acceptable salts, N-oxides or solvates of the compounds of Formula (I) (as well as Formulas (IA) and (IB)). Also within the scope of the invention are the pharmaceutically acceptable prodrugs of compounds of Formula (I) (as well as Formulas (IA) and (IB)), and pharmaceutically active metabolites of the compounds of Formula (I) (as well as Formulas (IA) and (IB)).

Also within the scope of the invention are isotopic variations of compounds of Formula (I) (as well as Formulas (IA) and (IB)), such as, e.g., deuterated compounds of Formula (I). Also within the scope of the invention are the pharmaceutically acceptable salts, N-oxides or solvates of the isotopic variations of the compounds of Formula (I) (as well as Formulas (IA) and (IB)).

Also within the scope of the invention are the pharmaceutically acceptable prodrugs of the isotopic variations of the compounds of Formula (I) (as well as Formulas (IA) and (IB)), and pharmaceutically active metabolites of the isotopic variations of the compounds of Formula (I) (as well as Formulas (IA) and (IB)).

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice.

Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent. By way of example, in the pharmaceutical compositions of embodiments of the present invention, the compounds of Formula (I) may be admixed with any suitable binder(s), lubricant(s), suspending agent(s), coating agent(s), solubilizing agent(s), and combinations thereof.

An embodiment of the invention relates to a pharmaceutical composition comprising an effective amount of at least one compound selected from compounds of Formula (I), and pharmaceutically acceptable salts, isotopes, N-oxides, solvates, and stereoisomers thereof, in accordance with any embodiment described herein; and at least one pharmaceutically acceptable excipient.

An additional embodiment of the invention is a pharmaceutical composition comprising: (A) an effective amount of at least one compound selected from compounds of Formula (I)

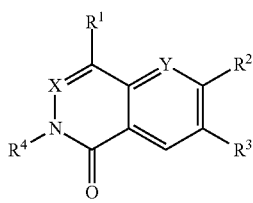

(I)

wherein
X is CH or N;
Y is CH or N;
$R^1$ is selected from the group consisting of: $C_{1-6}$alkyl; $C_{1-6}$alkyl substituted with OH, or $OCH_3$; $C_{2-6}$alkenyl; $C_{1-6}$haloalkyl; $C_{1-6}$haloalkyl substituted with OH, or $OCH_3$; $C_{2-6}$haloalkenyl; $N(CH_3)_2$; $C_{3-6}$cycloalkyl; $C_{3-6}$cycloalkyl substituted with $C_{1-6}$alkyl; and phenyl;
$R^2$ is

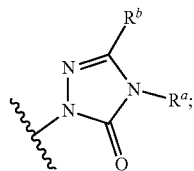

wherein
$R^a$ is selected from the group consisting of: $C_{1-6}$alkyl, $C_{1-6}$haloalkyl, and $C_{3-6}$cycloalkyl;
$R^b$ is $C_{1-6}$alkyl or $C_{1-6}$alkyl substituted with a member selected from the group consisting of: OH, halo, CN, $OC_{1-6}$alkyl, $OC_{1-6}$haloalkyl and $OC_{3-6}$cycloalkyl;
$R^3$ is selected from the group consisting of: H, halo, $CH_3$ and $OCH_3$;
$R^4$ is selected from the group consisting of:
(a) $C_{1-6}$alkyl; $C_{1-6}$alkyl substituted with one or two $OCH_3$; $C_{3-6}$cycloalkyl; $C_{3-6}$cycloalkyl substituted with $CH_3$, or $OCH_3$; $CH_2$—$C_{3-6}$cycloalkyl; and

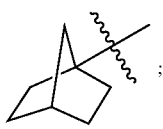

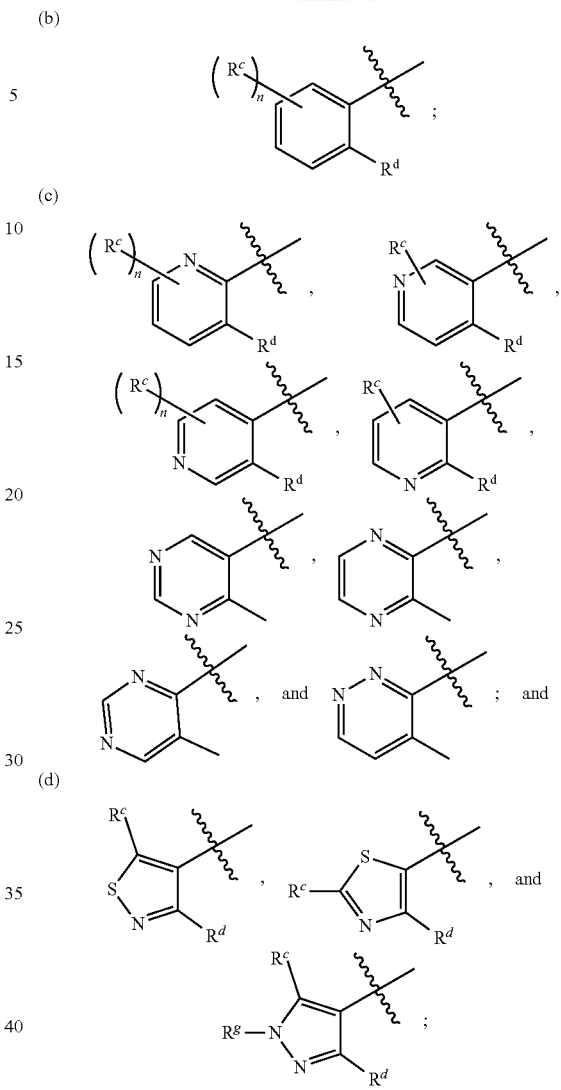

wherein
each $R^c$ is independently selected from the group consisting of: H; halo; $C_{1-6}$alkyl; $C_{1-6}$alkyl substituted with a member selected from the group consisting of: OH, $OCH_3$, $SCH_3$, and $OCF_3$; $C_{1-6}$haloalkyl; $C_{1-6}$haloalkyl substituted with a member selected from the group consisting of: OH, and $OCH_3$; $NO_2$; OH; O—$CH_2CH_2OH$; and $OC_{1-6}$alkyl;
$R^d$ is selected from the group consisting of: H; halo; $C_{1-6}$alkyl; $C_{1-6}$alkyl substituted with a member selected from the group consisting of: OH, $OCH_3$, $SCH_3$, and $OCF_3$; $C_{1-6}$haloalkyl; $C_{1-6}$haloalkyl substituted with a member selected from the group consisting of: OH, and $OCH_3$; CN; and $OC_{1-6}$alkyl;
$R^g$ is selected from the group consisting of: H; $C_{1-6}$alkyl; $C_{1-6}$alkyl substituted with a member selected from the group consisting of: OH, $OCH_3$, $SCH_3$, and $OCF_3$; $C_{1-6}$haloalkyl; and $C_{1-6}$haloalkyl substituted with a member selected from the group consisting of: OH, and $OCH_3$; and
n is 1, or 2;
or pharmaceutically acceptable salts, isotopes, N-oxides, solvates, or stereoisomers thereof;

and (B) at least one pharmaceutically acceptable excipient.

An additional embodiment of the invention is a pharmaceutical composition comprising an effective amount of a compound shown in Table 1 (e.g., a compound selected from Examples 1-142), or a pharmaceutically acceptable salt, isotope, N-oxide, solvate, or stereoisomer of the compound of Table 1, a pharmaceutically acceptable prodrug of the compound of Table 1, or a pharmaceutically active metabolite of the compound of Table 1; and at least one pharmaceutically acceptable excipient.

Solid oral dosage forms such as, tablets or capsules, containing one or more compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, one or more compounds of Formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

According to particular embodiments, a therapeutically effective amount of a compound of Formula (I) or a pharmaceutical composition thereof may comprise a dose range from about 0.1 mg to about 3000 mg, or any particular amount or range therein, in particular from about 1 mg to about 1000 mg, or any particular amount or range therein, of active ingredient in a regimen of about 1 to about (4x) per day for an average (70 kg) human; although, it is apparent to one skilled in the art that the therapeutically effective amount for a compound of Formula (I) will vary as will the diseases, syndromes, conditions, and disorders being treated.

An embodiment of the present invention is directed to a pharmaceutical composition for oral administration, comprising a compound of Formula (I) in an amount of from about 1 mg to about 500 mg.

Advantageously, a compound of Formula (I) may be administered in a single daily dose, or the total daily dosage may be administered in divided doses of two, three and (4x) daily.

Optimal dosages of a compound of Formula (I) to be administered may be readily determined and will vary with the particular compound used, the mode of administration, the strength of the preparation, and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) may be administered in any of the foregoing compositions and dosage regimens or by means of those compositions and dosage regimens established in the art whenever use of a compound of Formula (I) is administered to a subject in need thereof.

According to particular embodiments, one or more compounds of Formula (I) are useful in methods for treating, ameliorating and/or preventing a disease, a syndrome, a condition or a disorder that is affected by the inhibition of DHODH enzymatic activity.

An additional embodiment of the invention relates to the use of compounds of Formula (I), e.g., by inhibiting dihydroorotate oxygenase enzyme activity, in treating disorders like inflammatory disorders, autoimmune disorders, or cancer;

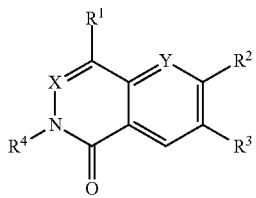

(I)

wherein
X is CH or N;
Y is CH or N;
R¹ is selected from the group consisting of: $C_{1-6}$alkyl; $C_{1-6}$alkyl substituted with OH, or $OCH_3$; $C_{2-6}$alkenyl; $C_{1-6}$haloalkyl; $C_{1-6}$haloalkyl substituted with OH, or $OCH_3$; $C_{2-6}$haloalkenyl; $N(CH_3)_2$; $C_{3-6}$cycloalkyl; $C_{3-6}$cycloalkyl substituted with $C_{1-6}$alkyl; and phenyl;
R² is

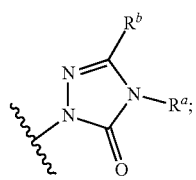

wherein
$R^a$ is selected from the group consisting of: $C_{1-6}$alkyl, $C_{1-6}$haloalkyl, and $C_{3-6}$cycloalkyl;
$R^b$ is $C_{1-6}$alkyl or $C_{1-6}$alkyl substituted with a member selected from the group consisting of: OH, halo, CN, $OC_{1-6}$alkyl, $OC_{1-6}$haloalkyl and $OC_{3-6}$cycloalkyl;
R³ is selected from the group consisting of: H, halo, $CH_3$ and $OCH_3$;
R⁴ is selected from the group consisting of:
(a) $C_{1-6}$alkyl; $C_{1-6}$alkyl substituted with one or two $OCH_3$; $C_{3-6}$cycloalkyl; $C_{3-6}$cycloalkyl substituted with $CH_3$, or $OCH_3$; $CH_2$—$C_{3-6}$cycloalkyl; and (b)
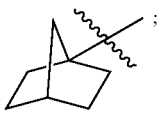

(c)
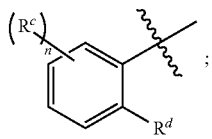

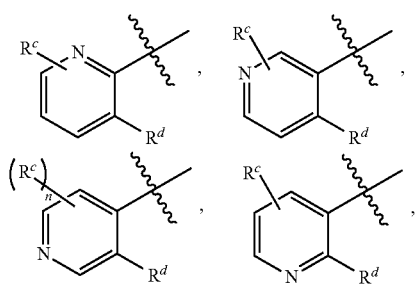

(d)
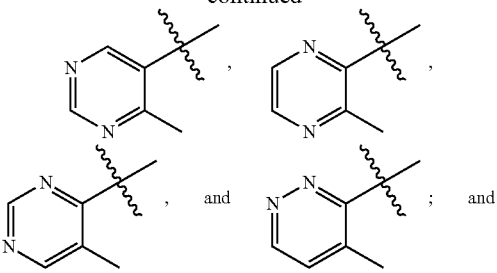

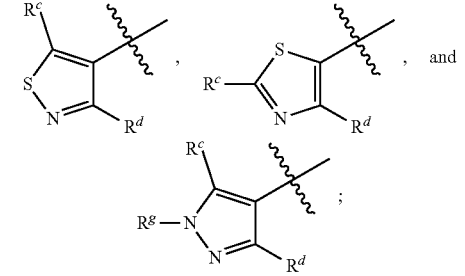

wherein
each $R^c$ is independently selected from the group consisting of: H; halo; $C_{1-6}$alkyl; $C_{1-6}$alkyl substituted with a member selected from the group consisting of: OH, $OCH_3$, $SCH_3$, and $OCF_3$; $C_{1-6}$haloalkyl; $C_{1-6}$haloalkyl substituted with a member selected from the group consisting of: OH, and $OCH_3$; $NO_2$; OH; O—$CH_2CH_2OH$; and $OC_{1-6}$alkyl;
$R^d$ is selected from the group consisting of: H; halo; $C_{1-6}$alkyl; $C_{1-6}$alkyl substituted with a member selected from the group consisting of: OH, $OCH_3$, $SCH_3$, and $OCF_3$; $C_{1-6}$haloalkyl; $C_{1-6}$haloalkyl substituted with a member selected from the group consisting of: OH, and $OCH_3$; CN; and $OC_{1-6}$alkyl;
$R^g$ is selected from the group consisting of: H; $C_{1-6}$alkyl; $C_{1-6}$alkyl substituted with a member selected from the group consisting of: OH, $OCH_3$, $SCH_3$, and $OCF_3$; $C_{1-6}$haloalkyl; and $C_{1-6}$haloalkyl substituted with a member selected from the group consisting of: OH, and $OCH_3$; and
n is 1, or 2;
or pharmaceutically acceptable salts, isotopes, N-oxides, solvates, or stereoisomers thereof.

In a further aspect the present invention provides a method for inhibiting or altering Dihydroorotate Dehydrogenase (DHODH) enzymatic activity, the method comprising contacting DHODH with any compound of Formula (I), aspect or embodiment disclosed herein, thereby inhibiting or otherwise altering DHODH enzymatic activity.

An additional embodiment of the present invention provides methods for treating diseases, disorders, or medical conditions mediated or otherwise affected by dihydroorotate dehydrogenase (DHODH) enzyme activity comprising administering a compound of Formula (I) to a subject in need thereof.

As used herein, the term "DHODH inhibitor" may refer to an agent that inhibits or reduces DHODH activity.

In one embodiment, the term "therapeutically effective amount" (or "effective amount") refers to the amount of a compound of the present invention that, when administered to a subject, is effective to (1) at least partially alleviate, inhibit, prevent, and/or ameliorate a condition, or a disorder or a disease (i) mediated by DHODH enzymatic activity; or (ii) associated with DHODH enzymatic activity; or (iii) characterized by activity (normal or abnormal) of DHODH enzyme; or (2) reduce or inhibit the activity of DHODH enzyme; or (3) reduce or inhibit the expression of DHODH; or (4) modify the protein levels of DHODH. Without being bound by a particular theory, DHODH inhibitors are believed to act by inhibiting nucleic acid synthesis, cell cycle arrest or altering post-translational glycosylation of proteins involved in regulating myeloid differentiation within progenitor tumor cells.

An additional embodiment of the invention is a method of treating a subject suffering from or diagnosed with a disease, disorder, or medical condition mediated or otherwise affected by DHODH enzymatic activity, comprising administering to a subject in need of such treatment an effective amount of at least one compound selected from: compounds of Formula (I) (as well as Formulas (IA), and (IB), such as a compound of Table 1), enantiomers and diastereomers of the compounds of Formula (I) (as well as Formulas (IA), and (IB), such as a compound of Table 1), isotopic variations of the compounds of Formula (I) (as well as Formulas (IA), and (IB), such as a compound of Table 1), and pharmaceutically acceptable salts of all of the foregoing. Stated another way, according to an embodiment, a method of treating a subject suffering from or diagnosed with a disease, disorder, or medical condition, such as cancer, comprises administering to the subject an effective amount of at least one compound selected from: compounds of Formula (I) (as well as Formulas (IA), and (IB), such as a compound of Table 1), and pharmaceutically acceptable salts of all the foregoing (e.g., by inhibiting or otherwise altering dihydroorotate oxygenase enzyme activity in the subject).

In another embodiment, inhibitors of DHODH of the present invention may be used for the treatment of immunological diseases including, but not limited to, autoimmune and inflammatory disorders, e.g. arthritis, inflammatory bowel disease, gastritis, ankylosing spondylitis, ulcerative colitis, pancreatitis, Crohn's disease, celiac disease, multiple sclerosis, systemic lupus erythematosus, lupus nephritis, rheumatic fever, gout, organ or transplant rejection, chronic allograft rejection, acute or chronic graft-versus-host disease, dermatitis including atopic, dermatomyositis, psoriasis, Behcet's diseases, uveitis, myasthenia gravis, Grave's disease, Hashimoto thyroiditis, Sjogren's syndrome, blistering disorders, antibody-mediated vasculitis syndromes, immune-complex vasculitides, allergic disorders, asthma, bronchitis, chronic obstructive pulmonary disease (COPD), cystic fibrosis, pneumonia, pulmonary diseases including edema, embolism, fibrosis, sarcoidosis, hypertension and emphysema, silicosis, respiratory failure, acute respiratory distress syndrome, BENTA disease, berylliosis, and polymyositis.

As used herein, unless otherwise noted, the term "affect" or "affected" (when referring to a disease, disorder, or medical condition that is affected by the inhibition or alteration of DHODH enzymatic activity) includes a reduction in the frequency and/or severity of one or more symptoms or manifestations of said disease, syndrome, condition or disorder; and/or includes the prevention of the development of one or more symptoms or manifestations of said disease, syndrome, condition or disorder or the development of the disease, condition, syndrome or disorder.

An additional embodiment of the invention provides a method of treatment of cancer comprising administering to a subject in need thereof, a therapeutically effective amount of a compound of Formula (I), or a pharmaceutically acceptable salt, isotope, N-oxide, solvate, or stereoisomer thereof.

According to an embodiment, the cancer is selected from but not limited to, lymphomas, leukemias, carcinomas, and sarcomas.

An additional embodiment of the invention provides the use of a compound of Formula (I), or a pharmaceutically acceptable salt, isotope, N-oxide, solvate, or stereoisomer thereof, for the treatment of one or more cancer types.

According to particular embodiments, the uses and methods of treatment described herein are directed to the treatment of cancer, wherein the cancer is selected from but not limited to:

leukemias including but not limited to acute lymphoblastic leukemia (ALL), acute myeloid leukemia (AML), (acute) T-cell leukemia, acute monocytic leukemia, acute promyelocytic leukemia (APL), bisphenotypic B myelomonocytic leukemia, chronic myeloid leukemia (CML), chronic myelomonocytic leukemia (CMML), large granular lymphocytic leukemia, plasma cell leukemia, and also myelodysplastic syndrome (MDS), which can develop into an acute myeloid leukemia, lymphomas including but not limited to AIDS-related lymphoma, Hodgkin lymphoma, non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell DLBCL, double-hit lymphoma and double-expressor lymphoma; anaplastic large cell lymphoma, marginal B cell lymphoma and primary mediastinal B-cell lymphoma, immunoblastic large cell lymphona, Burkitt lymphoma, follicular lymphoma, hairy cell leukemia, Hodgkin's disease, mantle cell lymphoma (MCL), lymphoplasmatic lymphoma, precursor B-lymphoblastic lymphoma, lymphoma of the central nervous system, small lymphocytic lymphoma (SLL) and chronic lymphocytic leukemia (CLL); T-cell NHL such as precursor T-lymphoblastic lymphoma/leukemia, peripheral T-cell lymphoma (PTCL), cutaneous T-cell lymphoma (CTCL), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma sarcomas including but not limited to sarcoma of the soft tissue, gliosarcoma, osteosarcoma, malignant fibrous histiocytoma, lymphosarcoma, and rhabdomyosarcoma;

and other cancers, such as solid tumors, including but not limited to breast cancer, colorectal carcinoma, gastric cancer, gliosarcoma, head & neck cancer, hepatocellular carcinoma, lung cancer, multiple myeloma, neuroblastoma, ovarian cancer, pancreatic cancer, prostate cancer, renal cell carcinoma and sarcoma.

In an embodiment, cancers that may benefit from a treatment with inhibitors of DHODH of the present invention include, but are not limited to, lymphomas, leukemias, carcinomas, and sarcomas, e.g. non-Hodgkin's lymphoma, diffuse large B-cell lymphoma (DLBCL), mantle cell lymphoma (MCL), follicular lymphoma (FL), marginal zone lymphoma, T-cell lymphoma, Hodgkin's lymphoma, Burkitt's lymphoma, multiple myeloma, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head & neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor).

In another embodiment of the present invention, the compounds of the present invention may be employed in combination with one or more other medicinal agents, more particularly with one or more anti-cancer agents, e.g. chemotherapeutic, anti-proliferative or immunomodulating agents, or with adjuvants in cancer therapy, e.g. immunosuppressive or anti-inflammatory agents. Additional non-limiting examples of anti-cancer agents that may be administered in combination with a compound of the present invention include biologic compounds, such as monoclonal antibodies (e.g., that mediate effector function upon binding to cancer cell-associated antigens, or block interaction of a receptor expressed on cancer cells with a soluble or cell bound ligand), bispecific antibodies that mediate immune cell redirection, etc. According to an embodiment, a method of treating cancer comprises administering an effective amount of a compound of the present invention (e.g., selected from compounds of Formula (I), such as a compound shown in Table 1, pharmaceutically acceptable salts, isotopes, N-oxides, solvates, and stereoisomers thereof) and an effective amount of one or more additional anti-cancer agents, wherein the method comprises administering the compound of the present invention and the additional anti-cancer agent(s) either simultaneously (e.g., as part of the same pharmaceutical composition) or sequentially. According to an embodiment, a pharmaceutical composition comprises an effective amount of a compound of the present invention (e.g., selected from compounds of Formula (I), such as a compound shown in Table 1, pharmaceutically acceptable salts, isotopes, N-oxides, solvates, and stereoisomers thereof), an effective amount of one or more additional anti-cancer agents, and optionally one or more excipients.

An additional embodiment of the invention provides the use of a compound of Formula (I), or pharmaceutically acceptable salts, isotopes, N-oxides, solvates, or stereoisomers thereof, as part of chemotherapeutic regimens for the treatment of cancers, lymphomas and leukemias alone or in combination with classic antitumoral compounds well known by the one skilled in the art.

General Synthetic Methods

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations used in the instant specification, particularly the schemes and examples, are as follows in Table 2:

TABLE 2

| Abbreviation | Name |
| --- | --- |
| Å | angstrom |
| ACN or MeCN | acetonitrile |
| AcOH | glacial acetic acid |
| AcOK | Potassium acetate |
| $AgBF_4$ | Silver tetrafluoroborate |
| $AlMe_3$ | Trimethylaluminium |
| Ar | Argon |
| aq. | aqueous |
| $AuCl_3$ | Gold(III) chloride |
| $BCl_3$ | Boron trichloride |
| Bn or Bzl | benzyl |
| Boc | tert-butyloxycarbonyl |
| $(Boc)_2O$ | Di-tert-butyl dicarbonate |
| Catacxium A Pd G2 | Chloro[(di(1-adamantyl)-N-butylphosphine)-2-(2-aminobiphenyl)]palladium(II) |
| $CdCl_2$ | Cadmium chloride |
| Celite ® | diatomaceous earth |
| conc. | concentrated |
| $CO_2$ | Carbon dioxide |
| $(COCl)_2$ | Oxalyl chloride |
| CuI | Copper(I) iodide |
| $Cu(OAc)_2$ | copper(II) acetate |
| $Cy_2NMe$ | N,N-Dicyclohexylmethylamine |
| $Cs_2CO_3$ | Cesium carbonate |
| DCC | N,N'-dicyclohexyl-carbodiimide |
| DCE | dichloroethane |
| DCM | dichloromethane |
| DIPEA or DIEA | diisopropyl-ethyl amine |
| DEAD | Diethyl azodicarboxylate |
| DEA | Diethanolamine |
| DHP | 3,4-Dihydropyran |
| DMA | dimethylaniline |

TABLE 2-continued

| Abbreviation | Name |
| --- | --- |
| DMAP | 4-dimethylaminopyridine |
| DME | dimethoxyethane |
| DMF | N,N-dimethylformamide |
| DMP | Dess-Martin periodinane or 1,1,1-Tris(acetyloxy)-1,1-dihydro-1,2-benziodoxol-3-(1H)-one |
| DMSO | dimethylsulfoxide |
| Dppf or DPPF | 1,1'-Bis(diphenylphosphino)ferrocene |
| EDCI | 1-ethyl-3-(3-dimethylaminopropyl) carbodiimide |
| ES-API | electrospray-atmospheric pressure ionization |
| ESI | electrospray ionization |
| $Et_3N \cdot 3HF$ | Triethylamine trihydrofluoride |
| EtOAc or EA | ethyl acetate |
| EtOH | ethanol |
| EtONa | sodium ethoxide |
| EtMgBr | Ethylmagnesium bromide |
| GCMS | gas chromatography-mass spectrometry |
| h or hr(s) | hour or hours |
| $H_2$ | Hydrogen gas |
| HCl | Hydrogen chloride |
| HPLC | high performance liquid chromatography |
| HPA | hypophosphorous acid |
| $H_2SO_4$ | Sulfuric acid |
| i-PrMgCl | Isopropylmagnesium chloride |
| IPA | Isopropylamine |
| iPrOH | Isopropyl alcohol or 2-propanol |
| isovaleraldehyde | 3-methylbutanal |
| KHMDS | Potassium bis(trimethylsilyl)amide |
| KI | Potassium iodide |
| $K_2OsO_4 \cdot 2H_2O$ | Potassium osmate (VI) dihydrate |
| $K_2CO_3$ | Potassium carbonate |
| $K_3PO_4$ | Potassium phosphate |
| LCMS or LC/MS | Liquid chromatography-mass spectrometry |
| LiHMDS | Lithium bis(trimethylsilyl)amide |
| MeOH | methanol |
| MeMgBr | methylmagnesium bromide |
| $Mg(ClO_4)_2$ | Magnesium perchlorate |
| $MgSO_4$ | Magnesium sulfate |
| MHz | megahertz |
| min | minute or minutes |
| MS | mass spectrometry |
| $NaBH_4$ | Sodium borohydride |
| NaHMDS | Sodium bis(trimethylsilyl)amide |
| NaOH | Sodium hydroxide |
| NaOEt | Sodium ethoxide |
| $NaHCO_3$ | Sodium bicarbonate |
| $Na_2CO_3$ | Sodium carbonate |
| $NaIO_4$ | Sodium periodate |
| $NaNO_2$ | Sodium nitrite |
| $Na_2SO_4$ | Sodium sulfate |
| $N_2$ | Nitrogen gas |
| NBS | N-Bromosuccinimide |
| NCS | N-chlorosuccinimide |
| $NH_2NH_2 \cdot H_2O$ | Hydrazine monohydrate |
| NIS | N-iodosuccinimide |
| $NH_4Cl$ | Ammonium chloride |
| $NH_4HCO_3$ | Ammonium bicarbonate |
| $NH_3 \cdot H_2O$ or $NH_4OH$ | Ammonium hydroxide |
| NMR | nuclear magnetic resonance |
| [Pd(allyl)Cl]$_2$ | Allylchloropalladium dimer or Bis(allyl)dichlorodipalladium or Bis(allyl)dichloropalladium or Bis(allylchloropalladium) or Diallyldichlorodipalladium |
| $PdCl_2(PPh_3)_2$ or $Pd(PPh_3)_2Cl_2$ | bis(triphenylphosphine)palladium(II) dichloride |
| $Pd(PPh_3)_4$ | tetrakis(triphenylphosphine)palladium |
| $Pd(OAc)_2$ | palladium (II) acetate |
| $P(tBu_3)PdG_2$ or $tBu_3PPdG_2$ | chloro[(tri-tert-butylphosphine)-2-(2-aminobiphenyl)] palladium(II) |
| PE | petrolum ether |
| $PPh_3$ | triphenylphosphine |
| ppm | parts per million |
| $Pd(dppf)Cl_2 \cdot CH_2Cl_2$ or $Pd(dppf)Cl_2 \cdot DCM$ | 1,1'-bis(diphenylphosphino)ferrocene-palladium(II)dichloride dichloromethane complex |
| Pd/C | Palladium on carbon |
| PG | Protecting group |
| RP | reverse-phase |
| rt or RT | room temperature |
| $R_t$ | retention time |

TABLE 2-continued

| Abbreviation | Name |
| --- | --- |
| RhCl(PPh$_3$)$_3$ or Rh(PPh$_3$)$_3$Cl | Wilkinson's Catalyst or Chlorotris(triphenylphosphine)rhodium(I) |
| Sec | second or seconds |
| SFC | supercritical fluid chromatography |
| SiO$_2$ | silica gel |
| SOCl$_2$ | Thionyl chloride |
| O$_2$ | Oxygen gas |
| TBAB | tetrabutylammonium bromide or tetra-n-butylammonium bromide |
| TBDPS | tert-Butyldiphenylchlorosilane |
| TBAF | tetrabutylammonium fluoride |
| TBHP | tert-butyl hydroperoxide |
| TBS | tert-Butyldimethylsilyl |
| TES | triethylsilane |
| TIPS | triisopropylsilane |
| TEA or Et$_3$N | triethylamine |
| TFA | trifluoroacetic acid |
| THF | tetrahydrofuran |
| TiCl$_4$ | Titanium tetrachloride |
| TLC | thin layer chromatography |
| TF$_2$NPh | N-phenylbis(trifluoromethanesufonimide) |
| triflate | trifluoromethanesulfonyl |
| Tf$_2$O | Triflic anhydride or Trifluoromethanesulfonic anhydride |
| TMSOiPr | Isopropoxytrimethylsilane |
| (PTSA or pTsOH) or tosylic acid | p-Toluenesulfonic acid |

Preparative Examples

Exemplary compounds useful in methods of the invention will now be described by reference to the illustrative synthetic schemes for their general preparation below and the specific examples to follow.

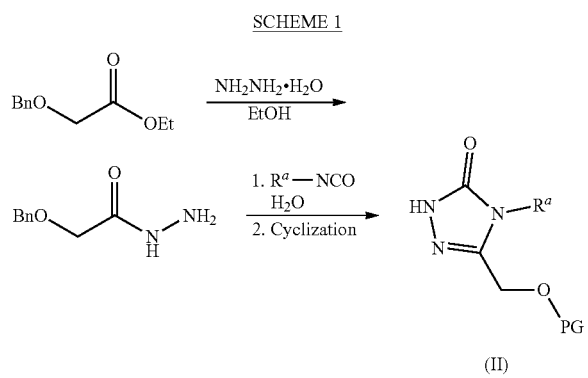

SCHEME 1

According to SCHEME 1, a 1,2,4-triazol-5(4H)-one compound of formula (II), where PG is Bn, is prepared from ethyl 2-(benzyloxy)acetate in three steps. In a first step 2-(benzyloxy)acetohydrazide is prepared by the reaction of ethyl 2-(benzyloxy)acetate with hydrazine hydrate, in a suitable solvent such as EtOH, and the like; at temperatures ranging from 70-85° C. Reaction of the hydrazide with an isocyanate of formula R$^a$—NCO, where R$^a$ is C$_{1-6}$alkyl, in a suitable solvent such as water, and the like; provides the corresponding semicarbazide. Subsequent cyclization of the semicarbazide with a suitable base such as NaOH, in a suitable solvent such as water, provides a compound of formula (II), where PG is Bn.

A compound of formula (II), where R$^a$ is C$_{1-6}$haloalkyl or C$_{3-6}$cycloalkyl; may be prepared as previously described employing a suitably substituted compound of formula R$^a$—NCO, where R$^a$ is C$_{1-6}$haloalkyl or C$_{3-6}$cycloalkyl.

Protecting group exchange of a compound of formula (II), where PG is Bn to a compound of formula (II) where PG is TBDPS, is achieved in two steps employing established methodologies, such as those described in T. W. Greene and P. G. M. Wuts, "Protective Groups in Organic Synthesis," 3 ed., John Wiley & Sons, 1999. In a first step, deprotection of benzyl group is achieved under hydrogenolytic conditions known to one skilled in the art provides the alcohol. For example, deprotection is achieved employing a palladium catalyst such Pd/C, and the like; under H$_2$; in a suitable solvent such as EtOH, MeOH, EtOAc, or a mixture thereof, preferably EtOH; with or without the presence HCl; for a period of 4 to 72 hrs. In a second step, protection of the corresponding alcohol as the silyl ether, is achieved with tert-butyldiphenylsilyl chloride, a suitable base such as imidazole, dimethylaminopyridine, pyridine, and the like; in a solvent such as DMF, DCM, and the like; at temperatures ranging from 0° C. to room temperature; affords a compound of formula (II) where PG is TBDPS.

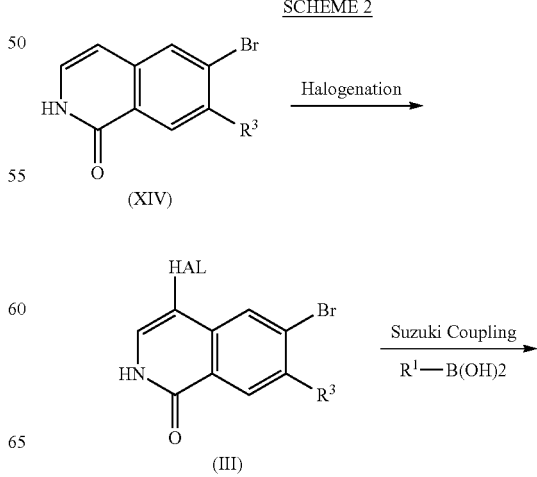

SCHEME 2

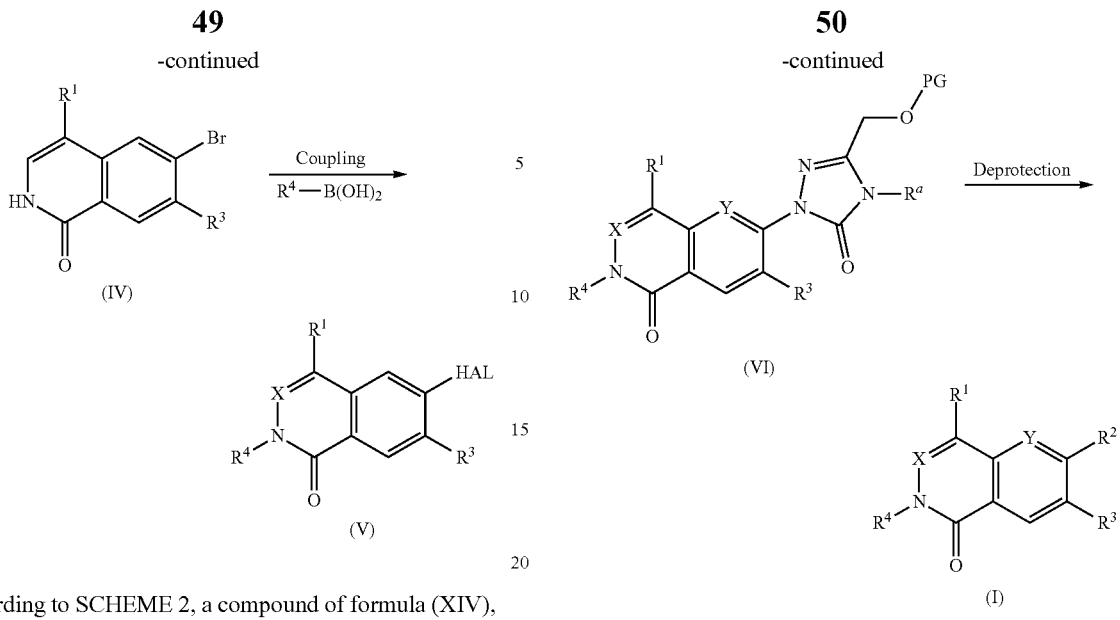

(IV)

(V)

According to SCHEME 2, a compound of formula (XIV), where $R^3$ is H is treated with a halogenating reagent such as N-iodosuccinimide (NIS), and the like; in an aprotic solvent such as acetonitrile, and the like; under heating conditions; to afford the halogenated compound of formula (III), where HAL is iodide. A compound of formula $R^1$—$B(OH)_2$; is reacted under Suzuki coupling conditions known to one skilled in the art with a compound of formula (III), to provide a compound of formula (IV). For example, a compound of formula (III), where HAL is iodide, is reacted a commercially available or synthetically accessible boronic acid (or boronic ester) such as $R^1$—$B(OH)_2$, where $R^1$ is an optionally substituted $C_{2-6}$alkenyl or aryl as defined in Embodiment #1; a palladium catalyst such as bis(triphenylphosphine)palladium(II) dichloride, tetrakis(triphenylphosphine)palladium, and the like; a suitable base such as potassium phosphate, $Cs_2CO_3$, and the like; in a suitable solvent such as dioxane, water, ethanol, or a mixture thereof; to provide a compound of formula compound (IV). A compound of formula (IV), where $R^3$ is H, is reacted with a compound of formula $R^4$—$B(OH)_2$; under copper (II) mediated Chan-Lam coupling conditions known to one skilled in the art, to provide a compound of formula (V), where HAL is bromide, X is CH and $R^3$ is H. For example, a compound of formula (IV) is reacted with a compound of formula $R^4$—$B(OH)_2$, where $R^4$ is as defined in Embodiment #1; a catalyst such as copper(II) acetate, and the like; a base such as pyridine, $NEt_3$, and the like; in a suitable solvent such as DCM, ACN, dioxane, THF, and the like; to afford a compound of formula (V).

SCHEME 3

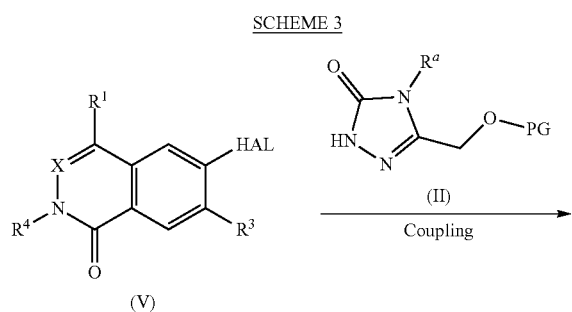

(VI)

Deprotection (I)

According to SCHEME 3, Ullmann-type aromatic amination reaction of compound of formula (V), where $R^1$ is optionally substituted $C_{2-6}$alkenyl, $R^3$ is H, $R^4$ is suitably substituted phenyl as described in claim 1, and HAL is Br; with a commercially available or synthetically accessible nucleophilic compound of formula (II), where $R^a$ is $C_{1-6}$alkyl; such as suitably protected triazolones, where PG is selected from: benzyl, 4-methoxy benzyl, or an alkyl or aryl silane such as TBDPS, TBS, TES, or TIPS; in the presence of catalytic CuI and a diamine such as trans-1,2-diaminocyclohexane, and a base such as $K_3PO_4$, $K_2CO_3$, $Cs_2CO_3$, $NaHCO_3$, triethylamine, and the like; in a suitable solvent such as 1,4-dioxane, DMSO, DMF, THF, ACN, and the like; provides a compound of formula (VI), where X is CH and Y is CH.

A compound of formula (VI), where PG is Bn and $R^1$ is $C_{2-6}$alkenyl, is reacted under Simmons-Smith cyclopropanation reaction conditions known to one skilled in the art to provide a compound of formula (VI) where $R^1$ is $C_{3-6}$cycloalkyl substituted with $C_{1-6}$alkyl. For example, a compound of formula (VI), where $R^1$ is

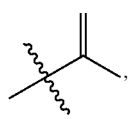

is reacted with diiodomethane; diethylzine; in a suitable solvent such as toluene, and the like; at temperatures ranging from 0° C. to room temperature; for a period of 3 to 26 h; to provide a compound of formula (VI), where $R^1$ is cyclopropyl substituted with $CH_3$.

Subsequent deprotection employing established methodologies, such as those described in T. W. Greene and P. G. M. Wuts, "Protective Groups in Organic Synthesis," 3 ed., John Wiley & Sons, 1999), provides a compound of Formula (I), where X and Y are CH. For example, compound of formula (VI), where $R^3$ is H, and PG is TBDPS, is deprotected employing conditions known to one skilled in the art, preferably with TBAF in a suitable solvent such as THF, and the like. In a preferred method, PG is TBDPS, and $R^a$ is $C_{1-6}$alkyl. Alternately, removal of a TBDPS protecting group is achieved employing triethylamine trihydrogen fluoride ($Et_3N \cdot 3HF$).

Removal of the Bn protecting group is achieved in the presence of hydrogen gas, in the presence of a catalyst such as Palladium on carbon (Pd/C). Removal of the protecting group Bn is also achieved employing TFA, at a temperature of about 80° C.

A compound of Formula (I), where X is CH; Y is CH; $R^2$, $R^3$, $R^4$ is each defined as described in Embodiment #1; and $R^1$ is $C_{2-6}$alkenyl, is reduced employing hydrogenation conditions known to one skilled in the art, for example, reaction with Pd/C or Wilkinson's Catalyst [$RhCl(PPh_3)_3$] under $H_2$; in a suitable solvent such as MeOH, THF, EtOAc, and the like; provides a compound of Formula (I) where $R^1$ is $C_{2-6}$alkyl.

According to SCHEME 4, reductive amination of a compound of formula (VII), with α, β-unsaturated aldehyde such as 3-methyl-2-butenal, 3-methylpent-2-enal, and the like; employing $TiCl_4$; and a base such as triethylamine; in an aprotic solvent such as dichloromethane (DCM), and the like; provides an enamine intermediate which is subsequently reduced employing a reducing agent such as $NaBH_4$, and the like; to afford a compound of formula (VIII) where $R^5$ is $C_{1-4}$alkyl, $R^4$ is as defined in Embodiment #1. A compound of formula (VIII) is coupled with commercially available or synthetically accessible 4-bromo-2-iodobenzoyl chloride employing a base such as triethylamine and 4-dimethylaminopyridine (DMAP); in an anhydrous aprotic solvent such as dichloromethane (DCM), and the like; to afford a compound of formula (IX). Treatment of a compound of formula (IX), with palladium (II) acetate, tetrabutylammonium bromide, and potassium acetate under heating Heck reaction conditions, affords the intramolecular cyclized compounds of formula (V), wherein $R^1$ is optionally substituted $C_{2-6}$alkyl, $R^3$ is H, X is CH, and HAL is Br; and (Va) wherein $R^1$ is optionally substituted $C_{2-6}$alkenyl, $R^3$ is H, X is $CH_2$, and HAL is Br.

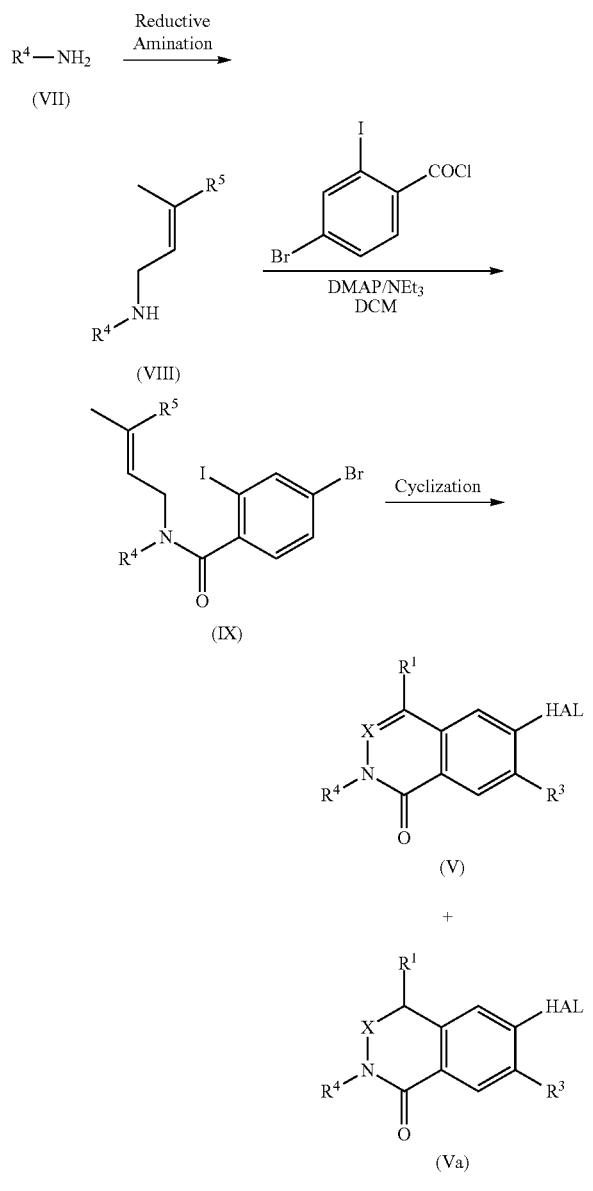

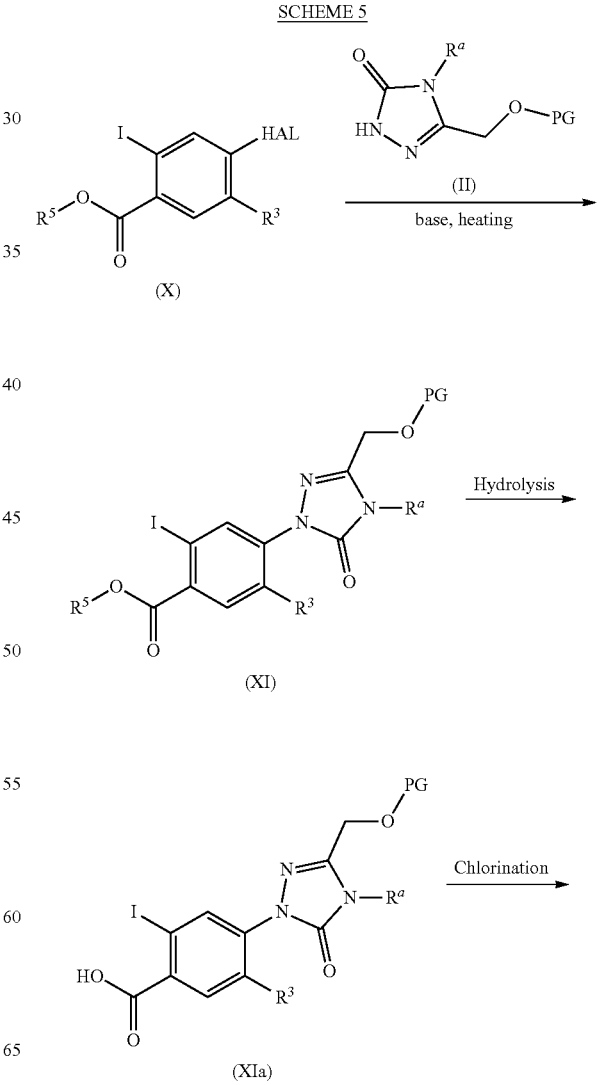

-continued

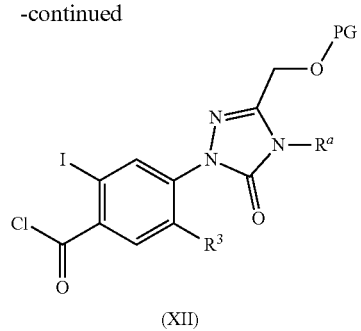

(XII)

-continued

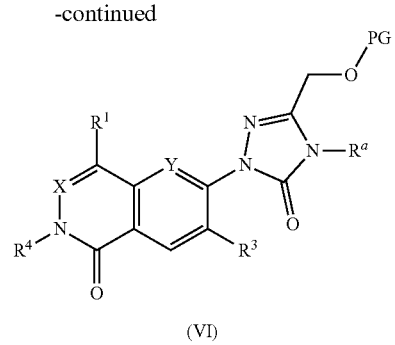

(VI)

According to SCHEME 5, the reaction of a commercially available or synthetically accessible compound of formula (X), where HAL is F, $R^3$ is F, and $R^5$ is H or $C_{1-4}$alkyl; with a commercially available or synthetically accessible nucleophilic compound of formula (II), where $R^a$ is $C_{1-6}$alkyl, such as suitably protected triazolones, where PG is selected from: benzyl, 4-methoxy benzyl, or an alkyl or aryl silane such as TBDPS, TBS, TES, or TIPS; in the presence of a base such as $K_3PO_4$, $K_2CO_3$, $Cs_2CO_3$, $NaHCO_3$, triethylamine, and the like; in a suitable solvent such as DMSO, DMF, THF, ACN, and the like; affords a compound of formula (XI). In a preferred method, PG is Bn, and $R^a$ is $C_{1-6}$alkyl. The ester of formula (XI), when $R^5$ is $C_1$-4alkyl, is hydrolyzed to its corresponding acid, under acidic or basic conditions. For example, the treatment of tert-butyl ester ($R^5$ is tert-Bu) with TFA; or alternately, hydrolysis with a base like NaOH, in an aqueous solvent, affords a compound of formula (XIa), where $R^5$ is H. A compound of formula (XIa) is chlorinated, employing conditions known to one skilled in the art, to provide the acyl chloride of formula (XII). For example, a compound of formula (XIa) is heated in $SOCl_2$; or treated with oxalyl chloride in DCM.

According to SCHEME 6, a compound of formula (XII), where $R^3$ is H or F, PG is Bn, and $R^a$ is $C_{1-6}$alkyl; is reacted with a compound of formula (VIII), where $R^5$ is $C_{1-4}$alkyl, employing a base such as a mixture of triethylamine (TEA) and 4-dimethylaminopyridine (DMAP); in an anhydrous aprotic solvent such as dichloromethane (DCM), and the like; to afford a compound of formula (XIII). A compound of formula (VI), where X is CH and Y is CH, is obtained by treatment of a compound of formula (XIII), where $R^1$ is optionally substituted $C_{1-6}$ alkyl as described in claim 1; with palladium (II) acetate, tetrabutylammonium bromide, and potassium acetate under heating Heck reaction conditions, that affords a mixture of intramolecular cyclized compounds, which is then separated to isolate an intermediate compound where $R^1$ is $C_{2-6}$alkyl, and $R^3$ is H or F.

SCHEME 6

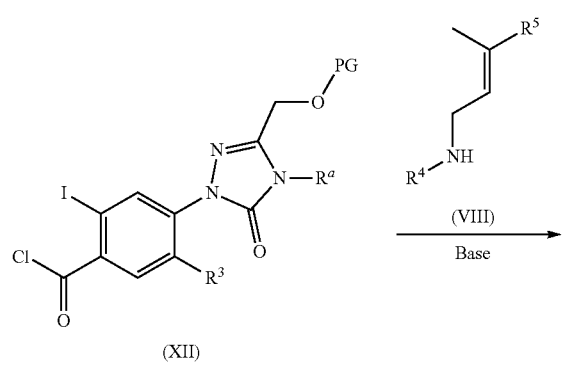

SCHEME 7

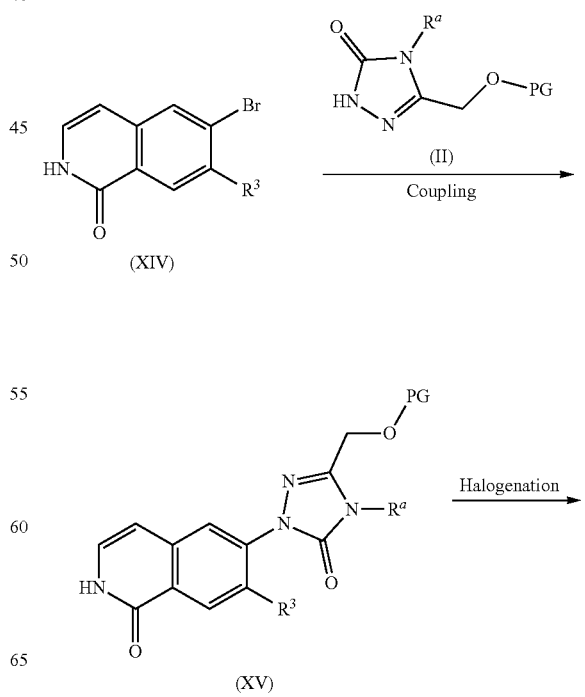

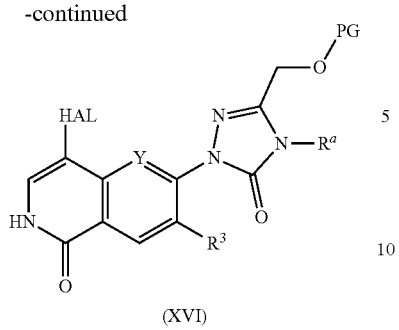

(XVI)

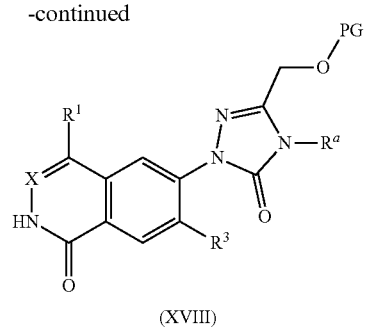

(XVIII)

According to SCHEME 7, Ullmann-type aromatic amination reaction of a compound of formula (XIV), where $R^3$ is H or F, with a compound of formula (II); such as suitably protected triazolones, where PG is selected from: benzyl, 4-methoxy benzyl, or an alkyl or aryl silane such as TBDPS, TBS, TES, or TIPS; according to methods previously described; affords a compound of formula (XV). In a preferred method, PG is Bn, and $R^a$ is $C_{1-6}$alkyl. A compound of formula (XV) is treated with a halogenating reagent such as N-iodosuccinimide (NIS), and the like; in an aprotic solvent such as acetonitrile, and the like; under heating conditions; affords a halogenated compound of formula (XVI), where Y is CH and HAL is iodide.

According to SCHEME 8, compounds of formula (XVIIa) and (XVIIb) are prepared from 5-bromoisobenzofuran-1,3-dione in two steps. 5-Bromoisobenzofuran-1,3-dione is reacted with a commercially available or synthetically accessible suitably substituted alkyl Grignard reagent such as i-PrMgCl, EtMgBr, and the like; in the presence of $CdCl_2$; in aprotic solvent like THF, and the like; followed by subsequent treatment with an alkylating agent of formula $R^5$—I, where $R^5$ is $C_{1-4}$alkyl (such as iodomethane or iodoethane); in the presence of base like $K_2CO_3$, $Cs_2CO_3$, and the like; in a aprotic solvent such as DMF, DMSO, and the like; affords a mixture of regio-isomeric esters of formula (XVIIa) and (XVIIb), where $R^1$ is an optionally substituted $C_{1-6}$alkyl. In a similar fashion, aryl Grignard reagents may be used to provide compounds of formula (XVIIa) and (VXIIb), where $R^1$ is a suitably substituted phenyl. The regio-isomers of formula (XVIIa) and (XVIIb) are not separated but are used directly and converted into the corresponding phthalazinone (mixture). For example, a mixture of formula (XVIIa) and formula (XVIIb) are treated with excess hydrazine; in a suitable solvent such as ethanol or methanol; at temperatures ranging from room temperature to 90° C.; for a period of 6 to 20 hours. The desired phthalazinone compound of formula (V) can be readily separated from the other regio-isomer by precipitation, crystallization, or purified by flash chromatography. Ullmann-type aromatic amination reaction of a compound of formula (V), with a suitably protected triazolone of formula (II), where $R^a$ is $C_{1-6}$alkyl, and PG is selected from: benzyl, 4-methoxy benzyl, or an alkyl or aryl silane such as TBDPS, TBS, TES, or TIPS; in the presence of catalytic CuI and a diamine such as trans-1,2-diaminocyclohexane, and a base such as $K_3PO_4$, $K_2CO_3$, $Cs_2CO_3$, $NaHCO_3$, triethylamine, and the like; in a suitable solvent such as 1,4-dioxane, DMSO, DMF, THF, ACN, and the like; affords a compound of formula (XVIII), where X is N.

A compound of formula (XVIII), where $R^1$ is $C_{2-6}$alkenyl, is reacted under Simmons-Smith cyclopropanation reaction conditions known to one skilled in the art, to provide a compound of formula (XVIII) where $R^1$ is $C_{3-6}$cycloalkyl substituted with $C_{1-6}$alkyl. For example, a compound of formula (XVIII), where $R^1$ is $C_{2-6}$alkenyl, is reacted with diiodomethane; diethylzinc; in a suitable solvent such as toluene, and the like; at temperatures ranging from 0° C. to room temperature; for a period of 24 to 26 h; to provide a compound of formula (XVIII), where $R^1$ is cyclopropyl substituted with $CH_3$.

SCHEME 8

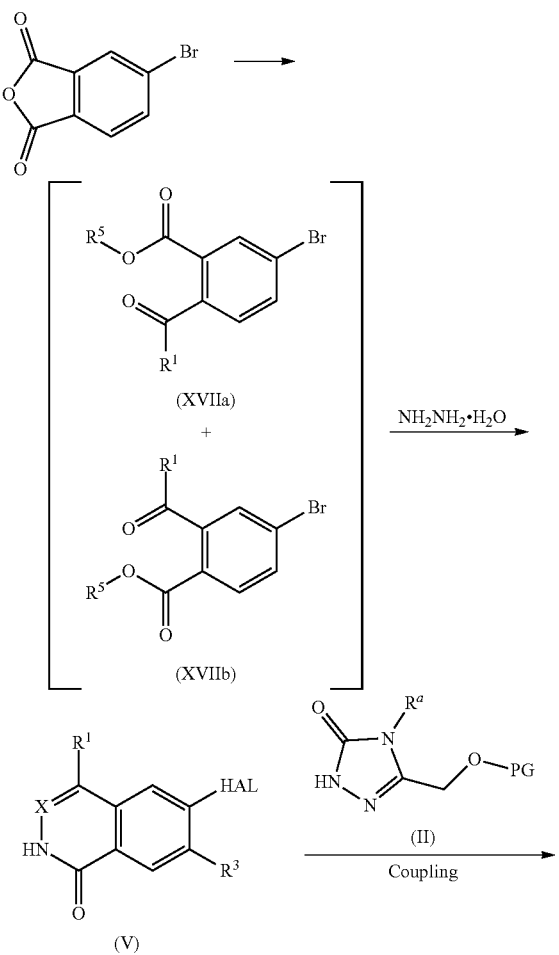

SCHEME 9

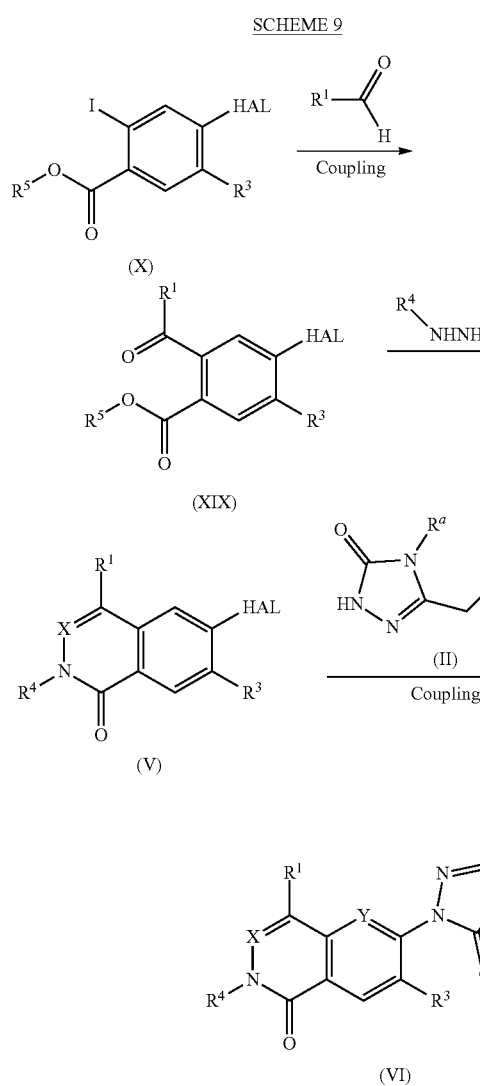

According to SCHEME 9, a compound of formula (X), where HAL is Br, $R^3$ is H, and $R^5$ is $CH_3$, is coupled in a palladium catalyzed carbonylation reaction with a commercially available or synthetically accessible aldehyde of formula $R^1$—CHO, where $R^1$ is $C_{1-6}$alkyl; to afford the corresponding ketone compound of formula (XIX), (similar transformation has been reported by Suchand et al, *J. Org. Chem.* 2016, 81, 6409-6423). For example, reaction of methyl 4-bromo-2-iodobenzoate with isobutylaldehye; in the presence of a palladium catalyst such as $Pd(OAc)_2$; $Ag_2O$; and an oxidizing agent such as aqueous solution of tert-butyl hydroperoxide (TBHP); at a temperature of about 120° C.; for a period of 10-14 h; provided methyl 4-bromo-2-isobutyrylbenzoate. A ketone compound of formula (XIX) is reacted with hydrazine $R^4$—$NHNH_2$, where $R^4$ is suitably substituted aryl such as 2-chloro-6-fluorophenylhydrazine; to afford a compound of formula (V), where X is N. Ullmann-type aromatic amination reaction of a compound of formula (V) with a suitably protected triazolone (II) as previously described, affords a compound of formula (VI), where Y is CH, and $R^1$ is selected from $C_{1-6}$alkyl.

A compound of formula (VI), where Y is CH, and $R^1$ is phenyl and X is N, may be prepared in a similar fashion, employing methods previously describe by coupling methyl 4-bromo-2-iodobenzoate with a commercially available or synthetically accessible aldehyde of formula $R^1$—CHO, where $R^1$ is phenyl.

SCHEME 10

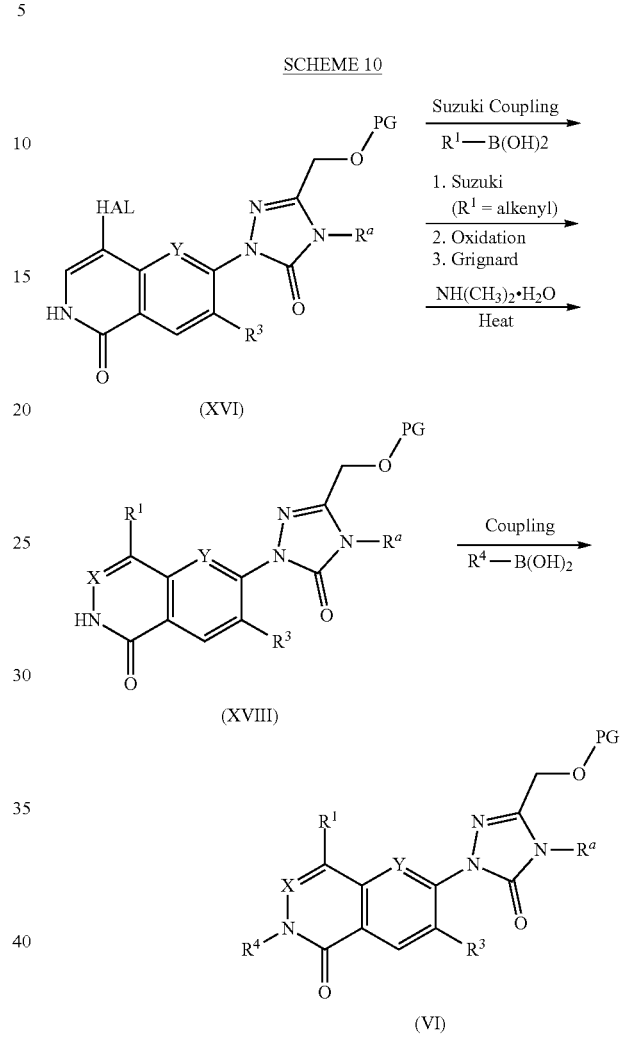

According to SCHEME 10, a compound of formula $R^1$—$B(OH)_2$; is reacted under Suzuki coupling conditions known to one skilled in the art, with a compound of formula (XVI), to provide a compound of formula (XVIII), where X is CH. For example, a compound of formula (XVI), where Y is CH and HAL is iodide, is reacted a commercially available or synthetically accessible boronic acid (or boronic ester) such as $R^1$—$B(OH)_2$, where $R^1$ is an optionally substituted $C_{2-6}$alkenyl, $C_{3-6}$cycloalkyl or aryl as defined in Embodiment #1; a palladium catalyst such as bis(triphenylphosphine)palladium(II) dichloride, and the like; a suitable base such a potassium phosphate, $Cs_2CO_3$, and the like; in a suitable solvent such as dioxane, water, ethanol, or a mixture thereof, to provide a compound of formula compound (XVIII), where X is CH. It has been noticed that during the coupling reaction as described above, loss of the iodide during the reaction conditions afforded a compound of formula compound (XVIII), where X is CH, and $R^1$ is H. A compound of formula (XVIII), where X is CH or N, is reacted with a compound of formula $R^4$—$B(OH)_2$; under copper (II) mediated Chan-Lam coupling conditions known to one skilled in the art, or as previously described, to provide a compound of formula (VI), where X is CH or N, $R^1$ is optionally substituted $C_{2-6}$alkenyl, $R^3$ is H or F, and $R^4$ is a suitably substituted phenyl as described in claim 1.

A compound of formula (XVIII), where $R^1$ is $N(CH_3)_2$ is prepared from a compound of formula (XVI), where HAL is Br and PG is Bn. Reaction of a compound of formula (XVI) with an amine bs such as $NH(CH_3)_2$ in water; at a temperature of about 110° C.; for a period of 96 hours h; affords a compound of formula (XVIII) where $R^1$ is $N(CH_3)_2$, and $R^a$ is $C_{1-6}$alkyl. A compound of Formula (I), where $R^1$ is $N(CH_3)_2$ is prepared according to methods described above.

A compound of formula (XVIII), where $R^1$ is $C_{1-6}$alkyl substituted with OH, is prepared from a compound of formula (XVIII), where $R^1$ is $C_{2-6}$alkenyl, and PG is Bn in two steps. In a first step, reaction of a compound of formula (XVIII), where $R^1$ is

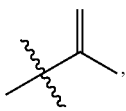

under oxidizing conditions such as NaIO4, and $K_2OsO_4 \cdot 2H_2O$ or $OsO_4$; in a suitable solvent such as $THF/H_2O$; at temperatures ranging from 0° C. to room temperature; for a period of 48 to 72 hours; affords a ketone intermediate compound. In a second step, reaction of the ketone intermediate compound with a Grignard reagent such as methylmagnesium bromide; in a suitable solvent such as diethyl ether; at temperatures ranging from 0° C. to room temperature; for a period of 3 to 30 hours; affords a compound of formula (XVIII), where $R^1$ is $C_{1-6}$alkyl substituted with OH.

SCHEME 11

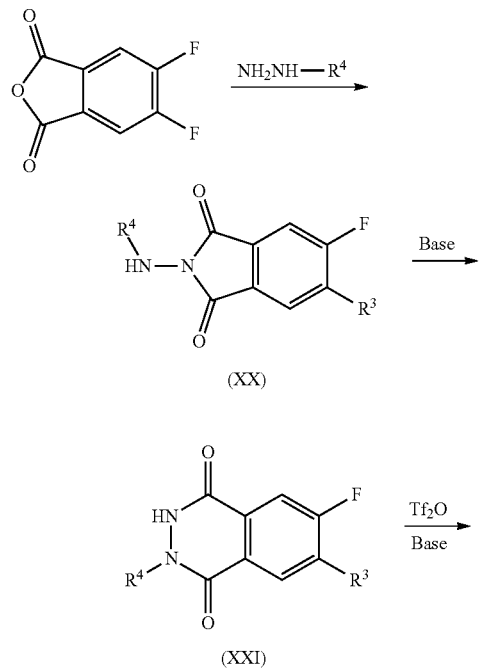

According to SCHEME 11, 4,5-difluorophthalic anhydride is reacted with a hydrazine compound of formula $R^4$—$NHNH_2$, where $R^4$ is a suitably substituted phenyl or heteroaryl such as (2-chloro-6-fluorophenyl)hydrazine hydrochloride; in acetic acid; at a temperature of about 125° C.; for a period of about 1.5 h to afford a compound of formula (XX), where $R^3$ is F. Rearrangement of a compound of formula (XX) affords a ring expansion compound of formula (XXI), under basic conditions such as sodium ethoxide or sodium methoxide; in a protic solvent such as ethanol, methanol, and the like; at room temperature; for a period of about 1.5 h. Derivation of a compound of formula (XXI), with a sulfonate-based leaving group such as trifluoromethanesulfonyl (triflate), is achieved by is by reaction with a triflating agent such as trifluoromethanesulfonic anhydride ($Tf_2O$), a base such as triethylamine (TEA), pyridine, and the like, in a suitable solvent such as DCM and the like, to provide a compound of formula (XXII). Milder triflating agents such as N-phenylbis(trifluoromethanesufonimide) ($TF_2NPh$), a base such as TEA, DIEA, and the like, in a suitable solvent such as DCM, and the like; may be used.

SCHEME 12

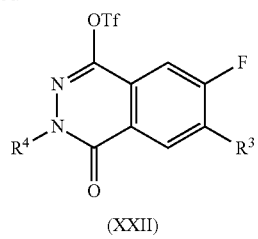

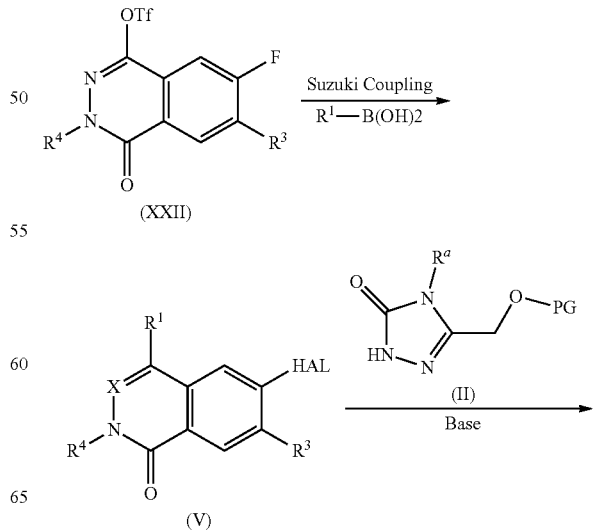

-continued

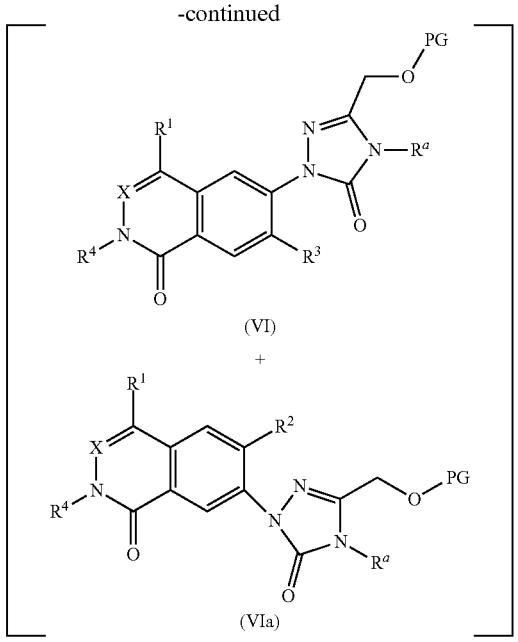

(VI)
+
(VIa)

According to SCHEME 12, a compound of formula R¹—B(OH)₂; is reacted under Suzuki coupling conditions previously described, with a compound of formula (XXII), to provide a compound of formula (V), where X is N. For example, a compound of formula (XXII), is reacted a commercially available or synthetically accessible boronic acid (or boronic ester) such as R¹—B(OH)₂, where R¹ is $C_{2-6}$alkenyl or $C_{2-6}$haloalkenyl as defined in Embodiment #1; a palladium catalyst such as 1,1'-bis(diphenylphosphino) ferrocene-palladium(II)dichloride or bis(triphenylphosphine)palladium(II) dichloride, and the like; a suitable base such a potassium phosphate, $Cs_2CO_3$, $K_2CO_3$, and the like; in a suitable solvent such as dioxane, water, ethanol, or a mixture thereof, to provide a compound of formula compound (V). A compound of formula (V), where R¹ is $C_{2-6}$alkyl or $C_{2-6}$haloalkyl, is readily prepared by selective hydrogenation of a compound of formula (V), where R¹ is $C_{2-6}$alkenyl or $C_{2-6}$haloalkenyl. For example, reaction of a compound of formula (V), where R¹ is

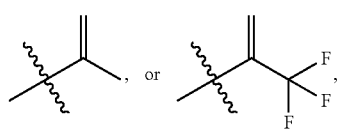

under hydrogenation conditions employing a catalyst such as Pd/C and the like, in a suitable solvent such as EtOAc, and the like; under an atmosphere of hydrogen gas (20-45 psi) at room temperature; for a period of 4 to 24 hours; affords a compound of formula (V), where R¹ is

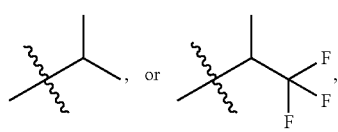

The reaction of a compound of formula (V), with a suitably protected triazolone of formula (II), employing conditions previously described, affords a mixture of compounds of formula (VI) and (VIa) which can be separated before or after deprotection of the protecting group.

SCHEME 13

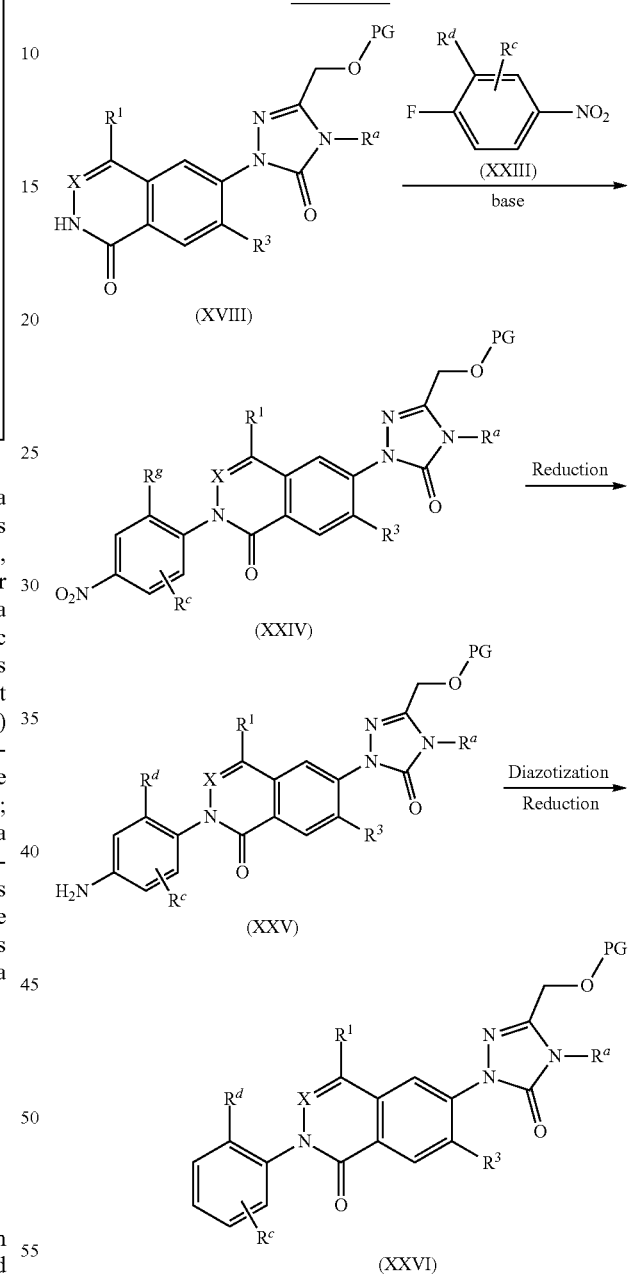

According to SCHEME 13, N-arylation of a compound of formula (XVIII) is achieved by reaction of suitably substituted commercially available or synthetically accessible fluoro compound of formula (XXIII), where $R^c$ and $R^d$ are as defined in Embodiment #1. A compound of formula (XVIII), where R¹ is H, $C_{2-6}$alkenyl, $C_{2-6}$haloalkenyl, $C_{3-6}$cycloalkyl, $C_{3-6}$cycloalkyl substituted with $C_{1-6}$alkyl, and X is CH or N, is reacted under nucleophilic displacement reaction conditions, with a commercially available or synthetically accessible fluoro compound of formula (XXIII); in the presence of a base like $K_2CO_3$, $Cs_2CO_3$, and the like; in aprotic solvent such as DMF, DMSO, and the like; at temperatures ranging from 65 to 100° C.; to afford a compound of formula (XXIV).

Reduction of compound of formula (XXIV) is achieved employing zinc or iron and $NH_4Cl$; in a mixed solvent of methanol and water; to provide an amino compound of formula (XXV).

Diazotization of a compound in formula (XXV) with $NaNO_2$; in an acidic aqueous solution or other nitrite reagents; in an organic solvent, such as EtOH, and the like; at a temperature of 0° C.; and subsequent the reduction of diazo group with zinc at temperatures ranging from 0 to 85° C.; or by treatment with $H_3PO_2$; affords a compound of formula (XXVI), where $R^c$ and $R^d$ are as defined as described in Embodiment #1.

formula (XXVIII), where $R^3$ is F, and HAL is F. A compound of formula (XXVIII), where $R^{1a}$ and $R^{1b}$ are each independently selected from $C_{1-4}$haloalkyl or $C_{3-6}$cycloalkyl may be made in a similar fashion. The reaction of an ester of formula (XXVIII) with a suitably protected triazolone compound of formula (II); in the presence of a base such as $K_3PO_4$, $K_2CO_3$, $Cs_2CO_3$, $NaHCO_3$, triethylamine, and the like; in a suitable solvent such as 1,4-dioxane, DMSO, DMF, THF, ACN, and the like; affords a compound of formula (XXIX). In a preferred method, PG is Bn, and $R^a$ is $C_{1-6}$alkyl. A compound of formula (XXIX), where $R^3$ is H or F, undergoes intramolecular cyclization under Heck reaction conditions, such as employing at catalyst such as chloro[(tri-tert-

SCHEME 14

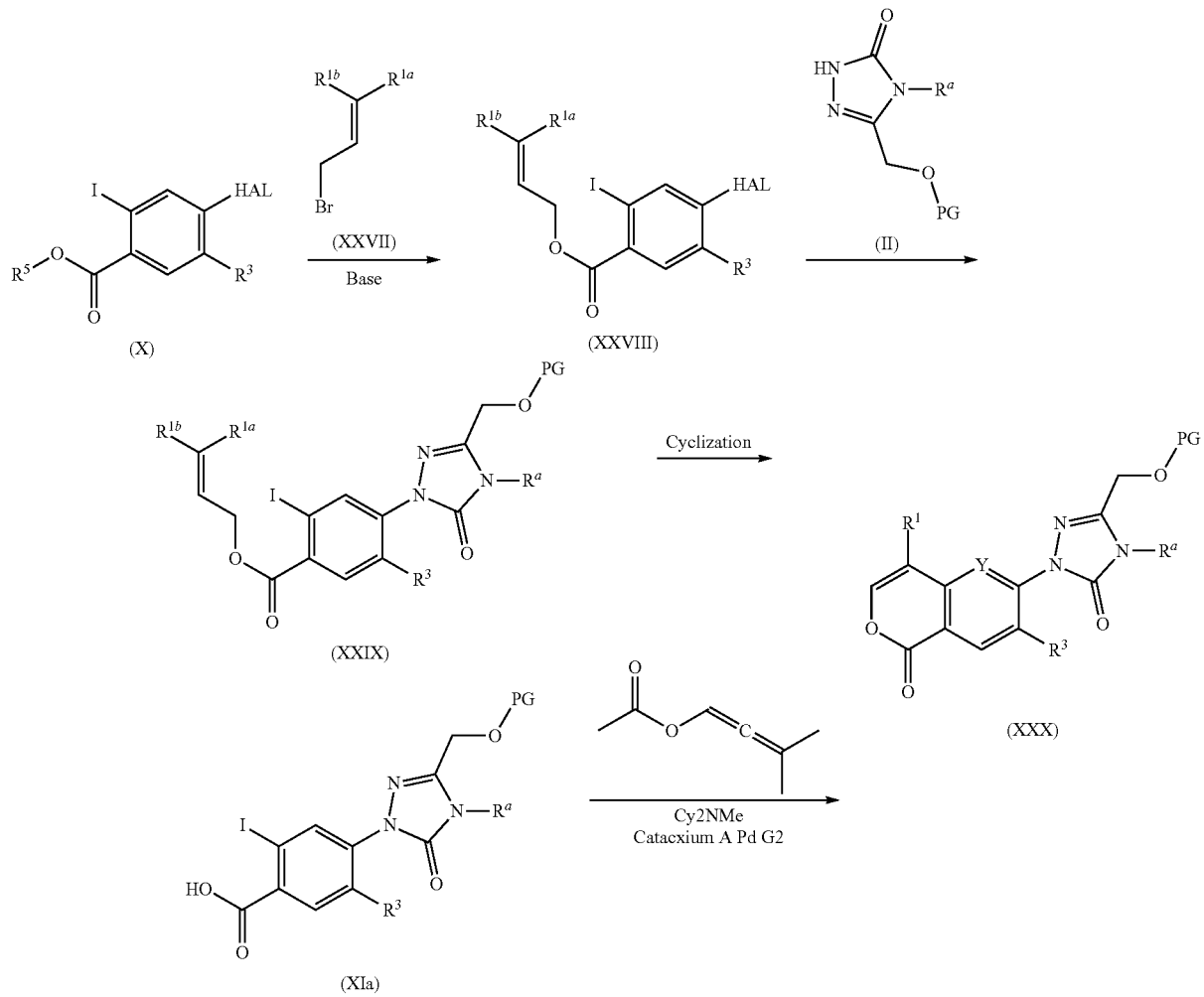

According to SCHEME 14, a compound of formula (X), where HAL is F, $R^5$ is H and $R^3$ is F, is reacted with a commercially available or synthetically accessible compound of formula (XXVII), where $R^{1a}$ and $R^{1b}$ are each independently H or $C_{1-4}$alkyl, such as 1-bromo-3-methyl-2-butene; in the presence of a base such as $K_2CO_3$, $Cs_2CO_3$, and the like; in a suitable solvent such as DMSO, DMF, THF, ACN, and the like; to afford an ester compound of butylphosphine)-2-(2-aminobiphenyl)] palladium(II) (P(tBu$_3$)PdG$_2$), N-cyclohexyl-N-methyl-cyclohexanamine, in a suitable solvent such as toluene, and the like; at a temperature of about 15 to 80° C.; for a period of about 18 to 36 hours; to provide an isocoumarin compound of formula (XXX), where Y is CH and $R^1$ is isopropyl, $R^3$ is H or F, $R^a$ and PG are defined as described above.

An isocoumarin compound of formula (XXX), where $R^1$ is

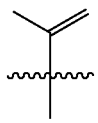 [SMILES: *C(=C)C]

is prepared from a compound of formula (XIa) and methylbuta-1,2-dien-1-yl acetate. Methylbuta-1,2-dien-1-yl acetate is commercially available or prepared in two steps from 2-methyl-3-butyn-2-ol. Acetic anhydride is reacted with 2-methyl-3-butyn-2-ol, in the presence of a catalyst such as $Mg(ClO_4)_2$; in a suitable solvent such as DCM, and the like; to afford 2-methylbut-3-yn-2-yl acetate. 2-Methylbut-3-yn-2-yl acetate is reacted with a catalytic amount of a Lewis acid such as $AgBF_4$, $AgClO_4$, $PtCl_2$, and the like; to provide 3-methylbuta-1,2-dien-1-yl acetate. 3-Methylbuta-1,2-dien-1-yl acetate is coupled with a compound of formula (XIa), where $R^5$ is H, employing intermolecular cyclization under Heck reaction conditions as previously described, such as employing at catalyst such as Catacxium A Pd G2, and $Cy_2NMe$ palladium (II) acetate, phase transfer reagent like tetrabutylammonium bromide, and a base like potassium acetate, in a suitable solvent such as DMF, and the like; at a temperature of 70 to 90° C.; for a period of 10 to 16 hours; to provide the isocoumarin compound of formula (XXX), where Y is CH and $R^1$ is

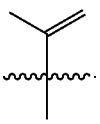

A compound of formula (XXX), where Y is CH and $R^1$ is

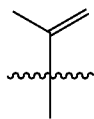

is selectively reduced under hydrogenation conditions employing at catalyst such as Wilkinson's Catalyst [RhCl$(PPh_3)_3$] and the like, in a suitable solvent such as THF, and the like; at room temperature, provide an isocoumarin compound of formula (XXX), where $R^1$ is isopropyl.

SCHEME 15

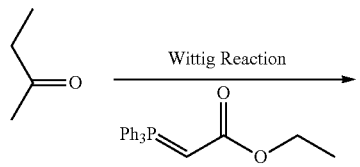

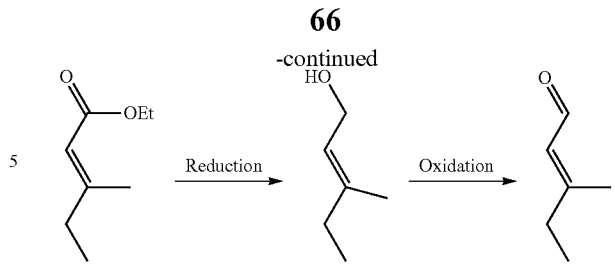

According to SCHEME 15, 2-butanone is converted to ethyl 3-methylpent-2-enoate employing Wittig reaction conditions known to one skilled in the art. For example, 2-butanone is reacted with a triphenyl phosphonium ylide such as (carbethoxymethylene) triphenylphosphorane, with or without an additive such as benzoic acid, LiCl, and sodium dodecyl sulfate (SDS), and the like, in a suitable solvent such as toluene, at temperatures ranging from rt to the reflux temperature of the solvent, for a period of 12-24 h. Ethyl 3-methylpent-2-enoate is reduced to 3-methylpent-2-en-1-ol employing a suitable reducing agent such as DIBAL-H, in a suitable solvent such as toluene, and the like, at temperatures ranging from −78° C. to room temperature. 3-Methylpent-2-en-1-ol is oxidized to 3-methylpent-2-enal employing oxidation conditions known to one skilled in the art, for example, DMP (Dess-Martin periodinane), $SO_3$-pyridine, Swern conditions [$(COCl)_2$, DMSO, $Et_3N$], PCC, and the like, in a solvent such as EtOAc, DMSO, DCM, and the like, at temperatures ranging from about −78° C. to room temperature (about 23° C.). In a preferred method, 3-methylpent-2-en-1-ol is oxidized to 3-methylpent-2-enal with Dess-Martin periodinane, in DCM, at 25° C. for a period of 1-4 h.

SCHEME 16

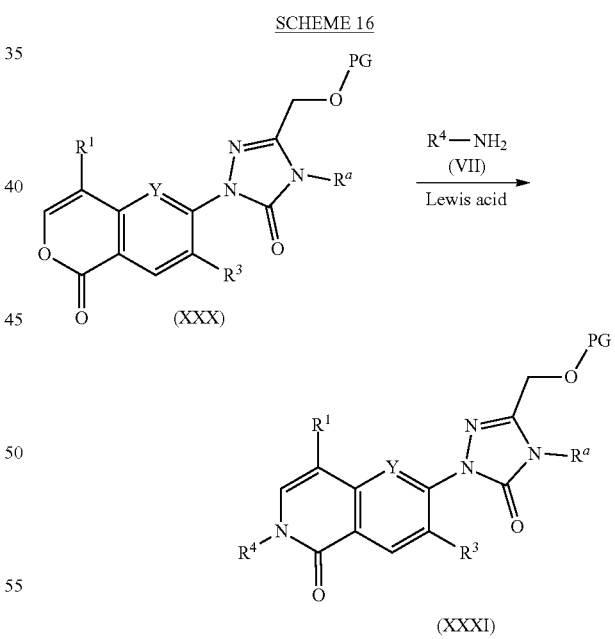

According to SCHEME 16, an isocoumarin of compound of formula (XXX), where Y is CH, is reacted with a commercially available or synthetically accessible amine compound of formula $R^4$—$NH_2$, where $R^4$ is as defined in Embodiment #1; a Lewis acid such as like $AlMe_3$, $AlCl_3$, and the like; in a suitable aprotic solvent such as DCM, toluene, and the like; to provide a compound of formula (XXXI), where Y is CH, and $R^1$, $R^3$, $R^4$ and $R^a$ are defined as described in Embodiment #1.

SCHEME 17

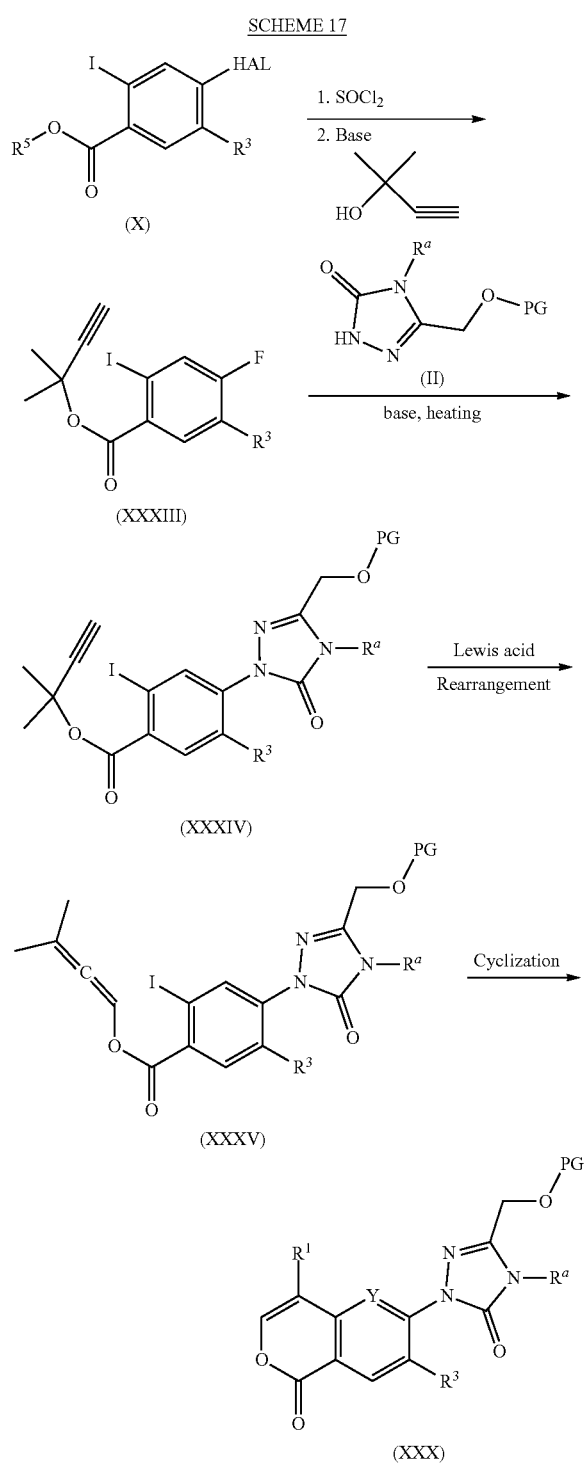

furan (THF), acetonitrile (ACN), toluene, and the like, at a temperatures ranging from 0° C. to room temperature to form 4,5-difluoro-2-iodobenzoyl chloride. 4,5-Difluoro-2-iodobenzoyl chloride may be reacted with commercially available or synthetically accessible 2-methylbut-3-yn-2-ol, in the presence of a base such as triethylamine and DMAP; in a suitable solvent such as DCM, and the like; to afford an ester compound of formula (XXXIII). A compound of formula (XXXIII) may be reacted with a compound of formula (II), employing methods as previously described to afford a compound of formula (XXXIV). Treatment of a compound of formula (XXXIV) with a catalytic amount of a Lewis acid such as $AgClO_4$, $PtCl_2$, and the like; may afford the rearranged compound of formula (XXXV). A compound of formula (XXXV), where $R^3$ is H or F, may undergoe an intramolecular cyclization under Heck reaction conditions, such as employing a catalyst such as palladium (II) acetate, a phase transfer reagent like tetrabutylammonium bromide, and a base like potassium acetate, in a suitable solvent such as DMF, and the like; at a temperature of 70 to 90° C.; for a period of 1 to 3 hours; to provide an isocoumarin compound of formula (XXX), where Y is CH.

SCHEME 18

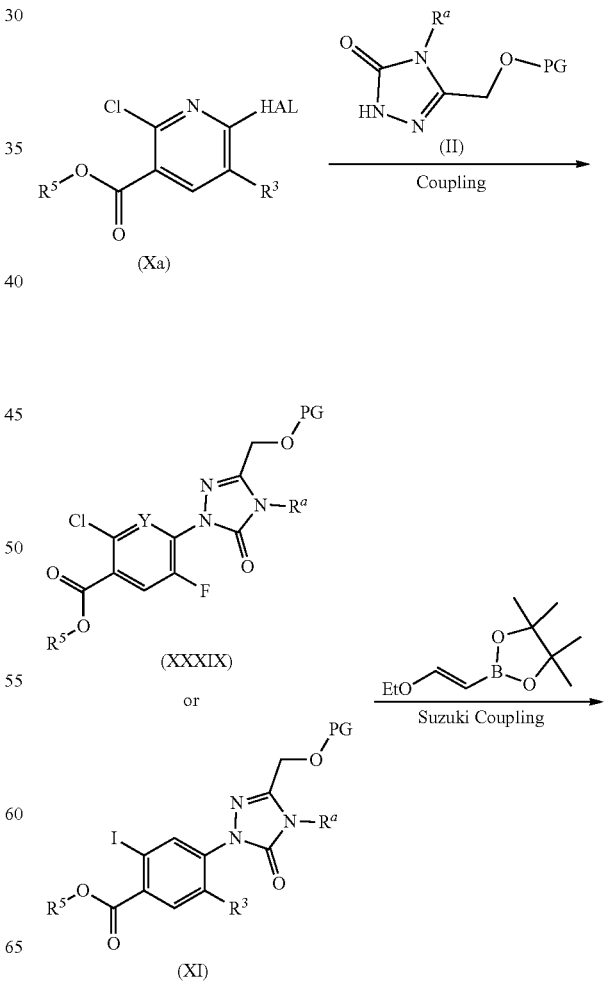

An isocoumarin compound of formula (XXX) may be prepared according to SCHEME 17. 4,5-Difluoro-2-iodobenzoyl chloride is prepared from a compound of formula (X), where HAL is F, $R^5$ is H and $R^3$ is F, employing conditions known to one skilled in the art such as oxalyl chloride or thionyl chloride, in the presence of a catalytic amount of DMF, in a suitable solvent such as an aprotic non polar solvent such as dichloromethane (DCM), tetrahydro- -continued

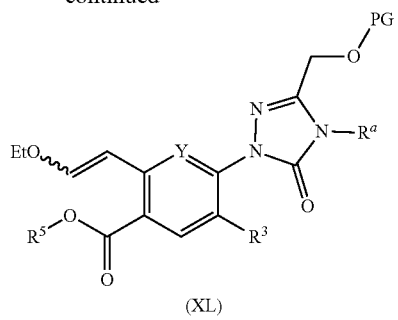

(XL)

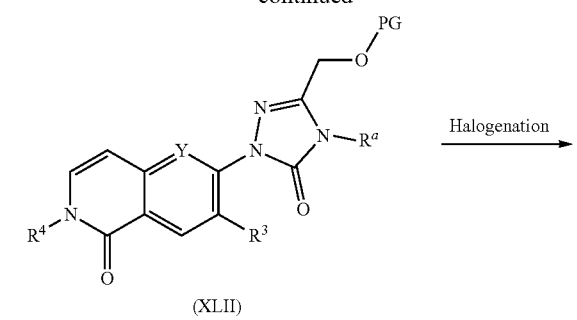

(XLII)

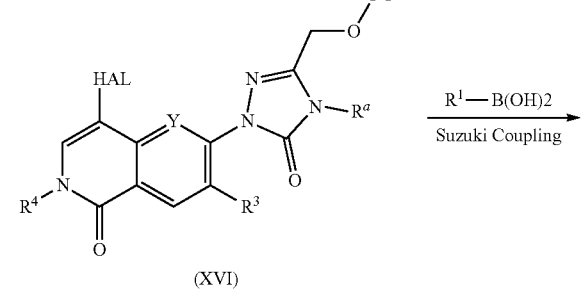

(XVI)

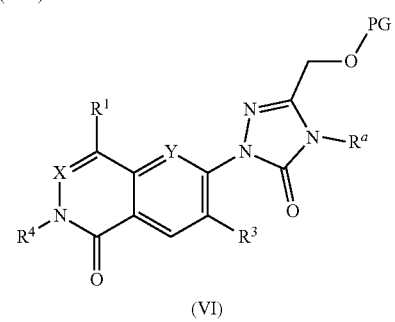

(VI)

According to SCHEME 18, a compound of formula (Xa), where HAL is Cl, $R^5$ is $CH(CH_3)_2$, and $R^3$ is F, is commercially available or synthetically accessible according to methods as described in Chen, et al, US Patent Publication No. US2016-0176869. Reaction of a compound of formula (Xa) with a commercially available or synthetically accessible nucleophilic compound of formula (II), where PG is benzyl, and $R^c$ is $C_{1-6}$alkyl; in the presence of a base such as $K_2CO_3$, $Cs_2CO_3$, $NaHCO_3$, triethylamine, and the like; in a suitable solvent such as dimethylsulfoxide (DMSO), DMF, THF, ACN, and the like; affords a compound of formula (XXXIX), where Y is N. A compound of formula (XXXIX) or formula (XI), where $R^3$ is F, and $R^5$ is $C_{1-4}$alkyl; is reacted a commercially available 1-ethoxyethene-2-boronic acid pinacol ester; a palladium catalyst such as bis(triphenylphosphine)palladium(II) dichloride, 1,1'-bis(diphenylphosphino)ferrocene-palladium(II)dichloride and the like; a suitable base such as $Cs_2CO_3$, and the like; in a suitable solvent such as dioxane, water, ethanol, or a mixture thereof; employing conventional or microwave heating; to provide a compound of formula (XL), where Y is N or CH.

SCHEME 19

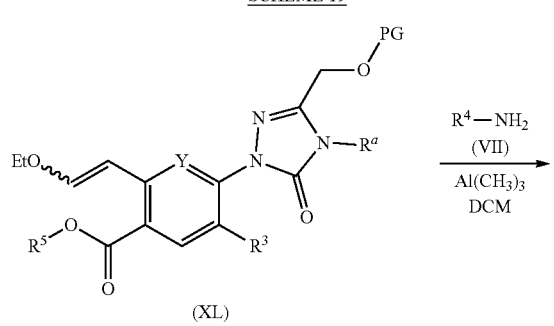

(XL)

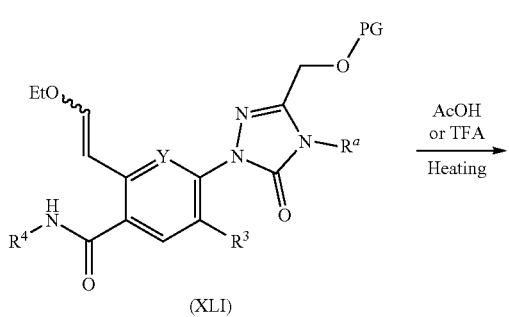

(XLI)

According to SCHEME 19, a compound of formula $R^4$—$NH_2$, where $R^4$ is as defined in Embodiment #1; is reacted with trimethyl aluminum; in a suitable solvent such as dichloromethane, toluene, or a mixture thereof; the resulting solution is combined with a compound of formula (XL), where Y is CH or N; to provide a compound of formula (XLI). A compound of formula (XLI), where Y is CH or N, is treated with acetic acid or trifluoroacetic acid under heating conditions between 50° C. to 90° C., to provide a compound of formula (XLII). A compound of formula (XLII) is halogenated employing N-bromosuccinimide in anhydrous dimethylformamide at room temperature, to provide a compound of formula (XVI), where HAL is Br. A compound of formula $R^1$—$B(OH)_2$; is reacted under Suzuki coupling conditions known to one skilled in the art, or as previously described with a compound of formula (XVI), to provide a compound of formula (VI), where $R^1$ is an optionally substituted $C_{2-6}$alkenyl, $C_{2-6}$haloalkenyl, or aryl as defined in Embodiment #1. A compound of formula (VI), where $R^1$ is an optionally substituted $C_{2-6}$alkenyl or $C_{2-6}$haloalkenyl is reacted under hydrogenation conditions using Wilkinson catalyst ((PPh$_3$)$_3$RhCl) to provide a compound of formula (VI), where $R^1$ is $C_{2-6}$alkyl or $C_{2-6}$haloalkyl.

SCHEME 20

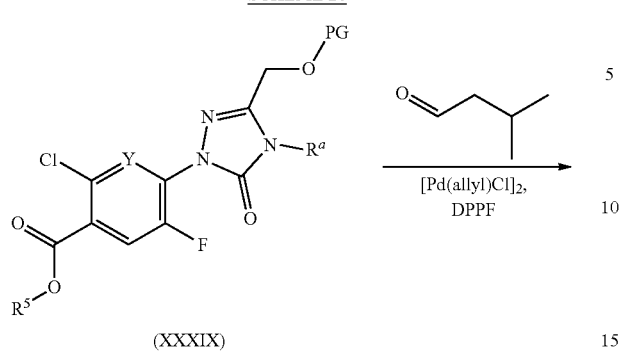

(XXXIX)

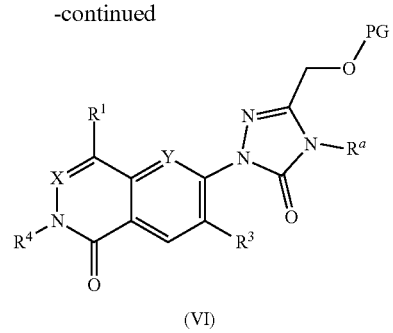

(VI)

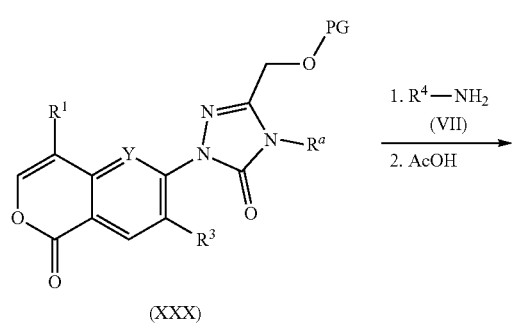

(XXX)

According to SCHEME 20, 3-methylbutanal is reacted with a compound of formula (XXXIX), where Y is N and $R^5$ is $CH(CH_3)_2$, with a palladium catalyst such as allylpalladium(II) chloride dimer, and the like; a ligand such as 1,1'-bis(diphenylphosphino)ferrocene (dppf), and the like; a suitable base such as $Cs_2CO_3$, and the like; in the presence of water scavenger such as molecular sieve (4A); in a suitable solvent such as dioxane thereof, to provide a compound of formula compound (XXX), where $R^1$ is isopropyl. A compound of formula $R^4$—$NH_2$, where $R^4$ is as defined in Embodiment #1; is reacted with trimethyl aluminum; in a suitable solvent such as dichloromethane, toluene, or a mixture thereof; the resulting solution is combined with a compound of formula (XXX), followed by subsequent treatment with acetic acid under heating temperature of 80-100° C. for a period of time ranging from 5 to 24 hours; to provide a compound of formula (VI); where X is CH, Y is N, $R^1$ is isopropyl, $R^3$ is F.

SCHEME 21

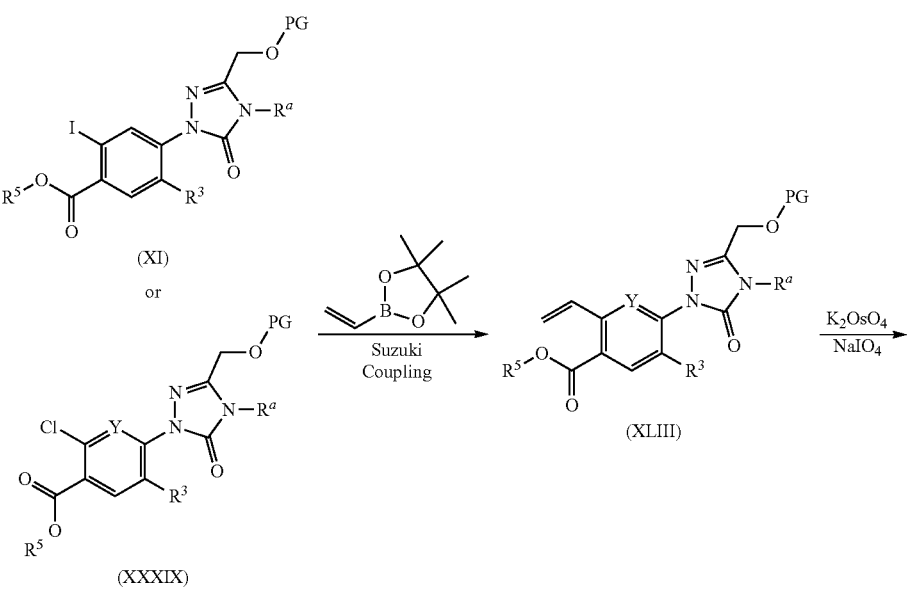

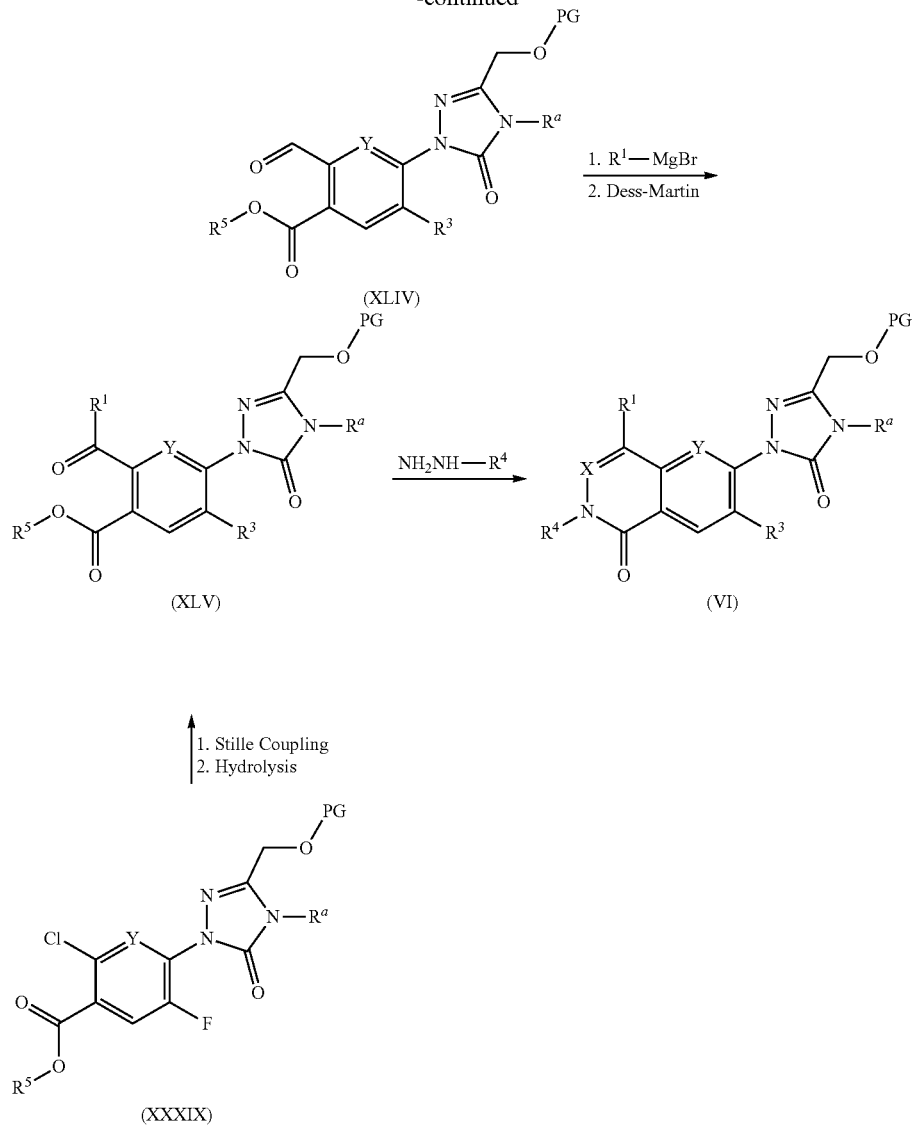

According to SCHEME 21, A compound of formula (XXXIX) or formula (XI), where $R^3$ is F, and $R^5$ is $C_{1-4}$alkyl; is reacted a commercially available vinylboronic acid pinacol ester; a palladium catalyst such as bis(triphenylphosphine)palladium(II) dichloride, or 1,1'-bis(diphenylphosphino)ferrocene-palladium(II)dichloride dichloromethane complex, and the like; a suitable base such as $Cs_2CO_3$, and the like; in a suitable solvent such as dioxane, water, ethanol, or a mixture thereof, to provide a compound of formula compound (XLIII), where Y is N or CH. The vinyl group in a compound of formula (XLIII) is selectively converted into an aldehyde group of formula (XLIV) employing potassium osmate (VI) dihydrate/sodium periodate, or ozonolysis, and the like. A compound of formula (XLIV) is reacted with a commercially available or synthetically accessible suitably substituted alkyl Grignard reagent such as i-PrMgCl, and the like; in aprotic solvent like THF, and the like; followed by subsequent treatment with an oxidizing reagent such as Dess-Martin reagent, or Swern oxidation conditions, and the like; to afford a ketone compound of formula (XLV).

A compound of formula (XLV) is prepared from a compound of formula (XXXIX) in two steps. A compound of formula (XXXIX), where $R^3$ is F, and $R^5$ is $C_{1-4}$alkyl; is reacted a commercially available tributyl(1-ethoxyvinyl)tin; a palladium catalyst such as bis(triphenylphosphine)palladium(II) dichloride, 1,1'-bis(diphenylphosphino)ferrocene-palladium(II)dichloride and the like; in a suitable solvent such as dioxane, water, ethanol, or a mixture thereof. Subsequent acidic hydrolysis employing conditions such as treatment with aqueous HCl solution at room temperature affords a compound of formula (XLV), where X is N, Y is N or CH, $R^1$ is methyl.

A commercially or synthetically available hydrazine $R^4$—$NHNH_2$, where $R^4$ is as defined in Embodiment #1, such as 2-chloro-6-fluorophenylhydrazine, o-tolylhydrazine; is condensed with a compound of formula (XLV); in the presence of a base such as potassium carbonate, and the like; under the heating conditions such as 70-120° C.; in a suitable solvent such as toluene, or a mixture thereof, afford a compound of formula (VI), where X is N, Y is CH or N, and $R^4$ is as defined in Embodiment #1.

SCHEME 22

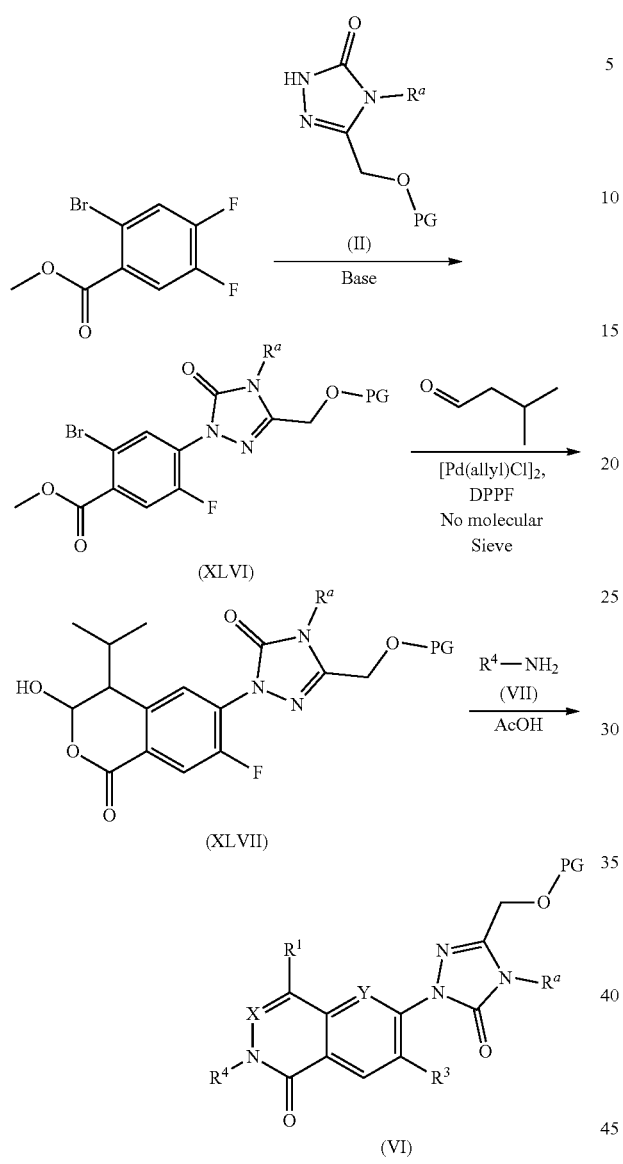

According to SCHEME 22, the reaction of methyl 2-bromo-4,5-difluorobenzoate with a suitably protected triazolone compound of formula (II); in the presence of a base such as $K_3PO_4$, $K_2CO_3$, $Cs_2CO_3$, $NaHCO_3$, triethylamine, and the like; in a suitable solvent such as 1,4-dioxane, DMSO, DMF, THF, ACN, and the like; affords a compound of formula (XLVI). In a preferred method, PG is Bn, and $R^a$ is $C_{1-6}$alkyl (as previously described in Scheme 14). 3-Methylbutanal is reacted with a compound of formula (XLVI), with a palladium catalyst such as allylpalladium(II) chloride dimer, and the like; a ligand such as 1,1'-bis(diphenylphosphino)ferrocene (dppf), and the like; a suitable base such as $Cs_2CO_3$, and the like; in the absence of water scavenger such as molecular sieve (4A); in a suitable solvent such as dioxane thereof; to provide a compound of formula compound (XLVII). A compound of formula $R^4$—$NH_2$, where $R^4$ is as defined in Embodiment #1; is reacted with trimethyl aluminum; in a suitable solvent such as dichloromethane, dichloroethane, toluene, or a mixture thereof; the resulting solution is combined with a compound of formula (XLVII), followed by subsequent treatment with acetic acid under heating temperature of 80-100° C. for a period of time ranging from 5 to 24 hours; to provide a compound of formula (VI); where X is CH, Y is CH, $R^1$ is isopropyl, $R^3$ is F. In certain cases, a compound of formula $R^4$—$NH_2$ such as o-toluidine and the like; is directly condensed with a compound of formula compound (XLVII) in acetic acid under heating temperature of 80-100° C. for a period of time ranging from 10 to 24 hours; to provide a compound of formula (VI); where X, Y, $R^1$, $R^3$ are defined above.

SCHEME 23

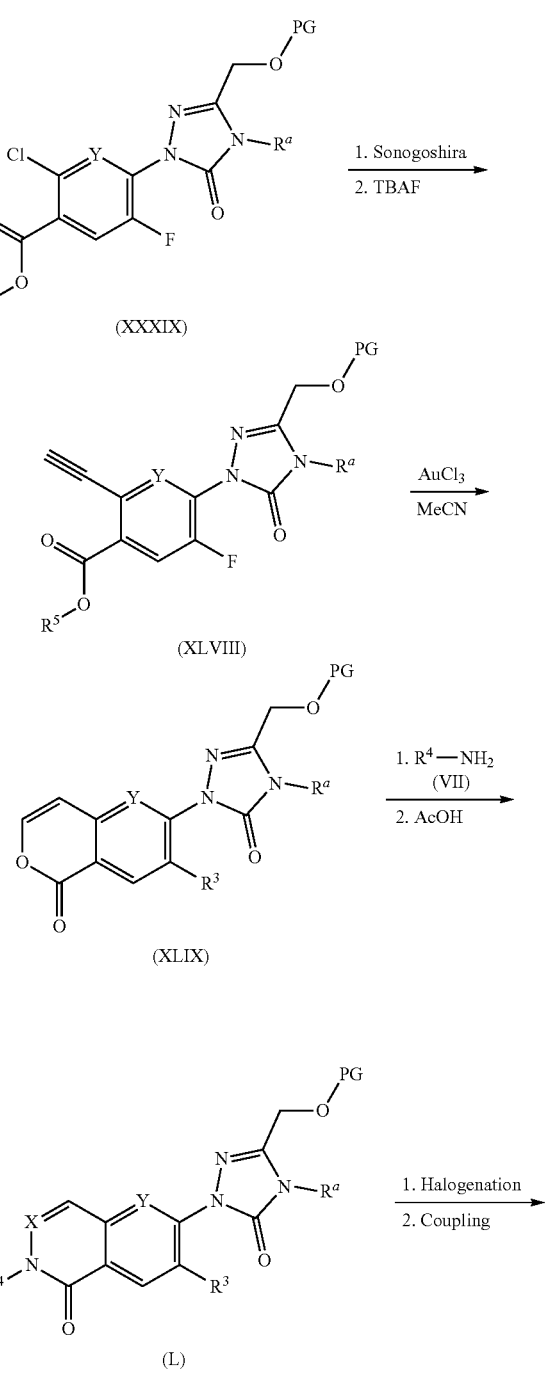

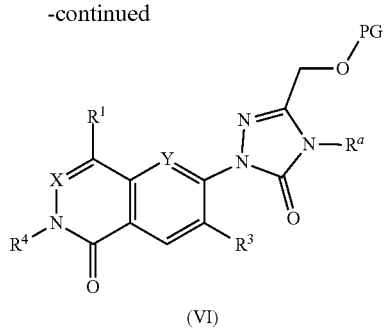

(VI)

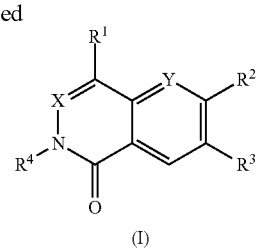

(I)

According to SCHEME 23, a compound of formula (XXXIX), where $R^5$ is $C_{1-4}$alkyl, Y is N, and $R^3$ is F, is subjected to a Sonogashira coupling reaction with a silyl protected alkyne, such as trimethylsilylacetylene, a palladium catalyst such as palladium(II)bis(triphenylphosphine) dichloride and the like; a copper catalyst such as copper iodide and the like; with a suitable base, such as triethylamine; in a suitable solvent such as ACN, toluene, and the like. Deprotection reaction employing TBAF in a suitable solvent such as THF, and the like; at room temperature affords a compound of formula (XLVIII). A compound of formula (XLIX) is obtained using a gold catalyst, preferably $AuCl_3$ in a suitable solvent mixture, such as MeCN. Similar transformation by $AuCl_3$-catalyzed cyclization has been described by Marchal, E. et al in *Tetrahedron* 2007, 63, 9979-9990. A compound of formula $R^4$—$NH_2$, where $R^4$ is as defined in Embodiment #1; is reacted with trimethylaluminum; in a suitable solvent such as dichloromethane, dichloroethane, toluene, or a mixture thereof; the resulting solution is combined with a compound of formula (XLIX), followed by subsequent treatment with acetic acid under heating temperature of 80-100° C. for a period of time ranging from 5 to 24 hours; to provide a compound of formula (L). Employing NBS in a suitable solvent, preferably DMF, at room temperature followed by cross coupling using conditions known to one skilled in the art, preferably a palladium catalyst such as palladium(II)bis(triphenylphosphine) dichloride, a base such as $Cs_2CO_3$, $Na_2CO_3$, and the like; in a solvent mixture composed of 1,4-dioxane and water; at a temperature of 100° C. provides a compound of formula (VI), where X is CH, Y is N, $R^3$ is F, and $R^1$, $R^a$ and PG are defined as previously described.

SCHEME 24

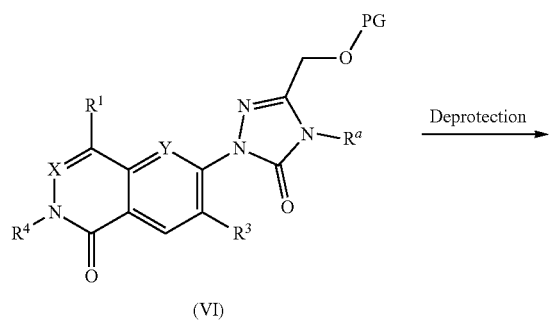

(VI)

Deprotection →

According to SCHEME 24, a compound of formula (VI), where PG is Bn, is deprotected employing conditions known to one skilled in the art, preferably in neat TFA in a sealed tube, at a temperature of about 60 to 90° C.; or employing $BCl_3$, at a temperature of about −78° C., in a suitable solvent such as in DCM; or treatment with hydrogen gas, in the presence of a catalyst such as Palladium on carbon (Pd/C), affords a compound of Formula (I).

In a similar fashion, N-arylation and in-situ TBDPS deprotection of a compound of formula (XVIII), where $R^1$ is I and PG is TBDPS, and Z is $NO_2$ and X is N; is achieved employing conditions known to one skilled in the art or as previously described, to afford a compound of Formula (I).

A compound of Formula (I), where $R^3$ is F is reacted in a nucleophilic aromatic substitution reaction to provide a compound of Formula (I), where $R^3$ is $OCH_3$. For example, reaction of a compound of Formula (I), where $R^3$ is F, with a suitable base such as NaOH, and the like; in a suitable solvent such as MeOH, and the like; to provide a compound of Formula (I) where Y is CH and $R^3$ is $OCH_3$.

Compounds of Formula (I) may be converted to their corresponding salts using methods known to one of ordinary skill in the art. For example, an amine of Formula (I) is treated with trifluoroacetic acid, HCl, or citric acid in a solvent such as $Et_2O$, $CH_2Cl_2$, THF, MeOH, chloroform, or isopropanol to provide the corresponding salt form. Alternately, trifluoroacetic acid or formic acid salts are obtained as a result of reverse phase HPLC purification conditions. Cyrstalline forms of pharmaceutically acceptable salts of compounds of Formula (I) may be obtained in crystalline form by recrystallization from polar solvents (including mixtures of polar solvents and aqueous mixtures of polar solvents) or from non-polar solvents (including mixtures of non-polar solvents).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure.

Normal-phase silica gel chromatography (FCC) was performed on silica gel ($SiO_2$) using prepacked cartridges.

Preparative reverse-phase high performance liquid chromatography (RP HPLC) was performed on either:
METHOD A. A Gilson GX-281 semi-prep-HPLC with Phenomenex Synergi C18 (10 μm, 150×25 mm), or Boston Green ODS C18 (5 μm, 150×30 mm), and mobile phase of 5-99% ACN in water (with 0.225% FA) over 10 min and then hold at 100% ACN for 2 min, at a flow rate of 25 mL/min.
or
METHOD B. A Gilson GX-281 semi-prep-HPLC with Phenomenex Synergi C18 (10 μm, 150×25 mm), or Boston Green ODS C18 (5 μm, 150×30 mm), and mobile phase of 5-99% ACN in water (0.1% TFA) over 10 min and then hold at 100% ACN for 2 min, at a flow rate of 25 mL/min.
or
METHOD C. A Gilson GX-281 semi-prep-HPLC with Phenomenex Synergi C18 (10 μm, 150×25 mm), or Boston Green ODS C18 (5 μm, 150×30 mm), and mobile phase of 5-99% ACN in water (0.05% HCl) over 10 min and then hold at 100% ACN for 2 min, at a flow rate of 25 mL/min.
or
METHOD D. a Gilson GX-281 semi-prep-HPLC with Phenomenex Gemini C18 (10 μm, 150×25 mm), AD (10 μm, 250 mm×30 mm), or Waters XBridge $C_{18}$ column (5 μm, 150×30 mm), mobile phase of 0-99% ACN in water (with 0.05% ammonia hydroxide v/v) over 10 min and then hold at 100% ACN for 2 min, at a flow rate of 25 mL/min.
or
METHOD E. a Gilson GX-281 semi-prep-HPLC with Phenomenex Gemini C18 (10 μm, 150×25 mm), or Waters XBridge $C_{18}$ column (5 μm, 150×30 mm), mobile phase of 5-99% ACN in water (10 mM $NH_4HCO_3$) over 10 min and then hold at 100% ACN for 2 min, at a flow rate of 25 mL/min.

Preparative supercritical fluid high performance liquid chromatography (SFC) was performed either on a Thar 80 Prep-SFC system, or Waters 80Q Prep-SFC system from Waters. The ABPR was set to 100 bar to keep the CO2 in SF conditions, and the flow rate may verify according to the compound characteristics, with a flow rate ranging from 50 g/min to 70 g/min. The column temperature was ambient temperature Mass spectra (MS) were obtained on a SHIMADZU LCMS-2020 MSD or Agilent 1200G6110A MSD using electrospray ionization (ESI) in positive mode unless otherwise indicated. Calculated (calcd) mass corresponds to the exact mass.

Nuclear magnetic resonance (NMR) spectra were obtained on Bruker model AVIII 400 spectrometers. Definitions for multiplicity are as follows: s=singlet, d=doublet, t=triplet, q=quartet, dd=doublet of doublets, ddd=doublet of doublet of doublets, td=triplet of doublets, dt=doublet of triplets, spt=septet, quin=quintet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 12.0, ChemDraw Ultra 14.0 (CambridgeSoft Corp., Cambridge, Mass.) or ACD/Name Version 10.01 (Advanced Chemistry).

Compounds designated as R* or S* are enantiopure compounds where the absolute configuration was not determined.

Intermediate 1: 3-((Benzyloxy)methyl)-4-ethyl-1H-1,2,4-triazol-5(4H)-one

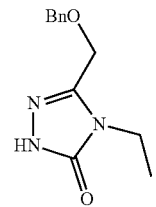

Step A. 2-(Benzyloxy)acetohydrazide. To a solution of ethyl 2-(benzyloxy)acetate (55 g, 283.17 mmol) in EtOH (500 mL) was added $NH_2NH_2·H_2O$ (28.3 g, 566 mmol, 27.5 mL). The reaction mixture was heated at 78° C. for 6 h. The reaction mixture was concentrated under reduced pressure to afford the title product (52 g, crude) as a colorless oil, which was used directly in the next step without further purification.

Step B. 3-((Benzyloxy)methyl)-4-ethyl-1H-1,2,4-triazol-5 (4H)-one. To a solution of 2-(benzyloxy)acetohydrazide (52 g, 288 mmol) in $H_2O$ (500 mL) was added dropwise isocyanatoethane (25.1 g, 346 mmol, 27.9 mL) at 0° C. After the addition was complete, the mixture was stirred at 25° C. for 12 hr. To the mixture was added $H_2O$ (20 mL), and an aqueous solution (120 mL) of NaOH (57.7 g, 1.44 mol). The mixture was stirred at 95° C. for 12 hr. The reaction mixture was cooled to rt, then quenched with HCl (12 M) at 0° C. and adjusted to "pH" 6. The solid was filtered and dried under reduced pressure to afford the title compound as a white solid (61 g, 91% yield). $^1H$ NMR (400 MHz, $CDCl_3$) δ 9.23-9.09 (m, 1H), 7.41-7.31 (m, 5H), 4.58-4.53 (m, 2H), 4.45-4.42 (m, 2H), 3.82-3.75 (m, 2H), 1.33-1.29 (m, 3H) ppm.

Intermediate 2: 5-(((tert-Butyldiphenylsilyl)oxy) methyl)-4-ethyl-2,4-dihydro-3H-1,2,4-triazol-3-one

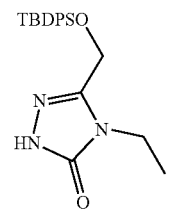

Step A. 4-Ethyl-5-(hydroxymethyl)-2,4-dihydro-3H-1,2,4-triazol-3-one.
To a solution of 5-[(benzyloxy)methyl]-4-methyl-2,4-dihydro-3H-1,2,4-triazol-3-one (8 g, 34.3 mmol, 1.0 eq.) in methanol (200 mL) was added Pd/C (2 g). The resulting mixture was maintained under hydrogen and stirred at rt for 6 h. Then the resulting mixture was filtered and the filtrate was concentrated to afford the crude product 4-ethyl-5-(hydroxymethyl)-2,4-dihydro-3H-1,2,4-triazol-3-one as a white solid (4.3 g, 88% yield). $^1$H NMR (400 MHz, DMSO-$d_6$) δ 11.52 (s, 1H), 5.55 (t, J=5.50 Hz, 1H), 4.32 (d, J=5.50 Hz, 2H), 3.64 (q, J=6.97 Hz, 2H), 1.18 (t, J=6.97 Hz, 3H) ppm.

Step B. 5-(((tert-Butyldiphenylsilyl)oxy)methyl)-4-ethyl-2,4-dihydro-3H-1,2,4-triazol-3-one.
To a solution of 4-ethyl-5-(hydroxymethyl)-2,4-dihydro-3H-1,2,4-triazol-3-one (3 g, 21 mmol, 1.0 eq.) in DCM (30 mL) was added tert-butylchlorodiphenylsilane (6.5 mL, 25 mmol, 1.2 eq.) and pyridine (1.86 mL, 23 mmol, 1.1 eq.). The resulting mixture was stirred at rt overnight. The reaction mixture was quenched with water (100 mL). The resulting mixture was extracted with DCM (3×100 mL). The organic layers were combined, dried over anhydrous sodium sulfate, filtered and concentrated. The residue was purified by silica gel chromatography (SiO$_2$, 50-80% ethyl acetate/petroleum ether) to afford 5-(((tert-butyldiphenylsilyl)oxy)methyl)-4-ethyl-2,4-dihydro-3H-1,2,4-triazol-3-one as a white solid (4.9 g, 61% yield). LCMS (ES-API): mass calcd. for $C_{21}H_{27}N_3O_2Si$, 381.2; m/z found, 382.2 [M+H]$^+$. $^1$H NMR (400 MHz, CDCl$_3$) δ 9.98 (s, 1H), 7.61-7.72 (m, 4H), 7.32-7.54 (m, 6H), 4.54 (s, 2H), 3.84 (q, J=7.34 Hz, 2H), 1.33 (t, J=7.34 Hz, 3H), 1.07 (s, 9H) ppm.

Intermediate 3: 5-((Benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one

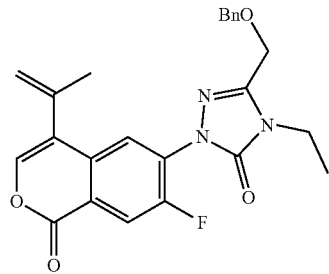 [SMILES: C=C(C)c1coc(=O)c2cc(F)c(-n3nc(COCc4ccccc4)n(CC)c3=O)cc12]

Step A. tert-Butyl 4,5-difluoro-2-iodobenzoate. 4,5-Difluoro-2-iodobenzoic acid (3 g, 11 mmol) was dissolved in THF (30 mL), then di-tert-butyl dicarbonate (4.6 g, 21 mmol) was added followed by DMAP (645 mg, 5.3 mmol). The reaction mixture was stirred under nitrogen at 50° C. overnight, then cooled down to room temperature. The solvent was evaporated under reduced pressure. The residue was diluted with EtOAc then washed with brine. The organic layer was separated, dried with Na$_2$SO$_4$, filtered, and concentrated. The residue was purified by silica column chromatography (gradient elution: 0-5% EtOAc in petroleum ether) to give the title compound as a yellow oil (2.9 g, yield: 79%). $^1$H NMR (400 MHz, CDCl$_3$) δ 7.77 (dd, J=10.2, 7.9 Hz, 1H), 7.63 (dd, J=10.2, 7.9 Hz, 1H), 1.62 (s, 9H) ppm; $^{19}$F NMR (376 MHz, CDCl$_3$) δ −131.55-131.13 (m, 1F), −136.97-136.65 (m, 1F) ppm.

Step B. tert-Butyl 4-(3-((benzyloxy)methyl)-4-ethyl-5-oxo-4,5-dihydro-1H-1,2,4-triazol-1-yl)-5-fluoro-2-iodobenzoate. A mixture of tert-butyl 4,5-difluoro-2-iodobenzoate (3.2 g, 9.4 mmol), 3-((benzyloxy)methyl)-4-ethyl-1H-1,2,4-triazol-5(4H)-one (Intermediate 1, 2.6 g, 11.2 mmol) and Cs$_2$CO$_3$ (6.1 g, 18.7 mmol) in anhydrous DMF (30 mL) was stirred under nitrogen at 75° C. for 1 h, then cooled to room temperature. The mixture was filtered through a pad of Celite®, and the pad was washed with EtOAc. The filtrate was combined, washed with brine, and concentrated. The residue was purified by silica column chromatography (gradient elution: 0-40% EtOAc in petroleum ether) to give the title compound as a colorless amorphous solid (5 g, yield: 96%). ESI-MS: mass calcd. for $C_{23}H_{25}FIN_3O_4$, 553.1; m/z found, 554.1 [M+H]$^+$. $^1$H NMR (400 MHz, CDCl$_3$) δ 8.16 (d, J=7.1 Hz, 1H), 7.62 (d, J=10.8 Hz, 1H), 7.29-7.45 (m, 5H), 4.61 (s, 2H), 4.50 (s, 2H), 3.84 (q, J=7.2 Hz, 2H), 1.63 (s, 9H), 1.35 (t, J=7.2 Hz, 3H) ppm; $^{19}$F NMR (376 MHz, CDCl$_3$) δ −119.09 (dd, J=10.6, 7.0 Hz, 1F) ppm.

Step C. 4-(3-((Benzyloxy)methyl)-4-ethyl-5-oxo-4,5-dihydro-1H-1,2,4-triazol-1-yl)-5-fluoro-2-iodobenzoic acid. To a solution of tert-butyl 4-(3-((benzyloxy)methyl)-4-ethyl-5-oxo-4,5-dihydro-1H-1,2,4-triazol-1-yl)-5-fluoro-2-iodobenzoate (5 g, 9 mmol) in DCM (50 mL) was slowly added TFA (10 mL). The reaction mixture was stirred at room temperature overnight. The reaction mixture was concentrated under vacuum. The obtained residue was triturated with petroleum ether at room temperature for 30 min. The mixture was filtered and the solid was rinsed with petroleum ether. The precipitate was collected and dried in vacuo to give the title compound as a white solid (4.1 g, yield: 91%). ESI-MS: mass calcd. for $C_{19}H_{17}FIN_3O_4$, 497.0; m/z found, 498.0 [M+H]$^+$. $^1$H NMR (400 MHz, DMSO-$d_6$) δ 8.16 (d, J=7.3 Hz, 1H), 7.78 (d, J=11.0 Hz, 1H), 7.28-7.43 (m, 5H), 4.60 (s, 2H), 4.57 (s, 2H), 3.74 (q, J=7.2 Hz, 2H), 1.23 (t, J=7.2 Hz, 3H) ppm; $^{19}$F NMR (376 MHz, DMSO-$d_6$) δ −119.91 (s, 1F) ppm.

Step D. 5-((Benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one. To a mixture of 3-methylbuta-1,2-dien-1-yl acetate (Intermediate 12, 280 mg, 2.2 mmol), 4-(3-((benzyloxy)methyl)-4-ethyl-5-oxo-4,5-dihydro-1H-1,2,4-triazol-1-yl)-5-fluoro-2-iodobenzoic acid (1.1 g, 2.2 mmol) and Cy$_2$NMe (867 mg, 4.4 mmol) in DMF (7 mL) was added Catacxium A Pd G2 (74.2 mg, 0.11 mmol) under nitrogen. The reaction mixture was stirred under nitrogen at 90° C. for overnight. The mixture was then cooled to room temperature, diluted with EtOAc and washed with brine. The organic layer was separated and the aqueous layer was combined and extracted with EtOAc. The combined organic layer was dried over Na$_2$SO$_4$, filtered and concentrated. The residue was purified by silica column chromatography (gradient elution: 0-80% EtOAc in petroleum ether) to give the title compound as yellow solid (240 mg, yield: 25%). ESI-MS: mass calcd. for $C_{24}H_{22}FN_3O_4$, 435.2; m/z 436.2 [M+H]$^+$. $^1$H NMR (400 MHz, CDCl$_3$) δ 8.15 (d, J=10.5 Hz, 1H), 7.86 (d, J=6.8 Hz, 1H), 7.30-7.45 (m, 5H), 7.19 (s, 1H), 5.37-5.39 (m, 1H), 5.18 (s, 1H), 4.62 (s, 2H), 4.53 (s, 2H), 3.87 (q, J=7.1 Hz, 2H), 2.11 (s, 3H), 1.37 (t, J=7.2 Hz, 3H) ppm;

Intermediate 4: 5-((Benzyloxy)methyl)-4-ethyl-2-(7-fluoro-4-isopropyl-1-oxo-1H-isochromen-6-yl)-2,4-dihydro-3H-1,2,4-triazol-3-one

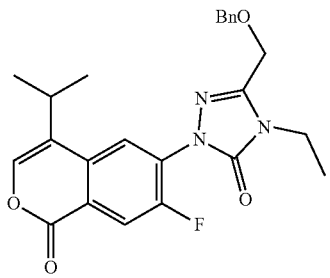 [SMILES: CCn1c(COCc2ccccc2)nn(-c2cc3c(C(C)C)coc(=O)c3cc2F)c1=O]

Method I:
Step A. 3-Methylbut-2-en-1-yl 4,5-difluoro-2-iodobenzoate. To the mixture of 4,5-difluoro-2-iodobenzoic acid (1.4 g, 4.9 mmol) and $Cs_2CO_3$ (4.8 g, 14.8 mmol) in anhydrous DMF (20 mL) was added 1-bromo-3-methyl-2-butene (1.5 g, 9.9 mmol). The reaction mixture was stirred at room temperature for 18 h. The mixture was diluted with water, and the mixture was extracted with DCM and EtOAc. The combined organic extract was dried over $Na_2SO_4$, filtered and concentrated. The residue was purified by flash chromatography ($SiO_2$, gradient elution: 10-20% EtOAc in heptane) to give the desired product as a colorless oil (1.6 g, yield: 92%). $^1$H NMR (400 MHz, $CDCl_3$) δ 7.80 (dd, J=7.58, 9.54 Hz, 1H), 7.73 (dd, J=7.83, 10.76 Hz, 1H), 5.42-5.52 (m, 1H), 4.82 (d, J=7.34 Hz, 2H), 1.80 (s, 3H), 1.78 (s, 3H) ppm.

Step B. 3-Methylbut-2-en-1-yl 4-(3-((benzyloxy)methyl)-4-ethyl-5-oxo-4,5-dihydro-1H-1,2,4-triazol-1-yl)-5-fluoro-2-iodobenzoate. To a mixture of 3-methylbut-2-en-1-yl 4,5-difluoro-2-iodobenzoate (1.6 g, 4.5 mmol), 3-((benzyloxy)methyl)-4-ethyl-1H-1,2,4-triazol-5(4H)-one (Intermediate 1, 2.1 g, 9.1 mmol) in anhydrous DMF (25 mL) was added $Cs_2CO_3$ (2.9 g, 9.1 mmol). The reaction mixture was heated under nitrogen at 85° C. for 1 h, then cooled to room temperature. The mixture was diluted with water, and the mixture was extracted with DCM and EtOAc. The combined organic extract was dried over $Na_2SO_4$, filtered and concentrated. The residue was purified by flash chromatography ($SiO_2$, gradient elution: 20-50% EtOAc in heptane) to give the title compound as a white solid (2.4 g, yield: 93%). LCMS (ES-API): mass calcd. for $C_{24}H_{25}FIN_3O_4$, 565.1; m/z found, 566.2 [M+H]$^+$. $^1$H NMR (400 MHz, $CDCl_3$) δ 8.21 (d, J=6.85 Hz, 1H), 7.73 (d, J=11.25 Hz, 1H), 7.29-7.44 (m, 5H), 5.41-5.53 (m, 1H), 4.84 (d, J=7.34 Hz, 2H), 4.60 (s, 2H), 4.50 (s, 2H), 3.84 (q, J=7.22 Hz, 2H), 1.80 (s, 3H), 1.78 (d, J=0.98 Hz, 3H), 1.34 (t, J=7.22 Hz, 3H) ppm.

Step C. 5-((Benzyloxy)methyl)-4-ethyl-2-(7-fluoro-4-isopropyl-1-oxo-1H-isochromen-6-yl)-2,4-dihydro-3H-1,2,4-triazol-3-one. To a mixture of 3-methylbut-2-en-1-yl 4-(3-((benzyloxy)methyl)-4-ethyl-5-oxo-4,5-dihydro-1H-1,2,4-triazol-1-yl)-5-fluoro-2-iodobenzoate (4 g, 6.86 mmol, 1 eq) in toluene (200 mL) was added $(tBu_3P)PdG_2$ (351 mg, 0.69 mmol, 0.1 eq), N-cyclohexyl-N-methyl-cyclohexanamine (1.60 mL, 7.54 mmol, 1.1 eq) respectively. The reaction mixture was degassed with nitrogen for three times, and then heated under nitrogen atmosphere at 80° C. for 18 h. LCMS analysis showed ~18% of starting material remained. The mixture was cooled to 15° C., and additional N-cyclohexyl-N-methyl-cyclohexanamine (0.72 mL, 3.43 mmol, 0.5 eq) and $tBu_3PPdG_2$ (176 mg, 0.34 mmol, 0.05 eq) were added. The reaction mixture was degassed with nitrogen, and then heated under nitrogen atmosphere at 80° C. for 16 h. The mixture was concentrated under reduced pressure, then diluted with $H_2O$ (200 mL), and extracted with EtOAc (150 mL×3). The combined organic layers were washed with brine (100 mL×2), dried over anhydrous $Na_2SO_4$, filtered, and concentrated under reduced pressure. The residue was purified by flash chromatography ($SiO_2$, Petroleum ether/Ethyl acetate=5/1 to 3/1) to give the title compound as a yellow oil (1.1 g, yield: 35%). ESI-MS: mass calcd. for $C_{24}H_{24}FN_3O_4$, 437.2; m/z found, 438.5 [M+H]$^+$. $^1$H NMR (400 MHz, $CDCl_3$) δ 8.16 (d, J=6.6 Hz, 1H), 7.96 (d, J=6.6 Hz, 1H), 7.42-7.34 (m, 5H), 7.13 (s, 1H), 4.63 (s, 2H), 4.54 (s, 2H), 3.88 (dd, J=7.2, 14.4 Hz, 2H), 3.13-3.06 (m, 1H), 1.38 (t, J=7.2 Hz, 3H), 1.32 (d, J=6.8 Hz, 6H) ppm.

Method II:
To a mixture of 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3, 5.9 g, 13.5 mmol) in THF (100 mL) at room temperature was added Wilkinson's Catalyst [$RhCl(PPh_3)_3$] (3.8 g, 4.1 mmol). The mixture was degassed and purged with hydrogen gas. The reaction mixture was stirred under an atmosphere of hydrogen (15 Psi) at room temperature for 12 h. The mixture was concentrated. The residue was purified by silica column chromatography (elution: 0-25% EtOAc in petroleum ether) to give the title compound as a yellow solid (1.5 g, yield: 77%). ESI-MS: mass calcd. for $C_{24}H_{24}FN_3O_4$, 437.2; m/z found 438.2 [M+H]$^+$. $^1$H NMR (400 MHz, DMSO-$d_6$) δ 8.10 (d, J=10.5 Hz, 1H), 8.01 (d, J=7.0 Hz, 1H), 7.46 (s, 1H), 7.26-7.42 (m, 5H), 4.61 (s, 2H), 4.59 (s, 2H), 3.77 (q, J=7.3 Hz, 2H), 3.08 (dt, J=13.4, 6.8 Hz, 1H), 1.22-1.28 (m, 9H) ppm; $^{19}$F NMR (376 MHz, DMSO-$d_6$) δ −118.29 (br s, 1F) ppm.

Intermediate 5: 4-(3-((Benzyloxy)methyl)-4-ethyl-5-oxo-4,5-dihydro-1H-1,2,4-triazol-1-yl)-5-fluoro-2-iodobenzoyl chloride

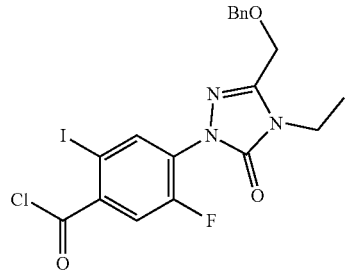 [SMILES: CCn1c(COCc2ccccc2)nn(-c2cc(I)c(C(=O)Cl)cc2F)c1=O]

Step A. tert-Butyl 4,5-difluoro-2-iodobenzoate. 4,5-Difluoro-2-iodobenzoic acid (3 g, 11 mmol) was dissolved in THF (30 mL), then di-tert-butyl dicarbonate (4.6 g, 21 mmol) was added followed by DMAP (645 mg, 5.3 mmol). The reaction mixture was stirred under nitrogen at 50° C. overnight, then cooled down to room temperature. The solvent was evaporated under reduced pressure. The residue was diluted with EtOAc then washed with brine. The organic layer was separated, dried with $Na_2SO_4$, filtered, and concentrated. The residue was purified by silica column chromatography (gradient elution: 0-5% EtOAc in petroleum ether) to give the title compound as a yellow oil (2.9 g, yield: 79%). $^1$H NMR (400 MHz, $CDCl_3$) δ 7.77 (dd, J=10.2, 7.9 Hz, 1H), 7.63 (dd, J=10.2, 7.9 Hz, 1H), 1.62 (s, 9H) ppm;

$^{19}$F NMR (376 MHz, CDCl$_3$) δ −131.55-131.13 (m, 1F), −136.97-136.65 (m, 1F) ppm.

Step B. tert-Butyl 4-(3-((benzyloxy)methyl)-4-ethyl-5-oxo-4,5-dihydro-1H-1,2,4-triazol-1-yl)-5-fluoro-2-iodobenzoate. A mixture of tert-butyl 4,5-difluoro-2-iodobenzoate (3.2 g, 9.4 mmol), 3-((benzyloxy)methyl)-4-ethyl-1H-1,2,4-triazol-5(4H)-one (Intermediate 1, 2.6 g, 11.2 mmol) and Cs$_2$CO$_3$ (6.1 g, 18.7 mmol) in anhydrous DMF (30 mL) was stirred under nitrogen at 75° C. for 1 h, then cooled to room temperature. The mixture was filtered through a pad of Celite®, and the pad was washed with EtOAc. The filtrate was combined, washed with brine, and concentrated. The residue was purified by silica column chromatography (gradient elution: 0-40% EtOAc in petroleum ether) to give the title compound as a colorless amorphous solid (5 g, yield: 96%).

ESI-MS: mass calcd. for C$_{23}$H$_{25}$FIN$_3$O$_4$, 553.1; m/z found, 554.1 [M+H]$^+$. $^1$H NMR (400 MHz, CDCl$_3$) δ 8.16 (d, J=7.1 Hz, 1H), 7.62 (d, J=10.8 Hz, 1H), 7.29-7.45 (m, 5H), 4.61 (s, 2H), 4.50 (s, 2H), 3.84 (q, J=7.2 Hz, 2H), 1.63 (s, 9H), 1.35 (t, J=7.2 Hz, 3H) ppm; $^{19}$F NMR (376 MHz, CDCl$_3$) δ −119.09 (dd, J=10.6, 7.0 Hz, 1F) ppm.

Step C. 4-(3-((Benzyloxy)methyl)-4-ethyl-5-oxo-4,5-dihydro-1H-1,2,4-triazol-1-yl)-5-fluoro-2-iodobenzoic acid. To a solution of tert-butyl 4-(3-((benzyloxy)methyl)-4-ethyl-5-oxo-4,5-dihydro-1H-1,2,4-triazol-1-yl)-5-fluoro-2-iodobenzoate (5 g, 9 mmol) in DCM (50 mL) was slowly added TFA (10 mL). The reaction mixture was stirred at room temperature overnight. The reaction mixture was concentrated under vacuum. The obtained residue was triturated with petroleum ether at room temperature for 30 min. The mixture was filtered and the solid was rinsed with petroleum ether. The precipitate was collected and dried in vacuo to give the title compound as a white solid (4.1 g, yield: 91%).

ESI-MS: mass calcd. for C$_{19}$H$_{17}$FIN$_3$O$_4$, 497.0; m/z found, 498.0 [M+H]$^+$. $^1$H NMR (400 MHz, DMSO-d$_6$) δ 8.16 (d, J=7.3 Hz, 1H), 7.78 (d, J=11.0 Hz, 1H), 7.28-7.43 (m, 5H), 4.60 (s, 2H), 4.57 (s, 2H), 3.74 (q, J=7.2 Hz, 2H), 1.23 (t, J=7.2 Hz, 3H) ppm; $^{19}$F NMR (376 MHz, DMSO-d$_6$) δ −119.91 (s, 1F) ppm.

Step D. 4-(3-((Benzyloxy)methyl)-4-ethyl-5-oxo-4,5-dihydro-1H-1,2,4-triazol-1-yl)-5-fluoro-2-iodobenzoyl chloride. A solution of 4-(3-((benzyloxy)methyl)-4-ethyl-5-oxo-4,5-dihydro-1H-1,2,4-triazol-1-yl)-5-fluoro-2-iodobenzoic acid (3.5 g, 7 mmol) in SOCl$_2$ (14 mL) was heated at reflux for 15 min. The reaction mixture was cooled to room temperature and concentrated. To the residue was added anhydrous toluene, then the mixture was evaporated to give the crude product as a yellow gum (3.6 g), which was directly used for the next step without further purification.

Intermediate 6: 2-Chloro-6-fluoro-N-(3-methylpent-2-en-1-yl)aniline

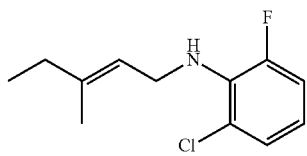

Step A. Ethyl 3-methylpent-2-enoate. To a solution of 2-butanone (52 g, 717.6 mmol) and (carbethoxymethylene) triphenylphosphorane (50 g, 143.5 mmol) in toluene (65 mL) was added benzoic acid (3.5 g, 28.7 mmol). The reaction mixture was heated at reflux for 16 h. The mixture was diluted with petroleum ether and filtered through a short pad of silica gel. The silica gel was washed with hexane. The filtrate was concentrated under reduced pressure at 0-2° C. The residue was purified by silica column chromatography (elution: 0-10% EtOAc in petroleum ether) to give the title compound as a colorless liquid (23.3 g crude). $^1$H NMR (400 MHz, CDCl$_3$) δ 5.58-5.69 (m, 1H), 4.13 (qd, J=7.1, 4.9 Hz, 2H), 2.62 (q, J=7.5 Hz, 1H), 2.09-2.20 (m, 3H), 1.86 (d, J=1.2 Hz, 1H), 1.24-1.28 (m, 3H), 1.01-1.09 (m, 3H) ppm.

Step B. 3-Methylpent-2-en-1-ol. To a toluene solution (1 M) of DIBAL-H (118 mL, 118 mmol) at −78° C. was added a toluene solution (40 mL) of ethyl 3-methylpent-2-enoate (20 g crude) dropwise under nitrogen. The reaction mixture was stirred at −78° C. for 2 h. The mixture was warmed to room temperature and slowly poured into saturated aqueous potassium sodium tartrate solution at 0° C. The mixture was stirred for 2 h and filtered through a short pad of Celite®. The pad was washed with DCM/EtOAc (v/v, 3/1), and the filtrate was extracted with DCM. The organic extract was separated, dried over Na$_2$SO$_4$, filtered and concentrated. The residue was purified by silica column chromatography (elution: 0-100% DCM in petroleum ether, then 0-30% EtOAc in DCM) to give the title compound as a colorless liquid (7 g, yield of two steps: 57%). $^1$H NMR (400 MHz, CDCl$_3$) δ 5.35-5.46 (m, 1H), 4.11-4.21 (m, 2H), 2.02-2.13 (m, 2H), 1.67-1.76 (m, 3H), 0.98-1.06 (m, 3H) ppm.

Step C. 3-Methylpent-2-enal. To a solution of 3-methylpent-2-en-1-ol (2 g, 20.0 mmol) in DCM (20 mL) was added Dess-martin periodinane (10 g, 24.0 mmol). The reaction mixture was stirred at room temperature for 1 h. The mixture was filtered through a short pad of Celite®. The pad was washed with DCM. The combined filtrate was washed with saturated aqueous NaHCO$_3$ solution. The organic layer was separated, dried over Na$_2$SO$_4$, filtered and concentrated under reduced pressure at 0-2° C. The crude was purified by silica column chromatography (elution: DCM) to give the title compound as a colorless liquid (1.5 g, yield: 77%). $^1$H NMR (400 MHz, CDCl$_3$) δ 9.91-10.04 (m, 1H), 5.78-5.90 (m, 1H), 2.58 (q, J=7.6 Hz, 1H), 2.23 (d, J=7.3 Hz, 1H), 2.16 (s, 2H), 1.96 (d, J=1.1 Hz, 1H), 1.16 (t, J=7.6 Hz, 1H), 1.09 (t, J=7.4 Hz, 2H) ppm.

Step D. N-(2-Chloro-6-fluorophenyl)-3-methylpent-2-en-1-imine. To a mixture of 2-chloro-6-fluoroaniline (1.2 g, 8.2 mmol) and 3-methylpent-2-enal (0.97 g, 9.9 mmol) in DCM (18 mL) under nitrogen at 0° C. was added triethylamine (4.6 mL, 33 mmol), followed by the addition of a DCM solution (1 M) of TiCl$_4$ (5 mL, 5 mmol) dropwise. The resulting mixture was stirred at 0° C. for 1 h, then warmed to room temperature and stirred for 4 h. The mixture was poured into saturated aqueous NH$_4$Cl solution. The mixture became cloudy and filtered through a pad of Celite®. The pad was washed with EtOAc. The combined filtrate was diluted with DCM and water. The organic layer was separated, and aqueous layer was extracted with DCM. The combined organic layers were washed with brine, dried over Na$_2$SO$_4$, filtered and concentrated. The residue product was purified by silica gel column chromatography (gradient elution: 0-5% DCM in petroleum ether) to give the title compound as a pale yellow oil (1.3 g, yield: 70%).

Step E. 2-Chloro-6-fluoro-N-(3-methylpent-2-en-1-yl)aniline. To a solution of N-(2-chloro-6-fluorophenyl)-3-methylpent-2-en-1-imine (1.3 g, 5.76 mmol) in MeOH (20 mL) was added NaBH$_4$ (218 mg, 5.8 mmol), and after 1 h, another batch of NaBH$_4$ (218 mg, 5.8 mmol) was added. A total of NaBH$_4$ (1.1 g, 29 mmol) was added. The reaction mixture was stirred at room temperature overnight. The mixture was concentrated, and then diluted with water and extracted with EtOAc. The organic layer was separated, washed with brine, dried over Na$_2$SO$_4$, filtered and concentrated. The residue was purified by combi flash column chromatography over silica gel (eluent: 0-5% DCM in petroleum ether) to give the title compound as a yellow oil (430 mg, yield: 33%). $^1$H NMR (400 MHz, CDCl$_3$) δ 6.95-7.02 (m, 1H), 6.84 (ddd, J=12.2, 8.3, 1.3 Hz, 1H), 6.52-6.63 (m, 1H), 5.17-5.28 (m, 1H), 3.85 (d, J=5.6 Hz, 2H), 3.73 (s, 1H), 1.91-2.07 (m, 2H), 1.58-1.68 (m, 3H), 0.89-0.96 (m, 3H)

Intermediate 7: 5-Chloro-3-methyl-1-(tetrahydro-2H-pyran-2-yl)-1H-pyrazol-4-amine

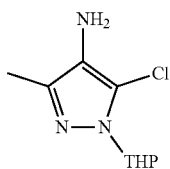

Step A. 5-Chloro-3-methyl-4-nitro-1-(tetrahydro-2H-pyran-2-yl)-1H-pyrazole. To a solution of 3-methyl-4-nitropyrazole (2 g, 15.7 mmol) in EtOAc (20 mL) was added DHP (2 g, 23.6 mmol) and TsOH·H$_2$O (150 mg, 0.79 mmol) at room temperature. The mixture was stirred at room temperature for overnight. Et$_3$N (0.4 mL) was added and the mixture was washed with brine. Then the organic layer was separated, dried over anhydrous Na$_2$SO$_4$, filtered and concentrated. The residue was dissolved in THF (45 mL) and the temperature was lowered to −78° C. A THF (1 M) solution of LiHMDS (10.6 mL, 13.8 mmol) was added to the mixture under nitrogen. After 45 minutes at −78° C., the solution of hexachloroethane (8.9 g, 37.8 mmol) in THF (20 mL) was added dropwise. The reaction mixture was warmed to room temperature and stirred for overnight. The mixture was poured into saturated aqueous NH$_4$Cl solution and extracted with EtOAc. The organic phase was separated, washed with brine, dried over anhydrous Na$_2$SO$_4$, filtered and concentrated. The residue was purified by silica column chromatography (gradient elution: 0-40% EtOAc in petroleum ether) to give the title compound as white solid (1.8 g, yield: 58%). $^1$H NMR (400 MHz, CDCl$_3$) δ 5.52 (dd, J=10.0, 2.7 Hz, 1H), 4.07-4.15 (m, 1H), 3.70 (td, J=11.3, 2.8 Hz, 1H), 2.57 (s, 3H), 2.37-2.47 (m, 1H), 2.11-2.19 (m, 1H), 1.86-1.90 (m, 1H), 1.72-1.75 (m, 1H), 1.64 (d, J=2.0 Hz, 1H), 1.53 (d, J=6.6 Hz, 1H) ppm.

Step B. 5-Chloro-3-methyl-1-(tetrahydro-2H-pyran-2-yl)-1H-pyrazol-4-amine. To a mixture of 5-chloro-3-methyl-4-nitro-1-(tetrahydro-2H-pyran-2-yl)-1H-pyrazole (100 mg, 0.4 mmol) in MeOH/THF/H$_2$O (v/v/v, 1/1/1, 3 mL) was added iron powder (114 mg, 2.0 mmol) and NH$_4$Cl (109 mg, 2.0 mmol). The mixture was stirred at 70° C. for 1.5 h. The mixture was cooled to room temperature and filtered through a pad of Celite®. The pad was washed with EtOAc. The combined filtrate was washed with saturated aqueous NaHCO$_3$ solution. The organic layer was separated, and the aqueous layer was extracted with EtOAc. The combined organic extract was washed with brine, dried over anhydrous Na$_2$SO$_4$, filtered and concentrated. The residue was purified by silica column chromatography (gradient elution: 0-50% EtOAc in petroleum ether) to give the title compound as a yellow oil (70 mg, yield: 79%). ESI-MS: mass calcd. for C$_9$H$_{14}$ClN$_3$O, 215.1; m/z found, 216.1 [M+H]$^+$.

Intermediate 8: 3-(2-((tert-Butyldiphenylsilyl)oxy)ethoxy)-2-chloroaniline

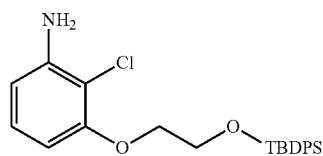

Step A. tert-Butyl(2-(2-chloro-3-nitrophenoxy)ethoxy)diphenylsilane. To a mixture of 2-chloro-3-nitrophenol (200 mg, 1.2 mmol), 2-((tert-butyldiphenylsilyl)oxy)ethan-1-ol (554 mg, 1.8 mmol) and PPh$_3$ (453 mg, 1.7 mmol) in THF (10 mL) was added DEAD (281 mg, 161 mmol) at 0° C. under nitrogen. The mixture was warmed to room temperature and stirred at room temperature for 12 h. Saturated aqueous NH$_4$Cl solution was added, and the mixture was extracted with EtOAc. The organic was separated, washed with brine, dried over anhydrous Na$_2$SO$_4$, filtered and concentrated. The residue was purified by silica column chromatography (gradient elution: 0-10% EtOAc in petroleum ether) to give the title compound as a yellow oil (240 mg, yield: 46%). $^1$H NMR (400 MHz, CDCl$_3$) δ 7.72 (dd, J=7.8, 1.5 Hz, 4H), 7.35-7.49 (m, 7H), 7.30 (t, J=8.2 Hz, 1H), 7.12 (dd, J=8.3, 1.2 Hz, 1H), 4.20-4.25 (m, 2H), 4.06 (t, J=4.9 Hz, 2H), 1.06 (s, 9H) ppm Step B. 3-(2-((tert-Butyldiphenylsilyl)oxy)ethoxy)-2-chloroaniline. To a mixture of tert-butyl(2-(2-chloro-3-nitrophenoxy)ethoxy)diphenylsilane (220 mg, 0.5 mmol), NH$_4$Cl (258 mg, 4.8 mmol) in THF (3 mL), MeOH (3 mL) and H$_2$O (3 mL) was added iron powder (269 mg, 4.8 mmol). The reaction mixture was stirred at 70° C. for 2 h. The mixture was cooled to room temperature, diluted with EtOAc, and filtered through a pad of Celite®. The Celite® was washed with EtOAc. The combined filtrate was washed with brine, dried over Na$_2$SO$_4$, filtered and concentrated. The residue was purified by silica column chromatography (gradient elution: 0-11% EtOAc in petroleum ether) to give the title compound as a yellow solid (192 mg, yield: 92%). ESI-MS: mass calcd. for C$_{24}$H$_{28}$ClNO$_2$Si, 425.2; m/z found, 426.1 [M+H]$^+$. $^1$H NMR (400 MHz, CDCl$_3$) δ 7.75 (dd, J=7.9, 1.6 Hz, 4H), 7.35-7.48 (m, 6H), 6.97 (t, J=8.1 Hz, 1H), 6.42 (dd, J=8.2, 1.1 Hz, 1H), 6.33 (dd, J=8.2, 1.1 Hz, 1H), 4.13-4.17 (m, 2H), 4.07-4.13 (m, 2H), 4.01-4.06 (m, 2H), 1.06 (s, 9H) ppm.

Intermediate 9: 5-((Benzyloxy)methyl)-4-ethyl-2-(7-methyl-1-oxo-4-(prop-1-en-2-yl)-1H-isochromen-6-yl)-2,4-dihydro-3H-1,2,4-triazol-3-one

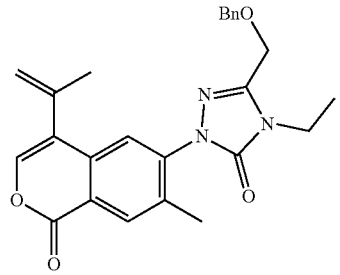 [SMILES: C=C(C)c1coc(=O)c2cc(C)c(-n3nc(COCc4ccccc4)n(CC)c3=O)cc12]

Step A. tert-Butyl 2-bromo-4-fluoro-5-methylbenzoate. To a solution of 2-bromo-4-fluoro-5-methylbenzoic acid (1 g, 4.3 mmol) in THF (10 mL) was added (Boc)$_2$O (1.9 g, 8.6 mmol), followed by the addition of DMAP (262 mg, 2.1 mmol). The reaction mixture turned orange and was stirred under nitrogen at 50° C. for overnight. The mixture was cooled to room temperature, diluted with EtOAc, and then washed with brine. The organic layer was separated, dried over Na$_2$SO$_4$, filtered and concentrated. The residue was purified by silica column chromatography (elution: 0-3% EtOAc in petroleum ether) to give the title compound as colorless oil (900 mg, yield: 72%). $^1$H NMR (400 MHz, CDCl$_3$) δ 7.57 (d, J=8.1 Hz, 1H), 7.24 (d, J=4.6 Hz, 1H), 2.22 (d, J=1.5 Hz, 3H), 1.58 (s, 9H) ppm.

Step B. tert-Butyl 4-(3-((benzyloxy)methyl)-4-ethyl-5-oxo-4,5-dihydro-1H-1,2,4-triazol-1-yl)-2-bromo-5-methylbenzoate. A mixture of tert-butyl 2-bromo-4-fluoro-5-methylbenzoate. (750 mg, 2.6 mmol), 5-((benzyloxy)methyl)-4-ethyl-2,4-dihydro-3H-1,2,4-triazol-3-one (800 mg, 3.4 mmol) and Cs$_2$CO$_3$ (1.7 g, 5.2 mmol) in DMF (8 mL) was stirred at 90° C. for 16 h. The reaction was quenched by the addition of aqueous saturated NH$_4$Cl solution. The mixture was extracted with EtOAc. The organic layer was separated, washed with brine, dried over Na$_2$SO$_4$, filtered and concentrated. The residue was purified by combi-flash chromatography (SiO$_2$, eluent: 0-22% EtOAc in petroleum ether) to give the title compound as colorless gum (1 g, yield: 71%). ESI-MS: mass calcd. for C$_{24}$H$_{28}$BrN$_3$O$_4$, 501.1; m/z found, 502.1 [M+H]$^+$. $^1$H NMR (400 MHz, CDCl$_3$) δ 7.64 (d, J=6.1 Hz, 2H), 7.33-7.43 (m, 5H), 4.61 (s, 2H), 4.50 (s, 2H), 3.85 (q, J=7.3 Hz, 2H), 2.31 (s, 3H), 1.62 (s, 9H), 1.36 (t, J=7.2 Hz, 3H) ppm.

Step C. 4-(3-((Benzyloxy)methyl)-4-ethyl-5-oxo-4,5-dihydro-1H-1,2,4-triazol-1-yl)-2-bromo-5-methylbenzoic acid. To a mixture of tert-butyl 4-(3-((benzyloxy)methyl)-4-ethyl-5-oxo-4,5-dihydro-1H-1,2,4-triazol-1-yl)-2-bromo-5-methylbenzoate (500 mg, 0.90 mmol) in DCM (5 mL) was added TFA (1 mL). The mixture was stirred at room temperature for 12 h. The mixture was concentrated. The residue was dissolved with DCM, and petroleum ether was added slowly. The mixture was stirred at room temperature for 30 min. The mixture was filtered, and the precipitate was rinsed with petroleum ether. The solid was collected and dried in vacuo to give the title compound as a white solid (360 mg, yield: 86%). ESI-MS: mass calcd. for C$_{20}$H$_{20}$BrN$_3$O$_4$, 445.1; m/z found, 446.0 [M+H]$^+$. $^1$H NMR (400 MHz, DMSO-d$_6$) δ 7.77 (s, 1H), 7.70 (s, 1H), 7.29-7.41 (m, 5H), 4.59 (s, 2H), 4.56 (s, 2H), 3.74 (q, J=7.0 Hz, 2H), 2.24 (s, 3H), 1.23 (t, J=7.2 Hz, 3H) ppm.

Step D. 5-((Benzyloxy)methyl)-4-ethyl-2-(7-methyl-1-oxo-4-(prop-1-en-2-yl)-1H-isochromen-6-yl)-2,4-dihydro-3H-1,2,4-triazol-3-one. To a mixture of 4-(3-((benzyloxy)methyl)-4-ethyl-5-oxo-4,5-dihydro-1H-1,2,4-triazol-1-yl)-2-bromo-5-methylbenzoic acid (560 mg, 1.26 mmol), 3-methylbuta-1,2-dien-1-yl acetate (Intermediate 12, 1.58 g, 12.5 mmol), AcOK (369 mg, 3.76 mmol) and TBAB (809 mg, 2.51 mmol) in DMF (3.9 mL) under nitrogen was added Pd(OAc)$_2$ (141 mg, 0.63 mmol). The reaction mixture was stirred under nitrogen at 90° C. for overnight. The mixture was cooled to room temperature, diluted with EtOAc, and washed with brine. The organic layer was separated, and the aqueous layer was extracted with EtOAc. The combined organic layers were combined, dried over Na$_2$SO$_4$, filtered, and concentrated. The residue was purified by silica column chromatography (gradient elution: 0-70% EtOAc in petroleum ether) to give the title compound as a yellow solid (410 mg, yield: 73%). ESI-MS: mass calcd. for C$_{25}$H$_{25}$N$_3$O$_4$, 431.2; m/z found, 432.1 [M+H]$^+$. $^1$H NMR (400 MHz, CDCl$_3$) δ 8.28 (s, 1H), 7.59 (s, 1H), 7.31-7.46 (m, 5H), 7.17 (s, 1H), 5.30-5.37 (m, 1H), 5.15 (s, 1H), 4.63 (s, 2H), 4.52 (s, 2H), 3.87 (q, J=7.1 Hz, 2H), 2.46 (s, 3H), 2.10 (s, 3H), 1.38 (t, J=7.2 Hz, 3H) ppm.

Intermediate 10: Isopropyl 6-(3-((benzyloxy)methyl)-4-ethyl-5-oxo-4,5-dihydro-1H-1,2,4-triazol-1-yl)-2-chloro-5-fluoronicotinate

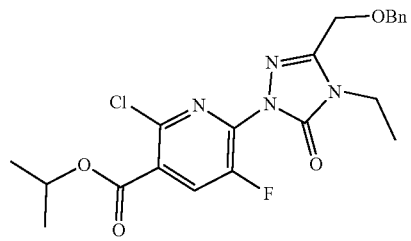 [SMILES: CCn1c(COCc2ccccc2)nn(-c2nc(Cl)c(C(=O)OC(C)C)cc2F)c1=O]

Step A. 2,6-Dichloro-5-fluoronicotinoyl chloride. To a solution of 2,6-dichloro-5-fluoronicotinic acid (20 g, 95 mmol) in THF (200 mL) was added (COCl)$_2$ (12.7 g, 10.0 mmol) and DMF (69.6 mg, 0.952 mmol) at 0° C. dropwise. The mixture was stirred at 0° C. for 30 min, then warmed to 25° C., and stirred for 1 h. The reaction mixture was concentrated under reduced pressure to afford desired product (21.7 g, crude) as a colorless oil, which was used without further purification.

Step B. Isopropyl 2,6-dichloro-5-fluoronicotinate. To a mixture of propan-2-ol (8.56 g, 142 mmol, 10.9 mL) and pyridine (9.02 g, 114 mmol) in THF (200 mL) was added a solution of 2,6-dichloro-5-fluoronicotinoyl chloride (21.7 g, 96.0 mmol) in THF (50 mL) at 0° C. The mixture was stirred at 25° C. for 1 h. The mixture was poured into water (300 mL). The aqueous phase was extracted with ethyl acetate (300 mL). The combined organic phase was dried with anhydrous Na$_2$SO$_4$, filtered and concentrated. The residue was purified by column chromatography (SiO$_2$, Petroleum ether/Ethyl acetate=1/1 to 10:1) to afford the title compound (21 g, 86.82% yield). MS (ESI): mass calcd. for C$_9$H$_8$Cl$_2$FNO$_2$, 250.1; m/z found, 252.0 [M+H]+. $^1$H NMR (400 MHz, CDCl$_3$) δ 7.97-7.95 (d, J=7.2 Hz, 1H), 5.32-5.25 (m, 1H), 1.58-1.39 (m, 6H) ppm.

Step C. Isopropyl 6-(3-((benzyloxy)methyl)-4-ethyl-5-oxo-4,5-dihydro-1H-1,2,4-triazol-1-yl)-2-chloro-5-fluoronicotinate. To a mixture of isopropyl 2,6-dichloro-5-fluoronicotinate (4 g, 15.87 mmol) in DMSO (40 mL) was added 3-((benzyloxy)methyl)-4-ethyl-1H-1,2,4-triazol-5(4H)-one (3.89 g, 16.66 mmol) and K$_2$CO$_3$ (3.29 g, 23.80 mmol). The mixture was stirred at 80° C. for 3 hr. LCMS showed the starting material was consumed and desired mass was detected. The mixture was diluted with H$_2$O (30 mL) and extracted with EtOAc (50 mL×3). The combined organic layers were washed with brine (100 mL), dried over Na$_2$SO$_4$, filtered and concentrated under reduced pressure. The residue was purified by column chromatography (SiO$_2$, Petroleum ether/Ethyl acetate=I/O to 1:1) to afford the title compound (5.7 g, 79.86% yield). MS (ESI): mass calcd. for C$_{21}$H$_{22}$ClFN$_4$O$_4$, 448.1; m/z found, 449.2 [M+H]+. $^1$H NMR (400 MHz, CDCl$_3$) δ 8.10 (d, J=8.8 Hz, 1H), 7.43-7.31 (m, 5H), 5.30 (td, J=6.3, 12.5 Hz, 1H), 4.61 (s, 2H), 4.54 (s, 2H), 3.85 (q, J=7.2 Hz, 2H), 1.41 (d, J=6.2 Hz, 6H), 1.37-1.31 (m, 3H) ppm.

Intermediate 11: 5-((Benzyloxy)methyl)-4-ethyl-2-(7-fluoro-3-hydroxy-4-isopropyl-1-oxoisochroman-6-yl)-2,4-dihydro-3H-1,2,4-triazol-3-one

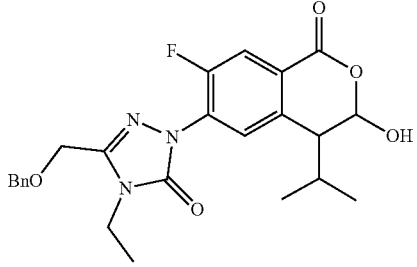 [SMILES: CCn1c(COCc2ccccc2)nn(-c2cc3c(cc2F)C(=O)OC(O)C3C(C)C)c1=O]

Step A. Methyl 4-(3-((benzyloxy)methyl)-4-ethyl-5-oxo-4,5-dihydro-1H-1,2,4-triazol-1-yl)-2-bromo-5-fluorobenzoate. To a flask charged with methyl 2-bromo-4,5-difluorobenzoate (100.0 g, 398 mmol), 5-((benzyloxy)methyl)-4-ethyl-2,4-dihydro-3H-1,2,4-triazol-3-one (Intermediate 1, 113.5 g, 508 mmol) and $K_2CO_3$ (100.0 g, 724 mmol) was added anhydrous DMF (1000 mL). The reaction mixture was heated under nitrogen at 50° C. for 16 h, and then additional 5-((benzyloxy)methyl)-4-ethyl-2,4-dihydro-3H-1,2,4-triazol-3-one (11 g, 51 mmol) was added. The reaction mixture continued to be stirred at 50° C. The mixture was cooled to room temperature and stirred for 10 min. Water (1000 mL) was added dropwise, and the mixture was stirred at room temperature for 2 h. The precipitate was collected by filtration and dried to give the crude product (190 g). The product was stirred in DMF (500 mL) for 30 min, then water (500 mL) was added. The mixture was stirred for 2 h. The precipitate was collected by filtration and dried to give the title compound (180 g, yield: 90%). $^1$H NMR (300 MHz, $CDCl_3$) δ 7.95 (d, J=6.7 Hz, 1H), 7.73 (d, J=10.7 Hz, 1H), 7.44-7.27 (m, 5H), 4.60 (s, 2H), 4.50 (s, 2H), 3.95 (s, 3H), 3.84 (q, J=7.2 Hz, 2H), 1.34 (t, J=7.2 Hz, 3H) ppm.

Step B. 5-((Benzyloxy)methyl)-4-ethyl-2-(7-fluoro-3-hydroxy-4-isopropyl-1-oxoisochroman-6-yl)-2,4-dihydro-3H-1,2,4-triazol-3-one. To a mixture of methyl 4-(3-((benzyloxy)methyl)-4-ethyl-5-oxo-4,5-dihydro-1H-1,2,4-triazol-1-yl)-2-bromo-5-fluorobenzoate (30 g, 65.9 mmol), Xantphos (4.02 g, 6.6 mmol), [Pd(allyl)Cl]$_2$ (1.38 g, 3.77 mmol), $Cs_2CO_3$ (42.6 g, 130 mmol) in dimethylacetamide (300 mL) was added 3-methylbutanal (41.4 mL, 386 mmol) slowly. The reaction mixture was heated under nitrogen at 80° C. for 22 h. The mixture was filtered and quenched with aqueous $NH_4Cl$ solution until "pH" turned 7-8. The mixture was extracted with ethyl acetate (2000 mL×2). The combined organic extract was concentrated. The residue was purified by column chromatography ($SiO_2$, gradient elution: 1-33% ethyl acetate in petroleum ether) to give the title compound as an oil (61.7 g, yield: 56%). $^1$H NMR (300 MHz, $CDCl_3$) δ 7.93 (d, J=10.4 Hz, 1H), 7.55 (d, J=6.7 Hz, 1H), 7.44-7.28 (m, 5H), 5.92 (s, 1H), 4.61 (s, 2H), 4.51 (s, 2H), 4.37 (br s, 1H), 3.85 (q, J=7.2 Hz, 2H), 2.80 (d, J=7.1 Hz, 1H), 1.92 (spt, J=6.8 Hz, 1H), 1.35 (t, J=7.2 Hz, 3H), 1.05 (d, J=6.8 Hz, 3H), 0.93 (d, J=6.8 Hz, 3H) ppm.

Intermediate 12: 3-Methylbuta-1,2-dien-1-yl acetate

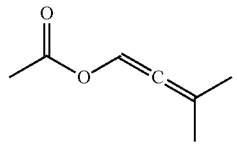

Step A. 2-Methylbut-3-yn-2-yl acetate. To a mixture of $Mg(ClO_4)_2$ (796 mg, 3.6 mmol) in acetic anhydride (38 g, 371 mmol) at 0° C. was added 2-methyl-3-butyn-2-ol (30 g, 357 mmol) dropwise. The reaction mixture was stirred at 0° C. for 10 min, then warmed to room temperature and stirred for overnight. The reaction mixture was diluted with DCM, then washed with aqueous saturated $NaHCO_3$ solution and aqueous saturated $Na_2CO_3$ solution. The organic layer was separated, dried over $Na_2SO_4$, filtered and concentrated at 0° C. The residue was purified by silica column chromatography (elution: DCM) to give the title compound as pale yellow oil (35.8 g, yield: 80%). $^1$H NMR (400 MHz, $CDCl_3$) δ 2.54 (s, 1H), 2.03 (s, 3H), 1.67 (s, 6H) ppm.

Step B. 3-Methylbuta-1,2-dien-1-yl acetate. To a solution of 2-methylbut-3-yn-2-yl acetate (2.5 g, 20 mmol) in DCM (20 mL) was added $AgBF_4$ (117 mg, 0.6 mmol) under nitrogen. The resulting colorless solution was stirred under nitrogen at 35° C. for 2 h until the mixture turned into a black solution. The mixture was washed with aqueous ammonia (10%). The organic layer was separated, and the aqueous layer was extracted with DCM. The combined organic layer was dried over $Na_2SO_4$, filtered and concentrated. The residue was purified by silica column chromatography (gradient elution: 0-3% EtOAc in petroleum ether) to give the title compound as yellow oil (650 mg, yield: 26%). $^1$H NMR (400 MHz, $CDCl_3$) δ 7.20 (dt, J=4.1, 2.0 Hz, 1H), 2.11 (s, 3H), 1.81 (d, J=2.0 Hz, 6H) ppm.

Example 2: 6-(4-Ethyl-3-(hydroxymethyl)-5-oxo-4,5-dihydro-1H-1,2,4-triazol-1-yl)-2-(3-fluorophenyl)-4-(prop-1-en-2-yl)isoquinolin-1(2H)-one

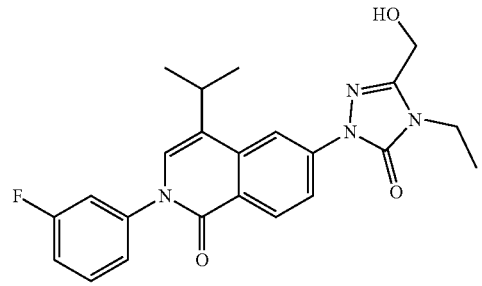 [SMILES: CCn1c(CO)nn(-c2ccc3c(=O)n(-c4cccc(F)c4)cc(C(C)C)c3c2)c1=O]

Step A. 6-Bromo-4-iodoisoquinolin-1(2H)-one. To a suspension of 6-bromo-2H-isoquinolin-1-one (2.9 g, 12.9 mmol) in anhydrous acetonitrile (ACN) (50 mL) was added N-iodosuccinimide (NIS) (4.4 g, 19.4 mmol). The reaction mixture was heated and stirred under nitrogen at 80° C. for 2 h, then cooled to 25° C. The mixture was filtered through a sintered funnel, and the precipitate was collected, washed with water, and dried in vacuo to afford the desired product (3.5 g, crude, 77%) as a brown solid, which was used crude in the next step without further purification. LCMS (ES-API): mass calcd. for $C_9H_5BrINO$, 348.9; m/z found, 349.8 $[M+H]^+$.

Step B. 6-Bromo-4-(prop-1-en-2-yl)isoquinolin-1(2H)-one. To a mixture of 6-bromo-4-iodoisoquinolin-1(2H)-one (0.7 g, 2 mmol) and $Cs_2CO_3$ (3.3 g, 10 mmol) in 1,4-dioxane (20 mL) and ethanol (20 mL) and water (10 mL) was added bis(triphenylphosphine)palladium(II) dichloride (0.7 g, 1 mmol) and isopropenylboronic acid pinacol ester (1.3 g, 4 mmol) respectively. The reaction mixture was degassed with nitrogen and then stirred at 25° C. for 24 h. The mixture was poured into water (50 mL). The aqueous phase was extracted with ethyl ether (100 mL) and ethyl acetate (EtOAc) (100 mL) sequentially. The combined organic extract was washed with brine, dried over anhydrous $Na_2SO_4$, filtered, and concentrated. The residue was purified by flash column chromatography ($SiO_2$, 10-70% ethyl acetate in heptane) to afford the desired product as a white solid (0.12 g, 23% yield). LCMS (ES-API): mass calcd. for $C_{12}H_{10}BrNO$, 263.0; m/z found, 264.0 $[M+H]^+$. $^1H$ NMR (400 MHz, $CDCl_3$) δ 11.15 (br s, 1H), 8.30 (d, J=8.42 Hz, 1H), 7.85 (d, J=1.59 Hz, 1H), 7.62 (br dd, J=1.59, 8.42 Hz, 1H), 7.06 (s, 1H), 5.37 (s, 1H), 5.09 (s, 1H), 2.11 (s, 3H) ppm.

Step C. 6-Bromo-2-(3-fluorophenyl)-4-(prop-1-en-2-yl)isoquinolin-1(2H)-one. To a mixture of 6-bromo-4-(prop-1-en-2-yl)isoquinolin-1(2H)-one (120 mg, 0.45 mmol) and 3-fluorophenylboronic acid (191 mg, 1.4 mmol) in dichloromethane (DCM) (20 mL) and triethylamine (3 mL) was added copper(II) acetate (82.5 mg, 0.45 mmol) and pyridine (0.11 mL, 1.36 mmol). The reaction mixture was stirred at 25° C. for 18 h. The mixture was filtered through a short pad of silica gel and the silica gel was washed with ethyl acetate (100 mL). The filtrate was concentrated. The residue was purified by flash column chromatography ($SiO_2$, 20-50% EtOAc in heptane) to afford the crude desired product as amorphous gum (118 mg, 72%). LCMS (ES-API): mass calcd. for $C_{18}H_{13}BrFNO$, 358.0; m/z found, 358.0 $[M]^+$.

Step D: 6-(3-(((tert-Butyldiphenylsilyl)oxy)methyl)-4-ethyl-5-oxo-4,5-dihydro-1H-1,2,4-triazol-1-yl)-2-(3-fluorophenyl)-4-(prop-1-en-2-yl)isoquinolin-1(2H)-one. To a mixture of 6-bromo-2-(3-fluorophenyl)-4-(prop-1-en-2-yl) isoquinolin-1(2H)-one (Example 1, product from Step C, 114 mg, 0.32 mmol) and $K_3PO_4$ (338 mg, 1.6 mmol) in anhydrous 1,4-dioxane (6 mL) was added 5-(((tert-butyldiphenylsilyl)oxy)methyl)-4-ethyl-2,4-dihydro-3H-1,2,4-triazol-3-one (Intermediate 2, 304 mg, 0.8 mmol), CuI (60 mg, 0.32 mmol), and trans-N,N'-dimethylcyclohexane-1,2-diamine (45 mg, 0.32 mmol), respectively. The mixture was slowly heated and stirred under nitrogen at 95° C. for 2 h, then cooled to 25° C. and quenched with addition of water. The mixture was extracted with ethyl acetate (50 mL×2). The combined organic extract was washed with brine, dried with anhydrous $Na_2SO_4$, filtered, and concentrated. The residue was purified by flash column chromatography (20-50% EtOAc in heptane) to afford the desired product as a white solid (125 mg, 60%). LCMS (ES-API): mass calcd. for $C_{39}H_{39}FN_4O_3Si$, 658.3; m/z found, 659.4 $[M+H]^+$.

Step E. 6-(4-Ethyl-3-(hydroxymethyl)-5-oxo-4,5-dihydro-1H-1,2,4-triazol-1-yl)-2-(3-fluorophenyl)-4-(prop-1-en-2-yl)isoquinolin-1(2H)-one. To a solution of 6-(3-(((tert-butyldiphenylsilyl)oxy)methyl)-4-ethyl-5-oxo-4,5-dihydro-1H-1, 2,4-triazol-1-yl)-2-(3-fluorophenyl)-4-(prop-1-en-2-yl) isoquinolin-1(2H)-one (92 mg, 0.14 mmol) in tetrahydrofuran (THF) (10 mL) was added a tetrahydrofuran (THF) solution (1 M) of tetrabutylammonium fluoride (0.14 mL, 0.14 mmol). The reaction mixture was stirred at 25° C. for 0.5 h. The mixture was diluted with $H_2O$ (15 mL) and extracted with ethyl acetate (50 mL×2). The combined organic extracts were washed with brine (20 mL), dried over $Na_2SO_4$, filtered, and concentrated. The residue was purified by flash column chromatography (30-100% EtOAc in heptane), then further purified by prep-HPLC ($C_{18}$ column, 10-90% gradient MeCN in water) to afford the title compound as a white solid (35 mg, yield 60%). LCMS (ES-API): mass calcd. for $C_{23}H_{21}FN_4O_3$, 420.2; m/z found, 421.2 $[M+H]^+$. $^1H$ NMR (400 MHz, DMSO-$d_6$) δ 8.40 (br s, 2H), 8.15 (br d, J=9.09 Hz, 1H), 7.55-7.59 (m, 1H), 7.49 (br d, J=9.60 Hz, 1H), 7.25-7.42 (m, 3H), 5.40 (br s, 1H), 5.17 (s, 1H), 4.53 (s, 2H), 3.81 (q, J=6.87 Hz, 2H), 2.14 (s, 3H), 1.29 (br t, J=6.87 Hz, 3H) ppm Example 2: 6-(4-Ethyl-3-(hydroxymethyl)-5-oxo-4, 5-dihydro-1H-1,2,4-triazol-1-yl)-2-(3-fluorophenyl)-4-isopropylisoquinolin-1(2H)-one

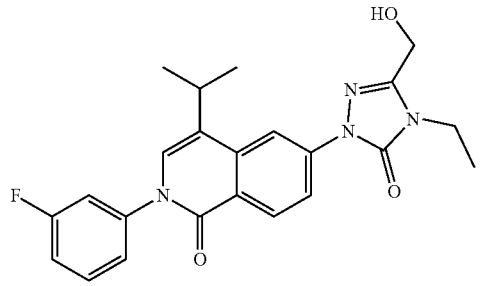 [SMILES: CCn1c(CO)nn(-c2ccc3c(=O)n(-c4cccc(F)c4)cc(C(C)C)c3c2)c1=O]

To a solution of 6-(4-ethyl-3-(hydroxymethyl)-5-oxo-4,5-dihydro-1H-1,2,4-triazol-1-yl)-2-(3-fluorophenyl)-4-(prop-1-en-2-yl)isoquinolin-1(2H)-one (35 mg, 0.08 mmol) in methanol (5 mL) was added Pd/C (18 mg, 10%). The mixture was degassed and purged with hydrogen gas for 3 times. The reaction mixture was then stirred under hydrogen atmosphere (15 psi) at 25° C. for 12 h. The mixture was filtered through a short pad of Celite®. The filtrate was concentrated. The residue was purified by prep-HPLC ($C_{18}$ column, 10-90% gradient ACN in water) to afford the title compound as a white solid (8 mg, yield 42%). LCMS (ES-API): mass calcd. for $C_{23}H_{23}FN_4O_3$, 422.2; m/z found, 423.1 $[M+H]^+$. $^1H$ NMR (400 MHz, DMSO-$d_6$) δ 8.51 (s, 1H), 8.41 (d, J=8.84 Hz, 1H), 8.13 (br d, J=8.84 Hz, 1H), 7.54-7.64 (m, 1H), 7.28-7.41 (m, 3H), 7.20 (s, 1H), 4.54 (s, 2H), 3.76-3.87 (m, 2H), 3.16-3.28 (m, 1H), 1.23-1.41 (m, 9H) ppm. Rac-6-(4-ethyl-3-(hydroxymethyl)-5-oxo-4,5-dihydro-1H-1,2,4-triazol-1-yl)-2-(3-fluorophenyl)-4-isopropyl-3,4-dihydroisoquinolin-1(2H)-one was also isolated as the other product: a white solid (15 mg, yield 42%). LCMS (ES-API): mass calcd. for $C_{23}H_{25}FN_4O_3$, 424.2; m/z found, 425.3 $[M+H]^+$. $^1H$ NMR (400 MHz, DMSO-$d_6$) δ 7.94-8.10 (m, 2H), 7.92 (s, 1H), 7.45-7.51 (m, 1H), 7.31 (br d, J=11.12 Hz, 1H), 7.26 (br d, J=8.08 Hz, 1H), 7.11 (br t, J=8.34 Hz, 1H), 5.82 (br s, 1H), 4.51 (s, 2H), 4.27 (br d, J=10.61 Hz, 1H), 3.59-3.98 (m, 3H), 1.92-2.16 (m, 1H), 1.28 (br t, J=6.82 Hz, 3H), 0.92 (br d, J=6.57 Hz, 3H), 0.88 (br d, J=6.57 Hz, 3H) ppm

Example 3: 2-(2-Chloro-6-fluorophenyl)-6-(4-ethyl-3-(hydroxymethyl)-5-oxo-4,5-dihydro-1H-1,2,4-triazol-1-yl)-4-isopropylisoquinolin-1(2H)-one

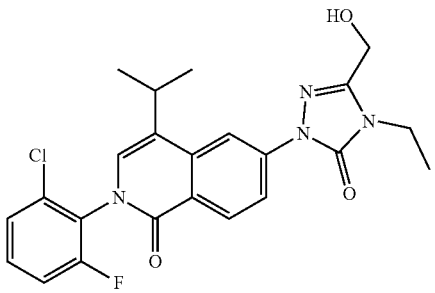 [SMILES: CCn1c(CO)nn(-c2ccc3c(=O)n(-c4c(F)cccc4Cl)cc(C(C)C)c3c2)c1=O]

Step A. N-(2-Chloro-6-fluorophenyl)-3-methylbut-2-en-1-imine. To a solution of 2-chloro-6-fluoroaniline (2.9 g, 20 mmol) and 3-methyl-2-butenal (2 g, 23.9 mmol) in anhydrous dichloromethane (50 mL) at 0° C. was added triethylamine (8.3 mL, 60 mmol), followed by the addition of TiCl$_4$ (3 g, 16 mmol) dropwise. The reaction mixture was stirred at 0° C. for 1 h, then warmed to 25° C. and stirred for 4 h. The mixture was filtered through a short pad of Celite®, and the filtrate was partitioned between dichloromethane and water. The organic layer was separated, and the aqueous layer was extracted with dichloromethane. The combined organic extract was dried over MgSO$_4$, filtered, and concentrated to give the crude desired product as a yellow oil (3.3 g, 78%), which was used crude in the next step without further purification. $^1$H NMR (400 MHz, CDCl$_3$) δ 8.36 (dd, J=2.20, 9.66 Hz, 1H), 7.20 (d, J=7.83 Hz, 1H), 6.94-7.09 (m, 2H), 6.32 (br d, J=9.66 Hz, 1H), 5.30 (s, 1H), 2.00 (s, 6H)

Step B. 2-Chloro-6-fluoro-N-(3-methylbut-2-en-1-yl)aniline. To a solution of crude N-(2-chloro-6-fluorophenyl)-3-methylbut-2-en-1-imine (3.3 g, 15.6 mmol) in methanol (25 mL) was added NaBH$_4$ (0.59 g, 15.6 mmol) at 25° C., and after 1 h interval, another batch of NaBH$_4$ (0.59 g, 15.6 mmol) was added. A total of three equivalents of NaBH$_4$ (1.8 g, 47 mmol) was added. The reaction mixture was stirred at 25° C. for 16 h. The reaction mixture was concentrated to dryness. The mixture was partitioned between ethyl acetate and water. The organic layer was separated, and the aqueous layer was extracted with ethyl acetate. The combined organic extract was dried over MgSO$_4$, filtered, and concentrated. The residue was purified by flash column chromatography (SiO$_2$, 5-25% EtOAc in heptane) to give the desired product as a yellow oil (yield, 1.9 g, 57%). $^1$H NMR (400 MHz, CDCl$_3$) δ 7.05 (br d, J=7.58 Hz, 1H), 6.83-6.97 (m, 1H), 6.55-6.73 (m, 1H), 5.32 (br s, 1H), 3.91 (br d, J=6.57 Hz, 2H), 3.82 (br s, 1H), 1.73 (s, 3H), 1.68 (s, 3H) ppm.

Step C. 4-Bromo-2-iodobenzoyl chloride. To a flask charged with 4-bromo-2-iodobenzoic acid (2.5 g, 7.7 mmol) was added SOCl$_2$ (7 mL). The mixture was heated at 80° C. for 15 min, then cooled to 25° C. and concentrated to afford the crude 4-bromo-2-iodobenzoyl chloride as an off white solid which was used in the next step without further purification.

Step D: 4-Bromo-N-(2-chloro-6-fluorophenyl)-2-iodo-N-(3-methylbut-2-en-1-yl)benzamide)-one. Crude 4-bromo-2-iodobenzoyl chloride was dissolved into dichloromethane (10 mL), and then added slowly dropwise to a pre-cooled dichloromethane solution (20 mL) of 2-chloro-6-fluoro-N-(3-methylbut-2-en-1-yl)aniline (1.1 g, 5.1 mmol) and triethylamine (2.1 mmol, 15 mmol) at 0° C., followed by the addition of a catalytic amount of 4-dimethylaminopyridine (DMAP) (6 mg, 0.05 mmol). The reaction mixture was warmed and stirred at 25° C. for 3 h. The reaction was quenched by the addition of aqueous saturated NaHCO$_3$ solution. The organic layer was separated, and the aqueous layer was extracted with ethyl acetate. The combined organic extract was washed with water, brine, dried over MgSO$_4$, filtered, and concentrated to afford the desired crude product as a brown oil (2.4 g, 89%). LCMS (ES-API): mass calcd. for C$_{18}$H$_{15}$BrClFINO, 520.9; m/z found, 522.0 [M+H]$^+$.

Step E. Racemic-6-bromo-2-(2-chloro-6-fluorophenyl)-4-(prop-1-en-2-yl)-3,4-dihydroisoquinolin-1(2H)-one and 6-bromo-2-(2-chloro-6-fluorophenyl)-4-isopropylisoquinolin-1(2H)-one. To a mixture of 4-bromo-N-(2-chloro-6-fluorophenyl)-2-iodo-N-(3-methylbut-2-en-1-yl)benzamide)-one (1.2 g, 2.3 mmol), tetrabutylammonium bromide (1.48 g, 4.6 mmol) and potassium acetate (0.68 g, 6.9 mmol) in anhydrous N,N-dimethylformamide (30 mL) was added palladium(II) acetate (0.26 g, 1.1 mmol) at 25° C. The reaction mixture was heated and stirred under nitrogen at 80° C. for 1.5 h, then cooled to 25° C. and water (100 mL) was added. The mixture was extracted with ethyl ether (100 mL) and ethyl acetate (100 mL). The combined organic extract was washed with brine, dried with anhydrous Na$_2$SO$_4$, filtered, and concentrated. The residue was purified by flash column chromatography (SiO$_2$, 30-60% EtOAc in heptane) to afford the two isomeric products as a mixture: a white solid (~3:1, 590 mg, 65%). The mixture was not further separated and used directly into the next step. LCMS (ES-API): mass calcd. for C$_{18}$H$_{14}$BrClFNO, 393.0; m/z found, 394.0 [M+H]$^+$.

Step F. Racemic-6-(3-(((tert-butyldiphenylsilyl)oxy)methyl)-4-ethyl-5-oxo-4,5-dihydro-1H-1,2,4-triazol-1-yl)-2-(2-chloro-6-fluorophenyl)-4-(prop-1-en-2-yl)-3,4-dihydroisoquinolin-1(2H)-one and 6-(3-(((tert-butyldiphenylsilyl)oxy)methyl)-4-ethyl-5-oxo-4,5-dihydro-1H-1,2,4-triazol-1-yl)-2-(2-chloro-6-fluorophenyl)-4-isopropylisoquinolin-1(2H)-one. To a mixture of racemic-6-bromo-2-(2-chloro-6-fluorophenyl)-4-(prop-1-en-2-yl)-3,4-dihydroisoquinolin-1(2H)-one and 6-bromo-2-(2-chloro-6-fluorophenyl)-4-isopropylisoquinolin-1(2H)-one (~3:1, 590 mg, 1.49 mmol) and K$_3$PO$_4$ (946 mg, 4.5 mmol) in anhydrous 1,4-dioxane (8 mL) was added 5-(((tert-butyldiphenylsilyl)oxy)methyl)-4-ethyl-2,4-dihydro-3H-1,2,4-triazol-3-one (Intermediate 2, 1063 mg, 2.8 mmol), CuI (212 mg, 1.1 mmol), and trans-N,N'-dimethylcyclohexane-1,2-diamine (159 mg, 1.1 mmol), respectively. The reaction mixture was slowly heated and stirred under nitrogen at 95° C. for 3 h, then cooled to 25° C. and quenched with addition of water (40 mL). The mixture was extracted with ethyl acetate (200 mL×2). The combined organic extract was washed with brine, dried with anhydrous Na$_2$SO$_4$, filtered, and concentrated. The residue was purified by flash column chromatography (SiO$_2$, 0-40% EtOAc in heptane) to afford two isomeric products as a mixture: a white foam (~4:1, 620 mg, 79%). LCMS (ES-API): mass calcd. for C$_{39}$H$_{40}$ClFN$_4$O$_3$Si, 694.3; m/z found, 695.4 [M+H]$^+$.

Step G. 2-(2-Chloro-6-fluorophenyl)-6-(4-ethyl-3-(hydroxymethyl)-5-oxo-4,5-dihydro-1H-1,2,4-triazol-1-yl)-4-isopropylisoquinolin-1(2H)-one. To a mixture of rac-6-(3-(((tert-butyldiphenylsilyl)oxy)methyl)-4-ethyl-5-oxo-4,5-dihydro-1H-1,2,4-triazol-1-yl)-2-(2-chloro-6-fluorophenyl)-4-(prop-1-en-2-yl)-3,4-dihydroisoquinolin-1(2H)-one and 6-(3-(((tert-butyldiphenylsilyl)oxy)methyl)-4-ethyl-5-oxo-4,5-dihydro-1H-1,2,4-triazol-1-yl)-2-(2-chloro-6-fluorophenyl)-4-isopropylisoquinolin-1(2H)-one (~4:1, 620 mg, 0.85 mmol) in tetrahydrofuran (THF) (10 mL) was added a tetrahydrofuran (THF) solution (1 M) of tetrabutylammonium fluoride (0.8 mL, 0.8 mmol). The reaction mixture was stirred at 25° C. for 0.5 h. The mixture was diluted with $H_2O$ and extracted with ethyl acetate. The combined organic extract washed with brine, dried over $Na_2SO_4$, filtered, and concentrated. The residue was purified by flash column chromatography (50-100% EtOAc in heptane), then further purified by prep-HPLC ($C_{18}$ column, 20-80% gradient MeCN in water) to afford 2-(2-chloro-6-fluorophenyl)-6-(4-ethyl-3-(hydroxymethyl)-5-oxo-4,5-dihydro-1H-1,2,4-triazol-1-yl)-4-isopropylisoquinolin-1(2H)-one as a white solid (36 mg, 11%). LCMS (ES-API): mass calcd. for $C_{23}H_{22}ClFN_4O_3$, 456.1; m/z found, 457.2[M+H]. $^1H$ NMR (400 MHz, $CDCl_3$) δ 8.61 (d, J=1.96 Hz, 1H), 8.56 (d, J=8.80 Hz, 1H), 8.10 (dd, J=1.96, 8.80 Hz, 1H), 7.34-7.46 (m, 1H), 7.16-7.33 (m, 2H), 6.77 (s, 1H), 4.70 (s, 2H), 3.85-3.97 (m, 2H), 3.27-3.44 (m, 1H), 1.40-1.46 (m, 3H), 1.30-1.40 (m, 6H) ppm. racemic-2-(2-chloro-6-fluorophenyl)-6-(4-ethyl-3-(hydroxymethyl)-5-oxo-4,5-dihydro-1H-1,2,4-triazol-1-yl)-4-(prop-1-en-2-yl)-3,4-dihydroisoquinolin-1(2H)-one was isolated as the second product: a white solid (280 mg, yield 85%). LCMS (ES-API): mass calcd. for $C_{23}H_{22}ClFN_4O_3$, 456.1; m/z found, 457.2[M+H]$^+$. $^1H$ NMR (400 MHz, $CDCl_3$) δ 8.24 (br d, J=9.09 Hz, 1H), 7.98 (br s, 2H), 7.27-7.35 (m, 2H), 7.06-7.16 (m, 1H), 5.15 (br d, J=4.04 Hz, 1H), 4.85, 4.75 (2 s, 1H), 4.68 (s, 2H), 3.97-4.07 (m, 1H), 3.84-3.95 (m, 4H), 1.87, 1.84 (2 s, 3H), 1.40 (br t, J=7.07 Hz, 3H) ppm.

Example 4: 6-(4-Ethyl-3-(hydroxymethyl)-5-oxo-4, 5-dihydro-1H-1,2,4-triazol-1-yl)-2-(3-fluorophenyl)-4-phenylisoquinolin-1(2H)-one

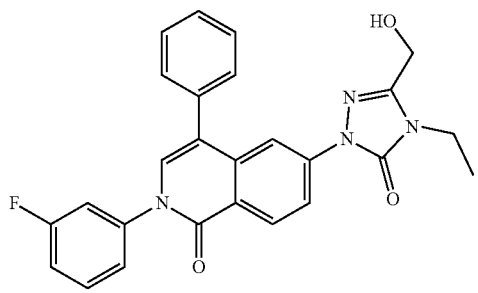 [SMILES: CCn1c(CO)nn(-c2ccc3c(=O)n(-c4cccc(F)c4)cc(-c4ccccc4)c3c2)c1=O]

Step A. 6-Bromo-4-phenylisoquinolin-1(2H)-one. To a mixture of 6-bromo-4-iodoisoquinolin-1(2H)-one (Example 1 Step A, 0.55 g, 1.7 mmol) and $Cs_2CO_3$ (1.3 g, 3.9 mmol) in 1,4-dioxane (20 mL) was added bis(triphenylphosphine) palladium(II) dichloride (0.22 g, 0.31 mmol) and phenylboronic acid (0.29 g, 2.4 mmol) respectively. The reaction mixture was degassed with nitrogen and then heated at 85° C. The progress of the reaction was closely monitored by TLC. After 0.5 h, TLC analysis indicated the almost complete consumption of starting material and the formation of the desired product. The mixture was cooled to 25° C. and filtered through a short pad of silica gel. The silica gel was washed with ethyl acetate. The combined filtrate was concentrated. The residue was purified by flash column chromatography ($SiO_2$, 10-70% Ethyl acetate in heptane) to afford the desired product as a white solid (0.16 g, 33% yield). LCMS (ES-API): mass calcd. for $C_{15}H_{10}BrNO$, 299.0; m/z found, 298.1 [M−H]+. $^1H$ NMR (400 MHz, DMSO-$d_6$) δ 11.65 (br d, J=4.04 Hz, 1H), 8.21 (d, J=8.59 Hz, 1H), 7.71 (br d, J=8.59 Hz, 1H), 7.56 (s, 1H), 7.41-7.53 (m, 5H), 7.18 (br d, J=5.56 Hz, 1H) ppm.

Step B. 6-Bromo-2-(3-fluorophenyl)-4-phenylisoquinolin-1(2H)-one. To a mixture of 6-bromo-4-phenylisoquinolin-1(2H)-one (160 mg, 0.53 mmol) and 3-fluorophenylboronic acid (224 mg, 1.6 mmol) in dichloromethane (DCM) (20 mL) and triethylamine (2 mL) was added copper(II) acetate (48 mg, 0.26 mmol) and pyridine (0.13 mL, 1.6 mmol). The reaction mixture was stirred at 25° C. for 48 h. The mixture was filtered through a short pad of silica gel and the silica gel was washed with ethyl acetate (100 mL). The filtrate was concentrated. The residue was purified by flash column chromatography ($SiO_2$, 20-50% EtOAc in heptane) to afford the crude desired product as a yellow amorphous gum (180 mg, 86%). LCMS (ES-API): mass calcd. for $C_{21}H_{13}BrFNO$, 393.0; m/z found, 394.0 [M+H]$^+$.

Step C. 6-(3-(((tert-Butyldiphenylsilyl)oxy)methyl)-4-ethyl-5-oxo-4,5-dihydro-1H-1,2,4-triazol-1-yl)-2-(3-fluorophenyl)-4-phenylisoquinolin-1(2H)-one. To a mixture of 6-bromo-2-(3-fluorophenyl)-4-phenylisoquinolin-1(2H)-one (100 mg, 0.25 mmol) and $K_3PO_4$ (161 mg, 0.7 mmol) in anhydrous 1,4-dioxane (6 mL) was added 5-(((tert-butyldiphenylsilyl)oxy)methyl)-4-ethyl-2,4-dihydro-3H-1,2,4-triazol-3-one (Intermediate 2, 194 mg, 0.5 mmol), CuI (48 mg, 0.25 mmol), and trans-N,N'-dimethylcyclohexane-1,2-diamine (36 mg, 0.25 mmol), respectively. The mixture was slowly heated and stirred under nitrogen at 95° C. for 2 h, then cooled to 25° C. and quenched with addition of water. The mixture was extracted with ethyl acetate (50 mL×2). The combined organic extract was washed with brine, dried with anhydrous $Na_2SO_4$, filtered, and concentrated. The residue was purified by flash column chromatography (20-50% EtOAc in heptane) to afford the desired product as a white solid (120 mg, 68%). LCMS (ES-API): mass calcd. for $C_{42}H_{39}FN_4O_3Si$, 694.3; m/z found, 695.4 [M+H]$^+$. $^1H$ NMR (400 MHz, $CDCl_3$) δ 8.60 (d, J=8.59 Hz, 1H), 8.28 (s, 1H), 8.15 (br d, J=8.59 Hz, 1H), 7.66 (br d, J=7.07 Hz, 4H), 7.34-7.53 (m, 12H), 7.27-7.33 (m, 2H), 7.08-7.19 (m, 2H), 4.62 (s, 2H), 3.88 (br q, J=6.82 Hz, 2H), 1.34 (br t, J=6.82 Hz, 3H), 1.07 (s, 9H) ppm Step D. 6-(4-Ethyl-3-(hydroxymethyl)-5-oxo-4,5-dihydro-1H-1,2,4-triazol-1-yl)-2-(3-fluorophenyl)-4-phenylisoquinolin-1(2H)-one. To a solution of 6-(3-(((tert-butyldiphenylsilyl)oxy)methyl)-4-ethyl-5-oxo-4,5-dihydro-1H-1,2,4-triazol-1-yl)-2-(3-fluorophenyl)-4-phenylisoquinolin-1(2H)-one (120 mg, 0.17 mmol) in tetrahydrofuran (THF) (10 mL) was added a tetrahydrofuran (THF) solution (1 M) of tetrabutylammonium fluoride (0.17 mL, 0.17 mmol). The reaction mixture was stirred at 25° C. for 0.5 h. The mixture was diluted with $H_2O$ (15 mL) and extracted with ethyl acetate (50 mL×2). The combined organic extract washed with brine (20 mL), dried over $Na_2SO_4$, filtered, and concentrated. The residue was purified by flash column chromatography (30-100% EtOAc in heptane) to afford the title compound as a white solid (50 mg, yield 63%). LCMS (ES-API): mass calcd. for $C_{26}H_{21}FN_4O_3$, 456.2; m/z found, 457.2 [M+H]$^+$. $^1H$ NMR (400 MHz, $CDCl_3$) δ 8.55-8.65 (m, 1H), 8.30 (s, 1H), 8.20 (br d, J=8.59 Hz, 1H), 7.39-7.56 (m, 6H), 7.28-7.32 (m, 2H), 7.17 (s, 1H), 7.10-7.16 (m, 1H), 4.64 (br d, J=6.19 Hz, 2H), 3.86 (q, J=7.07 Hz, 2H), 2.27 (t, J=6.19 Hz, 1H), 1.37 (br t, J=7.07 Hz, 3H) ppm Example 5: 2-(2-Chloro-6-fluorophenyl)-6-(4-ethyl-3-(hydroxymethyl)-5-oxo-4,5-dihydro-1H-1,2,4-triazol-1-yl)-4-(prop-1-en-2-yl)isoquinolin-1(2H)-one

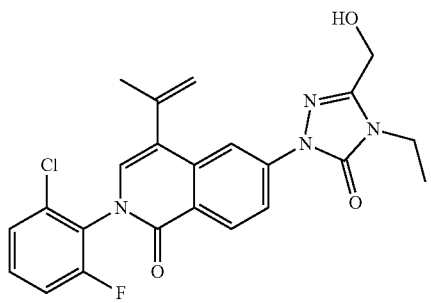 [SMILES: C=C(C)c1cn(-c2c(F)cccc2Cl)c(=O)c2ccc(-n3nc(CO)n(CC)c3=O)cc12]

Step A. 6-(3-((benzyloxy)methyl)-4-ethyl-5-oxo-4,5-dihydro-1H-1,2,4-triazol-1-yl)isoquinolin-1(2H)-one. To a mixture of 6-bromo-2-(3-fluorophenyl)-4-(prop-1-en-2-yl)isoquinolin-1(2H)-one (Example 1, product from Step C, 1.8 g, 8.0 mmol) and $K_3PO_4$ (3.4 g, 16 mmol) in anhydrous 1,4-dioxane (37 mL) was added 3-((benzyloxy)methyl)-4-ethyl-1H-1,2,4-triazol-5(4H)-one (Intermediate 1, 2.2 g, 9.6 mmol), CuI (1.5 g, 8.0 mmol), and trans-N,N'-dimethylcyclohexane-1,2-diamine (1.1 g, 8.0 mmol), respectively. The mixture was slowly heated and stirred under nitrogen at 95° C. for 24 h, then cooled to 25° C. and quenched with addition of water. The mixture was extracted with dichloromethane (200 mL×2) and ethyl acetate (200 mL). The combined organic extract was washed with brine, dried with anhydrous $Na_2SO_4$, filtered and concentrated. The residue was purified by flash column chromatography (50-100% EtOAc in heptane) to afford the desired product as a white solid (2.5 g, 82%). LCMS (ES-API): mass calcd. for $C_{21}H_{20}N_4O_3$, 376.2; m/z found, 377.3 [M+H]$^+$. $^1$H NMR (400 MHz, CDCl$_3$) δ 10.58 (br s, 1H), 8.47 (d, J=8.80 Hz, 1H), 8.29 (s, 1H), 8.17 (br d, J=8.80 Hz, 1H), 7.29-7.45 (m, 5H), 7.15 (br d, J=6.85 Hz, 1H), 6.60 (br d, J=6.85 Hz, 1H), 4.62 (s, 2H), 4.55 (s, 2H), 3.87 (q, J=6.92 Hz, 2H), 1.36 (t, J=6.92 Hz, 3H) ppm.

Step B. 6-(3-((Benzyloxy)methyl)-4-ethyl-5-oxo-4,5-dihydro-1H-1,2,4-triazol-1-yl)-4-iodoisoquinolin-1(2H)-one. To a suspension of 6-(3-((benzyloxy)methyl)-4-ethyl-5-oxo-4,5-dihydro-1H-1,2,4-triazol-1-yl)isoquinolin-1(2H)-one (2.5 g, 6.6 mmol) in anhydrous acetonitrile (60 mL) was added N-iodosuccinimide (NIS) (2.9 g, 13 mmol). The reaction mixture was heated and stirred under nitrogen at 80° C. for 2 h, then cooled to 25° C. The mixture was filtered through a sintered funnel, and the precipitate was collected, washed with water, and dried in vacuo to afford the desired product (1.2 g, crude, 36%) as an off white solid, which was used crude in the next step without further purification. LCMS (ES-API): mass calcd. for $C_{21}H_{19}IN_4O_3$, 502.1; m/z found, 503.1 [M+H]$^+$. $^1$H NMR (400 MHz, CDCl$_3$) δ 10.97 (br s, 1H), 8.55 (d, J=1.96 Hz, 1H), 8.44 (d, J=8.80 Hz, 1H), 8.23 (dd, J=1.96, 8.80 Hz, 1H), 7.61 (s, 1H), 7.30-7.48 (m, 5H), 4.63 (s, 2H), 4.57 (s, 2H), 3.88 (q, J=7.34 Hz, 2H), 1.37 (t, J=7.34 Hz, 3H) ppm.

Step C. 6-(3-((Benzyloxy)methyl)-4-ethyl-5-oxo-4,5-dihydro-1H-1,2,4-triazol-1-yl)-4-(prop-1-en-2-yl)isoquinolin-1(2H)-one. To a mixture of 6-(3-((benzyloxy)methyl)-4-ethyl-5-oxo-4,5-dihydro-1H-1,2,4-triazol-1-yl)-4-iodoisoquinolin-1(2H)-one (0.8 g, 1.6 mmol) and $Cs_2CO_3$ (1.6 g, 4.8 mmol) in 1,4-dioxane (20 mL) and ethanol (20 mL) and water (10 mL) was added bis(triphenylphosphine)palladium (II) dichloride (0.56 g, 0.8 mmol) and isopropenylboronic acid pinacol ester (0.67 g, 4 mmol) respectively. The reaction mixture was degassed with nitrogen and then heated at 85° C. for 1 h. The mixture was poured into water (50 mL). The aqueous phase was extracted with ethyl ether (100 mL) and ethyl acetate (EtOAc) (100 mL) sequentially. The combined organic extract was washed with brine, dried over anhydrous $Na_2SO_4$, filtered, and concentrated. The residue was purified by flash column chromatography (SiO$_2$, 50-100% ethyl acetate in heptane) to afford the desired product as a white solid (0.45 g, 68% yield). LCMS (ES-API): mass calcd. for $C_{24}H_{24}N_4O_3$, 416.2; m/z found, 417.3 [M+H]$^+$. $^1$H NMR (400 MHz, CDCl$_3$) δ 10.59 (br s, 1H), 8.51 (d, J=8.80 Hz, 1H), 8.48 (d, J=2.03 Hz, 1H), 8.14 (dd, J=2.03, 8.80 Hz, 1H), 7.30-7.43 (m, 5H), 7.06 (br s, 1H), 5.35-5.39 (m, 1H), 5.15 (d, J=0.98 Hz, 1H), 4.61 (s, 2H), 4.55 (s, 2H), 3.87 (q, J=7.22 Hz, 2H), 2.18 (s, 3H), 1.36 (t, J=7.22 Hz, 3H) ppm.

Step D. 6-(3-((Benzyloxy)methyl)-4-ethyl-5-oxo-4,5-dihydro-1H-1,2,4-triazol-1-yl)-2-(2-chloro-6-fluoro-4-nitrophenyl)-4-(prop-1-en-2-yl)isoquinolin-1(2H)-one. To a mixture of 6-(3-((benzyloxy)methyl)-4-ethyl-5-oxo-4,5-dihydro-1H-1,2,4-triazol-1-yl)-4-(prop-1-en-2-yl)isoquinolin-1(2H)-one (0.2 g, 0.48 mmol) and $Cs_2CO_3$ (0.47 g, 1.4 mmol) in anhydrous DMF (8 mL) was added 3-chloro-4,5-difluoronitrobenzene (0.17 g, 0.86 mmol). The reaction mixture was heated at 85° C. under nitrogen for 1 h. The mixture was poured into aqueous NaHCO$_3$ solution (50 mL). The aqueous phase was extracted with ethyl ether (50 mL) and ethyl acetate (EtOAc) (50 mL) sequentially. The combined organic extract was washed with brine, dried over anhydrous $Na_2SO_4$, filtered, and concentrated. The residue was purified by flash column chromatography (SiO$_2$, 20-50% ethyl acetate in heptane) to afford the desired product as a white solid (0.15 g, 53% yield). LCMS (ES-API): mass calcd. for $C_{30}H_{25}ClFN_5O_5$, 589.2; m/z found, 590.3 [M+H]$^+$. $^1$H NMR (400 MHz, CDCl$_3$) δ 8.53 (d, J=8.80 Hz, 1H), 8.51 (d, J=2.45 Hz, 1H), 8.29-8.32 (m, 1H), 8.17 (dd, J=1.96, 8.80 Hz, 1H), 8.09 (dd, J=2.45, 8.31 Hz, 1H), 7.29-7.46 (m, 5H), 6.80 (s, 1H), 5.40 (t, J=1.71 Hz, 1H), 5.14-5.25 (m, 1H), 4.63 (s, 2H), 4.55 (s, 2H), 3.87 (q, J=7.01 Hz, 2H), 2.21 (s, 3H), 1.37 (t, J=7.01 Hz, 3H) ppm.

Step E. 2-(4-Amino-2-chloro-6-fluorophenyl)-6-(3-((benzyloxy)methyl)-4-ethyl-5-oxo-4,5-dihydro-1H-1,2,4-triazol-1-yl)-4-(prop-1-en-2-yl)isoquinolin-1(2H)-one. To a mixture of 6-(3-((benzyloxy)methyl)-4-ethyl-5-oxo-4,5-dihydro-1H-1,2,4-triazol-1-yl)-2-(2-chloro-6-fluoro-4-nitrophenyl)-4-(prop-1-en-2-yl)isoquinolin-1(2H)-one (1.4 g, 2.4 mmol) in methanol (100 mL) and ethyl acetate (40 mL) was added an aqueous solution (20 mL) of NH$_4$Cl (1.1 g, 21 mmol) and zinc (1.55 g, 23 mmol) respectively. The reaction mixture was stirred at 25° C. for 1 h. The mixture was filtered through a short pad of Celite®. The filtrate was concentrated to a small volume, then partitioned between ethyl acetate (EtOAc) and water. The organic layer was separated, and the aqueous phase was extracted with ethyl acetate (EtOAc). The combined organic extract was washed with brine, dried over anhydrous Na$_2$SO$_4$, filtered, and concentrated to afford the crude product as a white foam (1.3 g, crude 97% yield), which was used crude in the next step without further purification. LCMS (ES-API): mass calcd. for $C_{30}H_{27}ClFN_5O_3$, 559.2; m/z found, 560.3 [M+H]$^+$.

Step F. 6-(3-((Benzyloxy)methyl)-4-ethyl-5-oxo-4,5-dihydro-1H-1,2,4-triazol-1-yl)-2-(2-chloro-6-fluorophenyl)-4-(prop-1-en-2-yl)isoquinolin-1(2H)-one. To a solution of crude 2-(4-amino-2-chloro-6-fluorophenyl)-6-(3-((benzyloxy)methyl)-4-ethyl-5-oxo-4,5-dihydro-1H-1,2,4-triazol-1-yl)-4-(prop-1-en-2-yl)isoquinolin-1(2H)-one (0.5 g, 0.89 mmol, estimated) in ethanol (25 mL) and concentrated $H_2SO_4$ (5 mL) at 0° C. was added an aqueous solution (10 mL) of $NaNO_2$ (0.22 g, 3.1 mmol). The reaction mixture was stirred at 0° C. for 0.5 h, then aqueous hypophosphorous acid (20 mL, 50% w/w) was added. The reaction mixture was stirred at 0° C. for 0.5 h, then room temperature for 1 h. The mixture was poured into water (50 mL), extracted with dichloromethane (50 mL) and ethyl acetate (EtOAc) (50 mL) sequentially. The combined organic extract was washed with brine, dried over anhydrous $Na_2SO_4$, filtered, and concentrated. The residue was purified by flash column chromatography ($SiO_2$, 20-70% Ethyl acetate in heptane) to afford the title compound as a white solid (0.11 g, 23% yield). LCMS (ES-API): mass calcd. for $C_{30}H_{26}ClFN_4O_3$, 544.2; m/z found, 545.3 [M+H]$^+$. $^1$H NMR (400 MHz, CDCl$_3$) δ 8.55 (d, J=8.80 Hz, 1H), 8.49 (d, J=1.96 Hz, 1H), 8.14 (dd, J=1.96, 8.80 Hz, 1H), 7.30-7.43 (m, 7H), 7.15-7.23 (m, 1H), 6.86 (s, 1H), 5.36-5.39 (m, 1H), 5.20 (dd, J=0.98, 1.96 Hz, 1H), 4.62 (s, 2H), 4.55 (s, 2H), 3.87 (q, J=7.22 Hz, 2H), 2.20 (s, 3H), 1.36 (t, J=7.22 Hz, 3H) ppm.

Step G. 2-(2-Chloro-6-fluorophenyl)-6-(4-ethyl-3-(hydroxymethyl)-5-oxo-4,5-dihydro-1H-1,2,4-triazol-1-yl)-4-(prop-1-en-2-yl)isoquinolin-1(2H)-one. 6-(3-((Benzyloxy)methyl)-4-ethyl-5-oxo-4,5-dihydro-1H-1,2,4-triazol-1-yl)-2-(2-chloro-6-fluorophenyl)-4-(prop-1-en-2-yl)isoquinolin-1(2H)-one (0.11 g, 0.2 mmol) was dissolved into trifluoroacetic acid (5 mL), and the reaction mixture was transferred into a sealed tube and heated at 80° C. for 17 h, then cooled to room temperature. The mixture was concentrated under reduced pressure. The residue was purified by flash column chromatography ($SiO_2$, 50-100% ethyl acetate in heptane), then further purified by prep-HPLC ($C_{18}$ column, 20-80% gradient MeCN in water) to afford the desired product as a white solid (45 mg, 49% yield). LCMS (ES-API): mass calcd. for $C_{23}H_{20}ClFN_4O_3$, 544.2; m/z found, 545.1 [M+H]$^+$. $^1$H NMR (400 MHz, CDCl$_3$) δ 8.55 (d, J=8.80 Hz, 1H), 8.48 (d, J=1.96 Hz, 1H), 8.12 (dd, J=1.96, 8.80 Hz, 1H), 7.31-7.46 (m, 2H), 7.16-7.25 (m, 1H), 6.86 (s, 1H), 5.37 (t, J=1.83 Hz, 1H), 5.30 (s, 1H), 5.20 (dd, J=0.98, 1.83 Hz, 1H), 4.70 (s, 2H), 3.92 (q, J=7.34 Hz, 2H), 2.20 (s, 3H), 1.42 (t, J=7.34 Hz, 3H) ppm.

Example 6: 2-(2-Chloro-6-fluorophenyl)-6-(4-ethyl-3-(hydroxymethyl)-5-oxo-4,5-dihydro-1H-1,2,4-triazol-1-yl)-4-(3,3,3-trifluoroprop-1-en-2-yl)isoquinolin-1(2H)-one

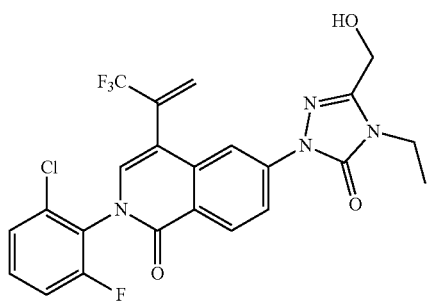 [SMILES: C=C(c1cn(-c2c(F)cccc2Cl)c(=O)c2ccc(-n3nc(CO)n(CC)c3=O)cc12)C(F)(F)F]

Step A. 6-(3-((Benzyloxy)methyl)-4-ethyl-5-oxo-4,5-dihydro-1H-1,2,4-triazol-1-yl)-4-(3,3,3-trifluoroprop-1-en-2-yl)isoquinolin-1(2H)-one. To a mixture of 6-(3-((benzyloxy)methyl)-4-ethyl-5-oxo-4,5-dihydro-1H-1,2,4-triazol-1-yl)-4-iodoisoquinolin-1(2H)-one (Example 5, product from Step B, 0.5 g, 1.0 mmol) and $Cs_2CO_3$ (0.97 g, 2.98 mmol) in 1,4-dioxane (20 mL) and ethanol (20 mL) and water (10 mL) was added bis(triphenylphosphine)palladium(II) dichloride (0.35 g, 0.5 mmol) and 1-(trifluoromethyl)vinylboronic acid hexylene glycol ester (0.55 g, 2.5 mmol) respectively. The reaction mixture was degassed with nitrogen and then heated at 85° C. for 2 h. The mixture was poured into water (50 mL). The aqueous phase was extracted with ethyl ether (100 mL) and ethyl acetate (EtOAc) (100 mL) sequentially. The combined organic extract was washed with brine, dried over anhydrous $Na_2SO_4$, filtered, and concentrated. The residue was purified by flash column chromatography ($SiO_2$, 30-100% Ethyl acetate in heptane) to afford the desired product as a white solid (0.45 g, 96% yield). LCMS (ES-API): mass calcd. for $C_{24}H_{21}F_3N_4O_3$, 470.2; m/z found, 417.3 [M+H]$^+$. $^1$H NMR (400 MHz, CDCl$_3$) δ 10.42 (br s, 1H), 8.51 (d, J=8.80 Hz, 1H), 8.35 (d, J=1.96 Hz, 1H), 8.14-8.28 (m, 1H), 7.30-7.50 (m, 5H), 7.15 (br d, J=4.40 Hz, 1H), 6.40 (d, J=1.24 Hz, 1H), 5.81 (d, J=1.24 Hz, 1H), 4.61 (s, 2H), 4.54 (s, 2H), 3.86 (q, J=7.17 Hz, 2H), 1.36 (t, J=7.17 Hz, 3H) ppm.

Step B. 6-(3-((Benzyloxy)methyl)-4-ethyl-5-oxo-4,5-dihydro-1H-1,2,4-triazol-1-yl)-2-(2-chloro-6-fluoro-4-nitrophenyl)-4-(3,3,3-trifluoroprop-1-en-2-yl)isoquinolin-1(2H)-one. To a mixture of -(3-((benzyloxy)methyl)-4-ethyl-5-oxo-4,5-dihydro-1H-1,2,4-triazol-1-yl)-4-(3,3,3-trifluoroprop-1-en-2-yl)isoquinolin-1(2H)-one (0.45 g, 0.96 mmol) and $Cs_2CO_3$ (0.93 g, 2.9 mmol) in anhydrous DMF (16 mL) was added 3-chloro-4,5-difluoronitrobenzene (0.33 g, 1.7 mmol). The reaction mixture was heated at 85° C. under nitrogen for 1 h. The mixture was poured into aqueous $NaHCO_3$ solution (100 mL). The aqueous phase was extracted with ethyl ether (100 mL) and ethyl acetate (EtOAc) (100 mL) sequentially. The combined organic extract was washed with brine, dried over anhydrous $Na_2SO_4$, filtered, and concentrated. The residue was purified by flash column chromatography ($SiO_2$, 20-50% ethyl acetate in heptane) to afford the desired product as a white solid (0.22 g, 35% yield). LCMS (ES-API): mass calcd. for $C_{30}H_{22}ClF_4N_5O_5$, 643.1; m/z found, 590.3 [M+H]$^+$. $^1$H NMR (400 MHz, CDCl$_3$) δ 8.54 (d, J=8.80 Hz, 1H), 8.41 (d, J=1.96 Hz, 1H), 8.30-8.32 (m, 1H), 8.26 (dd, J=1.96, 8.80 Hz, 1H), 8.10 (dd, J=2.45, 8.31 Hz, 1H), 7.31-7.41 (m, 5H), 6.94 (s, 1H), 6.44 (d, J=1.22 Hz, 1H), 5.90 (d, J=1.22 Hz, 1H), 4.62 (s, 2H), 4.55 (s, 2H), 3.87 (d, J=6.85 Hz, 3H), 1.36 (t, J=6.85 Hz, 3H) ppm.

Step C. 2-(4-Amino-2-chloro-6-fluorophenyl)-6-(3-((benzyloxy)methyl)-4-ethyl-5-oxo-4,5-dihydro-1H-1,2,4-triazol-1-yl)-4-(3,3,3-trifluoroprop-1-en-2-yl)isoquinolin-1(2H)-one. To a solution of 6-(3-((benzyloxy)methyl)-4-ethyl-5-oxo-4,5-dihydro-1H-1,2,4-triazol-1-yl)-2-(2-chloro-6-fluoro-4-nitrophenyl)-4-(3,3,3-trifluoroprop-1-en-2-yl)isoquinolin-1(2H)-one (0.22 g, 0.34 mmol) in methanol (40 mL) and ethyl acetate (20 mL) was added an aqueous solution (5 mL) of $NH_4Cl$ (0.16 g, 3 mmol) and zinc (0.22 g, 3.4 mmol) respectively. The reaction mixture was stirred at 25° C. for 1 h. The mixture was filtered through a short pad of Celite®. The filtrate was concentrated to a small volume, then partitioned between ethyl acetate (EtOAc) and water. The organic layer was separated, and the aqueous phase was extracted with ethyl acetate (EtOAc). The combined organic extract was washed with brine, dried over anhydrous $Na_2SO_4$, filtered, and concentrated to afford the crude product as a white foam (0.2 g, crude 97% yield), which was used crude in the next step without further purification. LCMS (ES-API): mass calcd. for $C_{30}H_{24}ClF_4N_5O_3$, 613.2; m/z found, 614.3 $[M+H]^+$.

Step D. 6-(3-((Benzyloxy)methyl)-4-ethyl-5-oxo-4,5-dihydro-1H-1,2,4-triazol-1-yl)-2-(2-chloro-6-fluorophenyl)-4-(3,3,3-trifluoroprop-1-en-2-yl)isoquinolin-1(2H)-one. To a solution of crude 2-(4-amino-2-chloro-6-fluorophenyl)-6-(3-((benzyloxy)methyl)-4-ethyl-5-oxo-4,5-dihydro-1H-1,2,4-triazol-1-yl)-4-(3,3,3-trifluoroprop-1-en-2-yl)isoquinolin-1(2H)-one (0.2 g, 0.33 mmol, estimated) in ethanol (20 mL) and concentrated $H_2SO_4$ (4 mL) at 0° C. was added an aqueous solution (10 mL) of $NaNO_2$ (0.03 g, 0.5 mmol). The reaction mixture was stirred at 0° C. for 0.5 h, then aqueous hypophosphorous acid (20 mL, 50% w/w) was added. The reaction mixture was stirred at 0° C. for 0.5 h, then room temperature for 1 h. The mixture was poured into water (50 mL), extracted with dichloromethane (50 mL) and ethyl acetate (EtOAc) (50 mL) sequentially. The combined organic extract was washed with brine, dried over anhydrous $Na_2SO_4$, filtered, and concentrated. The residue was purified by flash column chromatography ($SiO_2$, 20-70% ethyl acetate in heptane) to afford the desired product as a white solid (21 mg, 10% yield). LCMS (ES-API): mass calcd. for $C_{30}H_{23}ClF_4N_4O_3$, 598.1; m/z found, 599.3 $[M+H]^+$. $^1H$ NMR (400 MHz, $CDCl_3$) δ 8.56 (d, J=8.80 Hz, 1H), 8.38 (d, J=1.96 Hz, 1H), 8.22 (dd, J=1.96, 8.80 Hz, 1H), 7.33-7.44 (m, 7H), 7.13-7.28 (m, 1H), 7.00 (s, 1H), 6.41 (d, J=1.47 Hz, 1H), 5.89 (d, J=1.47 Hz, 1H), 4.62 (s, 2H), 4.55 (s, 2H), 3.86 (q, J=7.01 Hz, 3H), 1.36 (t, J=7.01 Hz, 3H) ppm.

Step E. 2-(2-Chloro-6-fluorophenyl)-6-(4-ethyl-3-(hydroxymethyl)-5-oxo-4,5-dihydro-1H-1,2,4-triazol-1-yl)-4-(3,3,3-trifluoroprop-1-en-2-yl)isoquinolin-1(2H)-one. 6-(3-((Benzyloxy)methyl)-4-ethyl-5-oxo-4,5-dihydro-1H-1,2,4-triazol-1-yl)-2-(2-chloro-6-fluorophenyl)-4-(3,3,3-trifluoroprop-1-en-2-yl)isoquinolin-1(2H)-one (21 mg, 0.03 mmol) was dissolved into trifluoroacetic acid (5 mL), and the reaction mixture was transferred into a sealed tube and heated at 80° C. for 17 h, then cooled to room temperature. The mixture was concentrated under reduced pressure. The residue was purified by flash column chromatography ($SiO_2$, 50-100% ethyl acetate in heptane), then further purified by prep-HPLC ($C_{18}$ column, 20-80% gradient MeCN in water) to afford the desired product as a white solid (9 mg, 50% yield). LCMS (ES-API): mass calcd. for $C_{23}H_{17}ClF_4N_4O_3$, 508.1; m/z found, 509.1 $[M+H]^+$. $^1H$ NMR (400 MHz, $CDCl_3$) δ 8.56 (br d, J=8.80 Hz, 1H), 8.36 (s, 1H), 8.21 (br dd, J=1.47, 8.80 Hz, 1H), 7.33-7.51 (m, 2H), 7.16-7.26 (m, 1H), 7.00 (s, 1H), 6.41 (s, 1H), 5.88 (s, 1H), 4.70 (br d, J=6.24 Hz, 2H), 3.90 (q, J=7.09 Hz, 2H), 2.14 (br t, J=6.24 Hz, 1H), 1.42 (br t, J=7.09 Hz, 3H) ppm.

Example 7: 2-(2,6-Dichlorophenyl)-6-(4-ethyl-3-(hydroxymethyl)-5-oxo-4,5-dihydro-1H-1,2,4-triazol-1-yl)-4-(1-methylcyclopropyl)isoquinolin-1(2H)-one

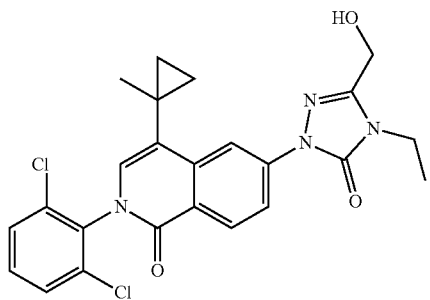 [SMILES: CCn1c(CO)nn(-c2ccc3c(=O)n(-c4c(Cl)cccc4Cl)cc(C4(C)CC4)c3c2)c1=O]

Step A. 6-(3-((Benzyloxy)methyl)-4-ethyl-5-oxo-4,5-dihydro-1H-1,2,4-triazol-1-yl)-4-(1-methylcyclopropyl)isoquinolin-1(2H)-one and 6-(3-((benzyloxy)methyl)-4-ethyl-5-oxo-4,5-dihydro-1H-1,2,4-triazol-1-yl)-4-(prop-1-en-2-yl)isoquinolin-1(2H)-one. To a mixture of diiodomethane (1.6 g, 6 mmol) in anhydrous toluene (10 mL) at 0° C. was added a toluene solution (15%) of diethylzinc (3.9 g, 4.8 mmol). The mixture was heated at 0° C. under nitrogen for 15 min, then a suspension of 6-(3-((benzyloxy)methyl)-4-ethyl-5-oxo-4,5-dihydro-1H-1,2,4-triazol-1-yl)-4-(prop-1-en-2-yl)isoquinolin-1(2H)-one (250 mg, 0.6 mmol) in toluene (20 mL). The reaction mixture was stirred at 0° C. for 0.5 h, then warmed to room temperature and stirred for 24 h. The mixture was poured into aqueous $NaHCO_3$ solution (50 mL). The aqueous phase was extracted with DCM (50 mL) and ethyl acetate (EtOAc) (50 mL) sequentially. The combined organic extract was washed with brine, dried over anhydrous $Na_2SO_4$, filtered, and concentrated. The residue was purified by flash column chromatography ($SiO_2$, 50-100% ethyl acetate in heptane) to afford 6-(3-((benzyloxy)methyl)-4-ethyl-5-oxo-4,5-dihydro-1H-1,2,4-triazol-1-yl)-4-(1-methylcyclopropyl)isoquinolin-1(2H)-one and unreacted 6-(3-((benzyloxy)methyl)-4-ethyl-5-oxo-4,5-dihydro-1H-1,2,4-triazol-1-yl)-4-(prop-1-en-2-yl)isoquinolin-1(2H)-one as a mixture, which was not further purified and used directly into the next step: a white solid (~1:4 ratio, 190 mg, 70% yield).

Step B. 6-(3-((Benzyloxy)methyl)-4-ethyl-5-oxo-4,5-dihydro-1H-1,2,4-triazol-1-yl)-2-(2,6-dichloro-4-nitrophenyl)-4-(1-methylcyclopropyl)isoquinolin-1(2H)-one and 6-(3-((benzyloxy)methyl)-4-ethyl-5-oxo-4,5-dihydro-1H-1,2,4-triazol-1-yl)-2-(2,6-dichloro-4-nitrophenyl)-4-(prop-1-en-2-yl)isoquinolin-1(2H)-one. To a mixture of 6-(3-((benzyloxy)methyl)-4-ethyl-5-oxo-4,5-dihydro-1H-1,2,4-triazol-1-yl)-4-(1-methylcyclopropyl)isoquinolin-1(2H)-one and 6-(3-((benzyloxy)methyl)-4-ethyl-5-oxo-4,5-dihydro-1H-1,2,4-triazol-1-yl)-4-(prop-1-en-2-yl)isoquinolin-1(2H)-one (~1:4, 0.19 g, 0.45 mmol) and $Cs_2CO_3$ (0.35 g, 1.1 mmol) in anhydrous DMF (6 mL) was added 3,5-dichloro-4-fluoronitrobenzene (0.19 g, 0.9 mmol). The reaction mixture was heated at 85° C. under nitrogen for 1 h. The mixture was poured into aqueous $NaHCO_3$ solution (50 mL). The aqueous phase was extracted with ethyl ether (50 mL) and ethyl acetate (EtOAc) (50 mL) sequentially. The combined organic extract was washed with brine, dried over anhydrous $Na_2SO_4$, filtered, and concentrated. The residue was purified by flash column chromatography ($SiO_2$, 20-50% ethyl acetate in heptane) to afford the two products as a mixture, which was not further purified and used directly into the next step: a white solid (112 mg, 51% yield).

6-(3-((benzyloxy)methyl)-4-ethyl-5-oxo-4,5-dihydro-1H-1,2,4-triazol-1-yl)-2-(2,6-dichloro-4-nitrophenyl)-4-(1-methylcyclopropyl)isoquinolin-1(2H)-one: LCMS (ES-API): mass calcd. for $C_{31}H_{27}Cl_2N_5O_5$, 619.1; m/z found, 620.2 $[M+H]^+$;

6-(3-((benzyloxy)methyl)-4-ethyl-5-oxo-4,5-dihydro-1H-1,2,4-triazol-1-yl)-2-(2,6-dichloro-4-nitrophenyl)-4-(prop-1-en-2-yl)isoquinolin-1(2H)-one: LCMS (ES-API): mass calcd. for $C_{30}H_{25}Cl_2N_5O_5$, 605.1; m/z found, 606.3 $[M+H]^+$.

Step C. 2-(4-Amino-2,6-dichlorophenyl)-6-(3-((benzyloxy)methyl)-4-ethyl-5-oxo-4,5-dihydro-1H-1,2,4-triazol-1-yl)-4-(1-methylcyclopropyl)isoquinolin-1(2H)-one and 2-(4-amino-2,6-dichlorophenyl)-6-(3-((benzyloxy)methyl)-4-ethyl-5-oxo-4,5-dihydro-1H-1,2,4-triazol-1-yl)-4-(prop-1-en-2-yl)isoquinolin-1(2H)-one. To a mixture of 6-(3-((benzyloxy)methyl)-4-ethyl-5-oxo-4,5-dihydro-1H-1,2,4- triazol-1-yl)-2-(2,6-dichloro-4-nitrophenyl)-4-(1-methylcyclopropyl)isoquinolin-1(2H)-one and 6-(3-((benzyloxy)methyl)-4-ethyl-5-oxo-4,5-dihydro-1H-1,2,4-triazol-1-yl)-2-(2,6-dichloro-4-nitrophenyl)-4-(prop-1-en-2-yl)isoquinolin-1(2H)-one (~1:4, 112 mg, 0.18 mmol) in methanol (40 mL) and ethyl acetate (20 mL) was added an aqueous solution (10 mL) of NH$_4$Cl (71 mg, 1.3 mmol) and zinc (97 mg, 1.5 mmol) respectively. The reaction mixture was stirred at 25° C. for 1 h. The mixture was filtered through a short pad of Celite®. The filtrate was concentrated to a small volume, then partitioned between ethyl acetate (EtOAc) and water. The organic layer was separated, and the aqueous phase was extracted with ethyl acetate (EtOAc). The combined organic extract was washed with brine, dried over anhydrous Na$_2$SO$_4$, filtered, and concentrated to afford the crude products as a mixture: a white foam (~1:5 ratio, 96 mg, crude 97% yield), which was used crude in the next step without further purification. 2-(4-amino-2,6-dichlorophenyl)-6-(3-((benzyloxy)methyl)-4-ethyl-5-oxo-4,5-dihydro-1H-1,2,4-triazol-1-yl)-4-(1-methylcyclopropyl)isoquinolin-1(2H)-one: LCMS (ES-API): mass calcd. for C$_{31}$H$_{29}$Cl$_2$N$_5$O$_3$, 589.2; m/z found, 590.2 [M+H]$^+$; 2-(4-amino-2,6-dichlorophenyl)-6-(3-((benzyloxy)methyl)-4-ethyl-5-oxo-4,5-dihydro-1H-1,2,4-triazol-1-yl)-4-(prop-1-en-2-yl)isoquinolin-1(2H)-one: LCMS (ES-API): mass calcd. for C$_{30}$H$_{27}$Cl$_2$N$_5$O$_3$, 575.2; m/z found, 576.3 [M+H]$^+$.

Step D. 6-(3-((Benzyloxy)methyl)-4-ethyl-5-oxo-4,5-dihydro-1H-1,2,4-triazol-1-yl)-2-(2,6-dichlorophenyl)-4-(1-methylcyclopropyl)isoquinolin-1(2H)-one and 6-(3-((benzyloxy)methyl)-4-ethyl-5-oxo-4,5-dihydro-1H-1,2,4-triazol-1-yl)-2-(2,6-dichlorophenyl)-4-(prop-1-en-2-yl)isoquinolin-1(2H)-one. To a mixture of crude 2-(4-amino-2,6-dichlorophenyl)-6-(3-((benzyloxy)methyl)-4-ethyl-5-oxo-4,5-dihydro-1H-1,2,4-triazol-1-yl)-4-(1-methylcyclopropyl)isoquinolin-1(2H)-one and 2-(4-amino-2,6-dichlorophenyl)-6-(3-((benzyloxy)methyl)-4-ethyl-5-oxo-4,5-dihydro-1H-1,2,4-triazol-1-yl)-4-(prop-1-en-2-yl)isoquinolin-1(2H)-one (~1:5 ratio, 96 mg, 0.17 mmol, estimated) in ethanol (20 mL) and concentrated H$_2$SO$_4$ (4 mL) at 0° C. was added an aqueous solution (4 mL) of NaNO$_2$ (34 mg, 0.49 mmol). The reaction mixture was stirred at 0° C. for 1 h, then zinc powder (91 mg, 1.4 mmol) was added. The reaction mixture was at room temperature for 0.5 h, then heated at 85° C. for 1 h. The mixture was cooled to room temperature, poured into water (50 mL), and the "pH" was adjusted to 7-8 by aqueous NaOH and NaHCO$_3$ solutions. The mixture was extracted with dichloromethane (50 mL) and ethyl acetate (EtOAc) (50 mL) sequentially. The combined organic extract was washed with brine, dried over anhydrous Na$_2$SO$_4$, filtered, and concentrated. The residue was purified by flash column chromatography (SiO$_2$, 20-70% ethyl acetate in heptane) to afford the two desired products as a mixture: a white solid (~1:4, 50 mg, 64% yield). 6-(3-((benzyloxy)methyl)-4-ethyl-5-oxo-4,5-dihydro-1H-1,2,4-triazol-1-yl)-2-(2,6-dichlorophenyl)-4-(1-methylcyclopropyl)isoquinolin-1(2H)-one: LCMS (ES-API): mass calcd. for C$_{31}$H$_{28}$Cl$_2$N$_4$O$_3$, 574.2; m/z found, 575.2 [M+H]$^+$; 6-(3-((benzyloxy)methyl)-4-ethyl-5-oxo-4,5-dihydro-1H-1,2,4-triazol-1-yl)-2-(2,6-dichlorophenyl)-4-(prop-1-en-2-yl)isoquinolin-1(2H)-one: LCMS (ES-API): mass calcd. for C$_{30}$H$_{26}$Cl$_2$N$_4$O$_3$, 560.1; m/z found, 561.1 [M+H]$^+$.

Step E. 2-(2,6-Dichlorophenyl)-6-(4-ethyl-3-(hydroxymethyl)-5-oxo-4,5-dihydro-1H-1,2,4-triazol-1-yl)-4-(1-methylcyclopropyl)isoquinolin-1(2H)-one. The mixture of 6-(3-((benzyloxy)methyl)-4-ethyl-5-oxo-4,5-dihydro-1H-1,2,4-triazol-1-yl)-2-(2,6-dichlorophenyl)-4-(1-methylcyclopropyl)isoquinolin-1(2H)-one and 6-(3-((benzyloxy)methyl)-4-ethyl-5-oxo-4,5-dihydro-1H-1,2,4-triazol-1-yl)-2-(2,6-dichlorophenyl)-4-(prop-1-en-2-yl)isoquinolin-1(2H)-one (~1:4, 50 mg, 0.09 mmol) was dissolved into trifluoroacetic acid (3 mL), and the reaction mixture was transferred into a sealed tube and heated at 80° C. for 17 h, then cooled to room temperature. The mixture was concentrated under reduced pressure. The residue was purified by flash column chromatography (SiO$_2$, 50-100% ethyl acetate in heptane), then further purified by prep-HPLC (C$_{18}$ column, 20-80% gradient MeCN in water) to afford the desired product as a white solid (2 mg, 24% yield). LCMS (ES-API): mass calcd. for C$_{24}$H$_{22}$Cl$_2$N$_4$O$_3$, 484.1; m/z found, 485.2 [M+H]$^+$. $^1$H NMR (400 MHz, CDCl$_3$) δ 8.92 (d, J=2.21 Hz, 1H), 8.54 (d, J=8.80 Hz, 1H), 8.09 (dd, J=2.21, 8.80 Hz, 2H), 7.48-7.54 (m, 2H), 7.32-7.39 (m, 1H), 6.89 (s, 1H), 4.72 (d, J=6.36 Hz, 2H), 3.94 (q, J=7.34 Hz, 2H), 2.17 (t, J=6.36 Hz, 1H), 1.50 (s, 3H), 1.44 (t, J=7.34 Hz, 3H), 0.81-0.97 (m, 4H) ppm.

Example 8: 2-(2,6-Dichlorophenyl)-6-(4-ethyl-3-(hydroxymethyl)-5-oxo-4,5-dihydro-1H-1,2,4-triazol-1-yl)-4-(prop-1-en-2-yl)isoquinolin-1(2H)-one

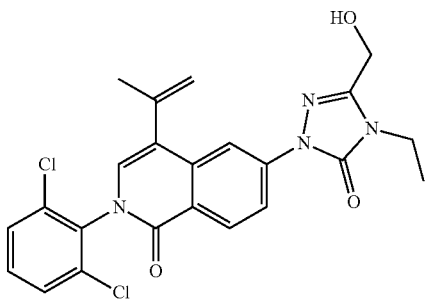 [SMILES: C=C(C)c1cn(-c2c(Cl)cccc2Cl)c(=O)c2ccc(-n3nc(CO)n(CC)c3=O)cc12]

In the preparation of 2-(2,6-dichlorophenyl)-6-(4-ethyl-3-(hydroxymethyl)-5-oxo-4,5-dihydro-1H-1,2,4-triazol-1-yl)-4-(1-methylcyclopropyl)isoquinolin-1(2H)-one (Example 7, step E), the title compound was obtained as the second product: a white solid (8 mg, yield 24%). LCMS (ES-API): mass calcd. for C$_{23}$H$_2$C$_{12}$N$_4$O$_3$, 470.1; m/z found, 471.1 [M+H]$^+$. $^1$H NMR (400 MHz, CDCl$_3$) δ 8.55 (d, J=8.80 Hz, 1H), 8.49 (d, J=2.21 Hz, 1H), 8.12 (dd, J=2.21, 8.80 Hz, 1H), 7.47-7.53 (m, 2H), 7.33-7.40 (m, 1H), 6.80 (s, 1H), 5.35-5.38 (m, 1H), 5.20 (s, 1H), 4.70 (d, J=6.36 Hz, 3H), 3.92 (q, J=7.34 Hz, 3H), 2.20 (t, J=6.36 Hz, 1H), 2.20 (s, 3H), 1.42 (t, J=7.34 Hz, 3H) ppm.

Example 9: 2-(2-Chloro-6-fluorophenyl)-4-cyclopropyl-6-(4-ethyl-3-(hydroxymethyl)-5-oxo-4,5-dihydro-1H-1,2,4-triazol-1-yl)isoquinolin-1(2H)-one

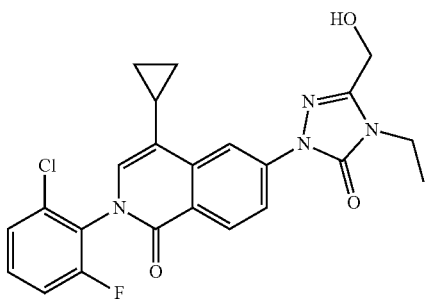 [SMILES: CCn1c(CO)nn(-c2ccc3c(=O)n(-c4c(F)cccc4Cl)cc(C4CC4)c3c2)c1=O]

Step A. 6-(3-((Benzyloxy)methyl)-4-ethyl-5-oxo-4,5-dihydro-1H-1,2,4-triazol-1-yl)-4-cyclopropylisoquinolin-1(2H)-one and 6-(3-((benzyloxy)methyl)-4-ethyl-5-oxo-4,5-dihydro-1H-1,2,4-triazol-1-yl)isoquinolin-1(2H)-one. To a mixture of 6-(3-((benzyloxy)methyl)-4-ethyl-5-oxo-4,5-dihydro-1H-1,2,4-triazol-1-yl)-4-iodoisoquinolin-1(2H)-one (Example 5, product from Step B, 0.6 g, 1.2 mmol) and Cs$_2$CO$_3$ (1.2 g, 3.6 mmol) in 1,4-dioxane (20 mL) and ethanol (20 mL) and water (10 mL) was added bis(triphenylphosphine)palladium(II) dichloride (0.42 g, 0.6 mmol) and cyclopropylboronic acid (0.26 g, 2.9 mmol) respectively. The reaction mixture was degassed with nitrogen and then heated at 85° C. for 24 h. The mixture was poured into water (50 mL). The aqueous phase was extracted with ethyl ether (100 mL) and ethyl acetate (EtOAc) (100 mL) sequentially. The combined organic extract was washed with brine, dried over anhydrous Na$_2$SO$_4$, filtered, and concentrated. The residue was purified by flash column chromatography (SiO$_2$, 30-100% Ethyl acetate in heptane) to afford the two products as a mixture, which was not further purified and used directly into the next step: a white solid (~1:2.5, 0.35 g, 75% yield). 6-(3-((benzyloxy)methyl)-4-ethyl-5-oxo-4,5-dihydro-1H-1,2,4-triazol-1-yl)-4-cyclopropylisoquinolin-1(2H)-one: LCMS (ES-API): mass calcd. for C$_{24}$H$_{24}$N$_4$O$_3$, 416.2; m/z found, 417.3 [M+H]$^+$; 6-(3-((benzyloxy)methyl)-4-ethyl-5-oxo-4,5-dihydro-1H-1,2,4-triazol-1-yl)isoquinolin-1(2H)-one: LCMS (ES-API): mass calcd. for C$_{21}$H$_2$MN$_4$O$_3$, 376.2; m/z found, 377.2 [M+H]$^+$.

Step B. 6-(3-((Benzyloxy)methyl)-4-ethyl-5-oxo-4,5-dihydro-1H-1,2,4-triazol-1-yl)-2-(2-chloro-6-fluoro-4-nitrophenyl)-4-cyclopropylisoquinolin-1(2H)-one and 6-(3-((benzyloxy)methyl)-4-ethyl-5-oxo-4,5-dihydro-1H-1,2,4-triazol-1-yl)-2-(2-chloro-6-fluoro-4-nitrophenyl)isoquinolin-1(2H)-one. To a mixture of 6-(3-((benzyloxy)methyl)-4-ethyl-5-oxo-4,5-dihydro-1H-1,2,4-triazol-1-yl)-4-cyclopropylisoquinolin-1(2H)-one and 6-(3-((benzyloxy)methyl)-4-ethyl-5-oxo-4,5-dihydro-1H-1,2,4-triazol-1-yl)isoquinolin-1(2H)-one (~1:2.5, 0.35 g, 0.9 mmol) and Cs$_2$CO$_3$ (0.39 g, 1.2 mmol) in anhydrous DMF (6 mL) was added 3-chloro-4,5-difluoronitrobenzene (0.16 g, 0.9 mmol). The reaction mixture was heated at 85° C. under nitrogen for 1 h. The mixture was poured into aqueous NaHCO$_3$ solution (50 mL). The aqueous phase was extracted with ethyl ether (50 mL) and ethyl acetate (EtOAc) (50 mL) sequentially. The combined organic extract was washed with brine, dried over anhydrous Na$_2$SO$_4$, filtered, and concentrated. The residue was purified by flash column chromatography (SiO$_2$, 20-50% ethyl acetate in heptane) to afford the two products as a mixture, which was not further purified and used directly into the next step: a white solid (~1:2.3, 330 mg, 70% yield). 6-(3-((benzyloxy)methyl)-4-ethyl-5-oxo-4,5-dihydro-1H-1,2,4-triazol-1-yl)-2-(2-chloro-6-fluoro-4-nitrophenyl)-4-cyclopropylisoquinolin-1(2H)-one: LCMS (ES-API): mass calcd. for C$_{30}$H$_{25}$ClFN$_5$O$_5$, 589.2; m/z found, 590.3 [M+H]$^+$; 6-(3-((benzyloxy)methyl)-4-ethyl-5-oxo-4,5-dihydro-1H-1,2,4-triazol-1-yl)-2-(2-chloro-6-fluoro-4-nitrophenyl)isoquinolin-1(2H)-one: LCMS (ES-API): mass calcd. for C$_{27}$H$_{21}$ClFN$_5$O$_5$, 549.1; m/z found, 550.2 [M+H]$^+$.

Step C. 2-(4-Amino-2-chloro-6-fluorophenyl)-6-(3-((benzyloxy)methyl)-4-ethyl-5-oxo-4,5-dihydro-1H-1,2,4-triazol-1-yl)-4-cyclopropylisoquinolin-1(2H)-one and 2-(4-amino-2-chloro-6-fluorophenyl)-6-(3-((benzyloxy)methyl)-4-ethyl-5-oxo-4,5-dihydro-1H-1,2,4-triazol-1-yl)isoquinolin-1(2H)-one. To a mixture of 6-(3-((benzyloxy)methyl)-4-ethyl-5-oxo-4,5-dihydro-1H-1,2,4-triazol-1-yl)-2-(2-chloro-6-fluoro-4-nitrophenyl)-4-cyclopropylisoquinolin-1(2H)-one and 6-(3-((benzyloxy)methyl)-4-ethyl-5-oxo-4,5-dihydro-1H-1,2,4-triazol-1-yl)-2-(2-chloro-6-fluoro-4-nitrophenyl)isoquinolin-1(2H)-one (~1:2.3, 330 mg, 0.58 mmol) in methanol (40 mL) and ethyl acetate (20 mL) was added an aqueous solution (10 mL) of NH$_4$Cl (82 mg, 1.5 mmol) and zinc (111 mg, 1.7 mmol) respectively. The reaction mixture was stirred at 25° C. for 1 h. The mixture was filtered through a short pad of Celite®. The filtrate was concentrated to a small volume, then partitioned between ethyl acetate (EtOAc) and water. The organic layer was separated, and the aqueous phase was extracted with ethyl acetate (EtOAc). The combined organic extract was washed with brine, dried over anhydrous Na$_2$SO$_4$, filtered, and concentrated to afford the crude two products as a mixture: a white foam (~1:2 ratio, 270 mg, crude 86% yield), which was used crude in the next step without further purification. 2-(4-amino-2-chloro-6-fluorophenyl)-6-(3-((benzyloxy)methyl)-4-ethyl-5-oxo-4,5-dihydro-1H-1,2,4-triazol-1-yl)-4-cyclopropylisoquinolin-1(2H)-one: LCMS (ES-API): mass calcd. for C$_{30}$H$_{27}$ClFN$_5$O$_3$, 559.2; m/z found, 560.3 [M+H]$^+$; 2-(4-amino-2-chloro-6-fluorophenyl)-6-(3-((benzyloxy)methyl)-4-ethyl-5-oxo-4,5-dihydro-1H-1,2,4-triazol-1-yl)isoquinolin-1(2H)-one: LCMS (ES-API): mass calcd. for C$_{27}$H$_{23}$ClFN$_5$O$_3$, 519.2; m/z found, 520.2 [M+H]$^+$.

Step D. 6-(3-((Benzyloxy)methyl)-4-ethyl-5-oxo-4,5-dihydro-1H-1,2,4-triazol-1-yl)-2-(2-chloro-6-fluorophenyl)-4-cyclopropylisoquinolin-1(2H)-one and 6-(3-((benzyloxy)methyl)-4-ethyl-5-oxo-4,5-dihydro-1H-1,2,4-triazol-1-yl)-2-(2-chloro-6-fluorophenyl)isoquinolin-1(2H)-one. To a mixture of crude 2-(4-amino-2-chloro-6-fluorophenyl)-6-(3-((benzyloxy)methyl)-4-ethyl-5-oxo-4,5-dihydro-1H-1,2,4-triazol-1-yl)-4-cyclopropylisoquinolin-1(2H)-one and 2-(4-amino-2-chloro-6-fluorophenyl)-6-(3-((benzyloxy)methyl)-4-ethyl-5-oxo-4,5-dihydro-1H-1,2,4-triazol-1-yl)isoquinolin-1(2H)-one (~1:2 ratio, 270 mg, 0.5 mmol, estimated) in ethanol (25 mL) and concentrated H$_2$SO$_4$ (5 mL) at 0° C. was added an aqueous solution (10 mL) of NaNO$_2$ (39 mg, 0.56 mmol). The reaction mixture was stirred at 0° C. for 1 h, then zinc powder (105 mg, 1.6 mmol) was added. The reaction mixture was at room temperature for 0.5 h, then heated at 85° C. for 1 h. The mixture was cooled to room temperature, poured into water (50 mL), and the "pH" was adjusted to 7-8 by aqueous NaOH and NaHCO$_3$ solutions. The mixture was extracted with dichloromethane (50 mL) and ethyl acetate (EtOAc) (50 mL) sequentially. The combined organic extract was washed with brine, dried over anhydrous Na$_2$SO$_4$, filtered, and concentrated. The residue was purified by flash column chromatography (SiO$_2$, 20-70% Ethyl acetate in heptane) to afford the two desired products as a mixture: a white solid (~1:2, 180 mg, 68% yield). 6-(3-((benzyloxy)methyl)-4-ethyl-5-oxo-4,5-dihydro-1H-1,2,4-triazol-1-yl)-2-(2-chloro-6-fluorophenyl)-4-cyclopropylisoquinolin-1(2H)-one: LCMS (ES-API): mass calcd. for C$_{30}$H$_{26}$ClFN$_4$O$_3$, 544.2; m/z found, 545.3 [M+H]$^+$; 6-(3-((benzyloxy)methyl)-4-ethyl-5-oxo-4,5-dihydro-1H-1,2,4-triazol-1-yl)-2-(2-chloro-6-fluorophenyl)isoquinolin-1(2H)-one: LCMS (ES-API): mass calcd. for C$_{27}$H$_{22}$ClFN$_4$O$_3$, 504.1; m/z found, 505.2 [M+H]$^+$.

Step E. 2-(2-Chloro-6-fluorophenyl)-4-cyclopropyl-6-(4-ethyl-3-(hydroxymethyl)-5-oxo-4,5-dihydro-1H-1,2,4-triazol-1-yl)isoquinolin-1(2H)-one. The mixture of 6-(3-((benzyloxy)methyl)-4-ethyl-5-oxo-4,5-dihydro-1H-1,2,4-triazol-1-yl)-2-(2-chloro-6-fluorophenyl)-4-cyclopropylisoquinolin-1(2H)-one and 6-(3-((benzyloxy)methyl)-4-ethyl-5-oxo-4,5-dihydro-1H-1,2,4-triazol-1-yl)-2-(2-chloro- 6-fluorophenyl)isoquinolin-1(2H)-one (~1:2, 180 mg, 0.35 mmol) was dissolved into trifluoroacetic acid (8 mL), and the reaction mixture was transferred into a sealed tube and heated at 80° C. for 17 h, then cooled to room temperature. The mixture was concentrated under reduced pressure. The residue was purified by flash column chromatography (SiO$_2$, 50-100% Ethyl acetate in heptane), then further purified by prep-HPLC (C$_{18}$ column, 20-80% gradient MeCN in water) to afford the desired product as a white solid (17 mg, 34% yield). LCMS (ES-API): mass calcd. for C$_{23}$H$_{20}$ClFN$_4$O$_3$, 454.1; m/z found, 455.1 [M+H]$^+$. $^1$H NMR (400 MHz, CDCl$_3$) δ 8.83 (d, J=1.96 Hz, 1H), 8.52 (d, J=8.80 Hz, 1H), 8.16 (dd, J=1.96, 8.80 Hz, 1H), 7.33-7.44 (m, 2H), 7.16-7.23 (m, 1H), 6.79 (d, J=0.98 Hz, 1H), 4.72 (d, J=6.36 Hz, 2H), 3.93 (q, J=7.25 Hz, 2H), 2.17 (t, J=6.36 Hz, 1H), 1.94-2.02 (m, 1H), 1.44 (t, J=7.25 Hz, 3H), 0.96-1.05 (m, 2H), 0.58-0.65 (m, 2H) ppm.

Example 10: 2-(2-Chloro-6-fluorophenyl)-6-(4-ethyl-3-(hydroxymethyl)-5-oxo-4,5-dihydro-1H-1,2,4-triazol-1-yl)isoquinolin-1(2H)-one

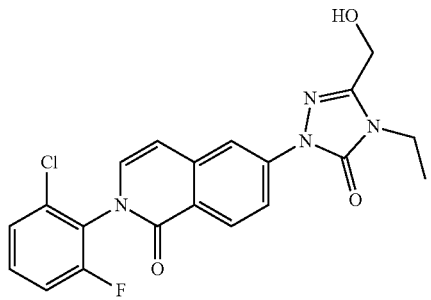 [SMILES: CCn1c(CO)nn(-c2ccc3c(=O)n(-c4c(F)cccc4Cl)ccc3c2)c1=O]

In the preparation of 2-(2-chloro-6-fluorophenyl)-4-cyclopropyl-6-(4-ethyl-3-(hydroxymethyl)-5-oxo-4,5-dihydro-1H-1,2,4-triazol-1-yl)isoquinolin-1(2H)-one (Example 9, step E), the title compound was obtained as the second product: a white solid (34 mg, yield 74%). LCMS (ES-API): mass calcd. for C$_{20}$H$_{16}$ClFN$_4$O$_3$, 414.1; m/z found, 415.2 [M+H]$^+$. $^1$H NMR (400 MHz, CDCl$_3$) δ 8.49 (d, J=8.80 Hz, 1H), 8.30 (d, J=1.96 Hz, 1H), 8.15 (dd, J=1.96, 8.80 Hz, 1H), 7.31-7.47 (m, 2H), 7.15-7.27 (m, 1H), 6.96 (d, J=7.59 Hz, 1H), 6.65 (d, J=7.59 Hz, 1H), 4.70 (s, 2H), 3.92 (d, J=7.22 Hz, 2H), 1.43 (t, J=7.22 Hz, 3H) ppm.

Example 11: 2-(2-Chloro-6-fluorophenyl)-6-(4-ethyl-3-(hydroxymethyl)-5-oxo-4,5-dihydro-1H-1,2,4-triazol-1-yl)-7-fluoro-4-isopropylisoquinolin-1(2H)-one

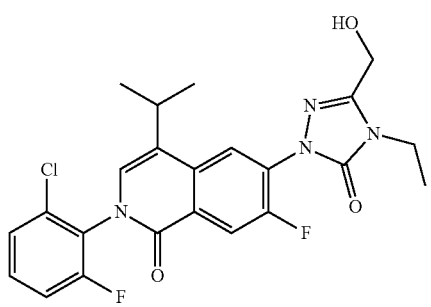 [SMILES: CCn1c(CO)nn(-c2cc3c(C(C)C)cn(-c4c(F)cccc4Cl)c(=O)c3cc2F)c1=O]

Step A. 6-(3-((Benzyloxy)methyl)-4-ethyl-5-oxo-4,5-dihydro-1H-1,2,4-triazol-1-yl)-2-(2-chloro-6-fluorophenyl)-7-fluoro-4-isopropylisoquinolin-1(2H)-one. To a stirred solution of 2-chloro-6-fluoroaniline (399 mg, 2.7 mmol) in DCM (6 mL) was added AlMe$_3$ (2 M in toluene, 1.03 mL, 2.06 mmol) under nitrogen. The mixture was stirred at room temperature for 0.5 h, then a DCM solution (6 mL) of 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4, 300 mg, 0.69 mmol) was added. The mixture was stirred at room temperature for overnight. Aqueous HCl (1N, 1.8 mL) was added, and the mixture was stirred for 2 min, then poured into water, and extracted with DCM. The organic extract was separated, washed with brine, dried over anhydrous Na$_2$SO$_4$, and concentrated. The residue was dissolved in AcOH (15 mL) and stirred at 90° C. for overnight. The mixture was poured into water and extracted with ethyl acetate. The combined organic extract was washed with brine, dried over anhydrous Na$_2$SO$_4$, and concentrated. The residue was purified by flash chromatography (SiO$_2$, gradient elution: 0-70% EtOAc in petroleum ether) to give the title compound as a yellow oil (320 mg, yield: 82%). MS (ESI): mass calcd. for C$_{30}$H$_{27}$ClF$_2$N$_4$O$_3$, 564.2; m/z found, 565.1 [M+H]$^+$. $^1$H NMR (400 MHz, CDCl$_3$) δ 8.33 (d, J=11.0 Hz, 1H), 8.09 (d, J=7.0 Hz, 1H), 7.36-7.45 (m, 7H), 7.19-7.26 (m, 1H), 6.74 (s, 1H), 4.64 (s, 2H), 4.56 (s, 2H), 3.90 (q, J=7.3 Hz, 2H), 3.28 (dt, J=13.6, 6.6 Hz, 1H), 1.40 (t, J=7.2 Hz, 3H), 1.34 (dd, J=6.8, 4.0 Hz, 6H); $^{19}$F NMR (376 MHz, CDCl$_3$) δ −116.47-116.23 (m, 1F), −120.52 (s, 1F) ppm.

Step B. 2-(2-Chloro-6-fluorophenyl)-6-(4-ethyl-3-(hydroxymethyl)-5-oxo-4,5-dihydro-1H-1,2,4-triazol-1-yl)-7-fluoro-4-isopropylisoquinolin-1(2H)-one. To a stirred solution of 6-(3-((benzyloxy)methyl)-4-ethyl-5-oxo-4,5-dihydro-1H-1,2,4-triazol-1-yl)-2-(2-chloro-6-fluorophenyl)-7-fluoro-4-isopropylisoquinolin-1(2H)-one (1.52 g, 2.7 mmol) in DCM (62 mL) was added BCl$_3$ (1 M in toluene, 13.4 mL, 13.4 mmol) at −78° C. The reaction mixture was stirred at −78° C. for 1 h. MeOH (17 mL) was added, and then the mixture was stirred at −78° C. for 0.5 h. The mixture was diluted with DCM, washed with saturated aqueous NaHCO$_3$ solution. The organic extract was separated, washed with brine, dried over anhydrous Na$_2$SO$_4$, filtered, and concentrated. The residue was purified by reverse phase prep-HPLC (Stationary phase: Boston Prime C18, 5 µm, 150×30 mm; Mobile phase: water (0.04% NH$_3$·H$_2$O+10 mM NH$_4$HCO$_3$) (A)—MeCN (B), gradient elution: 45-75% B in A over 8 min, flow rate: 25 mL/min) to give the title compound as a white powder (875 mg, yield: 69%). MS(ESI): mass calcd. for C$_{23}$H$_{21}$ClF$_2$N$_4$O$_3$, 474.1; m/z found, 475.2 [M+H]$^+$. $^1$H NMR (400 MHz, CDCl$_3$) δ 8.32 (d, J=11.0 Hz, 1H), 8.09 (d, J=6.8 Hz, 1H), 7.37-7.48 (m, 2H), 7.20-7.25 (m, 1H), 6.74 (s, 1H), 4.69 (d, J=6.2 Hz, 2H), 3.94 (q, J=7.1 Hz, 2H), 3.27 (dt, J=13.4, 6.6 Hz, 1H), 2.57 (t, J=6.4 Hz, 1H), 1.44 (t, J=7.3 Hz, 3H), 1.33 (dd, J=6.8, 4.0 Hz, 6H); $^{19}$F NMR (376 MHz, CDCl$_3$) δ ppm−116.37 (dd, J=9.5, 5.1 Hz, 1F), −120.58 (dd, J=11.7, 7.3 Hz, 1F) ppm.

Example 12: 6-(4-Ethyl-3-(hydroxymethyl)-5-oxo-4,5-dihydro-1H-1,2,4-triazol-1-yl)-4-(prop-1-en-2-yl)-2-(2-(trifluoromethyl)phenyl)isoquinolin-1(2H)-one

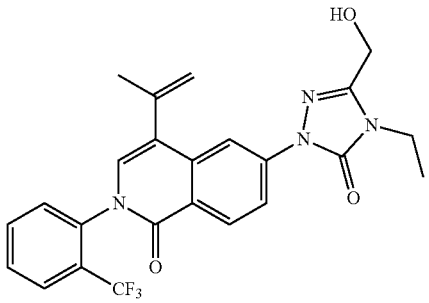 [SMILES: C=C(C)c1cn(-c2ccccc2C(F)(F)F)c(=O)c2ccc(-n3nc(CO)n(CC)c3=O)cc12]

Step A. 6-(3-((Benzyloxy)methyl)-4-ethyl-5-oxo-4,5-dihydro-1H-1,2,4-triazol-1-yl)-4-(prop-1-en-2-yl)-2-(2-(trifluoromethyl)phenyl)isoquinolin-1(2H)-one. To a solution of 6-(3-((benzyloxy)methyl)-4-ethyl-5-oxo-4,5-dihydro-1H-1,2,4-triazol-1-yl)-4-(prop-1-en-2-yl)isoquinolin-1(2H)-one (300 mg, 0.57 mmol) and $Cs_2CO_3$ (369 mg, 1.13 mmol) in anhydrous DMF (1.5 mL) was added 2-fluorobenzotrifluoride (111 mg, 0.68 mmol). The mixture was stirred under nitrogen at 130° C. for 4 d, then cooled to room temperature. Water was added and the mixture was extracted with DCM. The combined organic layer was dried over anhydrous $Na_2SO_4$, filtered, and concentrated. The residue was purified by silica column chromatography (eluent: 0-1% MeOH in DCM) to give the title compound as a yellow solid (177 mg, yield: 49%). ESI-MS: mass calcd. for $C_{31}H_{27}F_3N_4O_3$, 560.2; m/z found, 561.2 $[M+H]^+$.

Step B. 6-(4-Ethyl-3-(hydroxymethyl)-5-oxo-4,5-dihydro-1H-1,2,4-triazol-1-yl)-4-(prop-1-en-2-yl)-2-(2-(trifluoromethyl)phenyl)isoquinolin-1(2H)-one. The mixture of 6-(3-((benzyloxy)methyl)-4-ethyl-5-oxo-4,5-dihydro-1H-1,2,4-triazol-1-yl)-4-(prop-1-en-2-yl)-2-(2-(trifluoromethyl)phenyl)isoquinolin-1(2H)-one (177 mg, 0.26 mmol) in TFA (3 mL) was heated in a sealed tube under nitrogen at 70° C. overnight, then cooled down to room temperature. The solution was quenched with saturated aqueous $NaHCO_3$ solution. The aqueous layer was extracted with DCM. The combined organic layers were dried over $Na_2SO_4$, filtered, and concentrated. The residue was purified by silica column chromatography (gradient elution: 0-40% EtOAc in DCM), then further purified by preparative reversed phase HPLC (Stationary phase: Boston Prime C18, 5 μm, 150×25 mm; Mobile phase: water (0.04% $NH_3 \cdot H_2O$+10 mM $NH_4HCO_3$) (A)—MeCN (B), gradient elution: 45-75% B in A over 8 min, flow rate: 25 mL/min) to give the title compound as a white solid (50 mg, yield: 35%). ESI-MS: mass calcd. for $C_{24}H_{21}F_3N_4O_3$, 470.2; m/z found, 471.2 $[M+H]^+$. $^1H$ NMR (400 MHz, DMSO-$d_6$) δ 8.42 (d, J=2.1 Hz, 1H), 8.35 (d, J=8.8 Hz, 1H), 8.13 (dd, J=8.8, 2.1 Hz, 1H), 7.94 (d, J=8.2 Hz, 1H), 7.84-7.90 (m, 1H), 7.72-7.78 (m, 1H), 7.67 (d, J=8.2 Hz, 1H), 7.27 (s, 1H), 5.83 (t, J=5.8 Hz, 1H), 5.36 (s, 1H), 5.07 (s, 1H), 4.52 (d, J=5.8 Hz, 2H), 3.80 (q, J=7.0 Hz, 2H), 2.10 (s, 3H), 1.28 (t, J=7.0 Hz, 3H) ppm; $^{19}F$ NMR (376 MHz, DMSO-$d_6$) δ −59.37 (s, 1F) ppm.

Example 13: 2-(6-(4-Ethyl-3-(hydroxymethyl)-5-oxo-4,5-dihydro-1H-1,2,4-triazol-1-yl)-1-oxo-4-(prop-1-en-2-yl)isoquinolin-2(1H)-yl)benzonitrile

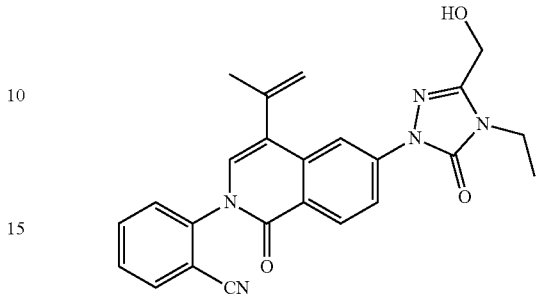

Step A. 2-(6-(3-((Benzyloxy)methyl)-4-ethyl-5-oxo-4,5-dihydro-1H-1,2,4-triazol-1-yl)-1-oxo-4-(prop-1-en-2-yl)isoquinolin-2(1H)-yl)benzonitrile. To a mixture of 6-(3-((benzyloxy)methyl)-4-ethyl-5-oxo-4,5-dihydro-1H-1,2,4-triazol-1-yl)-4-(prop-1-en-2-yl)isoquinolin-1(2H)-one (300 mg, 0.57 mmol) and $Cs_2CO_3$ (369 mg, 1.13 mmol) in DMF (1.5 mL) was added 2-fluorobenzonitrile (82.2 mg, 0.68 mmol) under nitrogen. Then the reaction mixture was heated at 85° C. for 20 h. The mixture was cooled to room temperature, poured into water, and extracted with EtOAc. The combined organic layer was dried over $Na_2SO_4$ and concentrated to dryness. The residue was purified by silica column chromatography (gradient elution: 0-10% EtOAc in DCM) to give the title compound as the crude product, which was used without further purification: a red gum (580 mg, crude). ESI-MS: mass calcd. for $C_{31}H_{27}N_5O_3$, 517.2; m/z found, 518.2 $[M+H]^+$. $^1H$ NMR (400 MHz, CDCl$_3$) δ 8.56 (d, J=8.8 Hz, 1H), 8.49 (d, J=2.0 Hz, 1H), 8.16 (dd, J=8.8, 2.0 Hz, 1H), 7.82-7.86 (m, 1H), 7.77 (td, J=7.9, 1.3 Hz, 1H), 7.54-7.60 (m, 2H), 7.34-7.42 (m, 5H), 7.01 (s, 1H), 5.38 (s, 1H), 5.22 (s, 1H), 4.62 (s, 2H), 4.55 (s, 2H), 3.87 (q, J=7.3 Hz, 2H), 2.21 (s, 3H), 1.36 (t, J=7.3 Hz, 3H) ppm.

Step B. 2-(6-(4-Ethyl-3-(hydroxymethyl)-5-oxo-4,5-dihydro-1H-1,2,4-triazol-1-yl)-1-oxo-4-(prop-1-en-2-yl)isoquinolin-2(1H)-yl)benzonitrile. To a solution of 2-(6-(3-((benzyloxy)methyl)-4-ethyl-5-oxo-4,5-dihydro-1H-1,2,4-triazol-1-yl)-1-oxo-4-(prop-1-en-2-yl)isoquinolin-2(1H)-yl)benzonitrile (500 mg crude, 0.89 mmol) in DCM (27 mL) at −78° C. was added a toluene solution (1 M) of $BCl_3$ (4.5 mL, 4.5 mmol) under nitrogen. The reaction mixture was stirred at −78° C. for 1 h. MeOH (3 mL) was added at −78° C. and then the mixture was stirred for 0.5 h. The mixture was diluted with DCM, washed with saturated aqueous $NaHCO_3$ solution. The organic layer was separated, dried with $Na_2SO_4$, filtered, and concentrated. The residue was purified by preparative reversed phase HPLC (Stationary phase: Boston Prime C18, 5 μm, 150×25 mm; Mobile phase: $H_2O$ (0.04% $NH_3 \cdot H_2O$+10 mM $NH_4HCO_3$) (A)—MeCN (B), gradient elution: 40-70% B in A over 8 min, flow rate: 25 mL/min) to give the title compound as a white solid (48 mg, yield: 14% for two steps). ESI-MS: mass calcd. for $C_{24}H_{21}N_5O_3$, 427.2; m/z found, 428.2 $[M+H]^+$. $^1H$ NMR (400 MHz, DMSO-$d_6$) δ 8.41 (d, J=2.0 Hz, 1H), 8.37 (d, J=8.8 Hz, 1H), 8.17 (dd, J=8.8, 2.0 Hz, 1H), 8.06 (d, J=8.0 Hz, 1H), 7.88-7.94 (m, 1H), 7.75 (d, J=8.0 Hz, 1H), 7.66 (t, J=7.7 Hz, 1H), 7.44 (s, 1H), 5.79 (br t, J=5.0 Hz, 1H), 5.42 (s, 1H), 5.17 (s, 1H), 4.53 (br d, J=5.0 Hz, 2H), 3.81 (q, J=7.2 Hz, 2H), 2.14 (s, 3H), 1.29 (t, J=7.2 Hz, 3H) ppm.

Example 14: 2-(2-Chlorophenyl)-6-(4-ethyl-3-(hydroxymethyl)-5-oxo-4,5-dihydro-1H-1,2,4-triazol-1-yl)-4-(prop-1-en-2-yl)isoquinolin-1(2H)-one

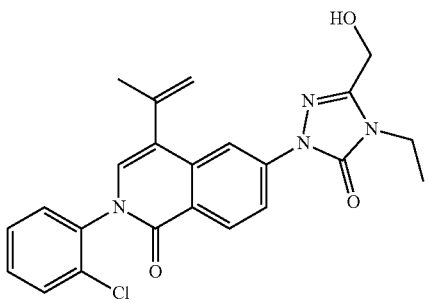 [SMILES: C=C(C)c1cn(-c2ccccc2Cl)c(=O)c2ccc(-n3nc(CO)n(CC)c3=O)cc12]

Step A. 6-(3-(((tert-Butyldiphenylsilyl)oxy)methyl)-4-ethyl-5-oxo-4,5-dihydro-1H-1,2,4-triazol-1-yl)isoquinolin-1(2H)-one. To a mixture of 6-bromo-2H-isoquinolin-1-one (1 g, 4.5 mmol) in anhydrous 1,4-dioxane (10 mL) was added 5-(((tert-butyldiphenylsilyl)oxy)methyl)-4-ethyl-2,4-dihydro-3H-1,2,4-triazol-3-one (Intermediate 2, 2.1 g, 5.4 mmol), $Cs_2CO_3$ (2.6 g, 8 mmol), CuI (0.4 g, 2.2 mmol), KI (0.5 mg, 3.1 mmol) and trans-1,2-diaminocyclohexane (0.3 g, 2.7 mmol) under nitrogen. The reaction was heated under nitrogen at 110° C. overnight. The mixture was filtered through a short pad of Celite® and the filtrate was evaporated under reduced pressure. The crude was purified by silica column chromatography (gradient elution: 0-30% EtOAc in petroleum ether) to give the title compound as a yellow solid (1.2 g, yield: 46%). ESI-MS: mass calcd. for $C_{30}H_{32}N_4O_3Si$, 524.2; m/z found, 525.1 [M+H]$^+$. $^1$H NMR (400 MHz, DMSO-d$_6$) δ 11.23 (br d, J=5.1 Hz, 1H), 8.23 (d, J=8.8 Hz, 1H), 8.06 (d, J=2.0 Hz, 1H), 7.97 (dd, J=8.8, 2.0 Hz, 1H), 7.62-7.70 (m, 4H), 7.41-7.51 (m, 6H), 7.14-7.22 (m, 1H), 6.57 (d, J=7.1 Hz, 1H), 4.75 (s, 2H), 3.82 (q, J=7.1 Hz, 2H), 1.29 (t, J=7.1 Hz, 3H), 1.03 (s, 9H) ppm.

Step B. 6-(3-(((tert-Butyldiphenylsilyl)oxy)methyl)-4-ethyl-5-oxo-4,5-dihydro-1H-1,2,4-triazol-1-yl)-4-iodoisoquinolin-1(2H)-one. A mixture of 6-(3-(((tert-butyldiphenylsilyl)oxy)methyl)-4-ethyl-5-oxo-4,5-dihydro-1H-1,2,4-triazol-1-yl)isoquinolin-1(2H)-one (1.2 g, 2 mmol) in anhydrous acetonitrile (MeCN) (30 mL) was added N-iodosuccinimide (NIS) (0.5 g, 2.4 mmol). The reaction mixture was heated at reflux for 3 h. Then the mixture was cooled to room temperature and evaporated under reduced pressure. The residue was purified by silica column chromatography (gradient elution: 0-30% EtOAc in petroleum ether) to give the title compound as a yellow solid (1.1 g, yield: 74%). ESI-MS: mass calcd. for $C_{30}H_{31}IN_4O_3Si$, 650.1; m/z found, 651.1 [M+H]$^+$. $^1$H NMR (400 MHz, DMSO-d$_6$) δ 11.49 (br s, 1H), 8.22-8.31 (m, 2H), 8.03 (dd, J=8.8, 2.0 Hz, 1H), 7.64-7.72 (m, 5H), 7.44-7.49 (m, 6H), 4.77 (s, 2H), 3.83 (q, J=7.2 Hz, 2H), 1.30 (t, J=7.2 Hz, 3H), 1.04 (s, 9H) ppm.

Step C. 6-(4-Ethyl-3-(hydroxymethyl)-5-oxo-4,5-dihydro-1H-1,2,4-triazol-1-yl)-4-(prop-1-en-2-yl)isoquinolin-1(2H)-one. To a mixture of 6-(3-(((tert-butyldiphenylsilyl)oxy)methyl)-4-ethyl-5-oxo-4,5-dihydro-1H-1,2,4-triazol-1-yl)-4-iodoisoquinolin-1(2H)-one (500 mg, 0.69 mmol) in EtOH (20 mL) and $H_2O$ (5 mL) under nitrogen was added isopropenylboronic acid pinacol ester (288 mg, 1.71 mmol), $PdCl_2(PPh_3)_2$ (241 mg, 0.34 mmol) and $Cs_2CO_3$ (670 mg, 2.06 mmol) respectively. The reaction mixture was heated under nitrogen at 100° C. for 12 h. The mixture was concentrated to a small volume, and then water was added. The mixture was extracted with EtOAc. The organic layers were separated, washed with brine, dried over $Na_2SO_4$, filtered and evaporated under reduced pressure. The residue was purified by silica column chromatography (gradient elution: 0-10% MeOH in DCM) to give the title compound as a yellow solid (105 mg, yield: 47%). ESI-MS: mass calcd. for $C_{17}H_{18}N_4O_3$, 326.1; m/z found, 327.2 [M+H]$^+$. $^1$H NMR (400 MHz, DMSO-d$_6$) δ 11.27 (br d, J=5.3 Hz, 1H), 8.23-8.39 (m, 2H), 8.06 (dd, J=8.8, 2.0 Hz, 1H), 7.03 (d, J=5.8 Hz, 1H), 5.79 (t, J=5.9 Hz, 1H), 5.34 (s, 1H), 5.07 (s, 1H), 4.51 (d, J=5.9 Hz, 2H), 3.79 (q, J=7.3 Hz, 2H), 2.09 (s, 3H), 1.27 (t, J=7.3 Hz, 3H) ppm.

Step D. 2-(2-Chlorophenyl)-6-(4-ethyl-3-(hydroxymethyl)-5-oxo-4,5-dihydro-1H-1,2,4-triazol-1-yl)-4-(prop-1-en-2-yl)isoquinolin-1(2H)-one. To a mixture of 6-(4-ethyl-3-(hydroxymethyl)-5-oxo-4,5-dihydro-1H-1,2,4-triazol-1-yl)-4-(prop-1-en-2-yl)isoquinolin-1(2H)-one (105 mg, 0.32 mmol) in DMF (6 mL) was added 2-chlorophenylboronic acid (201 mg, 1.3 mmol), $Et_3N$ (65 mg, 0.64 mmol) and $Cu(OAc)_2$ (58 mg, 0.32 mmol), respectively. The reaction mixture was stirred under 02 (15 Psi) at room temperature for 72 h. The reaction was quenched by the addition of saturated aqueous $NH_4Cl$ solution. The mixture was extracted with EtOAc. The organic layer was separated, washed with brine, dried over $Na_2SO_4$, filtered, and concentrated. The residue was purified by preparative reversed phase HPLC (Stationary phase: Xtimate $C_{18}$, 5 µm, 150×25 mm; Mobile phase: water (0.225% formic acid) (A)—MeCN (B), gradient elution: 57-87% B in A over 7 min, flow rate: 30 mL/min) to give the title compound as a yellow solid (4.7 mg, yield: 3%).

ESI-MS: mass calcd. for $C_{23}H_{21}C_1N_4O_3$, 436.1; m/z found, 437.1 [M+H]$^+$. $^1$H NMR (400 MHz, DMSO-d$_6$) δ 8.40 (d, J=1.96 Hz, 1H), 8.35 (d, J=8.80 Hz, 1H), 8.12 (dd, J=1.96, 8.80 Hz, 1H), 7.64-7.70 (m, 1H), 7.55-7.61 (m, 1H), 7.47-7.53 (m, 2H), 7.22 (s, 1H), 5.79 (t, J=5.87 Hz, 1H), 5.37 (s, 1H), 5.11 (s, 1H), 4.50 (d, J=5.87 Hz, 2H), 3.78 (q, J=7.09 Hz, 2H), 2.10 (s, 3H), 1.26 (br t, J=7.09 Hz, 3H) ppm.

Example 15: 6-(4-Ethyl-3-(hydroxymethyl)-5-oxo-4,5-dihydro-1H-1,2,4-triazol-1-yl)-4-(prop-1-en-2-yl)-2-(o-tolyl)isoquinolin-1(2H)-one

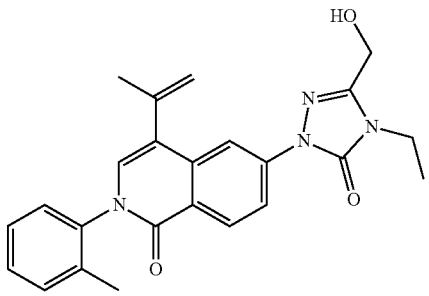 [SMILES: C=C(C)c1cn(-c2ccccc2C)c(=O)c2ccc(-n3nc(CO)n(CC)c3=O)cc12]

To a mixture of 6-(4-ethyl-3-(hydroxymethyl)-5-oxo-4,5-dihydro-1H-1,2,4-triazol-1-yl)-4-(prop-1-en-2-yl)isoquinolin-1(2H)-one (200 mg, 0.6 mmol) in DMF (6 mL) was added 2-methylphenyl boronic acid (304 mg, 2.2 mmol), $Et_3N$ (227 mg, 2.2 mmol) and $Cu(OAc)_2$ (102 mg, 0.6 mmol), respectively. The reaction mixture was stirred under 02 (15 Psi) at room temperature for 72 h. The reaction was quenched by the addition of saturated aqueous $NH_4Cl$ solution. The mixture was extracted with EtOAc. The organic layer was separated, washed with brine, dried over Na$_2$SO$_4$, filtered, and concentrated. The residue was purified by preparative reversed phase HPLC (Stationary phase: Phenomenex Gemini-NX, 5 μm, 150×30 mm; Mobile phase: water (0.04% NH$_3$·H$_2$O+10 mM NH$_4$HCO$_3$) (A)—MeCN (B), gradient elution: 42-72% B in A over 8 min, flow rate: 25 mL/min) to give the title compound as a yellow solid (28 mg, yield: 12%). ESI-MS: mass calcd. for C$_{24}$H$_{24}$N$_4$O$_3$, 416.2; m/z found, 417.3 [M+H]$^+$. $^1$H NMR (400 MHz, DMSO-d$_6$) δ 8.39 (d, J=1.71 Hz, 1H), 8.35 (d, J=8.80 Hz, 1H), 8.10 (dd, J=1.71, 8.80 Hz, 1H), 7.27-7.42 (m, 4H), 7.16 (s, 1H), 5.79 (t, J=5.87 Hz, 1H), 5.35 (s, 1H), 5.11 (s, 1H), 4.49 (d, J=5.87 Hz, 2H), 3.77 (q, J=7.09 Hz, 2H), 2.09 (s, 3H), 2.05 (s, 3H), 1.25 (t, J=7.09 Hz, 3H) ppm.

Example 16: 6-(4-Ethyl-3-(hydroxymethyl)-5-oxo-4,5-dihydro-1H-1,2,4-triazol-1-yl)-2-(2-fluoro-4-nitrophenyl)-4-iodoisoquinolin-1(2H)-one

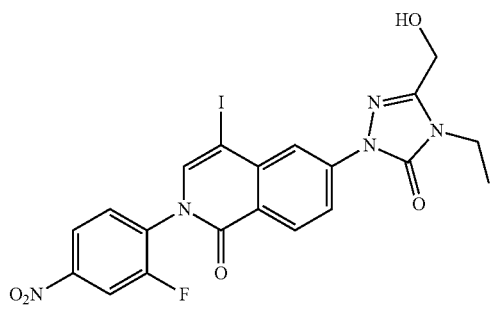 [SMILES: CCn1c(CO)nn(-c2ccc3c(=O)n(-c4ccc([N+](=O)[O-])cc4F)cc(I)c3c2)c1=O]

To a mixture of 6-(3-((((tert-butyldiphenylsilyl)oxy)methyl)-4-ethyl-5-oxo-4,5-dihydro-1H-1,2,4-triazol-1-yl)-4-iodo-isoquinolin-1(2H)-one (120 mg, 0.18 mmol) and Cs$_2$CO$_3$ (63 mg, 0.45 mmol) in anhydrous DMF (1.2 mL) was added 3,4-difluoronitrobenzene (29 mg, 0.18 mmol) under nitrogen. The reaction mixture was stirred under nitrogen at room temperature for 2 d. The mixture was filtered through a pad of Celite® and the pad was washed with EtOAc. The filtrate was combined and concentrated. The residue was purified by preparative reversed phase HPLC (Stationary phase: Boston Green ODS, 5 μm, 150×30 mm; Mobile phase: H$_2$O (0.04% NH$_3$·H$_2$O+10 mM NH$_4$HCO$_3$) (A)—MeCN (B), gradient elution: 45-75% B in A over 8 min, flow rate: 25 mL/min) to give the title compound as a yellow solid (25 mg, yield: 29%). ESI-MS: mass calcd. for C$_{20}$H$_{15}$IN$_5$O$_5$, 551.0; m/z found, 551.8 [M+H]$^+$. $^1$H NMR (400 MHz, DMSO-d$_6$) δ 8.43 (d, J=1.96 Hz, 1H), 8.37 (dd, J=2.27, 9.24 Hz, 1H), 8.32 (d, J=8.80 Hz, 1H), 8.21-8.25 (m, 1H), 8.19 (dd, J=2.27, 9.24 Hz, 1H), 8.04 (s, 1H), 7.91-7.98 (m, 1H), 4.51 (s, 2H), 3.79 (q, J=7.09 Hz, 2H), 1.27 (t, J=7.09 Hz, 3H) ppm; $^{19}$F NMR (376 MHz, DMSO-d$_6$) δ −115.27 (br t, J=8.4 Hz, 1F) ppm.

Example 17: 2-(2-Chlorophenyl)-6-(4-ethyl-3-(hydroxymethyl)-5-oxo-4,5-dihydro-1H-1,2,4-triazol-1-yl)-4-isopropylphthalazin-1(2H)-one

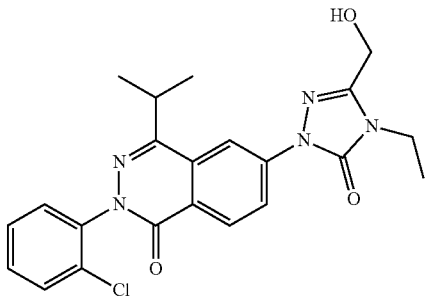 [SMILES: CCn1c(CO)nn(-c2ccc3c(=O)n(-c4ccccc4Cl)nc(C(C)C)c3c2)c1=O]

Step A. 4-Bromo-2-isobutyrylbenzoic acid and 5-bromo-2-isobutyrylbenzoic acid. To a suspension of CdCl$_2$ (3.8 g, 20.5 mmol) in THF (30 mL) was added a THF solution (2 M) of i-PrMgCl (20.5 mL, 41 mmol) at 0° C. The mixture was heated under nitrogen at 45° C. for 1 h, then cooled to 0° C., followed by the addition of a THF solution (7 mL) of 4-bromophthalic anhydride (3.5 g, 15.4 mmol) under nitrogen. The reaction mixture was stirred at 45° C. for 12 h, then concentrated. Then aqueous HCl solution (1 M) was added, and the mixture was extracted with EtOAc twice. The combined organic extract was dried over anhydrous Na$_2$SO$_4$, filtered and concentrated to give the crude regio-isomeric mixture of two title compounds as a yellow oil (4.9 g), which was used in the next step without further purification.

Step B. Ethyl 4-bromo-2-isobutyrylbenzoate and ethyl 5-bromo-2-isobutyrylbenzoate. To a solution of the mixture of crude 4-bromo-2-isobutyrylbenzoic acid and 5-bromo-2-isobutyrylbenzoic acid (4.9 g mixture, 9.1 mmol) in DMF (14 mL) was added K$_2$CO$_3$ (3.8 g, 27 mmol) and iodoethane (2.2 mL, 27 mmol). The reaction was stirred at room temperature overnight. The mixture was filtered through a short pad of Celite® and the filtrate was concentrated. The residue was purified by silica column chromatography (gradient elution: 0-4% EtOAc in petroleum ether) to give the regio-isomeric mixture of two title compounds as an orange oil (4 g).

Step C. 6-Bromo-4-isopropylphthalazin-1(2H)-one. To a stirred solution of ethyl 4-bromo-2-isobutyrylbenzoate and ethyl 5-bromo-2-isobutyrylbenzoate (4 g mixture, 6.7 mmol) in EtOH (28 mL) was added NH$_2$NH$_2$·H$_2$O (6.1 mL, 107 mmol, 98%) at room temperature. The reaction mixture was refluxed at 90° C. for overnight. The mixture was cooled to room temperature and the precipitate was collected by filtration. The filtrate was concentrated, and the residue was triturated with EtOAc. The precipitate was collected by filtration. The two batches of the precipitates were combined, rinsed with water, dried in vacuo to give the title compound as a yellow solid (819 mg, yield of three steps: 20%). ESI-MS: mass calcd. for C$_{11}$H$_{11}$BrN$_2$O, 266.0; m/z found, 267.0 [M+H]$^+$. $^1$H NMR (400 MHz, DMSO-d$_6$) δ 12.63 (s, 1H), 8.25 (s, J=1.47 Hz, 1H), 8.18 (d, J=8.56 Hz, 1H), 8.02 (dd, J=1.47, 8.56 Hz, 1H), 3.58 (q, J=6.51 Hz, 1H), 1.25 (d, J=6.51 Hz, 6H) ppm.

The filtrate was concentrated, and the residue was purified by flash column chromatography (20-75% EtOAc in heptane) to give the second compound 7-bromo-4-isopropylphthalazin-1(2H)-one as a white solid (320 mg, yield of three steps: 8%). ESI-MS: mass calcd. for $C_{11}H_{11}BrN_2O$, 266.0; m/z found, 267.0 [M+H]$^+$. $^1$H NMR (400 MHz, DMSO-d$_6$) δ 12.68 (s, 1H), 8.36 (s, 1H), 8.09-8.17 (m, 1H), 7.95-8.07 (m, 1H), 3.46-3.63 (m, 1H), 1.26 (d, J=6.57 Hz, 6H) ppm.

Step D. 6-(3-(((tert-Butyldiphenylsilyl)oxy)methyl)-4-ethyl-5-oxo-4,5-dihydro-1H-1,2,4-triazol-1-yl)-4-isopropylphthalazin-1(2H)-one. To a solution of 6-bromo-4-isopropylphthalazin-1(2H)-one (619 mg, 2.3 mmol) in 1,4-dioxane (18.5 mL) was added 5-(((tert-butyldiphenylsilyl)oxy)methyl)-4-ethyl-2,4-dihydro-3H-1,2,4-triazol-3-one (Intermediate 2, 1.06 g, 2.8 mmol), Cs$_2$CO$_3$ (1.4 g, 4.2 mmol), CuI (221 mg, 1.2 mmol), KI (269 mg, 1.6 mmol) and trans-1,2-diaminocyclohexane (159 mg, 1.4 mmol) under nitrogen. The reaction was heated under nitrogen at 110° C. for overnight. The mixture was cooled to room temperature, diluted with water, and then extracted with EtOAc. The combined organic extract was dried over anhydrous Na$_2$SO$_4$, filtered and concentrated. The residue was purified by silica column chromatography (gradient elution: 0-32% EtOAc in petroleum ether) to give the title compound as a yellow solid (410 mg, yield: 31%). ESI-MS: mass calcd. for $C_{32}H_{37}N_5O_3Si$, 567.3; m/z found, 568.3 [M+H]$^+$. $^1$H NMR (400 MHz, CDCl$_3$) δ 9.89 (s, 1H), 8.65 (d, J=1.9 Hz, 1H), 8.50 (d, J=8.8 Hz, 1H), 8.31 (dd, J=8.8, 1.9 Hz, 1H), 7.71 (dd, J=7.8, 1.5 Hz, 4H), 7.38-7.52 (m, 6H), 4.70 (s, 2H), 3.94 (q, J=7.0 Hz, 2H), 3.53 (q, J=7.0 Hz, 1H), 1.35-1.44 (m, 9H), 1.11 (s, 9H) ppm.

Step E. 6-(3-(((tert-Butyldiphenylsilyl)oxy)methyl)-4-ethyl-5-oxo-4,5-dihydro-1H-1,2,4-triazol-1-yl)-2-(2-chlorophenyl)-4-isopropylphthalazin-1(2H)-one. To a solution of 6-(3-(((tert-butyldiphenylsilyl)oxy)methyl)-4-ethyl-5-oxo-4,5-dihydro-1H-1,2,4-triazol-1-yl)-4-isopropylphthalazin-1 (2H)-one (881 mg, 1.6 mmol) in DMF (10 mL) was added 2-chlorophenylboronic acid (971 mg, 6.2 mmol), Cu(OAc)$_2$ (282 mg, 1.6 mmol) and Et$_3$N (0.4 mL, 3.1 mmol). The reaction mixture was stirred under O2 (15 Psi) at room temperature for 5 d. The reaction was quenched by the addition of saturated aqueous NH$_4$Cl solution. The mixture was extracted with EtOAc twice and the organic layer was separated. The combined organic extract was dried over anhydrous Na$_2$SO$_4$, filtered and concentrated. The residue was purified by silica column chromatography (gradient elution: 0-32% EtOAc in petroleum ether) to give the title compound as a brown oil (36 mg, yield: 3%). ESI-MS: mass calcd. for $C_{38}H_{40}ClN_5O_3Si$, 677.3; m/z found, 678.2 [M+H]$^+$. $^1$H NMR (400 MHz, CDCl$_3$) δ 8.64 (d, J=1.9 Hz, 1H), 8.52 (d, J=8.8 Hz, 1H), 8.29 (dd, J=8.8, 1.9 Hz, 1H), 7.63-7.71 (m, 4H), 7.33-7.56 (m, 10H), 4.67 (s, 2H), 3.91 (q, J=7.0 Hz, 2H), 3.54 (q, J=6.7 Hz, 1H), 1.33-1.41 (m, 9H), 1.08 (s, 9H) ppm.

Step F. 2-(2-Chlorophenyl)-6-(4-ethyl-3-(hydroxymethyl)-5-oxo-4,5-dihydro-1H-1,2,4-triazol-1-yl)-4-isopropylphthalazin-1(2H)-one. To a solution of 6-(3-(((tert-butyldiphenylsilyl)oxy)methyl)-4-ethyl-5-oxo-4,5-dihydro-1H-1,2,4-triazol-1-yl)-2-(2-chlorophenyl)-4-isopropylphthalazin-1 (2H)-one (18 mg, 0.03 mmol) in THF (2.5 mL) was added triethylamine trihydrogen fluoride (Et$_3$N·3HF) (64.2 mg, 0.40 mmol). The reaction mixture was stirred at 60° C. for 4 h. The mixture was cooled to room temperature and concentrated. The residue was diluted with water and the mixture was extracted with EtOAc twice. The organic layers were combined, dried, filtered and concentrated. The residue was purified by preparative reversed phase HPLC (Stationary phase: HT C18 Highload, 5 μm, 150×25 mm; Mobile phase: water (0.04% NH$_3$·H$_2$O+10 mM NH$_4$HCO$_3$) (A)—MeCN (B), gradient elution: 38-68% B in A over 7.5 min, flow rate: 30 mL/min) to give the title compound as a white solid (2.6 mg, yield: 22%). ESI-MS: mass calcd. for $C_{22}H_{22}Cl_1N_5O_3$, 439.1; m/z found, 440.2 [M+H]$^+$. $^1$H NMR (400 MHz, CDCl$_3$) δ 8.73 (d, J=1.8 Hz, 1H), 8.58 (d, J=8.8 Hz, 1H), 8.38 (dd, J=8.7, 1.8 Hz, 1H), 7.54-7.60 (m, 1H), 7.49-7.54 (m, 1H), 7.37-7.47 (m, 2H), 4.72 (s, 2H), 3.94 (q, J=7.3 Hz, 2H), 3.59 (q, J=6.7 Hz, 1H), 2.37 (s, 1H), 1.45 (t, J=7.3 Hz, 3H), 1.39 (d, J=6.7 Hz, 6H) ppm.

Example 18: 6-(4-Ethyl-3-(hydroxymethyl)-5-oxo-4,5-dihydro-1H-1,2,4-triazol-1-yl)-2-(3-fluorophenyl)-4-isopropylphthalazin-1(2H)-one

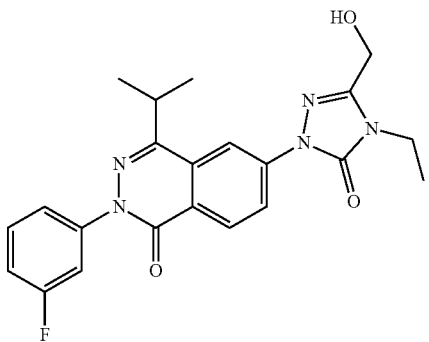 [SMILES: CCn1c(CO)nn(-c2ccc3c(=O)n(-c4cccc(F)c4)nc(C(C)C)c3c2)c1=O]

Step A. 6-Bromo-2-(3-fluorophenyl)-4-isopropylphthalazin-1(2H)-one. To a solution of 6-bromo-4-isopropylphthalazin-1(2H)-one (300 mg, 1.1 mmol) in DCM (20 mL) was added 3-fluorophenylboronic acid (471 mg, 3.4 mmol), Cu(OAc)$_2$ (245 mg, 1.3 mmol), pyridine (0.27 mL, 3.3 mmol) and Et$_3$N (3 mL, 22 mmol). The reaction mixture was stirred under air at room temperature for 18 h. The reaction was filtered through a short pad of silica gel and the silica gel was washed with EtOAc. The combined filtrate was concentrated. The residue was purified by silica column chromatography (gradient elution: 20-50% EtOAc in heptane) to give the title compound as a colorless gum (250 mg, yield: 62%). LCMS (ES-API): mass calcd. for $C_{17}H_{14}BrFN_2O$, 360.0; m/z found, 361.0 [M+H]$^+$.

Step B. 6-(3-(((tert-Butyldiphenylsilyl)oxy)methyl)-4-ethyl-5-oxo-4,5-dihydro-1H-1,2,4-triazol-1-yl)-2-(3-fluorophenyl)-4-isopropylphthalazin-1(2H)-one. To a mixture of 6-bromo-2-(3-fluorophenyl)-4-isopropylphthalazin-1(2H)-one (250 mg, 0.69 mmol) and K$_3$PO$_4$ (441 mg, 2.1 mmol) in anhydrous 1,4-dioxane (8 mL) was added 5-(((tert-butyldiphenylsilyl)oxy)methyl)-4-ethyl-2,4-dihydro-3H-1,2,4-triazol-3-one (Intermediate 2, 528 mg, 1.4 mmol), CuI (132 mg, 0.69 mmol), and trans-N,N'-dimethylcyclohexane-1,2-diamine (98 mg, 0.69 mmol), respectively. The mixture was slowly heated and stirred under nitrogen at 95° C. for 2 h, then cooled to 25° C. and quenched with addition of water. The mixture was extracted with ethyl acetate (50 mL×2). The combined organic extract was washed with brine, dried with anhydrous Na$_2$SO$_4$, filtered, and concentrated. The residue was purified by silica gel chromatography (20-50% EtOAc in heptane) to afford the desired product as a white solid (200 mg, 43%). LCMS (ES-API): mass calcd. for $C_{38}H_{40}FN_5O_3Si$, 661.3; m/z found, 662.4 [M+H]$^+$. $^1$H NMR (400 MHz, CDCl$_3$) δ 8.66 (br s, 1H), 8.58 (d, J=8.59 Hz, 1H), 8.33 (br d, J=8.59 Hz, 1H), 7.70 (br d, J=6.57 Hz, 4H), 7.65 (br d, J=8.08 Hz, 1H), 7.58 (br d, J=10.61 Hz, 1H), 7.38-7.51 (m, 7H), 7.05 (br t, J=8.08 Hz, 1H), 4.70 (s, 2H), 3.94 (q, J=7.07 Hz, 2H), 3.59 (q, J=6.76 Hz, 1H), 1.36-1.46 (m, 9H), 1.11 (s, 9H) ppm.

Step C. 6-(4-Ethyl-3-(hydroxymethyl)-5-oxo-4,5-dihydro-1H-1,2,4-triazol-1-yl)-2-(3-fluorophenyl)-4-isopropylphthalazin-1(2H)-one. To a solution of 6-(3-(((tert-butyldiphenylsilyl)oxy)methyl)-4-ethyl-5-oxo-4,5-dihydro-1H-1,2,4-triazol-1-yl)-2-(3-fluorophenyl)-4-isopropylphthalazin-1(2H)-one (200 mg, 0.3 mmol) in tetrahydrofuran (THF) (10 mL) was added a tetrahydrofuran (THF) solution (1 M) of tetrabutylammonium fluoride (0.45 mL, 0.45 mmol). The reaction mixture was stirred at 25° C. for 0.5 h. The mixture was diluted with H$_2$O (15 mL) and extracted with ethyl acetate (50 mL×2). The combined organic extract washed with brine (20 mL), dried over Na$_2$SO$_4$, filtered, and concentrated. The residue was purified by flash column chromatography (SiO$_2$, 30-70% EtOAc in heptane) to afford the title compound as a white solid (120 mg, yield 94%). LCMS (ES-API): mass calcd. for C$_{22}$H$_{22}$FN$_5$O$_3$, 423.2; m/z found, 424.2 [M+H]$^+$. $^1$H NMR (400 MHz, DMSO-d$_6$) δ 8.65 (d, J=1.96 Hz, 1H), 8.49 (d, J=8.80 Hz, 1H), 8.42 (dd, J=1.96, 8.80 Hz, 1H), 7.52-7.64 (m, 3H), 7.22-7.31 (m, 1H), 5.87 (br s, 1H), 4.55 (br s, 2H), 3.83 (q, J=7.18 Hz, 2H), 3.54 (q, J=6.56 Hz, 1H), 1.35 (d, J=6.56 Hz, 6H), 1.31 (t, J=7.18 Hz, 3H) ppm.

Example 19: 2-(2-Chloro-6-fluorophenyl)-6-(4-ethyl-3-(hydroxymethyl)-5-oxo-4,5-dihydro-1H-1,2,4-triazol-1-yl)-4-isopropylphthalazin-1(2H)-one

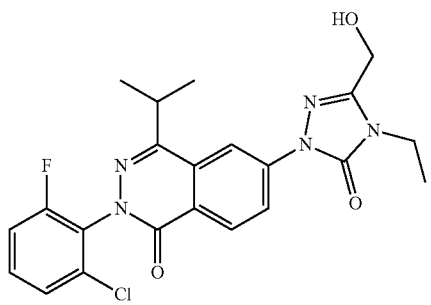 [SMILES: CCn1c(CO)nn(-c2ccc3c(=O)n(-c4c(F)cccc4Cl)nc(C(C)C)c3c2)c1=O]

Step A. Methyl 4-bromo-2-isobutyrylbenzoate. To a tube charged with methyl 4-bromo-2-iodobenzoate (1420 mg, 4.2 mmol) was added isobutyraldehyde (1201 mg, 17 mmol), Pd(OAc)$_2$ (94 mg, 0.4 mmol), Ag$_2$O (1255 mg, 5.4 mmol) and an aqueous solution (70% w/w) of tert-butyl hydroperoxide (TBHP) (2681 mg, 21 mmol). The reaction mixture was degassed with nitrogen, sealed and heated with stirring at 120° C. for 12 h. The reaction was cooled to room temperature, diluted with aqueous NaHCO$_3$ solution (50 mL) and extracted with ethyl acetate (100 mL×2). The combined organic extract washed with brine (20 mL), dried over Na$_2$SO$_4$, filtered, and concentrated. The residue was purified by silica column chromatography (gradient elution: 10-30% EtOAc in heptane) to give the title compound as a white solid (167 mg, yield: 14%). LCMS (ES-API): mass calcd. for C$_{12}$H$_{13}$BrO$_3$, 284.0; m/z found, 285.0 [M+H]$^+$. $^1$H NMR (400 MHz, CDCl$_3$) δ 7.83 (d, J=8.31 Hz, 1H), 7.62 (dd, J=1.96, 8.31 Hz, 1H), 7.42 (d, J=1.96 Hz, 1H), 3.88 (s, 3H), 3.02 (spt, J=6.89 Hz, 1H), 1.21 (d, J=6.89 Hz, 6H) ppm.

Step B. 6-Bromo-2-(2-chloro-6-fluorophenyl)-4-isopropylphthalazin-1(2H)-one. To a solution of methyl 4-bromo-2-isobutyrylbenzoate (167 mg, 0.6 mmol) in anhydrous ethanol (20 mL) was added 2-chloro-6-fluorophenylhydrazine (658 mg, 4.1 mmol) and conc. H$_2$SO$_4$ (10 mL). The reaction mixture was heated at 70° C. for 2 d. The reaction was cooled to room temperature, diluted with water (50 mL) and extracted with DCM (50 mL) and ethyl acetate (100 mL×2). The combined organic extract washed with brine (75 mL), dried over Na$_2$SO$_4$, filtered, and concentrated. The residue was purified by silica gel column chromatography (gradient elution: 20-50% EtOAc in heptane) to give the title compound as a white solid (21 mg, yield: 9%). LCMS (ES-API): mass calcd. for C$_{17}$H$_{13}$BrClFN$_2$O, 394.0; m/z found, 395.0 [M+H]$^+$. $^1$H NMR (400 MHz, CDCl$_3$) δ 8.40 (br d, J=8.34 Hz, 1H), 8.06 (s, 1H), 7.90 (br d, J=8.34 Hz, 1H), 7.32-7.45 (m, 2H), 7.19 (br t, J=8.34 Hz, 1H), 3.47 (spt, J=7.14 Hz, 1H), 1.36 (br d, J=7.14 Hz, 6H) ppm.

Step C. 6-(3-(((tert-Butyldiphenylsilyl)oxy)methyl)-4-ethyl-5-oxo-4,5-dihydro-1H-1,2,4-triazol-1-yl)-2-(2-chloro-6-fluorophenyl)-4-isopropylphthalazin-1(2H)-one. To a mixture of 6-bromo-2-(2-chloro-6-fluorophenyl)-4-isopropylphthalazin-1(2H)-one (17 mg, 0.04 mmol) and K$_3$PO$_4$ (36 mg, 0.17 mmol) in anhydrous 1,4-dioxane (3 mL) was added 5-(((tert-butyldiphenylsilyl)oxy)methyl)-4-ethyl-2,4-dihydro-3H-1,2,4-triazol-3-one (Intermediate 2, 49 mg, 0.12 mmol), CuI (16 mg, 0.08 mmol), and trans-N,N'-dimethylcyclohexane-1,2-diamine (12 mg, 0.08 mmol), respectively. The mixture was slowly heated and stirred under nitrogen at 95° C. for 3 h, then cooled to 25° C. and quenched with addition of water. The mixture was extracted with ethyl acetate (50 mL×2). The combined organic extract was washed with brine, dried with anhydrous Na$_2$SO$_4$, filtered, and concentrated. The residue was purified by silica gel column chromatography (SiO$_2$, 20-50% EtOAc in heptane) to afford the desired product as a white solid (17 mg, 57%). LCMS (ES-API): mass calcd. for C$_{38}$H$_{39}$ClFN$_5$O$_3$Si, 695.3; m/z found, 696.3 [M+H]$^+$. $^1$H NMR (400 MHz, CDCl$_3$) δ 8.68 (s, 1H), 8.56 (br d, J=8.59 Hz, 1H), 8.32 (br d, J=8.59 Hz, 1H), 7.70 (br d, J=6.06 Hz, 4H), 7.33-7.51 (m, 8H), 7.20 (br d, J=8.08 Hz, 1H), 4.70 (s, 2H), 3.94 (br d, J=7.07 Hz, 3H), 3.57 (spt, J=7.01 Hz, 1H), 1.34-1.44 (m, 9H), 1.10 (br s, 9H) ppm.

Step D. 2-(2-Chloro-6-fluorophenyl)-6-(4-ethyl-3-(hydroxymethyl)-5-oxo-4,5-dihydro-1H-1,2,4-triazol-1-yl)-4-isopropylphthalazin-1(2H)-one. To a solution of 6-(3-(((tert-butyldiphenylsilyl)oxy)methyl)-4-ethyl-5-oxo-4,5-dihydro-1H-1,2,4-triazol-1-yl)-2-(2-chloro-6-fluorophenyl)-4-isopropylphthalazin-1(2H)-one (17 mg, 0.02 mmol) in tetrahydrofuran (THF) (1 mL) was added a tetrahydrofuran (THF) solution (1 M) of tetrabutylammonium fluoride (0.1 mL, 0.1 mmol). The reaction mixture was stirred at 25° C. for 0.5 h. The mixture was diluted with H$_2$O (15 mL) and extracted with ethyl acetate (50 mL×2). The combined organic extract washed with brine (20 mL), dried over Na$_2$SO$_4$, filtered, and concentrated. The residue was purified by silica gel column chromatography (SiO$_2$, 30-70% EtOAc in heptane), then further purified by prep-HPLC (C$_{18}$ column, 10-90% gradient MeCN in water) to afford the title compound as a white solid (8 mg, yield: 71%). LCMS (ES-API): mass calcd. for C$_{22}$H$_{21}$ClFN$_5$O$_3$, 457.1; m/z found, 458.1 [M+H]$^+$. $^1$H NMR (400 MHz, CDCl$_3$) δ 8.74 (br s, 1H), 8.58 (br d, J=8.59 Hz, 1H), 8.39 (br d, J=8.59 Hz, 1H), 7.34-7.45 (m, 2H), 7.20 (br d, J=8.08 Hz, 1H), 4.73 (br s, 2H), 3.94 (t, J=6.57 Hz, 2H), 3.52-3.65 (m, 1H), 2.06 (br s, 1H), 1.44 (br t, J=6.57 Hz, 3H), 1.38 (br d, J=7.14 Hz, 6H) ppm.

Example 20: 4-Ethyl-6-(4-ethyl-3-(hydroxymethyl)-5-oxo-4,5-dihydro-1H-1,2,4-triazol-1-yl)-2-(3-fluorophenyl)phthalazin-1(2H)-one

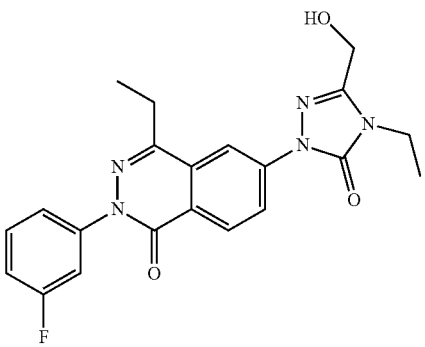 [SMILES: CCc1nn(-c2cccc(F)c2)c(=O)c2ccc(-n3nc(CO)n(CC)c3=O)cc12]

Step A. 4-Bromo-2-propionylbenzoic acid and 5-bromo-2-propionylbenzoic acid. To a mixture of CdCl$_2$ (3.6 g, 20 mmol) in THF (10 mL) was added a diethyl ether solution (3 M) of EtMgBr (13.3 mL, 40 mmol) at 0° C. The mixture was stirred at 45° C. for 1 h, then a THF solution (5 mL) of 4-bromophthalic anhydride (3.4 g, 15 mmol) was added under nitrogen. The reaction mixture was stirred at 45° C. for 12 h. The mixture was cooled to room temperature and concentrated. An aqueous HCl solution (1N) was added and the mixture was extracted with EtOAc. The combined organic layer was separated, dried with anhydrous Na$_2$SO$_4$, filtered, and concentrated to give the crude regio-isomeric mixture of two title compounds as a yellow oil (4.0 g), which was used in next step without further purification.

Step B. Ethyl 4-bromo-2-propionylbenzoate and ethyl 5-bromo-2-propionylbenzoate. To the mixture of 4-bromo-2-propionylbenzoic acid and 5-bromo-2-propionylbenzoic acid (4 g mixture, 7.7 mmol) in anhydrous DMF (15 mL) was added iodoethane (1.9 mL, 23 mmol) and K$_2$CO$_3$ (3.2 g, 23 mmol). The reaction mixture was stirred at room temperature for overnight. The mixture was filtered through a short pad of silica gel and the silica gel was washed with EtOAc. The filtrate was combined and concentrated. The residue was purified by silica column chromatography (SiO$_2$, gradient elution: 0-3% EtOAc in petroleum ether) to give the regio-isomeric mixture of two title compounds as a yellow oil (2.7 g, yield of two steps: 54%), which was used in the next step without further purification.

Step C. 6-Bromo-4-ethylphthalazin-1(2H)-one. To the mixture of ethyl 4-bromo-2-propionylbenzoate and ethyl 5-bromo-2-propionylbenzoate (2.4 g, 4.2 mmol) in EtOH (15 mL) was added NH$_2$NH$_2$·H$_2$O (924 mg, 18 mmol, 98%). The reaction mixture was stirred at room temperature for 6 h. The precipitate was collected by filtration. The filtrate was concentrated, and the residue was triturated with petroleum ether. The precipitate was collected. The collected precipitates were combined, washed with water, and dried in vacuo to give the title compound as a white solid (320 mg, yield: 24%). ESI-MS: mass calcd. for C$_{10}$H$_9$BrN$_2$O, 252.0; m/z found, 252.8 [M+H]$^+$. $^1$H NMR (400 MHz, DMSO-d$_6$) δ 12.55 (s, 1H), 8.11-8.15 (m, 2H), 7.98 (dd, J=8.3, 1.7 Hz, 1H), 2.92 (q, J=7.5 Hz, 2H), 1.20 (t, J=7.4 Hz, 3H) ppm. The second product 7-bromo-4-ethylphthalazin-1(2H)-one can be obtained from purification of the filtrate by flash column chromatography (20-75% EtOAc in heptane) but not characterized.

Step D. 6-Bromo-4-ethyl-2-(3-fluorophenyl)phthalazin-1(2H)-one. To a mixture of 6-bromo-4-ethylphthalazin-1(2H)-one (50 mg, 0.16 mmol) in DCM (2 mL) was added 3-fluorophenylboronic acid (45 mg, 0.32 mmol), Et$_3$N (32 mg, 0.32 mmol) and Cu(OAc)$_2$ (29 mg, 0.16 mmol). The reaction mixture was stirred under O2 (15 Psi) at room temperature for 12 h. Water was added, and the mixture was extracted with EtOAc. The organic layer was separated, dried over Na$_2$SO$_4$, filtered and evaporated under reduced pressure. The residue was purified by flash chromatography (SiO$_2$, gradient elution: 0-5% EtOAc in petroleum ether) to give the title compound as a white solid (60 mg, yield: 95%). ESI-MS: mass calcd. for C$_{16}$H$_{12}$BrFN$_2$O, 346.0; m/z found, 347.0 [M+H]$^+$.

Step E. 6-(3-(((tert-Butyldiphenylsilyl)oxy)methyl)-4-ethyl-5-oxo-4,5-dihydro-1H-1,2,4-triazol-1-yl)-4-ethyl-2-(3-fluorophenyl)phthalazin-1(2H)-one. To a mixture of 6-bromo-4-ethyl-2-(3-fluorophenyl)phthalazin-1(2H)-one (120 mg, 0.3 mmol) in anhydrous 1,4-dioxane (4 mL) was added 5-(((tert-butyldiphenylsilyl)oxy)methyl)-4-ethyl-2,4-dihydro-3H-1,2,4-triazol-3-one (Intermediate 2, 141 mg, 0.36 mmol), Cs$_2$CO$_3$ (177 mg, 0.54 mmol), CuI (29 mg, 0.15 mmol), KI (35 mg, 0.21 mmol) and trans-1,2-diaminocyclohexane (21 mg, 0.18 mmol) under nitrogen. The reaction mixture was heated under nitrogen at 110° C. for overnight. The mixture was cooled to room temperature, filtered through a short pad of Celite®. The filtrate was evaporated under reduced pressure. The residue was purified by flash chromatography (SiO$_2$, gradient elution: 0-14% EtOAc in petroleum ether) to give the title compound as a colorless gum (130 mg, yield: 66%). ESI-MS: mass calcd. for C$_{37}$H$_{38}$FN$_5$O$_3$Si, 647.3; m/z found, 648.3 [M+H]$^+$.

Step F. 4-Ethyl-6-(4-ethyl-3-(hydroxymethyl)-5-oxo-4,5-dihydro-1H-1,2,4-triazol-1-yl)-2-(3-fluorophenyl)phthalazin-1(2H)-one. To the solution of 6-(3-(((tert-butyldiphenylsilyl)oxy)methyl)-4-ethyl-5-oxo-4,5-dihydro-1H-1,2,4-triazol-1-yl)-4-ethyl-2-(3-fluorophenyl)phthalazin-1(2H)-one (20 mg, 0.03 mmol) in THF (2 mL) was added Et$_3$N·3HF (74 mg, 0.46 mmol). The reaction mixture was stirred at 60° C. for 1.5 h. The mixture was cooled to room temperature and concentrated. The residue was purified by preparative reversed phase HPLC (Stationary phase: Boston Prime C18, 5 μm, 150×30 mm; Mobile phase: water (0.05% ammonia hydroxide) (A)—MeCN (B), gradient elution: 45-75% B in A over 9 min, flow rate: 25 mL/min) to give the title compound as a yellow solid (9 mg, yield: 71%). ESI-MS: mass calcd. for C$_{21}$H$_{20}$FN$_5$O$_3$, 409.2; m/z found, 410.2 [M+H]$^+$. $^1$H NMR (400 MHz, DMSO-d$_6$) δ 8.51 (s, 1H), 8.37-8.46 (m, 2H), 7.47-7.60 (m, 3H), 7.16-7.28 (m, 1H), 5.82 (br s, 1H), 4.52 (br d, J=3.91 Hz, 2H), 3.80 (q, J=6.85 Hz, 2H), 2.98 (q, J=7.42 Hz, 2H), 1.28 (q, J=7.42 Hz, 6H) ppm; $^{19}$F NMR (376 MHz, DMSO-d$_6$) δ −112.70 (br s, 1F) ppm.

Example 21: 4-Ethyl-6-(4-ethyl-3-(hydroxymethyl)-5-oxo-4,5-dihydro-1H-1,2,4-triazol-1-yl)-2-(o-tolyl)phthalazin-1(2H)-one

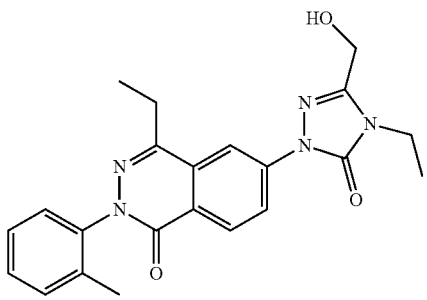 [SMILES: CCc1nn(-c2ccccc2C)c(=O)c2ccc(-n3nc(CO)n(CC)c3=O)cc12]

Step A. 6-Bromo-4-ethyl-2-(o-tolyl)phthalazin-1(2H)-one. To a mixture of 6-bromo-4-ethylphthalazin-1(2H)-one (50 mg, 0.16 mmol) in DCM (2 mL) was added 2-methylphenylboronic acid (43 mg, 0.32 mmol), Et$_3$N (32 mg, 032 mmol) and Cu(OAc)$_2$ (29 mg, 0.16 mmol). The reaction mixture was stirred under O2 (15 Psi) at room temperature for 12 h. Aqueous saturated NH$_4$Cl solution was added, and the mixture was extracted with EtOAc. The organic layer was separated, dried over Na$_2$SO$_4$, filtered and evaporated under vacuum. The residue was purified by prep-TLC (17% EtOAc in petroleum ether) to give the title compound as a yellow gum (23 mg, yield: 36%). ESI-MS: mass calcd. for C$_{17}$H$_{15}$BrN$_2$O, 342.0; m/z found, 343.0 [M+H]$^+$.

Step B. 6-(3-(((tert-Butyldiphenylsilyl)oxy)methyl)-4-ethyl-5-oxo-4,5-dihydro-1H-1,2,4-triazol-1-yl)-4-ethyl-2-(o-tolyl)phthalazin-1(2H)-one. To a mixture of 6-bromo-4-ethyl-2-(o-tolyl)phthalazin-1(2H)-one (23 mg, 0.06 mmol) in anhydrous 1,4-dioxane (1.5 mL) was added 5-(((tert-butyldiphenylsilyl)oxy)methyl)-4-ethyl-2,4-dihydro-3H-1,2,4-triazol-3-one (Intermediate 2, 27 mg, 0.07 mmol), Cs$_2$CO$_3$ (33 mg, 0.1 mmol), CuI (5 mg, 0.03 mmol), KI (7 mg, 0.04 mmol) and trans-1,2-diaminocyclohexane (4 mg, 0.03 mmol). The reaction was heated under nitrogen at 110° C. for overnight. The mixture was cooled to room temperature, filtered through a short pad of silica gel and the silica gel was washed with EtOAc. The combined filtrate was concentrated. The residue was purified by prep-TLC (25% EtOAc in petroleum ether) to give the title compound as a white solid (15 mg, yield: 35%). ESI-MS: mass calcd. for C$_{38}$H$_{41}$N$_5$O$_3$Si, 643.3; m/z found, 644.3 [M+H]$^+$.

Step C. 4-Ethyl-6-(4-ethyl-3-(hydroxymethyl)-5-oxo-4,5-dihydro-1H-1,2,4-triazol-1-yl)-2-(o-tolyl)phthalazin-1(2H)-one. To the solution of 6-(3-(((tert-butyldiphenylsilyl)oxy)methyl)-4-ethyl-5-oxo-4,5-dihydro-1H-1,2,4-triazol-1-yl)-4-ethyl-2-(o-tolyl)phthalazin-1(2H)-one (15 mg, 0.02 mmol) in THF (2 mL) was added Et$_3$N·3HF (49 mg, 0.3 mmol). The reaction mixture was stirred at 60° C. for 1 h. The mixture was cooled to room temperature and concentrated. The residue was purified by preparative reversed phase HPLC (Stationary phase: Xtimate C$_{18}$, 5 μm, 150×25 mm; Mobile phase: water (0.225% formic acid) (A)—MeCN (B), gradient elution: 44-74% B in A over 7 min, flow rate: 30 mL/min) to give the title compound as a yellow solid (7.3 mg, yield: 89%). ESI-MS: mass calcd. for C$_{22}$H$_{23}$N$_5$O$_3$, 405.2; m/z found, 406.2 [M+H]$^+$. $^1$H NMR (400 MHz, DMSO-d$_6$) δ 8.58 (s, 1H), 8.45 (s, 2H), 7.31-7.42 (m, 4H), 5.86 (t, J=5.9 Hz, 1H), 4.56 (d, J=5.9 Hz, 2H), 3.84 (q, J=7.1 Hz, 2H), 3.00 (q, J=7.4 Hz, 2H), 2.09 (s, 3H), 1.30-1.34 (m, 3H), 1.26-1.30 (m, 3H) ppm.

Example 22: 6-(4-Ethyl-3-(hydroxymethyl)-5-oxo-4,5-dihydro-1H-1,2,4-triazol-1-yl)-7-fluoro-4-isopropyl-2-(o-tolyl)isoquinolin-1(2H)-one

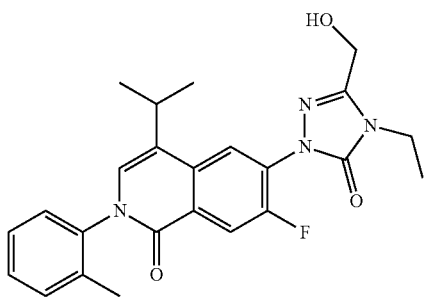 [SMILES: CCn1c(CO)nn(-c2cc3c(C(C)C)cn(-c4ccccc4C)c(=O)c3cc2F)c1=O]

Step A. 6-(3-((Benzyloxy)methyl)-4-ethyl-5-oxo-4,5-dihydro-1H-1,2,4-triazol-1-yl)-7-fluoro-4-isopropyl-2-(o-tolyl)isoquinolin-1(2H)-one. To a mixture of 5-((benzyloxy)methyl)-4-ethyl-2-(7-fluoro-3-hydroxy-4-isopropyl-1-oxoisochroman-6-yl)-2,4-dihydro-3H-1,2,4-triazol-3-one (Intermediate 11, 56 g, 123 mmol) in AcOH (160 mL) was added o-toluidine (14.8 g, 138 mmol). The reaction mixture was heated at 80° C. for 16 h. The mixture was concentrated, and then the "pH" was adjusted to 7-8 with aqueous NaHCO$_3$ solution. The mixture was extracted with ethyl acetate (160 mL×2). The combined organic extract was concentrated. The residue was purified by flash chromatography (SiO$_2$, 0-20% Ethyl acetate in DCM) to give the title compound as an oil (32.5 g, yield: 50%). MS (ESI): mass calcd. for C$_{31}$H$_{31}$FN$_4$O$_3$, 526.2; m/z found, 527.4 [M+H]$^+$. $^1$H NMR (300 MHz, CDCl$_3$) δ 8.33 (d, J=10.9 Hz, 1H), 8.07 (d, J=6.8 Hz, 1H), 7.44-7.27 (m, 9H), 6.84 (s, 1H), 4.64 (s, 2H), 4.55 (s, 2H), 3.89 (q, J=7.2 Hz, 2H), 3.23 (spt, J=6.8 Hz, 1H), 2.16 (s, 3H), 1.39 (t, J=7.2 Hz, 3H), 1.31 (dd, J=6.8, 2.1 Hz, 6H) ppm Step B. 6-(4-Ethyl-3-(hydroxymethyl)-5-oxo-4,5-dihydro-1H-1,2,4-triazol-1-yl)-7-fluoro-4-isopropyl-2-(o-tolyl)isoquinolin-1(2H)-one. To a stirred solution of 6-(3-((benzyloxy)methyl)-4-ethyl-5-oxo-4,5-dihydro-1H-1,2,4-triazol-1-yl)-7-fluoro-4-isopropyl-2-(o-tolyl)isoquinolin-1(2H)-one (26.5 g, 50.3 mmol) in DCM (230 mL) at −78° C. was added a DCM solution (1 M) of BCl$_3$ (290 mL, 290 mmol) under nitrogen. The reaction mixture was stirred at 15° C. for 0.5 h. The reaction was quenched by MeOH (100 mL) at −78° C. to −20° C. The mixture was partitioned between water and DCM. The organic layer was separated, and the aqueous layer was extracted with DCM (110 mL×2). The combined organic extract was washed with brine (30 mL×2), dried with anhydrous Na$_2$SO$_4$, filtered, and concentrated to give a crude product (27.5 g). The product was triturated with methyl ethyl ketone (82 mL) and heptane (290 mL) to give a pure product (17.5 g), which was re-crystallized in ethanol and water to give the title compound as a white solid (16 g, yield: 73%). MS (ESI): mass calcd. for C$_{24}$H$_{25}$FN$_4$O$_3$, 436.2; m/z found, 437.2 [M+H]$^+$. $^1$H NMR (400 MHz, CDCl$_3$) δ 8.33 (d, J=11.2, 1H), 8.08 (d, J=6.8, 1H), 7.39-7.33 (m, 3H), 7.28 (s, 1H), 6.85 (s, 1H), 4.69 (br s, 2H), 3.94 (q, J=7.11 Hz, 2H), 3.27 (td, J=13.66, 6.82 Hz, 1H), 2.32 (br s, 1H), 2.17 (s, 3H), 1.45 (t, J=7.11 Hz, 3H), 1.32 (dd, J=6.82, 1.83 Hz, 6H) ppm.

Example 23: 2-(2-Chloro-4-methylpyridin-3-yl)-6-(4-ethyl-3-(hydroxymethyl)-5-oxo-4,5-dihydro-1H-1,2,4-triazol-1-yl)-7-fluoro-4-isopropylisoquinolin-1(2H)-one

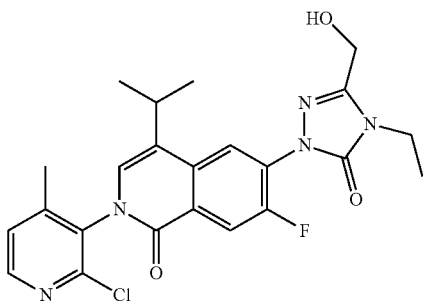 [SMILES: CCn1c(CO)nn(-c2cc3c(C(C)C)cn(-c4c(C)ccnc4Cl)c(=O)c3cc2F)c1=O]

Step A. 4-(3-((Benzyloxy)methyl)-4-ethyl-5-oxo-4,5-dihydro-1H-1,2,4-triazol-1-yl)-N-(2-chloro-4-methylpyridin-3-yl)-5-fluoro-2-(1-hydroxy-3-methylbut-1-en-2-yl)benzamide. To a solution of 3-amino-2-chloro-4-methylpyridine (310 mg, 2.2 mmol) in DCM (4.0 mL) at 0° C. under nitrogen atmosphere was added trimethylaluminum (0.82 mL, 2 M in toluene, 1.6 mmol). The mixture was stirred for 5 min, then a DCM solution (1.0 mL) of 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4, 238 mg, 0.5 mmol) was added. The reaction mixture was slowly warmed to room temperature then heated to 60° C. and stirred overnight. The reaction was carefully quenched by dropwise addition of MeOH followed by water. The organics were extracted with EtOAc (3×). The combined organics layers were washed with brine, dried over sodium sulfate, filtered and concentrated. The crude material was used without further purification. LCMS (ES-API): mass calcd. for $C_{30}H_{31}ClFN_5O_4$, 579.2; m/z found, 580.2 $[M+H]^+$.

Step B. 6-(3-((Benzyloxy)methyl)-4-ethyl-5-oxo-4,5-dihydro-1H-1,2,4-triazol-1-yl)-2-(2-chloro-4-methylpyridin-3-yl)-7-fluoro-4-isopropylisoquinolin-1(2H)-one. A mixture of 4-(3-((benzyloxy)methyl)-4-ethyl-5-oxo-4,5-dihydro-1H-1,2,4-triazol-1-yl)-N-(2-chloro-4-methylpyridin-3-yl)-5-fluoro-2-(1-hydroxy-3-methylbut-1-en-2-yl)benzamide (316 mg, 0.54 mmol) in EtOH was stirred at 90° C. for 48 h, then cooled to rt and concentrated. The residue was purified by silica gel column chromatography (SiO$_2$, 20-70% EtOAc/heptane) to afford the title compound (155 mg, 51% over two steps). LCMS (ES-API): mass calcd. for $C_{30}H_{29}ClFN_5O_3$, 561.2; m/z found, 562.2 $[M+H]^+$. $^1$H NMR (400 MHz, CDCl$_3$) δ: 8.28-8.39 (m, 2H), 8.11 (d, J=6.8 Hz, 1H), 7.32-7.44 (m, 5H), 7.29 (d, J=5.4 Hz, 1H), 6.67 (s, 1H), 4.64 (s, 2H), 4.56 (s, 2H), 3.83-3.96 (m, 2H), 3.21-3.38 (m, 1H), 2.24 (s, 3H), 1.39 (t, J=7.3 Hz, 3H), 1.33 (t, J=7.1 Hz, 6H) ppm.

Step C. 2-(2-Chloro-4-methylpyridin-3-yl)-6-(4-ethyl-3-(hydroxymethyl)-5-oxo-4,5-dihydro-1H-1,2,4-triazol-1-yl)-7-fluoro-4-isopropylisoquinolin-1(2H)-one. To a solution of 6-(3-((benzyloxy)methyl)-4-ethyl-5-oxo-4,5-dihydro-1H-1,2,4-triazol-1-yl)-2-(2-chloro-4-methylpyridin-3-yl)-7-fluoro-4-isopropylisoquinolin-1(2H)-one (100 mg, 0.18 mmol) in DCM at −78° C. was added boron trichloride (0.53 mL, 1 M DCM, 0.53 mmol). The mixture was stirred for 1.5 h then an additional 0.25 mL of boron trichloride was added. After stirring for an additional 1 h, the reaction was quenched carefully by dropwise addition of MeOH followed by water. The organics were extracted with DCM, washed with brine, dried over sodium sulfate, filtered and concentrated. Purification by column chromatography (SiO$_2$, 60-100% EtOAc/heptane) afforded the title compound with minor impurities (72 mg, yield: 86%). The impure product was re-purified by RP HPLC (Isco AcuuPrep, 30×100 mm C18, 10-70% ACN/10 mM NH$_4$OH in water). The pure title compound was obtained as a white solid (36.5 mg, 43% yield). LCMS (ES-API): mass calcd. for $C_{23}H_{23}ClFN_5O_3$, 471.2; m/z found, 472.2 $[M+H]^+$. $^1$H NMR (400 MHz, CDCl$_3$) δ: 8.24-8.44 (m, 2H), 8.11 (d, J=6.8 Hz, 1H), 7.29 (d, J=4.9 Hz, 1H), 6.67 (s, 1H), 4.72 (d, J=6.4 Hz, 2H), 3.95 (q, J=7.3 Hz, 2H), 3.19-3.36 (m, 1H), 2.24 (s, 3H), 2.10 (t, J=6.4 Hz, 1H), 1.45 (t, J=7.3 Hz, 3H), 1.33 (app. t, J=6.8 Hz, 6H) ppm.

Example 24: 2-(2-Chloro-6-fluorophenyl)-6-(4-ethyl-3-(hydroxymethyl)-5-oxo-4,5-dihydro-1H-1,2,4-triazol-1-yl)-4-(1-methylcyclopropyl)isoquinolin-1(2H)-one

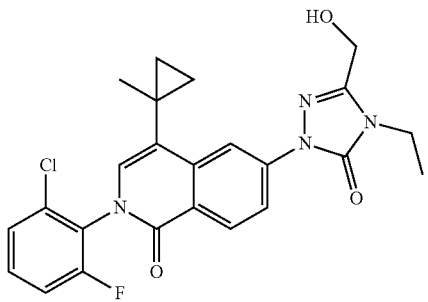 [SMILES: CCn1c(CO)nn(-c2ccc3c(=O)n(-c4c(F)cccc4Cl)cc(C4(C)CC4)c3c2)c1=O]

Step A. 6-(3-((Benzyloxy)methyl)-4-ethyl-5-oxo-4,5-dihydro-1H-1,2,4-triazol-1-yl)-2-(2-chloro-6-fluorophenyl)-4-(1-methylcyclopropyl)isoquinolin-1(2H)-one. To a mixture of diiodomethane (373 mg, 0.14 mmol) in anhydrous toluene (20 mL) at 0° C. was added a toluene solution (15%) of diethylzinc (918 mg, 1.1 mmol). The mixture was heated at 0° C. under nitrogen for 15 min, then a suspension of 6-(3-((benzyloxy)methyl)-4-ethyl-5-oxo-4,5-dihydro-1H-1,2,4-triazol-1-yl)-2-(2-chloro-6-fluorophenyl)-4-(1-methylcyclopropyl)isoquinolin-1(2H)-one (38 mg, 0.6 mmol) in toluene (20 mL). The reaction mixture was stirred at 0° C. for 0.5 h, then warmed to room temperature and stirred for 24 h. The mixture was poured into aqueous NaHCO$_3$ solution (50 mL). The aqueous phase was extracted with DCM (50 mL) and ethyl acetate (EtOAc) (50 mL) sequentially. The combined organic extract was washed with brine, dried over anhydrous Na$_2$SO$_4$, filtered, and concentrated. The residue was purified by flash column chromatography (SiO$_2$, 50-100% ethyl acetate in heptane) to afford the title compound and unreacted 6-(3-((benzyloxy)methyl)-4-ethyl-5-oxo-4,5-dihydro-1H-1,2,4-triazol-1-yl)-2-(2-chloro-6-fluorophenyl)-4-(1-methylcyclopropyl)isoquinolin-1(2H)-one as a mixture, which was not further purified and used directly into the next step: a white solid (~1:4 ratio, 15 mg, 38% yield).

Step B. 2-(2-Chloro-6-fluorophenyl)-6-(4-ethyl-3-(hydroxymethyl)-5-oxo-4,5-dihydro-1H-1,2,4-triazol-1-yl)-4-(1-methylcyclopropyl)isoquinolin-1(2H)-one. The mixture of 6-(3-((benzyloxy)methyl)-4-ethyl-5-oxo-4,5-dihydro-1H-1,2,4-triazol-1-yl)-2-(2-chloro-6-fluorophenyl)-4-(1- methylcyclopropyl)isoquinolin-1(2H)-one and 6-(3-((benzyloxy)methyl)-4-ethyl-5-oxo-4,5-dihydro-1H-1,2,4-triazol-1-yl)-2-(2-chloro-6-fluorophenyl)-4-(1-methylcyclopropyl)isoquinolin-1(2H)-one (~1:4, 15 mg, 0.03 mmol) was dissolved into trifluoroacetic acid (3 mL), and the reaction mixture was transferred into a sealed tube and heated at 80° C. for 17 h, then cooled to room temperature. The mixture was concentrated under reduced pressure. The residue was purified by flash column chromatography (SiO₂, 50-100% ethyl acetate in heptane), then further purified by prep-HPLC (C₁₈ column, 20-80% gradient MeCN in water) to afford the desired product as a white solid (1 mg, 11% yield). LCMS (ES-API): mass calcd. for $C_{24}H_{22}ClFN_4O_3$, 468.1; m/z found, 469.2 [M+H]⁺. ¹H NMR (400 MHz, CDCl₃) δ 8.91 (d, J=2.08 Hz, 1H), 8.52 (d, J=8.80 Hz, 1H), 8.09 (dd, J=2.08, 8.80 Hz, 1H), 7.33-7.48 (m, 2H), 7.17-7.24 (m, 1H), 6.95 (s, 1H), 4.71 (d, J=6.61 Hz, 2H), 3.84-4.02 (m, 2H), 2.41 (t, J=6.61 Hz, 1H), 1.49 (s, 3H), 1.44 (t, J=7.34 Hz, 3H), 0.78-0.88 (m, 4H) ppm.

Example 25: 6-(4-Ethyl-3-(hydroxymethyl)-5-oxo-4,5-dihydro-1H-1,2,4-triazol-1-yl)-2-(3-fluorophenyl)-4-(2-hydroxypropan-2-yl)isoquinolin-1(2H)-one

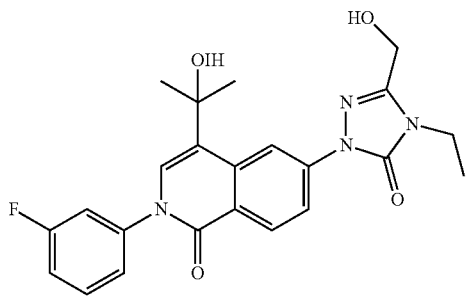

Step A. 4-Acetyl-6-(3-((benzyloxy)methyl)-4-ethyl-5-oxo-4,5-dihydro-1H-1,2,4-triazol-1-yl)isoquinolin-1(2H)-one. To a solution of 6-(3-((benzyloxy)methyl)-4-ethyl-5-oxo-4,5-dihydro-1H-1,2,4-triazol-1-yl)-4-(prop-1-en-2-yl)isoquinolin-1(2H)-one (100 mg, 0.19 mmol) in THF/H₂O (v/v, 4:1, 5 mL) was added NaIO₄ (121 mg, 0.57 mmol) and K₂OsO₄·2H₂O (3.5 mg, 0.01 mmol) under nitrogen at 0° C. The resulting pale brown suspension was stirred at room temperature for 3 days. The mixture was diluted with water, stirred at room temperature for 30 min, and then filtered. The solid was collected and dried in vacuo. The crude product was further purified by preparative reversed phase HPLC (Stationary phase: Phenomenex Gemini-NX, 5 µm, 150×30 mm; Mobile phase: water (0.05% HCl) (A)—MeCN (B), gradient elution: 40-70% B in A over 8 min, flow rate: 25 mL/min) to give the title compound as off-white solid (20 mg, yield: 23%). ESI-MS: mass calcd. for $C_{23}H_{22}N_4O_4$, 418.2; m/z found, 419.1 [M+H]⁺; ¹H NMR (400 MHz, DMSO-d₆) δ 11.96 (br d, J=5.6 Hz, 1H), 9.48 (d, J=2.0 Hz, 1H), 8.31 (d, J=8.8 Hz, 1H), 8.17-8.23 (m, 2H), 7.36-7.41 (m, 4H), 7.29-7.36 (m, 1H), 4.62 (d, J=3.9 Hz, 4H), 3.77 (q, J=7.1 Hz, 2H), 2.54 (s, 3H), 1.24 (t, J=7.1 Hz, 3H) ppm.
Step B. 6-(3-((Benzyloxy)methyl)-4-ethyl-5-oxo-4,5-dihydro-1H-1,2,4-triazol-1-yl)-4-(2-hydroxypropan-2-yl)isoquinolin-1(2H)-one. To a stirring solution of 4-acetyl-6-(3-((benzyloxy)methyl)-4-ethyl-5-oxo-4,5-dihydro-1H-1,2,4-triazol-1-yl)isoquinolin-1(2H)-one (20 mg, 0.043 mmol) at 0° C. was added a diethyl ether solution (3 M) of methylmagnesium bromide (21 µL, 0.06 mmol) in THF (0.2 mL) dropwise. The resulting yellow suspension was stirred at 0° C. for 3 h, then slowly warmed to room temperature and stirred for 24 h. The mixture was slowly poured into aqueous saturated NH₄Cl solution and extracted with EtOAc. The organic layer was separated, dried with Na₂SO₄, filtered, and concentrated. The residue was purified by flash chromatography (SiO₂, gradient elution: 1-4% MeOH in DCM) to give the title as white solid (10 mg, yield: 50%). ESI-MS: mass calcd. for $C_{24}H_{26}N_4O_4$, 434.2; m/z found, 435.2 [M+H]⁺. ¹H NMR (400 MHz, DMSO-d₆) δ 11.13 (br d, J=5.8 Hz, 1H), 9.03 (s, 1H), 8.32 (d, J=8.8 Hz, 1H), 8.01 (d, J=9.0 Hz, 1H), 7.26-7.45 (m, 5H), 7.10 (d, J=5.8 Hz, 1H), 5.12 (s, 1H), 4.61 (s, 4H), 3.77 (q, J=7.0 Hz, 2H), 1.60 (s, 6H), 1.23-1.27 (m, 3H) ppm.
Step C. 6-(3-((Benzyloxy)methyl)-4-ethyl-5-oxo-4,5-dihydro-1H-1,2,4-triazol-1-yl)-2-(3-fluorophenyl)-4-(2-hydroxypropan-2-yl)isoquinolin-1(2H)-one. To a mixture of 6-(3-((benzyloxy)methyl)-4-ethyl-5-oxo-4,5-dihydro-1H-1,2,4-triazol-1-yl)-4-(2-hydroxypropan-2-yl)isoquinolin-1(2H)-one (100 mg, 0.23 mmol), Et₃N (64 µL, 0.46 mmol), 3-fluorophenylboronic acid (64.4 mg, 0.46 mmol) in DCM (3 mL) was added 4 Å MS powder (0.1 g) and Cu(OAc)₂ (41.8 mg, 0.23 mmol). The reaction mixture was stirred under O₂ at room temperature for 2 days. The mixture was diluted with EtOAc and filtered through a short pad of Celite®. The pad was washed with EtOAc, and the combined filtrate was washed with H₂O. The organic layer was separated, dried over Na₂SO₄, filtered, and concentrated. The residue was purified by flash chromatography (SiO₂, gradient elution: 1-5% MeOH in DCM) to give the title compound as a yellow solid (40 mg, yield: 25%). ESI-MS: mass calcd. for $C_{30}H_{29}FN_4O_4$, 528.2; m/z found, 529.3 [M+H]⁺; ¹H NMR (400 MHz, CDCl₃) δ 9.15 (d, J=1.8 Hz, 1H), 8.61 (d, J=8.9 Hz, 1H), 8.11 (dd, J=8.9, 1.8 Hz, 1H), 7.83-8.05 (m, 1H), 7.44-7.55 (m, 2H), 7.36-7.40 (m, 5H), 7.22-7.26 (m, 1H), 7.13-7.19 (m, 1H), 4.63 (s, 2H), 4.57 (s, 2H), 3.89 (q, J=7.1 Hz, 2H), 1.85 (s, 6H), 1.38 (t, J=7.1 Hz, 3H) ppm; ¹⁹F NMR (376 MHz, CDCl₃) δ −111.17 (s, 1F) ppm.
Step D. 6-(4-Ethyl-3-(hydroxymethyl)-5-oxo-4,5-dihydro-1H-1,2,4-triazol-1-yl)-2-(3-fluorophenyl)-4-(2-hydroxypropan-2-yl)isoquinolin-1(2H)-one. To a solution of 6-(3-((benzyloxy)methyl)-4-ethyl-5-oxo-4,5-dihydro-1H-1,2,4-triazol-1-yl)-2-(3-fluorophenyl)-4-(2-hydroxypropan-2-yl)isoquinolin-1(2H)-one (40 mg, 0.057 mmol) in DCM (2 mL) at −78° C. was added BCl₃ (1 M solution in toluene, 283 µL, 0.28 mmol) under nitrogen. The reaction mixture was stirred at −78° C. for 1 h. The mixture was quenched with MeOH (1 mL) at −78° C. and stirred for 0.5 hour. The mixture was diluted with DCM and washed with saturated aqueous NaHCO₃ solution. The organic layer was separated, dried over Na₂SO₄, filtered, and concentrated. The residue was purified by preparative reversed phase HPLC (Stationary phase: Waters Xbridge Prep OBD C18, 10 µm, 150×40 mm; Mobile phase: H₂O (10 mM NH₄HCO₃) (A)—MeCN (B), gradient elution: 0-70% B in A over 25 min, flow rate: 25 mL/min) to give the title compound as a white solid (20 mg, yield: 40%). ESI-MS: mass calcd. for $C_{23}H_{23}FN_4O_4$, 438.2; m/z found, 439.2 [M+H]⁺; ¹H NMR (400 MHz, DMSO-d₆) δ 9.08 (d, J=2.0 Hz, 1H), 8.41 (d, J=8.8 Hz, 1H), 8.11 (dd, J=9.0, 2.0 Hz, 1H), 7.55-7.64 (m, 1H), 7.47 (dt, J=9.9, 2.2 Hz, 1H), 7.29-7.39 (m, 3H), 5.83 (t, J=5.9 Hz, 1H), 5.25 (s, 1H), 4.52 (d, J=5.9 Hz, 2H), 3.82 (q, J=7.1 Hz, 2H), 1.64 (s, 6H), 1.29 (t, J=7.1 Hz, 3H) ppm.

Example 26: 4-(Dimethylamino)-6-(4-ethyl-3-(hydroxymethyl)-5-oxo-4,5-dihydro-1H-1,2,4-triazol-1-yl)-2-(o-tolyl)isoquinolin-1(2H)-one

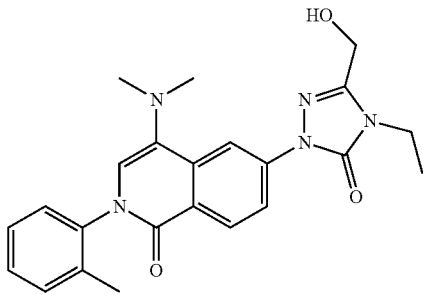 [SMILES: CCn1c(CO)nn(-c2ccc3c(=O)n(-c4ccccc4C)cc(N(C)C)c3c2)c1=O]

Step A. 6-(3-((Benzyloxy)methyl)-4-ethyl-5-oxo-4,5-dihydro-1H-1,2,4-triazol-1-yl)-4-bromoisoquinolin-1(2H)-one. A mixture of 6-(3-((benzyloxy)methyl)-4-ethyl-5-oxo-4,5-dihydro-1H-1,2,4-triazol-1-yl)isoquinolin-1(2H)-one (2 g, 3.9 mmol) in MeCN (20 mL) was added NBS (842 mg, 4.7 mmol). The reaction mixture was heated at reflux for 16 h. The mixture was cooled to room temperature and filtered. The collected precipitate was washed with DCM to give the title compound as a yellow solid (980 mg, yield: 55%). ESI-MS: mass calcd. for $C_{21}H_{19}BrN_4O_3$, 454.1; m/z found, 455.1 [M+H]+; 1H NMR (400 MHz, DMSO-$d_6$) δ 11.59 (br d, J=5.8 Hz, 1H), 8.42 (d, J=2.1 Hz, 1H), 8.32 (d, J=8.9 Hz, 1H), 8.17 (dd, J=8.9, 2.1 Hz, 1H), 7.61 (d, J=5.8 Hz, 1H), 7.37-7.62 (m, 5H), 4.64 (s, 2H), 4.62 (s, 2H), 3.78 (q, J=7.3 Hz, 2H), 1.25 (t, J=7.3 Hz, 3H) ppm.

Step B. 6-(3-((Benzyloxy)methyl)-4-ethyl-5-oxo-4,5-dihydro-1H-1,2,4-triazol-1-yl)-4-(dimethylamino)isoquinolin-1(2H)-one. To a flask charged with 6-(3-((benzyloxy)methyl)-4-ethyl-5-oxo-4,5-dihydro-1H-1,2,4-triazol-1-yl)-4-bromoisoquinolin-1(2H)-one (930 mg, 2 mmol) was added dimethylamine (40% aqueous solution, 5 mL). The reaction mixture was heated in a 30 mL autoclave at 110° C. for 4 days. The mixture was cooled down to room temperature, then diluted with DCM and water. The organic layer was separated, and the aqueous layer was extracted with DCM. The combined organic extract was dried over $Na_2SO_4$, filtered and concentrated. The residue was purified by silica column chromatography ($SiO_2$, gradient elution: 0-1% MeOH in DCM) to give the title compound as a yellow solid (161 mg, yield: 18%). ESI-MS: mass calcd. for $C_{23}H_{25}N_5O_3$, 419.2; m/z found, 420.2 [M+H]+.

Step C. 6-(3-((Benzyloxy)methyl)-4-ethyl-5-oxo-4,5-dihydro-1H-1,2,4-triazol-1-yl)-4-(dimethylamino)-2-(o-tolyl)isoquinolin-1(2H)-one. To a mixture of 6-(3-((benzyloxy)methyl)-4-ethyl-5-oxo-4,5-dihydro-1H-1,2,4-triazol-1-yl)-4-(dimethylamino)isoquinolin-1(2H)-one (160 mg, 0.36 mmol), $Et_3N$ (72 mg, 0.71 mmol), 2-methylphenylboronic acid (97 mg, 0.71 mmol) in DCM (9 mL) was added 4A MS powder (300 mg) and $Cu(OAc)_2$ (64 mg, 0.36 mmol). The reaction mixture was stirred under O2 at 30° C. for 2 days. Then $H_2O$ was added, and the mixture was extracted with DCM. The organic layer was separated, dried over $Na_2SO_4$, filtered and concentrated. The residue was purified by flash chromatography ($SiO_2$, gradient elution: 0-100% EtOAc in petroleum ether) to give the title compound as a yellow solid (31 mg, yield: 14%). ESI-MS: mass calcd. for $C_{30}H_{31}N_5O_3$ 509.2; m/z found, 510.3 [M+H]+; 1H NMR (400 MHz, CDCl$_3$) δ 8.68 (d, J=2.2 Hz, 1H), 8.55 (d, J=8.8 Hz, 1H), 8.16 (dd, J=8.8, 2.2 Hz, 1H), 7.33-7.43 (m, 9H), 6.68 (s, 1H), 4.64 (s, 2H), 4.57 (s, 2H), 3.89 (q, J=7.0 Hz, 2H), 2.78 (s, 6H), 2.20 (s, 3H), 1.36-1.41 (m, 3H) ppm.

Step D. 4-(Dimethylamino)-6-(4-ethyl-3-(hydroxymethyl)-5-oxo-4,5-dihydro-1H-1,2,4-triazol-1-yl)-2-(o-tolyl)isoquinolin-1(2H)-one. To a solution of 6-(3-((benzyloxy)methyl)-4-ethyl-5-oxo-4,5-dihydro-1H-1,2,4-triazol-1-yl)-4-(dimethylamino)-2-(o-tolyl)isoquinolin-1(2H)-one (31 mg, 0.05 mmol) in DCM (2 mL) at −78° C. under nitrogen was added $BCl_3$ (1 M solution in toluene, 254 μL, 0.25 mmol). The reaction mixture was stirred at −78° C. for 1 h. Then reaction was quenched with MeOH (1 mL) at −78° C., and the mixture was stirred at −78° C. for 0.5 h. Then aqueous saturated $NaHCO_3$ solution was added, and the mixture was extracted with DCM. The organic layer was dried over $Na_2SO_4$, filtered and concentrated. The residue was purified by preparative reversed phase HPLC (Stationary phase: Waters Xbridge Prep OBD C18, 10 μm, 150×40 mm; Mobile phase: $H_2O$ (10 mM $NH_4HCO_3$) (A)—MeCN (B), gradient elution: 0-60% B in A over 30 min, flow rate: 25 mL/min) to give the title compound as a white solid (13 mg, yield: 53%). ESI-MS: mass calcd. for $C_{23}H_{25}N_5O_3$, 419.2; m/z found, 420.3 [M+H]+. 1H NMR (400 MHz, DMSO-$d_6$) δ 8.54 (d, J=2.1 Hz, 1H), 8.35 (d, J=9.0 Hz, 1H), 8.15 (dd, J=9.0, 2.1 Hz, 1H), 7.29-7.44 (m, 4H), 6.93 (s, 1H), 5.83 (br t, J=5.8 Hz, 1H), 4.54 (d, J=5.8 Hz, 2H), 3.82 (q, J=7.2 Hz, 2H), 3.31 (s, 6H), 2.69 (s, 3H), 1.30 (t, J=7.2 Hz, 3H) ppm.

Example 27: 2-(2-Chloro-6-fluorophenyl)-6-(4-ethyl-3-(hydroxymethyl)-5-oxo-4,5-dihydro-1H-1,2,4-triazol-1-yl)-7-fluoro-4-(prop-1-en-2-yl)phthalazin-1(2H)-one

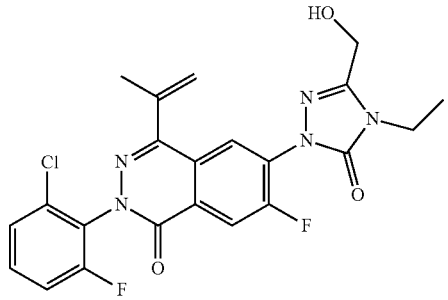 [SMILES: C=C(C)c1nn(-c2c(F)cccc2Cl)c(=O)c2cc(F)c(-n3nc(CO)n(CC)c3=O)cc12]

Step A. 2-((2-Chloro-6-fluorophenyl)amino)-5,6-difluoroisoindoline-1,3-dione. A reaction mixture of 4,5-difluorophthalic anhydride (1.83 g, 9.94 mmol) and (2-chloro-6-fluorophenyl)hydrazine hydrochloride (2.40 g, 12.2 mmol) in AcOH (45 mL) was heated at 125° C. for 1.5 h, and then concentrated to ~ 15 mL. The clear mixture was poured into 50 mL of water. The formed off-white solid was filtered, and then stirred in $NaHCO_3$ aqueous solution for a while, filtered again, washed with water, and dried under vacuum over night to give the title compound (2.93 g, 90%). LCMS (ES-API): mass calcd. for $C_{14}H_6ClF_3N_2O_2$, 326.0; m/z found, 327.0 [M+H]+. 1H NMR (400 MHz, CDCl$_3$) δ 7.73 (t, J=7.3 Hz, 2H), 7.20-7.13 (m, 1H), 6.97-6.90 (m, 2H), 6.48 (d, J=2.9 Hz, 1H) ppm.

Step B. 2-(2-Chloro-6-fluorophenyl)-6,7-difluoro-2,3-dihydrophthalazine-1,4-dione. To a suspension of 2-((2-chloro-6-fluorophenyl)amino)-5,6-difluoroisoindoline-1,3-dione (1.51 g, 4.62 mmol) in EtOH (28 mL) was added a solution of EtONa in EtOH (21%, 2.6 mL, 6.96 mmol). After stirring at room temperature for 1.5 h, a few drops of water were added followed by the addition of 3.8 mL of 2N HCl to adjust "pH" to ~4. After removal of the solvent in vacuo, DCM and water was added to the residue. After filtering off the white solid, the filtrate was separated, and the aqueous layer was extracted with DCM. The combined organic layers were dried over Na$_2$SO$_4$, filtered, concentrated. The residue was purified by solid loading flash column chromatography (SiO$_2$, 0-60% EtOAc in heptanes) to give the title compound as white crystalline solid (250 mg, 17%). LCMS (ES-API): mass calcd. for C$_{14}$H$_6$ClF$_3$N$_2$O$_2$, 326.0; m/z found, 327.0 [M+H]$^+$. $^1$H NMR (400 MHz, CDCl$_3$) δ 9.26 (br s, 1H), 8.23 (dd, J=7.6, 9.5 Hz, 1H), 7.68 (dd, J=7.3, 9.3 Hz, 1H), 7.47 (dt, J=5.9, 8.3 Hz, 1H), 7.43-7.35 (m, 1H), 7.23 (dt, J=1.5, 8.6 Hz, 1H) ppm.

Step C. 3-(2-Chloro-6-fluorophenyl)-6,7-difluoro-4-oxo-3,4-dihydrophthalazin-1-yl trifluoromethanesulfonate. To a mixture of 2-(2-chloro-6-fluorophenyl)-6,7-difluoro-2,3-dihydrophthalazine-1,4-dione (377 mg, 1.15 mmol) in DCM (35 mL) at 4° C. was added Tf$_2$O (0.30 mL, 1.83 mmol) followed by the addition of Et$_3$N (0.42 mL, 3.03 mmol). The reaction mixture was stirred at room temperature for 17.5 h and then concentrated. The residue was purified by flash column chromatography (SiO$_2$, 0-50% EtOAc in heptane) to give the title compound as a thick yellow oil (460 mg, 87%). LCMS (ES-API): mass calcd. for C$_{15}$H$_5$ClF$_6$N$_2$O$_4$S, 458.0; m/z found, 459.0 [M+H]$^+$. $^1$H NMR (400 MHz, CDCl$_3$) δ 8.32 (dd, J=7.3, 9.3 Hz, 1H), 7.72 (dd, J=6.8, 9.3 Hz, 1H), 7.47 (dt, J=5.9, 8.3 Hz, 1H), 7.42-7.36 (m, 1H), 7.22 (dt, J=1.0, 8.6 Hz, 1H) ppm.

Step D. 2-(2-Chloro-6-fluorophenyl)-6,7-difluoro-4-(prop-1-en-2-yl)phthalazin-1(2H)-one. To a mixture of 3-(2-chloro-6-fluorophenyl)-6,7-difluoro-4-oxo-3,4-dihydrophthalazin-1-yl trifluoromethanesulfonate (141 mg, 0.310 mmol), isopropenylboronic acid pinacol ester (78 mg, 0.46 mmol), bis(triphenylphosphine)palladium(ii) dichloride (25 mg, 0.036 mmol) in dioxane (3 mL) was added an aqueous solution of K$_2$CO$_3$ (2 M, 0.30 mL, 0.60 mmol). The reaction mixture was purged with argon for ~5 min, and then heated at 85° C. for 3 h. The mixture was filtered, and the filtrate was concentrated. The residue was partitioned between DCM and water. The organic layer was dried over Na$_2$SO$_4$, filtered, concentrated. The residue was purified by flash column chromatography (SiO$_2$, 0-50% EtOAc in heptanes) to give the title compound as an off-white solid (101 mg, 94%). LCMS (ES-API): mass calcd. for C$_{17}$H$_{10}$ClF$_3$N$_2$O, 350.0; m/z found, 351.1 [M+H]$^+$. $^1$H NMR (400 MHz, CDCl$_3$) δ 8.32 (dd, J=7.6, 10.0 Hz, 1H), 7.78 (dd, J=7.3, 10.8 Hz, 1H), 7.47-7.32 (m, 2H), 7.24-7.13 (m, 1H), 5.67-5.58 (m, 1H), 5.34 (t, J=1.0 Hz, 1H), 2.19 (s, 3H) ppm.

Step E. 6-(3-((Benzyloxy)methyl)-4-ethyl-5-oxo-4,5-dihydro-1H-1,2,4-triazol-1-yl)-2-(2-chloro-6-fluorophenyl)-7-fluoro-4-(prop-1-en-2-yl)phthalazin-1(2H)-one and 7-(3-((benzyloxy)methyl)-4-ethyl-5-oxo-4,5-dihydro-1H-1,2,4-triazol-1-yl)-2-(2-chloro-6-fluorophenyl)-6-fluoro-4-(prop-1-en-2-yl)phthalazin-1(2H)-one. A reaction mixture of 2-(2-chloro-6-fluorophenyl)-6,7-difluoro-4-(prop-1-en-2-yl)phthalazin-1(2H)-one (56 mg, 0.16 mmol), 5-((benzyloxy)methyl)-4-ethyl-2,4-dihydro-3H-1,2,4-triazol-3-one (51 mg, 0.22 mmol) and K$_2$CO$_3$ (45 mg, 0.33 mmol) in DMF (2 mL) was heated at 85° C. for 4 h and then cooled to rt and concentrated. The crude residue was purified by flash column chromatography (SiO$_2$, 0-50% EtOAc in heptanes) to give the two title compounds (58 mg, 64%) and (19 mg, 21%), respectively.
6-(3-((benzyloxy)methyl)-4-ethyl-5-oxo-4,5-dihydro-1H-1,2,4-triazol-1-yl)-2-(2-chloro-6-fluorophenyl)-7-fluoro-4-(prop-1-en-2-yl)phthalazin-1(2H)-one: LCMS (ES-API): mass calcd. for C$_{29}$H$_{24}$ClF$_2$N$_5$O$_3$, 563.2; m/z found, 564.2 [M+H]$^+$. $^1$H NMR (400 MHz, CDCl$_3$) δ 8.34 (s, 1H), 8.32 (d, J=3.9 Hz, 1H), 7.44-7.31 (m, 7H), 7.23-7.16 (m, 1H), 5.67-5.60 (m, 1H), 5.41 (t, J=1.0 Hz, 1H), 4.63 (s, 2H), 4.54 (s, 2H), 3.88 (q, J=7.2 Hz, 2H), 2.21 (t, J=1.2 Hz, 3H), 1.38 (t, J=7.3 Hz, 3H) ppm.
7-(3-((benzyloxy)methyl)-4-ethyl-5-oxo-4,5-dihydro-1H-1,2,4-triazol-1-yl)-2-(2-chloro-6-fluorophenyl)-6-fluoro-4-(prop-1-en-2-yl)phthalazin-1(2H)-one: LCMS (ES-API): mass calcd. for C$_{29}$H$_{24}$ClF$_2$N$_5$O$_3$, 563.2; m/z found, 564.3 [M+H]$^+$. $^1$H NMR (400 MHz CDCl$_3$) δ 8.72 (d, J=7.3 Hz, 1H), 7.78 (d, J=10.8 Hz, 1H), 7.46-7.29 (m, 7H), 7.23-7.12 (m, 1H), 5.67-5.60 (m, 1H), 5.37 (t, J=1.0 Hz, 1H), 4.62 (s, 2H), 4.52 (s, 2H), 3.87 (q, J=7.2 Hz, 2H), 2.20 (s, 3H), 1.37 (t, J=7.1 Hz, 3H) ppm.

Step F. 2-(2-Chloro-6-fluorophenyl)-6-(4-ethyl-3-(hydroxymethyl)-5-oxo-4,5-dihydro-1H-1,2,4-triazol-1-yl)-7-fluoro-4-(prop-1-en-2-yl)phthalazin-1(2H)-one. A solution of 6-(3-((benzyloxy)methyl)-4-ethyl-5-oxo-4,5-dihydro-1H-1,2,4-triazol-1-yl)-2-(2-chloro-6-fluorophenyl)-7-fluoro-4-(prop-1-en-2-yl)phthalazin-1(2H)-one and 7-(3-((benzyloxy)methyl)-4-ethyl-5-oxo-4,5-dihydro-1H-1,2,4-triazol-1-yl)-2-(2-chloro-6-fluorophenyl)-6-fluoro-4-(prop-1-en-2-yl)phthalazin-1(2H)-one (40 mg, 0.071 mmol) in TFA (0.3 mL) was heated at 70° C. for 8 h and then cooled to rt and concentrated. The residue in 0.5 mL of MeOH and 0.5 mL of THF was treated with 0.15 mL of 3 M NaOH for 1.5 h. After concentration, the residue was purified by RP-HPLC (Gemini C18 110A, 5 uM 100×30 mm, 20-100% CH$_3$CN in water with 10 mM NH$_4$OH, 60 mL/min) to provide one of the two products as the title compound (15 mg, 45%). LCMS (ES-API): mass calcd. for C$_{22}$H$_{18}$ClF$_2$N$_5$O$_3$, 473.1; m/z found, 474.1 [M+H]$^+$. $^1$H NMR (400 MHz, CDCl$_3$) δ 8.39-8.27 (m, 2H), 7.50-7.28 (m, 2H), 7.20 (t, J=8.5 Hz, 1H), 5.70-5.56 (m, 1H), 5.40 (s, 1H), 4.67 (d, J=5.9 Hz, 2H), 3.93 (q, J=7.0 Hz, 2H), 2.71-2.55 (m, 1H), 2.20 (s, 3H), 1.42 (t, J=7.3 Hz, 3H) ppm.

Example 28: 2-(2-Chloro-6-fluorophenyl)-7-(4-ethyl-3-(hydroxymethyl)-5-oxo-4,5-dihydro-1H-1,2,4-triazol-1-yl)-6-fluoro-4-(prop-1-en-2-yl)phthalazin-1(2H)-one

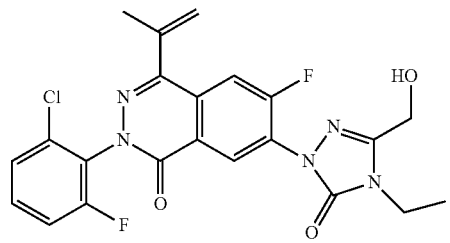 [SMILES: C=C(C)c1nn(-c2c(F)cccc2Cl)c(=O)c2cc(-n3nc(CO)n(CC)c3=O)c(F)cc12]

In the preparation of 2-(2-chloro-6-fluorophenyl)-6-(4-ethyl-3-(hydroxymethyl)-5-oxo-4,5-dihydro-1H-1,2,4-triazol-1-yl)-7-fluoro-4-(prop-1-en-2-yl)phthalazin-1(2H)-one (Example 27, step F), the title compound was obtained as the second product (3 mg). LCMS (ES-API): mass calcd. for C$_{22}$H$_{18}$ClF$_2$N$_5$O$_3$, 473.1; m/z found, 474.1 [M+H]$^+$. $^1$H NMR (400 MHz, CDCl$_3$) δ 8.69 (d, J=7.3 Hz, 1H), 7.78 (d, J=10.8 Hz, 1H), 7.46-7.28 (m, 2H), 7.25-7.13 (m, 1H), 5.68-5.55 (m, 1H), 5.37 (s, 1H), 4.67 (s, 2H), 3.91 (q, J=7.2 Hz, 2H), 2.37 (br s, 1H), 2.20 (s, 3H), 1.42 (t, J=7.3 Hz, 3H) ppm.

Example 29: 2-(2-Chloro-6-fluorophenyl)-6-(4-ethyl-3-(hydroxymethyl)-5-oxo-4,5-dihydro-1H-1,2,4-triazol-1-yl)-7-methoxy-4-(prop-1-en-2-yl)phthalazin-1(2H)-one

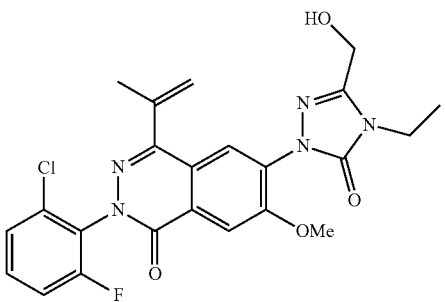 [SMILES: C=C(C)c1nn(-c2c(F)cccc2Cl)c(=O)c2cc(OC)c(-n3nc(CO)n(CC)c3=O)cc12]

Step A: 2-(2-Chloro-6-fluorophenyl)-6-(4-ethyl-3-(hydroxymethyl)-5-oxo-4,5-dihydro-1H-1,2,4-triazol-1-yl)-7-fluoro-4-(prop-1-en-2-yl)phthalazin-1(2H)-one and (1-(2-(2-chloro-6-fluorophenyl)-7-fluoro-1-oxo-4-(prop-1-en-2-yl)-1,2-dihydrophthalazin-6-yl)-4-ethyl-5-oxo-4,5-dihydro-1H-1,2,4-triazol-3-yl)methyl 2,2,2-trifluoroacetate. A solution of 6-(3-((benzyloxy)methyl)-4-ethyl-5-oxo-4,5-dihydro-1H-1,2,4-triazol-1-yl)-2-(2-chloro-6-fluorophenyl)-7-fluoro-4-(prop-1-en-2-yl)phthalazin-1(2H)-one (25 mg, 0.044 mmol) in TFA (0.3 mL) was heated at 70° C. for 8 h, then cooled to rt, and concentrated to give the crude title compounds, which were used directly in the next step without further purification.

Step B: 2-(2-Chloro-6-fluorophenyl)-6-(4-ethyl-3-(hydroxymethyl)-5-oxo-4,5-dihydro-1H-1,2,4-triazol-1-yl)-7-methoxy-4-(prop-1-en-2-yl)phthalazin-1(2H)-one. A solution of 2-(2-chloro-6-fluorophenyl)-6-(4-ethyl-3-(hydroxymethyl)-5-oxo-4,5-dihydro-1H-1,2,4-triazol-1-yl)-7-fluoro-4-(prop-1-en-2-yl)phthalazin-1(2H)-one and (1-(2-(2-chloro-6-fluorophenyl)-7-fluoro-1-oxo-4-(prop-1-en-2-yl)-1,2-dihydrophthalazin-6-yl)-4-ethyl-5-oxo-4,5-dihydro-1H-1,2,4-triazol-3-yl)methyl 2,2,2-trifluoroacetate (crude from Step A) in 0.5 mL of MeOH and 0.5 mL of THF was treated with 0.10 mL of 3 M NaOH for 1.5 h. After concentration, the residue was purified by RP-HPLC (Gemini C18 110A, 5 uM 100×30 mm, 20-100% CH$_3$CN in water with 10 mM NH$_4$OH, 60 mL/min) to give the title compound (6.7 mg, 31%). LCMS (ES-API): mass calcd. for C$_{23}$H$_{21}$ClFN$_5$O$_4$, 485.1; m/z found, 486.1 [M+H]$^+$. $^1$H NMR (400 MHz, CDCl$_3$) δ 8.05 (d, J=9.3 Hz, 2H), 7.45-7.33 (m, 2H), 7.25-7.14 (m, 1H), 5.58 (s, 1H), 5.37 (s, 1H), 4.67 (d, J=4.9 Hz, 2H), 4.04 (s, 3H), 3.92 (q, J=7.3 Hz, 2H), 2.32 (br t, J=5.6 Hz, 1H), 2.19 (s, 3H), 1.43 (t, J=7.1 Hz, 3H) ppm.

Example 30: 2-(2-Chloro-6-fluorophenyl)-7-(4-ethyl-3-(hydroxymethyl)-5-oxo-4,5-dihydro-1H-1,2,4-triazol-1-yl)-6-methoxy-4-(prop-1-en-2-yl)phthalazin-1(2H)-one

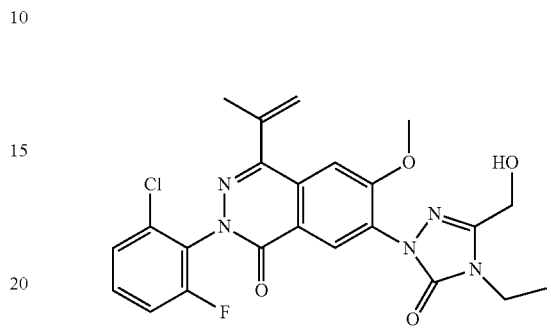

Step A: 2-(2-Chloro-6-fluorophenyl)-7-(4-ethyl-3-(hydroxymethyl)-5-oxo-4,5-dihydro-1H-1,2,4-triazol-1-yl)-6-fluoro-4-(prop-1-en-2-yl)phthalazin-1(2H)-one and (1-(3-(2-chloro-6-fluorophenyl)-7-fluoro-4-oxo-1-(prop-1-en-2-yl)-3,4-dihydrophthalazin-6-yl)-4-ethyl-5-oxo-4,5-dihydro-1H-1,2,4-triazol-3-yl)methyl 2,2,2-trifluoroacetate. A solution of 7-(3-((benzyloxy)methyl)-4-ethyl-5-oxo-4,5-dihydro-1H-1,2,4-triazol-1-yl)-2-(2-chloro-6-fluorophenyl)-6-fluoro-4-(prop-1-en-2-yl)phthalazin-1(2H)-one (12 mg, 0.021 mmol) in TFA (0.3 mL) was heated at 70° C. for 8 h, cooled to rt and concentrated to give the crude title compounds, which were used directly in the next step without further purification.

Step B: 2-(2-Chloro-6-fluorophenyl)-7-(4-ethyl-3-(hydroxymethyl)-5-oxo-4,5-dihydro-1H-1,2,4-triazol-1-yl)-6-methoxy-4-(prop-1-en-2-yl)phthalazin-1(2H)-one. A solution of 2-(2-chloro-6-fluorophenyl)-7-(4-ethyl-3-(hydroxymethyl)-5-oxo-4,5-dihydro-1H-1,2,4-triazol-1-yl)-6-fluoro-4-(prop-1-en-2-yl)phthalazin-1(2H)-one and (1-(3-(2-chloro-6-fluorophenyl)-7-fluoro-4-oxo-1-(prop-1-en-2-yl)-3,4-dihydrophthalazin-6-yl)-4-ethyl-5-oxo-4,5-dihydro-1H-1,2,4-triazol-3-yl)methyl 2,2,2-trifluoroacetate (crude from Step A) in 0.5 mL of MeOH and 0.5 mL of THF was treated with 0.10 mL of 3 M NaOH for 1.5 h. After concentration, the residue was purified by RP-HPLC (Gemini C18 110A, 5 uM 100×30 mm, 20-100% CH$_3$CN in water with 10 mM NH$_4$OH, 60 mL/min) to give the title compound (3 mg, 29%). LCMS (ES-API): mass calcd. for C$_{23}$H$_{21}$ClFN$_5$O$_4$, 485.1; m/z found, 486.1 [M+H]$^+$. $^1$H NMR (400 MHz, CDCl$_3$) δ 8.51 (s, 1H), 7.43 (s, 1H), 7.42-7.32 (m, 2H), 7.24-7.12 (m, 1H), 5.64-5.60 (m, 1H), 5.39 (s, 1H), 4.66 (d, J=6.4 Hz, 2H), 4.00 (s, 3H), 3.90 (q, J=7.3 Hz, 2H), 2.22 (s, 3H), 2.18 (br s, 1H), 1.46-1.38 (m, 3H) ppm.

Example 31: 2-(5-Chloro-3-methyl-1H-pyrazol-4-yl)-6-(4-ethyl-3-(hydroxymethyl)-5-oxo-4,5-dihydro-1H-1,2,4-triazol-1-yl)-7-fluoro-4-isopropylisoquinolin-1(2H)-one

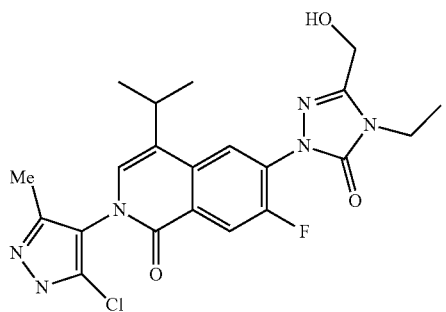 [SMILES: CCn1c(CO)nn(-c2cc3c(C(C)C)cn(-c4c(C)n[nH]c4Cl)c(=O)c3cc2F)c1=O]

Step A. 6-(3-((Benzyloxy)methyl)-4-ethyl-5-oxo-4,5-dihydro-1H-1,2,4-triazol-1-yl)-2-(5-chloro-3-methyl-1H-pyrazol-4-yl)-7-fluoro-4-isopropylisoquinolin-1(2H)-one.
To a solution of 5-chloro-3-methyl-4-amino-1H-pyrazole (260 mg, 2.0 mmol) in DCM (3.0 mL) at 0° C. under a $N_2$ atmosphere was added $AlMe_3$ (0.74 mL, 2 M in toluene, 1.5 mmol). The mixture was stirred for 5 min then 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4, 216 mg, 0.5 mmol) in DCM (1.5 mL) was added. The reaction was slowly warmed to room temperature then heated to 60° C. overnight. The reaction was cooled to 0° C. then carefully quenched by dropwise addition of MeOH followed by water. The organics were extracted with DCM (2×). The combined organics layers were washed with brine, dried over sodium sulfate, filtered and concentrated. The crude mixture was dissolved in AcOH (1.0 mL) and heated at 90° C. for 24 h. The mixture was then cooled to room temperature and neutralized with $K_2CO_3$. The organics were extracted with EtOAc (3×), washed with brine, dried over sodium sulfate, filtered and concentrated. The crude oil was purified by flash column chromatography ($SiO_2$, 50-70% EtOAc/heptane) to afford the title compound as a colorless oil (183 mg, 67% yield over two steps). LCMS (ES-API): mass calcd. for $C_{28}H_{28}ClFN_6O_3$, 550.2; m/z found, 551.3 [M+H]$^+$.
Step B. 2-(5-Chloro-3-methyl-1H-pyrazol-4-yl)-6-(4-ethyl-3-(hydroxymethyl)-5-oxo-4,5-dihydro-1H-1,2,4-triazol-1-yl)-7-fluoro-4-isopropylisoquinolin-1(2H)-one. To a solution of 6-(3-((benzyloxy)methyl)-4-ethyl-5-oxo-4,5-dihydro-1H-1,2,4-triazol-1-yl)-2-(5-chloro-3-methyl-1H-pyrazol-4-yl)-7-fluoro-4-isopropylisoquinolin-1(2H)-one (180 mg, 0.33 mmol) in DCM (3.3 mL) at −78° C. was added $BCl_3$ (0.98 mL, 1 M in DCM, 0.98 mmol). The mixture was stirred for 2 h then quenched by dropwise addition of MeOH followed by water. The mixture was diluted with EtOAc and transferred to a separatory funnel. The organics were extracted with EtOAc (2×). The combined organic layers were washed with sat. aq. $NaHCO_3$, dried over sodium sulfate, filtered and concentrated. The crude oil was adsorbed onto silica and purified by column chromatography ($SiO_2$, 60-80% EtOAc/heptane) to provide the title compound (147 mg) with minor impurities as a colorless oil. The material was re-purified by RP HPLC (Isco Acuuprep, 30-100 mm Gemini C18, 20-40% ACN/10 mM $NH_4OH$ in water) followed by additional column chromatography ($SiO_2$, 60-80% EtOAc/heptane) to provide the title compound (17 mg, yield 11%) as a white solid. LCMS (ES-API): mass calcd. for $C_{21}H_{22}ClFN_6O_3$, 460.1; m/z found, 461.3 [M+H]$^+$. $^1$H NMR (400 MHz, CDCl$_3$) δ 9.81-9.99 (m, 1H), 8.32 (d, J=11.2 Hz, 1H), 8.08 (d, J=6.8 Hz, 1H), 6.83 (s, 1H), 4.71 (d, J=6.4 Hz, 2H), 3.94 (q, J=7.0 Hz, 2H), 3.25 (m, 1H), 2.28 (s, 3H), 2.03-2.16 (m, 1H), 1.45 (t, J=7.3 Hz, 3H), 1.33 (m, 6H) ppm.

Example 32: 2-(4-Ethyl-3-(hydroxymethyl)-5-oxo-4,5-dihydro-1H-1,2,4-triazol-1-yl)-3-fluoro-8-(prop-1-en-2-yl)-6-(o-tolyl)-1,6-naphthyridin-5(6H)-one

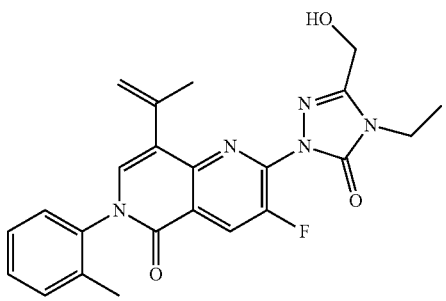 [SMILES: C=C(C)c1cn(-c2ccccc2C)c(=O)c2cc(F)c(-n3nc(CO)n(CC)c3=O)nc12]

Step A. Methyl 6-(3-((benzyloxy)methyl)-4-ethyl-5-oxo-4,5-dihydro-1H-1,2,4-triazol-1-yl)-2-chloro-5-fluoronicotinate. Methyl 2,6-dichloro-5-fluoronicotinate (7.48 g, 33.4 mmol), 5-((benzyloxy)methyl)-4-ethyl-2,4-dihydro-3H-1,2,4-triazol-3-one (7.945 g, 34.1 mmol), $K_2CO_3$ (6.92 g, 50.1 mmol) in DMSO (160 mL) was stirred at 80° C. for 1 h. The mixture was diluted with EtOAc and water and transferred to a separatory funnel. The organics were extracted with EtOAc (2×). The combined organic layers were washed with brine (3×), dried over sodium sulfate, filtered and concentrated. The crude material was purified by column chromatography ($SiO_2$, 20-50% EtOAc/heptane) to provide the title compound as a white solid (26.6 g, 90% yield). LCMS (ES-API): mass calcd. for $C_{19}H_{18}ClFN_4O_4$, 420.1; m/z found, 421.0 [M+H]$^+$. $^1$H NMR (400 MHz, CDCl$_3$) δ 8.15 (d, J=8.8 Hz, 1H), 7.28-7.50 (m, 5H), 4.60 (s, 2H), 4.54 (s, 2H), 3.99 (s, 3H), 3.85 (q, J=7.2 Hz, 2H), 1.34 (t, J=7.3 Hz, 3H) ppm.
Step B. Methyl 6-(3-((benzyloxy)methyl)-4-ethyl-5-oxo-4,5-dihydro-1H-1,2,4-triazol-1-yl)-5-fluoro-2-((trimethylsilyl)ethynyl)nicotinate. Methyl 6-(3-((benzyloxy)methyl)-4-ethyl-5-oxo-4,5-dihydro-1H-1,2,4-triazol-1-yl)-2-chloro-5-fluoronicotinate (1.8 g, 4.2 mmol), trimethylsilylacetylene (2.94 mL, 0.709 g/mL, 21.2 mmol), $PdCl_2(PPh_3)_2$ (298 mg, 0.43 mmol), CuI (121 mg, 0.64 mmol), TEA (1.18 mL, 0.728 g/mL, 8.5 mmol) and MeCN (4 mL) was added to a microwave vial. The mixture was stirred at 100° C. for 2 h then cooled to room temperature. The mixture was filtered over Celite® then purified by flash column chromatography ($SiO_2$, 10-60% EtOAc/heptane) to provide the title compound as a dark sticky oil (1.65 g, 80% yield). LCMS (ES-API): mass calcd. for $C_{24}H_{27}FN_4O_4Si$, 482.2; m/z found, 483.1 [M+H]$^+$. $^1$H NMR (400 MHz, CDCl$_3$) δ 8.14 (d, J=9.3 Hz, 1H), 7.29-7.50 (m, 5H), 4.60 (s, 2H), 4.54 (s, 2H), 3.97 (s, 3H), 3.84 (q, J=7.0 Hz, 2H), 1.32 (t, J=7.3 Hz, 3H), 0.27 (s, 9H) ppm.
Step C. Methyl 6-(3-((benzyloxy)methyl)-4-ethyl-5-oxo-4,5-dihydro-1H-1,2,4-triazol-1-yl)-2-ethynyl-5-fluoronicotinate. To a solution of methyl 6-(3-((benzyloxy)methyl)-4-ethyl-5-oxo-4,5-dihydro-1H-1,2,4-triazol-1-yl)-5-fluoro-2-

((trimethylsilyl)ethynyl)nicotinate (6.6 g, 13.7 mmol) in THF (110 mL) was added TBAF (15.0 mL, 1 M in THF, 15.0 mmol). The reaction was stirred at room temperature for 0.5 h then diluted with water and EtOAc. The organics were extracted with EtOAc, washed with brine, dried over sodium sulfate, filtered and concentrated. Purification by flash column chromatography (SiO$_2$, 20-60% EtOAc heptane) afforded the title compound as a tan solid (5.6 g, quantitative yield). LCMS (ES-API): mass calcd. for $C_{21}H_{19}FN_4O_4$, 410.1; m/z found, 411.1 [M+H]$^+$.

Step D. 2-(3-((Benzyloxy)methyl)-4-ethyl-5-oxo-4,5-dihydro-1H-1,2,4-triazol-1-yl)-3-fluoro-5H-pyrano[4,3-b]pyridin-5-one. To a vial with a stir bar was added methyl 6-(3-((benzyloxy)methyl)-4-ethyl-5-oxo-4,5-dihydro-1H-1,2,4-triazol-1-yl)-2-ethynyl-5-fluoronicotinate (1.58 g, 3.85 mmol) and AuCl$_3$ (117 mg, 0.39 mmol). The vial was evacuated and backfilled with nitrogen then water (139 µL, 7.71 mmol) and MeCN (40 mL) were added. The mixture was heated to 50° C. for 1.5 h then filtered over a pad of Celite® and concentrated. The crude residue was purified by flash column chromatography (SiO$_2$, 40-70% EtOAc/heptane) to provide the title compound as a sticky oil (1.2 g, 78% yield). LCMS (ES-API): mass calcd. for $C_{20}H_{17}FN_4O_4$, 396.1; m/z found, 397.2 [M+H]$^+$.

Step E. 2-(3-((Benzyloxy)methyl)-4-ethyl-5-oxo-4,5-dihydro-1H-1,2,4-triazol-1-yl)-3-fluoro-6-(o-tolyl)-1,6-naphthyridin-5(6H)-one. To a solution of o-toluidine (1.2 mL, 1.008 g/mL, 11.1 mmol) in DCM (27.0 mL) at 0° C. was added AlMe$_3$ (4.2 mL, 2 M in toluene, 8.3 mmol). The mixture was stirred for 5 min then 2-(3-((benzyloxy)methyl)-4-ethyl-5-oxo-4,5-dihydro-1H-1,2,4-triazol-1-yl)-3-fluoro-5H-pyrano[4,3-b]pyridin-5-one (1.1 g, 2.8 mmol) in a solution of DCM (5.0 mL) was added. The mixture was warmed to room temperature and stirred overnight. The reaction was carefully quenched by dropwise addition of MeOH then diluted with water and DCM and transferred to a separatory funnel. Diluted HCl (0.5N) was added. The organics were extracted with DCM (3×), washed with brine, dried over sodium sulfate, filtered and concentrated. The crude residue was dissolved in AcOH (6.0 mL) and stirred at 90° C. for 3 h then cooled to room temperature and diluted with EtOAc and water. The reaction was neutralized with K$_2$CO$_3$ then the organics extracted with EtOAc (2×). The combined organic layers were dried over sodium sulfate, filtered and concentrated. The crude product was purified by flash column chromatography (SiO$_2$, 30-70% EtOAc/heptane) to provide the title compound (710 mg, 53% yield). LCMS (ES-API): mass calcd. for $C_{27}H_{24}FN_5O_3$, 485.2; m/z found, 486.1 [M+H]$^+$.

Step F. 2-(3-((Benzyloxy)methyl)-4-ethyl-5-oxo-4,5-dihydro-1H-1,2,4-triazol-1-yl)-8-bromo-3-fluoro-6-(o-tolyl)-1,6-naphthyridin-5(6H)-one. 2-(3-((Benzyloxy)methyl)-4-ethyl-5-oxo-4,5-dihydro-1H-1,2,4-triazol-1-yl)-3-fluoro-6-(o-tolyl)-1,6-naphthyridin-5(6H)-one (111 mg, 0.23 mmol) and NBS (49 mg, 0.27 mmol) in DMF (1.7 mL) was stirred at room temperature for 3 h. The mixture was concentrated and purified by flash column chromatography (SiO$_2$, 20-40% EtOAc/heptane) to provide the title compound as a white solid (107 mg, 83% yield). LCMS (ES-API): mass calcd. for $C_{27}H_{23}BrFN_5O_3$, 563.1; m/z found, 564.0 [M+H]$^+$.

Step G. 2-(3-((Benzyloxy)methyl)-4-ethyl-5-oxo-4,5-dihydro-1H-1,2,4-triazol-1-yl)-3-fluoro-8-(prop-1-en-2-yl)-6-(o-tolyl)-1,6-naphthyridin-5(6H)-one. 2-(3-((Benzyloxy)methyl)-4-ethyl-5-oxo-4,5-dihydro-1H-1,2,4-triazol-1-yl)-8-bromo-3-fluoro-6-(o-tolyl)-1,6-naphthyridin-5(6H)-one (105 mg, 0.186 mmol), isopropenylboronic acid pinacol ester (105 µL, 0.894 g/mL, 0.56 mmol), PdCl$_2$(PPh$_3$)$_2$ (13 mg, 0.02 mmol), Cs$_2$CO$_3$ (121 mg, 0.37 mmol) in 1,4-dioxane (3.7 mL) and water (1.9 mL) were stirred at 100° C. for 3 h. The mixture was cooled to room temperature and diluted with EtOAc and water. The organics were extracted with EtOAc, washed with brine, dried over sodium sulfate, filtered and concentrated. The crude product was purified by flash column chromatography (SiO$_2$, 20-40% EtOAc/heptane) to provide the title compound as a yellow oil (91 mg, 93% yield). LCMS (ES-API): mass calcd. for $C_{30}H_{28}FN_5O_3$, 525.2; m/z found, 526.2 [M+H]$^+$.

Step H. 2-(4-Ethyl-3-(hydroxymethyl)-5-oxo-4,5-dihydro-1H-1,2,4-triazol-1-yl)-3-fluoro-8-(prop-1-en-2-yl)-6-(o-tolyl)-1,6-naphthyridin-5(6H)-one. To a solution of 2-(3-((benzyloxy)methyl)-4-ethyl-5-oxo-4,5-dihydro-1H-1,2,4-triazol-1-yl)-3-fluoro-8-(prop-1-en-2-yl)-6-(o-tolyl)-1,6-naphthyridin-5(6H)-one (90 mg, 0.17 mmol) in DCM (1.0 mL) at −78° C. was added BCl$_3$ (0.51 mL, 1 M in DCM, 0.51 mmol). The reaction was stirred for 1 h then quenched with MeOH and water. The organics were extracted with DCM, dried over sodium sulfate, filtered and concentrated. Purification by column chromatography (SiO$_2$, 50-80% EtOAc/heptane) provided the title compound as a pale yellow solid (41 mg, 55% yield). LCMS (ES-API): mass calcd. for $C_{23}H_{22}FN_5O_3$, 435.2; m/z found, 436.0 [M+H]$^+$. $^1$H NMR (400 MHz, CDCl$_3$) δ 8.56 (d, J=9.8 Hz, 1H), 7.28-7.44 (m, 5H), 5.40 (s, 1H), 5.22 (s, 1H), 4.70 (d, J=6.4 Hz, 2H), 3.92 (q, J=7.3 Hz, 2H), 2.33 (s, 3H), 2.19 (s, 3H), 1.43 (t, J=7.1 Hz, 3H) ppm.

Example 33: 2-(4-Ethyl-3-(hydroxymethyl)-5-oxo-4,5-dihydro-1H-1,2,4-triazol-1-yl)-3-fluoro-8-methyl-6-(o-tolyl)pyrido[2,3-d]pyridazin-5(6H)-one

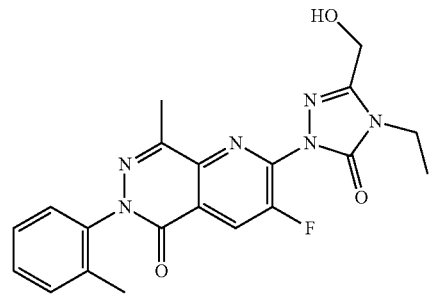 [SMILES: CCn1c(CO)nn(-c2nc3c(C)nn(-c4ccccc4C)c(=O)c3cc2F)c1=O]

Step A. Isopropyl 2-acetyl-6-(3-((benzyloxy)methyl)-4-ethyl-5-oxo-4,5-dihydro-1H-1,2,4-triazol-1-yl)-5-fluoronicotinate. Isopropyl 6-(3-((benzyloxy)methyl)-4-ethyl-5-oxo-4,5-dihydro-1H-1,2,4-triazol-1-yl)-2-chloro-5-fluoronicotinate (Intermediate 10, 564 mg, 1.26 mmol), PdCl$_2$(PPh$_3$)$_2$ (88 mg, 0.13 mmol), tributyl(1-ethoxyvinyl)tin (0.64 mL, 1.069 g/mL, 1.9 mmol) and toluene (5.6 mL) were added to a microwave vial. The mixture was sparged with argon then sealed and heated at 100° C. for 1.5 h. The mixture was diluted with EtOAc and water. The organics were extracted with EtOAc, washed with brine, dried over sodium sulfate, filtered and concentrated. The crude residue was dissolved in acetone (2 mL) and HCl (3N, 2 mL) and stirred vigorously for 2 h. The mixture was neutralized with K$_2$CO$_3$ then diluted with water and EtOAc. The organics were extracted with EtOAc (2×). The combined layers were washed with sat. aq. NaHCO$_3$ followed by brine. The organics were dried over sodium sulfate, filtered and concentrated. Purification by flash column chromatography (SiO$_2$, 30-50% EtOAc/heptane) provided the title compound as a pale yellow oil (614 mg, 99% yield). LCMS (ES-API): mass calcd. for C$_{23}$H$_{25}$FN$_4$O$_5$, 456.2; m/z found, 457.2 [M+H]$^+$. $^1$H NMR (400 MHz, CDCl$_3$) δ 7.89 (d, J=8.8 Hz, 1H), 7.29-7.47 (m, 5H), 5.27 (spt, J=6.4 Hz, 1H), 4.62 (s, 2H), 4.54 (s, 2H), 3.86 (q, J=7.0 Hz, 2H), 2.68 (s, 3H), 1.32-1.42 (m, 9H) ppm.

Step B. 2-(3-((Benzyloxy)methyl)-4-ethyl-5-oxo-4,5-dihydro-1H-1,2,4-triazol-1-yl)-3-fluoro-8-methyl-6-(o-tolyl)pyrido[2,3-d]pyridazin-5(6H)-one. Isopropyl 2-acetyl-6-(3-((benzyloxy)methyl)-4-ethyl-5-oxo-4,5-dihydro-1H-1,2,4-triazol-1-yl)-5-fluoronicotinate (107 mg, 0.23 mmol), o-tolylhydrazine hydrochloride (74 mg, 0.47 mmol), K$_2$CO$_3$ (162 mg, 1.2 mmol) in toluene (0.8 mL) were stirred at 110° C. for overnight. The mixture was filtered and concentrated. The crude mixture was purified by column chromatography (SiO$_2$, 20-40% EtOAc/heptane) to provide the title compound as a pale yellow solid (92 mg, 78% yield). LCMS (ES-API): mass calcd. for C$_{27}$H$_{25}$FN$_6$O$_3$, 500.2; m/z found, 501.1 [M+H]$^+$. $^1$H NMR (400 MHz, CDCl$_3$) δ 8.57 (d, J=8.8 Hz, 1H), 7.30-7.51 (m, 9H), 4.65 (s, 2H), 4.57 (s, 2H), 3.89 (q, J=7.0 Hz, 2H), 2.72 (s, 3H), 2.19 (s, 3H), 1.39 (t, J=7.3 Hz, 3H) ppm.

Step C. 2-(4-Ethyl-3-(hydroxymethyl)-5-oxo-4,5-dihydro-1H-1,2,4-triazol-1-yl)-3-fluoro-8-methyl-6-(o-tolyl)pyrido[2,3-d]pyridazin-5(6H)-one. To a solution of 2-(3-((benzyloxy)methyl)-4-ethyl-5-oxo-4,5-dihydro-1H-1,2,4-triazol-1-yl)-3-fluoro-8-methyl-6-(o-tolyl)pyrido[2,3-d]pyridazin-5(6H)-one (92 mg, 0.18 mmol) in DCM (2.0 mL) at −78° C. was added BCl$_3$ (0.368 mL, 1 M in DCM, 0.37 mmol). The mixture was stirred for 1.5 h at −78° C. then quenched with water. The organics were extracted with DCM, washed with brine, dried over sodium sulfate, filtered and concentrated. The crude material was purified by column chromatography (SiO$_2$, 30-50% EtOAc/heptane) followed by re-purification by RP HPLC (Isco Acuuprep, C$_{18}$ column 100×30 mm Gemini, 20-100% ACN/10 mM NH$_4$OH in water) to afford the title compound as a white solid (57 mg, 75% yield). LCMS (ES-API): mass calcd. for C$_{20}$H$_{19}$FN$_6$O$_3$, 410.2; m/z found, 411.1 [M+H]$^+$. $^1$H NMR (400 MHz, CDCl$_3$) δ 8.57 (d, J=8.8 Hz, 1H), 7.29-7.46 (m, 4H), 4.73 (d, J=6.4 Hz, 2H), 3.95 (q, J=7.2 Hz, 2H), 2.72 (s, 3H), 2.19 (m, 4H), 1.45 (t, J=7.1 Hz, 3H) ppm.

Example 34: 2-(4-Ethyl-3-(hydroxymethyl)-5-oxo-4,5-dihydro-1H-1,2,4-triazol-1-yl)-3-fluoro-8-isopropyl-6-(o-tolyl)pyrido[2,3-d]pyridazin-5(6H)-one

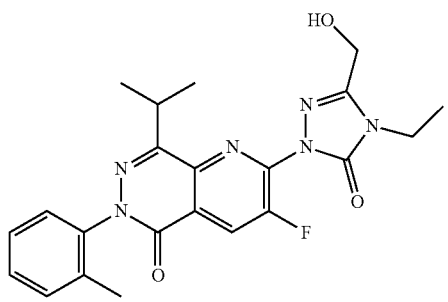 [SMILES: CCn1c(CO)nn(-c2nc3c(C(C)C)nn(-c4ccccc4C)c(=O)c3cc2F)c1=O]

Step A. Isopropyl 6-(3-((benzyloxy)methyl)-4-ethyl-5-oxo-4,5-dihydro-1H-1,2,4-triazol-1-yl)-5-fluoro-2-vinylnicotinate. Isopropyl 6-(3-((benzyloxy)methyl)-4-ethyl-5-oxo-4, 5-dihydro-1H-1,2,4-triazol-1-yl)-2-chloro-5-fluoronicotinate (Intermediate 10, 7.64 g, 17.0 mmol), vinylboronic acid pinacol ester (3.5 mL, 0.908 g/mL, 20.4 mmol), 1,1'-bis(diphenylphosphino)ferrocene-palladium(II)dichloride dichloromethane complex (278 mg, 0.34 mmol), Na$_2$CO$_3$ (7.22 g, 68.1 mmol), 1,4-dioxane (15 mL) and water (15 mL) were added to a pressure vessel. The mixture was sparged with Ar then heated to 100° C. and stirred overnight. The mixture was then diluted with EtOAc and water. The organics were extracted (3×) with EtOAc then washed with brine, dried over sodium sulfate and filtered. The crude material was purified by flash column chromatography (SiO$_2$, 20-40% EtOAc/heptane) to provide the title compound as a dark oil (7.68 g, quantitative). LCMS (ES-API): mass calcd. for C$_{23}$H$_{25}$FN$_4$O$_4$, 440.2; m/z found, 441.1.

Step B. Isopropyl 6-(3-((benzyloxy)methyl)-4-ethyl-5-oxo-4,5-dihydro-1H-1,2,4-triazol-1-yl)-5-fluoro-2-formylnicotinate. Isopropyl 6-(3-((benzyloxy)methyl)-4-ethyl-5-oxo-4, 5-dihydro-1H-1,2,4-triazol-1-yl)-5-fluoro-2-vinylnicotinate (2.4 g, 5.5 mmol), sodium periodate (2.4 g, 11.0 mmol), potassium osmate(VI) dihydrate (203 mg, 0.55 mmol) in dioxane (40 mL) and water (40 mL) was stirred at room temperature overnight. The mixture was diluted with EtOAc and water and transferred to a separatory funnel. The organics were extracted with EtOAc, dried over sodium sulfate, filtered and concentrated. The crude mixture was purified by column chromatography (SiO$_2$, 40-100% EtOAc/heptane) to provide the title compound as a yellow oil (887 mg, 36% yield). LCMS (ES-API): mass calcd. for C$_{22}$H$_{23}$FN$_4$O$_5$, 442.2 m/z found, 443.1.

Step C. Mixture of isopropyl 6-(3-((benzyloxy)methyl)-4-ethyl-5-oxo-4,5-dihydro-1H-1,2,4-triazol-1-yl)-5-fluoro-2-(1-hydroxy-2-methylpropyl)nicotinate and 2-(3-((benzyloxy)methyl)-4-ethyl-5-oxo-4,5-dihydro-1H-1,2,4-triazol-1-yl)-3-fluoro-7-isopropylfuro[3,4-b]pyridin-5(7H)-one. To a solution of isopropyl 6-(3-((benzyloxy)methyl)-4-ethyl-5-oxo-4,5-dihydro-1H-1,2,4-triazol-1-yl)-5-fluoro-2-formylnicotinate (300 mg, 0.68 mmol) in THF (6.4 mL) at −78° C. was added isopropylmagnesium bromide (0.99 mL, 0.75 M in THF, 0.75 mmol) dropwise. The mixture was stirred for 2 h at the same temperature then slowly warmed to 0° C. The mixture was quenched with sat aq NH$_4$Cl. The organics were extracted with EtOAc, washed with brine, dried over sodium sulfate, filtered and concentrated. Purification by column chromatography (SiO$_2$, 0-50% EtOAc/heptane) afforded a mixture of the title compounds (80 mg) as a white solid.

Step D. Isopropyl 6-(3-((benzyloxy)methyl)-4-ethyl-5-oxo-4,5-dihydro-1H-1,2,4-triazol-1-yl)-5-fluoro-2-isobutyrylnicotinate. To a solution of a mixture of isopropyl 6-(3-((benzyloxy)methyl)-4-ethyl-5-oxo-4,5-dihydro-1H-1,2,4-triazol-1-yl)-5-fluoro-2-(1-hydroxy-2-methylpropyl)nicotinate and 2-(3-((benzyloxy)methyl)-4-ethyl-5-oxo-4,5-dihydro-1H-1,2,4-triazol-1-yl)-3-fluoro-7-isopropylfuro[3,4-b]pyridin-5(7H)-one (78 mg) in DCM (2.0 mL) was added DMP (75 mg, 0.18 mmol). The reaction was stirred at room temperature for 16 h. The mixture was diluted with DCM and filtered over Celite® then concentrated. Purification by column chromatography (SiO$_2$, 10-40% EtOAc/heptane) afforded the title compound (57 mg, 73% yield). LCMS (ES-API): mass calcd. for C$_{25}$H$_{29}$FN$_4$O$_5$, 484.2; m/z found, 485.3 [M+H]$^+$.

Step E. 2-(3-((Benzyloxy)methyl)-4-ethyl-5-oxo-4,5-dihydro-1H-1,2,4-triazol-1-yl)-3-fluoro-8-isopropyl-6-(o-tolyl)pyrido[2,3-d]pyridazin-5(6H)-one. Isopropyl 6-(3-((benzyloxy)methyl)-4-ethyl-5-oxo-4,5-dihydro-1H-1,2,4-triazol-1-yl)-5-fluoro-2-isobutyrylnicotinate (97 mg, 0.2 mmol), o-tolylhydrazine hydrochloride (63.5 mg, 0.4 mmol), and K$_2$CO$_3$ (138 mg, 1.0 mmol) in toluene (0.68 mL) was stirred at 110° C. overnight. The mixture was filtered and concentrated. The crude mixture was purified by column chromatography (SiO$_2$, 20-40% EtOAc/heptane) to provide the title compound (60 mg, 44% yield). LCMS (ES-API): mass calcd. for C$_{29}$H$_{29}$FN$_6$O$_3$, 528.2; m/z found, 529.2 [M+H]$^+$.

Step F. 2-(4-Ethyl-3-(hydroxymethyl)-5-oxo-4,5-dihydro-1H-1,2,4-triazol-1-yl)-3-fluoro-8-isopropyl-6-(o-tolyl)pyrido[2,3-d]pyridazin-5(6H)-one. To a solution of 2-(3-((benzyloxy)methyl)-4-ethyl-5-oxo-4,5-dihydro-1H-1,2,4-triazol-1-yl)-3-fluoro-8-isopropyl-6-(o-tolyl)pyrido[2,3-d]pyridazin-5(6H)-one (58 mg, 0.11 mmol) in DCM (2.0 mL) at −78° C. was added BCl$_3$ (0.33 mL, 1 M in DCM, 0.33 mmol) dropwise. The mixture was stirred for 1.5 h then quenched with MeOH followed by water. The organics were extracted with DCM, dried over sodium sulfate, filtered and concentrated. The crude residue was purified by RP HPLC (Isco Acuuprep, C18 Gemini 30×100 column, 10-100% ACN/10 mM NH$_4$OH in water) to provide the title compound as a white solid (27 mg, 56% yield). LCMS (ES-API): mass calcd. for C$_{22}$H$_{23}$FN$_6$O$_3$, 438.2; m/z found, 439.2 [M+H]$^+$. $^1$H NMR (400 MHz, CDCl$_3$) δ 8.56 (d, J=9.3 Hz, 1H), 7.32-7.42 (m, 4H), 4.73 (d, J=6.4 Hz, 2H), 3.80-4.01 (m, 3H), 2.13-2.22 (m, 4H), 1.45 (t, J=7.3 Hz, 3H), 1.35 (d, J=6.8 Hz, 6H) ppm.

Example 35: 6-(2-Chloro-6-fluorophenyl)-2-(4-ethyl-3-(hydroxymethyl)-5-oxo-4,5-dihydro-1H-1,2,4-triazol-1-yl)-3-fluoro-8-(prop-1-en-2-yl)-1,6-naphthyridin-5(6H)-one

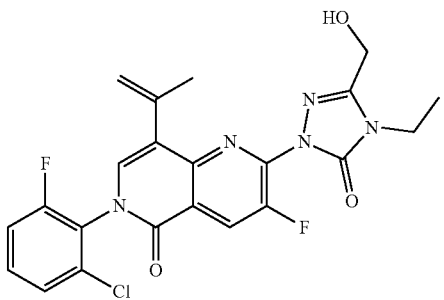 [SMILES: C=C(C)c1cn(-c2c(F)cccc2Cl)c(=O)c2cc(F)c(-n3nc(CO)n(CC)c3=O)nc12]

Step A. Isopropyl 6-(3-((benzyloxy)methyl)-4-ethyl-5-oxo-4,5-dihydro-1H-1,2,4-triazol-1-yl)-2-(2-ethoxyvinyl)-5-fluoronicotinate. Isopropyl 6-(3-((benzyloxy)methyl)-4-ethyl-5-oxo-4,5-dihydro-1H-1,2,4-triazol-1-yl)-2-chloro-5-fluoronicotinate (Intermediate 10, 1.37 g, 3.1 mmol), 1-ethoxyethene-2-boronic acid pinacol ester (725 mg, 3.7 mmol), 1,1'-bis(diphenylphosphino)ferrocene-palladium(II) dichloride dichloromethane complex (187 mg, 0.23 mmol), Na$_2$CO$_3$ (1.3 g, 12.2 mmol), 1,4-dioxane (5.5 mL) and water (5.5 mL) were added to a microwave vial. The mixture was sparged with Ar then heated to 100° C. and stirred overnight. The mixture was then diluted with EtOAc and water. The organics were extracted (3×) with EtOAc then washed with brine, dried over sodium sulfate and filtered. The crude material was purified by column chromatography (SiO$_2$, 20-50% EtOAc/heptane) to provide the title compound as a yellow orange oil (1.58 g, quantitative). LCMS (ES-API): mass calcd. for C$_{25}$H$_{29}$FN$_4$O$_5$, 484.2; m/z found, 485.3 [M+H]$^+$.

Step B. 2-(3-((Benzyloxy)methyl)-4-ethyl-5-oxo-4,5-dihydro-1H-1,2,4-triazol-1-yl)-6-(2-chloro-6-fluorophenyl)-3-fluoro-1,6-naphthyridin-5(6H)-one. To a solution of 2-chloro-6-fluoroaniline (676 mg, 4.6 mmol) in DCM (3.0 mL) at 0° C. was added AlMe$_3$ (3.1 mL, 2 M in toluene, 6.2 mmol). The mixture was stirred for 5 minutes then a solution of isopropyl-6-(3-((benzyloxy)methyl)-4-ethyl-5-oxo-4,5-dihydro-1H-1,2,4-triazol-1-yl)-2-(2-ethoxyvinyl)-5-fluoronicotinate (730 mg, 1.5 mmol) in DCM (3.0 mL) was added. The mixture was stirred at room temperature overnight. The mixture was heated to 50° C. and stirred for 6 h then cooled to rt and quenched by careful addition of MeOH. Dilute HCl was added to solubilize solids and the organics were extracted with DCM, dried over sodium sulfate, filtered and concentrated. The crude residue was dissolved in AcOH (4.0 mL) and heated at 90° C. for 1 h. The mixture was diluted with EtOAc and transferred to a separatory funnel. The organics were washed with brine, dried over sodium sulfate, filtered and concentrated. The crude product was purified by column chromatography (SiO$_2$, 40-70% EtOAc/heptane) to provide the title compound as a yellow/orange solid (675 mg, 86% yield). LCMS (ES-API): mass calcd. for C$_{26}$H$_{20}$ClF$_2$N$_5$O$_3$, 523.1; m/z found, 524.1 [M+H]$^+$.

Step C. 2-(3-((Benzyloxy)methyl)-4-ethyl-5-oxo-4,5-dihydro-1H-1,2,4-triazol-1-yl)-8-bromo-6-(2-chloro-6-fluorophenyl)-3-fluoro-1,6-naphthyridin-5(6H)-one. To a solution of 2-(3-((benzyloxy)methyl)-4-ethyl-5-oxo-4,5-dihydro-1H-1,2,4-triazol-1-yl)-6-(2-chloro-6-fluorophenyl)-3-fluoro-1,6-naphthyridin-5(6H)-one (675 mg, 1.3 mmol) in DMF (9.3 mL) was added NBS (275 mg, 1.5 mmol). The mixture was stirred overnight at room temperature. EtOAc and water were added. The organics were extracted with EtOAc, washed with brine, dried over sodium sulfate, filtered and concentrated. Purification by flash column chromatography (SiO$_2$, 20-50% EtOAc/heptane) provided the title compound as a tan solid (443 mg, 57% yield). LCMS (ES-API): mass calcd. for C$_{26}$H$_{19}$BrClF$_2$N$_5$O$_3$, 601.0; m/z found, 602.1 [M+H]$^+$.

Step D. 2-(3-((Benzyloxy)methyl)-4-ethyl-5-oxo-4,5-dihydro-1H-1,2,4-triazol-1-yl)-6-(2-chloro-6-fluorophenyl)-3-fluoro-8-(prop-1-en-2-yl)-1,6-naphthyridin-5(6H)-one. 2-(3-((Benzyloxy)methyl)-4-ethyl-5-oxo-4,5-dihydro-1H-1,2,4-triazol-1-yl)-8-bromo-6-(2-chloro-6-fluorophenyl)-3-fluoro-1,6-naphthyridin-5(6H)-one (178 mg, 0.3 mmol), 4,4,5,5-tetramethyl-2-(prop-1-en-2-yl)-1,3,2-dioxaborolane (0.17 mL, 0.894 g/mL, 0.89 mmol), Pd(PPh$_3$)$_2$Cl$_2$ (21 mg, 0.03 mmol), Cs$_2$CO$_3$ (192 mg, 0.59 mmol) in 1,4-dioxane (4.1 mL) and water (1.7 mL) were sparged with Ar then stirred at 100° C. for 3 h. The mixture was cooled to room temperature and diluted with EtOAc and water. The organics were extracted with EtOAc, washed with brine, dried over sodium sulfate, filtered and concentrated. The crude product was purified by flash column chromatography (SiO$_2$, 20-40% EtOAc/heptane) to provide the title compound as an oil (149 mg, 90% yield). LCMS (ES-API): mass calcd. for C$_{29}$H$_{24}$ClF$_2$N$_5$O$_3$, 563.2; m/z found, 564.2 [M+H]$^+$.

Step E. 6-(2-Chloro-6-fluorophenyl)-2-(4-ethyl-3-(hydroxymethyl)-5-oxo-4,5-dihydro-1H-1,2,4-triazol-1-yl)-3-fluoro-8-(prop-1-en-2-yl)-1,6-naphthyridin-5(6H)-one To a solution of 2-(3-((Benzyloxy)methyl)-4-ethyl-5-oxo-4,5-dihydro-1H-1,2,4-triazol-1-yl)-6-(2-chloro-6-fluorophenyl)-3-fluoro-8-(prop-1-en-2-yl)-1,6-naphthyridin-5(6H)-one (64 mg, 0.11 mmol) in DCM (2.0 mL) at −78° C. was added BCl$_3$ (0.57 mL, 1 M in DCM, 0.57 mmol). The mixture was stirred for 1.5 h then quenched carefully by dropwise addition of MeOH followed by water. The organics were extracted with DCM, washed with brine, dried over sodium sulfate, filtered and concentrated. Purification by column chromatography (SiO$_2$, 40-70% EtOAc/heptane) afforded the title compound with minor impurities. The product was re-purified by RP HPLC (Isco AcuuPrep, 30×100 mm Gemini C$_{18}$ column, 20-70% ACN/water (10 mM NH$_4$OH) to afford the title compound as a pale yellow solid (22 mg, 41% yield). LCMS (ES-API): mass calcd. for C$_{22}$H$_{18}$ClF$_2$N$_5$O$_3$, 473.1; m/z found, 474.1 [M+H]$^+$. $^1$H NMR (400 MHz, CDCl$_3$) δ 8.55 (d, J=9.8 Hz, 1H), 7.36-7.50 (m, 2H), 7.20-7.25 (m, 1H), 7.15 (s, 1H), 5.38 (s, 1H), 5.23 (s, 1H), 4.69 (br d, J=4.9 Hz, 2H), 3.92 (q, J=7.3 Hz, 2H), 2.34 (s, 3H), 2.18-2.28 (m, 1H), 1.42 (t, J=7.1 Hz, 3H) ppm.

Example 36. 6-(2-Chloro-6-fluorophenyl)-2-(4-ethyl-3-(hydroxymethyl)-5-oxo-4,5-dihydro-1H-1,2,4-triazol-1-yl)-3-fluoro-8-isopropyl-1,6-naphthyridin-5(6H)-one

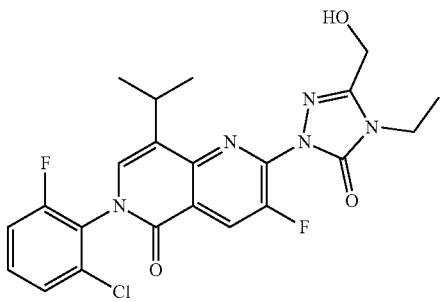 [SMILES: CCn1c(CO)nn(-c2nc3c(C(C)C)cn(-c4c(F)cccc4Cl)c(=O)c3cc2F)c1=O]

Step A. 2-(3-((Benzyloxy)methyl)-4-ethyl-5-oxo-4,5-dihydro-1H-1,2,4-triazol-1-yl)-6-(2-chloro-6-fluorophenyl)-3-fluoro-8-isopropyl-1,6-naphthyridin-5(6H)-one. To a solution of 2-(3-((benzyloxy)methyl)-4-ethyl-5-oxo-4,5-dihydro-1H-1,2,4-triazol-1-yl)-6-(2-chloro-6-fluorophenyl)-3-fluoro-8-(prop-1-en-2-yl)-1,6-naphthyridin-5(6H)-one (65 mg, 0.12 mmol) in THF (3.0 mL) was added Rh(PPh$_3$)$_3$C$_1$ (32 mg, 0.0346 mmol). H$_2$ was bubbled through the mixture for 5 minutes then allowed to stir overnight. The mixture was concentrated and purified by column chromatography (SiO$_2$, 20-50% EtOAc/heptane) to provide the title compound (55 mg, 84% yield). LCMS (ES-API): mass calcd. for C$_{29}$H$_{26}$ClF$_2$N$_5$O$_3$, 565.2; m/z found, 566.2 [M+H]$^+$.
Step B. 6-(2-Chloro-6-fluorophenyl)-2-(4-ethyl-3-(hydroxymethyl)-5-oxo-4,5-dihydro-1H-1,2,4-triazol-1-yl)-3-fluoro-8-isopropyl-1,6-naphthyridin-5(6H)-one. To a solution of 2-(3-((benzyloxy)methyl)-4-ethyl-5-oxo-4,5-dihydro-1H-1,2,4-triazol-1-yl)-6-(2-chloro-6-fluorophenyl)-3-fluoro-8-isopropyl-1,6-naphthyridin-5(6H)-one (55 mg, 0.1 mmol) in DCM (1.1 mL) at −78° C. was added BCl$_3$ (0.34 mL, 1 M in DCM, 0.34 mmol) dropwise. The reaction was stirred for 1 h then quenched by addition of MeOH followed by water. The organics were extracted with DCM, dried over sodium sulfate, filtered and concentrated. Purification by reverse phase HPLC (10-100% MeCN/10 mM NH$_4$OH in water, Gemini C18 5 µM C18 100Å 100×30 mm column) afforded the title compound as a white solid after lyophilization (30 mg, 65% yield). LCMS (ES-API): mass calcd. for C$_{22}$H$_{20}$ClF$_2$N$_5$O$_3$, 475.1; m/z found, 476.1 [M+H]$^+$. $^1$H NMR (400 MHz, CDCl$_3$) δ 8.54 (d, J=9.8 Hz, 1H), 7.55-7.35 (m, 2H), 7.26-7.20 (m, 1H), 6.93 (s, 1H), 4.70 (d, J=6.4 Hz, 2H), 3.94 (q, J=7.2 Hz, 2H), 3.74-3.55 (m, 1H), 2.39 (t, J=6.4 Hz, 1H), 1.44 (t, J=7.1 Hz, 3H), 1.32 (dd, J=3.2, 6.6 Hz, 6H) ppm.

Example 37. (S)-2-(4-Ethyl-3-(hydroxymethyl)-5-oxo-4,5-dihydro-1H-1,2,4-triazol-1-yl)-3-fluoro-6-(o-tolyl)-8-(1,1,1-trifluoropropan-2-yl)-1,6-naphthyridin-5(6H)-one

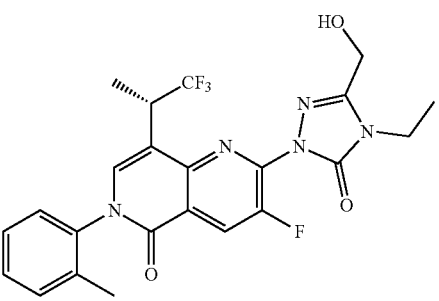 [SMILES: CCn1c(CO)nn(-c2nc3c([C@H](C)C(F)(F)F)cn(-c4ccccc4C)c(=O)c3cc2F)c1=O]

Step A. 2-(3-((Benzyloxy)methyl)-4-ethyl-5-oxo-4,5-dihydro-1H-1,2,4-triazol-1-yl)-3-fluoro-6-(o-tolyl)-8-(3,3,3-trifluoroprop-1-en-2-yl)-1,6-naphthyridin-5(6H)-one. 2-(3-((Benzyloxy)methyl)-4-ethyl-5-oxo-4,5-dihydro-1H-1,2,4-triazol-1-yl)-8-bromo-3-fluoro-6-(o-tolyl)-1,6-naphthyridin-5(6H)-one (100 mg, 0.18 mmol) (Example 32, Step F), 1-(trifluoromethyl)vinylboronic acid hexylene glycol ester (118 mg, 0.53 mmol), Pd(PPh$_3$)$_2$Cl$_2$ (12 mg, 0.018 mmol), Cs$_2$CO$_3$ (115 mg, 0.35 mmol) in 1,4-dioxane (2.5 mL) and water (1.0 mL) were stirred at 100° C. for 3 h. Additional Pd(PPh$_3$)$_2$Cl$_2$ (6 mg), Cs$_2$CO$_3$ (60 mg) and 1-(trifluoromethyl)vinylboronic acid hexylene glycol ester (50 mg) added and the reaction continued to stir overnight at 100° C. The mixture was cooled to room temperature then diluted with EtOAc and water. The organics were extracted with EtOAc, washed with brine, dried over sodium sulfate, filtered and concentrated. The crude product was purified by flash column chromatography (SiO$_2$, 0-40% EtOAc/heptane) to provide the title compound as a yellow-orange oil (97 mg, 95% yield). LCMS (ES-API): mass calcd. for C$_{30}$H$_{25}$F$_4$N$_5$O$_3$, 579.2; m/z found, 580.2 [M+H]$^+$.
Step B. 2-(3-((Benzyloxy)methyl)-4-ethyl-5-oxo-4,5-dihydro-1H-1,2,4-triazol-1-yl)-3-fluoro-6-(o-tolyl)-8-(1,1,1-trifluoropropan-2-yl)-1,6-naphthyridin-5(6H)-one. To a solution of 2-(3-((benzyloxy)methyl)-4-ethyl-5-oxo-4,5-dihydro-1H-1,2,4-triazol-1-yl)-3-fluoro-6-(o-tolyl)-8-(3,3,3-trifluoroprop-1-en-2-yl)-1,6-naphthyridin-5(6H)-one (97 mg, 0.17 mmol) in THF (4.4 mL) was added (PPh$_3$)$_3$RhCl (46 mg, 0.05 mmol). Hydrogen was bubbled through the mixture for 5 minutes then allowed to stir overnight. The mixture was adsorbed onto silica and purified by column chromatography (SiO$_2$, 20-50% EtOAc/heptane) to provide the title compound as a yellow/orange oil (63 mg, 65% yield). LCMS (ES-API): mass calcd. for C$_{30}$H$_{27}$F$_4$N$_5$O$_3$, 581.2; m/z found, 582.2 [M+H]$^+$.
Step C. (S)-2-(4-Ethyl-3-(hydroxymethyl)-5-oxo-4,5-dihydro-1H-1,2,4-triazol-1-yl)-3-fluoro-6-(o-tolyl)-8-(1,1,1-trifluoropropan-2-yl)-1,6-naphthyridin-5(6H)-one. To a solution of 2-(3-((benzyloxy)methyl)-4-ethyl-5-oxo-4,5-dihydro-1H-1,2,4-triazol-1-yl)-3-fluoro-6-(o-tolyl)-8-(1,1,1-trifluoropropan-2-yl)-1,6-naphthyridin-5(6H)-one (62 mg, 0.11 mmol) in DCM (1.0 mL) at −78° C. was added BCl$_3$ (0.43 mL, 1 M in DCM, 0.43 mmol). The mixture was stirred for 0.5 h then quenched by addition of MeOH followed by water. The organics were extracted with DCM, dried over sodium sulfate, filtered and concentrated. Purification by column chromatography (SiO₂, 50% EtOAc/heptane) provided the racemic compound (46 mg, 87% yield). A purification was performed via chiral SFC (Stationary phase: CHIRALPAK AD-H 5 μm 250*21.2 mm, Mobile phase: 85% CO₂, 15% iPrOH) to provide the title compound (15 mg, 29% yield). LCMS (ES-API): mass calcd. for $C_{23}H_{21}F_4N_5O_3$, 491.2; m/z found, 492.4 [M+H]⁺. ¹H NMR (400 MHz, CDCl₃) δ 8.56 (d, J=9.8 Hz, 1H), 7.27-7.46 (m, 5H), 4.64-4.77 (m, 3H), 3.94 (q, J=6.8 Hz, 2H), 2.15 (s, 3H), 1.41-1.52 (m, 6H) ppm.

Example 38. (R)-2-(4-Ethyl-3-(hydroxymethyl)-5-oxo-4,5-dihydro-1H-1,2,4-triazol-1-yl)-3-fluoro-6-(o-tolyl)-8-(1,1,1-trifluoropropan-2-yl)-1,6-naphthyridin-5(6H)-one

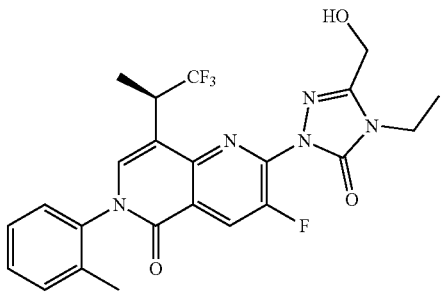 [SMILES: CCn1c(CO)nn(-c2nc3c([C@@H](C)C(F)(F)F)cn(-c4ccccc4C)c(=O)c3cc2F)c1=O]

A purification of 2-(4-ethyl-3-(hydroxymethyl)-5-oxo-4,5-dihydro-1H-1,2,4-triazol-1-yl)-3-fluoro-6-(o-tolyl)-8-(1,1,1-trifluoropropan-2-yl)-1,6-naphthyridin-5(6H)-one (Example 37, Step C) was performed via chiral SFC (Stationary phase: CHIRALPAK AD-H 5 μm 250*21.2 mm, Mobile phase: 85% CO₂, 15% iPrOH) to provide the title compound (19 mg, 36% yield). LCMS (ES-API): mass calcd. for $C_{23}H_{21}F_4N_5O_3$, 491.2; m/z found, 492.4 [M+H]⁺. ¹H NMR (400 MHz, CDCl₃) δ 8.56 (d, J=9.8 Hz, 1H), 7.27-7.46 (m, 5H), 4.64-4.77 (m, 3H), 3.94 (q, J=6.8 Hz, 2H), 2.15 (s, 3H), 1.41-1.52 (m, 6H) ppm.

Example 39. 6-(4-Ethyl-3-(hydroxymethyl)-5-oxo-4,5-dihydro-1H-1,2,4-triazol-1-yl)-7-fluoro-4-isopropyl-2-(4-methylthiazol-5-yl)isoquinolin-1(2H)-one

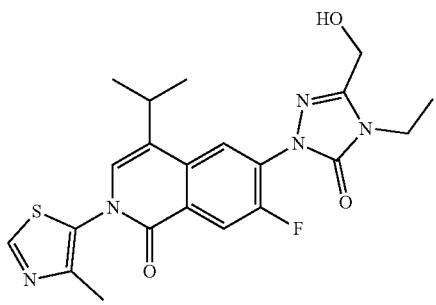 [SMILES: CCn1c(CO)nn(-c2cc3c(C(C)C)cn(-c4scnc4C)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 4-methyl-1,3-thiazol-5-amine instead of 5-chloro-3-methyl-4-amino-1H-pyrazole in Step A. LCMS (ES-API): mass calcd. for $C_{21}H_{22}FN_5O_3S$, 443.1; m/z found, 441.1 [M+H]⁺. ¹H NMR (400 MHz, CDCl₃) δ 8.80 (s, 1H), 8.30 (d, J=11.2 Hz, 1H), 8.09 (d, J=6.4 Hz, 1H), 6.86 (s, 1H), 4.71 (d, J=6.4 Hz, 2H), 3.94 (q, J=7.2 Hz, 2H), 3.18-3.34 (m, 1H), 2.33-2.45 (m, 3H), 1.45 (t, J=7.1 Hz, 3H), 1.33 (d, J=6.4 Hz, 6H) ppm.

Example 40. 2-(4-Ethyl-3-(hydroxymethyl)-5-oxo-4,5-dihydro-1H-1,2,4-triazol-1-yl)-3-fluoro-8-isopropyl-6-(o-tolyl)-1,6-naphthyridin-5(6H)-one

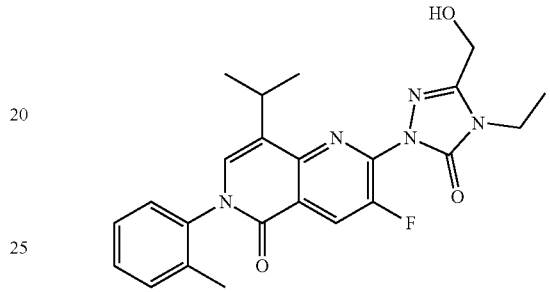

Step A. 2-(3-((Benzyloxy)methyl)-4-ethyl-5-oxo-4,5-dihydro-1H-1,2,4-triazol-1-yl)-3-fluoro-8-isopropyl-6-(o-tolyl)-1,6-naphthyridin-5(6H)-one. To a solution of 2-(3-((benzyloxy)methyl)-4-ethyl-5-oxo-4,5-dihydro-1H-1,2,4-triazol-1-yl)-3-fluoro-8-(prop-1-en-2-yl)-6-(o-tolyl)-1,6-naphthyridin-5(6H)-one (Example 32, Step G) (139 mg, 0.26 mmol) in THF (7.0 ml) was added (PPh₃)₃RhCl (73 mg, 0.08 mmol). Hydrogen was bubbled through the mixture for 5 minutes then allowed to stir overnight. The mixture was concentrated and purified by column chromatography (SiO₂, 20-50% EtOAc/heptane) to provide the title compound as a yellow/orange oil (139 mg, 100% yield). LCMS (ES-API): mass calcd. for $C_{30}H_{30}FN_5O_3$, 527.2; m/z found, 528.3 [M+H]⁺.

Step B. 2-(4-Ethyl-3-(hydroxymethyl)-5-oxo-4,5-dihydro-1H-1,2,4-triazol-1-yl)-3-fluoro-8-isopropyl-6-(o-tolyl)-1,6-naphthyridin-5(6H)-one. To a solution of 2-(3-((benzyloxy)methyl)-4-ethyl-5-oxo-4,5-dihydro-1H-1,2,4-triazol-1-yl)-3-fluoro-8-isopropyl-6-(o-tolyl)-1,6-naphthyridin-5(6H)-one (130 mg, 0.25 mmol) in DCM (2.0 mL) at −78° C. was added BCl₃ (0.86 mL, 1 M in DCM, 0.86 mmol). The mixture was stirred for 1 h then quenched with MeOH followed by water. The organics were extracted with DCM, dried over sodium sulfate, filtered and concentrated. Purification by reverse phase HPLC (Isco Acuuprep, 100×30 mm Gemini C₁₈ column, 20-100% ACN/10 mM NH₄OH) afforded the title compound as a white solid (84 mg, 77% yield). LCMS (ES-API): mass calcd. for $C_{23}H_{24}FN_5O_3$, 437.2; m/z found, 438.3 [M+H]⁺. 1H NMR (400 MHz, CDCl₃) δ 8.55 (d, J=9.7 Hz, 1H), 7.44-7.34 (m, 3H), 7.28 (s, 1H), 7.04 (s, 1H), 4.69 (d, J=6.4 Hz, 2H), 3.94 (q, J=7.2 Hz, 2H), 3.66 (spt, J=6.9 Hz, 1H), 2.59-2.52 (m, 1H), 2.16 (s, 3H), 1.44 (t, J=7.2 Hz, 3H), 1.31 (dd, J=1.8, 6.9 Hz, 6H); ¹⁹F NMR (376 MHz, CDCl₃) δ −125.65 (s, 1F) ppm.

Example 41: 6-(4-Ethyl-3-(hydroxymethyl)-5-oxo-4,5-dihydro-1H-1,2,4-triazol-1-yl)-7-fluoro-2-(2-fluoro-5-methylphenyl)-4-isopropylisoquinolin-1(2H)-one

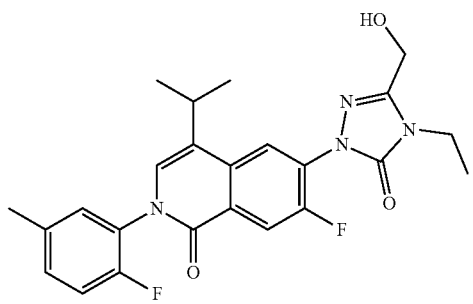 [SMILES: CCn1c(CO)nn(-c2cc3c(C(C)C)cn(-c4cc(C)ccc4F)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2-fluoro-5-methylaniline instead of 5-chloro-3-methyl-4-amino-1H-pyrazole in Step A. ESI-MS: mass calcd. for $C_{24}H_{24}F_2N_4O_3$, 454.2; m/z found, 455.2 [M+H]$^+$. $^1$H NMR (400 MHz, CDCl$_3$) δ 8.07-8.16 (m, 2H), 7.40 (d, J=7.5 Hz, 1H), 7.29-7.35 (m, 2H), 7.16 (s, 1H), 5.82 (t, J=5.8 Hz, 1H), 4.51 (d, J=5.8 Hz, 2H), 3.81 (q, J=7.2 Hz, 2H), 3.23 (dt, J=13.6, 6.9 Hz, 1H), 2.36 (s, 3H), 1.23-1.33 (m, 9H) ppm. 19F NMR (376 MHz, CDCl$_3$) δ −120.38 (s, 1F), −125.87 (s, 1F) ppm.

Example 42: 6-(4-Ethyl-3-(hydroxymethyl)-5-oxo-4,5-dihydro-1H-1,2,4-triazol-1-yl)-7-fluoro-2-(2-fluoro-5-methylphenyl)-4-(prop-1-en-2-yl)isoquinolin-1(2H)-one

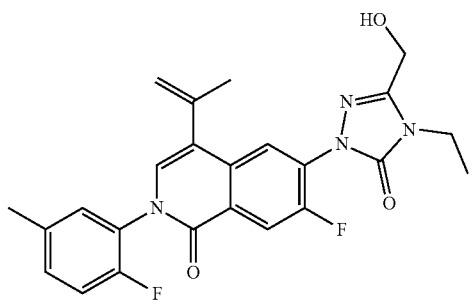 [SMILES: C=C(C)c1cn(-c2cc(C)ccc2F)c(=O)c2cc(F)c(-n3nc(CO)n(CC)c3=O)cc12]

Step A. 6-(3-((Benzyloxy)methyl)-4-ethyl-5-oxo-4,5-dihydro-1H-1,2,4-triazol-1-yl)-7-fluoro-2-(2-fluoro-5-methylphenyl)-4-(prop-1-en-2-yl)isoquinolin-1(2H)-one. To a stirred solution of 2-fluoro-5-methylaniline (115 mg, 0.92 mmol) in DCM (2 mL) was added AlMe$_3$ (2 M, 0.34 mL, 0.68 mmol) under nitrogen. The mixture was stirred at 16° C. for 0.5 h, then a DCM solution (2 mL) of 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3, 100 mg, 0.23 mmol) was added. The mixture was stirred at room temperature for overnight. Aqueous HCl (1N, 0.6 mL) was added, and the mixture was stirred for 2 min, then poured into water (15 mL), and extracted with DCM (15 mL×2). The combined organic extract was washed with brine (20 mL×2), dried with anhydrous Na$_2$SO$_4$, and concentrated. The residue was dissolved in AcOH (5 mL) and stirred at 90° C. for overnight. The mixture was poured into water (20 mL) and extracted with ethyl acetate (15 mL×2). The combined organic extract was washed with brine (20 mL×3), dried with anhydrous Na$_2$SO$_4$, and concentrated. The residue was purified by flash chromatography (SiO$_2$, Petroleum ether/Ethyl acetate from 5/1 to 1/1) to give the title compound as a yellow oil (70 mg, yield: 56%). ESI-MS: mass calcd. for $C_{31}H_{28}F_2N_4O_3$, 542.2; m/z found, 543.2 [M+H]$^+$. $^1$H NMR (400 MHz, CDCl$_3$) δ 8.31 (d, J=11.0 Hz, 1H), 7.99 (d, J=7.0 Hz, 1H), 7.33-7.42 (m, 5H), 7.21-7.26 (m, 2H), 7.13-7.18 (m, 1H), 6.98 (s, 1H), 5.35-5.37 (m, 1H), 5.18 (s, 1H), 4.63 (s, 2H), 4.55 (s, 2H), 3.89 (q, J=7.0 Hz, 2H), 2.40 (s, 3H), 2.16 (s, 3H), 1.38 (t, J=7.3 Hz, 3H) ppm; $^{19}$F NMR (376 MHz, CDCl$_3$) δ −120.06 (s, 1F), −125.51 (s, 1F) ppm.

Step B. 6-(4-Ethyl-3-(hydroxymethyl)-5-oxo-4,5-dihydro-1H-1,2,4-triazol-1-yl)-7-fluoro-2-(2-fluoro-5-methylphenyl)-4-(prop-1-en-2-yl)isoquinolin-1(2H)-one. To a stirred solution of 6-(3-((benzyloxy)methyl)-4-ethyl-5-oxo-4,5-dihydro-1H-1,2,4-triazol-1-yl)-7-fluoro-2-(2-fluoro-5-methylphenyl)-4-(prop-1-en-2-yl)isoquinolin-1(2H)-one (70 mg, 0.12 mmol) in DCM (5 mL) was added BCl$_3$ (1 M, 0.6 mL, 0.6 mmol) at −78° C. The reaction was stirred at −78° C. for 1 h. The mixture was quenched with MeOH (1.5 mL) at −78° C. The mixture was diluted with DCM, washed with saturated aqueous NaHCO$_3$ solution. The organic extract was separated, washed with brine (30 mL×2), dried over anhydrous Na$_2$SO$_4$, filtered, and concentrated. The residue was purified by reverse phase prep-HPLC (Stationary phase: Boston Prime C18, 5 μm, 150×30 mm; Mobile phase: water (0.04% NH$_3$·H$_2$O+10 mM NH$_4$HCO$_3$) (A)—MeCN (B), gradient elution: 45-75% B in A over 8 min, flow rate: 25 mL/min) to give the title compound as a white powder (30 mg, yield: 55%). ESI-MS: mass calcd. for $C_{24}H_{22}F_2N_4O_3$, 452.2; m/z found, 453.2 [M+H]$^+$. $^1$H NMR (400 MHz, DMSO-d$_6$) δ 8.15 (d, J=10.8 Hz, 1H), 7.98 (d, J=7.0 Hz, 1H), 7.42 (d, J=7.3 Hz, 1H), 7.39 (s, 1H), 7.31-7.37 (m, 2H), 5.82 (t, J=5.8 Hz, 1H), 5.41 (s, 1H), 5.15 (s, 1H), 4.50 (d, J=5.8 Hz, 2H), 3.81 (q, J=6.9 Hz, 2H), 2.36 (s, 3H), 2.11 (s, 3H), 1.30 (t, J=7.2 Hz, 3H) ppm. $^{19}$F NMR (376 MHz, DMSO-d$_6$) δ −119.50 (s, 1F), −125.79 (s, 1F) ppm.

Example 43: 2-(2-Chloro-5-methylphenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one

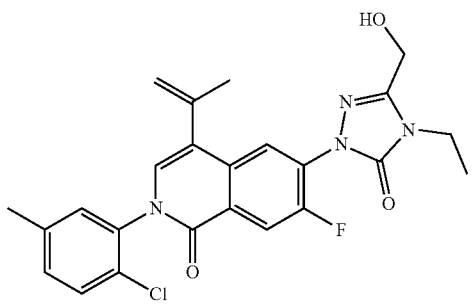 [SMILES: C=C(C)c1cn(-c2cc(C)ccc2Cl)c(=O)c2cc(F)c(-n3nc(CO)n(CC)c3=O)cc12]

The title compound was prepared in a manner analogous to Example 42, Steps A-B using 5-((benzyloxy)methyl)-4-- ethyl-2-(7-fluoro-1-oxo-4-(prop-1-en-2-yl)-1H-isochromen-6-yl)-2,4-dihydro-3H-1,2,4-triazol-3-one (Intermediate 3) and using 2-chloro-5-methylaniline instead of 2-fluoro-5-methylaniline in Step A. ESI-MS: mass calcd. for $C_{24}H_{22}ClFN_4O_3$, 468.1; m/z found, 469.2 [M+H]$^+$. $^1$H NMR (400 MHz, DMSO-d$_6$) δ 8.30 (d, J=11.0 Hz, 1H), 8.00 (d, J=7.0 Hz, 1H), 7.46 (d, J=8.0 Hz, 1H), 7.23 (d, J=8.3 Hz, 2H), 6.90 (s, 1H), 5.36 (s, 1H), 5.18 (s, 1H), 4.68 (d, J=6.3 Hz, 2H), 3.93 (q, J=7.1 Hz, 2H), 2.36-2.41 (m, 4H), 2.15 (s, 3H), 1.43 (t, J=7.3 Hz, 3H) ppm. $^{19}$F NMR (376 MHz, DMSO-d$_6$) δ −120.23 (s, 1F) ppm.

Example 44: 6-(4-Ethyl-3-(hydroxymethyl)-5-oxo-4,5-dihydro-1H-1,2,4-triazol-1-yl)-7-fluoro-2-(2-fluoro-5-methoxyphenyl)-4-(prop-1-en-2-yl)isoquinolin-1(2H)-one

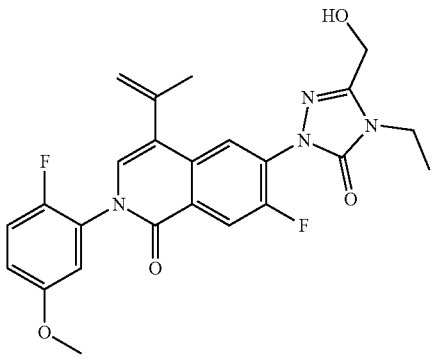 [SMILES: C=C(C)c1cn(-c2cc(OC)ccc2F)c(=O)c2cc(F)c(-n3nc(CO)n(CC)c3=O)cc12]

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using 2-fluoro-5-methoxyaniline instead of 2-fluoro-5-methylaniline in Step A. ESI-MS: mass calcd. for $C_{24}H_{22}F_2N_4O_4$, 468.2; m/z found, 469.2 [M+H]$^+$. $^1$H NMR (400 MHz, CDCl$_3$) δ 8.30 (d, J=11.0 Hz, 1H), 8.00 (d, J=7.0 Hz, 1H), 7.15-7.22 (m, 1H), 6.93-7.00 (m, 3H), 5.36 (s, 1H), 5.17 (s, 1H), 4.67 (d, J=6.3 Hz, 2H), 3.92 (q, J=7.1 Hz, 2H), 3.83 (s, 3H), 2.63 (t, J=6.4 Hz, 1H), 2.15 (s, 3H), 1.42 (t, J=7.3 Hz, 3H) ppm. $^{19}$F NMR (376 MHz, CDCl$_3$) δ −119.92 (s, 1F), −131.06 (s, 1F) ppm.

Example 45: 2-(2-Chlorophenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one

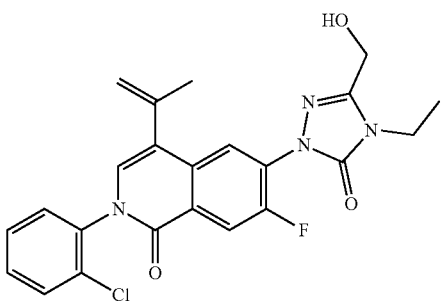

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using 2-chloroaniline instead of 2-fluoro-5-methylaniline in Step A. ESI-MS: mass calcd. for $C_{23}H_{20}ClFN_4O_3$, 454.1; m/z found, 455.1 [M+H]$^+$. $^1$H NMR (400 MHz, CDCl$_3$) δ 8.30 (d, J=11.0 Hz, 1H), 8.01 (d, J=7.0 Hz, 1H), 7.59 (dd, J=5.5, 3.5 Hz, 1H), 7.41-7.48 (m, 3H), 6.91 (s, 1H), 5.35-5.37 (m, 1H), 5.18 (s, 1H), 4.68 (d, J=6.5 Hz, 2H), 3.93 (q, J=7.3 Hz, 2H), 2.45 (t, J=6.3 Hz, 1H), 2.15 (s, 3H), 1.43 (t, J=7.2 Hz, 3H) ppm. $^{19}$F NMR (376 MHz, CDCl$_3$) δ −120.14 (s, 1F) ppm.

Example 46: 6-(4-Ethyl-3-(hydroxymethyl)-5-oxo-4,5-dihydro-1H-1,2,4-triazol-1-yl)-7-fluoro-4-(prop-1-en-2-yl)-2-(o-tolyl)isoquinolin-1(2H)-one

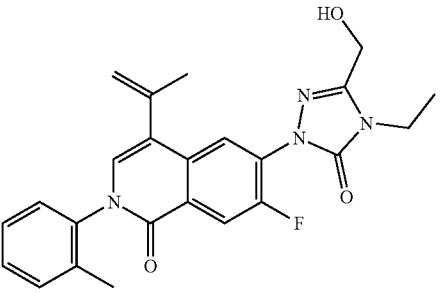 [SMILES: C=C(C)c1cn(-c2ccccc2C)c(=O)c2cc(F)c(-n3nc(CO)n(CC)c3=O)cc12]

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using o-toluidine instead of 2-fluoro-5-methylaniline in Step A. ESI-MS: mass calcd. for $C_{24}H_{23}FN_4O_3$, 434.2; m/z found, 435.2 [M+H]$^+$. $^1$H NMR (400 MHz, CDCl$_3$) δ 8.31 (d, J=11.0 Hz, 1H), 8.01 (d, J=7.0 Hz, 1H), 7.36-7.40 (m, 2H), 7.32-7.36 (m, 1H), 7.29 (s, 1H), 6.95 (s, 1H), 5.35 (s, 1H), 5.16 (s, 1H), 4.68 (d, J=6.3 Hz, 2H), 3.93 (q, J=7.3 Hz, 2H), 2.38 (t, J=6.3 Hz, 1H), 2.19 (s, 3H), 2.15 (s, 3H), 1.43 (t, J=7.3 Hz, 3H) ppm. $^{19}$F NMR (376 MHz, CDCl$_3$) δ −120.40 (s, 1F) ppm.

Example 47: 2-(2-Chloro-5-methoxyphenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one

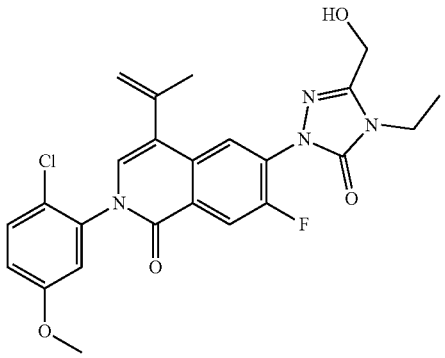 [SMILES: C=C(C)c1cn(-c2cc(OC)ccc2Cl)c(=O)c2cc(F)c(-n3nc(CO)n(CC)c3=O)cc12]

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using 2-chloro-5-methoxyaniline instead of 2-fluoro-5-methylaniline in Step A. ESI-MS: mass calcd. for $C_{24}H_{22}ClFN_4O_4$, 484.1; m/z found, 485.2 [M+H]$^+$. $^1$H NMR (400 MHz, CDCl$_3$) δ 8.31 (d, J=11.0 Hz, 1H), 8.01 (d, J=7.0 Hz, 1H), 7.46 (d, J=9.5 Hz, 1H), 6.96-7.01 (m, 2H), 6.90 (s, 1H), 5.36 (d, J=1.5 Hz, 1H), 5.18 (s, 1H), 4.69 (d, J=6.5 Hz, 2H), 3.93 (q, J=7.3 Hz, 2H), 3.84 (s, 3H), 2.36 (t, J=6.4 Hz, 1H), 2.15 (s, 3H), 1.43 (t, J=7.2 Hz, 3H) ppm. $^{19}$F NMR (376 MHz, CDCl$_3$) δ −120.16 (s, 1F) ppm.

Example 48: Racemic-4-(sec-Butyl)-2-(2-chloro-6-fluorophenyl)-6-(4-ethyl-3-(hydroxymethyl)-5-oxo-4,5-dihydro-1H-1,2,4-triazol-1-yl)-7-fluoroisoquinolin-1(2H)-one

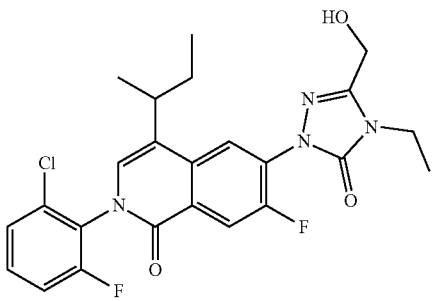 [SMILES: CCC(C)c1cn(-c2c(F)cccc2Cl)c(=O)c2cc(F)c(-n3nc(CO)n(CC)c3=O)cc12]

Step A. 4-(3-((Benzyloxy)methyl)-4-ethyl-5-oxo-4,5-dihydro-1H-1,2,4-triazol-1-yl)-N-(2-chloro-6-fluorophenyl)-5-fluoro-2-iodo-N-(3-methylpent-2-en-1-yl)benzamide. To a solution of 4-(3-((benzyloxy)methyl)-4-ethyl-5-oxo-4,5-dihydro-1H-1,2,4-triazol-1-yl)-5-fluoro-2-iodobenzoyl chloride (Intermediate 5, 917 mg, 1.8 mmol) in DCM (4 mL) at 0° C. was slowly added a pre-cooled solution of 2-chloro-6-fluoro-N-(3-methylpent-2-en-1-yl)aniline (Intermediate 6, 270 mg, 1.19 mmol) dropwise, followed by the careful addition of Et$_3$N (0.5 mL, 3.6 mmol) in DCM (5 mL) and DMAP (14.5 mg, 0.12 mmol) under nitrogen. The reaction mixture was stirred at room temperature for 3 h. The reaction was quenched by the addition of aqueous saturated NaHCO$_3$ solution. The organic layer was separated, and the aqueous layer was extracted with DCM. The combined organic extract was washed with brine, dried over Na$_2$SO$_4$, filtered and concentrated. The residue was purified by combi-flash column chromatography over silica gel (eluent: 0-40% EtOAc in petroleum ether) to give the title compound as a yellow gum (730 mg, yield: 80%). ESI-MS: mass calcd. for $C_{31}H_{30}ClF_2IN_4O_3$, 706.1; m/z found 707.1 [M+H]$^+$.

Step B. 6-(3-((Benzyloxy)methyl)-4-ethyl-5-oxo-4,5-dihydro-1H-1,2,4-triazol-1-yl)-4-(sec-butyl)-2-(2-chloro-6-fluorophenyl)-7-fluoroisoquinolin-1(2H)-one. To a solution of 4-(3-((benzyloxy)methyl)-4-ethyl-5-oxo-4,5-dihydro-1H-1,2,4-triazol-1-yl)-N-(2-chloro-6-fluorophenyl)-5-fluoro-2-iodo-N-(3-methylpent-2-en-1-yl)benzamide (730 mg, 0.95 mmol) in DMF (7.3 mL) was added TBAB (916 mg, 2.8 mmol), AcOK (186 mg, 1.9 mmol), Pd(OAc)$_2$ (213 mg, 0.95 mmol) respectively. The reaction mixture was heated under nitrogen at 80° C. for overnight. The mixture was cooled down to room temperature, then filtered through a pad of Celite®. The pad was washed with EtOAc. The combined filtrate was washed with brine, dried over Na$_2$SO$_4$, filtered and concentrated under vacuum. The crude product was purified by combi-flash column chromatography over silica gel (eluent: 0-70% EtOAc in petroleum ether). The crude product was further purified by preparative reversed phase HPLC (Stationary phase: Boston Uni C18, 5 μm, 150×40 mm; Mobile phase: water (0.04% NH$_3$·H$_2$O+10 mM NH$_4$HCO$_3$) (A)—MeCN (B), gradient elution: 70-100% B in A over 8 min, flow rate: 25 mL/min) to give the mixture of the desired product and other isomers as a pale yellow solid (290 mg, yield: 45%), which was used directly to the next step without further purification. ESI-MS: mass calcd. for $C_{31}H_{29}ClF_2N_4O_3$, 578.2; m/z found 579.1 [M+H]$^+$.

Step C. 4-(sec-Butyl)-2-(2-chloro-6-fluorophenyl)-6-(4-ethyl-3-(hydroxymethyl)-5-oxo-4,5-dihydro-1H-1,2,4-triazol-1-yl)-7-fluoroisoquinolin-1(2H)-one. To a solution of 6-(3-((benzyloxy)methyl)-4-ethyl-5-oxo-4,5-dihydro-1H-1,2,4-triazol-1-yl)-4-(sec-butyl)-2-(2-chloro-6-fluorophenyl)-7-fluoroisoquinolin-1(2H)-one and other isomers (290 mg, 0.13 mmol) in EtOAc (18 mL) was added Pd/C (10%, 133 mg, 0.13 mmol). The suspension was degassed under vacuum and purged with H$_2$ several times. The mixture was vigorously stirred under H$_2$ (15 psi) at room temperature for 4 h. The mixture was filtered and concentrated. The residue was purified by preparative reversed phase HPLC (Stationary phase: Boston Uni C18, 5 μm, 150×40 mm; Mobile phase: water (0.04% NH$_3$·H$_2$O+10 mM NH$_4$HCO$_3$) (A)—MeCN (B), gradient elution: 45-75% B in A over 8 min, flow rate: 25 mL/min). The product was further separated by SFC (Stationary phase: Phenomenex-Cellulose-2, 10 μm, 250×30 mm; Mobile phase: Supercritical CO$_2$ (A)—MeOH (0.1% NH$_3$·H$_2$O) (B), gradient elution: 30% B in A at 60 mL/min) to give the title compound as white solid (23 mg, 36%). ESI-MS: mass calcd. for $C_{24}H_{23}ClF_2N_4O_3$, 488.1; m/z found 489.2 [M+H]$^+$; $^1$H NMR (400 MHz, CDCl$_3$) δ 8.33 (d, J=11.3 Hz, 1H), 8.09 (d, J=7.0 Hz, 1H), 7.37-7.46 (m, 2H), 7.18-7.25 (m, 1H), 6.71 (s, 1H), 4.65-4.74 (m, 2H), 3.94 (q, J=7.3 Hz, 2H), 3.05 (dd, J=10.2, 6.7 Hz, 1H), 2.21-2.28 (m, 1H), 1.65-1.82 (m, 2H), 1.45 (t, J=7.2 Hz, 3H), 1.30 (t, J=6.9 Hz, 3H), 0.96 (td, J=7.3, 1.9 Hz, 3H); $^{19}$F NMR (376 MHz, CDCl$_3$) δ −116.26 (s, 1F), −116.56 (s, 1F), −120.66 (s, 1F) ppm.

Example 49: 2-(3-Chloro-6-methoxypyridin-2-yl)-6-(4-ethyl-3-(hydroxymethyl)-5-oxo-4,5-dihydro-1H-1,2,4-triazol-1-yl)-7-fluoro-4-isopropylisoquinolin-1(2H)-one

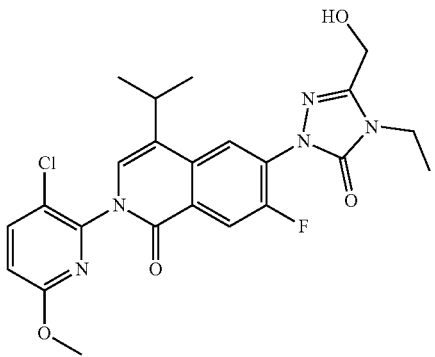 [SMILES: CCn1c(CO)nn(-c2cc3c(C(C)C)cn(-c4nc(OC)ccc4Cl)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 3-chloro-6-methoxypyridin-2-amine instead of 5-chloro-3-methyl-4-amino-1H-pyrazole in Step A. ESI-MS: mass calcd. for $C_{23}H_{23}ClFN_5O_4$, 487.1; m/z found, 488.3 [M+H]$^+$. $^1$H NMR (400 MHz, CDCl$_3$) δ 8.34 (d, J=11.3 Hz, 1H), 8.09 (d, J=6.8 Hz, 1H), 7.76 (d, J=8.5 Hz, 1H), 6.92 (s, 1H), 6.86 (d, J=8.8 Hz, 1H), 4.70 (d, J=6.3 Hz, 2H), 3.91-3.98 (m, 5H), 3.27 (quin, J=6.7 Hz, 1H), 2.36 (t, J=6.3 Hz, 1H), 1.45 (t, J=7.3 Hz, 3H), 1.35 (dd, J=6.8, 2.8 Hz, 6H) ppm. $^{19}$F NMR (376 MHz, CDCl$_3$) δ −120.86 (s, 1F) ppm.

Example 50: 6-(4-Ethyl-3-(hydroxymethyl)-5-oxo-4,5-dihydro-1H-1,2,4-triazol-1-yl)-7-fluoro-4-isopropyl-2-(2-methoxy-4-methylpyridin-3-yl)isoquinolin-1(2H)-one

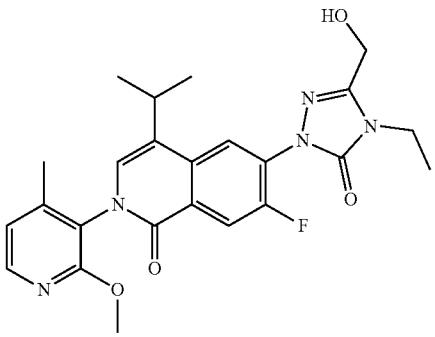 [SMILES: CCn1c(CO)nn(-c2cc3c(C(C)C)cn(-c4c(C)ccnc4OC)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2-methoxy-4-methylpyridin-3-amine instead of 5-chloro-3-methyl-4-amino-1H-pyrazole in Step A. ESI-MS: mass calcd. for $C_{24}H_{26}FN_5O_4$, 467.2; m/z found, 468.1 [M+H]$^+$. $^1$H NMR (400 MHz, CDCl$_3$) δ 8.31 (d, J=11.0 Hz, 1H), 8.04-8.16 (m, 2H), 6.91 (d, J=5.3 Hz, 1H), 6.68 (s, 1H), 4.68 (d, J=5.8 Hz, 2H), 3.89-4.00 (m, 5H), 3.26 (dt, J=13.4, 6.7 Hz, 1H), 2.64 (br t, J=6.1 Hz, 1H), 2.15 (s, 3H), 1.44 (t, J=7.2 Hz, 3H), 1.32 (t, J=5.9 Hz, 6H) ppm. $^{19}$F NMR (376 MHz, CDCl$_3$) δ −121.09 (br s, 1F) ppm.

Example 51: 2-(2-Chloro-6-fluoro-3-methoxyphenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one

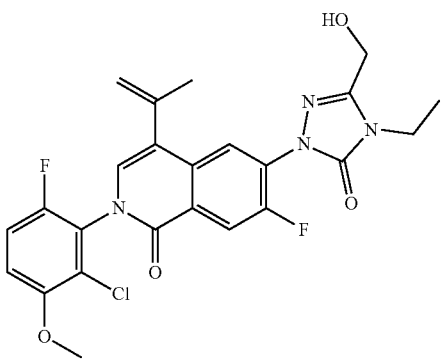

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using 2-chloro-6-fluoro-3-methoxyaniline instead of 2-fluoro-5-methylaniline in Step A. ESI-MS: mass calcd. for $C_{24}H_{21}ClF_2N_4O_4$, 502.1; m/z found, 503.2 [M+H]$^+$. $^1$H NMR (400 MHz, CDCl$_3$) δ 8.31 (d, J=10.8 Hz, 1H), 8.01 (d, J=6.8 Hz, 1H), 7.16-7.22 (m, 1H), 7.03 (dd, J=9.3, 4.5 Hz, 1H), 6.84 (s, 1H), 5.35-5.37 (m, 1H), 5.19 (s, 1H), 4.69 (d, J=5.3 Hz, 2H), 3.89-3.98 (m, 5H), 2.22 (br s, 1H), 2.15 (s, 3H), 1.44 (t, J=7.3 Hz, 3H) ppm. $^{19}$F NMR (376 MHz, CDCl$_3$) δ −120.06 (s, 1F), −127.09 (s, 1F) ppm.

Example 52: 2-(2-Chloro-6-fluorophenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one

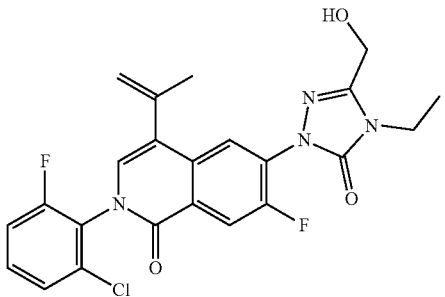

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using 2-chloro-6-fluoroaniline instead of 2-fluoro-5-methylaniline in Step A. ESI-MS: mass calcd. for $C_{23}H_{19}ClF_2N_4O_3$, 472.1; m/z found, 473.1 [M+H]$^+$. $^1$H NMR (400 MHz, CDCl$_3$) δ 8.16 (d, J=10.8 Hz, 1H), 8.02 (d, J=7.0 Hz, 1H), 7.59-7.67 (m, 2H), 7.51-7.57 (m, 1H), 7.45 (s, 1H), 5.82 (t, J=5.9 Hz, 1H), 5.43 (s, 1H), 5.15 (s, 1H), 4.50 (d, J=6.0 Hz, 2H), 3.81 (q, J=7.3 Hz, 2H), 2.10 (s, 3H), 1.30 (t, J=7.2 Hz, 3H) ppm. $^{19}$F NMR (376 MHz, CDCl$_3$) δ −120.06 (s, 1F), −127.09 (s, 1F) ppm.

Example 53: 6-(4-Ethyl-3-(hydroxymethyl)-5-oxo-4,5-dihydro-1H-1,2,4-triazol-1-yl)-7-fluoro-4-isopropyl-2-(o-tolyl)phthalazin-1(2H)-one

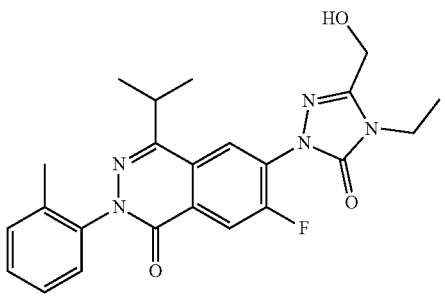 [SMILES: CCn1c(CO)nn(-c2cc3c(C(C)C)nn(-c4ccccc4C)c(=O)c3cc2F)c1=O]

Step A: 5,6-Difluoro-2-(o-tolylamino)isoindoline-1,3-dione and 6,7-difluoro-2-(o-tolyl)-2,3-dihydrophthalazine-1,4-dione. A reaction mixture of 4,5-difluorophthalic anhydride (12.0 g, 65.2 mmol) and o-tolylhydrazine hydrochloride (15.0 g, 94.6 mmol) in AcOH (110 mL) was heated at 120° C. for 2 h and allowed to cool to RT. The precipitated yellow solid was filtered, washed with NaHCO$_3$ aqueous solution and then water, and dried in high vacuum to give 5,6-difluoro-2-(o-tolylamino)isoindoline-1,3-dione (7.32 g, 39.0%). LCMS (ES-API): mass calcd. for $C_{15}H_{10}F_2N_2O_2$, 288.07; m/z found, 289.0 [M+H]$^+$. $^1$H NMR (400 MHz, CDCl$_3$) δ 7.76 (t, J=7.1 Hz, 2H), 7.14 (d, J=7.3 Hz, 1H), 7.07 (t, J=7.8 Hz, 1H), 6.90 (t, J=7.3 Hz, 1H), 6.54 (d, J=7.8 Hz, 1H), 6.06 (s, 1H), 2.39 (s, 3H) ppm.

The filtrate was concentrated in vacuo, and to the residue water was added and then filtered. The filtered solid was washed with NaHCO$_3$ aqueous solution and then water, dried, and purified by flash column chromatography (100% DCM, 10-70% EtOAc in heptane) to give 5,6-difluoro-2-(o-tolylamino)isoindoline-1,3-dione (2.48 g, 13%) and 6,7-difluoro-2-(o-tolyl)-2,3-dihydrophthalazine-1,4-dione (3.01 g, 16%).

Step B: 6,7-Difluoro-2-(o-tolyl)-2,3-dihydrophthalazine-1,4-dione. To a suspension of 5,6-difluoro-2-(o-tolylamino)isoindoline-1,3-dione (10.96 g, 38.0 mmol) in EtOH (360 mL) at −20 to −25° C. was slowly added a solution of NaOEt in EtOH (21%, 17.5 mL, 46.9 mmol), and the yellow suspension gradually dissolved. After completion of the addition, all solid dissolved. The mixture was stirred at −25° C. to RT for 4.5 h, and a few drops of water were added followed by 24 mL of 2N HCl to pH~ 2. After removal of the solvents in vacuo, to the solid residue was added 250 mL of DCM and 50 mL of water, and the mixture was heated at 40 to 50° C. for ~30 min. After filtering off the solid, the filtrate was separated, and the aqueous layer was extracted with DCM. The combined organic layers were dried over Na$_2$SO$_4$, filtered, concentrated, and purified by solid loading flash column chromatography (100% DCM, 20-100% EtOAc in heptane) to give the title compound as an off-white solid (3.92 g, 36%). LCMS (ES-API): mass calcd. for $C_{15}H_{10}F_2N_2O_2$, 288.07; m/z found, 289.0 [M+H]$^+$. $^1$H NMR (400 MHz, CDCl$_3$) δ 8.23 (dd, J=7.8, 9.3 Hz, 1H), 7.90-7.68 (m, 1H), 7.47-7.28 (m, 4H), 2.22 (s, 3H) ppm.

Step C: 6,7-Difluoro-4-oxo-3-(o-tolyl)-3,4-dihydrophthalazin-1-yl trifluoromethanesulfonate. To a mixture of 6,7-difluoro-2-(o-tolyl)-2,3-dihydrophthalazine-1,4-dione (6.90 g, 23.9 mmol) in DCM (225 mL) at 4° C. was added a solution of Tf$_2$O in DCM (1.0 M, 38.0 mL, 38.0 mmol) followed by Et$_3$N (8.4 mL, 61 mmol). The mixture was stirred at 4° C. to room temperature for 17 h and concentrated. The residue was purified by flash column chromatography (10-30% EtOAc in heptane) to give the title compound as a yellow solid (5.75 g, 57%). LCMS (ES-API): mass calcd. for $C_{16}H_9F_5N_2O_4S$, 420.02; m/z found, 421.0 [M+H]$^+$. $^1$H NMR (400 MHz, CDCl$_3$) δ 8.32 (dd, J=7.6, 9.5 Hz, 1H), 7.70 (dd, J=7.1, 9.0 Hz, 1H), 7.46-7.28 (m, 4H), 2.20 (s, 3H).

Step D: 6,7-Difluoro-4-(prop-1-en-2-yl)-2-(o-tolyl)phthalazin-1(2H)-one. A reaction mixture of 6,7-difluoro-4-oxo-3-(o-tolyl)-3,4-dihydrophthalazin-1-yl trifluoromethanesulfonate (5.02 g, 11.9 mmol), isopropenylboronic acid pinacol ester (2.81 g, 16.7 mmol), bis(triphenylphosphine)palladium(II) dichloride (500 mg, 0.710 mmol), and an aqueous solution of K$_2$CO$_3$ (2.0 M, 10 mL, 20 mmol) in dioxane (90 mL) was purged with Argon for 30 min, and then heated at 85° C. for 3.5 h. After concentration, the residue was partitioned between DCM and water. The organic layer was dried over Na$_2$SO$_4$, filtered, concentrated, and purified by flash column chromatography (0-30% EtOAc in heptane) to give the title compound as an off-white solid (3.55 g, 95%). LCMS (ES-API): mass calcd. for $C_{18}H_{14}F_2N_2O$, 312.11; m/z found, 313.0 [M+H]$^+$. $^1$H NMR (400 MHz, CDCl$_3$) δ 8.32 (dd, J=7.8, 9.8 Hz, 1H), 7.79 (dd, J=7.3, 10.3 Hz, 1H), 7.39-7.27 (m, 4H), 5.64-5.54 (m, 1H), 5.31 (s, 1H), 2.22-2.15 (m, 6H) ppm.

Step E: 6,7-Difluoro-4-isopropyl-2-(o-tolyl)phthalazin-1(2H)-one. A mixture of 6,7-difluoro-4-(prop-1-en-2-yl)-2-(o-tolyl)phthalazin-1(2H)-one (3.55 g, 11.4 mmol) and 10% Pd/C (500 mg, 0.470 mmol) in EtOAc (80 mL) was hydrogenated under 20 psi H$_2$ for 16 h. After removal of the solid by filtration through silica gel, the filtrate was concentrated to give the title compound as a clear solid (3.57 g, 99%). LCMS (ES-API): mass calcd. for $C_{18}H_{16}F_2N_2O$, 314.12; m/z found, 315.1 [M+H]$^+$. $^1$H NMR (400 MHz, CDCl$_3$) δ 8.32 (dd, J=7.8, 9.8 Hz, 1H), 7.68 (dd, J=7.3, 10.8 Hz, 1H), 7.39-7.27 (m, 4H), 3.46-3.32 (m, 1H), 2.17 (s, 3H), 1.35 (d, J=6.4 Hz, 6H) ppm.

Step F: 6-(3-((Benzyloxy)methyl)-4-ethyl-5-oxo-4,5-dihydro-1H-1,2,4-triazol-1-yl)-7-fluoro-4-isopropyl-2-(o-tolyl)phthalazin-1(2H)-one. A reaction mixture of 6,7-difluoro-4-isopropyl-2-(o-tolyl)phthalazin-1(2H)-one (2.89 g, 9.19 mmol), 5-((benzyloxy)methyl)-4-ethyl-2,4-dihydro-3H-1,2,4-triazol-3-one (3.00 g, 12.9 mmol) and K$_2$CO$_3$ (2.29 g, 16.6 mmol) in DMF (110 mL) was heated at 60° C. for 14 h and concentrated. The crude was purified by flash column chromatography (10-40% EtOAc in heptane) to give the title compound as a white solid (3.05 g, 63%). LCMS (ES-API): mass calcd. for $C_{30}H_{30}FN_5O_3$, 527.23; m/z found, 528.2 [M+H]$^+$. $^1$H NMR (400 MHz, CDCl$_3$) δ 8.33 (d, J=10.8 Hz, 1H), 8.26 (d, J=6.8 Hz, 1H), 7.46-7.29 (m, 9H), 4.64 (s, 2H), 4.55 (s, 2H), 3.90 (q, J=7.0 Hz, 2H), 3.57-3.44 (m, 1H), 2.18 (s, 3H), 1.43-1.33 (m, 9H) ppm.

Step G: 6-(4-Ethyl-3-(hydroxymethyl)-5-oxo-4,5-dihydro-1H-1,2,4-triazol-1-yl)-7-fluoro-4-isopropyl-2-(o-tolyl)phthalazin-1(2H)-one. A solution of 6-(3-((benzyloxy)methyl)-4-ethyl-5-oxo-4,5-dihydro-1H-1,2,4-triazol-1-yl)-7-fluoro-4-isopropyl-2-(o-tolyl)phthalazin-1(2H)-one (3.05 g, 5.78 mmol) and TFA (30 mL) was heated at 65° C. for 8 h and concentrated. To the residue 10 mL of toluene was added and then concentrated in vacuo, and the process was repeated once. The residue was dissolved in 30 mL of THF and treated with 8.7 mL of 2N K$_2$CO$_3$ for 7 h. After concentration, the residue was partitioned between DCM and water. The organic layer was dried over Na$_2$SO$_4$, filtered, concentrated, and purified by flash column chromatography (30-80% EtOAc in heptane) to provide the title compound as a white foam (1.88 g, 74%). LCMS (ES-API): mass calcd. for $C_{23}H_{24}FN_5O_3$, 437.19; m/z found, 438.3 [M+H]$^+$. $^1$H NMR (400 MHz, CDCl$_3$) δ 8.32 (d, J=10.8 Hz, 1H), 8.27 (d, J=6.8 Hz, 1H), 7.42-7.29 (m, 4H), 4.69 (d, J=6.4 Hz, 2H), 3.94 (q, J=7.3 Hz, 2H), 3.56-3.40 (m, 1H), 2.47-2.34 (m, 1H), 2.18 (s, 3H), 1.44 (t, J=7.1 Hz, 3H), 1.36 (d, J=6.8 Hz, 6H) ppm.

Example 54: 2-(2-Chloro-6-fluorophenyl)-6-(4-ethyl-3-(hydroxymethyl)-5-oxo-4,5-dihydro-1H-1,2,4-triazol-1-yl)-7-fluoro-4-isopropylphthalazin-1(2H)-one

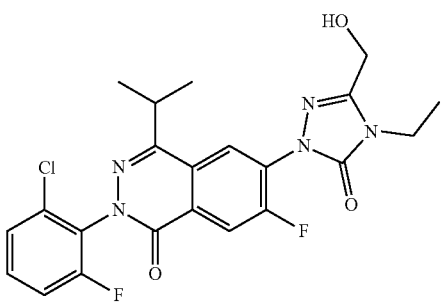 [SMILES: CCn1c(CO)nn(-c2cc3c(C(C)C)nn(-c4c(F)cccc4Cl)c(=O)c3cc2F)c1=O]

A mixture of 2-(2-chloro-6-fluorophenyl)-6-(4-ethyl-3-(hydroxymethyl)-5-oxo-4,5-dihydro-1H-1,2,4-triazol-1-yl)-7-fluoro-4-(prop-1-en-2-yl)phthalazin-1(2H)-one (Example 27, 20 mg, 0.042 mmol) and 10% Pd/C (5.5 mg, 0.0052 mmol) in EtOAc (8.5 mL) was stirred under 1 atm $H_2$ balloon for 4.5 h. After filtering through a syringe filter, the filtrate was concentrated and purified by flash column chromatography (20-70% EtOAc in heptane) to give the title compound (17 mg, 85%). LCMS (ES-API): mass calcd. for $C_{22}H_{20}ClF_2N_5O_3$, 475.12; m/z found, 476.1 [M+H]$^+$. $^1$H NMR (400 MHz, CDCl$_3$) δ 8.30 (dd, J=10.3, 12.2 Hz 2H), 7.47-7.31 (m, 2H), 7.25-7.13 (m, 1H), 4.70 (br s, 2H), 3.94 (q, J=7.3 Hz, 2H), 3.57-3.39 (m, 1H), 2.54-2.33 (m, 1H), 1.44 (t, J=7.1 Hz, 3H), 1.36 (dd, J=4.9, 6.8 Hz, 6H).

Example 55: Racemic 6-(4-Ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)phthalazin-1(2H)-one

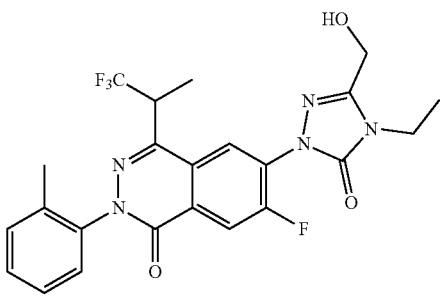 [SMILES: CCn1c(CO)nn(-c2cc3c(C(C)C(F)(F)F)nn(-c4ccccc4C)c(=O)c3cc2F)c1=O]

Step A: 6,7-Difluoro-2-(o-tolyl)-4-(3,3,3-trifluoroprop-1-en-2-yl)phthalazin-1(2H)-one. A reaction mixture of 6,7-difluoro-4-oxo-3-(o-tolyl)-3,4-dihydrophthalazin-1-yl trifluoromethanesulfonate (Example 53, Step C, 450 mg, 1.07 mmol), 1-(trifluoromethyl)vinylboronic acid hexylene glycol ester (480 mg, 2.16 mmol), bis(triphenylphosphine)palladium(II) dichloride (75 mg, 0.11 mmol), and an aqueous solution of $K_2CO_3$ (2.0 M, 1.1 mL, 2.2 mmol) in dioxane (10 mL) was purged with Argon for 10 min, and then heated at 85° C. for 5 h. After concentration, the residue was partitioned between DCM and NH$_4$Cl aqueous solution. The organic layer was dried over Na$_2$SO$_4$, filtered, concentrated, and purified by flash column chromatography (0-40% EtOAc in heptane) to give the title compound as a clear oil (321 mg, 82%). LCMS (ES-API): mass calcd. for $C_{18}H_{11}F_5N_2O$, 366.08; m/z found, 367.0 [M+H]$^+$. $^1$H NMR (400 MHz, CDCl$_3$) δ 8.41-8.25 (m, 1H), 7.54 (dd, J=7.3, 9.8 Hz, 1H), 7.45-7.30 (m, 4H), 6.48 (s, 1H), 5.97 (s, 1H), 2.18 (s, 3H) ppm.

Step B: Racemic 6,7-Difluoro-2-(o-tolyl)-4-(1,1,1-trifluoropropan-2-yl)phthalazin-1(2H)-one. A mixture of 6,7-difluoro-2-(o-tolyl)-4-(3,3,3-trifluoroprop-1-en-2-yl)phthalazin-1(2H)-one (320 mg, 0.870 mmol) and 10% Pd/C (91 mg, 0.086 mmol) in EtOAc (17 mL) was hydrogenated under 20 psi H$_2$ for 3 h. After filtering off the solid through a pad of silica gel, the filtrate was concentrated to give the title compound as a clear solid (315 mg, 98%). LCMS (ES-API): mass calcd. for $C_{18}H_{13}F_5N_2O$, 368.09; m/z found, 369.1 [M+H]$^+$. $^1$H NMR (400 MHz, CDCl$_3$) δ 8.34 (t, J=8.8 Hz, 1H), 7.67 (dd, J=6.8, 10.3 Hz, 1H), 7.49-7.27 (m, 4H), 4.09-3.96 (m, 1H), 2.16 (s, 3H), 1.67-1.53 (m, 3H) ppm.

Step C: Racemic 6-(3-((Benzyloxy)methyl)-4-ethyl-5-oxo-4,5-dihydro-1H-1,2,4-triazol-1-yl)-7-fluoro-2-(o-tolyl)-4-(1,1,1-trifluoropropan-2-yl)phthalazin-1(2H)-one. A reaction mixture of 6,7-difluoro-2-(o-tolyl)-4-(1,1,1-trifluoropropan-2-yl)phthalazin-1(2H)-one (315 mg, 0.860 mmol), 5-((benzyloxy)methyl)-4-ethyl-2,4-dihydro-3H-1,2,4-triazol-3-one (260 mg, 1.11 mmol) and K$_2$CO$_3$ (209 mg, 1.51 mmol) in DMF (10 mL) was stirred at RT for 23 h and filtered. The filtrate was concentrated and purified by flash column chromatography (20-50% EtOAc in heptane) to give the title compound (233 mg, 47%). LCMS (ES-API): mass calcd. for $C_{30}H_{27}F_4N_5O_3$, 581.21; m/z found, 582.2 [M+H]$^+$. $^1$H NMR (400 MHz, CDCl$_3$) δ 8.35 (d, J=10.8 Hz, 1H), 8.23 (d, J=6.8 Hz, 1H), 7.44-7.30 (m, 9H), 4.65 (s, 2H), 4.56 (s, 2H), 4.22-4.03 (m, 1H), 3.89 (q, J=7.2 Hz, 2H), 2.17 (s, 3H), 1.59 (d, J=7.3 Hz, 3H), 1.40 (t, J=7.1 Hz, 3H) ppm.

Step D: Racemic 6-(4-Ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)phthalazin-1(2H)-one. A solution of 6-(3-((benzyloxy)methyl)-4-ethyl-5-oxo-4,5-dihydro-1H-1,2,4-triazol-1-yl)-7-fluoro-2-(o-tolyl)-4-(1,1,1-trifluoropropan-2-yl)phthalazin-1(2H)-one (233 mg, 0.400 mmol) in TFA (3.5 mL) was heated at 65° C. for 10 h and concentrated. To the residue 2 mL of toluene was added and then concentrated in vacuo, and the process was repeated. The residue was dissolved in 2 mL of THF and treated with 0.6 mL of 2N K$_2$CO$_3$ for 2 h. After concentration, the residue was partitioned between DCM and water. The organic layer was dried over Na$_2$SO$_4$, filtered, concentrated, and purified by flash column chromatography (40-60% EtOAc in heptane) to provide the title compound as a white solid (164 mg, 83%). LCMS (ES-API): mass calcd. for $C_{23}H_{21}F_4N_5O_3$, 491.16; m/z found, 492.1 [M+H]$^+$. $^1$H NMR (400 MHz, CDCl$_3$) δ 8.34 (d, J=10.3 Hz, 1H), 8.24 (d, J=6.4 Hz, 1H), 7.46-7.30 (m, 4H), 4.72 (d, J=5.9 Hz, 2H), 4.20-4.08 (m, 1H), 3.95 (q, J=7.3 Hz, 2H), 2.21 (t, J=6.4 Hz, 1H), 2.17 (s, 3H), 1.66-1.59 (m, 3H), 1.46 (t, J=7.3 Hz, 3H) ppm.

Example 56: (S*)-6-(4-Ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)phthalazin-1(2H)-one

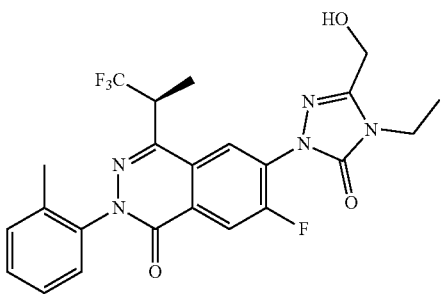 [SMILES: CCn1c(CO)nn(-c2cc3c([C@H](C)C(F)(F)F)nn(-c4ccccc4C)c(=O)c3cc2F)c1=O]

A purification of 6-(4-ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)phthalazin-1(2H)-one (Example 55, 155 mg) was performed via chiral SFC (stationary phase: CHIRACEL OJ-H 5 μm 250×20 mm, mobile phase: 85% $CO_2$, 15% MeOH) to give the first peak as the title compound (70 mg, 45%). LCMS (ES-API): mass calcd. for $C_{23}H_{21}F_4N_5O_3$, 491.16; m/z found, 492.1 [M+H]$^+$. $^1$H NMR (400 MHz, CDCl$_3$) δ 8.34 (d, J=10.8 Hz, 1H), 8.24 (d, J=6.8 Hz, 1H), 7.44-7.29 (m, 4H), 4.71 (d, J=6.4 Hz, 2H), 4.23-4.07 (m, 1H), 3.95 (q, J=7.2 Hz, 2H), 2.23 (t, J=6.4 Hz, 1H), 2.17 (s, 3H), 1.63-1.53 (m, 3H), 1.45 (t, J=7.3 Hz, 3H).

Example 57: (R*)-6-(4-Ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)phthalazin-1(2H)-one

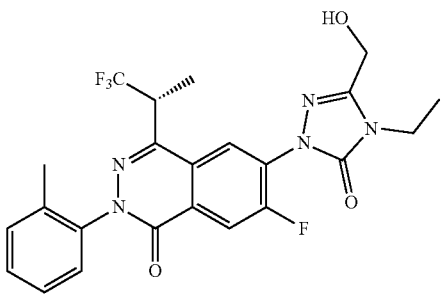 [SMILES: CCn1c(CO)nn(-c2cc3c([C@@H](C)C(F)(F)F)nn(-c4ccccc4C)c(=O)c3cc2F)c1=O]

The title compound (70 md, 45%) was isolated as the second peak from chiral SFC purification of 6-(4-ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)phthalazin-1(2H)-one (155 mg, Example 55, Step D). LCMS (ES-API): mass calcd. for $C_{23}H_{21}F_4N_5O_3$, 491.16; m/z found, 492.0 [M+H]$^+$. $^1$H NMR (400 MHz, CDCl$_3$) δ 8.34 (d, J=10.3 Hz, 1H), 8.24 (d, J=6.4 Hz, 1H), 7.44-7.30 (m, 4H), 4.70 (d, J=5.9 Hz, 2H), 4.25-4.05 (m, 1H), 3.94 (q, J=7.2 Hz, 2H), 2.39 (t, J=6.1 Hz, 1H), 2.17 (s, 3H), 1.69-1.53 (m, 3H), 1.45 (t, J=7.3 Hz, 3H).

Example 58: 2-(2-Chloro-6-fluorophenyl)-6-(4-ethyl-3-(hydroxymethyl)-5-oxo-4,5-dihydro-1H-1,2,4-triazol-1-yl)-7-fluoro-4-(1-methylcyclopropyl)isoquinolin-1(2H)-one

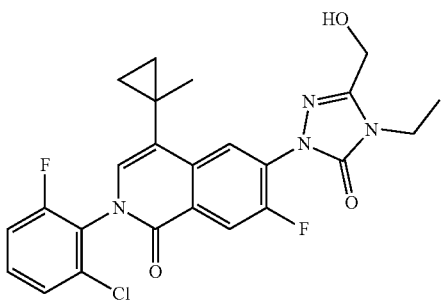 [SMILES: CCn1c(CO)nn(-c2cc3c(C4(C)CC4)cn(-c4c(F)cccc4Cl)c(=O)c3cc2F)c1=O]

Step A. 5-((Benzyloxy)methyl)-4-ethyl-2-(7-fluoro-4-(1-methylcyclopropyl)-1-oxo-1H-isochromen-6-yl)-2,4-dihydro-3H-1,2,4-triazol-3-one. To a mixture of diiodomethane (3.7 g, 14 mmol) in anhydrous toluene (20 mL) at 0° C. was added a toluene solution (15%) of diethylzinc (9.2 g, 11 mmol). The mixture was stirred at 0° C. under nitrogen for 15 min, followed by the addition of a suspension of 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3, 300 mg, 0.69 mmol) in toluene (20 mL). The reaction mixture was stirred at 0° C. for 0.5 h, then warmed to room temperature and stirred for 24 h. The mixture was poured into aqueous NaHCO$_3$ solution (50 mL). The aqueous phase was extracted with DCM (50 mL) and ethyl acetate (EtOAc) (50 mL) sequentially. The combined organic extract was washed with brine, dried over anhydrous Na$_2$SO$_4$, and concentrated. The residue was purified by ISCO chromatography (SiO$_2$, 50-100% ethyl acetate in heptane) to afford the title compound and unreacted 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one as a mixture, which was not further purified and used directly into the next step: a white solid (1:1.5 ratio, estimated 60 mg, yield: 19%). LCMS (ES-API): mass calcd. for $C_{25}H_{24}FN_3O_4$, 449.2; m/z found, 450.1 [M+H]$^+$.

Step B. 6-(3-((Benzyloxy)methyl)-4-ethyl-5-oxo-4,5-dihydro-1H-1,2,4-triazol-1-yl)-2-(2-chloro-6-fluorophenyl)-7-fluoro-4-(1-methylcyclopropyl)isoquinolin-1(2H)-one. To a stirred solution of 2-chloro-6-fluoroaniline (194 mg, 1.3 mmol) in DCM (6 mL) was added AlMe$_3$ (2 M, 0.5 mL, 1.0 mmol) under nitrogen. The mixture was stirred at room temperature for 0.5 h, followed by the addition of a DCM solution (2 mL) of the mixture of 5-((benzyloxy)methyl)-4-ethyl-2-(7-fluoro-4-(1-methylcyclopropyl)-1-oxo-1H-isochromen-6-yl)-2,4-dihydro-3H-1,2,4-triazol-3-one and (60 mg, 0.13 mmol) and 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3, 90 mg, 0.21 mmol). The mixture was stirred at room temperature for overnight. MeOH (1 mL) was added. The mixture was poured into water and extracted with EtOAc. The organic layer was separated, washed with brine, dried over anhydrous MgSO$_4$, filtered and concentrated. The residue was dissolved in AcOH (20 mL) and stirred at 100° C. for 20 h. The mixture was poured into water and extracted with EtOAc. The organic layer was separated, washed with brine, dried over anhydrous MgSO$_4$, filtered and concentrated. The residue was purified by ISCO chromatography (SiO$_2$, 40 g, gradient elution: 0-70% EtOAc in heptane) to give the title compound as a yellow solid (33 mg, yield: 56%). LCMS (ES-API): mass calcd. for C$_{31}$H$_{27}$ClF$_2$N$_4$O$_3$, 576.2; m/z found, 577.2 [M+H]$^+$. $^1$H NMR (400 MHz, CDCl$_3$) δ 8.52 (d, J=6.36 Hz, 1H), 7.79 (d, J=8.80 Hz, 1H), 7.30-7.50 (m, 8H), 7.19 (ddd, J=1.71, 7.95, 8.93 Hz, 1H), 4.64 (s, 2H), 4.55 (s, 2H), 3.72-4.00 (m, 2H), 1.31-1.46 (m, 6H), 0.65-0.82 (m, 4H) ppm.

Step C. 2-(2-Chloro-6-fluorophenyl)-6-(4-ethyl-3-(hydroxymethyl)-5-oxo-4,5-dihydro-1H-1,2,4-triazol-1-yl)-7-fluoro-4-(1-methylcyclopropyl)isoquinolin-1(2H)-one. To a stirred solution of 6-(3-((benzyloxy)methyl)-4-ethyl-5-oxo-4,5-dihydro-1H-1,2,4-triazol-1-yl)-2-(2-chloro-6-fluorophenyl)-7-fluoro-4-(1-methylcyclopropyl)isoquinolin-1(2H)-one (30 mg, 0.05 mmol) in DCM (5 mL) at −78° C. was added BCl$_3$ (1 M, 0.26 mL, 0.26 mmol). The reaction was stirred at −78° C. for 0.5 h. The mixture was quenched with MeOH (1 mL) at −78° C. The mixture was diluted with DCM, washed with saturated aqueous NaHCO$_3$ solution. The organic extract was separated, washed with brine, dried over anhydrous Na$_2$SO$_4$, filtered, and concentrated. The residue was purified by reverse phase prep-HPLC [ISCO C$_{18}$ (5 μm, 150×30 mm), and mobile phase of 10-99% MeCN in water over 15 min and then hold at 100% MeCN for 2 min, at a flow rate of 25 mL/min] to give the title compound as a white powder (15 mg, yield: 59%). LCMS (ES-API): mass calcd. for C$_{24}$H$_{21}$ClF$_2$N$_4$O$_3$, 486.1; m/z found, 487.2 [M+H]$^+$. $^1$H NMR (400 MHz, CDCl$_3$) δ 8.52 (d, J=6.36 Hz, 1H), 7.79 (d, J=8.80 Hz, 1H), 7.32-7.49 (m, 3H), 7.20 (dt, J=1.71, 8.44 Hz, 1H), 5.32 (s, 1H), 4.71 (d, J=6.36 Hz, 2H), 3.82-4.04 (m, 2H), 1.44 (t, J=7.09 Hz, 3H), 1.36 (s, 3H), 0.65-0.82 (m, 4H) ppm.

Example 59: 6-(4-Ethyl-3-(hydroxymethyl)-5-oxo-4,5-dihydro-1H-1,2,4-triazol-1-yl)-7-fluoro-2-(2-methoxy-4-methylpyridin-3-yl)-4-(prop-1-en-2-yl)isoquinolin-1(2H)-one

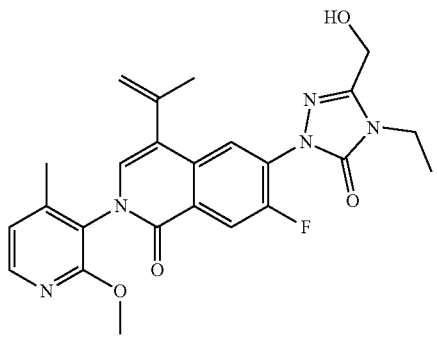 [SMILES: C=C(C)c1cn(-c2c(C)ccnc2OC)c(=O)c2cc(F)c(-n3nc(CO)n(CC)c3=O)cc12]

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using 2-methoxy-4-methyl-pyridin-3-ylamine instead of 2-fluoro-5-methylaniline in Step A. ESI-MS: mass calcd. for C$_{24}$H$_{24}$FN$_5$O$_4$, 465.2; m/z found, 466.2 [M+H]$^+$. $^1$H NMR (400 MHz, CDCl$_3$) δ 8.30 (d, J=11.0 Hz, 1H), 8.12 (d, J=5.3 Hz, 1H), 8.01 (d, J=7.0 Hz, 1H), 6.91 (d, J=5.3 Hz, 1H), 6.79 (s, 1H), 5.35 (s, 1H), 5.18 (s, 1H), 4.69 (d, J=6.0 Hz, 2H), 3.89-3.97 (m, 5H), 2.41 (br t, J=6.0 Hz, 1H), 2.17 (s, 3H), 2.15 (s, 3H), 1.44 (t, J=7.2 Hz, 3H) ppm. $^{19}$F NMR (376 MHz, CDCl$_3$) δ −120.55 (s, 1F) ppm.

Example 60: 2-(5-Chloro-3-methyl-1H-pyrazol-4-yl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one

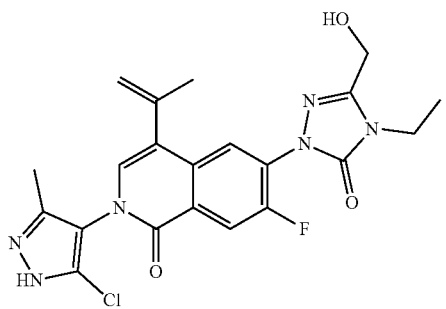 [SMILES: C=C(C)c1cn(-c2c(C)n[nH]c2Cl)c(=O)c2cc(F)c(-n3nc(CO)n(CC)c3=O)cc12]

Step A. 6-(3-((Benzyloxy)methyl)-4-ethyl-5-oxo-4,5-dihydro-1H-1,2,4-triazol-1-yl)-2-(5-chloro-3-methyl-1H-pyrazol-4-yl)-7-fluoro-4-(prop-1-en-2-yl)isoquinolin-1(2H)-one. To a stirred solution of 5-chloro-3-methyl-1-(tetrahydro-2H-pyran-2-yl)-1H-pyrazol-4-amine (Intermediate 7, 186 mg, 0.86 mmol) in DCM (2.5 mL) was added AlMe$_3$ (2 M, 0.32 mL, 0.64 mmol) under nitrogen. The mixture was stirred at room temperature for 0.5 h, then a DCM solution (2.5 mL) of 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3, 95 mg, 0.22 mmol) was added. The mixture was stirred at room temperature for overnight. Aqueous HCl solution (1 M, 0.4 mL) was added and the mixture was stirred at room temperature for 2 min. The mixture was poured into water and extracted with DCM. The organic phase was separated, washed with brine, dried over anhydrous Na$_2$SO$_4$, filtered and concentrated. The residue was dissolved in AcOH (7 mL) and stirred at 90° C. for overnight. The mixture was cooled to room temperature, and then methanesulfonic acid (138 mg, 1.4 mmol) was added under nitrogen. The reaction mixture was stirred at room temperature for overnight. The mixture was poured into water and extracted with EtOAc. The combined organic phase was washed with brine, dried over anhydrous Na$_2$SO$_4$, filtered and concentrated. The residue was purified by flash chromatography (SiO$_2$, 0-70% EtOAc in petroleum ether) to give the title compound as a yellow oil (50 mg, yield: 42%). ESI-MS: mass calcd. for C$_{28}$H$_{26}$ClFN$_6$O$_3$, 548.2; m/z found, 549.1 [M+H]$^+$. $^1$H NMR (400 MHz, CDCl$_3$) δ 8.31 (d, J=10.8 Hz, 1H), 8.02 (d, J=7.0 Hz, 1H), 7.34-7.40 (m, 5H), 6.93 (s, 1H), 5.37-5.40 (m, 1H), 5.19 (s, 1H), 4.63 (s, 2H), 4.55 (s, 2H), 3.89 (q, J=7.1 Hz, 2H), 2.25 (s, 3H), 2.16 (s, 3H), 1.35-1.40 (m, 3H); $^{19}$F NMR (376 MHz, CDCl$_3$) δ −119.73 (s, 1F) ppm.

Step B. 2-(5-Chloro-3-methyl-1H-pyrazol-4-yl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one. To a stirred solution of 6-(3-((benzyloxy)methyl)-4-ethyl-5-oxo-4,5-dihydro-1H-1,2,4-triazol-1-yl)-2-(5-chloro-3-methyl-1H-pyrazol-4-yl)-7-fluoro-4-(prop-1-en-2-yl)isoquinolin-1(2H)-one (50 mg, 0.09 mmol) in DCM (5 mL) at −78° C. was added BCl$_3$ (1 M, 0.45 mL, 0.45 mmol). The reaction was stirred at −78° C. for 1 h. The mixture was quenched with MeOH (2 mL) at −78° C. The mixture was diluted with DCM, washed with saturated aqueous NaHCO₃ solution. The organic extract was separated, washed with brine, dried over anhydrous Na₂SO₄, filtered, and concentrated. The residue was purified by reverse phase prep-HPLC (Stationary phase: Boston Prime C18, 5 μm, 150×30 mm; Mobile phase: water (0.04% NH₃·H₂O+10 mM NH₄HCO₃) (A)—MeCN (B), gradient elution: 30-60% B in A over 8 min, flow rate: 25 mL/min) to give the title compound as a white powder (33 mg, yield: 79%). ESI-MS: mass calcd. for $C_{21}H_{20}ClFN_6O_3$, 458.1; m/z found, 459.1 [M+H]⁺. ¹H NMR (400 MHz, CDCl₃) δ 10.57 (br s, 1 H), 8.30 (d, J=11.0 Hz, 1H), 8.02 (d, J=7.0 Hz, 1H), 6.92 (s, 1H), 5.38 (t, J=1.5 Hz, 1H), 5.18 (s, 1H), 4.70 (d, J=3.3 Hz, 2H), 3.94 (q, J=7.3 Hz, 2H), 2.48 (br s, 1H), 2.26 (s, 3H), 2.16 (s, 3H), 1.44 (t, J=7.3 Hz, 3H) ppm. ¹⁹F NMR (376 MHz, CDCl₃) δ −119.96 (s, 1F) ppm.

Example 61: 2-(3-Chloro-2-methoxy-5-methylpyridin-4-yl)-6-(4-ethyl-3-(hydroxymethyl)-5-oxo-4,5-dihydro-1H-1,2,4-triazol-1-yl)-7-fluoro-4-isopropylisoquinolin-1(2H)-one

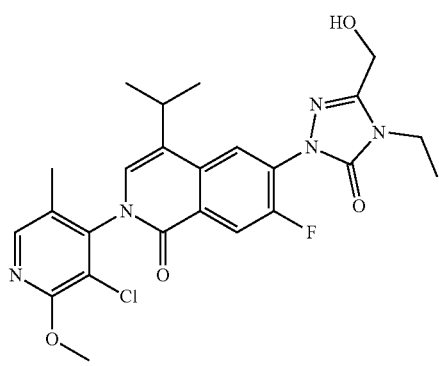 [SMILES: CCn1c(CO)nn(-c2cc3c(C(C)C)cn(-c4c(C)cnc(OC)c4Cl)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 3-chloro-2-methoxy-5-methylpyridin-4-amine instead of 5-chloro-3-methyl-4-amino-1H-pyrazole in Step A. ESI-MS: mass calcd. for $C_{24}H_{25}ClFN_5O_4$, 501.2; m/z found, 502.1 [M+H]⁺. ¹H NMR (400 MHz, CDCl₃) δ 8.32 (d, J=11.0 Hz, 1H), 8.07-8.14 (m, 2H), 6.62 (s, 1H), 4.70 (d, J=6.3 Hz, 2H), 4.07 (s, 3H), 3.94 (q, J=7.3 Hz, 2H), 3.27 (spt, J=6.6 Hz, 1H), 2.45 (t, J=6.3 Hz, 1H), 2.09 (s, 3H), 1.44 (t, J=7.2 Hz, 3H), 1.31 (dd, J=6.8, 3.5 Hz, 6H) ppm. ¹⁹F NMR (376 MHz, CDCl₃) δ −120.25 (s, 1 F) ppm.

Example 62: 2-(3-Chloro-2-methoxy-5-methylpyridin-4-yl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one

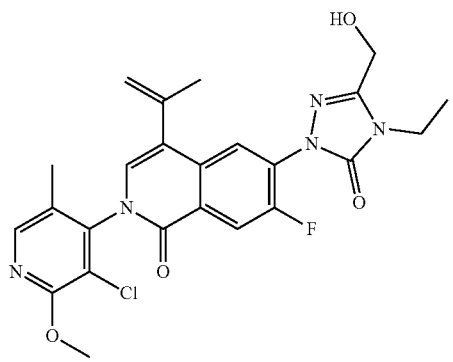 [SMILES: C=C(C)c1cn(-c2c(C)cnc(OC)c2Cl)c(=O)c2cc(F)c(-n3nc(CO)n(CC)c3=O)cc12]

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using 3-chloro-2-methoxy-5-methylpyridin-4-amine instead of 2-fluoro-5-methylaniline in Step A. ESI-MS: mass calcd. for $C_{24}H_{23}ClFN_5O_4$, 499.1; m/z found, 500.0 [M+H]⁺. ¹H NMR (400 MHz, CDCl₃) δ 8.30 (d, J=11.0 Hz, 1H), 8.08 (s, 1H), 8.03 (d, J=7.0 Hz, 1H), 6.72 (s, 1H), 5.37 (s, 1H), 5.18 (s, 1H), 4.68 (s, 2H), 4.06 (s, 3H), 3.93 (q, J=7.3 Hz, 2H), 2.48 (br s, 1H), 2.15 (s, 3H), 2.11 (s, 3H), 1.43 (t, J=7.3 Hz, 3H) ppm. ¹⁹F NMR (376 MHz, CDCl₃) δ −119.58 (s, 1F) ppm.

Example 63: 6-(4-Ethyl-3-(hydroxymethyl)-5-oxo-4,5-dihydro-1H-1,2,4-triazol-1-yl)-7-fluoro-2-(2-fluoro-5-methoxyphenyl)-4-isopropylisoquinolin-1(2H)-one

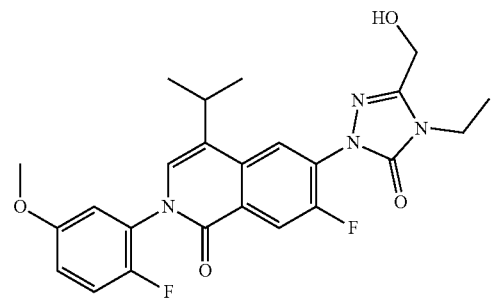 [SMILES: CCn1c(CO)nn(-c2cc3c(C(C)C)cn(-c4cc(OC)ccc4F)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2-fluoro-5-methoxyaniline instead of 5-chloro-3-methyl-4-amino-1H-pyrazole in Step A. ESI-MS: mass calcd. for $C_{24}H_{24}F_2N_4O_4$, 470.2; m/z found, 471.1 [M+H]⁺. ¹H NMR (400 MHz, CDCl₃) δ 8.32 (d, J=11.0 Hz, 1H), 8.08 (d, J=6.8 Hz, 1H), 7.16-7.23 (m, 1H), 6.92-7.00 (m, 2H), 6.88 (s, 1H), 4.70 (d, J=6.3 Hz, 2H), 3.94 (q, J=7.3 Hz, 2H), 3.83 (s, 3H), 3.17-3.32 (m, 1H), 2.28 (t, J=6.4 Hz, 1H), 1.44

(t, J=7.3 Hz, 3H), 1.32 (d, J=6.8 Hz, 6H) ppm. $^{19}$F NMR (376 MHz, CDCl$_3$) δ −120.66 (s, 1F) (s, 1F) ppm.

Example 64: 6-(4-Ethyl-3-(hydroxymethyl)-5-oxo-4,5-dihydro-1H-1,2,4-triazol-1-yl)-7-fluoro-2-(4-fluoro-2-methylphenyl)-4-isopropylisoquinolin-1(2H)-one

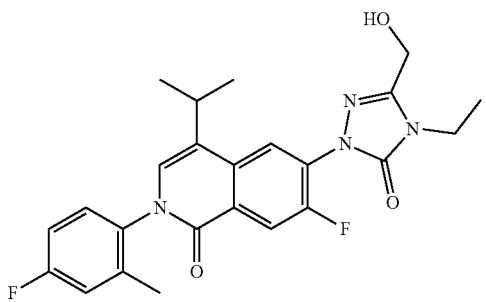 [SMILES: CCn1c(CO)nn(-c2cc3c(C(C)C)cn(-c4ccc(F)cc4C)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 4-fluoro-2-methylaniline instead of 5-chloro-3-methyl-4-amino-1H-pyrazole in Step A. ESI-MS: mass calcd. for C$_{24}$H$_{24}$F$_2$N$_4$O$_3$, 454.2; m/z found, 455.1 [M+H]$^+$. $^1$H NMR (400 MHz, CDCl$_3$) δ 8.30 (d, J=11.3 Hz, 1H), 8.08 (d, J=6.8 Hz, 1H), 7.24 (dd, J=8.5, 5.3 Hz, 1H), 6.99-7.11 (m, 2H), 6.79 (s, 1H), 4.66 (s, 2H), 3.93 (q, J=7.3 Hz, 2H), 3.26 (dt, J=13.5, 6.7 Hz, 1H), 2.82 (br s, 1H), 2.14 (s, 3H), 1.43 (t, J=7.2 Hz, 3H), 1.31 (d, J=6.8 Hz, 6H) ppm. $^{19}$F NMR (376 MHz, CDCl$_3$) δ −112.96 (s, 1F), −120.59 (s, 1F) ppm.

Example 65: 2-(2-Chloro-3-(2-hydroxyethoxy)phenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one

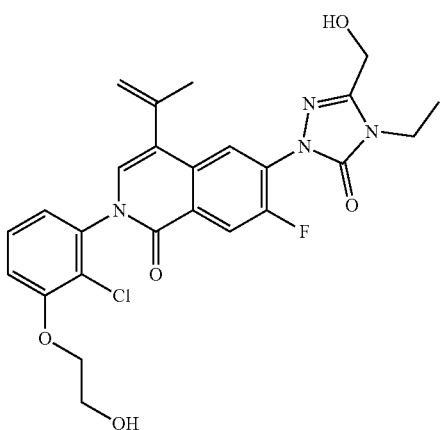 [SMILES: C=C(C)c1cn(-c2cccc(OCCO)c2Cl)c(=O)c2cc(F)c(-n3nc(CO)n(CC)c3=O)cc12]

Step A. 6-(3-((Benzyloxy)methyl)-4-ethyl-5-oxo-4,5-dihydro-1H-1,2,4-triazol-1-yl)-2-(3-(2-((tert-butyldiphenylsilyl)oxy)ethoxy)-2-chlorophenyl)-7-fluoro-4-(prop-1-en-2-yl)isoquinolin-1(2H)-one. The title compound was prepared in a manner analogous to Example 42, Step A, using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using 3-(2-((tert-butyldiphenylsilyl)oxy)ethoxy)-2-chloroaniline (Intermediate 8) instead of 2-fluoro-5-methylaniline in Step A. ESI-MS: mass calcd. for C$_{48}$H$_{48}$ClFN$_4$O$_5$Si, 842.3; m/z found, 843.4 [M+H]$^+$. $^1$H NMR (400 MHz, CDCl$_3$) δ 8.33 (d, J=11.0 Hz, 1H), 8.02 (d, J=7.1 Hz, 1H), 7.67-7.80 (m, 4H), 7.29-7.49 (m, 12H), 7.06 (dd, J=10.9, 8.2 Hz, 2H), 6.90 (s, 1H), 5.36 (s, 1H), 5.19 (s, 1H), 4.64 (s, 2H), 4.55 (s, 2H), 4.18-4.29 (m, 2H), 4.01-4.10 (m, 2H), 3.89 (q, J=7.1 Hz, 2H), 2.16 (s, 3H), 1.39 (t, J=7.2 Hz, 3H), 1.07 (s, 9H) ppm.

Step B. 6-(3-((Benzyloxy)methyl)-4-ethyl-5-oxo-4,5-dihydro-1H-1,2,4-triazol-1-yl)-2-(2-chloro-3-(2-hydroxyethoxy)phenyl)-7-fluoro-4-(prop-1-en-2-yl)isoquinolin-1(2H)-one. To a mixture of 6-(3-((benzyloxy)methyl)-4-ethyl-5-oxo-4,5-dihydro-1H-1,2,4-triazol-1-yl)-2-(3-(2-((tert-butyldiphenylsilyl)oxy)ethoxy)-2-chlorophenyl)-7-fluoro-4-(prop-1-en-2-yl)isoquinolin-1(2H)-one (35 mg, 0.035 mmol) in THF (2 mL) was added Et$_3$N·3HF (86 mg, 0.53 mmol). The reaction mixture was stirred at 60° C. for 1 h. The mixture was cooled to room temperature. Isopropoxytrimethylsilane (TMSOiPr) (187 mg, 1.4 mmol) was added. The reaction mixture was stirred at room temperature for 2 h. The mixture was evaporated under reduced pressure. The residue was purified by silica column chromatography (gradient elution: 0-30% EtOAc in petroleum ether) to give the title compound as yellow gum (20 mg, yield: 93%). ESI-MS: mass calcd. for C$_{32}$H$_{30}$ClFN$_4$O$_5$, 604.2; m/z found, 605.2 [M+H]$^+$. $^1$H NMR (400 MHz, CDCl$_3$) δ 8.31 (d, J=11.0 Hz, 1H), 8.01 (d, J=6.8 Hz, 1H), 7.32-7.44 (m, 6H), 7.10 (t, J=9.0 Hz, 2H), 6.90 (s, 1H), 5.36 (s, 1H), 5.19 (s, 1H), 4.63 (s, 2H), 4.55 (s, 2H), 4.22 (t, J=4.4 Hz, 2H), 4.03 (br s, 2H), 3.89 (q, J=7.2 Hz, 2H), 2.21 (br s, 1H), 2.16 (s, 3H), 1.38 (t, J=7.1 Hz, 3H) ppm.

Step C. 2-(2-Chloro-3-(2-hydroxyethoxy)phenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one. The title compound was prepared in a manner analogous to Example 42, Step C. ESI-MS: mass calcd. for C$_{25}$H$_{24}$ClFN$_4$O$_5$, 514.1; m/z found, 515.0 [M+H]$^+$. $^1$H NMR (400 MHz, DMSO-d$_6$) δ 8.14 (d, J=10.8 Hz, 1H), 7.99 (d, J=7.0 Hz, 1H), 7.40-7.53 (m, 1H), 7.33 (d, J=8.0 Hz, 1H), 7.27 (s, 1H), 7.19 (d, J=7.8 Hz, 1H), 5.80 (s, 1H), 5.40 (s, 1H), 5.12 (s, 1H), 4.95 (t, J=5.0 Hz, 1H), 4.49 (s, 2H), 4.09-4.22 (m, 2H), 3.73-3.85 (m, 4H), 2.09 (s, 3H), 1.29 (t, J=7.2 Hz, 3H) ppm. $^{19}$F NMR (376 MHz, DMSO-d$_6$) δ −119.68 (br s, 1F) ppm.

Example 66: 6-(4-Ethyl-3-(hydroxymethyl)-5-oxo-4,5-dihydro-1H-1,2,4-triazol-1-yl)-7-fluoro-2-(2-fluorophenyl)-4-(prop-1-en-2-yl)isoquinolin-1(2H)-one

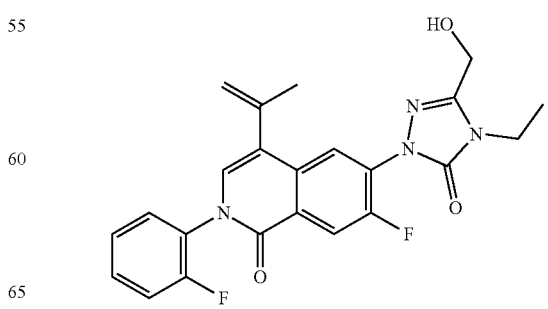

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using 2-fluoroaniline instead of 2-fluoro-5-methylaniline in Step A. ESI-MS: mass calcd. for $C_{23}H_{20}F_2N_4O_3$, 438.2; m/z found, 439.2 [M+H]$^+$. $^1$H NMR (400 MHz, CDCl$_3$) δ 8.13 (d, J=11.0 Hz, 1H), 7.83 (d, J=7.0 Hz, 1H), 7.25-7.34 (m, 2H), 7.09-7.16 (m, 2H), 6.83 (s, 1H), 5.18-5.21 (m, 1H), 5.01 (s, 1H), 4.49 (s, 2H), 3.75 (q, J=7.3 Hz, 2H), 2.73 (br s, 1H), 1.98 (s, 3H), 1.25 (t, J=7.3 Hz, 3H) ppm. $^{19}$F NMR (376 MHz, CDCl$_3$) δ −119.88 (s, 1F), −120.06 (s, 1F) ppm.

Example 67: 6-(4-Ethyl-3-(hydroxymethyl)-5-oxo-4,5-dihydro-1H-1,2,4-triazol-1-yl)-7-fluoro-2-(5-fluoro-2-methylphenyl)-4-isopropylisoquinolin-1(2H)-one

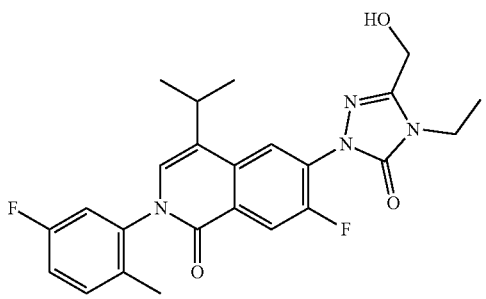 [SMILES: CCn1c(CO)nn(-c2cc3c(C(C)C)cn(-c4cc(F)ccc4C)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 5-fluoro-2-methylaniline instead of 5-chloro-3-methyl-4-amino-1H-pyrazole in Step A. ESI-MS: mass calcd. for $C_{24}H_{24}F_2N_4O_3$, 454.2; m/z found, 455.1 [M+H]$^+$. $^1$H NMR (400 MHz, CDCl$_3$) δ 8.31 (d, J=11.0 Hz, 1H), 8.08 (d, J=6.8 Hz, 1H), 7.33 (dd, J=8.3, 6.0 Hz, 1H), 7.10 (td, J=8.3, 2.8 Hz, 1H), 7.03 (dd, J=8.7, 2.6 Hz, 1H), 6.80 (s, 1H), 4.66 (s, 2H), 3.93 (q, J=7.3 Hz, 2H), 3.26 (spt, J=6.8 Hz, 1H), 2.78 (br s, 1H), 2.11 (s, 3H), 1.43 (t, J=7.3 Hz, 3H), 1.31 (dd, J=6.8, 1.8 Hz, 6H) ppm. $^{19}$F NMR (376 MHz, CDCl$_3$) δ −115.24 (s, 1F), −120.46 (s, 1F) ppm.

Example 68: 2-(2,5-Difluorophenyl)-6-(4-ethyl-3-(hydroxymethyl)-5-oxo-4,5-dihydro-1H-1,2,4-triazol-1-yl)-7-fluoro-4-isopropylisoquinolin-1(2H)-one

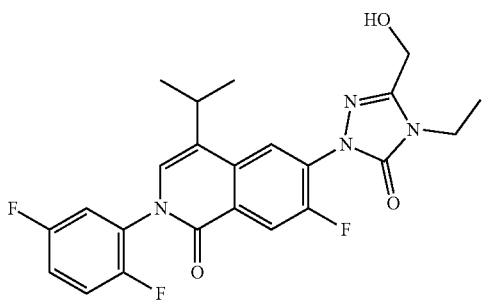 [SMILES: CCn1c(CO)nn(-c2cc3c(C(C)C)cn(-c4cc(F)ccc4F)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2,5-difluoroaniline instead of 5-chloro-3-methyl-4-amino-1H-pyrazole in Step A. ESI-MS: mass calcd. for $C_{23}H_{21}F_3N_4O_3$, 458.2; m/z found, 459.1 [M+H]$^+$. $^1$H NMR (400 MHz, CDCl$_3$) δ 8.30 (d, J=11.0 Hz, 1H), 8.08 (d, J=6.8 Hz, 1H), 7.12-7.26 (m, 3H), 6.85 (s, 1H), 4.69 (br s, 2H), 3.93 (q, J=7.2 Hz, 2H), 3.25 (spt, J=6.8 Hz, 1H), 2.50-2.60 (m, 1H), 1.43 (t, J=7.3 Hz, 3H), 1.32 (d, J=6.8 Hz, 6H) ppm. $^{19}$F NMR (376 MHz, CDCl$_3$) δ −116.63-116.45 (m, 1F), −120.22 (s, 1F), −125.43 (br d, J=17.2 Hz, 1F) ppm.

Example 69: 6-(4-Ethyl-3-(hydroxymethyl)-5-oxo-4,5-dihydro-1H-1,2,4-triazol-1-yl)-7-fluoro-2-(2-fluoro-6-methylphenyl)-4-isopropylisoquinolin-1(2H)-one

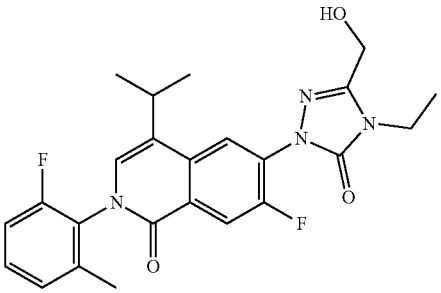 [SMILES: CCn1c(CO)nn(-c2cc3c(C(C)C)cn(-c4c(C)cccc4F)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2-fluoro-6-methylaniline instead of 5-chloro-3-methyl-4-amino-1H-pyrazole in Step A. ESI-MS: mass calcd. for $C_{24}H_{24}F_2N_4O_3$, 454.2; m/z found, 455.1 [M+H]$^+$. $^1$H NMR (400 MHz, CDCl$_3$) δ 8.32 (d, J=11.0 Hz, 1H), 8.08 (d, J=6.8 Hz, 1H), 7.35 (td, J=8.0, 5.5 Hz, 1H), 7.07-7.21 (m, 2H), 6.75 (s, 1H), 4.68 (d, J=6.3 Hz, 2H), 3.94 (q, J=7.2 Hz, 2H), 3.21-3.34 (m, 1H), 2.54 (t, J=6.4 Hz, 1H), 2.18 (s, 3H), 1.44 (t, J=7.2 Hz, 3H), 1.31 (d, J=6.8 Hz, 6H) ppm. $^{19}$F NMR (376 MHz, CDCl$_3$) δ −120.79 (s, 1F), −121.83 (s, 1F) ppm.

Example 70: 2-(2-Chloro-3-methoxyphenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one

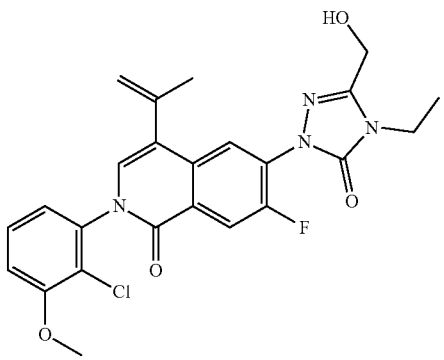 [SMILES: C=C(C)c1cn(-c2cccc(OC)c2Cl)c(=O)c2cc(F)c(-n3nc(CO)n(CC)c3=O)cc12]

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using 2-chloro-3-methoxyaniline instead of 2-fluoro-5-methylaniline in Step A. ESI-MS: mass calcd. for $C_{24}H_{22}ClFN_4O_4$, 484.1; m/z found, 485.0 [M+H]$^+$. $^1$H NMR (400 MHz, CDCl$_3$) δ 8.31 (d, J=11.0 Hz, 1H), 8.01 (d, J=7.0 Hz, 1H), 7.37-7.41 (m, 1H), 7.05-7.10 (m, 2H), 6.90 (s, 1H), 5.35 (d, J=1.5 Hz, 1H), 5.18 (s, 1H), 4.68 (s, 2H), 3.97 (s, 3H), 3.93 (q, J=7.3 Hz, 2H), 2.38 (br s, 1H), 2.15 (s, 3H), 1.43 (t, J=7.3 Hz, 3H) ppm. $^{19}$F NMR (376 MHz, CDCl$_3$) δ −120.31 (s, 1F) ppm.

Example 71: 6-(4-Ethyl-3-(hydroxymethyl)-5-oxo-4,5-dihydro-1H-1,2,4-triazol-1-yl)-7-fluoro-2-(2-methoxy-3,5-dimethylpyridin-4-yl)-4-(prop-1-en-2-yl)isoquinolin-1(2H)-one

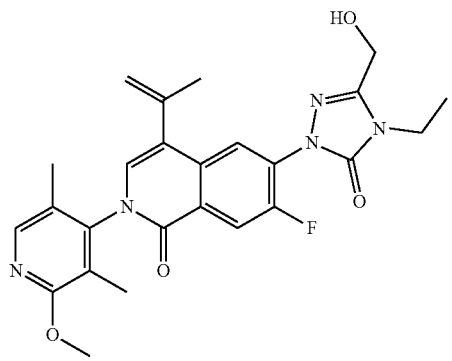 [SMILES: C=C(C)c1cn(-c2c(C)cnc(OC)c2C)c(=O)c2cc(F)c(-n3nc(CO)n(CC)c3=O)cc12]

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using 2-methoxy-3,5-dimethylpyridin-4-amine instead of 2-fluoro-5-methylaniline in Step A. ESI-MS: mass calcd. for $C_{25}H_{26}FN_5O_4$, 479.2; m/z found, 480.1 [M+H]$^+$. $^1$H NMR (400 MHz, CDCl$_3$) δ 8.31 (d, J=11.0 Hz, 1H), 8.00-8.05 (m, 2H), 6.73 (s, 1H), 5.36 (s, 1H), 5.14-5.19 (m, 1H), 4.69 (s, 2H), 3.99 (s, 3H), 3.93 (q, J=7.2 Hz, 2H), 2.46 (br s, 1H), 2.15 (s, 3H), 2.03 (s, 3H), 1.99 (s, 3H), 1.44 (t, J=7.3 Hz, 3H) ppm; $^{19}$F NMR (376 MHz, CDCl$_3$) δ −119.85 (s, 1F) ppm.

Example 72: 2-(2,5-Difluorophenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one

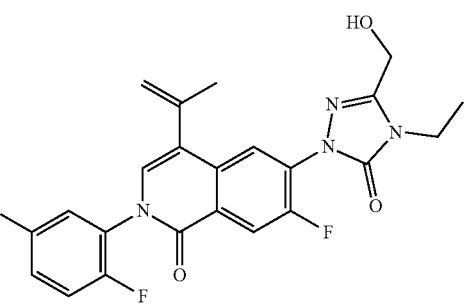

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using 2,5-difluoroaniline instead of 2-fluoro-5-methylaniline in Step A. ESI-MS: mass calcd. for $C_{23}H_{19}F_3N_4O_3$, 456.1; m/z found, 457.0 [M+H]$^+$. $^1$H NMR (400 MHz, CDCl$_3$) δ 8.29 (d, J=11.0 Hz, 1H), 8.00 (d, J=6.8 Hz, 1H), 7.13-7.26 (m, 3H), 6.96 (s, 1H), 5.37 (s, 1H), 5.18 (s, 1H), 4.68 (br s, 2H), 3.93 (q, J=7.3 Hz, 2H), 2.55 (br s, 1H), 2.15 (s, 3H), 1.43 (t, J=7.2 Hz, 3H) ppm; $^{19}$F NMR (376 MHz, CDCl$_3$) δ −116.47 (br d, J=17.2 Hz, 1F), −119.57 (s, 1F), −125.38 (br d, J=17.2 Hz, 1F) ppm.

Example 73: 6-(4-Ethyl-3-(hydroxymethyl)-5-oxo-4,5-dihydro-1H-1,2,4-triazol-1-yl)-7-fluoro-2-(2-fluoro-6-methylphenyl)-4-(prop-1-en-2-yl)isoquinolin-1(2H)-one

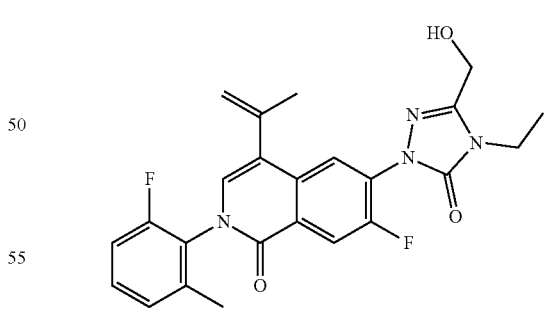

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using 2-fluoro-6-methylaniline instead of 2-fluoro-5-methylaniline in Step A. ESI-MS: mass calcd. for $C_{24}H_{22}F_2N_4O_3$, 452.2; m/z found, 453.1 [M+H]$^+$. $^1$H NMR (400 MHz, CDCl$_3$) δ 8.30 (d, J=10.8 Hz, 1H), 8.01 (d, J=6.8 Hz, 1H), 7.31-7.40 (m, 1H), 7.06-7.19 (m, 2H), 6.86 (s, 1H), 5.35 (s, 1H), 5.17 (s, 1H), 4.65 (s, 2H), 3.92 (d, J=7.3 Hz, 2H), 2.90 (br s, 1H), 2.20 (s, 3H), 2.14 (s, 3H), 1.41 (t, J=6.9 Hz, 3H) ppm; $^{19}$F NMR (376 MHz, CDCl$_3$) δ −120.02 (s, 1F), −121.86 (s, 1F) ppm.

Example 74: 6-(4-Ethyl-3-(hydroxymethyl)-5-oxo-4,5-dihydro-1H-1,2,4-triazol-1-yl)-7-fluoro-2-(3-fluoro-2-methylphenyl)-4-isopropylisoquinolin-1(2H)-one

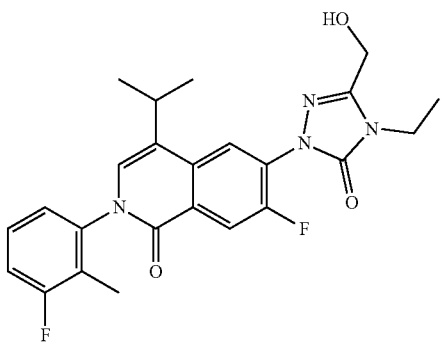 [SMILES: CCn1c(CO)nn(-c2cc3c(C(C)C)cn(-c4cccc(F)c4C)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 3-fluoro-2-methylaniline instead of 5-chloro-3-methyl-4-amino-1H-pyrazole in Step A. ESI-MS: mass calcd. for C$_{24}$H$_{24}$F$_2$N$_4$O$_3$, 454.2; m/z found, 455.1 [M+H]$^+$. $^1$H NMR (400 MHz, CDCl$_3$) δ 8.32 (d, J=11.3 Hz, 1H), 8.09 (d, J=7.0 Hz, 1H), 7.28-7.35 (m, 1H), 7.13-7.20 (m, 1H), 7.10 (d, J=8.0 Hz, 1H), 6.81 (s, 1H), 4.70 (d, J=6.3 Hz, 2H), 3.94 (q, J=7.3 Hz, 2H), 3.27 (dt, J=13.6, 6.8 Hz, 1H), 2.39 (t, J=6.3 Hz, 1H), 2.07 (d, J=1.8 Hz, 3H), 1.45 (t, J=7.2 Hz, 3H), 1.31 (dd, J=6.8, 1.3 Hz, 6H) ppm. 19F NMR (376 MHz, CDCl$_3$) δ −113.88 (s, 1F), −120.66 (s, 1F) ppm.

Example 75: 2-(2,5-Dimethylphenyl)-6-(4-ethyl-3-(hydroxymethyl)-5-oxo-4,5-dihydro-1H-1,2,4-triazol-1-yl)-7-fluoro-4-isopropylisoquinolin-1(2H)-one

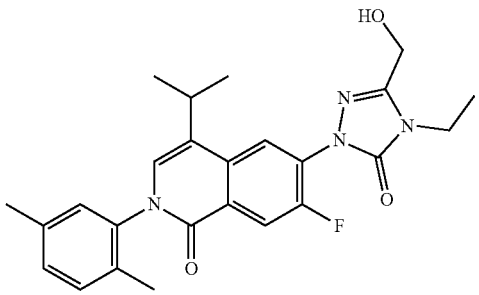

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2,5-dimethylaniline instead of 5-chloro-3-methyl-4-amino-1H-pyrazole in Step A. ESI-MS: mass calcd. for C$_{25}$H$_{27}$FN$_4$O$_3$, 450.2; m/z found, 451.1 [M+H]$^+$. $^1$H NMR (400 MHz, CDCl$_3$) δ 8.31 (d, J=11.3 Hz, 1H), 8.07 (d, J=6.8 Hz, 1H), 7.25 (s, 1H), 7.15-7.22 (m, 1H), 7.08 (s, 1H), 6.83 (s, 1H), 4.65 (d, J=2.8 Hz, 2H), 3.92 (q, J=7.2 Hz, 2H), 3.26 (spt, J=6.7 Hz, 1H), 2.94 (br s, 1H), 2.38 (s, 3H), 2.10 (s, 3H), 1.42 (t, J=7.2 Hz, 3H), 1.30 (dd, J=6.8, 3.3 Hz, 6H) ppm. $^{19}$F NMR (376 MHz, CDCl$_3$) δ −120.96 (s, 1F) ppm.

Example 76: 6-(4-Ethyl-3-(hydroxymethyl)-5-oxo-4,5-dihydro-1H-1,2,4-triazol-1-yl)-7-fluoro-2-(4-fluoro-2-methylphenyl)-4-(prop-1-en-2-yl)isoquinolin-1(2H)-one

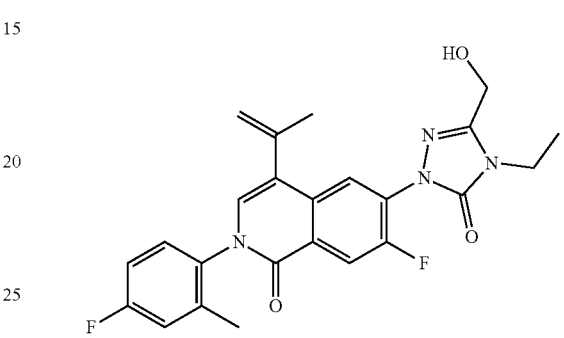

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using 3-fluoro-2-methylaniline instead of 2-fluoro-5-methylaniline in Step A. ESI-MS: mass calcd. for C$_{24}$H$_{22}$F$_2$N$_4$O$_3$, 452.2; m/z found, 453.2 [M+H]$^+$. $^1$H NMR (400 MHz, CDCl$_3$) δ 8.29 (d, J=11.0 Hz, 1H), 8.01 (d, J=7.0 Hz, 1H), 7.27-7.35 (m, 1H), 7.08-7.19 (m, 2H), 6.92 (s, 1H), 5.35 (s, 1H), 5.16 (s, 1H), 4.66 (s, 2 H), 3.92 (q, J=7.3 Hz, 2H), 2.55-2.66 (m, 1H), 2.14 (s, 3H), 2.09 (d, J=1.8 Hz, 3H), 1.42 (t, J=7.2 Hz, 3H) ppm; $^{19}$F NMR (376 MHz, CDCl$_3$) δ −113.79 (s, 1F), −119.93 (s, 1F) ppm.

Example 77: 6-(4-Ethyl-3-(hydroxymethyl)-5-oxo-4,5-dihydro-1H-1,2,4-triazol-1-yl)-7-fluoro-2-(2-fluorophenyl)-4-isopropylisoquinolin-1(2H)-one

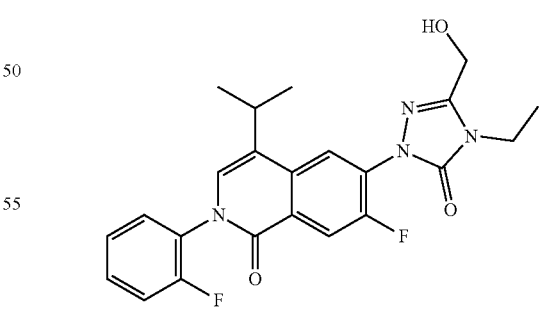

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2-fluoroaniline instead of 5-chloro-3-methyl-4-amino-1H-pyrazole in Step A. ESI-MS: mass calcd. for C$_{23}$H$_{22}$F$_2$N$_4$O$_3$, 440.2; m/z found, 441.2 [M+H]$^+$. $^1$H NMR (400 MHz, CDCl$_3$) δ 8.32 (d, J=11.0 Hz, 1H), 8.08 (d, J=6.8 Hz, 1H), 7.40-7.49 (m, 2H), 7.27-7.33 (m, 2H), 6.89 (s, 1H), 4.69 (br s, 2H), 3.93 (q, J=7.2 Hz, 2H), 3.26 (dt, J=13.4, 6.8 Hz, 1H), 2.47 (br s, 1H), 1.44 (t, J=7.2 Hz, 3H), 1.32 (d, J=6.8 Hz, 6H) ppm. $^{19}$F NMR (376 MHz, CDCl$_3$) δ −120.12 (s, 1F), −120.65 (s, 1F) ppm.

Example 78: 6-(4-Ethyl-3-(hydroxymethyl)-5-oxo-4,5-dihydro-1H-1,2,4-triazol-1-yl)-7-fluoro-4-isopropyl-2-(2-methoxy-3,5-dimethylpyridin-4-yl)isoquinolin-1(2H)-one

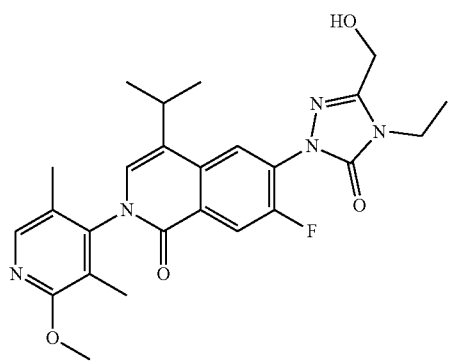

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2-methoxy-3,5-dimethylpyridin-4-amine instead of 5-chloro-3-methyl-4-amino-1H-pyrazole in Step A. ESI-MS: mass calcd. for C$_{25}$H$_{28}$FN$_5$O$_4$, 481.2; m/z found, 482.1[M+H]$^+$. $^1$H NMR (400 MHz, CDCl$_3$) δ 8.33 (d, J=11.3 Hz, 1H), 8.10 (d, J=6.8 Hz, 1H), 8.01 (s, 1H), 6.63 (s, 1H), 4.72 (d, J=6.3 Hz, 2H), 4.00 (s, 3H), 3.95 (q, J=7.1 Hz, 2H), 3.25-3.31 (m, 1H), 2.13 (t, J=6.4 Hz, 1H), 2.01 (s, 3H), 1.97 (s, 3H), 1.45 (t, J=7.2 Hz, 3H), 1.31 (d, J=6.8 Hz, 6H) ppm. $^{19}$F NMR (376 MHz, CDCl$_3$) δ −120.52 (br s, 1F) ppm.

Example 79: 6-(4-Ethyl-3-(hydroxymethyl)-5-oxo-4,5-dihydro-1H-1,2,4-triazol-1-yl)-7-methyl-4-(prop-1-en-2-yl)-2-(o-tolyl)isoquinolin-1(2H)-one

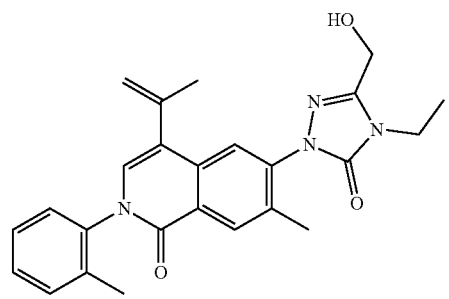 [SMILES: C=C(C)c1cn(-c2ccccc2C)c(=O)c2cc(C)c(-n3nc(CO)n(CC)c3=O)cc12]

The title compound was prepared in a manner analogous to Example 42, Steps A-B using 5-((benzyloxy)methyl)-4-ethyl-2-(7-methyl-1-oxo-4-(prop-1-en-2-yl)-1H-isochromen-6-yl)-2,4-dihydro-3H-1,2,4-triazol-3-one (Intermediate 7) instead of 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using o-toluidine instead of 2-fluoro-5-methylaniline in Step A. ESI-MS: mass calcd. for C$_{25}$H$_{26}$N$_4$O$_3$, 430.2; m/z found, 431.2 [M+H]$^+$. $^1$H NMR (400 MHz, CDCl$_3$) δ 8.44 (s, 1H), 7.76 (s, 1H), 7.35-7.37 (m, 2H), 7.31-7.35 (m, 1H), 7.29 (s, 1H), 6.91 (s, 1H), 5.31 (s, 1H), 5.14 (s, 1H), 4.67 (d, J=6.0 Hz, 2H), 3.92 (q, J=7.3 Hz, 2H), 2.44 (s, 3H), 2.32 (t, J=6.1 Hz, 1H), 2.17 (s, 3H), 2.13 (s, 3H), 1.43 (t, J=7.3 Hz, 3H) ppm.

Example 80: 2-(2-Chloro-6-fluoro-3-methoxyphenyl)-6-(4-ethyl-3-(hydroxymethyl)-5-oxo-4,5-dihydro-1H-1,2,4-triazol-1-yl)-7-fluoro-4-isopropylisoquinolin-1(2H)-one

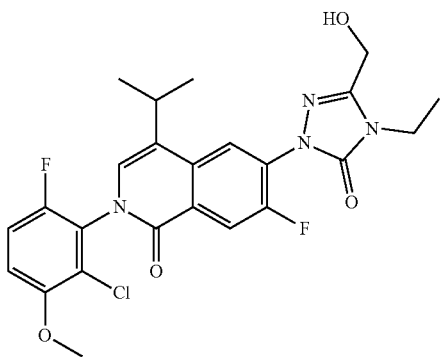 [SMILES: CCn1c(CO)nn(-c2cc3c(C(C)C)cn(-c4c(F)ccc(OC)c4Cl)c(=O)c3cc2F)c1=O]

To a solution of 2-(2-chloro-6-fluoro-3-methoxyphenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one (Example 51, 35 mg, 0.07 mmol) in THF (0.7 mL) was added Wilkinson's Catalyst [RhCl(PPh$_3$)$_3$](19.2 mg, 0.02 mmol). The suspension was degassed and purged with H$_2$ several times. The reaction mixture was stirred under an atmosphere of H$_2$ (15 psi) at room temperature overnight. The mixture was filtered through a short pad of Celite®. The filtrate was diluted with H$_2$O and extracted with EtOAc. The organic layer was separated, washed with brine, dried over anhydrous Na$_2$SO$_4$, filtered, and concentrated. The residue was purified by reversed phase prep-HPLC (Stationary phase: Boston Prime C18, 5 μm, 150×30 mm; Mobile phase: water (0.04% NH$_3$·H$_2$O+10 mM NH$_4$HCO$_3$) (A)—MeCN (B), gradient elution: 40-70% B in A over 7 min, flow rate: 25 mL/min) to give the title compound as an off-white powder (20.7 mg, yield: 59%). ESI-MS: mass calcd. for C$_{24}$H$_{23}$ClF$_2$N$_4$O$_4$, 504.1; m/z found, 505.1. $^1$H NMR (400 MHz, CDCl$_3$) δ 8.32 (d, J=11.0 Hz, 1H), 8.09 (d, J=7.0 Hz, 1H), 7.15-7.22 (m, 1H), 7.03 (dd, J=9.3, 4.5 Hz, 1H), 6.73 (s, 1H), 4.70 (s, 2H), 3.89-3.99 (m, 5H), 3.21-3.30 (m, 1H), 2.47 (br s, 1H), 1.44 (t, J=7.3 Hz, 3H), 1.32 (dd, J=6.8, 4.0 Hz, 6H ppm); $^{19}$F NMR (376 MHz, CDCl$_3$) δ −120.69 (br s, 1F), −127.05 (s, 1F) ppm.

Example 81: 6-(4-Ethyl-3-(hydroxymethyl)-5-oxo-4,5-dihydro-1H-1,2,4-triazol-1-yl)-7-fluoro-2-(o-tolyl)-4-(3,3,3-trifluoroprop-1-en-2-yl)isoquinolin-1(2H)-one

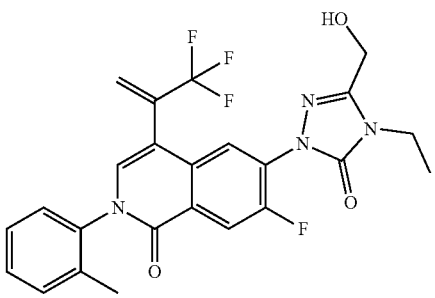 [SMILES: C=C(c1cn(-c2ccccc2C)c(=O)c2cc(F)c(-n3nc(CO)n(CC)c3=O)cc12)C(F)(F)F]

Step A. tert-Butyl (E)-4-(3-((benzyloxy)methyl)-4-ethyl-5-oxo-4,5-dihydro-1H-1,2,4-triazol-1-yl)-2-(2-ethoxyvinyl)-5-fluorobenzoate. To a mixture of tert-butyl 4-(3-((benzyloxy)methyl)-4-ethyl-5-oxo-4,5-dihydro-1H-1,2,4-triazol-1-yl)-5-fluoro-2-iodobenzoate (3.6 g, 6.5 mmol) and $Cs_2CO_3$ (6.36 g, 19.5 mmol) in 1,4-dioxane (34 mL) was added 2-(2-ethoxyvinyl)-4,4,5,5-tetramethyl-1,3,2-dioxaborolane (3.2 g, 16.3 mmol) and bis(triphenylphosphine)palladium(ii) dichloride (2.28 g, 3.25 mmol) under nitrogen. The reaction mixture was heated at 85° C. for 8 h. The mixture was cooled to room temperature, partitioned between water and ethyl acetate. The organic layer was separated, and the aqueous layer was extracted with ethyl acetate. The combined organic extract was washed with brine, dried over $MgSO_4$, filtered, and concentrated. The reside was purified by ISCO chromatography ($SiO_2$ 80 g, 30-100% EtOAc in heptane) to give the desired product as a white solid. LCMS (ES-API): mass calcd. for $C_{27}H_{32}FN_3O_5$, 497.2; m/z found, 498.1 [M+H]$^+$. $^1$H NMR (400 MHz, CDCl$_3$) δ 7.66 (d, J=11.25 Hz, 1H), 7.56 (d, J=7.34 Hz, 1H), 7.29-7.46 (m, 5H), 6.88 (d, J=12.97 Hz, 1H), 6.64 (d, J=12.97 Hz, 1H), 4.60 (s, 2H), 4.51 (s, 2H), 3.93 (q, J=7.17 Hz, 2H), 3.85 (q, J=7.01 Hz, 2H), 1.59 (s, 8H), 1.32-1.37 (m, 6H) ppm.

Step B. 4-(3-((Benzyloxy)methyl)-4-ethyl-5-oxo-4,5-dihydro-1H-1,2,4-triazol-1-yl)-2-(2-ethoxyvinyl)-5-fluoro-N-(o-tolyl)benzamide. To a solution of o-toluidine (1.6 mL, 15 mmol) in DCM (25 mL) was added a toluene solution (2 M) of AlMe$_3$ (10 mL, 20 mmol) under nitrogen. The mixture was stirred for 5 min, then the solution of tert-butyl (E)-4-(3-((benzyloxy)methyl)-4-ethyl-5-oxo-4,5-dihydro-1H-1,2,4-triazol-1-yl)-2-(2-ethoxyvinyl)-5-fluorobenzoate (2.5 g, 5 mmol) in DCM (25 mL) was added. The reaction mixture was stirred at 60° C. for 16 h. The mixture was cooled to room temperature and MeOH (2 mL) was carefully added. The mixture was partitioned between aqueous HCl solution (0.5N) and DCM. The organic layer was separated, and the aqueous layer was extracted with DCM. The combined organic extract was dried over anhydrous $MgSO_4$, filtered and concentrated to give the crude product (2.1 g, 78%), which was used directly to the next step without further purification. LCMS (ES-API): mass calcd. for $C_{30}H_{31}FN_4O_4$, 530.2; m/z found, 531.2 [M+H]$^+$.

Step C. 6-(3-((Benzyloxy)methyl)-4-ethyl-5-oxo-4,5-dihydro-1H-1,2,4-triazol-1-yl)-7-fluoro-2-(o-tolyl)isoquinolin-1(2H)-one. 4-(3-((benzyloxy)methyl)-4-ethyl-5-oxo-4,5-dihydro-1H-1,2,4-triazol-1-yl)-2-(2-ethoxyvinyl)-5-fluoro-N-(o-tolyl)benzamide (2.1 g, 4 mmol) was dissolved in trifluoroacetic acid (17 mL). The reaction mixture was stirred at 50° C. for 1 h. LCMS indicated almost complete consumption of the starting material and the formation of one major product. The mixture was poured into water (200 mL) and extracted with ethyl acetate (200 mL×2). The combined organic extract was dried over $MgSO_4$, filtered, and concentrated. The residue was purified by ISCO chromatography ($SiO_2$, 80 g, 30-70% ethyl acetate in heptane) to give the title compound as a yellow solid (1.08 g, yield: 56%). LCMS (ES-API): mass calcd. for $C_{28}H_{25}FN_4O_3$, 484.2; m/z found, 485.1 [M+H]$^+$. $^1$H NMR (400 MHz, CDCl$_3$) δ 8.27 (d, J=11.25 Hz, 1H), 7.87 (d, J=6.85 Hz, 1H), 7.29-7.44 (m, 8H), 7.15-7.25 (m, 1H), 7.03 (d, J=7.34 Hz, 1H), 6.57 (d, J=7.34 Hz, 1H), 4.63 (s, 2H), 4.54 (s, 2H), 3.88 (q, J=7.25 Hz, 2H), 2.17 (s, 3H), 1.38 (t, J=7.25 Hz, 3H) ppm.

Step D. 6-(3-((Benzyloxy)methyl)-4-ethyl-5-oxo-4,5-dihydro-1H-1,2,4-triazol-1-yl)-4-bromo-7-fluoro-2-(o-tolyl)isoquinolin-1(2H)-one. To a solution of 6-(3-((benzyloxy)methyl)-4-ethyl-5-oxo-4,5-dihydro-1H-1,2,4-triazol-1-yl)-7-fluoro-2-(o-tolyl)isoquinolin-1(2H)-one (1.08 g, 2.2 mmol) in DMF (18 mL) was added NBS (0.72 g, 4 mmol) at 0° C. Then the mixture was stirred at room temperature for 3 h. The mixture was poured into water and extracted with DCM. The organic layer was separated, and the aqueous layer was extracted with ethyl acetate. The combined organic extract was dried over $MgSO_4$, filtered, and concentrated. The residue was purified by ISCO chromatography ($SiO_2$, 80 g, 20-40% EtOAc in heptane) to give the title compound as a white solid (1.01 g, yield: 80%). LCMS (ES-API): mass calcd. for $C_{28}H_{24}BrFN_4O_3$, 562.1; m/z found, 563.0 [M+H]$^+$. $^1$H NMR (400 MHz, CDCl$_3$) δ 8.31 (d, J=10.27 Hz, 1H), 8.17-8.21 (m, 1H), 7.30-7.45 (m, 9H), 7.25 (s, 1H), 4.64 (s, 2H), 4.55 (s, 2H), 3.89 (q, J=7.34 Hz, 2H), 2.19 (s, 3H), 1.39 (t, J=7.34 Hz, 3H) ppm.

Step E. 6-(3-((Benzyloxy)methyl)-4-ethyl-5-oxo-4,5-dihydro-1H-1,2,4-triazol-1-yl)-7-fluoro-2-(o-tolyl)-4-(3,3,3-trifluoroprop-1-en-2-yl)isoquinolin-1(2H)-one. To a mixture of 6-(3-((benzyloxy)methyl)-4-ethyl-5-oxo-4,5-dihydro-1H-1,2,4-triazol-1-yl)-4-bromo-7-fluoro-2-(o-tolyl)isoquinolin-1(2H)-one (1.01 g, 1.79 mmol) and $Cs_2CO_3$ (1.75 g, 5.38 mmol) in 1,4-dioxane (20 mL), ethanol (10 mL), and water (10 mL) was added 1-(trifluoromethyl)vinylboronic acid hexylene glycol ester (0.99 g, 4.4 mmol) and bis(triphenylphosphine)palladium(II) dichloride (0.63 g, 0.9 mmol) under nitrogen. The reaction mixture was heated at 85° C. for 8 h. The mixture was cooled to room temperature, partitioned between water and ethyl acetate. The organic layer was separated, and the aqueous layer was extracted with ethyl acetate. The combined organic extract was washed with brine, dried over $MgSO_4$, filtered, and concentrated. The reside was purified by ISCO chromatography ($SiO_2$ 80 g, 30-100% EtOAc in heptane) to give the desired product as a white solid (0.67 g, yield: 64%). LCMS (ES-API): mass calcd. for $C_{31}H_{26}F_4N_4O_3$, 578.2; m/z found, 579.2 [M+H]$^+$. $^1$H NMR (400 MHz, CDCl$_3$) δ 8.32 (d, J=10.76 Hz, 1H), 7.89 (d, J=6.85 Hz, 1H), 7.28-7.48 (m, 9H), 7.08 (s, 1H), 6.37 (d, J=1.23 Hz, 1H), 5.86 (d, J=1.23 Hz, 1H), 4.63 (s, 2H), 4.54 (s, 2H), 3.87 (q, J=7.05 Hz, 2H), 2.18 (s, 3H), 1.37 (t, J=7.05 Hz, 3H) ppm.

Step F. 6-(4-Ethyl-3-(hydroxymethyl)-5-oxo-4,5-dihydro-1H-1,2,4-triazol-1-yl)-7-fluoro-2-(o-tolyl)-4-(3,3,3-trifluoroprop-1-en-2-yl)isoquinolin-1(2H)-one. To a stirred solution of 6-(3-((benzyloxy)methyl)-4-ethyl-5-oxo-4,5-dihydro-1H-1,2,4-triazol-1-yl)-7-fluoro-2-(o-tolyl)-4-(3,3,3-trifluoroprop-1-en-2-yl)isoquinolin-1(2H)-one (78 mg, 0.14 mmol) in DCM (5 mL) was added BCl$_3$ (1 M, 0.4 mL, 0.4 mmol) at −78° C. The reaction mixture was stirred at −78° C. for 0.5 h. The mixture was diluted with DCM, washed with saturated aqueous NaHCO$_3$ solution. The organic extract was separated, washed with brine, dried over anhydrous Na$_2$SO$_4$, filtered, and concentrated. The residue was purified by ISCO chromatography (SiO$_2$ 40 g, 50-100% EtOAc in heptane). The product was further purified by ISCO reverse phase prep-HPLC [C18, 10-90% MeCN in water (0.2% NH$_4$OH)] to give the title compound as a white powder (25 mg, yield: 38%). LCMS (ES-API): mass calcd. for $C_{24}H_{20}F_4N_4O_3$, 488.1; m/z found, 489.0 [M+H]$^+$. $^1$H NMR (400 MHz, CDCl$_3$) δ 8.32 (d, J=10.76 Hz, 1H), 7.88 (d, J=6.85 Hz, 1H), 7.28-7.43 (m, 4H), 7.08 (s, 1H), 6.37 (s, 1H), 5.86 (s, 1H), 4.68 (d, J=6.12 Hz, 2H), 3.92 (q, J=7.05 Hz, 2H), 2.29 (br t, J=6.12 Hz, 1H), 2.18 (s, 3H), 1.43 (t, J=7.05 Hz, 3H) ppm.

Example 82: 6-(4-Ethyl-3-(hydroxymethyl)-5-oxo-4,5-dihydro-1H-1,2,4-triazol-1-yl)-7-fluoro-2-(5-fluoro-2-methylphenyl)-4-(prop-1-en-2-yl)isoquinolin-1(2H)-one

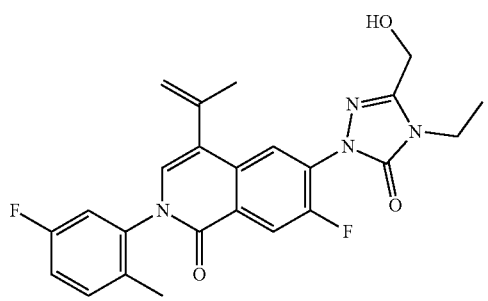 [SMILES: C=C(C)c1cn(-c2cc(F)ccc2C)c(=O)c2cc(F)c(-n3nc(CO)n(CC)c3=O)cc12]

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using 5-fluoro-2-methylaniline instead of 2-fluoro-5-methylaniline in Step A. ESI-MS: mass calcd. for $C_{24}H_{22}F_2N_4O_3$, 452.2; m/z found, 453.1 [M+H]$^+$. $^1$H NMR (400 MHz, CDCl$_3$) δ 8.30 (d, J=11.0 Hz, 1H), 8.01 (d, J=7.0 Hz, 1H), 7.33 (dd, J=8.3, 6.3 Hz, 1H), 7.02-7.14 (m, 2H), 6.90 (s, 1H), 5.36 (s, 1H), 5.16 (s, 1H), 4.70 (d, J=6.0 Hz, 2H), 3.93 (q, J=7.3 Hz, 2H), 2.15-2.19 (m, 1H), 2.14 (s, 6H), 1.44 (t, J=7.3 Hz, 3H) ppm; $^{19}$F NMR (376 MHz, CDCl$_3$) δ −115.26 (s, 1F), −119.98 (br s, 1F) ppm.

Example 83: 6-(4-Ethyl-3-(hydroxymethyl)-5-oxo-4,5-dihydro-1H-1,2,4-triazol-1-yl)-7-fluoro-2-(2-methoxyphenyl)-4-(prop-1-en-2-yl)isoquinolin-1(2H)-one

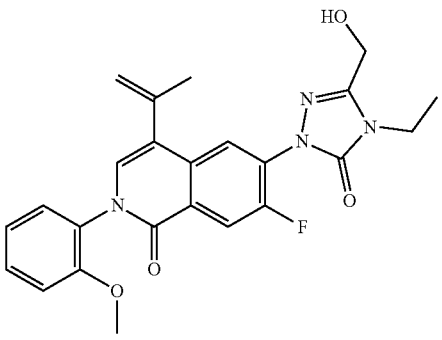 [SMILES: C=C(C)c1cn(-c2ccccc2OC)c(=O)c2cc(F)c(-n3nc(CO)n(CC)c3=O)cc12]

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using o-anisidine instead of 2-fluoro-5-methylaniline in Step A. ESI-MS: mass calcd. for $C_{24}H_{23}FN_4O_4$, 450.2; m/z found, 451.1 [M+H]$^+$. $^1$H NMR (400 MHz, CDCl$_3$) δ 8.30 (d, J=11.3 Hz, 1H), 7.99 (d, J=6.8 Hz, 1H), 7.41-7.47 (m, 1H), 7.34 (d, J=7.8 Hz, 1H), 7.08 (d, J=8.0 Hz, 2H), 6.95 (s, 1H), 5.34 (s, 1H), 5.17 (s, 1H), 4.69 (d, J=5.0 Hz, 2H), 3.93 (q, J=7.2 Hz, 2H), 3.83 (s, 3H), 2.30 (br s, 1H), 2.15 (s, 3H), 1.44 (t, J=7.2 Hz, 3H) ppm; $^{19}$F NMR (376 MHz, CDCl$_3$) δ −121.07 (br s, 1 F) ppm.

Example 84: 2-(2-Chloro-5-methylpyridin-3-yl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one

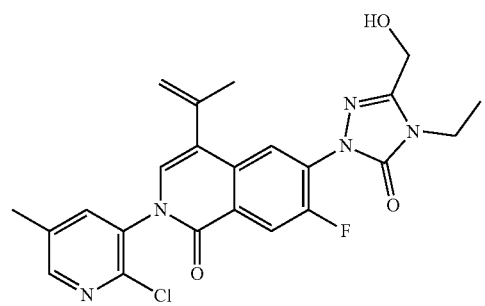 [SMILES: C=C(C)c1cn(-c2cc(C)cnc2Cl)c(=O)c2cc(F)c(-n3nc(CO)n(CC)c3=O)cc12]

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using 3-amino-2-chloro-5-methylpyridine instead of 2-fluoro-5-methylaniline in Step A. ESI-MS: mass calcd. for $C_{23}H_{21}ClFN_5O_3$, 469.1; m/z found, 470.0 [M+H]$^+$. $^1$H NMR (400 MHz, CDCl$_3$) δ 8.35 (s, 1H), 8.29 (d, J=11.0 Hz, 1H), 8.02 (d, J=7.0 Hz, 1H), 7.67 (s, 1H), 6.87 (s, 1H), 5.37 (s, 1H), 5.19 (s, 1H), 4.70 (d, J=6.0 Hz, 2H), 3.94 (q, J=7.2 Hz, 2H), 2.43 (s, 3H), 2.25 (t, J=6.1 Hz, 1H), 2.16 (s, 3H), 1.44 (t, J=7.2 Hz, 3H) ppm; $^{19}$F NMR (376 MHz, CDCl$_3$) δ −119.61 (s, 1F) ppm.

Example 85: 6-(4-Ethyl-3-(hydroxymethyl)-5-oxo-4,5-dihydro-1H-1,2,4-triazol-1-yl)-7-fluoro-2-(5-fluoro-2-methoxypyridin-4-yl)-4-(prop-1-en-2-yl)isoquinolin-1(2H)-one

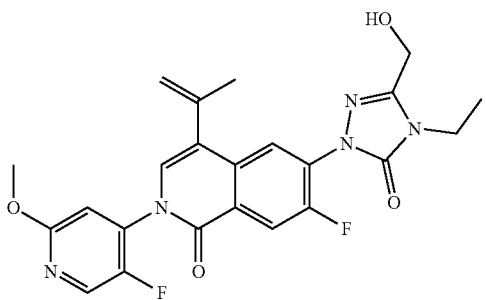 [SMILES: C=C(C)c1cn(-c2cc(OC)ncc2F)c(=O)c2cc(F)c(-n3nc(CO)n(CC)c3=O)cc12]

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using 5-fluoro-2-methoxypyridin-4-amine instead of 2-fluoro-5-methylaniline in Step A. ESI-MS: mass calcd. for $C_{23}H_{21}F_2N_5O_4$, 469.2; m/z found, 470.1 [M+H]$^+$. $^1$H NMR (400 MHz, CDCl$_3$) δ 8.29 (d, J=11.0 Hz, 1H), 8.19 (d, J=1.0 Hz, 1H), 8.00 (d, J=7.0 Hz, 1H), 6.94 (s, 1H), 6.86 (d, J=4.8 Hz, 1H), 5.37 (s, 1H), 5.17 (s, 1H), 4.68 (s, 2H), 3.95-4.00 (m, 3H), 3.89-3.95 (m, 2H), 2.59 (br s, 1H), 2.14 (s, 3H), 1.43 (t, J=7.3 Hz, 3H) ppm; $^{19}$F NMR (376 MHz, CDCl$_3$) δ −119.20 (s, 1F), −145.32 (s, 1F) ppm.

Example 86: 6-(4-Ethyl-3-(hydroxymethyl)-5-oxo-4,5-dihydro-1H-1,2,4-triazol-1-yl)-7-fluoro-2-(3-fluoro-2-methylphenyl)-4-(prop-1-en-2-yl)isoquinolin-1(2H)-one

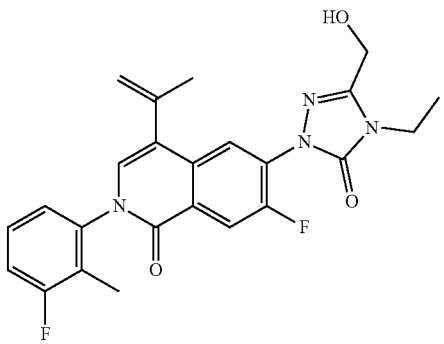 [SMILES: C=C(C)c1cn(-c2cccc(F)c2C)c(=O)c2cc(F)c(-n3nc(CO)n(CC)c3=O)cc12]

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using 3-fluoro-2-methylaniline instead of 2-fluoro-5-methylaniline in Step A. ESI-MS: mass calcd. for $C_{24}H_{22}F_2N_4O_3$, 452.2; m/z found, 453.1 [M+H]$^+$. $^1$H NMR (400 MHz, CDCl$_3$) δ 8.30 (d, J=11.0 Hz, 1H), 8.01 (d, J=7.0 Hz, 1H), 7.29-7.36 (m, 1H), 7.08-7.21 (m, 2H), 6.92 (s, 1H), 5.36 (s, 1H), 5.16 (s, 1H), 4.70 (d, J=6.3 Hz, 2H), 3.93 (q, J=7.4 Hz, 2H), 2.18 (t, J=6.3 Hz, 1H), 2.15 (s, 3H), 2.09 (d, J=2.0 Hz, 3H), 1.44 (t, J=7.3 Hz, 3H) ppm; $^{19}$F NMR (376 MHz, CDCl$_3$) δ −113.79 (s, 1F), −119.93 (s, 1F) ppm.

Example 87: 2-(2,5-Dimethylphenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one

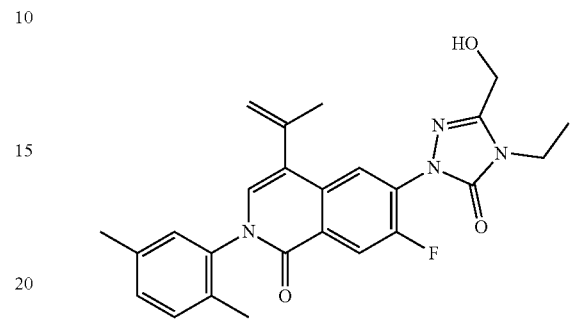

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using 2,5-dimethylaniline instead of 2-fluoro-5-methylaniline in Step A. ESI-MS: mass calcd. for $C_{25}H_{25}FN_4O_3$, 448.2; m/z found, 449.1 [M+H]$^+$. $^1$H NMR (400 MHz, CDCl$_3$) δ 8.31 (d, J=11.0 Hz, 1H), 8.00 (d, J=7.0 Hz, 1H), 7.24 (s, 1H), 7.15-7.20 (m, 1H), 7.09 (s, 1H), 6.93 (s, 1H), 5.35 (s, 1H), 5.16 (s, 1H), 4.69 (d, J=6.5 Hz, 2H), 3.93 (q, J=7.2 Hz, 2H), 2.37 (s, 3H), 2.27 (br t, J=6.3 Hz, 1H), 2.13 (d, J=6.8 Hz, 6H), 1.43 (t, J=7.3 Hz, 3H) ppm; $^{19}$F NMR (376 MHz, CDCl$_3$) δ −120.54 (s, 1F) ppm.

Example 88: Racemic-6-(4-Ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)isoquinolin-1(2H)-one

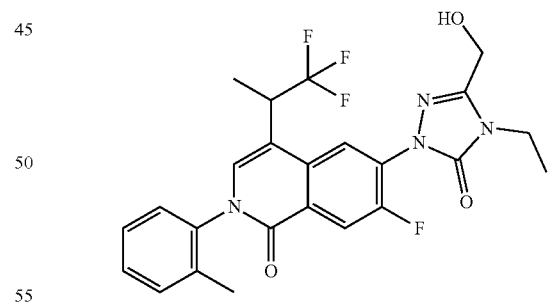

Step A. Racemic-6-(3-((benzyloxy)methyl)-4-ethyl-5-oxo-4,5-dihydro-1H-1,2,4-triazol-1-yl)-7-fluoro-2-(o-tolyl)-4-(1,1,1-trifluoropropan-2-yl)isoquinolin-1(2H)-one. To a solution of 6-(3-((benzyloxy)methyl)-4-ethyl-5-oxo-4,5-dihydro-1H-1,2,4-triazol-1-yl)-7-fluoro-2-(o-tolyl)-4-(3,3,3-trifluoroprop-1-en-2-yl)isoquinolin-1(2H)-one (Example 81, product from Step E, 0.67 g, 1.16 mmol) in THF (30 mL) at room temperature was added Wilkinson's Catalyst (RhCl(PPh$_3$)$_3$) (0.5 g, 0.6 mmol). The mixture was degassed and purged with hydrogen gas. The reaction mixture was stirred under an atmosphere of hydrogen (15 Psi) at room temperature for 12 h. The mixture was concentrated. The residue was purified by ISCO chromatography (SiO$_2$, 80 g, 30-60% EtOAc in heptane) to give the title compound as a white foam (0.56 g, yield: 83%). ESI-MS: mass calcd. for C$_{31}$H$_{28}$F$_4$N$_4$O$_3$, 580.2; m/z found 581.1 [M+H]$^+$.

Step B. Racemic-6-(4-ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)isoquinolin-1(2H)-one. To a stirred solution of racemic-6-(3-((benzyloxy)methyl)-4-ethyl-5-oxo-4,5-dihydro-1H-1,2,4-triazol-1-yl)-7-fluoro-2-(o-tolyl)-4-(1,1,1-trifluoropropan-2-yl)isoquinolin-1(2H)-one (63 mg, 0.11 mmol) in DCM (5 mL) was added BCl$_3$ (1 M in DCM, 0.33 mL, 0.33 mmol) at −78° C. The reaction mixture was stirred at 1. The mixture was diluted with DCM, washed with saturated aqueous NaHCO$_3$ solution. The organic extract was separated, washed with brine, dried over anhydrous Na$_2$SO$_4$, filtered, and concentrated. The residue was purified by ISCO chromatography (SiO$_2$ 40 g, 50-80% EtOAc in heptane). The product was further purified by ISCO reverse phase prep-HPLC [C18, 10-90% MeCN in water (0.2% NH$_4$OH)] to give the title compound as a white powder (26 mg, yield: 49%). LCMS (ES-API): mass calcd. for C$_{24}$H$_{22}$F$_4$N$_4$O$_3$, 490.2; m/z found, 491.1 [M+H]$^+$. $^1$H NMR (400 MHz, CDCl$_3$) δ 8.35 (d, J=11.25 Hz, 1H), 8.04 (d, J=6.85 Hz, 1H), 7.11-7.39 (s, 4H), 7.10 (s, 1H), 4.71 (br d, J=4.89 Hz, 2H), 3.83-4.01 (m, 4H), 2.16 (s, 3H) 1.53 (d, J=7.34 Hz, 3H), 1.45 (t, J=7.34 Hz, 3H) ppm.

Example 89: 6-(4-Ethyl-3-(hydroxymethyl)-5-oxo-4,5-dihydro-1H-1,2,4-triazol-1-yl)-2-(2-ethylphenyl)-7-fluoro-4-isopropylisoquinolin-1(2H)-one

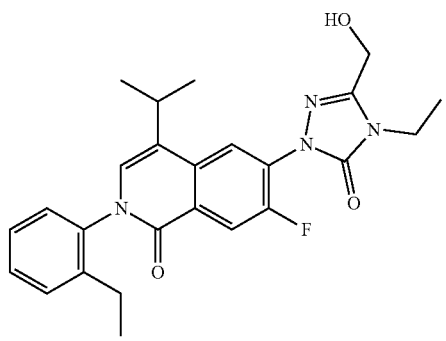

The title compound was prepared in a manner analogous to Example 42, Steps A-B using 5-((benzyloxy)methyl)-4-ethyl-2-(7-fluoro-1-oxo-4-(prop-1-en-2-yl)-1H-isochromen-6-yl)-2,4-dihydro-3H-1,2,4-triazol-3-one (Intermediate 3) and using 2-ethylaniline instead of 2-fluoro-5-methylaniline in Step A. ESI-MS: mass calcd. for C$_{25}$H$_{27}$FN$_4$O$_3$, 450.2; m/z found, 451.2 [M+H]$^+$. $^1$H NMR (400 MHz, CDCl$_3$) δ 8.30 (d, J=11.0 Hz, 1H), 8.05 (d, J=6.8 Hz, 1H), 7.37-7.44 (m, 2H), 7.30-7.36 (m, 1H), 7.22 (s, 1H), 6.83 (s, 1H), 4.65 (br d, J=5.1 Hz, 2H), 3.91 (q, J=7.1 Hz, 2H), 3.24 (dt, J=13.5, 6.8 Hz, 1H), 2.53 (br d, J=7.3 Hz, 1H), 2.36-2.51 (m, 2H), 1.41 (t, J=7.2 Hz, 3H), 1.28 (d, J=6.8 Hz, 6H), 1.12 (t, J=7.6 Hz, 3H) ppm; $^{19}$F NMR (376 MHz, CDCl$_3$) δ −121.02 (dd, J=11.0, 6.6 Hz, 1F) ppm.

Example 90: 6-(4-Ethyl-3-(hydroxymethyl)-5-oxo-4,5-dihydro-1H-1,2,4-triazol-1-yl)-7-fluoro-4-isopropyl-2-(2-methoxypyridin-3-yl)isoquinolin-1(2H)-one

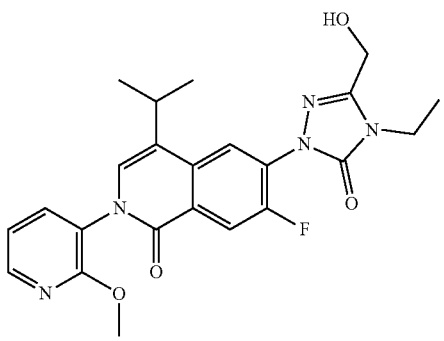

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2-methoxypyridin-3-amine instead of 5-chloro-3-methyl-4-amino-1H-pyrazole in Step A. ESI-MS: mass calcd. for C$_{23}$H$_{24}$FN$_5$O$_4$, 453.2; m/z found, 454.1 [M+H]$^+$. $^1$H NMR (400 MHz, CDCl$_3$) δ 8.25-8.34 (m, 2H), 8.07 (d, J=7.0 Hz, 1H), 7.68 (dd, J=7.5, 1.5 Hz, 1H), 7.06 (dd, J=7.5, 5.0 Hz, 1H), 6.81 (s, 1H), 4.69 (d, J=6.0 Hz, 2H), 3.89-3.99 (m, 5H), 3.25 (dt, J=13.6, 6.6 Hz, 1H), 2.47 (t, J=6.3 Hz, 1H), 1.44 (t, J=7.2 Hz, 3H), 1.32 (d, J=6.8 Hz, 6H) ppm; $^{19}$F NMR (376 MHz, CDCl$_3$) δ −123.28-119.32 (m, 1F) ppm.

Example 91: 6-(4-Ethyl-3-(hydroxymethyl)-5-oxo-4,5-dihydro-1H-1,2,4-triazol-1-yl)-7-fluoro-2-(5-fluoro-2-methoxypyridin-4-yl)-4-isopropylisoquinolin-1(2H)-one

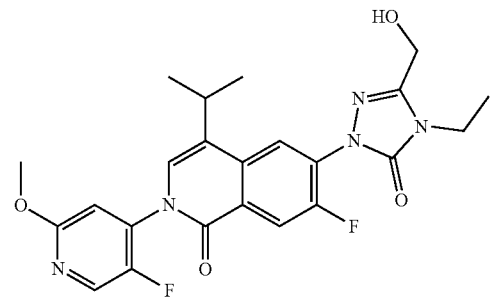

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 5-fluoro-2-methoxypyridin-4-amine instead of 5-chloro-3-methyl-4-amino-1H-pyrazole in Step A. ESI-MS: mass calcd. for C$_{23}$H$_{23}$F$_2$N$_5$O$_4$, 471.2; m/z found, 472.1 [M+H]$^+$. $^1$H NMR (400 MHz, CDCl$_3$) δ 8.32 (d, J=11.0 Hz, 1H), 8.20 (d, J=1.5 Hz, 1H), 8.10 (d, J=6.8 Hz, 1H), 6.87-6.83 (m, 2H), 4.71 (s, 2H), 3.98 (s, 3H), 3.96-3.89 (m, 2H), 3.30-3.21 (m, 1H), 2.33 (br d, J=16.1 Hz, 1H), 1.45 (t, J=7.3 Hz, 3H), 1.33 (d, J=6.8 Hz, 6H); $^{19}$F NMR (376 MHz, CDCl$_3$) δ −119.93 (s, 1F), −145.28 (s, 1F) ppm.

Example 92: 2-(2-Chloro-5-methylpyridin-3-yl)-6-(4-ethyl-3-(hydroxymethyl)-5-oxo-4,5-dihydro-1H-1,2,4-triazol-1-yl)-7-fluoro-4-isopropylisoquinolin-1(2H)-one

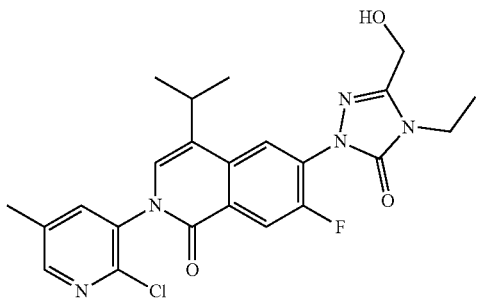 [SMILES: CCn1c(CO)nn(-c2cc3c(C(C)C)cn(-c4cc(C)cnc4Cl)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2-chloro-5-methylpyridin-3-amine instead of 5-chloro-3-methyl-4-amino-1H-pyrazole in Step A. ESI-MS: mass calcd. for $C_{23}H_{23}ClFN_5O_3$, 471.1; m/z found, 472.2 [M+H]+. 1H NMR (400 MHz, CDCl3) δ 8.35 (d, J=1.5 Hz, 1H), 8.30 (d, J=11.0 Hz, 1H), 8.10 (d, J=6.8 Hz, 1H), 7.66 (d, J=1.5 Hz, 1H), 6.77 (s, 1H), 4.69 (br d, J=4.8 Hz, 2H), 3.94 (q, J=7.1 Hz, 2H), 3.27 (spt, J=6.8 Hz, 1H), 2.78-2.71 (m, 1H), 2.43 (s, 3H), 1.44 (t, J=7.2 Hz, 3H), 1.32 (t, J=7.4 Hz, 6H) ppm; 19F NMR (376 MHz, CDCl3) δ −120.17 (s, 1F) ppm.

Example 93: 6-(4-Ethyl-3-(hydroxymethyl)-5-oxo-4,5-dihydro-1H-1,2,4-triazol-1-yl)-7-fluoro-4-isopropyl-2-(2-(methyl-d3)phenyl)isoquinolin-1(2H)-one

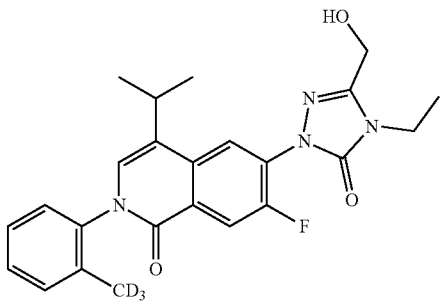

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2-(methyl-d3)-aniline instead of 5-chloro-3-methyl-4-amino-1H-pyrazole in Step A. ESI-MS: mass calcd. for $C_{24}H_{22}D_3FN_4O_3$, 439.2; m/z found, 440.1 [M+H]+. 1H NMR (400 MHz, CDCl3) δ 8.33 (d, J=11.0 Hz, 1H), 8.08 (d, J=7.0 Hz, 1H), 7.41-7.33 (m, 3H), 7.28 (s, 1H), 6.85 (s, 1H), 4.69 (d, J=6.3 Hz, 2H), 3.94 (q, J=7.3 Hz, 2H), 3.27 (quin, J=6.8 Hz, 1H), 2.49 (t, J=6.4 Hz, 1H), 1.45 (t, J=7.3 Hz, 3H), 1.31 (dd, J=1.8, 6.8 Hz, 6H) ppm; 19F NMR (376 MHz, CDCl3) δ −121.02 (s, 1F) ppm.

Example 94: 6-(4-Ethyl-3-(hydroxymethyl)-5-oxo-4,5-dihydro-1H-1,2,4-triazol-1-yl)-7-fluoro-4-isopropyl-2-(4-methylpyrimidin-5-yl)isoquinolin-1(2H)-one

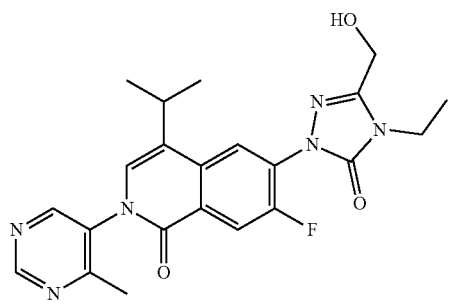 [SMILES: CCn1c(CO)nn(-c2cc3c(C(C)C)cn(-c4cncnc4C)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 5-amino-4-methylpyrimidine instead of 5-chloro-3-methyl-4-amino-1H-pyrazole in Step A. ESI-MS: mass calcd. for $C_{22}H_{23}FN_6O_3$, 438.2; m/z found, 439.1 [M+H]+. 1H NMR (400 MHz, CDCl3) δ 9.17 (s, 1H), 8.66 (s, 1H), 8.26 (d, J=11.0 Hz, 1H), 8.15 (d, J=7.0 Hz, 1H), 6.76 (s, 1H), 4.70 (br d, J=3.3 Hz, 2H), 3.95 (q, J=7.3 Hz, 2H), 3.29 (td, J=6.8, 13.6 Hz, 1H), 2.82 (br s, 1H), 2.45 (s, 3H), 1.45 (t, J=7.2 Hz, 3H), 1.33 (d, J=6.8 Hz, 6H) ppm; 19F NMR (376 MHz, CDCl3) δ −119.53 (s, 1F) ppm.

Example 95: 6-(4-Ethyl-3-(hydroxymethyl)-5-oxo-4,5-dihydro-1H-1,2,4-triazol-1-yl)-7-fluoro-4-isopropyl-2-(2-methoxyphenyl)isoquinolin-1(2H)-one

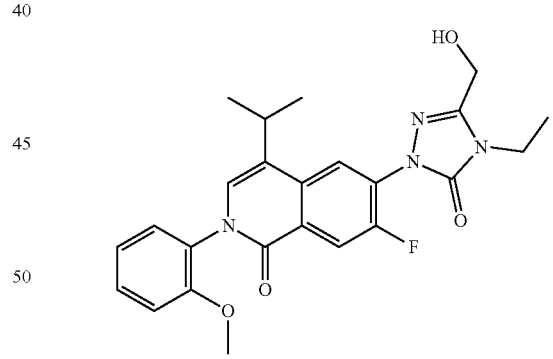

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using o-anisidine instead of 5-chloro-3-methyl-4-amino-1H-pyrazole in Step A. ESI-MS: mass calcd. for $C_{24}H_{25}FN_4O_4$, 452.2; m/z found, 453.1 [M+H]+. 1H NMR (400 MHz, CDCl3) δ 8.32 (d, J=11.3 Hz, 1H), 8.05 (d, J=7.0 Hz, 1H), 7.41-7.47 (m, 1H), 7.33 (d, J=7.5 Hz, 1H), 7.04-7.12 (m, 2H), 6.85 (s, 1H), 4.69 (d, J=5.5 Hz, 2H), 3.94 (q, J=7.3 Hz, 2H), 3.82 (s, 3H), 3.25 (dt, J=13.6, 6.8 Hz, 1H), 2.36 (br s, 1H), 1.44 (t, J=7.3 Hz, 3H), 1.31 (d, J=6.8 Hz, 6H) ppm; 19F NMR (376 MHz, CDCl3) δ −121.56 (s, 1F) ppm.

Example 96: 6-(4-Ethyl-3-(hydroxymethyl)-5-oxo-4,5-dihydro-1H-1,2,4-triazol-1-yl)-7-fluoro-2-(3-fluoro-6-methoxypyridin-2-yl)-4-isopropylisoquinolin-1(2H)-one

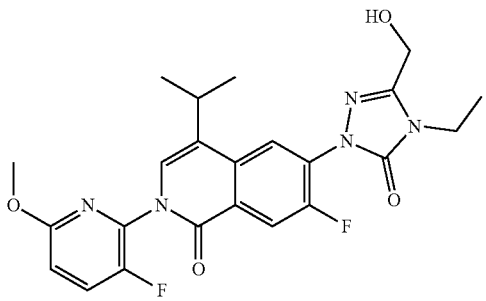

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 3-fluoro-6-methoxypyridin-2-amine instead of 5-chloro-3-methyl-4-amino-1H-pyrazole in Step A. ESI-MS: mass calcd. for $C_{23}H_{23}F_2N_5O_4$, 471.2; m/z found, 472.1 [M+H]$^+$. $^1$H NMR (400 MHz, CDCl$_3$) δ 8.33 (d, J=11.3 Hz, 1H), 8.08 (d, J=6.8 Hz, 1H), 7.55 (t, J=8.5 Hz, 1H), 7.10 (s, 1H), 6.85 (dd, J=8.8, 2.8 Hz, 1H), 4.70 (d, J=6.3 Hz, 2H), 3.90-3.98 (m, 5H), 3.26 (dt, J=13.7, 6.8 Hz, 1H), 2.34 (t, J=6.5 Hz, 1H), 1.44 (t, J=7.3 Hz, 3H), 1.35 (d, J=6.8 Hz, 6H); $^{19}$F NMR (376 MHz, CDCl$_3$) δ −120.61 (s, 1F), −133.15 (s, 1F) ppm.

Example 97: 6-(4-Ethyl-3-(hydroxymethyl)-5-oxo-4,5-dihydro-1H-1,2,4-triazol-1-yl)-7-fluoro-4-isopropyl-2-(3-methylpyrazin-2-yl)isoquinolin-1(2H)-one

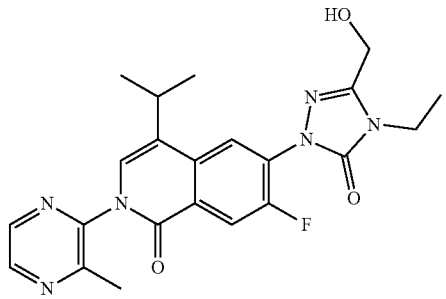 [SMILES: CCn1c(CO)nn(-c2cc3c(C(C)C)cn(-c4nccnc4C)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 3-methylpyrazin-2-amine instead of 5-chloro-3-methyl-4-amino-1H-pyrazole in Step A. ESI-MS: mass calcd. for $C_{22}H_{23}FN_6O_3$, 438.2; m/z found, 439.2 [M+H]$^+$. $^1$H NMR (400 MHz, CDCl$_3$) δ 8.34 (d, J=11.0 Hz, 1H), 8.24 (d, J=2.5 Hz, 1H), 8.21 (d, J=2.5 Hz, 1H), 7.83 (d, J=6.8 Hz, 1H), 6.84 (s, 1H), 4.70 (d, J=6.3 Hz, 2H), 3.94 (q, J=7.3 Hz, 2H), 3.02 (dt, J=13.4, 6.8 Hz, 1H), 2.49 (s, 3H), 2.44-2.48 (m, 1H), 1.44 (t, J=7.3 Hz, 3H), 1.26 (d, J=6.8 Hz, 6H); $^{19}$F NMR (376 MHz, CDCl$_3$) δ −118.42 (s, 1F) ppm.

Example 98: 2-(2-Chloro-5-methylpyridin-3-yl)-6-(4-ethyl-3-(hydroxymethyl)-5-oxo-4,5-dihydro-1H-1,2,4-triazol-1-yl)-7-fluoro-4-isopropylisoquinolin-1(2H)-one

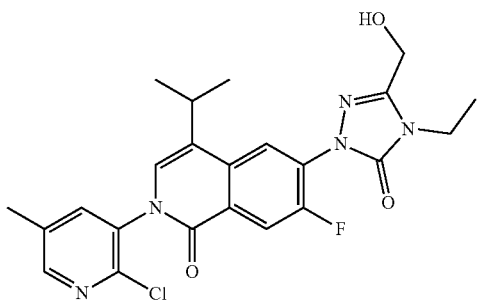 [SMILES: CCn1c(CO)nn(-c2cc3c(C(C)C)cn(-c4cc(C)cnc4Cl)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2-chloro-5-methylpyridin-3-amine instead of 5-chloro-3-methyl-4-amino-1H-pyrazole in Step A. ESI-MS: mass calcd. for $C_{23}H_{23}ClFN_5O_3$, 471.1; m/z found, 472.2 [M+H]$^+$. $^1$H NMR (400 MHz, CDCl$_3$) δ 8.35 (d, J=1.5 Hz, 1H), 8.30 (d, J=11.0 Hz, 1H), 8.10 (d, J=6.8 Hz, 1H), 7.66 (d, J=1.5 Hz, 1H), 6.77 (s, 1H), 4.69 (br d, J=4.8 Hz, 2H), 3.94 (q, J=7.1 Hz, 2H), 3.27 (spt, J=6.8 Hz, 1H), 2.78-2.71 (m, 1H), 2.43 (s, 3H), 1.44 (t, J=7.2 Hz, 3H), 1.32 (t, J=7.4 Hz, 6H); $^{19}$F NMR (376 MHz, CDCl$_3$) δ −120.17 (s, 1F) ppm.

Example 99: 2-(4-Ethyl-3-(hydroxymethyl)-5-oxo-4,5-dihydro-1H-1,2,4-triazol-1-yl)-3-fluoro-6-(2-fluoro-5-methylphenyl)-8-isopropyl-1,6-naphthyridin-5(6H)-one

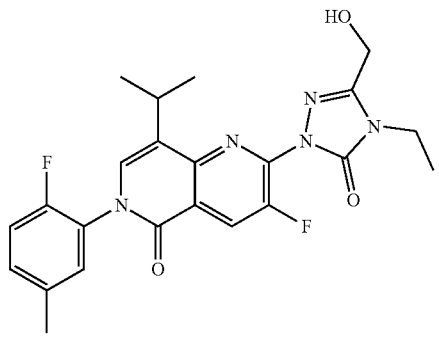 [SMILES: CCn1c(CO)nn(-c2nc3c(C(C)C)cn(-c4cc(C)ccc4F)c(=O)c3cc2F)c1=O]

Step A. 6-(3-((Benzyloxy)methyl)-4-ethyl-5-oxo-4,5-dihydro-1H-1,2,4-triazol-1-yl)-2-(2-ethoxyvinyl)-5-fluoro-N-(2-fluoro-5-methylphenyl)nicotinamide. 2-Fluoro-5-methylaniline (101 mg, 0.808 mmol) was dissolved in toluene (2 mL), and AlMe$_3$ (2 M solution in toluene, 0.30 mL, 0.60 mmol) was added under N$_2$. After stirring 0.5 hour, the mixture of isopropyl 6-(3-((benzyloxy)methyl)-4-ethyl-5-oxo-4,5-dihydro-1H-1,2,4-triazol-1-yl)-2-(2-ethoxyvinyl)-5-fluoronicotinate (100 mg, 206.39 μmol) in toluene (2 mL) was added. The mixture was stirred at 90° C. overnight. 1 M aqueous HCl solution (0.6 mL) was added and stirred at room temperature for 2 minutes. The mixture was poured into water (20 mL) and extracted with DCM (25 mL×2). The combined organic phase was washed with brine (20 mL×2), dried with anhydrous $Na_2SO_4$, filtered and concentrated in vacuum. The residue was purified by column chromatography ($SiO_2$, petroleum ether/ethyl acetate=1/0 to ¼) to give the title compound (64 mg, 116.45 μmol, 58% yield, 100% purity) as a yellow oil. MS (ESI): mass calcd. for $C_{29}H_{29}F_2N_5O_4$, 549.2; m/z found, 550.2 [M+H]$^+$.

Step B. 2-(3-((Benzyloxy)methyl)-4-ethyl-5-oxo-4,5-dihydro-1H-1,2,4-triazol-1-yl)-3-fluoro-6-(2-fluoro-5-methylphenyl)-1,6-naphthyridin-5(6H)-one. 6-(3-((benzyloxy)methyl)-4-ethyl-5-oxo-4,5-dihydro-1H-1,2,4-triazol-1-yl)-2-(2-ethoxyvinyl)-5-fluoro-N-(2-fluoro-5-methylphenyl) nicotinamide (64 mg, 116.45 μmol) was dissolved in AcOH (3 mL) and stirred at 90° C. overnight. The mixture was poured into water (10 mL) and extracted with EtOAc (12 mL×2). The combined organic phase was washed with brine (15 mL×2), dried with anhydrous $Na_2SO_4$, filtered and concentrated in vacuum. The residue was purified by column chromatography ($SiO_2$, petroleum ether/ethyl acetate=1/0 to ¼) to give the title compound (45 mg, 85.8 μmol, 74% yield, 96% purity) as a yellow oil. MS (ESI): mass calcd. for $C_{27}H_{23}F_2N_5O_3$, 503.2; m/z found, 504.2 [M+H]$^+$. $^1$H NMR (400 MHz, CDCl$_3$) δ 8.54 (d, J=9.3 Hz, 1H), 7.42-7.34 (m, 6H), 7.31 (d, J=7.8 Hz, 1H), 7.24-7.14 (m, 2H), 6.89 (d, J=7.8 Hz, 1H), 4.63 (s, 2H), 4.58 (s, 2H), 3.89 (q, J=7.3 Hz, 2H), 2.40 (s, 3H), 1.37 (t, J=7.2 Hz, 3H); $^{19}$F NMR (376 MHz, CDCl$_3$) δ −123.41 (s, 1F), −125.59 (s, 1F) ppm.

Step C. 2-(3-((Benzyloxy)methyl)-4-ethyl-5-oxo-4,5-dihydro-1H-1,2,4-triazol-1-yl)-8-bromo-3-fluoro-6-(2-fluoro-5-methylphenyl)-1,6-naphthyridin-5(6H)-one. A mixture of 2-(3-((benzyloxy)methyl)-4-ethyl-5-oxo-4,5-dihydro-1H-1,2,4-triazol-1-yl)-3-fluoro-6-(2-fluoro-5-methylphenyl)-1,6-naphthyridin-5(6H)-one (65 mg, 129.1 μmol) and NBS (24.6 mg, 138.2 μmol) in DMF (3.5 mL) was stirred at room temperature overnight. The reaction mixture was added water (12 mL) and extracted with EtOAc (15 mL×3). The organic layer was combined, dried with $Na_2SO_4$, filtered and concentrated under vacuum. The residue was purified by column chromatography ($SiO_2$, petroleum ether/ethyl acetate=1/0 to 1/1) to give the title compound (55 mg, 94 μmol, 76% yield, 100% purity) as a yellow oil. MS (ESI): mass calcd. for $C_{27}H_{22}BrF_2N_5O_3$, 581.1; m/z found, 582.0 [M+H]$^+$. $^1$H NMR (400 MHz, CDCl$_3$) δ 8.56 (d, J=9.3 Hz, 1H), 7.66 (s, 1H), 7.40-7.32 (m, 5H), 7.31-7.27 (m, 1H), 7.24-7.15 (m, 2H), 4.64 (s, 2H), 4.58 (s, 2H), 3.88 (q, J=7.3 Hz, 2H), 2.40 (s, 3H), 1.37 (t, J=7.2 Hz, 3H); $^{19}$F NMR (376 MHz, CDCl$_3$) δ −122.15 (s, 1F), −125.27 (s, 1F) ppm.

Step D. 2-(3-((Benzyloxy)methyl)-4-ethyl-5-oxo-4,5-dihydro-1H-1,2,4-triazol-1-yl)-3-fluoro-6-(2-fluoro-5-methylphenyl)-8-(prop-1-en-2-yl)-1,6-naphthyridin-5(6H)-one. PdCl$_2$(PPh$_3$)$_2$ (34 mg, 49 μmol) was added to a stirring mixture of 2-(3-((benzyloxy)methyl)-4-ethyl-5-oxo-4,5-dihydro-1H-1,2,4-triazol-1-yl)-8-bromo-3-fluoro-6-(2-fluoro-5-methylphenyl)-1,6-naphthyridin-5(6H)-one (95 mg, 163.12 μmol), isopropenylboronic acid pinacol ester (54.8 mg, 326.11 μmol) and Cs$_2$CO$_3$ (159.4 mg, 489.23 μmol) in dioxane/water (v/v, 4/1, 3 mL) under N$_2$. The reaction mixture was stirred at 100° C. for 12 hours then cooled down to room temperature. The reaction mixture was filtered through a pad of Celite® and the filter cake was washed with DCM (15 mL). The filtrate was diluted with H$_2$O (20 mL) and extracted with DCM (30 mL×2). Organic layers were dried with Na$_2$SO$_4$, filtered and concentrated under vacuum. The crude was purified by column chromatography (SiO$_2$, petroleum ether/ethyl acetate=I/O to ⅔) to give the title compound (50 mg, 88.3 μmol, 54% yield, 96% purity) as a yellow solid. MS (ESI): mass calcd. for $C_{30}H_{27}F_2N_5O_3$, 543.2; m/z found, 544.2 [M+H]$^+$. $^1$H NMR (400 MHz, CDCl$_3$) δ 8.55 (d, J=9.5 Hz, 1H), 7.42-7.33 (m, 5H), 7.29 (s, 1H), 7.26-7.22 (m, 2H), 7.20-7.14 (m, 1H), 5.39 (s, 1H), 5.23 (s, 1H), 4.62 (s, 2H), 4.54 (s, 2H), 3.88 (q, J=7.3 Hz, 2H), 2.40 (s, 3H), 2.34 (s, 3H), 1.37 (t, J=7.2 Hz, 3H); $^{19}$F NMR (376 MHz, CDCl$_3$) δ −124.86 (s, 1F), −125.48 (s, 1F) ppm.

Step E. 2-(3-((Benzyloxy)methyl)-4-ethyl-5-oxo-4,5-dihydro-1H-1,2,4-triazol-1-yl)-3-fluoro-6-(2-fluoro-5-methylphenyl)-8-isopropyl-1,6-naphthyridin-5(6H)-one. Wilkinson's Catalyst (38.3 mg, 41.40 μmol) was added to a solution of 2-(3-((benzyloxy)methyl)-4-ethyl-5-oxo-4,5-dihydro-1H-1,2,4-triazol-1-yl)-3-fluoro-6-(2-fluoro-5-methylphenyl)-8-(prop-1-en-2-yl)-1,6-naphthyridin-5(6H)-one (75 mg, 137.98 μmol) in THF (4.5 mL). The suspension was degassed under vacuum and purged with H$_2$ several times. The mixture was stirred under H$_2$ (15 psi) at room temperature over two days. The mixture was evaporated under vacuum. The crude was purified by column chromatography (SiO$_2$, petroleum ether/ethyl acetate=I/O to 1/1) to give the title compound (30 mg, 54.99 μmol, 40% yield, 100% purity) as a yellow gum. MS (ESI): mass calcd. for $C_{30}H_{29}F_2N_5O_3$, 545.2; m/z found, 546.2 [M+H]$^+$. $^1$H NMR (400 MHz, CDCl$_3$) δ 8.52 (d, J=9.5 Hz, 1H), 7.39-7.31 (m, 5H), 7.22-7.11 (m, 3H), 7.04 (s, 1H), 4.61 (s, 2H), 4.54 (s, 2H), 3.87 (d, J=7.3 Hz, 2H), 3.65-3.61 (m, 1H), 2.38 (s, 3H), 1.36 (t, J=7.3 Hz, 3H), 1.30 (d, J=7.1 Hz, 6H); $^{19}$F NMR (376 MHz, CDCl$_3$) δ −125.44 (d, J=9.5 Hz, 1F), −125.57 (br s, 1F) ppm.

Step F. 2-(4-Ethyl-3-(hydroxymethyl)-5-oxo-4,5-dihydro-1H-1,2,4-triazol-1-yl)-3-fluoro-6-(2-fluoro-5-methylphenyl)-8-isopropyl-1,6-naphthyridin-5(6H)-one. BCl$_3$ (1 M solution in toluene, 0.28 mL, 0.28 mmol) was added to a stirred solution of 2-(3-((benzyloxy)methyl)-4-ethyl-5-oxo-4,5-dihydro-1H-1,2,4-triazol-1-yl)-3-fluoro-6-(2-fluoro-5-methylphenyl)-8-isopropyl-1,6-naphthyridin-5(6H)-one (30 mg, 54.99 μmol) in DCM (3 mL) at −78° C., and the mixture was stirred at −78° C. for 1 hour. The reaction was quenched with MeOH (1 mL) at −78° C. and stirred at −78° C. for 0.5 hour. The mixture was diluted with DCM (10 mL) and washed with sat. aq. NaHCO$_3$ solution (12 mL). The combined organic phase was dried with anhydrous Na$_2$SO$_4$, filtered and concentrated in vacuum. The crude product was purified by preparative reversed phase HPLC (Stationary phase: Boston Prime C18, 5 μm, 150×30 mm; Mobile phase: water (0.04% NH$_3$H$_2$O+10 mM NH$_4$HCO$_3$) (A)—MeCN (B), gradient elution: 45-75% B in A over 7 min, flow rate: 25 mL/min) to give the title compound (19 mg, 41.72 μmol, 76% yield, 100% purity) as white powder. MS (ESI): mass calcd. for $C_{23}H_{23}F_2N_5O_3$, 455.2; m/z found, 456.1 [M+H]$^+$. $^1$H NMR (400 MHz, CDCl$_3$) δ 8.54 (d, J=9.5 Hz, 1H), 7.26-7.14 (m, 3H), 7.07 (s, 1H), 4.71 (d, J=5.8 Hz, 2H), 3.94 (q, J=7.2 Hz, 2H), 3.64 (td, J=6.8, 13.7 Hz, 1H), 2.44-2.42 (m, 1H), 2.41 (s, 3H), 1.45 (t, J=7.3 Hz, 3H), 1.32 (d, J=7.0 Hz, 6H); $^{19}$F NMR (376 MHz, CDCl$_3$) δ −125.44 (s, 1F), −125.55 (s, 1F) ppm.

Example 100: 6-(4-Ethyl-3-(hydroxymethyl)-5-oxo-4,5-dihydro-1H-1,2,4-triazol-1-yl)-7-fluoro 4-isopropyl-2-(4-methylpyridazin-3-yl)isoquinolin-1(2H)-one

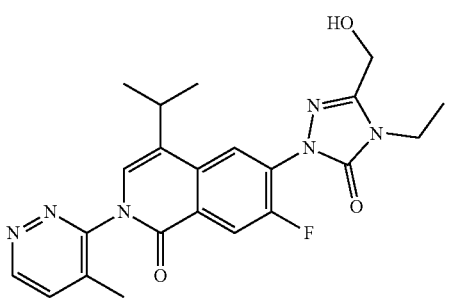 [SMILES: CCn1c(CO)nn(-c2cc3c(C(C)C)cn(-c4nnccc4C)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 4-methylpyridazin-3-amine instead of 5-chloro-3-methyl-4-amino-1H-pyrazole in Step A. ESI-MS: mass calcd. for $C_{22}H_{23}FN_6O_3$, 438.2; m/z found, 439.0 [M+H]$^+$. $^1$H NMR (400 MHz, CDCl$_3$) δ 9.15 (br d, J=4.8 Hz, 1H), 8.30 (br d, J=11.0 Hz, 1H), 8.11 (br d, J=6.8 Hz, 1H), 7.54 (br d, J=4.8 Hz, 1H), 7.15 (s, 1H), 4.69 (br s, 2H), 3.94 (q, J=6.9 Hz, 2H), 3.38-3.19 (m, 1H), 2.97 (br s, 1H), 2.32 (s, 3H), 1.43 (br t, J=7.0 Hz, 3H), 1.34 (br dd, J=6.8, 11.3 Hz, 6H); $^{19}$F NMR (376 MHz, CDCl$_3$) δ −120.04 (br s, 1F) ppm.

Example 101: (S)-6-(4-Ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)isoquinolin-1(2H)-one

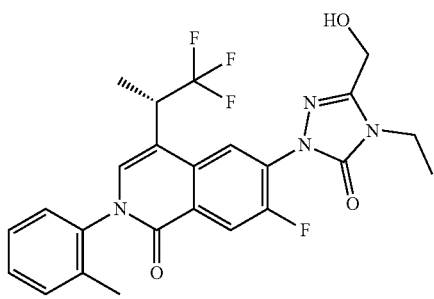 [SMILES: CCn1c(CO)nn(-c2cc3c([C@H](C)C(F)(F)F)cn(-c4ccccc4C)c(=O)c3cc2F)c1=O]

To a stirred solution of racemic 6-(3-((benzyloxy)methyl)-4-ethyl-5-oxo-4,5-dihydro-1H-1,2,4-triazol-1-yl)-7-fluoro-2-(o-tolyl)-4-(1,1,1-trifluoropropan-2-yl)isoquinolin-1(2H)-one (Example 88, 490 mg, 0.84 mmol) in DCM (20 mL) was added BCl$_3$ (1 M in DCM, 2.5 mL, 2.5 mmol) at −78° C. The reaction mixture was stirred at −78° C. for 0.5 h. The mixture was diluted with DCM, washed with saturated aqueous NaHCO$_3$ solution. The organic extract was separated, washed with brine, dried over anhydrous Na$_2$SO$_4$, filtered, and concentrated. The residue was purified by ISCO chromatography (SiO$_2$ 40 g, 50-80% EtOAc in heptane). The racemic product (350 mg) was separated into two chiral enantiomers by SFC [AD-H (3×25 cm), 15% isopropanol (0.1% DEA)/CO$_2$, 100 bar, 40 mL/min, 220 nm, inj vol: 0.5 mL, 15 mg/mL ethanol: DCM](S)-6-(4-Ethyl-5-(hydroxymethyl)-5-oxo-4,5-dihydro-1H-1,2,4-triazol-1-yl)-7-fluoro-2-(o-tolyl)-4-(1,1,1-trifluoropropan-2-yl)isoquinolin-1(2H)-one: 135 mg, yield: 33%. [99% ee by SFC (ret: 3.21 min, the second peak)]. LCMS (ES-API): mass calcd. for $C_{24}H_{22}F_4N_4O_3$, 490.2; m/z found, 491.1 [M+H]$^+$. $^1$H NMR (400 MHz, CDCl$_3$) δ 8.34 (d, J=11.25 Hz, 1H), 7.87-8.14 (m, 1H), 7.34-7.45 (m, 3H), 7.26 (s, 1H), 7.10 (s, 1H), 4.69 (s, 2H), 3.94 (q, J=7.34 Hz, 3H), 2.15 (s, 3H), 1.58-1.69 (m, 1H), 1.53 (d, J=6.85 Hz, 3H), 1.44 (t, J=7.34 Hz, 3H) ppm.

Example 102: (R)-6-(4-Ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)isoquinolin-1(2H)-one

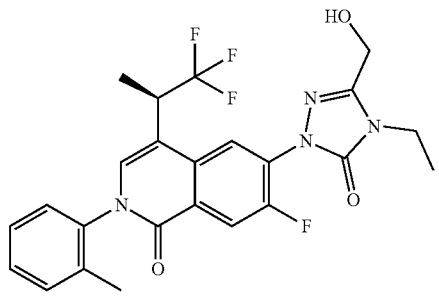 [SMILES: CCn1c(CO)nn(-c2cc3c([C@@H](C)C(F)(F)F)cn(-c4ccccc4C)c(=O)c3cc2F)c1=O]

In the chiral separation of racemic 6-(4-ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)isoquinolin-1(2H)-one (Example 88, 350 mg) by SFC [AD-H (3×25 cm), 15% isopropanol (0.1% DEA)/CO$_2$, 100 bar, 40 mL/min, 220 nm, inj vol: 0.5 mL, 15 mg/mL ethanol: DCM], the title compound was obtained as a white solid (145 mg, 35%). [100% ee by SFC (ret: 2.39 min, the first peak, absolute (R)-configuration was confirmed by X-ray crystallography]. LCMS (ES-API): mass calcd. for $C_{24}H_{22}F_4N_4O_3$, 490.2; m/z found, 491.3 [M+H]$^+$. $^1$H NMR (400 MHz, CDCl$_3$) δ 8.34 (d, J=11.25 Hz, 1H), 7.93-8.14 (m, 1H), 7.30-7.47 (m, 3H), 7.28 (br d, J=1.47 Hz, 1H), 7.10 (s, 1H), 4.69 (d, J=6.36 Hz, 2H), 3.94 (q, J=7.34 Hz, 3H), 2.36 (br t, J=6.36 Hz, 1H), 2.15 (s, 3H) 1.53 (d, J=7.34 Hz, 3H), 1.44 (t, J=7.34 Hz, 3H) ppm.

Example 103: 6-(4-Ethyl-3-(hydroxymethyl)-5-oxo-4,5-dihydro-1H-1,2,4-triazol-1-yl)-7-fluoro-4-isopropyl-2-(2-(trifluoromethyl)phenyl)isoquinolin-1(2H)-one

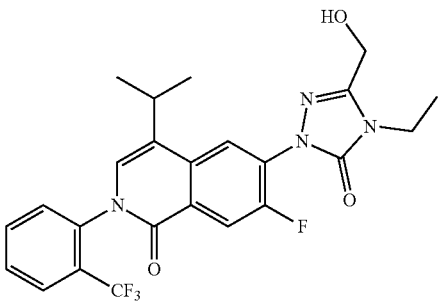 [SMILES: CCn1c(CO)nn(-c2cc3c(C(C)C)cn(-c4ccccc4C(F)(F)F)c(=O)c3cc2F)c1=O]

Step A. 6-(3-((Benzyloxy)methyl)-4-ethyl-5-oxo-4,5-dihydro-1H-1,2,4-triazol-1-yl)-7-fluoro-4-isopropyl-2-(2-(trifluoromethyl)phenyl)isoquinolin-1(2H)-one. To a stirred solution of 3-((benzyloxy)methyl)-4-ethyl-1-(7-fluoro-4-isopropyl-1-oxo-1H-isochromen-6-yl)-1H-1,2,4-triazol-5(4H)-one 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4, 100 mg, 0.23 mmol) and 2-aminobenzotrifluoride (92.1 mg, 0.57 mmol) in THF (5 mL) was added LiHMDS (1 M in THF, 0.68 mL, 0.68 mmol) by dropwise under nitrogen at −78° C. Then the reaction mixture was stirred at room temperature overnight. aqueous HCl solution (1 M, 0.6 mL) was added to quench the reaction. The mixture was poured into water (10 mL) and extracted with EtOAc (20 mL×3). The combined organic phase was dried over anhydrous $Na_2SO_4$, filtered and concentrated. The residue was dissolved in AcOH (5 mL) and stirred at 90° C. for overnight. The mixture was poured into water and extracted with EtOAc. The combined organic phase was washed with brine, dried over anhydrous $Na_2SO_4$, filtered and concentrated. The residue was purified by flash chromatography ($SiO_2$, 0-50% EtOAc in petroleum ether) to give the title compound as a yellow gum (80 mg, 60%). MS (ESI): mass calcd. for $C_{31}H_{28}F_4N_4O_3$, 580.2; m/z found, 581.2 [M+H]$^+$. $^1$H NMR (400 MHz, CDCl$_3$) δ 8.30 (d, J=11.0 Hz, 1H), 8.08 (d, J=7.0 Hz, 1H), 7.87 (d, J=8.0 Hz, 1H), 7.78-7.71 (m, 1H), 7.67-7.60 (m, 1H), 7.48 (d, J=8.0 Hz, 1H), 7.42-7.35 (m, 5H), 6.82 (s, 1H), 4.64 (s, 2H), 4.56 (s, 2H), 3.90 (q, J=7.0 Hz, 2H), 3.27 (td, J=6.5, 13.4 Hz, 1H), 1.40 (t, J=7.3 Hz, 3H), 1.30 (d, J=6.8 Hz, 6H); $^{19}$F NMR (376 MHz, CDCl$_3$) δ −60.66 (s, 1F), −120.58 (s, 1F) ppm.

Step B. 6-(4-Ethyl-3-(hydroxymethyl)-5-oxo-4,5-dihydro-1H-1,2,4-triazol-1-yl)-7-fluoro-4-isopropyl-2-(2-(trifluoromethyl)phenyl)isoquinolin-1(2H)-one. To a stirred solution of 6-(3-((benzyloxy)methyl)-4-ethyl-5-oxo-4,5-dihydro-1H-1,2,4-triazol-1-yl)-7-fluoro-4-isopropyl-2-(2-(trifluoromethyl)phenyl)isoquinolin-1(2H)-one (95 mg, 0.16 mmol) in DCM (5 mL) at −78° C. was added BCl$_3$ (1 M in toluene, 0.82 mL, 0.82 mmol). The reaction was stirred at −78° C. for 1 h. The mixture was quenched with MeOH (2 mL) at −78° C. The mixture was diluted with DCM, washed with saturated aqueous NaHCO$_3$ solution. The organic extract was separated, washed with brine, dried over anhydrous $Na_2SO_4$, filtered, and concentrated. The residue was purified by reverse phase prep-HPLC (Stationary phase: Boston Prime C18, 5 μm, 150×30 mm; Mobile phase: water (0.04% NH$_3$·H$_2$O+10 mM NH$_4$HCO$_3$) (A)—MeCN (B), gradient elution: 45-75% B in A over 8 min, flow rate: 25 mL/min) to give the title compound as a white powder (46.8 mg, yield: 56%). ESI-MS: mass calcd. for $C_{24}H_{22}F_4N_4O_3$, 490.2; m/z found, 491.2 [M+H]$^+$. $^1$H NMR (400 MHz, CDCl$_3$) δ 8.30 (d, J=11.0 Hz, 1H), 8.08 (d, J=6.8 Hz, 1H), 7.87 (d, J=7.5 Hz, 1H), 7.78-7.72 (m, 1H), 7.67-7.61 (m, 1H), 7.48 (d, J=7.8 Hz, 1H), 6.82 (s, 1H), 4.69 (br d, J=5.0 Hz, 2H), 3.94 (q, J=7.1 Hz, 2H), 3.26 (td, J=6.8, 13.4 Hz, 1H), 2.47 (br s, 1H), 1.44 (t, J=7.3 Hz, 3H), 1.30 (d, J=6.8 Hz, 6H); $^{19}$F NMR (376 MHz, CDCl$_3$) δ −60.65 (s, 1F), −120.70 (br d, J=11.4 Hz, 1F) ppm.

Example 104: 6-(4-Ethyl-3-(hydroxymethyl)-5-oxo-4,5-dihydro-1H-1,2,4-triazol-1-yl)-7-fluoro-4-isopropyl-2-(5-methylpyrimidin-4-yl)isoquinolin-1(2H)-one

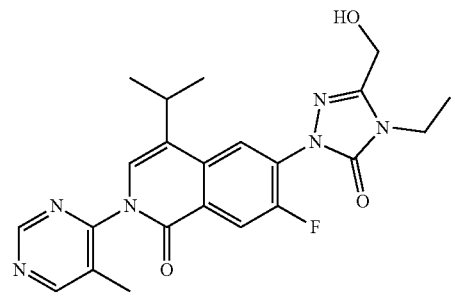 [SMILES: CCn1c(CO)nn(-c2cc3c(C(C)C)cn(-c4ncncc4C)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 4-amino-5-methylpyrimidine instead of 5-chloro-3-methyl-4-amino-1H-pyrazole in Step A; using DCE instead of DCM and heating at 90° C. for 48 h in Step A. MS (ESI): mass calcd. for $C_{22}H_{23}FN_6O_3$, 438.2; m/z found, 439.1 [M+H]$^+$. $^1$H NMR (400 MHz, CDCl$_3$) δ 9.12 (s, 1H), 8.77 (s, 1H), 8.31 (d, J=11.0 Hz, 1H), 8.11 (d, J=6.8 Hz, 1H), 7.09 (s, 1H), 4.69 (d, J=5.0 Hz, 2H), 3.94 (q, J=7.1 Hz, 2H), 3.27 (td, J=6.8, 13.6 Hz, 1H), 2.64 (br s, 1H), 2.27 (s, 3H), 1.44 (t, J=7.3 Hz, 3H), 1.35 (d, J=6.8 Hz, 6H); $^{19}$F NMR (376 MHz, CDCl$_3$) δ −120.03 (s, 1F) ppm.

Example 105: 2-(2-(Difluoromethyl)phenyl)-6-(4-ethyl-3-(hydroxymethyl)-5-oxo-4,5-dihydro-1H-1,2,4-triazol-1-yl)-7-fluoro-4-isopropylisoquinolin-1(2H)-one

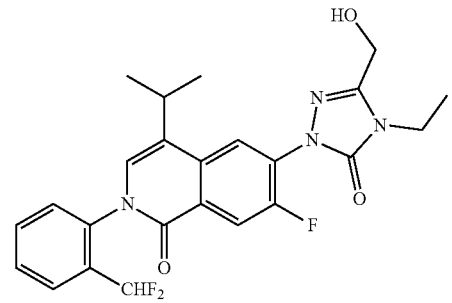

The title compound was prepared in a manner analogous to Example 103, Steps A-B; using 3-((benzyloxy)methyl)-4-ethyl-1-(7-fluoro-4-isopropyl-1-oxo-1H-isochromen-6-yl)-1H-1,2,4-triazol-5(4H)-one 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2-(difluoromethyl)aniline hydrochloride instead of 2-aminobenzotrifluoride in Step A. ESI-MS: mass calcd. for $C_{24}H_{23}F_3N_4O_3$, 472.2; m/z found, 473.1 [M+H]$^+$. $^1$H NMR (400 MHz, CDCl$_3$) δ 8.31 (d, J=11.0 Hz, 1H), 8.11 (d, J=6.8 Hz, 1H), 7.84-7.79 (m, 1H), 7.69-7.57 (m, 2H), 7.38 (d, J=7.5 Hz, 1H), 6.88 (s, 1H), 6.81-6.50 (m, 1H), 4.71 (d, J=6.3 Hz, 2H), 3.95 (q, J=7.2 Hz, 2H), 3.27 (td, J=6.8, 13.6

Hz, 1H), 2.32 (t, J=6.4 Hz, 1H), 1.45 (t, J=7.2 Hz, 3H), 1.32 (t, J=6.4 Hz, 6H); $^{19}$F NMR (376 MHz, CDCl$_3$) δ –107.33 (br d, J=301.7 Hz, 1F), –120.34 (s, 1F), –121.58 (br d, J=301.7 Hz, 1F) ppm.

Example 106: 2-(3-Chloro-2-methoxypyridin-4-yl)-6-(4-ethyl-3-(hydroxymethyl)-5-oxo-4,5-dihydro-1H-1,2,4-triazol-1-yl)-7-fluoro-4-isopropylisoquinolin-1(2H)-one

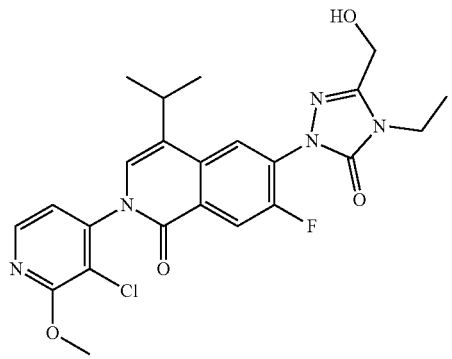

Step A. 3-Chloro-2-methoxypyridin-4-amine. To a solution of 2-methoxypyridin-4-amine (2 g, 16 mmol) in DCM (40 mL) at 0° C. was added NCS (1.94 g, 14.5 mmol). Then the reaction mixture was stirred at 20° C. for 40 min. The mixture was poured into water (50 mL), extracted with DCM (20 mL). The organic layer was dried over Na$_2$SO$_4$, filtered and concentrated. The residue was purified by column chromatography (SiO$_2$, petroleum ether/ethyl acetate=50/1 to 5/1) to give the title compound as brown oil (1.7 g, 61%). MS (ESI): mass calcd. for C$_6$H$_7$ClN$_2$O, 158.0; m/z found, 159.1 [M+H]$^+$. $^1$H NMR (400 MHz, CDCl$_3$) δ 7.71 (d, J=5.7 Hz, 1H), 6.31 (d, J=5.7 Hz, 1H), 4.55 (br s, 2H), 3.98 (s, 3H) ppm.

Step B. 2-(3-Chloro-2-methoxypyridin-4-yl)-6-(4-ethyl-3-(hydroxymethyl)-5-oxo-4,5-dihydro-1H-1,2,4-triazol-1-yl)-7-fluoro-4-isopropylisoquinolin-1(2H)-one. The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 3-chloro-2-methoxypyridin-4-amine instead of 5-chloro-3-methyl-4-amino-1H-pyrazole in Step A. ESI-MS: mass calcd. for C$_{23}$H$_{23}$ClFN$_5$O$_4$, 487.1; m/z found, 488.1 [M+H]$^+$. $^1$H NMR (400 MHz, CDCl$_3$) δ 8.32 (d, J=11.0 Hz, 1H), 8.22 (d, J=5.3 Hz, 1H), 8.10 (d, J=6.8 Hz, 1H), 7.04 (d, J=5.3 Hz, 1H), 6.75 (s, 1H), 4.71 (d, J=5.8 Hz, 2H), 4.10 (s, 3H), 3.94 (q, J=7.3 Hz, 2H), 3.26 (td, J=6.8, 13.4 Hz, 1H), 2.34 (br t, J=6.1 Hz, 1H), 1.45 (t, J=7.2 Hz, 3H), 1.32 (dd, J=5.3, 6.5 Hz, 6H); $^{19}$F NMR (376 MHz, CDCl$_3$) δ –120.22 (s, 1F) ppm.

Example 107: 2-Cyclohexyl-6-(4-ethyl-3-(hydroxymethyl)-5-oxo-4,5-dihydro-1H-1,2,4-triazol-1-yl)-7-fluoro-4-isopropylisoquinolin-1(2H)-one

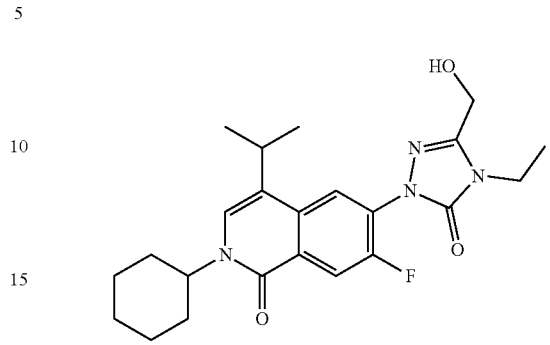

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using cyclohexanamine instead of 5-chloro-3-methyl-4-amino-1H-pyrazole in Step A. ESI-MS: mass calcd. for C$_{23}$H$_{29}$FN$_4$O$_3$, 428.2; m/z found, 429.1 [M+H]$^+$. $^1$H NMR (400 MHz, CDCl$_3$) δ 8.28 (d, J=11.3 Hz, 1H), 7.99 (d, J=6.8 Hz, 1H), 6.97 (s, 1H), 4.97 (br s, 1H), 4.68 (br s, 2H), 3.93 (q, J=7.1 Hz, 2H), 3.30-3.16 (m, 1H), 2.91 (br s, 1H), 1.93 (br s, 4H), 1.78 (br d, J=13.6 Hz, 2H), 1.62-1.48 (m, 4H), 1.42 (t, J=7.2 Hz, 3H), 1.32 (d, J=6.8 Hz, 6H); $^{19}$F NMR (376 MHz, CDCl$_3$) δ –121.78 (s, 1F) ppm.

Example 108: 2-(3-Chloro-6-methylpyridin-2-yl)-6-(4-ethyl-3-(hydroxymethyl)-5-oxo-4,5-dihydro-1H-1,2,4-triazol-1-yl)-7-fluoro-4-isopropylisoquinolin-1(2H)-one

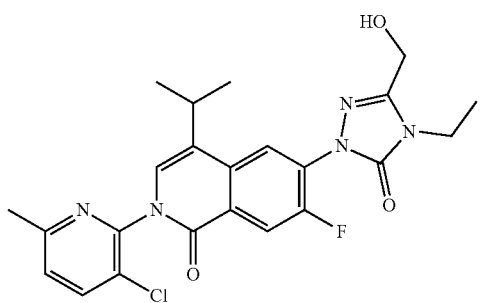 [SMILES: CCn1c(CO)nn(-c2cc3c(C(C)C)cn(-c4nc(C)ccc4Cl)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 3-chloro-6-methylpyridin-2-amine instead of 5-chloro-3-methyl-4-amino-1H-pyrazole in Step A. MS (ESI): mass calcd. for C$_{23}$H$_{23}$ClFN$_5$O$_3$, 471.1; m/z found, 472.0 [M+H]$^+$. $^1$H NMR (400 MHz, CDCl$_3$) δ 8.33 (d, J=11.3 Hz, 1H), 8.08 (d, J=7.0 Hz, 1H), 7.81 (d, J=8.0 Hz, 1H), 7.28 (s, 1H), 6.92 (s, 1H), 4.71 (s, 2H), 3.95 (q, J=7.3 Hz, 2H), 3.27 (td, J=6.7, 13.5 Hz, 1H), 2.62 (s, 3H), 2.36-2.19 (m, 1H), 1.45 (t, J=7.3 Hz, 3H), 1.34 (dd, J=2.5, 6.8 Hz, 6H); $^{19}$F NMR (376 MHz, CDCl$_3$) δ –120.79 (s, 1F) ppm.

Example 109: 2-Cyclopentyl-6-(4-ethyl-3-(hydroxymethyl)-5-oxo-4,5-dihydro-1H-1,2,4-triazol-1-yl)-7-fluoro-4-isopropylisoquinolin-1(2H)-one

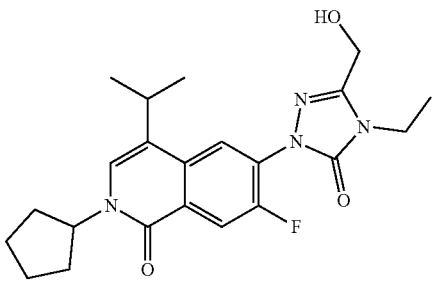 [SMILES: CCn1c(CO)nn(-c2cc3c(C(C)C)cn(C4CCCC4)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using cyclopentanamine instead of 5-chloro-3-methyl-4-amino-1H-pyrazole in Step A. MS (ESI): mass calcd. for $C_{22}H_{27}FN_4O_3$, 414.2; m/z found, 415.1 [M+H]$^+$. $^1$H NMR (400 MHz, CDCl$_3$) δ 8.27 (d, J=11.3 Hz, 1H), 7.98 (d, J=7.0 Hz, 1H), 6.94 (s, 1H), 5.42 (quin, J=7.9 Hz, 1H), 4.67 (s, 2H), 3.92 (q, J=7.3 Hz, 2H), 3.22 (quin, J=6.7 Hz, 2H), 2.24-2.12 (m, 2H), 1.95-1.84 (m, 2H), 1.77-1.66 (m, 4H), 1.41 (t, J=7.3 Hz, 3H), 1.31 (d, J=7.0 Hz, 6H); $^{19}$F NMR (376 MHz, CDCl$_3$) δ −121.43 (s, 1F) ppm.

Example 110: 2-(3-Chloro-4-methoxypyridin-2-yl)-6-(4-ethyl-3-(hydroxymethyl)-5-oxo-4,5-dihydro-1H-1,2,4-triazol-1-yl)-7-fluoro-4-isopropylisoquinolin-1(2H)-one

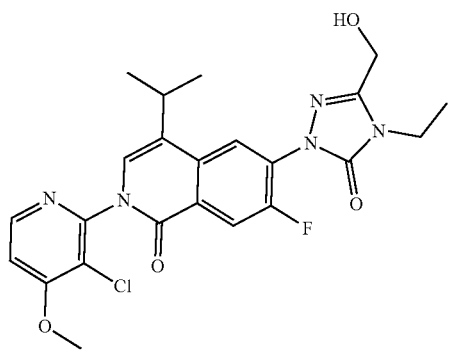 [SMILES: CCn1c(CO)nn(-c2cc3c(C(C)C)cn(-c4nccc(OC)c4Cl)c(=O)c3cc2F)c1=O]

Step A. 3-Chloro-4-methoxypyridin-2-amine. To a solution of 4-methoxypyridin-2-amine (3 g, 24.17 mmol) in MeCN (60 mL) at 0° C. was added NCS (3 g, 22.47 mmol) in portions. Then the reaction mixture was stirred at 20° C. for 1.5 h. The mixture was poured into water (50 mL), extracted with DCM (20 mL). The organic layer was dried over Na$_2$SO$_4$, filtered and concentrated. The residue was purified by column chromatography (SiO$_2$, petroleum ether/ethyl acetate=3/1 to 1/1) to give the title compound as brown solid (0.6 g, 15%). MS (ESI): mass calcd. for $C_6H_7ClN_2O$, 158.0; m/z found, 159.0 [M+H]$^+$. $^1$H NMR (400 MHz, CDCl$_3$) δ 7.90 (d, J=5.8 Hz, 1H), 6.34 (d, J=5.8 Hz, 1H), 4.86 (br s, 2H), 3.92 (s, 3H) ppm.

Step B. 2-(3-Chloro-4-methoxypyridin-2-yl)-6-(4-ethyl-3-(hydroxymethyl)-5-oxo-4,5-dihydro-1H-1,2,4-triazol-1-yl)-7-fluoro-4-isopropylisoquinolin-1(2H)-one. The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 3-chloro-4-methoxypyridin-2-amine instead of 5-chloro-3-methyl-4-amino-1H-pyrazole in Step A. MS (ESI): mass calcd. for $C_{23}H_{23}ClFN_5O_4$, 487.1; m/z found, 488.1 [M+H]$^+$. $^1$H NMR (400 MHz, CDCl$_3$) δ 8.44 (d, J=5.5 Hz, 1H), 8.33 (d, J=11.0 Hz, 1H), 8.08 (d, J=6.8 Hz, 1H), 7.01 (d, J=5.5 Hz, 1H), 6.93 (s, 1H), 4.69 (br s, 2H), 4.05 (s, 3H), 3.94 (q, J=7.2 Hz, 2H), 3.26 (td, J=6.5, 13.4 Hz, 1H), 2.54 (br s, 1H), 1.44 (t, J=7.2 Hz, 3H), 1.33 (d, J=6.5 Hz, 6H); $^{19}$F NMR (376 MHz, CDCl$_3$) δ −120.76 (s, 1F) ppm.

Example 111: 6-(4-Ethyl-3-(hydroxymethyl)-5-oxo-4,5-dihydro-1H-1,2,4-triazol-1-yl)-7-fluoro-4-isopropyl-2-((1R,2S)-2-methylcyclohexyl)isoquinolin-1(2H)-one

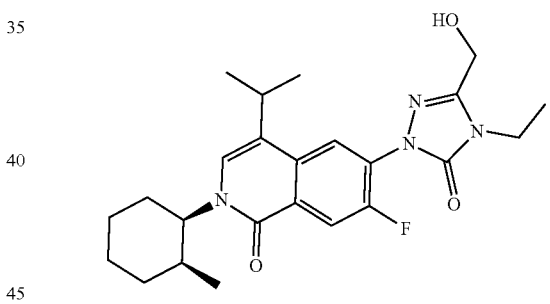

The title compound was prepared in a manner analogous to Example 103, Steps A-B; using 3-((benzyloxy)methyl)-4-ethyl-1-(7-fluoro-4-isopropyl-1-oxo-1H-isochromen-6-yl)-1H-1,2,4-triazol-5(4H)-one 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using (1R,2S)-2-methylcyclohexanamine hydrochloride instead of 2-aminobenzotrifluoride in Step A. MS (ESI): mass calcd. for $C_{24}H_{31}FN_4O_3$, 442.2; m/z found, 443.1 [M+H]$^+$. $^1$H NMR (400 MHz, CDCl$_3$) δ 8.29 (d, J=11.3 Hz, 1H), 7.99 (d, J=7.0 Hz, 1H), 6.96 (s, 1H), 5.03 (td, J=3.8, 13.1 Hz, 1H), 4.69 (br d, J=2.5 Hz, 2H), 3.93 (q, J=7.2 Hz, 2H), 3.24 (td, J=6.8, 13.6 Hz, 1H), 2.55 (br s, 1H), 2.49-2.39 (m, 1H), 2.07-1.95 (m, 2H), 1.91-1.79 (m, 1H), 1.67 (br s, 2H), 1.58-1.49 (m, 3H), 1.44 (t, J=7.2 Hz, 3H), 1.31 (dd, J=1.8, 6.8 Hz, 6H), 0.87 (d, J=7.2 Hz, 3H); $^{19}$F NMR (376 MHz, CDCl$_3$) δ −122.01 (s, 1F) ppm.

Example 112: 2-(1,3-Dimethoxypropan-2-yl)-6-(4-ethyl-3-(hydroxymethyl)-5-oxo-4,5-dihydro-1H-1,2,4-triazol-1-yl)-7-fluoro-4-isopropylisoquinolin-1(2H)-one

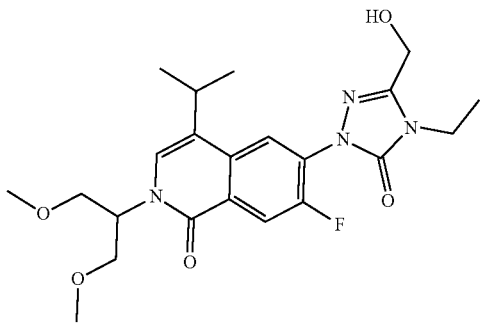 [SMILES: CCn1c(CO)nn(-c2cc3c(C(C)C)cn(C(COC)COC)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 1,3-dimethoxypropan-2-amine instead of 5-chloro-3-methyl-4-amino-1H-pyrazole in Step A. MS (ESI): mass calcd. for $C_{22}H_{29}FN_4O_5$, 448.2; m/z found, 449.1 [M+H]$^+$. $^1$H NMR (400 MHz, CDCl$_3$) δ 8.27 (d, J=11.3 Hz, 1H), 7.99 (d, J=7.0 Hz, 1H), 7.23 (s, 1H), 5.32 (quin, J=5.3 Hz, 1H), 4.67 (s, 2H), 3.93 (q, J=7.2 Hz, 2H), 3.86-3.81 (m, 2H), 3.76-3.71 (m, 2H), 3.36 (s, 6H), 3.25-3.17 (m, 1H), 2.84 (br s, 1H), 1.43 (t, J=7.2 Hz, 3H), 1.31 (d, J=6.8 Hz, 6H); $^{19}$F NMR (376 MHz, CDCl$_3$) δ −121.82 (br s, 1F) ppm.

Example 113: 6-(4-Ethyl-3-(hydroxymethyl)-5-oxo-4,5-dihydro-1H-1,2,4-triazol-1-yl)-7-fluoro-4-isopropyl-2-(2-methoxy-5-methylpyridin-4-yl)isoquinolin-1(2H)-one

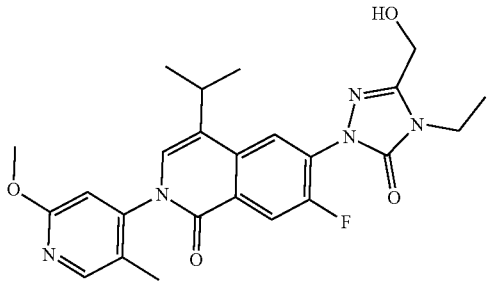 [SMILES: CCn1c(CO)nn(-c2cc3c(C(C)C)cn(-c4cc(OC)ncc4C)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2-methoxy-5-methylpyridin-4-amine instead of 5-chloro-3-methyl-4-amino-1H-pyrazole in Step A. MS (ESI): mass calcd. for $C_{24}H_{26}FN_5O_4$, 467.2; m/z found, 468.1 [M+H]$^+$. $^1$H NMR (400 MHz, CDCl$_3$) δ 8.32 (d, J=11.1 Hz, 1H), 8.17 (s, 1H), 8.10 (d, J=6.9 Hz, 1H), 6.76 (s, 1H), 6.72 (s, 1H), 4.71 (s, 2H), 3.98 (s, 3H), 3.97-3.91 (m, 2H), 3.26 (td, J=6.8, 13.5 Hz, 1H), 2.38 (br s, 1H), 2.08 (s, 3H), 1.45 (t, J=7.3 Hz, 3H), 1.31 (d, J=6.8 Hz, 6H); $^{19}$F NMR (376 MHz, CDCl$_3$) δ −120.31 (s, 1F) ppm.

Example 114: 6-(4-Ethyl-3-(hydroxymethyl)-5-oxo-4,5-dihydro-1H-1,2,4-triazol-1-yl)-7-fluoro-4-isopropyl-2-((1S,2R)-2-methylcyclohexyl)isoquinolin-1(2H)-one

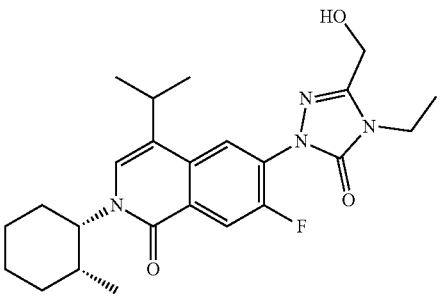 [SMILES: CCn1c(CO)nn(-c2cc3c(C(C)C)cn([C@H]4CCCC[C@H]4C)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using (1S,2R)-2-methylcyclohexanamine instead of 5-chloro-3-methyl-4-amino-1H-pyrazole in Step A. MS (ESI): mass calcd. for $C_{24}H_{31}FN_4O_3$, 442.2; m/z found, 443.1 [M+H]$^+$. $^1$H NMR (400 MHz, CDCl$_3$) δ 8.29 (d, J=11.3 Hz, 1H), 7.99 (d, J=6.9 Hz, 1H), 6.96 (s, 1H), 5.03 (td, J=3.7, 13.0 Hz, 1H), 4.69 (s, 2H), 3.93 (q, J=7.3 Hz, 2H), 3.24 (spt, J=6.8 Hz, 1H), 2.75-2.62 (m, 1H), 2.44 (br dd, J=3.2, 6.9 Hz, 1H), 2.08-1.92 (m, 2H), 1.90-1.80 (m, 1H), 1.63 (br s, 2H), 1.58-1.48 (m, 3H), 1.43 (t, J=7.2 Hz, 3H), 1.30 (dd, J=1.9, 6.8 Hz, 6H), 0.87 (d, J=7.3 Hz, 3H); $^{19}$F NMR (376 MHz, CDCl$_3$) δ −121.96 (s, 1F) ppm.

Example 115: 2-(Cyclopropylmethyl)-6-(4-ethyl-3-(hydroxymethyl)-5-oxo-4,5-dihydro-1H-1,2,4-triazol-1-yl)-7-fluoro-4-isopropylisoquinolin-1(2H)-one

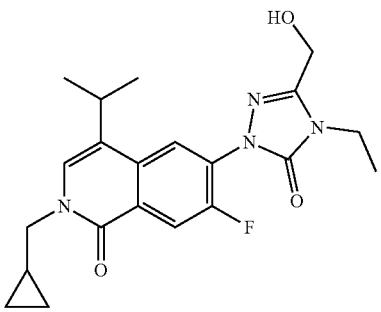 [SMILES: CCn1c(CO)nn(-c2cc3c(C(C)C)cn(CC4CC4)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using cyclopropylmethanamine instead of 5-chloro-3-methyl-4-amino-1H-pyrazole in Step A. MS (ESI): mass calcd. For $C_{21}H_{25}FN_4O_3$, 400.2; m/z found, 401.1 [M+H]$^+$. $^1$H NMR (400 MHz, CDCl$_3$) δ 8.28 (d, J=11.2 Hz, 1H), 8.01 (d, J=6.8 Hz, 1H), 6.97 (s, 1H), 4.68 (s, 2H), 4.02-3.77 (m, 4H), 3.36-3.13 (m, 1H), 2.90 (br d, J=1.8 Hz, 1H), 1.43 (t, J=7.2 Hz, 3H), 1.32 (d, J=6.8 Hz, 7H), 0.67-0.56 (m, 2H), 0.42 (q, J=4.9 Hz, 2H); ¹⁹F NMR (376 MHz, CDCl₃) δ −121.57 (br dd, J=7.0, 11.4 Hz, 1F) ppm.

Example 116: 6-(4-Ethyl-3-(hydroxymethyl)-5-oxo-4,5-dihydro-1H-1,2,4-triazol-1-yl)-7-fluoro-4-isopropyl-2-(1-methoxybutan-2-yl)isoquinolin-1(2H)-one

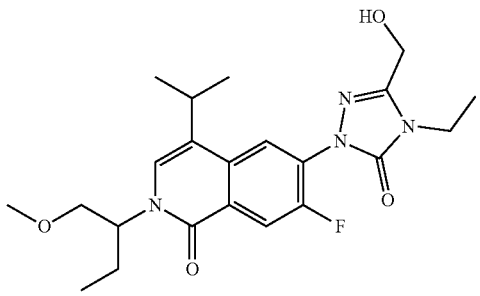 [SMILES: CCC(COC)n1cc(C(C)C)c2cc(-n3nc(CO)n(CC)c3=O)c(F)cc2c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 1-methoxybutan-2-amine instead of 5-chloro-3-methyl-4-amino-1H-pyrazole in Step A. MS (ESI): mass calcd. for C₂₂H₂₉FN₄O₄, 432.2; m/z found, 433.2 [M+H]⁺. ¹H NMR (400 MHz, CDCl₃) δ 8.30 (d, J=11.3 Hz, 1H), 8.04-7.96 (m, 1H), 7.10 (s, 1H), 5.15 (br s, 1H), 4.70 (s, 2H), 3.93 (q, J=7.2 Hz, 2H), 3.78-3.71 (m, 1H), 3.59 (dd, J=3.7, 10.5 Hz, 1H), 3.34 (s, 3H), 3.28-3.16 (m, 1H), 2.23 (br s, 1H), 2.06-1.78 (m, 2H), 1.44 (t, J=7.2 Hz, 3H), 1.32 (d, J=6.9 Hz, 6H), 0.91 (t, J=7.4 Hz, 3H); ¹⁹F NMR (376 MHz, CDCl₃) δ −122.05 (s, 1F) ppm.

Example 117: 2-(2-Chlorophenyl)-6-(4-ethyl-3-(hydroxymethyl)-5-oxo-4,5-dihydro-1H-1,2,4-triazol-1-yl)-7-fluoro-4-isopropylisoquinolin-1(2H)-one

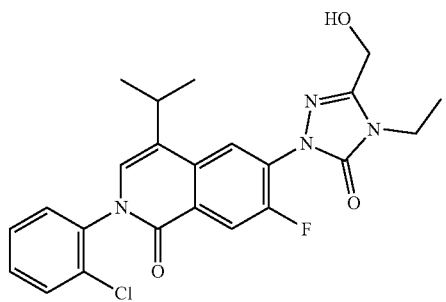 [SMILES: CCn1c(CO)nn(-c2cc3c(C(C)C)cn(-c4ccccc4Cl)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2-chloroaniline instead of 5-chloro-3-methyl-4-amino-1H-pyrazole in Step A. MS (ESI): mass calcd. for C₂₃H₂₂ClFN₄O₃, 456.1; m/z found, 457.1 [M+H]⁺. ¹H NMR (400 MHz, CDCl₃) δ 8.33 (d, J=11.1 Hz, 1H), 8.09 (d, J=6.9 Hz, 1H), 7.63-7.57 (m, 1H), 7.47-7.41 (m, 3H), 6.81 (s, 1H), 4.71 (br s, 2H), 3.95 (q, J=7.3 Hz, 2H), 3.27 (td, J=6.9, 13.4 Hz, 1H), 2.32 (br s, 1H), 1.45 (t, J=7.3 Hz, 3H), 1.33 (dd, J=3.9, 6.7 Hz, 6H); ¹⁹F NMR (376 MHz, CDCl₃) δ −120.84 (s, 1F) ppm.

Example 118: 6-(4-Ethyl-3-(hydroxymethyl)-5-oxo-4,5-dihydro-1H-1,2,4-triazol-1-yl)-7-fluoro-4-isopropyl-2-(3-methylpyridin-2-yl)isoquinolin-1(2H)-one

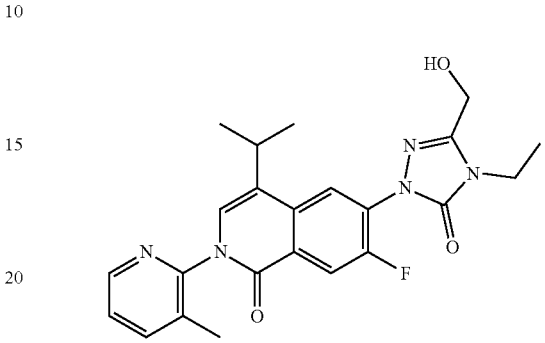

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 3-methylpyridin-2-amine instead of 5-chloro-3-methyl-4-amino-1H-pyrazole in Step A. MS (ESI): mass calcd. For C₂₃H₂₄FN₅O₃, 437.2; m/z found, 438.1 [M+H]⁺. ¹H NMR (400 MHz, CDCl₃) δ 8.49 (br d, J=3.5 Hz, 1H), 8.32 (d, J=11.1 Hz, 1H), 8.08 (d, J=6.9 Hz, 1H), 7.74 (d, J=7.0 Hz, 1H), 7.36 (dd, J=4.8, 7.6 Hz, 1H), 7.02 (s, 1H), 4.68 (br s, 2H), 3.94 (q, J=7.2 Hz, 2H), 3.27 (td, J=6.8, 13.6 Hz, 1H), 2.65-2.53 (m, 1H), 2.24 (s, 3H), 1.44 (t, J=7.2 Hz, 3H), 1.34 (t, J=7.0 Hz, 6H); ¹⁹F NMR (376 MHz, CDCl₃) δ −120.84 (br s, 1F) ppm.

Example 119: Racemic 6-(4-Ethyl-3-(hydroxymethyl)-5-oxo-4,5-dihydro-1H-1,2,4-triazol-1-yl)-7-fluoro-4-isopropyl-2-((cis)-3-methoxycyclopentyl)isoquinolin-1(2H)-one

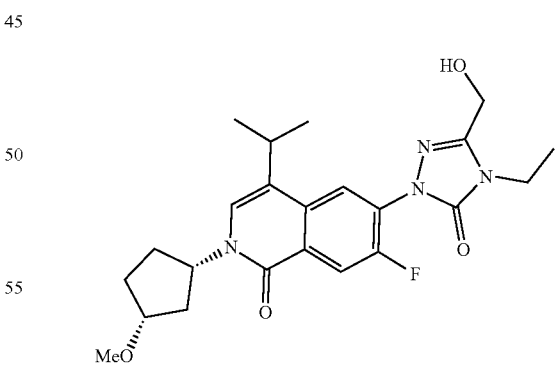

The title compound was prepared in a manner analogous to Example 103, Steps A-B; using 3-((benzyloxy)methyl)-4-ethyl-1-(7-fluoro-4-isopropyl-1-oxo-1H-isochromen-6-yl)-1H-1,2,4-triazol-5(4H)-one 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using (cis)-3-methoxycyclopentanamine hydrochloride instead of 2-aminobenzotrifluoride in Step A. MS (ESI): mass calcd.

for C₂₃H₂₉FN₄O₄, 444.2; m/z found, 445.1 [M+H]⁺. ¹H NMR (400 MHz, CDCl₃) δ 8.28 (d, J=11.2 Hz, 1H), 7.98 (d, J=7.1 Hz, 1H), 7.41 (s, 1H), 5.78-5.68 (m, 1H), 4.69 (s, 2H), 3.93 (q, J=7.3 Hz, 3H), 3.39 (s, 3H), 3.22 (td, J=6.7, 13.6 Hz, 1H), 2.62 (br s, 1H), 2.39 (ddd, J=5.4, 10.4, 15.3 Hz, 1H), 2.31-2.22 (m, 1H), 2.10 (br dd, J=7.2, 11.6 Hz, 1H), 1.88-1.80 (m, 2H), 1.75-1.67 (m, 1H), 1.43 (t, J=7.2 Hz, 3H), 1.31 (dd, J=3.9, 6.7 Hz, 6H); ¹⁹F NMR (376 MHz, CDCl₃) δ −121.93 (dd, J=7.3, 11.7 Hz, 1F) ppm.

Example 120: 6-(4-Ethyl-3-(hydroxymethyl)-5-oxo-4,5-dihydro-1H-1,2,4-triazol-1-yl)-7-fluoro-4-isopropyl-2-((1R*,2R*)-2-methylcyclohexyl)isoquinolin-1(2H)-one

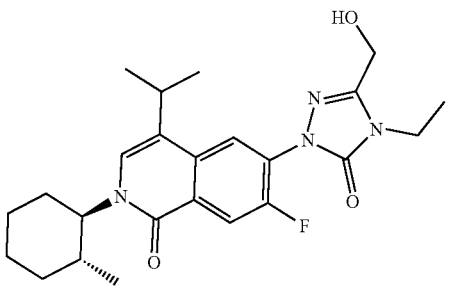 [SMILES: CCn1c(CO)nn(-c2cc3c(C(C)C)cn([C@@H]4CCCC[C@H]4C)c(=O)c3cc2F)c1=O]

Step A. Racemic trans-6-(3-((Benzyloxy)methyl)-4-ethyl-5-oxo-4,5-dihydro-1H-1,2,4-triazol-1-yl)-7-fluoro-4-isopropyl-2-(2-methylcyclohexyl)isoquinolin-1(2H)-one. To a stirred solution of trans-2-methyl-cyclohexylamine hydrochloride (369 mg, 2.47 mmol) in DCM (3 mL) was added Et₃N (0.34 mL, 2.47 mmol) at 0° C., followed by the addition of AlMe₃ (2 M in toluene, 0.93 mL, 1.86 mmol) under nitrogen. The mixture was stirred at room temperature for 0.5 h, then a DCM solution (2 mL) of 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4, 270 mg, 0.61 mmol) was added. The mixture was stirred at room temperature for overnight. The mixture was poured into water and extracted with DCM. The organic phase was separated, washed with brine, dried over anhydrous Na₂SO₄, filtered and concentrated. The residue was dissolved in AcOH (5 mL) and stirred at 90° C. for overnight. The mixture was poured into water and extracted with EtOAc. The combined organic phase was washed with brine, dried over anhydrous Na₂SO₄, filtered and concentrated. The residue was purified by flash chromatography (SiO₂, 0-50% EtOAc in petroleum ether) to give the title compound as a light yellow gum (325 mg, 99%). MS (ESI): mass calcd. for C₃₁H₃₇FN₄O₃, 532.3; m/z found, 533.3 [M+H]⁺. ¹H NMR (400 MHz, CDCl₃) δ 8.28 (d, J=11.5 Hz, 1H), 7.97 (d, J=6.8 Hz, 1H), 7.40-7.30 (m, 5H), 6.88 (s, 1H), 4.75 (br s, 1H), 4.60 (s, 2H), 4.52 (s, 2H), 3.86 (q, J=7.3 Hz, 2H), 3.30-3.14 (m, 1H), 1.88 (br s, 4H), 1.77 (br d, J=8.8 Hz, 2H), 1.72-1.66 (m, 1H), 1.39-1.35 (m, 3H), 1.34 (s, 2H), 1.30 (dd, J=2.3, 6.7 Hz, 6H), 0.73 (d, J=6.4 Hz, 3H); ¹⁹F NMR (376 MHz, CDCl₃) δ −121.85 (br dd, J=7.0, 11.4 Hz, 1F) ppm.

Step B. 6-(4-Ethyl-3-(hydroxymethyl)-5-oxo-4,5-dihydro-1H-1,2,4-triazol-1-yl)-7-fluoro-4-isopropyl-2-((1R*,2R*)-2-methylcyclohexyl)isoquinolin-1(2H)-one. To a stirred solution of racemic trans-6-(3-((benzyloxy)methyl)-4-ethyl-5-oxo-4,5-dihydro-1H-1,2,4-triazol-1-yl)-7-fluoro-4-isopropyl-2-(2-methylcyclohexyl)isoquinolin-1(2H)-one (325 mg, 0.6 mmol) in DCM (4 mL) at −78° C. was added BCl₃ (1 M in toluene, 3.05 mL, 3.05 mmol). The reaction was stirred at −78° C. for 1 h. The mixture was quenched with MeOH (2 mL) at −78° C. The mixture was diluted with DCM, washed with saturated aqueous NaHCO₃ solution. The organic extract was separated, washed with brine, dried over anhydrous Na₂SO₄, filtered, and concentrated. The residue was purified by column chromatography (SiO₂, gradient elution: 0-50% ethyl acetate in petroleum ether) to give the trans racemate compound as a white powder (230 mg, yield: 80.40%). The racemic product was separated by chiral SFC: (Column: (S,S) Whelk-01 100×4.6 mm I.D., 5 µm; mobile phase: CO₂ (A)—IPA (0.05% DEA) (B); isocratic: 40% B in A; flow rate: 2.5 mL/min; column temp: 40° C.; ABPR: 100 bar) to give the title compound as a white powder (56.5 mg, yield: 21%). [99% ee, retention time 2.280 min; SFC analytical method: (S,S) Whelk-01_IPA (DEA)_4]. MS (ESI): mass calcd. for C₂₄H₃₁FN₄O₃, 442.2; m/z found, 443.1 [M+H]⁺. ¹H NMR (400 MHz, CDCl₃) δ 8.31 (d, J=11.3 Hz, 1H), 8.00 (d, J=6.8 Hz, 1H), 6.90 (s, 1H), 4.85-4.72 (m, 1H), 4.70 (br d, J=3.8 Hz, 2H), 3.93 (q, J=7.3 Hz, 2H), 3.30-3.20 (m, 1H), 2.29 (br s, 1H), 1.91 (br d, J=10.3 Hz, 3H), 1.80 (br d, J=11.3 Hz, 2H), 1.55-1.48 (m, 2H), 1.44 (t, J=7.3 Hz, 3H), 1.36-1.34 (m, 1H), 1.33 (dd, J=2.3, 6.8 Hz, 6H), 1.27 (br s, 1H), 0.76 (d, J=6.5 Hz, 3H); ¹⁹F NMR (376 MHz, CDCl₃) δ −121.89 (s, 1F) ppm.

Example 121: 6-(4-Ethyl-3-(hydroxymethyl)-5-oxo-4,5-dihydro-1H-1,2,4-triazol-1-yl)-7-fluoro-4-isopropyl-2-((1S*,2S*)-2-methylcyclohexyl)isoquinolin-1(2H)-one

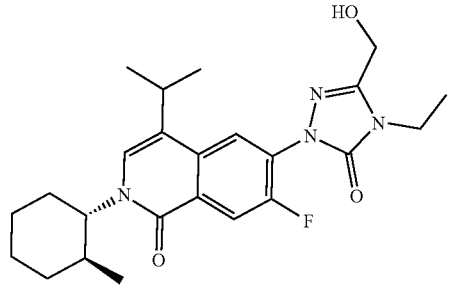 [SMILES: CCn1c(CO)nn(-c2cc3c(C(C)C)cn([C@H]4CCCC[C@@H]4C)c(=O)c3cc2F)c1=O]

In the separation for 6-(4-ethyl-3-(hydroxymethyl)-5-oxo-4,5-dihydro-1H-1,2,4-triazol-1-yl)-7-fluoro-4-isopropyl-2-((1R*,2R*)-2-methylcyclohexyl)isoquinolin-1(2H)-one (Example 120) by chiral SFC: (Column: (S,S) Whelk-01 100×4.6 mm I.D., 5 µm; mobile phase: CO₂ (A)—IPA (0.05% DEA) (B); isocratic: 40% B in A; flow rate: 2.5 mL/min; column temp: 40° C.; ABPR: 100 bar), the title compound was obtained as the second product: a white solid (61.7 mg, yield: 23%) [98% ee, retention time 2.662 min; SFC analytical method: (S,S) Whelk-01_IPA(DEA)_4.]MS (ESI): mass calcd. for C₂₄H₃₁FN₄O₃, 442.2; m/z found, 443.1 [M+H]⁺. ¹H NMR (400 MHz, CDCl₃) δ 8.30 (d, J=11.3 Hz, 1H), 8.00 (d, J=6.8 Hz, 1H), 6.90 (s, 1H), 4.76 (br s, 1H), 4.70 (s, 2H), 3.93 (q, J=7.3 Hz, 2H), 3.24 (quin, J=6.8 Hz, 1H), 2.38 (br s, 1H), 1.91 (br d, J=8.5 Hz, 3H), 1.84-1.71 (m, 2H), 1.54 (br s, 1H), 1.44 (t, J=7.3 Hz, 3H), 1.36-1.34 (m, 1H), 1.33 (dd, J=2.3, 6.8 Hz, 6H), 1.28 (br d, J=15.1 Hz, 1H), 0.76 (d, J=6.5 Hz, 3H); ¹⁹F NMR (376 MHz, CDCl₃) δ −121.87 (s, 1F) ppm.

Example 122: 6-(4-Ethyl-3-(hydroxymethyl)-5-oxo-4,5-dihydro-1H-1,2,4-triazol-1-yl)-7-fluoro-4-isopropyl-2-(pentan-3-yl)isoquinolin-1(2H)-one

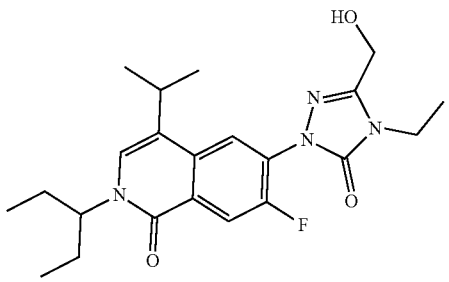 [SMILES: CCC(CC)n1cc(C(C)C)c2cc(-n3nc(CO)n(CC)c3=O)c(F)cc2c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 3-aminopentane instead of 5-chloro-3-methyl-4-amino-1H-pyrazole in Step A. MS (ESI): mass calcd. for $C_{22}H_{29}FN_4O_3$, 416.2; m/z found, 417.1 $[M+H]^+$. $^1H$ NMR (400 MHz, CDCl$_3$) δ 8.40-8.20 (m, 1H), 8.08-7.90 (m, 1H), 6.82 (d, J=5.3 Hz, 1H), 5.00 (s, 1H), 4.69 (s, 2H), 3.94 (t, J=6.6 Hz, 2H), 3.36-3.15 (m, 1H), 3.06 (s, 1H), 1.85-1.79 (m, 2H), 1.69 (d, J=8.2 Hz, 2H), 1.47-1.40 (m, 3H), 1.36-1.25 (m, 6H), 0.91-0.79 (m, 6H); $^{19}F$ NMR (376 MHz, CDCl$_3$) δ −121.54-121.75 (m, 1F) ppm.

Example 123: 6-(4-Ethyl-3-(hydroxymethyl)-5-oxo-4,5-dihydro-1H-1,2,4-triazol-1-yl)-7-fluoro-4-isopropyl-2-((1R*,2R*)-2-methylcyclopentyl)isoquinolin-1(2H)-one

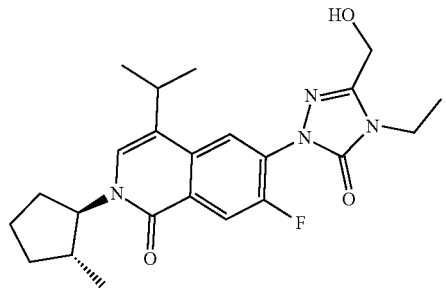 [SMILES: CCn1c(CO)nn(-c2cc3c(C(C)C)cn([C@@H]4CCC[C@H]4C)c(=O)c3cc2F)c1=O]

Step A. Racemic and diastereomeric 6-(3-((Benzyloxy)methyl)-4-ethyl-5-oxo-4,5-dihydro-1H-1,2,4-triazol-1-yl)-7-fluoro-4-isopropyl-2-(2-methylcyclopentyl)isoquinolin-1(2H)-one. To a stirred solution of 2-methylcyclopentanamine hydrochloride (248 mg, 1.83 mmol) in DCM (3 mL) was added Et$_3$N (0.38 mL, 2.74 mmol) at 0° C., followed by the addition of AlMe$_3$ (2 M in toluene, 0.69 mL, 1.38 mmol) under nitrogen. The mixture was stirred at room temperature for 0.5 h, then a DCM solution (3 mL) of 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4, 200 mg, 0.46 mmol) was added. The mixture was stirred at room temperature for overnight. The mixture was poured into water and extracted with DCM. The organic phase was separated, washed with brine, dried over anhydrous Na$_2$SO$_4$, filtered and concentrated. The residue was dissolved in AcOH (6 mL) and stirred at 50° C. for overnight. The mixture was poured into water and extracted with EtOAc. The combined organic phase was washed with brine, dried over anhydrous Na$_2$SO$_4$, filtered and concentrated. The residue was purified by flash chromatography (SiO$_2$, 0-50% EtOAc in petroleum ether) to give the title compound as a yellow oil (201.9 mg, 85%). MS (ESI): mass calcd. for $C_{30}H_{35}FN_4O_3$, 518.2; m/z found, 519.2 $[M+H]^+$. $^1H$ NMR (400 MHz, CDCl$_3$) δ 8.31 (br d, J=10.8 Hz, 1H), 8.03-7.95 (m, 1H), 7.41-7.33 (m, 5H), 6.92 (br d, J=3.3 Hz, 1H), 5.51-4.93 (m, 1H), 4.63 (s, 2H), 4.55 (s, 2H), 3.93-3.85 (m, 2H), 3.32-3.18 (m, 1H), 2.26-2.03 (m, 3H), 1.91-1.67 (m, 3H), 1.39 (br t, J=7.1 Hz, 4H), 1.35-1.29 (m, 6H), 1.02 (br d, J=6.2 Hz, 2H), 0.72 (br d, J=7.1 Hz, 3H); $^{19}F$ NMR (376 MHz, CDCl$_3$) δ −121.70-121.95 (m, 1F) ppm.

Step B. 6-(4-Ethyl-3-(hydroxymethyl)-5-oxo-4,5-dihydro-1H-1,2,4-triazol-1-yl)-7-fluoro-4-isopropyl-2-((1R*,2R*)-2-methylcyclopentyl)isoquinolin-1(2H)-one. To a stirred solution of racemic and diastereomeric 6-(3-((benzyloxy)methyl)-4-ethyl-5-oxo-4,5-dihydro-1H-1,2,4-triazol-1-yl)-7-fluoro-4-isopropyl-2-(2-methylcyclopentyl)isoquinolin-1(2H)-one (201.9 mg, 0.4 mmol) in DCM (6 mL) at −78° C. was added BCl$_3$ (1 M in toluene, 3.0 mL, 3.0 mmol). The reaction was stirred at −78° C. for 1 h. The mixture was quenched with MeOH (2 mL) at −78° C. The mixture was diluted with DCM, washed with saturated aqueous NaHCO$_3$ solution. The organic extract was separated, washed with brine, dried over anhydrous Na$_2$SO$_4$, filtered, and concentrated. The residue was purified by preparative reversed phase HPLC (Stationary phase: Boston Prime C18, 5 µm, 150×30 mm; Mobile phase: water (0.05% NH$_3$H$_2$O+10 mM NH$_4$HCO$_3$) (A)—MeCN (B), gradient elution: 50-80% B in A over 7 min, flow rate: 25 mL/min) to give the racemate diastereomeric mixture as a white powder (90.1 mg, yield: 54%). The racemate diastereomeric mixture was separated by chiral SFC: chiral SFC: (Column: Chiralpak AS-3 100× 4.6 mm I.D., 3 um; Mobile phase: A: CO$_2$B: ethanol (0.05% DEA); Gradient: from 5% to 40% of B in 4 min and hold 40% for 2.5 min, then 5% of B for 1.5 min; Flow rate: 2.8 mL/min; Column temp: 35° C.; ABPR: 1500 psi) to give the title compound as a white powder (11.5 mg, yield: 13%). [99.5% ee, retention time 1.808 min, SFC analytical method: AS_ETOH_DEA_5_40_28ML_8 MIN]. MS (ESI): mass calcd. for $C_{23}H_{29}FN_4O_3$, 428.2; m/z found, 429.1 $[M+H]^+$. $^1H$ NMR (400 MHz, CDCl$_3$) δ 8.30 (d, J=11.3 Hz, 1H), 8.00 (d, J=6.8 Hz, 1H), 6.92 (s, 1H), 5.01 (q, J=8.9 Hz, 1H), 4.70 (d, J=6.3 Hz, 2H), 3.94 (q, J=7.3 Hz, 2H), 3.24 (td, J=6.8, 13.6 Hz, 1H), 2.27-2.17 (m, 2H), 2.17-2.09 (m, 1H), 2.04 (dt, J=6.5, 12.4 Hz, 1H), 1.90-1.81 (m, 2H), 1.79-1.69 (m, 1H), 1.44 (t, J=7.2 Hz, 3H), 1.40 (br d, J=9.3 Hz, 1H), 1.33 (dd, J=3.8, 6.8 Hz, 6H), 1.02 (d, J=6.5 Hz, 3H); $^{19}F$ NMR (376 MHz, CDCl$_3$) δ −121.75 (br s, 1F) ppm.

Example 124: 6-(4-Ethyl-3-(hydroxymethyl)-5-oxo-4,5-dihydro-1H-1,2,4-triazol-1-yl)-7-fluoro-4-isopropyl-2-((1S*,2S*)-2-methylcyclopentyl)isoquinolin-1(2H)-one

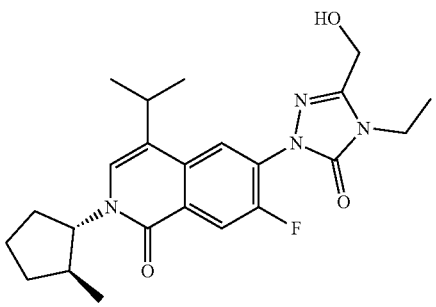 [SMILES: CCn1c(CO)nn(-c2cc3c(C(C)C)cn([C@H]4CCC[C@@H]4C)c(=O)c3cc2F)c1=O]

In the separation of racemic diastereomeric mixture of 6-(4-ethyl-3-(hydroxymethyl)-5-oxo-4,5-dihydro-1H-1,2,4-triazol-1-yl)-7-fluoro-4-isopropyl-2-(2-methylcyclopentyl)isoquinolin-1(2H)-one (Example 123, 90.1 mg) by chiral SFC: (Column: Chiralpak AS-3 100×4.6 mm I.D., 3 um; Mobile phase: A: $CO_2$B: ethanol (0.05% DEA); Gradient: from 5% to 40% of B in 4 min and hold 40% for 2.5 min, then 5% of B for 1.5 min; Flow rate: 2.8 mL/min; Column temp: 35° C.; ABPR: 1500 psi), the title compound was obtained as the second product: a white solid (14.4 mg, yield: 16%) [97.9% ee, retention time 1.889 min; SFC analytical method: AS_ETOH_DEA_5_40_28ML_8 MIN]. MS (ESI): mass calcd. for $C_{23}H_{29}FN_4O_3$, 428.2; m/z found, 429.1 [M+H]$^+$. $^1$H NMR (400 MHz, CDCl$_3$) δ 8.30 (d, J=11.3 Hz, 1H), 8.00 (d, J=6.8 Hz, 1H), 6.92 (s, 1H), 5.00 (q, J=8.9 Hz, 1H), 4.69 (br d, J=3.3 Hz, 2H), 3.93 (q, J=7.3 Hz, 2H), 3.24 (td, J=6.8, 13.7 Hz, 1H), 2.48 (br s, 1H), 2.27-2.17 (m, 1H), 2.16-2.08 (m, 1H), 2.08-1.98 (m, 1H), 1.90-1.81 (m, 2H), 1.80-1.68 (m, 1H), 1.47-1.42 (m, 3H), 1.42-1.38 (m, 1H), 1.33 (dd, J=3.5, 6.8 Hz, 6H), 1.02 (d, J=6.5 Hz, 3H); $^{19}$F NMR (376 MHz, CDCl$_3$) δ −121.66 (s, 1F) ppm.

Example 125: 6-(4-Ethyl-3-(hydroxymethyl)-5-oxo-4,5-dihydro-1H-1,2,4-triazol-1-yl)-7-fluoro-4-isopropyl-2-((1R*,2S*)-2-methylcyclopentyl)isoquinolin-1(2H)-one

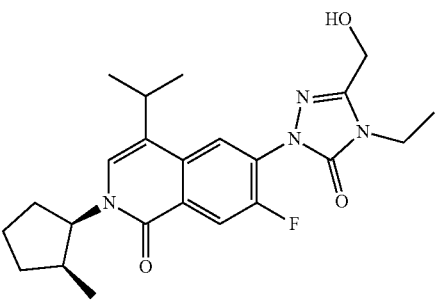 [SMILES: CCn1c(CO)nn(-c2cc3c(C(C)C)cn([C@@H]4CCC[C@@H]4C)c(=O)c3cc2F)c1=O]

In the separation of racemic diastereomeric mixture of 6-(4-ethyl-3-(hydroxymethyl)-5-oxo-4,5-dihydro-1H-1,2,4-triazol-1-yl)-7-fluoro-4-isopropyl-2-(2-methylcyclopentyl)isoquinolin-1(2H)-one (Example 123, 90.1 mg) by chiral SFC: (Column: Chiralpak AS-3 100×4.6 mm I.D., 3 um; Mobile phase: A: $CO_2$B: ethanol (0.05% DEA); Gradient: from 5% to 40% of B in 4 min and hold 40% for 2.5 min, then 5% of B for 1.5 min; Flow rate: 2.8 mL/min; Column temp: 35° C.; ABPR: 1500 psi), the title compound was obtained as the third product: a white solid (11.1 mg, yield: 12%) [98.9% ee, retention time 1.994 min; SFC analytical method: AS_ETOH_DEA_5_40_28ML_8 MIN]. MS (ESI): mass calcd. for $C_{23}H_{29}FN_4O_3$, 428.2; m/z found, 429.1 [M+H]$^+$. $^1$H NMR (400 MHz, CDCl$_3$) δ 8.31 (d, J=11.3 Hz, 1H), 7.99 (d, J=7.0 Hz, 1H), 6.93 (s, 1H), 5.49-5.40 (m, 1H), 4.70 (d, J=6.0 Hz, 2H), 3.94 (q, J=7.3 Hz, 2H), 3.24 (td, J=6.8, 13.6 Hz, 1H), 2.51 (td, J=7.6, 15.4 Hz, 1H), 2.29-2.16 (m, 2H), 2.08-1.93 (m, 3H), 1.83-1.69 (m, 1H), 1.47-1.43 (m, 3H), 1.42-1.39 (m, 1H), 1.32 (dd, J=1.8, 6.8 Hz, 6H), 0.73 (d, J=7.0 Hz, 3H); $^{19}$F NMR (376 MHz, CDCl$_3$) δ −121.89 (s, 1F) ppm.

Example 126: 6-(4-Ethyl-3-(hydroxymethyl)-5-oxo-4,5-dihydro-1H-1,2,4-triazol-1-yl)-7-fluoro-4-isopropyl-2-((1S*,2R*)-2-methylcyclopentyl)isoquinolin-1(2H)-one

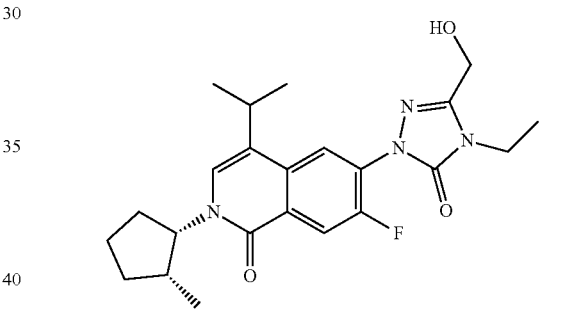

In the separation of racemic diastereomeric mixture of 6-(4-ethyl-3-(hydroxymethyl)-5-oxo-4,5-dihydro-1H-1,2,4-triazol-1-yl)-7-fluoro-4-isopropyl-2-(2-methylcyclopentyl)isoquinolin-1(2H)-one (Example 123, 90.1 mg) by chiral SFC: (Column: Chiralpak AS-3 100×4.6 mm I.D., 3 um; Mobile phase: A: $CO_2$B: ethanol (0.05% DEA); Gradient: from 5% to 40% of B in 4 min and hold 40% for 2.5 min, then 5% of B for 1.5 min; Flow rate: 2.8 mL/min; Column temp: 35° C.; ABPR: 1500 psi), the title compound was obtained as the fourth product: a white solid (10.6 mg, yield: 12%) [100% ee, retention time 2.034 min; SFC analytical method: AS_ETOH_DEA_5_40_28ML_8 MIN]. MS (ESI): mass calcd. for $C_{23}H_{29}FN_4O_3$, 428.2; m/z found, 429.1 [M+H]$^+$. $^1$H NMR (400 MHz, CDCl$_3$) δ 8.31 (d, J=11.5 Hz, 1H), 7.99 (d, J=7.0 Hz, 1H), 6.93 (s, 1H), 5.45 (q, J=7.6 Hz, 1H), 4.70 (br d, J=4.3 Hz, 2H), 3.94 (q, J=7.2 Hz, 2H), 3.24 (td, J=6.7, 13.5 Hz, 1H), 2.56-2.46 (m, 1H), 2.27-2.15 (m, 2H), 2.08-1.93 (m, 3H), 1.83-1.70 (m, 1H), 1.47-1.42 (m, 3H), 1.42-1.38 (m, 1H), 1.32 (dd, J=1.8, 6.8 Hz, 6H), 0.73 (d, J=7.0 Hz, 3H); $^{19}$F NMR (376 MHz, CDCl$_3$) δ −121.89 (s, 1F) ppm.

Example 127: Racemic 6-(4-Ethyl-3-(hydroxymethyl)-5-oxo-4,5-dihydro-1H-1,2,4-triazol-1-yl)-7-fluoro-4-isopropyl-2-((cis)-3-methoxycyclohexyl)isoquinolin-1(2H)-one

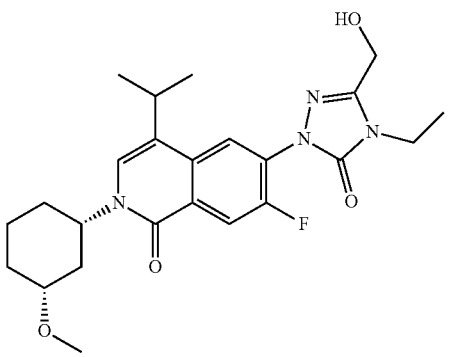 [SMILES: CCn1c(CO)nn(-c2cc3c(C(C)C)cn([C@H]4CCC[C@@H](OC)C4)c(=O)c3cc2F)c1=O]

The title compound was prepared in a manner analogous to Example 120 Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using cis-3-methoxycyclohexanamine hydrochloride instead of trans-2-methyl-cyclohexylamine hydrochloride in Step A. MS (ESI): mass calcd. for $C_{24}H_{31}FN_4O_4$, 458.2; m/z found, 459.2 [M+H]⁺. ¹H NMR (400 MHz, CDCl₃) δ 8.29 (d, J=11.3 Hz, 1H), 8.00 (d, J=6.8 Hz, 1H), 6.95 (s, 1H), 5.10-4.99 (m, 1H), 4.68 (br d, J=5.0 Hz, 2H), 3.93 (q, J=7.3 Hz, 2H), 3.43-3.32 (m, 4H), 3.27-3.18 (m, 1H), 2.67-2.61 (m, 1H), 2.35 (br d, J=11.3 Hz, 1H), 2.18 (br d, J=12.3 Hz, 1H), 1.99-1.88 (m, 2H), 1.54-1.47 (m, 3H), 1.43 (t, J=7.2 Hz, 3H), 1.31 (d, J=_6.8 Hz, 6H), 1.26-1.20 (m, 1H); ¹⁹F NMR (376 MHz, CDCl₃) δ -121.43 (s, 1F) ppm.

Example 128: 2-(Bicyclo[2.2.1]heptan-1-yl)-6-(4-ethyl-3-(hydroxymethyl)-5-oxo-4,5-dihydro-1H-1,2,4-triazol-1-yl)-7-fluoro-4-isopropylisoquinolin-1(2H)-one

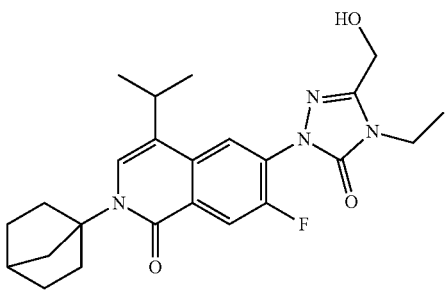 [SMILES: CCn1c(CO)nn(-c2cc3c(C(C)C)cn(C45CCC(CC4)C5)c(=O)c3cc2F)c1=O]

The title compound was prepared in a manner analogous to Example 120 Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using bicyclo[2.2.1]heptan-1-amine instead of trans-2-methyl-cyclohexylamine hydrochloride in Step A. MS (ESI): mass calcd. for $C_{24}H_{29}FN_4O_3$, 440.2; m/z found, 441.1 [M+H]⁺. ¹H NMR (400 MHz, CDCl₃) δ 8.26 (d, J=11.5 Hz, 1H), 7.97 (d, J=7.0 Hz, 1H), 7.13 (s, 1H), 4.69 (d, J=6.3 Hz, 2H), 3.93 (q, J=7.3 Hz, 2H), 3.22 (quin, J=6.8 Hz, 1H), 2.70-2.62 (m, 2H), 2.39 (t, J=6.4 Hz, 1H), 2.34 (br s, 1H), 2.04 (s, 2H), 1.92-1.83 (m, 2H), 1.76-1.68 (m, 2H), 1.56 (br s, 2H), 1.44 (t, J=7.2 Hz, 3H), 1.31 (d, J=6.8 Hz, 6H); ¹⁹F NMR (376 MHz, CDCl₃) δ -122.09 (s, 1F) ppm.

Example 129: 6-(4-Ethyl-3-(hydroxymethyl)-5-oxo-4,5-dihydro-1H-1,2,4-triazol-1-yl)-7-fluoro-4-isopropyl-2-(2-methoxy-3-methylpyridin-4-yl)isoquinolin-1(2H)-one

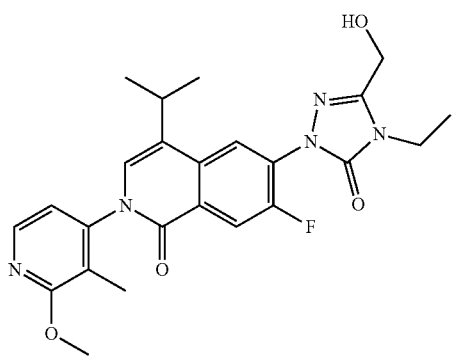 [SMILES: CCn1c(CO)nn(-c2cc3c(C(C)C)cn(-c4ccnc(OC)c4C)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2-methoxy-3-methylpyridin-4-amine instead of 5-chloro-3-methyl-4-amino-1H-pyrazole in Step A; using DCE instead of DCM and heating at 90° C. for 40 h in Step A. MS (ESI): mass calcd. for $C_{24}H_{26}FN_5O_4$, 467.2; m/z found, 468.2 [M+H]⁺. ¹H NMR (400 MHz, CDCl₃) δ 8.32 (d, J=11.0 Hz, 1H), 8.19-8.06 (m, 2H), 6.86 (d, J=5.3 Hz, 1H), 6.77 (s, 1H), 4.71 (s, 2H), 4.03 (s, 3H), 3.95 (q, J=7.3 Hz, 2H), 3.27 (td, J=6.9, 13.6 Hz, 1H), 2.34 (br s, 1H), 2.02 (s, 3H), 1.45 (t, J=7.2 Hz, 3H), 1.32 (d, J=6.8 Hz, 6H); ¹⁹F NMR (376 MHz, CDCl₃) δ -120.39 (s, 1F) ppm.

Example 130: 2-(4-Ethyl-3-(hydroxymethyl)-5-oxo-4,5-dihydro-1H-1,2,4-triazol-1-yl)-3-fluoro-8-isopropyl-6-(2-methoxyphenyl)-1,6-naphthyridin-5(6H)-one

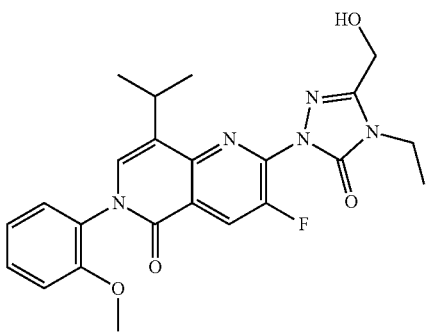 [SMILES: CCn1c(CO)nn(-c2nc3c(C(C)C)cn(-c4ccccc4OC)c(=O)c3cc2F)c1=O]

Step A. 6-(3-((Benzyloxy)methyl)-4-ethyl-5-oxo-4,5-dihydro-1H-1,2,4-triazol-1-yl)-2-(2-ethoxyvinyl)-5-fluoro-N-(2-methoxyphenyl)nicotinamide. To a solution of 2-methoxyaniline (318 mg, 2.58 mmol) in toluene (5 mL) was added a toluene solution (2 M) of AlMe₃ (1.55 mL, 3.10 mmol) under nitrogen. The mixture was stirred for 5 min, then the solution of isopropyl 6-(3-((benzyloxy)methyl)-4-ethyl-5-oxo-4,5-dihydro-1H-1,2,4-triazol-1-yl)-2-(2-ethoxyvinyl)-5-fluoronicotinate (550 mg, 1.14 mmol) in toluene (5 mL) was added. The reaction mixture was stirred at 90° C. for 3 h. The mixture was cooled to room temperature and aqueous HCl solution (1N, 3 mL) was carefully added. The mixture was partitioned between water and ethyl acetate. The organic layer was separated, and the aqueous layer was extracted with ethyl acetate. The combined organic extract was dried over anhydrous $MgSO_4$, filtered and concentrated. The residue was purified by column chromatography ($SiO_2$, 0-50% ethyl acetate in petroleum ether) to give the title compound as a yellow gum (480 mg, yield: 63%). MS (ESI): mass calcd. for $C_{29}H_{30}FN_5O_5$, 547.2; m/z found, 548.3 $[M+H]^+$.

Step B. 2-(3-((Benzyloxy)methyl)-4-ethyl-5-oxo-4,5-dihydro-1H-1,2,4-triazol-1-yl)-3-fluoro-6-(2-methoxyphenyl)-1,6-naphthyridin-5(6H)-one. 6-(3-((benzyloxy)methyl)-4-ethyl-5-oxo-4,5-dihydro-1H-1,2,4-triazol-1-yl)-2-(2-ethoxyvinyl)-5-fluoro-N-(2-methoxyphenyl)nicotinamide (480 mg, 0.72 mmol) was dissolved in AcOH (10 mL). The reaction mixture was stirred at 90° C. for overnight. LCMS indicated almost complete consumption of the starting material and the formation of one major product. The mixture was poured into water (30 mL) and extracted with ethyl acetate (200 mL×2). The combined organic extract was washed with water, aqueous saturated $NaHCO_3$ solution, dried over $Na_2SO_4$, filtered, and concentrated. The residue was purified by column chromatography ($SiO_2$, 0-50% ethyl acetate in petroleum ether) to give the title compound as a yellow gum (360 mg, yield: 97%). MS (ESI): mass calcd. for $C_{27}H_{24}FN_5O_4$, 501.2; m/z found, 502.3 $[M+H]^+$. $^1$H NMR (400 MHz, $CDCl_3$) δ 8.55 (d, J=9.5 Hz, 1H), 7.46 (dt, J=1.6, 8.0 Hz, 1H), 7.42-7.31 (m, 6H), 7.26 (s, 1H), 7.14-7.07 (m, 2H), 6.85 (d, J=7.8 Hz, 1H), 4.63 (s, 2H), 4.59 (s, 2H), 3.89 (q, J=7.3 Hz, 2H), 3.82 (s, 3H), 1.38 (t, J=7.3 Hz, 3H) ppm.

Step C. 2-(3-((Benzyloxy)methyl)-4-ethyl-5-oxo-4,5-dihydro-1H-1,2,4-triazol-1-yl)-8-bromo-3-fluoro-6-(2-methoxyphenyl)-1,6-naphthyridin-5(6H)-one. To a solution of 2-(3-((benzyloxy)methyl)-4-ethyl-5-oxo-4,5-dihydro-1H-1,2,4-triazol-1-yl)-3-fluoro-6-(2-methoxyphenyl)-1,6-naphthyridin-5(6H)-one (360 mg, 0.69 mmol) in DMF (5 mL) was added NBS (123.5 mg, 0.69 mmol) at 0° C. Then the mixture was stirred at room temperature for 3 h. The mixture was poured into water (30 mL) and extracted with ethyl acetate (30 mL×2). The combined organic layers were dried over anhydrous $Na_2SO_4$, filtered and concentrated. The residue was purified by column chromatography ($SiO_2$, gradient elution: 0-50% ethyl acetate in petroleum ether) to give the title compound as a light yellow solid (190 mg, yield: 45%). MS (ESI): mass calcd. for $C_{27}H_{23}BrFN_5O_4$, 579.1; m/z found, 580.2 $[M+H]^+$. $^1$H NMR (400 MHz, $CDCl_3$) δ 8.56 (d, J=9.3 Hz, 1H), 7.61 (s, 1H), 7.51-7.45 (m, 1H), 7.41-7.37 (m, 4H), 7.37-7.32 (m, 2H), 7.14-7.07 (m, 2H), 4.64 (s, 2H), 4.58 (s, 2H), 3.89 (q, J=7.1 Hz, 2H), 3.84 (s, 3H), 1.38 (t, J=7.2 Hz, 3H) ppm.

Step D. 2-(3-((Benzyloxy)methyl)-4-ethyl-5-oxo-4,5-dihydro-1H-1,2,4-triazol-1-yl)-3-fluoro-6-(2-methoxyphenyl)-8-(prop-1-en-2-yl)-1,6-naphthyridin-5(6H)-one. To a mixture of 2-(3-((benzyloxy)methyl)-4-ethyl-5-oxo-4,5-dihydro-1H-1,2,4-triazol-1-yl)-8-bromo-3-fluoro-6-(2-methoxyphenyl)-1,6-naphthyridin-5(6H)-one (190 mg, 0.31 mmol) and $Na_2CO_3$ (100 mg, 0.94 mmol) in 1,4-dioxane/water (v/v, 4/1, 5 mL) was added isopropenyl boronic acid pinacol ester (106 mg, 0.63 mmol) and $Pd(dppf)Cl_2 \cdot DCM$ (46 mg, 0.062 mmol) under nitrogen. The reaction mixture was heated at 90° C. for 5 h. The mixture was cooled to room temperature, partitioned between water and ethyl acetate. The organic layer was separated, and the aqueous layer was extracted with ethyl acetate. The combined organic extract was washed with brine, dried over $Na_2SO_4$, filtered, and concentrated. The reside was purified by column chromatography ($SiO_2$, 0-45% ethyl acetate in petroleum ether) to give the title compound as a brown gum (130 mg, yield: 76%). MS (ESI): mass calcd. for $C_{30}H_{28}FN_5O_4$, 541.2; m/z found, 542.3 $[M+H]^+$.

Step E. 2-(3-((Benzyloxy)methyl)-4-ethyl-5-oxo-4,5-dihydro-1H-1,2,4-triazol-1-yl)-3-fluoro-8-isopropyl-6-(2-methoxyphenyl)-1,6-naphthyridin-5(6H)-one. To a solution of 2-(3-((benzyloxy)methyl)-4-ethyl-5-oxo-4,5-dihydro-1H-1,2,4-triazol-1-yl)-3-fluoro-6-(2-methoxyphenyl)-8-(prop-1-en-2-yl)-1,6-naphthyridin-5(6H)-one (130 mg, 0.24 mmol) in THF (6 mL) at room temperature was added Wilkinson's Catalyst [$RhCl(PPh_3)_3$] (66.6 mg, 0.07 mmol). The mixture was degassed and purged with hydrogen gas. The reaction mixture was stirred under an atmosphere of hydrogen (15 Psi) at room temperature for 40 h. The mixture was concentrated. The residue was purified by column chromatography ($SiO_2$, 0-40% ethyl acetate in petroleum ether) to give the title compound as a off white solid (90 mg, yield: 69%). MS (ESI): mass calcd. for $C_{30}H_{30}FN_5O_4$, 543.2; m/z found, 544.2 $[M+H]^+$.

Step F. 2-(4-Ethyl-3-(hydroxymethyl)-5-oxo-4,5-dihydro-1H-1,2,4-triazol-1-yl)-3-fluoro-8-isopropyl-6-(2-methoxyphenyl)-1,6-naphthyridin-5(6H)-one. To a stirred solution of 2-(3-((benzyloxy)methyl)-4-ethyl-5-oxo-4,5-dihydro-1H-1,2,4-triazol-1-yl)-3-fluoro-8-isopropyl-6-(2-methoxyphenyl)-1,6-naphthyridin-5(6H)-one (90 mg, 0.17 mmol) in DCM (5 mL) was added $BCl_3$ (1 M in toluene, 0.91 mL, 0.91 mmol) at −78° C. The reaction mixture was stirred at −78° C. for 0.5 h. MeOH (3 mL) was carefully added. The mixture was diluted with DCM, washed with saturated aqueous $NaHCO_3$ solution. The organic layer was separated, washed with brine, dried over anhydrous $Na_2SO_4$, filtered, and concentrated. The residue was purified by preparative reversed phase HPLC (Stationary phase: Boston Prime C18, 5 μm, 150×30 mm; Mobile phase: water (0.05% $NH_3H_2O$+ 10 mM $NH_4HCO_3$) (A)—MeCN (B), gradient elution: 45-75% B in A over 7 min, flow rate: 25 mL/min) to give the title compound as a white powder (41 mg, yield: 55%). MS (ESI): mass calcd. For $C_{23}H_{24}FN_5O_4$, 453.2; m/z found, 454.1 $[M+H]^+$. $^1$H NMR (400 MHz, $CDCl_3$) δ 8.54 (d, J=9.6 Hz, 1H), 7.46 (dt, J=1.8, 7.9 Hz, 1H), 7.34 (dd, J=1.6, 7.7 Hz, 1H), 7.14-7.07 (m, 2H), 7.04 (s, 1H), 4.69 (d, J=5.9 Hz, 2H), 3.93 (q, J=7.2 Hz, 2H), 3.82 (s, 3H), 3.64 (spt, J=6.9 Hz, 1H), 2.57 (br t, J=6.1 Hz, 1H), 1.44 (t, J=7.2 Hz, 3H), 1.31 (d, J=7.0 Hz, 6H); $^{19}$F NMR (377 MHz, $CDCl_3$) δ −126.27 (s, 1F) ppm.

Example 131: 6-(4-Ethyl-3-(hydroxymethyl)-5-oxo-4,5-dihydro-1H-1,2,4-triazol-1-yl)-7-fluoro-4-isopropyl-2-(3-methylisothiazol-4-yl)isoquinolin-1(2H)-one

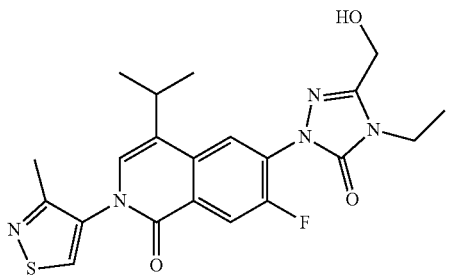 [SMILES: CCn1c(CO)nn(-c2cc3c(C(C)C)cn(-c4csnc4C)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 3-methylisothiazol-4-amine instead of 5-chloro-3-methyl-4-amino-1H-pyrazole in Step A. MS (ESI): mass calcd. for $C_{21}H_{22}FN_5O_3S$, 443.1; m/z found, 444.0 [M+H]$^+$. $^1$H NMR (400 MHz, CDCl$_3$) δ 8.69 (s, 1H), 8.31 (d, J=11.1 Hz, 1H), 8.10 (d, J=6.8 Hz, 1H), 6.82 (s, 1H), 4.71 (d, J=5.8 Hz, 2H), 3.95 (q, J=7.2 Hz, 2H), 3.33-3.19 (m, 1H), 2.38 (s, 3H), 2.24 (br t, J=6.2 Hz, 1H), 1.45 (t, J=7.2 Hz, 3H), 1.33 (d, J=6.8 Hz, 6H); $^{19}$F NMR (376 MHz, CDCl$_3$) δ −120.07 (s, 1F) ppm.

Example 132: 6-(4-Ethyl-3-(hydroxymethyl)-5-oxo-4,5-dihydro-1H-1,2,4-triazol-1-yl)-7-fluoro-4-isopropyl-2-(5-methylisothiazol-4-yl)isoquinolin-1(2H)-one

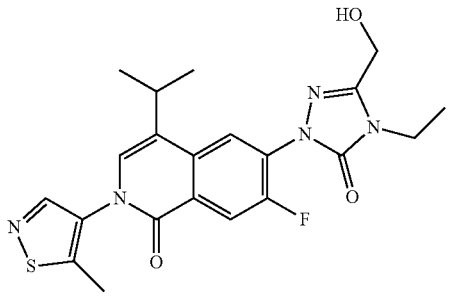 [SMILES: CCn1c(CO)nn(-c2cc3c(C(C)C)cn(-c4cnsc4C)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 5-methylisothiazol-4-amine instead of 5-chloro-3-methyl-4-amino-1H-pyrazole in Step A. MS (ESI): mass calcd. for $C_{21}H_{22}FN_5O_3S$, 443.1; m/z found, 444.1 [M+H]$^+$. $^1$H NMR (400 MHz, CDCl$_3$) δ 8.47 (s, 1H), 8.32 (d, J=11.0 Hz, 1H), 8.10 (d, J=6.8 Hz, 1H), 6.83 (s, 1H), 4.72 (d, J=6.3 Hz, 2H), 3.95 (q, J=7.3 Hz, 2H), 3.31-3.21 (m, 1H), 2.46 (s, 3H), 2.17 (t, J=6.3 Hz, 1H), 1.46 (t, J=7.3 Hz, 3H), 1.33 (d, J=7.0 Hz, 6H); $^{19}$F NMR (376 MHz, CDCl$_3$) δ −120.09 (s, 1F) ppm.

Example 133: 2-(4-Ethyl-3-(hydroxymethyl)-5-oxo-4,5-dihydro-1H-1,2,4-triazol-1-yl)-3-fluoro-8-isopropyl-6-(2-(trifluoromethyl)phenyl)-1,6-naphthyridin-5(6H)-one

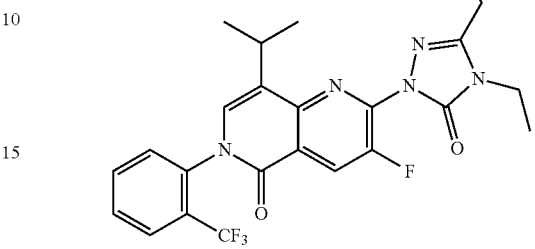

Step A. 6-(3-((Benzyloxy)methyl)-4-ethyl-5-oxo-4,5-dihydro-1H-1,2,4-triazol-1-yl)-2-(2-ethoxyvinyl)-5-fluoro-N-(2-(trifluoromethyl)phenyl)nicotinamide. To a stirred solution of isopropyl 6-(3-((benzyloxy)methyl)-4-ethyl-5-oxo-4,5-dihydro-1H-1,2,4-triazol-1-yl)-2-(2-ethoxyvinyl)-5-fluoronicotinate (1.2 g, 2.48 mmol) and 2-(trifluoromethyl)aniline (998 mg, 6.19 mmol) in THF (25 mL) was added LiHMDS (1 M in THF, 7.4 mL, 7.4 mmol) by dropwise under nitrogen at −78° C. Then the reaction mixture was slowly warmed to 0° C. and stirred at 0° C. for 5 h. Aqueous HCl solution (1 M, 8 mL) was added. The mixture was poured into water (20 mL) and extracted with EtOAc (40 mL×3). The combined organic extract was dried over anhydrous Na$_2$SO$_4$, filtered and concentrated. The residue was dissolved in AcOH (5 mL) and stirred at 90° C. for overnight. The mixture was poured into water and extracted with EtOAc. The combined organic phase was washed with brine, dried over anhydrous Na$_2$SO$_4$, filtered and concentrated. The residue was purified by column chromatography (SiO$_2$, 0-80% ethyl acetate in petroleum ether) to give the title compound as a yellow gum (700 mg, crude). MS (ESI): mass calcd. for $C_{29}H_{27}F_4N_5O_4$, 585.2; m/z found, 586.2 [M+H]$^+$.

Step B. 2-(3-((Benzyloxy)methyl)-4-ethyl-5-oxo-4,5-dihydro-1H-1,2,4-triazol-1-yl)-3-fluoro-6-(2-(trifluoromethyl)phenyl)-1,6-naphthyridin-5(6H)-one. 6-(3-((benzyloxy)methyl)-4-ethyl-5-oxo-4,5-dihydro-1H-1,2,4-triazol-1-yl)-2-(2-ethoxyvinyl)-5-fluoro-N-(2-(trifluoromethyl)phenyl)nicotinamide (700 mg, crude) was dissolved in AcOH (10 mL). The reaction mixture was stirred at 90° C. for 16 h. LCMS indicated almost complete consumption of the starting material and the formation of one major product. The mixture was poured into water (30 mL) and extracted with ethyl acetate (30 mL×2). The combined organic extract was washed with water, aqueous saturated NaHCO$_3$ solution, brine, dried over Na$_2$SO$_4$, filtered, and concentrated. The residue was purified by column chromatography (SiO$_2$, 0-50% ethyl acetate in petroleum ether) to give the title compound as a yellow gum (340 mg, yield: 24% for two steps). MS (ESI): mass calcd. for $C_{27}H_{21}F_4N_5O_3$, 539.2; m/z found, 540.3 [M+H]$^+$. $^1$H NMR (400 MHz, CDCl$_3$) δ 8.52 (d, J=9.4 Hz, 1H), 7.88 (d, J=7.9 Hz, 1H), 7.80-7.73 (m, 1H), 7.70-7.63 (m, 1H), 7.46 (d, J=7.9 Hz, 1H), 7.42-7.39 (m, 1H), 7.38-7.32 (m, 4H), 7.24 (d, J=7.7 Hz, 1H), 6.89 (d, J=7.6 Hz, 1H), 4.63 (s, 2H), 4.59 (s, 2H), 3.90 (q, J=7.2 Hz, 2H), 1.38 (t, J=7.2 Hz, 3H); $^{19}$F NMR (376 MHz, CDCl$_3$) δ −60.60 (s, 1F), −123.27 (s, 1F) ppm.

Step C. 2-(3-((Benzyloxy)methyl)-4-ethyl-5-oxo-4,5-dihydro-1H-1,2,4-triazol-1-yl)-8-bromo-3-fluoro-6-(2-(trifluoromethyl)phenyl)-1,6-naphthyridin-5(6H)-one. To a solution of 2-(3-((benzyloxy)methyl)-4-ethyl-5-oxo-4,5-dihydro-1H-1,2,4-triazol-1-yl)-3-fluoro-6-(2-(trifluoromethyl)phenyl)-1,6-naphthyridin-5(6H)-one (340 mg, 0.61 mmol) in DMF (5 mL) was added NBS (108.5 mg, 0.61 mmol) at 0° C. Then the mixture was stirred at room temperature for 3 h. The mixture was poured into water (30 mL) and extracted with ethyl acetate (30 mL×2). The combined organic layers were dried over anhydrous $Na_2SO_4$, filtered and concentrated. The residue was purified by column chromatography ($SiO_2$, gradient elution: 0-50% ethyl acetate in petroleum ether) to give the title compound as an orange gum (220 mg, yield: 58%). MS (ESI): mass calcd. for $C_{27}H_{20}BrF_4N_5O_3$, 617.1; m/z found, 618.1 [M+H]$^+$. $^1$H NMR (400 MHz, CDCl$_3$) δ 8.54 (d, J=9.1 Hz, 1H), 7.89 (d, J=7.6 Hz, 1H), 7.81-7.74 (m, 1H), 7.72-7.66 (m, 1H), 7.60 (s, 1H), 7.48 (d, J=7.6 Hz, 1H), 7.41-7.33 (m, 5H), 4.64 (s, 2H), 4.58 (s, 2H), 3.89 (q, J=7.2 Hz, 2H), 1.38 (t, J=7.2 Hz, 3H); $^{19}$F NMR (376 MHz, CDCl$_3$) δ −60.52 (br s, 1F), −122.01 (br s, 1F) ppm.

Step D. 2-(3-((Benzyloxy)methyl)-4-ethyl-5-oxo-4,5-dihydro-1H-1,2,4-triazol-1-yl)-3-fluoro-8-(prop-1-en-2-yl)-6-(2-(trifluoromethyl)phenyl)-1,6-naphthyridin-5(6H)-one. To a mixture of 2-(3-((benzyloxy)methyl)-4-ethyl-5-oxo-4,5-dihydro-1H-1,2,4-triazol-1-yl)-8-bromo-3-fluoro-6-(2-(trifluoromethyl)phenyl)-1,6-naphthyridin-5(6H)-one (210 mg, 0.34 mmol) and $Na_2CO_3$ (108 mg, 1.02 mmol) in 1,4-dioxane/water (v/v, 4/1, 5 mL) was added isopropenyl boronic acid pinacol ester (114 mg, 0.68 mmol) and Pd(dppf)Cl$_2$.DCM (50 mg, 0.068 mmol) under nitrogen. The reaction mixture was heated at 90° C. for 5 h. The mixture was cooled to room temperature, partitioned between water and ethyl acetate. The organic layer was separated, and the aqueous layer was extracted with ethyl acetate. The combined organic extract was washed with brine, dried over $Na_2SO_4$, filtered, and concentrated. The reside was purified by column chromatography ($SiO_2$, 0-45% ethyl acetate in petroleum ether) to give the title compound as a yellow gum (160 mg, yield: 81%). MS (ESI): mass calcd. for $C_{30}H_{25}F_4N_5O_3$, 579.2; m/z found, 580.2 [M+H]$^+$. $^1$H NMR (400 MHz, CDCl$_3$) δ 8.53 (d, J=9.7 Hz, 1H), 7.88 (d, J=7.7 Hz, 1H), 7.81-7.74 (m, 1H), 7.70-7.64 (m, 1H), 7.50 (d, J=7.7 Hz, 1H), 7.43-7.32 (m, 5H), 7.23 (s, 1H), 5.38 (s, 1H), 5.22 (s, 1H), 4.63 (s, 2H), 4.55 (s, 2H), 3.89 (q, J=7.2 Hz, 2H), 2.34 (s, 3H), 1.38 (t, J=7.2 Hz, 3H); $^{19}$F NMR (376 MHz, CDCl$_3$) δ −60.55 (s, 1F), −124.72 (br s, 1F) ppm.

Step E. 2-(3-((Benzyloxy)methyl)-4-ethyl-5-oxo-4,5-dihydro-1H-1,2,4-triazol-1-yl)-3-fluoro-8-isopropyl-6-(2-(trifluoromethyl)phenyl)-1,6-naphthyridin-5(6H)-one. To a solution of 2-(3-((benzyloxy)methyl)-4-ethyl-5-oxo-4,5-dihydro-1H-1,2,4-triazol-1-yl)-3-fluoro-8-(prop-1-en-2-yl)-6-(2-(trifluoromethyl)phenyl)-1,6-naphthyridin-5(6H)-one (160 mg, 0.276 mmol) in THF (10 mL) at room temperature was added Wilkinson's Catalyst [RhCl(PPh$_3$)$_3$] (76.6 mg, 0.082 mmol). The mixture was degassed and purged with hydrogen gas. The reaction mixture was stirred under an atmosphere of hydrogen (15 Psi) at room temperature for 24 h. The mixture was concentrated. The residue was purified by column chromatography ($SiO_2$, 0-35% ethyl acetate in petroleum ether) to give the title compound as an off white solid (100 mg, yield: 62%). MS (ESI): mass calcd. for $C_{30}H_{27}F_4N_5O_3$, 581.2; m/z found, 582.1 [M+H]$^+$. $^1$H NMR (400 MHz, CDCl$_3$) δ 8.52 (d, J=9.5 Hz, 1H), 7.88 (d, J=7.7 Hz, 1H), 7.80-7.72 (m, 1H), 7.70-7.62 (m, 1H), 7.49 (d, J=7.9 Hz, 1H), 7.43-7.31 (m, 5H), 7.01 (s, 1H), 4.64 (s, 2H), 4.57 (s, 2H), 3.90 (q, J=7.2 Hz, 2H), 3.67 (td, J=6.8, 13.6 Hz, 1H), 1.40 (t, J=7.2 Hz, 3H), 1.30 (dd, J=0.9, 6.9 Hz, 6H); $^{19}$F NMR (376 MHz, CDCl$_3$) δ −60.62 (s, 1F), −125.29 (s, 1F) ppm.

Step F. 2-(4-Ethyl-3-(hydroxymethyl)-5-oxo-4,5-dihydro-1H-1,2,4-triazol-1-yl)-3-fluoro-8-isopropyl-6-(2-(trifluoromethyl)phenyl)-1,6-naphthyridin-5(6H)-one. To a stirred solution of 2-(3-((benzyloxy)methyl)-4-ethyl-5-oxo-4,5-dihydro-1H-1,2,4-triazol-1-yl)-3-fluoro-8-isopropyl-6-(2-(trifluoromethyl)phenyl)-1,6-naphthyridin-5(6H)-one (100 mg, 0.17 mmol) in DCM (5 mL) was added BCl$_3$ (1 M in toluene, 0.95 mL, 0.95 mmol) at −78° C. The reaction mixture was stirred at −78° C. for 0.5 h. MeOH (3 mL) was carefully added. The mixture was diluted with DCM, washed with saturated aqueous NaHCO$_3$ solution. The organic layer was separated, washed with brine, dried over anhydrous $Na_2SO_4$, filtered, and concentrated. The residue was purified by preparative reversed phase HPLC (Stationary phase: Boston Prime C18, 5 μm, 150×30 mm; Mobile phase: water (0.05% NH$_3$H$_2$O+10 mM NH$_4$HCO$_3$) (A)—MeCN (B), gradient elution: 45-75% B in A over 7 min, flow rate: 25 mL/min) to give the title compound as a white powder (49 mg, yield: 58%). MS (ESI): mass calcd. for $C_{23}H_{21}F_4N_5O_3$, 491.2; m/z found, 492.4 [M+H]$^+$. $^1$H NMR (400 MHz, CDCl$_3$) δ 8.52 (d, J=9.4 Hz, 1H), 7.88 (br d, J=7.7 Hz, 1H), 7.80-7.72 (m, 1H), 7.70-7.61 (m, 1H), 7.48 (br d, J=7.7 Hz, 1H), 7.01 (s, 1H), 4.70 (s, 2H), 3.94 (q, J=7.2 Hz, 2H), 3.66 (td, J=6.9, 13.6 Hz, 1H), 2.48 (br s, 1H), 1.44 (t, J=7.2 Hz, 3H), 1.29 (br d, J=6.8 Hz, 6H); $^{19}$F NMR (376 MHz, CDCl$_3$) δ −60.61 (s, 1F), −125.30 (br s, 1F) ppm.

Example 134: 2-(3,6-Dimethylpyridin-2-yl)-6-(4-ethyl-3-(hydroxymethyl)-5-oxo-4,5-dihydro-1H-1,2,4-triazol-1-yl)-7-fluoro-4-isopropylisoquinolin-1(2H)-one

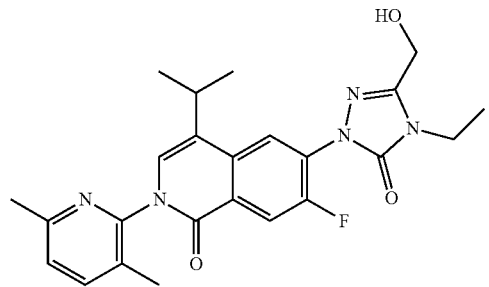 [SMILES: CCn1c(CO)nn(-c2cc3c(C(C)C)cn(-c4nc(C)ccc4C)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 3,6-dimethylpyridin-2-amine instead of 5-chloro-3-methyl-4-amino-1H-pyrazole in Step A. MS (ESI): mass calcd. for $C_{24}H_{26}FN_5O_3$, 451.2; m/z found, 452.1 [M+H]$^+$. $^1$H NMR (400 MHz, CDCl$_3$) δ 8.31 (d, J=11.1 Hz, 1H), 8.07 (d, J=6.9 Hz, 1H), 7.62 (d, J=7.7 Hz, 1H), 7.21 (d, J=7.7 Hz, 1H), 6.96 (s, 1H), 4.68 (d, J=6.2 Hz, 2H), 3.94 (q, J=7.3 Hz, 2H), 3.26 (spt, J=6.7 Hz, 1H), 2.64-2.51 (m, 4H), 2.16 (s, 3H), 1.44 (t, J=7.2 Hz, 3H), 1.33 (t, J=7.3 Hz, 6H); $^{19}$F NMR (376 MHz, CDCl$_3$) δ −120.96 (s, 1F) ppm.

Example 135: 2-(2,5-Dimethylpyridin-4-yl)-6-(4-ethyl-3-(hydroxymethyl)-5-oxo-4,5-dihydro-1H-1,2,4-triazol-1-yl)-7-fluoro-4-isopropylisoquinolin-1(2H)-one

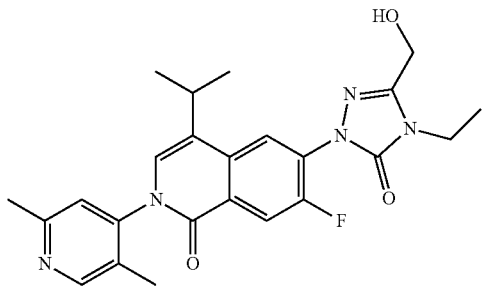 [SMILES: CCn1c(CO)nn(-c2cc3c(C(C)C)cn(-c4cc(C)ncc4C)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2,5-dimethylpyridin-4-amine instead of 5-chloro-3-methyl-4-amino-1H-pyrazole in Step A; using DCE instead of DCM and heating at 75° C. for 24 h in Step A. MS (ESI): mass calcd. for $C_{24}H_{26}FN_5O_3$, 451.2; m/z found, 452.2 [M+H]+. 1H NMR (400 MHz, CDCl3) δ 8.52 (s, 1H), 8.30 (d, J=11.1 Hz, 1H), 8.10 (d, J=6.9 Hz, 1H), 7.12 (s, 1H), 6.75 (s, 1H), 4.69 (s, 2H), 3.95 (q, J=7.2 Hz, 2H), 3.27 spt, J=6.8, 13.6 Hz, 1H), 2.60 (s, 3H), 2.14 (s, 3H), 1.75 (br s, 1H), 1.45 (t, J=7.2 Hz, 3H), 1.32 (br d, J=5.7 Hz, 6H); 19F NMR (376 MHz, CDCl3) δ −120.06 (s, 1F) ppm.

Example 136: 6-(4-Ethyl-3-(hydroxymethyl)-5-oxo-4,5-dihydro-1H-1,2,4-triazol-1-yl)-7-fluoro-4-isopropyl-2-(4-methylpyridin-3-yl)isoquinolin-1(2H)-one

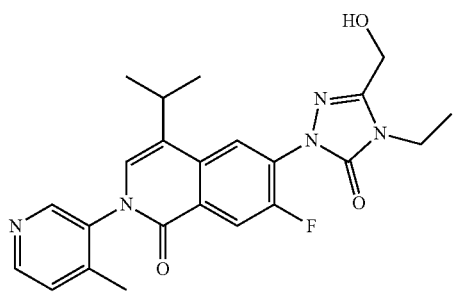 [SMILES: CCn1c(CO)nn(-c2cc3c(C(C)C)cn(-c4cnccc4C)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 4-methylpyridin-3-amine instead of 5-chloro-3-methyl-4-amino-1H-pyrazole in Step A; using DCE instead of DCM and heating at 85° C. for 4 h in Step A. MS (ESI): mass calcd. for $C_{23}H_{24}FN_5O_3$, 437.5; m/z found, 438.1 [M+H]+. 1H NMR (400 MHz, CDCl3) δ 8.56-8.49 (m, 2H), 8.17-8.08 (m, 2H), 7.34 (d, J=5.0 Hz, 1H), 6.77 (s, 1H), 4.66 (s, 2H), 3.94 (q, J=7.2 Hz, 2H), 3.25 (td, J=6.7, 13.5 Hz, 1H), 2.20 (s, 3H), 1.92 (br s, 1H), 1.41 (t, J=7.2 Hz, 3H), 1.30 (dd, J=3.2, 6.6 Hz, 6H); 19F NMR (376 MHz, CDCl3) δ −120.15 (br s, 1F) ppm.

Example 137: 6-(4-Ethyl-3-(hydroxymethyl)-5-oxo-4,5-dihydro-1H-1,2,4-triazol-1-yl)-7-fluoro-4-isopropyl-2-(3-methylpyridin-4-yl)isoquinolin-1(2H)-one

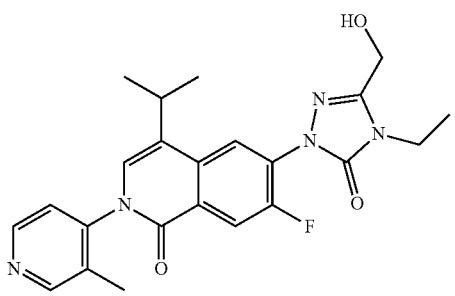 [SMILES: CCn1c(CO)nn(-c2cc3c(C(C)C)cn(-c4ccncc4C)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 3-methylpyridin-4-amine instead of 5-chloro-3-methyl-4-amino-1H-pyrazole in Step A; using DCE instead of DCM and heating at 85° C. for 24 h in Step A. MS (ESI): mass calcd. for $C_{23}H_{24}FN_5O_3$, 437.2; m/z found, 438.1 [M+H]+. 1H NMR (400 MHz, CDCl3) δ 8.67 (s, 1H), 8.63 (d, J=5.1 Hz, 1H), 8.32 (d, J=11.0 Hz, 1H), 8.13 (d, J=6.9 Hz, 1H), 7.29 (s, 1H), 6.78 (s, 1H), 4.71 (s, 2H), 3.97 (q, J=7.3 Hz, 2H), 3.36-3.24 (m, 1H), 3.05 (br s, 1H), 2.22 (s, 3H), 1.46 (t, J=7.2 Hz, 3H), 1.34 (d, J=6.8 Hz, 6H); 19F NMR (376 MHz, CDCl3) δ −120.00 (s, 1F) ppm.

Example 138: 6-(4-Ethyl-3-(hydroxymethyl)-5-oxo-4,5-dihydro-1H-1,2,4-triazol-1-yl)-7-fluoro-4-isopropyl-2-(2-methylpyridin-3-yl)isoquinolin-1(2H)-one

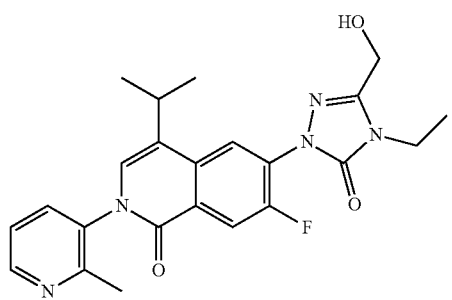 [SMILES: CCn1c(CO)nn(-c2cc3c(C(C)C)cn(-c4cccnc4C)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2-methylpyridin-3-amine instead of 5-chloro-3-methyl-4-amino-1H-pyrazole in Step A; using DCE instead of DCM and heating at 90° C. for 24 h in Step A. MS (ESI): mass calcd. for $C_{23}H_{24}FN_5O_3$, 437.1; m/z found, 438.1 [M+H]+. 1H NMR (400 MHz, CDCl3) δ 8.63 (dd, J=1.3, 4.8 Hz, 1H), 8.32 (d, J=11.1 Hz, 1H), 8.11 (d, J=6.9 Hz, 1H), 7.64 (dd, J=1.3, 7.9 Hz, 1H), 7.34 (dd, J=4.9, 7.9 Hz, 1H), 6.79 (s, 1H), 4.71 (s, 2H), 3.95 (q, J=7.3 Hz, 2H), 3.28 (td, J=6.9, 13.6 Hz, 1H), 2.42 (s, 4H), 1.46 (t, J=7.3 Hz, 3H), 1.33 (dd, J=1.6, 6.7 Hz, 6H); $^{19}$F NMR (376 MHz, CDCl$_3$) δ −120.25 (s, 1F) ppm.

Example 139: 6-(4-Ethyl-3-(hydroxymethyl)-5-oxo-4,5-dihydro-1H-1,2,4-triazol-1-yl)-7-fluoro-2-(2-hydroxy-5-methylpyridin-4-yl)-4-isopropylisoquinolin-1(2H)-one

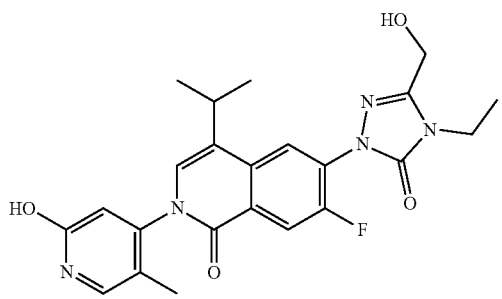 [SMILES: CCn1c(CO)nn(-c2cc3c(C(C)C)cn(-c4cc(O)ncc4C)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2-methoxy-5-methylpyridin-4-amine instead of 5-chloro-3-methyl-4-amino-1H-pyrazole in Step A; using DCE instead of DCM and heating at 90° C. for 24 h in Step A. MS (ESI): mass calcd. for C$_{23}$H$_{24}$FN$_5$O$_4$, 453.1; m/z found, 454.0 [M+H]$^+$. $^1$H NMR (400 MHz, CDCl$_3$) δ 12.18 (br s, 1H), 8.30 (d, J=11.0 Hz, 1H), 8.11 (d, J=6.8 Hz, 1H), 7.32 (s, 1H), 6.79 (s, 1H), 6.61 (s, 1H), 4.72 (s, 2H), 3.95 (q, J=7.2 Hz, 2H), 3.27 (td, J=6.7, 13.5 Hz, 1H), 2.52 (br s, 1H), 1.93 (s, 3H), 1.45 (t, J=7.2 Hz, 3H), 1.33 (dd, J=2.1, 6.7 Hz, 6H); $^{19}$F NMR (376 MHz, CDCl$_3$) δ −119.99 (s, 1F) ppm.

Example 140: 6-(2-(Difluoromethyl)phenyl)-2-(4-ethyl-3-(hydroxymethyl)-5-oxo-4,5-dihydro-1H-1,2,4-triazol-1-yl)-3-fluoro-8-isopropyl-1,6-naphthyridin-5(6H)-one

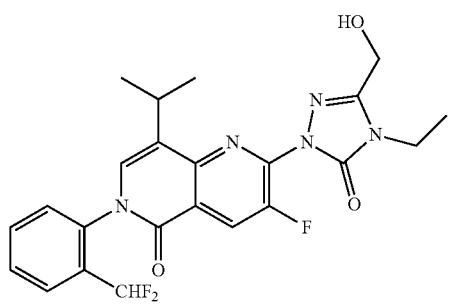 [SMILES: CCn1c(CO)nn(-c2nc3c(C(C)C)cn(-c4ccccc4C(F)F)c(=O)c3cc2F)c1=O]

Step A. 2-(3-((Benzyloxy)methyl)-4-ethyl-5-oxo-4,5-dihydro-1H-1,2,4-triazol-1-yl)-3-fluoro-8-isopropyl-5H-pyrano[4,3-b]pyridin-5-one. To a flask charged with isopropyl 6-(3-((benzyloxy)methyl)-4-ethyl-5-oxo-4,5-dihydro-1H-1,2,4-triazol-1-yl)-2-chloro-5-fluoronicotinate (Intermediate 10, 1 g, 2.23 mmol), DPPF (61.7 mg, 111.30 μmol), [Pd(allyl)Cl]$_2$ (16.3 mg, 44.56 μmol), Cs$_2$CO$_3$ (1.45 g, 4.46 mmol) and 4A MS (1 g) in glovebox was added a solution of 3-methylbutanal (1.19 mL, 11.14 mmol) in dioxane (15 mL) slowly by syringe. The reaction mixture was heated to 100° C. for 16 h. The mixture was filtered and the filtrate was concentrated. The residue was purified by column chromatography (SiO$_2$, gradient elution: 10-25% ethyl acetate in petroleum ether) to give the title compound as light yellow solid (370 mg, 37.6% yield). MS (ESI): mass calcd. for C$_{23}$H$_{23}$FN$_4$O$_4$, 438.2; m/z found, 439.1 [M+H]$^+$. $^1$H NMR (400 MHz, CDCl$_3$) δ 8.37 (d, J=9.2 Hz, 1H), 7.43-7.34 (m, 5H), 7.31 (s, 1H), 4.63 (s, 2H), 4.55 (s, 2H), 3.88 (q, J=7.2 Hz, 2H), 3.44 (td, J=7.0, 13.8 Hz, 1H), 1.38 (t, J=7.2 Hz, 3H), 1.32 (d, J=6.9 Hz, 6H); $^{19}$F NMR (376 MHz, CDCl$_3$) δ −122.48 (s, 1F) ppm.

Step B. 2-(3-((Benzyloxy)methyl)-4-ethyl-5-oxo-4,5-dihydro-1H-1,2,4-triazol-1-yl)-6-(2-(difluoromethyl)phenyl)-3-fluoro-8-isopropyl-1,6-naphthyridin-5(6H)-one. To a solution of 2-(3-((benzyloxy)methyl)-4-ethyl-5-oxo-4,5-dihydro-1H-1,2,4-triazol-1-yl)-3-fluoro-8-isopropyl-5H-pyrano[4,3-b]pyridin-5-one (150 mg, 0.34 mmol) and 2-(difluoromethyl)aniline hydrochloride (152 mg, 0.85 mmol) in anhydrous THF (6 ml) was added a THF (1 M) of LiHMDS (1.01 ml, 1.01 mmol) under nitrogen at −78° C. The reaction mixture was stirred at −78° C. for 0.5 h, and then allowed to warm to room temperature and stirred for overnight. Aqueous HCl (1 M, 0.6 mL) was added. The mixture was poured into water (20 mL) and extracted with DCM (20 mL×3). The combined organic extract was washed with brine (20 mL×2), dried over anhydrous Na$_2$SO$_4$, filtered, and concentrated. The residue was dissolved in AcOH (5 mL) and stirred at 90° C. for overnight. The mixture was poured into water (15 mL) and extracted with ethyl acetate (20 mL×3). The combined organic layer was washed with brine (15 mL×3), dried over anhydrous Na$_2$SO$_4$, filtered, and concentrated. The residue was purified by column chromatography (SiO$_2$, gradient elution: 0-50% ethyl acetate in petroleum ether) to the title compound as light yellow gum (162.8 mg, 82.5% yield). MS (ESI): mass calcd. for C$_{30}$H$_{28}$F$_3$N$_5$O$_3$, 563.2; m/z found, 564.2 [M+H]$^+$. $^1$H NMR (400 MHz, CDCl$_3$) δ 8.53 (d, J=9.7 Hz, 1H), 7.81 (d, J=7.5 Hz, 1H), 7.72-7.57 (m, 2H), 7.44-7.34 (m, 6H), 7.08 (s, 1H), 6.83-6.46 (m, 1H), 4.65 (s, 2H), 4.57 (s, 2H), 3.90 (q, J=7.2 Hz, 2H), 3.67 (td, J=6.7, 13.6 Hz, 1H), 1.40 (t, J=7.2 Hz, 3H), 1.34-1.29 (m, 6H); $^{19}$F NMR (376 MHz, CDCl$_3$) δ −108.02 (br d, J=301.7 Hz, 1F), −121.04 (br d, J=301.7 Hz, 1F), −124.99 (s, 1F) ppm.

Step C. 6-(2-(Difluoromethyl)phenyl)-2-(4-ethyl-3-(hydroxymethyl)-5-oxo-4,5-dihydro-1H-1,2,4-triazol-1-yl)-3-fluoro-8-isopropyl-1,6-naphthyridin-5(6H)-one. To a stirred solution of 2-(3-((benzyloxy)methyl)-4-ethyl-5-oxo-4,5-dihydro-1H-1,2,4-triazol-1-yl)-6-(2-(difluoromethyl)phenyl)-3-fluoro-8-isopropyl-1,6-naphthyridin-5(6H)-one (162.8 mg, 0.28 mmol) in DCM (6 mL) was added BCl$_3$ (1 M in toluene, 1.38 mL, 1.38 mmol) at −78° C. The reaction mixture was stirred at −78° C. for 1 h. MeOH (2 mL) was carefully added. The mixture was diluted with DCM, washed with saturated aqueous NaHCO$_3$ solution. The organic layer was separated, washed with brine, dried over anhydrous Na$_2$SO$_4$, filtered, and concentrated. The residue was purified by preparative reversed phase HPLC (Stationary phase: Boston Prime C$_{18}$, 5 μm, 150×30 mm; Mobile phase: water (0.05% NH$_3$H$_2$O+10 mM NH$_4$HCO$_3$) (A)—MeCN (B), gradient elution: 45-75% B in A over 7 min, flow rate: 25 mL/min) to give the title compound as a white powder (43 mg, yield: 33%). MS (ESI): mass calcd. for C$_{23}$H$_{22}$F$_3$N$_5$O$_3$, 473.2; m/z found, 474.1 [M+H]$^+$. $^1$H NMR (400 MHz, CDCl$_3$) δ 8.53 (d, J=9.5 Hz, 1H), 7.81 (d, J=7.5 Hz, 1H), 7.72-7.60 (m, 2H), 7.38 (d, J=7.5 Hz, 1H), 7.08 (s, 1H), 6.83-6.48 (m, 1H), 4.71 (br d, J=3.3 Hz, 2H), 3.95 (q, J=7.3 Hz, 2H), 3.71-3.62 (m, 1H), 2.32 (br s, 1H), 1.45 (t, J=7.2 Hz, 3H), 1.37-1.27 (m, 6H); $^{19}$F NMR (376 MHz, CDCl$_3$) δ −108.03 (br d, J=301.7 Hz, 1F), −120.92 (br d, J=301.7 Hz, 1F), −125.00 (s, 1F) ppm.

Example 141: 6-(4-Ethyl-3-(hydroxymethyl)-5-oxo-4,5-dihydro-1H-1,2,4-triazol-1-yl)-7-fluoro-2-(2-hydroxy-3-methylpyridin-4-yl)-4-isopropylisoquinolin-1(2H)-one

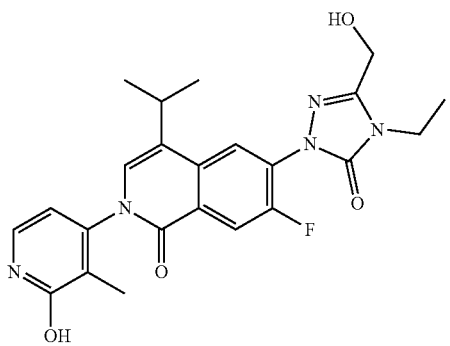 [SMILES: CCn1c(CO)nn(-c2cc3c(C(C)C)cn(-c4ccnc(O)c4C)c(=O)c3cc2F)c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2-methoxy-3-methylpyridin-4-amine instead of 5-chloro-3-methyl-4-amino-1H-pyrazole in Step A; using DCE instead of DCM and heating at 90° C. for 25 h in Step A. MS (ESI): mass calcd. for C$_{23}$H$_{24}$FN$_5$O$_4$, 453.5; m/z found, 454.4 [M+H]$^+$. $^1$H NMR (400 MHz, CDCl$_3$) δ 12.56 (br s, 1H), 8.31 (d, J=11.1 Hz, 1H), 8.12 (d, J=6.9 Hz, 1H), 7.39 (d, J=6.9 Hz, 1H), 6.77 (s, 1H), 6.32 (d, J=6.9 Hz, 1H), 4.70 (s, 2H), 4.03-3.86 (m, 2H), 3.36-3.21 (m, 1H), 3.15 (br s, 1H), 2.01 (s, 3H), 1.44 (t, J=7.2 Hz, 3H), 1.33 (dd, J=3.2, 6.8 Hz, 6H); $^{19}$F NMR (376 MHz, CDCl$_3$) δ −120.09 (s, 1F) ppm.

Example 142: 2-(4-Ethyl-3-(hydroxymethyl)-5-oxo-4,5-dihydro-1H-1,2,4-triazol-1-yl)-3-fluoro-8-isopropyl-6-(o-D$_3$-tolyl)-1,6-naphthyridin-5(6H)-one

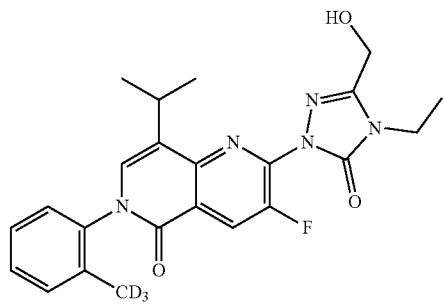 [SMILES: [2H]C([2H])([2H])c1ccccc1-n1cc(C(C)C)c2nc(-n3nc(CO)n(CC)c3=O)c(F)cc2c1=O]

The title compound was prepared in a manner analogous to Example 31, Steps A-B, using 5-((benzyloxy)methyl)-4-ethyl-2-(7-fluoro-4-isopropyl-1-oxo-1H-isochromen-6-yl)-2,4-dihydro-3H-1,2,4-triazol-3-one (Intermediate 4) and using 2-(methyl-D$_3$)aniline instead of 5-chloro-3-methyl-4-amino-1H-pyrazole in Step A. MS (ESI): mass calcd. for C$_{23}$H$_{21}$D$_3$FN$_5$O$_3$, 440.2; m/z found, 441.1 [M+H]$^+$. $^1$H NMR (400 MHz, CDCl$_3$) δ 8.55 (d, J=9.7 Hz, 1H), 7.39 (s, 2H), 7.37-7.28 (m, 1H), 7.27 (s, 1H), 7.04 (s, 1H), 4.70 (br d, J=5.0 Hz, 2H), 3.94 (q, J=7.2 Hz, 2H), 3.75-3.62 (m, 1H), 2.40 (br s, 1H), 1.45 (t, J=7.3 Hz, 3H), 1.31 (dd, J=1.8, 6.9 Hz, 6H); $^{19}$F NMR (376 MHz, CDCl$_3$) δ −125.68 (br s, 1F) ppm.

Biological Data

DHODH inhibitory activities of the compounds of Examples 1-142 were assessed using the following assays. The half maximal inhibitory concentration values (IC$_{50}$) are summarized in Table 3.

Biological Assays

In Vitro Assay: DHODH Enzymatic Assay

The following assay is referred to herein as the "DHODH Enzymatic Assay." To detect DHODH enzyme activities, dichloroindophenol (DCIP) is added as the final electron acceptor in the assay. DCIP can accept electrons from the reduced coenzyme Q generated in the assay, or from dihydroorotate (DHO) via FMN by binding presumably to the ubiquinone pocket. DCIP solutions are blue, with an intense absorbance around 600 nm, but becomes colorless upon reduction (J. Biol. Chem. (1986) 261, 11386). The assay buffer contained 50 nM HEPES, pH 7.5, 150 mM NaCl, 0.5 mM EDTA, and 0.1% Triton X-100 in MilliQ water. Substrate consisting of 20 mM DHO, 5 mM CoQ$_6$, and 1 mM DCIP in assay buffer, initiates the reaction. The assay is run in end-point mode by quenching the reaction with the potent DHODH inhibitor brequinar. Absorbance measurements were obtained using the BMG Phera Star plate-reading spectrophotomer. Purified human DHODH was purchased from Proteros (cat. No. PR-0044). Chemicals were purchased from Sigma-Aldrich, Teknova, and Avanti Polar Lipids. Liquid handling was performed using Labcyte Echo and Formulatrix Tempest.

In Vitro Assay: MOLM-13 Cellular Assay

The following assay is referred to herein as the "MOLM-13 Cellular Assay." MOLM-13 cells (human acute myeloid leukemia cells) were obtained from DSMZ and were maintained in RPMI 1640+Glutamax+25 mM HEPES (Invitrogen, catalog number 72400) supplemented with 10% heat inactivated fetal bovine serum (FBS; Invitrogen, catalog number 16140). The day prior to assay set-up, cells were pelleted, resuspended in fresh media, counted, and cells were plated at 0.4×10$^6$ cell/mL in a T150 flask. On the day of the assay, cells were pelleted, resuspend in fresh media, counted and seeded at 5,000 cells/well in white opaque 96-well tissue culture treated microplates (Perkin Elmer, catalog number 6005680). Cells were exposed to different concentrations of test compounds at 37° C., 5% CO$_2$ for 72 hours immediately after seeding. Cell viability was acquired on a Perkin Elmer Envision 2104 multilabel reader using the CellTiter-Glo assay (Promega) according to the manufacturer's instructions.

TABLE 3

| Example # | Compound Name | MOLM-13 IC$_{50}$ (nM) | hDHODH IC$_{50}$ (nM) |
|---|---|---|---|
| 1 | 6-(4-Ethyl-3-(hydroxymethyl)-5-oxo-4,5-dihydro-1H-1,2,4-triazol-1-yl)-2-(3-fluorophenyl)-4-(prop-1-en-2-yl)isoquinolin-1(2H)-one; | 6 | 9.89 |
| 2 | 6-(4-Ethyl-3-(hydroxymethyl)-5-oxo-4,5-dihydro-1H-1,2,4-triazol-1-yl)-2-(3-fluorophenyl)-4-isopropylisoquinolin-1(2H)-one; | 40 | 75.9 |
| 3 | 2-(2-Chloro-6-fluorophenyl)-6-(4-ethyl-3-(hydroxymethyl)-5-oxo-4,5-dihydro-1H-1,2,4-triazol-1-yl)-4-isopropylisoquinolin-1(2H)-one; | 2 | 3.46 |
| 4 | 6-(4-Ethyl-3-(hydroxymethyl)-5-oxo-4,5-dihydro-1H-1,2,4-triazol-1-yl)-2-(3-fluorophenyl)-4-phenylisoquinolin-1(2H)-one; | 100 | 177 |
| 5 | 2-(2-Chloro-6-fluorophenyl)-6-(4-ethyl-3-(hydroxymethyl)-5-oxo-4,5-dihydro-1H-1,2,4-triazol-1-yl)-4-(prop-1-en-2-yl)isoquinolin-1(2H)-one; | 0.9 | 1.29 |
| 6 | 2-(2-Chloro-6-fluorophenyl)-6-(4-ethyl-3-(hydroxymethyl)-5-oxo-4,5-dihydro-1H-1,2,4-triazol-1-yl)-4-(3,3,3-trifluoroprop-1-en-2-yl)isoquinolin-1(2H)-one; | 1 | 1.94 |
| 7 | 2-(2,6-Dichlorophenyl)-6-(4-ethyl-3-(hydroxymethyl)-5-oxo-4,5-dihydro-1H-1,2,4-triazol-1-yl)-4-(1-methylcyclopropyl)isoquinolin-1(2H)-one; | 2 | 0.965 |
| 8 | 2-(2,6-Dichlorophenyl)-6-(4-ethyl-3-(hydroxymethyl)-5-oxo-4,5-dihydro-1H-1,2,4-triazol-1-yl)-4-(prop-1-en-2-yl)isoquinolin-1(2H)-one; | 0.7 | 0.839 |
| 9 | 2-(2-Chloro-6-fluorophenyl)-4-cyclopropyl-6-(4-ethyl-3-(hydroxymethyl)-5-oxo-4,5-dihydro-1H-1,2,4-triazol-1-yl)isoquinolin-1(2H)-one; | 5 | 11.5 |
| 10 | 2-(2-Chloro-6-fluorophenyl)-6-(4-ethyl-3-(hydroxymethyl)-5-oxo-4,5-dihydro-1H-1,2,4-triazol-1-yl)isoquinolin-1(2H)-one; | 100 | 344 |
| 11 | 2-(2-Chloro-6-fluorophenyl)-6-(4-ethyl-3-(hydroxymethyl)-5-oxo-4,5-dihydro-1H-1,2,4-triazol-1-yl)-7-fluoro-4-isopropylisoquinolin-1(2H)-one; | 0.2 | 0.222 |
| 12 | 6-(4-Ethyl-3-(hydroxymethyl)-5-oxo-4,5-dihydro-1H-1,2,4-triazol-1-yl)-4-(prop-1-en-2-yl)-2-(2-(trifluoromethyl)phenyl)isoquinolin-1(2H)-one; | 2 | 2.29 |
| 13 | 2-(6-(4-Ethyl-3-(hydroxymethyl)-5-oxo-4,5-dihydro-1H-1,2,4-triazol-1-yl)-1-oxo-4-(prop-1-en-2-yl)isoquinolin-2(1H)-yl)benzonitrile; | 6 | 5.49 |
| 14 | 2-(2-Chlorophenyl)-6-(4-ethyl-3-(hydroxymethyl)-5-oxo-4,5-dihydro-1H-1,2,4-triazol-1-yl)-4-(prop-1-en-2-yl)isoquinolin-1(2H)-one; | 0.4 | 0.724 |
| 15 | 6-(4-Ethyl-3-(hydroxymethyl)-5-oxo-4,5-dihydro-1H-1,2,4-triazol-1-yl)-4-(prop-1-en-2-yl)-2-(o-tolyl)isoquinolin-1(2H)-one; | 0.4 | 0.634 |
| 16 | 6-(4-Ethyl-3-(hydroxymethyl)-5-oxo-4,5-dihydro-1H-1,2,4-triazol-1-yl)-2-(2-fluoro-4-nitrophenyl)-4-iodoisoquinolin-1(2H)-one; | 300 | 1183 |
| 17 | 2-(2-Chlorophenyl)-6-(4-ethyl-3-(hydroxymethyl)-5-oxo-4,5-dihydro-1H-1,2,4-triazol-1-yl)-4-isopropylphthalazin-1(2H)-one; | 3 | 3.21 |
| 18 | 6-(4-Ethyl-3-(hydroxymethyl)-5-oxo-4,5-dihydro-1H-1,2,4-triazol-1-yl)-2-(3-fluorophenyl)-4-isopropylphthalazin-1(2H)-one; | 30 | 80.7 |
| 19 | 2-(2-Chloro-6-fluorophenyl)-6-(4-ethyl-3-(hydroxymethyl)-5-oxo-4,5-dihydro-1H-1,2,4-triazol-1-yl)-4-isopropylphthalazin-1(2H)-one; | 4 | 4.96 |
| 20 | 4-Ethyl-6-(4-ethyl-3-(hydroxymethyl)-5-oxo-4,5-dihydro-1H-1,2,4-triazol-1-yl)-2-(3-fluorophenyl)phthalazin-1(2H)-one; | 100 | 83.5 |
| 21 | 4-Ethyl-6-(4-ethyl-3-(hydroxymethyl)-5-oxo-4,5-dihydro-1H-1,2,4-triazol-1-yl)-2-(o-tolyl)phthalazin-1(2H)-one; | 10 | 31.2 |
| 22 | 6-(4-Ethyl-3-(hydroxymethyl)-5-oxo-4,5-dihydro-1H-1,2,4-triazol-1-yl)-7-fluoro-4-isopropyl-2-(o-tolyl)isoquinolin-1(2H)-one; | 0.2 | 0.396 |
| 23 | 2-(2-Chloro-4-methylpyridin-3-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; | 3 | 3.57 |

TABLE 3-continued

| Example # | Compound Name | MOLM-13 IC$_{50}$ (nM) | hDHODH IC$_{50}$ (nM) |
|---|---|---|---|
| 24 | 2-(2-Chloro-6-fluorophenyl)-6-(4-ethyl-3-(hydroxymethyl)-5-oxo-4,5-dihydro-1H-1,2,4-triazol-1-yl)-4-(1-methylcyclopropyl)isoquinolin-1(2H)-one; | 1 | 1.65 |
| 25 | 6-(4-Ethyl-3-(hydroxymethyl)-5-oxo-4,5-dihydro-1H-1,2,4-triazol-1-yl)-2-(3-fluorophenyl)-4-(2-hydroxypropan-2-yl)isoquinolin-1(2H)-one; | NT | 4264 |
| 26 | 4-(Dimethylamino)-6-(4-ethyl-3-(hydroxymethyl)-5-oxo-4,5-dihydro-1H-1,2,4-triazol-1-yl)-2-(o-tolyl)isoquinolin-1(2H)-one; | 20 | 46.5 |
| 27 | 2-(2-Chloro-6-fluorophenyl)-6-(4-ethyl-3-(hydroxymethyl)-5-oxo-4,5-dihydro-1H-1,2,4-triazol-1-yl)-7-fluoro-4-(prop-1-en-2-yl)phthalazin-1(2H)-one; | NT | 0.32 |
| 28 | 2-(2-Chloro-6-fluorophenyl)-7-(4-ethyl-3-(hydroxymethyl)-5-oxo-4,5-dihydro-1H-1,2,4-triazol-1-yl)-6-fluoro-4-(prop-1-en-2-yl)phthalazin-1(2H)-one; | NT | 5.03 |
| 29 | 2-(2-Chloro-6-fluorophenyl)-6-(4-ethyl-3-(hydroxymethyl)-5-oxo-4,5-dihydro-1H-1,2,4-triazol-1-yl)-7-methoxy-4-(prop-1-en-2-yl)phthalazin-1(2H)-one; | NT | 82.6 |
| 30 | 2-(2-Chloro-6-fluorophenyl)-7-(4-ethyl-3-(hydroxymethyl)-5-oxo-4,5-dihydro-1H-1,2,4-triazol-1-yl)-6-methoxy-4-(prop-1-en-2-yl)phthalazin-1(2H)-one; | NT | 3480 |
| 31 | 2-(5-Chloro-3-methyl-1H-pyrazol-4-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; | 6 | 0.764 |
| 32 | 2-(4-Ethyl-3-(hydroxymethyl)-5-oxo-4,5-dihydro-1H-1,2,4-triazol-1-yl)-3-fluoro-8-(prop-1-en-2-yl)-6-(o-tolyl)-1,6-naphthyridin-5(6H)-one; | 2 | 1.01 |
| 33 | 2-(4-Ethyl-3-(hydroxymethyl)-5-oxo-4,5-dihydro-1H-1,2,4-triazol-1-yl)-3-fluoro-8-methyl-6-(o-tolyl)pyrido[2,3-d]pyridazin-5(6H)-one; | >100 | 240 |
| 34 | 2-(4-Ethyl-3-(hydroxymethyl)-5-oxo-4,5-dihydro-1H-1,2,4-triazol-1-yl)-3-fluoro-8-isopropyl-6-(o-tolyl)pyrido[2,3-d]pyridazin-5(6H)-one; | 4 | 1.97 |
| 35 | 6-(2-Chloro-6-fluorophenyl)-2-(4-ethyl-3-(hydroxymethyl)-5-oxo-4,5-dihydro-1H-1,2,4-triazol-1-yl)-3-fluoro-8-(prop-1-en-2-yl)-1,6-naphthyridin-5(6H)-one; | 1 | 1.15 |
| 36 | 6-(2-Chloro-6-fluorophenyl)-2-(4-ethyl-3-(hydroxymethyl)-5-oxo-4,5-dihydro-1H-1,2,4-triazol-1-yl)-3-fluoro-8-isopropyl-1,6-naphthyridin-5(6H)-one; | 0.4 | 0.356 |
| 37 | (S)-2-(4-Ethyl-3-(hydroxymethyl)-5-oxo-4,5-dihydro-1H-1,2,4-triazol-1-yl)-3-fluoro-6-(o-tolyl)-8-(1,1,1-trifluoropropan-2-yl)-1,6-naphthyridin-5(6H)-one; | 3 | 1.88 |
| 38 | (R)-2-(4-Ethyl-3-(hydroxymethyl)-5-oxo-4,5-dihydro-1H-1,2,4-triazol-1-yl)-3-fluoro-6-(o-tolyl)-8-(1,1,1-trifluoropropan-2-yl)-1,6-naphthyridin-5(6H)-one; | 0.5 | 0.464 |
| 39 | 6-(4-Ethyl-3-(hydroxymethyl)-5-oxo-4,5-dihydro-1H-1,2,4-triazol-1-yl)-7-fluoro-4-isopropyl-2-(4-methylthiazol-5-yl)isoquinolin-1(2H)-one; | 40 | 13 |
| 40 | 2-(4-Ethyl-3-(hydroxymethyl)-5-oxo-4,5-dihydro-1H-1,2,4-triazol-1-yl)-3-fluoro-8-isopropyl-6-(o-tolyl)-1,6-naphthyridin-5(6H)-one; | 0.8 | 0.802 |
| 41 | 6-(4-Ethyl-3-(hydroxymethyl)-5-oxo-4,5-dihydro-1H-1,2,4-triazol-1-yl)-7-fluoro-2-(2-fluoro-5-methylphenyl)-4-isopropylisoquinolin-1(2H)-one; | 2 | 2.98 |
| 42 | 6-(4-Ethyl-3-(hydroxymethyl)-5-oxo-4,5-dihydro-1H-1,2,4-triazol-1-yl)-7-fluoro-2-(2-fluoro-5-methylphenyl)-4-(prop-1-en-2-yl)isoquinolin-1(2H)-one; | 0.9 | 1.69 |
| 43 | 2-(2-Chloro-5-methylphenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; | 0.4 | 0.917 |
| 44 | 6-(4-Ethyl-3-(hydroxymethyl)-5-oxo-4,5-dihydro-1H-1,2,4-triazol-1-yl)-7-fluoro-2-(2-fluoro-5-methoxyphenyl)-4-(prop-1-en-2-yl)isoquinolin-1(2H)-one; | 0.7 | 2.22 |

TABLE 3-continued

| Example # | Compound Name | MOLM-13 IC$_{50}$ (nM) | hDHODH IC$_{50}$ (nM) |
|---|---|---|---|
| 45 | 2-(2-Chlorophenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; | 0.3 | 1.41 |
| 46 | 6-(4-Ethyl-3-(hydroxymethyl)-5-oxo-4,5-dihydro-1H-1,2,4-triazol-1-yl)-7-fluoro-4-(prop-1-en-2-yl)-2-(o-tolyl)isoquinolin-1(2H)-one; | 0.3 | 0.746 |
| 47 | 2-(2-Chloro-5-methoxyphenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; | 0.7 | 1.21 |
| 48 | racemic-4-(sec-Butyl)-2-(2-chloro-6-fluorophenyl)-6-(4-ethyl-3-(hydroxymethyl)-5-oxo-4,5-dihydro-1H-1,2,4-triazol-1-yl)-7-fluoroisoquinolin-1(2H)-one; | 0.6 | 0.907 |
| 49 | 2-(3-Chloro-6-methoxypyridin-2-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; | 2 | 1.09 |
| 50 | 6-(4-Ethyl-3-(hydroxymethyl)-5-oxo-4,5-dihydro-1H-1,2,4-triazol-1-yl)-7-fluoro-4-isopropyl-2-(2-methoxy-4-methylpyridin-3-yl)isoquinolin-1(2H)-one; | 7 | 2.75 |
| 51 | 2-(2-Chloro-6-fluoro-3-methoxyphenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; | 0.1 | 0.267 |
| 52 | 2-(2-Chloro-6-fluorophenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; | 0.1 | 0.265 |
| 53 | 6-(4-Ethyl-3-(hydroxymethyl)-5-oxo-4,5-dihydro-1H-1,2,4-triazol-1-yl)-7-fluoro-4-isopropyl-2-(o-tolyl)phthalazin-1(2H)-one; | 0.7 | 0.778 |
| 54 | 2-(2-Chloro-6-fluorophenyl)-6-(4-ethyl-3-(hydroxymethyl)-5-oxo-4,5-dihydro-1H-1,2,4-triazol-1-yl)-7-fluoro-4-isopropylphthalazin-1(2H)-one; | 0.4 | 0.433 |
| 55 | Racemic 6-(4-Ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)phthalazin-1(2H)-one; | 0.5 | 1.2 |
| 56 | (S*)-6-(4-Ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)phthalazin-1(2H)-one; | 2 | 2.31 |
| 57 | (R*)-6-(4-Ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)phthalazin-1(2H)-one; | 1 | 1.15 |
| 58 | 2-(2-Chloro-6-fluorophenyl)-6-(4-ethyl-3-(hydroxymethyl)-5-oxo-4,5-dihydro-1H-1,2,4-triazol-1-yl)-7-fluoro-4-(1-methylcyclopropyl)isoquinolin-1(2H)-one; | 4 | 8.81 |
| 59 | 6-(4-Ethyl-3-(hydroxymethyl)-5-oxo-4,5-dihydro-1H-1,2,4-triazol-1-yl)-7-fluoro-2-(2-methoxy-4-methylpyridin-3-yl)-4-(prop-1-en-2-yl)isoquinolin-1(2H)-one; | 5 | 2.23 |
| 60 | 2-(5-Chloro-3-methyl-1H-pyrazol-4-yl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; | 4 | 0.286 |
| 61 | 2-(3-Chloro-2-methoxy-5-methylpyridin-4-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; | 2 | 0.617 |
| 62 | 2-(3-Chloro-2-methoxy-5-methylpyridin-4-yl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; | 2 | 0.836 |
| 63 | 6-(4-Ethyl-3-(hydroxymethyl)-5-oxo-4,5-dihydro-1H-1,2,4-triazol-1-yl)-7-fluoro-2-(2-fluoro-5-methoxyphenyl)-4-isopropylisoquinolin-1(2H)-one; | 2 | 2.76 |
| 64 | 6-(4-Ethyl-3-(hydroxymethyl)-5-oxo-4,5-dihydro-1H-1,2,4-triazol-1-yl)-7-fluoro-2-(4-fluoro-2-methylphenyl)-4-isopropylisoquinolin-1(2H)-one; | 0.5 | 0.459 |
| 65 | 2-(2-Chloro-3-(2-hydroxyethoxy)phenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; | 20 | 1.65 |

TABLE 3-continued

| Example # | Compound Name | MOLM-13 IC$_{50}$ (nM) | hDHODH IC$_{50}$ (nM) |
|---|---|---|---|
| 66 | 6-(4-Ethyl-3-(hydroxymethyl)-5-oxo-4,5-dihydro-1H-1,2,4-triazol-1-yl)-7-fluoro-2-(2-fluorophenyl)-4-(prop-1-en-2-yl)isoquinolin-1(2H)-one; | 0.3 | <0.169 |
| 67 | 6-(4-Ethyl-3-(hydroxymethyl)-5-oxo-4,5-dihydro-1H-1,2,4-triazol-1-yl)-7-fluoro-2-(5-fluoro-2-methylphenyl)-4-isopropylisoquinolin-1(2H)-one; | 0.9 | 0.605 |
| 68 | 2-(2,5-Difluorophenyl)-6-(4-ethyl-3-(hydroxymethyl)-5-oxo-4,5-dihydro-1H-1,2,4-triazol-1-yl)-7-fluoro-4-isopropylisoquinolin-1(2H)-one; | 3 | 2.2 |
| 69 | 6-(4-Ethyl-3-(hydroxymethyl)-5-oxo-4,5-dihydro-1H-1,2,4-triazol-1-yl)-7-fluoro-2-(2-fluoro-6-methylphenyl)-4-isopropylisoquinolin-1(2H)-one; | 0.7 | 0.435 |
| 70 | 2-(2-Chloro-3-methoxyphenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; | 0.4 | 0.24 |
| 71 | 6-(4-Ethyl-3-(hydroxymethyl)-5-oxo-4,5-dihydro-1H-1,2,4-triazol-1-yl)-7-fluoro-2-(2-methoxy-3,5-dimethylpyridin-4-yl)-4-(prop-1-en-2-yl)isoquinolin-1(2H)-one; | 10 | 2.02 |
| 72 | 2-(2,5-Difluorophenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; | 2 | 0.946 |
| 73 | 6-(4-Ethyl-3-(hydroxymethyl)-5-oxo-4,5-dihydro-1H-1,2,4-triazol-1-yl)-7-fluoro-2-(2-fluoro-6-methylphenyl)-4-(prop-1-en-2-yl)isoquinolin-1(2H)-one; | 0.7 | 0.562 |
| 74 | 6-(4-Ethyl-3-(hydroxymethyl)-5-oxo-4,5-dihydro-1H-1,2,4-triazol-1-yl)-7-fluoro-2-(3-fluoro-2-methylphenyl)-4-isopropylisoquinolin-1(2H)-one; | 7 | 2.24 |
| 75 | 2-(2,5-Dimethylphenyl)-6-(4-ethyl-3-(hydroxymethyl)-5-oxo-4,5-dihydro-1H-1,2,4-triazol-1-yl)-7-fluoro-4-isopropylisoquinolin-1(2H)-one; | 1 | 0.58 |
| 76 | 6-(4-Ethyl-3-(hydroxymethyl)-5-oxo-4,5-dihydro-1H-1,2,4-triazol-1-yl)-7-fluoro-2-(4-fluoro-2-methylphenyl)-4-(prop-1-en-2-yl)isoquinolin-1(2H)-one; | 4 | 1.5 |
| 77 | 6-(4-Ethyl-3-(hydroxymethyl)-5-oxo-4,5-dihydro-1H-1,2,4-triazol-1-yl)-7-fluoro-2-(2-fluorophenyl)-4-isopropylisoquinolin-1(2H)-one; | 3 | 1.86 |
| 78 | 6-(4-Ethyl-3-(hydroxymethyl)-5-oxo-4,5-dihydro-1H-1,2,4-triazol-1-yl)-7-fluoro-4-isopropyl-2-(2-methoxy-3,5-dimethylpyridin-4-yl)isoquinolin-1(2H)-one; | 20 | 2.34 |
| 79 | 6-(4-Ethyl-3-(hydroxymethyl)-5-oxo-4,5-dihydro-1H-1,2,4-triazol-1-yl)-7-methyl-4-(prop-1-en-2-yl)-2-(o-tolyl)isoquinolin-1(2H)-one; | 10 | 17.1 |
| 80 | 2-(2-Chloro-6-fluoro-3-methoxyphenyl)-6-(4-ethyl-3-(hydroxymethyl)-5-oxo-4,5-dihydro-1H-1,2,4-triazol-1-yl)-7-fluoro-4-isopropylisoquinolin-1(2H)-one; | 0.3 | 0.273 |
| 81 | 6-(4-Ethyl-3-(hydroxymethyl)-5-oxo-4,5-dihydro-1H-1,2,4-triazol-1-yl)-7-fluoro-2-(o-tolyl)-4-(3,3,3-trifluoroprop-1-en-2-yl)isoquinolin-1(2H)-one; | 0.3 | 0.226 |
| 82 | 6-(4-Ethyl-3-(hydroxymethyl)-5-oxo-4,5-dihydro-1H-1,2,4-triazol-1-yl)-7-fluoro-2-(5-fluoro-2-methylphenyl)-4-(prop-1-en-2-yl)isoquinolin-1(2H)-one; | 0.09 | 0.249 |
| 83 | 6-(4-Ethyl-3-(hydroxymethyl)-5-oxo-4,5-dihydro-1H-1,2,4-triazol-1-yl)-7-fluoro-2-(2-methoxyphenyl)-4-(prop-1-en-2-yl)isoquinolin-1(2H)-one; | 0.2 | 0.444 |
| 84 | 2-(2-Chloro-5-methylpyridin-3-yl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; | 70 | 6.58 |
| 85 | 6-(4-Ethyl-3-(hydroxymethyl)-5-oxo-4,5-dihydro-1H-1,2,4-triazol-1-yl)-7-fluoro-2-(5-fluoro-2-methoxypyridin-4-yl)-4-(prop-1-en-2-yl)isoquinolin-1(2H)-one; | 20 | 6.55 |
| 86 | 6-(4-Ethyl-3-(hydroxymethyl)-5-oxo-4,5-dihydro-1H-1,2,4-triazol-1-yl)-7-fluoro-2-(3-fluoro-2-methylphenyl)-4-(prop-1-en-2-yl)isoquinolin-1(2H)-one; | 3 | 1.19 |

TABLE 3-continued

| Example # | Compound Name | MOLM-13 IC$_{50}$ (nM) | hDHODH IC$_{50}$ (nM) |
|---|---|---|---|
| 87 | 2-(2,5-Dimethylphenyl)-6-(4-ethyl-3-(hydroxymethyl)-5-oxo-4,5-dihydro-1H-1,2,4-triazol-1-yl)-7-fluoro-4-(prop-1-en-2-yl)isoquinolin-1(2H)-one; | 0.9 | 0.292 |
| 88 | Racemic-6-(4-Ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)isoquinolin-1(2H)-one; | 0.9 | 0.52 |
| 89 | 6-(4-Ethyl-3-(hydroxymethyl)-5-oxo-4,5-dihydro-1H-1,2,4-triazol-1-yl)-2-(2-ethylphenyl)-7-fluoro-4-isopropylisoquinolin-1(2H)-one; | 2 | 1.21 |
| 90 | 6-(4-Ethyl-3-(hydroxymethyl)-5-oxo-4,5-dihydro-1H-1,2,4-triazol-1-yl)-7-fluoro-4-isopropyl-2-(2-methoxypyridin-3-yl)isoquinolin-1(2H)-one; | NT | 20.7 |
| 91 | 6-(4-Ethyl-3-(hydroxymethyl)-5-oxo-4,5-dihydro-1H-1,2,4-triazol-1-yl)-7-fluoro-2-(5-fluoro-2-methoxypyridin-4-yl)-4-isopropylisoquinolin-1(2H)-one; | 30 | 6.05 |
| 92 | 2-(2-Chloro-5-methylpyridin-3-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; | >100 | 14.8 |
| 93 | 6-(4-Ethyl-3-(hydroxymethyl)-5-oxo-4,5-dihydro-1H-1,2,4-triazol-1-yl)-7-fluoro-4-isopropyl-2-(2-(methyl-d$_3$)phenyl)isoquinolin-1(2H)-one; | 0.6 | 0.463 |
| 94 | 6-(4-Ethyl-3-(hydroxymethyl)-5-oxo-4,5-dihydro-1H-1,2,4-triazol-1-yl)-7-fluoro-4-isopropyl-2-(4-methylpyrimidin-5-yl)isoquinolin-1(2H)-one; | >100 | 566 |
| 95 | 6-(4-Ethyl-3-(hydroxymethyl)-5-oxo-4,5-dihydro-1H-1,2,4-triazol-1-yl)-7-fluoro-4-isopropyl-2-(2-methoxyphenyl)isoquinolin-1(2H)-one; | 1 | 0.772 |
| 96 | 6-(4-Ethyl-3-(hydroxymethyl)-5-oxo-4,5-dihydro-1H-1,2,4-triazol-1-yl)-7-fluoro-2-(3-fluoro-6-methoxypyridin-2-yl)-4-isopropylisoquinolin-1(2H)-one; | 9 | 6.14 |
| 97 | 6-(4-Ethyl-3-(hydroxymethyl)-5-oxo-4,5-dihydro-1H-1,2,4-triazol-1-yl)-7-fluoro-4-isopropyl-2-(3-methylpyrazin-2-yl)isoquinolin-1(2H)-one; | >100 | >10000 |
| 98 | 2-(2-Chloro-5-methylpyridin-3-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; | 50 | 6.29 |
| 99 | 2-(4-Ethyl-3-(hydroxymethyl)-5-oxo-4,5-dihydro-1H-1,2,4-triazol-1-yl)-3-fluoro-6-(2-fluoro-5-methylphenyl)-8-isopropyl-1,6-naphthyridin-5(6H)-one; | 7 | 6.1 |
| 100 | 6-(4-Ethyl-3-(hydroxymethyl)-5-oxo-4,5-dihydro-1H-1,2,4-triazol-1-yl)-7-fluoro-4-isopropyl-2-(4-methylpyridazin-3-yl)isoquinolin-1(2H)-one; | >100 | 70.7 |
| 101 | (S)-6-(4-Ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)isoquinolin-1(2H)-one; | 0.4 | 1.19 |
| 102 | (R)-6-(4-Ethyl-3-(hydroxymethyl)-5-oxo-4,5-dihydro-1H-1,2,4-triazol-1-yl)-7-fluoro-2-(o-tolyl)-4-(1,1,1-trifluoropropan-2-yl)isoquinolin-1(2H)-one; | 0.3 | 0.26 |
| 103 | 6-(4-Ethyl-3-(hydroxymethyl)-5-oxo-4,5-dihydro-1H-1,2,4-triazol-1-yl)-7-fluoro-4-isopropyl-2-(2-(trifluoromethyl)phenyl)isoquinolin-1(2H)-one; | 0.3 | 0.669 |
| 104 | 6-(4-Ethyl-3-(hydroxymethyl)-5-oxo-4,5-dihydro-1H-1,2,4-triazol-1-yl)-7-fluoro-4-isopropyl-2-(5-methylpyrimidin-4-yl)isoquinolin-1(2H)-one; | >100 | 43.5 |
| 105 | 2-(2-(Difluoromethyl)phenyl)-6-(4-ethyl-3-(hydroxymethyl)-5-oxo-4,5-dihydro-1H-1,2,4-triazol-1-yl)-7-fluoro-4-isopropylisoquinolin-1(2H)-one; | 0.2 | 0.528 |
| 106 | 2-(3-Chloro-2-methoxypyridin-4-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; | 10 | 4.88 |
| 107 | 2-Cyclohexyl-6-(4-ethyl-3-(hydroxymethyl)-5-oxo-4,5-dihydro-1H-1,2,4-triazol-1-yl)-7-fluoro-4-isopropylisoquinolin-1(2H)-one; | 6 | 2.07 |
| 108 | 2-(3-Chloro-6-methylpyridin-2-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; | 6 | 3.07 |

TABLE 3-continued

| Example # | Compound Name | MOLM-13 IC$_{50}$ (nM) | hDHODH IC$_{50}$ (nM) |
|---|---|---|---|
| 109 | 2-Cyclopentyl-6-(4-ethyl-3-(hydroxymethyl)-5-oxo-4,5-dihydro-1H-1,2,4-triazol-1-yl)-7-fluoro-4-isopropylisoquinolin-1(2H)-one; | 9 | 5.37 |
| 110 | 2-(3-Chloro-4-methoxypyridin-2-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; | 20 | 10.4 |
| 111 | 6-(4-Ethyl-3-(hydroxymethyl)-5-oxo-4,5-dihydro-1H-1,2,4-triazol-1-yl)-7-fluoro-4-isopropyl-2-((1R,2S)-2-methylcyclohexyl)isoquinolin-1(2H)-one; | 0.7 | 3.54 |
| 112 | 2-(1,3-Dimethoxypropan-2-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; | 30 | 35.3 |
| 113 | 6-(4-Ethyl-3-(hydroxymethyl)-5-oxo-4,5-dihydro-1H-1,2,4-triazol-1-yl)-7-fluoro-4-isopropyl-2-(2-methoxy-5-methylpyridin-4-yl)isoquinolin-1(2H)-one; | 3 | 2.1 |
| 114 | 6-(4-Ethyl-3-(hydroxymethyl)-5-oxo-4,5-dihydro-1H-1,2,4-triazol-1-yl)-7-fluoro-4-isopropyl-2-((1S,2R)-2-methylcyclohexyl)isoquinolin-1(2H)-one; | 3 | 11.6 |
| 115 | 2-(Cyclopropylmethyl)-6-(4-ethyl-3-(hydroxymethyl)-5-oxo-4,5-dihydro-1H-1,2,4-triazol-1-yl)-7-fluoro-4-isopropylisoquinolin-1(2H)-one; | 80 | 50.9 |
| 116 | 6-(4-Ethyl-3-(hydroxymethyl)-5-oxo-4,5-dihydro-1H-1,2,4-triazol-1-yl)-7-fluoro-4-isopropyl-2-(1-methoxybutan-2-yl)isoquinolin-1(2H)-one; | 20 | 30.7 |
| 117 | 2-(2-Chlorophenyl)-6-(4-ethyl-3-(hydroxymethyl)-5-oxo-4,5-dihydro-1H-1,2,4-triazol-1-yl)-7-fluoro-4-isopropylisoquinolin-1(2H)-one; | 0.3 | 0.418 |
| 118 | 6-(4-Ethyl-3-(hydroxymethyl)-5-oxo-4,5-dihydro-1H-1,2,4-triazol-1-yl)-7-fluoro-4-isopropyl-2-(3-methylpyridin-2-yl)isoquinolin-1(2H)-one; | 10 | 14.8 |
| 119 | Racemic 6-(4-Ethyl-3-(hydroxymethyl)-5-oxo-4,5-dihydro-1H-1,2,4-triazol-1-yl)-7-fluoro-4-isopropyl-2-((cis)-3-methoxycyclopentyl)isoquinolin-1(2H)-one; | 10 | 10.1 |
| 120 | 6-(4-Ethyl-3-(hydroxymethyl)-5-oxo-4,5-dihydro-1H-1,2,4-triazol-1-yl)-7-fluoro-4-isopropyl-2-((1R*,2R*)-2-methylcyclohexyl)isoquinolin-1(2H)-one; | 1 | 1.68 |
| 121 | 6-(4-Ethyl-3-(hydroxymethyl)-5-oxo-4,5-dihydro-1H-1,2,4-triazol-1-yl)-7-fluoro-4-isopropyl-2-((1S*,2S*)-2-methylcyclohexyl)isoquinolin-1(2H)-one; | 4 | 7.41 |
| 122 | 6-(4-Ethyl-3-(hydroxymethyl)-5-oxo-4,5-dihydro-1H-1,2,4-triazol-1-yl)-7-fluoro-4-isopropyl-2-(pentan-3-yl)isoquinolin-1(2H)-one; | 10 | 13.4 |
| 123 | 6-(4-Ethyl-3-(hydroxymethyl)-5-oxo-4,5-dihydro-1H-1,2,4-triazol-1-yl)-7-fluoro-4-isopropyl-2-((1R*,2R*)-2-methylcyclopentyl)isoquinolin-1(2H)-one; | 9 | 16.8 |
| 124 | 6-(4-Ethyl-3-(hydroxymethyl)-5-oxo-4,5-dihydro-1H-1,2,4-triazol-1-yl)-7-fluoro-4-isopropyl-2-((1S*,2S*)-2-methylcyclopentyl)isoquinolin-1(2H)-one; | 0.9 | 1.36 |
| 125 | 6-(4-Ethyl-3-(hydroxymethyl)-5-oxo-4,5-dihydro-1H-1,2,4-triazol-1-yl)-7-fluoro-4-isopropyl-2-((1R*,2S*)-2-methylcyclopentyl)isoquinolin-1(2H)-one; | 6 | 15.5 |
| 126 | 6-(4-Ethyl-3-(hydroxymethyl)-5-oxo-4,5-dihydro-1H-1,2,4-triazol-1-yl)-7-fluoro-4-isopropyl-2-((1S*,2R*)-2-methylcyclopentyl)isoquinolin-1(2H)-one; | 1 | 1.32 |
| 127 | Racemic 6-(4-Ethyl-3-(hydroxymethyl)-5-oxo-4,5-dihydro-1H-1,2,4-triazol-1-yl)-7-fluoro-4-isopropyl-2-((cis)-3-methoxycyclohexyl)isoquinolin-1(2H)-one; | >100 | 181 |
| 128 | 2-(Bicyclo[2.2.1]heptan-1-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; | 7 | 19 |

TABLE 3-continued

| Example # | Compound Name | MOLM-13 IC$_{50}$ (nM) | hDHODH IC$_{50}$ (nM) |
|---|---|---|---|
| 129 | 6-(4-Ethyl-3-(hydroxymethyl)-5-oxo-4,5-dihydro-1H-1,2,4-triazol-1-yl)-7-fluoro-4-isopropyl-2-(2-methoxy-3-methylpyridin-4-yl)isoquinolin-1(2H)-one; | 50 | 29.2 |
| 130 | 2-(4-Ethyl-3-(hydroxymethyl)-5-oxo-4,5-dihydro-1H-1,2,4-triazol-1-yl)-3-fluoro-8-isopropyl-6-(2-methoxyphenyl)-1,6-naphthyridin-5(6H)-one; | 0.9 | 0.885 |
| 131 | 6-(4-Ethyl-3-(hydroxymethyl)-5-oxo-4,5-dihydro-1H-1,2,4-triazol-1-yl)-7-fluoro-4-isopropyl-2-(3-methylisothiazol-4-yl)isoquinolin-1(2H)-one; | 50 | 33.7 |
| 132 | 6-(4-Ethyl-3-(hydroxymethyl)-5-oxo-4,5-dihydro-1H-1,2,4-triazol-1-yl)-7-fluoro-4-isopropyl-2-(5-methylisothiazol-4-yl)isoquinolin-1(2H)-one; | 4 | 3.72 |
| 133 | 2-(4-Ethyl-3-(hydroxymethyl)-5-oxo-4,5-dihydro-1H-1,2,4-triazol-1-yl)-3-fluoro-8-isopropyl-6-(2-(trifluoromethyl)phenyl)-1,6-naphthyridin-5(6H)-one; | 2 | NT |
| 134 | 2-(3,6-Dimethylpyridin-2-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; | 8 | NT |
| 135 | 2-(2,5-Dimethylpyridin-4-yl)-6-(4-ethyl-3-(hydroxymethyl)-5-oxo-4,5-dihydro-1H-1,2,4-triazol-1-yl)-7-fluoro-4-isopropylisoquinolin-1(2H)-one; | 50 | 6.93 |
| 136 | 6-(4-Ethyl-3-(hydroxymethyl)-5-oxo-4,5-dihydro-1H-1,2,4-triazol-1-yl)-7-fluoro-4-isopropyl-2-(4-methylpyridin-3-yl)isoquinolin-1(2H)-one; | 8 | 4.79 |
| 137 | 6-(4-Ethyl-3-(hydroxymethyl)-5-oxo-4,5-dihydro-1H-1,2,4-triazol-1-yl)-7-fluoro-4-isopropyl-2-(3-methylpyridin-4-yl)isoquinolin-1(2H)-one; | 8 | 8.08 |
| 138 | 6-(4-Ethyl-3-(hydroxymethyl)-5-oxo-4,5-dihydro-1H-1,2,4-triazol-1-yl)-7-fluoro-4-isopropyl-2-(2-methylpyridin-3-yl)isoquinolin-1(2H)-one; | >100 | 80.4 |
| 139 | 6-(4-Ethyl-3-(hydroxymethyl)-5-oxo-4,5-dihydro-1H-1,2,4-triazol-1-yl)-7-fluoro-2-(2-hydroxy-5-methylpyridin-4-yl)-4-isopropylisoquinolin-1(2H)-one; | >100 | 35.4 |
| 140 | 6-(2-(Difluoromethyl)phenyl)-2-(4-ethyl-3-(hydroxymethyl)-5-oxo-4,5-dihydro-1H-1,2,4-triazol-1-yl)-3-fluoro-8-isopropyl-1,6-naphthyridin-5(6H)-one; | 1 | 1.13 |
| 141 | 6-(4-Ethyl-3-(hydroxymethyl)-5-oxo-4,5-dihydro-1H-1,2,4-triazol-1-yl)-7-fluoro-2-(2-hydroxy-3-methylpyridin-4-yl)-4-isopropylisoquinolin-1(2H)-one; and | >100 | 10.5 |
| 142 | 2-(4-Ethyl-3-(hydroxymethyl)-5-oxo-4,5-dihydro-1H-1,2,4-triazol-1-yl)-3-fluoro-8-isopropyl-6-(o-D$_3$-tolyl)-1,6-naphthyridin-5(6H)-one. | 0.4 | 0.623 |

NT means Not Tested.

An additional embodiment of the current invention is a compound selected from those compounds shown above in Table 3 which have an IC$_{50}$ (nM) value of 0.7 or less according to the DHODH Enzymatic Assay, and/or an IC$_{50}$ (nM) value of 0.6 or less according to the MOLM-13 Cellular Assay; and, optionally, one or more of pharmaceutically acceptable salts, isotopes, N-oxides, solvates, and stereoisomers thereof. An additional embodiment of the current invention is a compound selected from those compounds shown above in Table 3 which have an IC$_{50}$ (nM) value of 0.5 or less according to the DHODH Enzymatic Assay, and/or an IC$_{50}$ (nM) value of 0.4 or less according to the MOLM-13 Cellular Assay; and, optionally, one or more of pharmaceutically acceptable salts, isotopes, N-oxides, solvates, and stereoisomers thereof. An additional embodiment of the current invention is a compound selected from those compounds shown above in Table 3 which have an IC$_{50}$ (nM) value of 0.4 or less (or from 0.1 to 0.4) according to the DHODH Enzymatic Assay (i.e., selected from compounds 11, 81, 70, 82, 102, 52, 51, 80, 60, 87, 27, 36, 22); or an IC$_{50}$ (nM) value of 0.2 or less (or from 0.01 to 0.2) according to the MOLM-13 Cellular Assay (i.e., selected from compounds 82, 52, 51, 11, 22, 83, 105); and, optionally, one or more of pharmaceutically acceptable salts, isotopes, N-oxides, solvates, and stereoisomers thereof. An additional embodiment of the current invention is a compound selected from those compounds shown above in Table 3 which have an IC$_{50}$ (nM) value of 0.4 or less (or from 0.1 to 0.4) according to the DHODH Enzymatic Assay, and an IC$_{50}$ (nM) value of 0.2 or less (or from 0.01 to 0.2) according to the MOLM-13 Cellular Assay (i.e., selected from compounds 82, 52, 51, 11, 22); and, optionally, one or more of pharmaceutically acceptable salts, isotopes, N-oxides, solvates, and stereoisomers thereof.

Illustrative Embodiments of the Invention

The present invention may be further understood by reference to the embodiments provided below.

Embodiment #1: A compound having the structure of Formula (I):

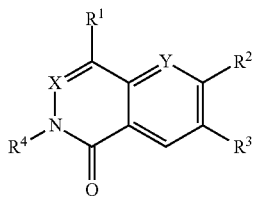
(I)

wherein
X is CH or N;
Y is CH or N;
$R^1$ is selected from the group consisting of: $C_{1-6}$alkyl; $C_{1-6}$alkyl substituted with one substituent selected from the group consisting of: OH, and $OCH_3$; $C_{2-6}$alkenyl; $C_{1-6}$haloalkyl; $C_{1-6}$ haloalkyl substituted with one substituent selected from the group consisting of OH, and $OCH_3$; $C_{2-6}$haloalkenyl; $N(CH_3)_2$; $C_{3-6}$cycloalkyl; $C_{3-6}$cycloalkyl substituted with one $C_{1-6}$ alkyl substituent; and phenyl;
$R^2$ is

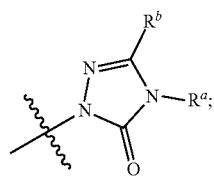

wherein
$R^a$ is selected from the group consisting of: $C_{1-6}$alkyl, $C_{1-6}$haloalkyl, and $C_{3-6}$cycloalkyl;
$R^b$ is $C_{1-6}$alkyl or $C_{1-6}$alkyl substituted with a member selected from the group consisting of: OH, halo, CN, $OC_{1-6}$alkyl, $OC_{1-6}$haloalkyl and $OC_{3-6}$cycloalkyl;
$R^3$ is selected from the group consisting of: H, halo, $CH_3$ and $OCH_3$;
$R^4$ is selected from the group consisting of:
(a) $C_{1-6}$alkyl; $C_{1-6}$alkyl substituted with one or two $OCH_3$; $C_{3-6}$cycloalkyl; $C_{3-6}$cycloalkyl substituted with $CH_3$, or $OCH_3$; $CH_2$—$C_{3-6}$cycloalkyl; and (b)
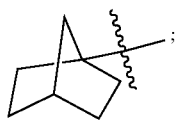

(c)
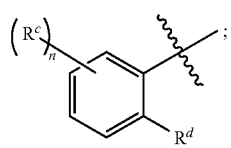

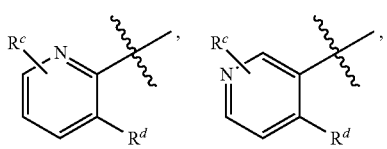

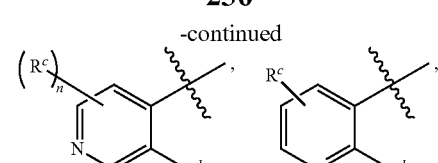

(d)

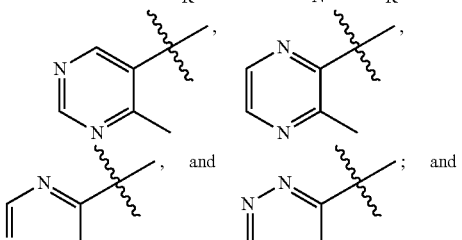

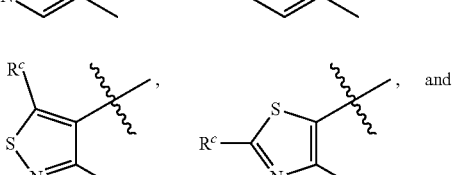

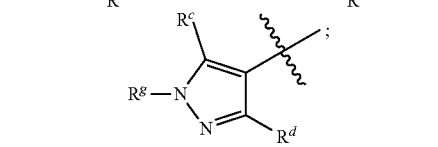

wherein
each $R^c$ is independently selected from the group consisting of: H; halo; $C_{1-6}$alkyl; $C_{1-6}$alkyl substituted with a member selected from the group consisting of: OH, $OCH_3$, $SCH_3$, and $OCF_3$; $C_{1-6}$haloalkyl; $C_{1-6}$haloalkyl substituted with a member selected from the group consisting of: OH, and $OCH_3$; $NO_2$; OH; O—$CH_2CH_2OH$; and $OC_{1-6}$alkyl;
$R^d$ is selected from the group consisting of: H; halo; $C_{1-6}$alkyl; $C_{1-6}$alkyl substituted with a member selected from the group consisting of: OH, $OCH_3$, $SCH_3$, and $OCF_3$; $C_{1-6}$haloalkyl; $C_{1-6}$haloalkyl substituted with a member selected from the group consisting of: OH, and $OCH_3$; CN; and $OC_{1-6}$alkyl;
$R^g$ is selected from the group consisting of: H; $C_{1-6}$alkyl; $C_{1-6}$alkyl substituted with a member selected from the group consisting of: OH, $OCH_3$, $SCH_3$, and $OCF_3$; $C_{1-6}$ haloalkyl; and $C_{1-6}$haloalkyl substituted with a member selected from the group consisting of: OH, and $OCH_3$; and
n is 1, or 2;
or a pharmaceutically acceptable salt, isotope, N-oxide, solvate, or stereoisomer thereof.

Embodiment #2: The compound according to Embodiment #1 above, wherein X is CH; or a pharmaceutically acceptable salt, solvate, stereoisomer, isotopic variant, or N-oxide thereof.

Embodiment #3: The compound according to Embodiment #1 above, wherein X is N; or a pharmaceutically acceptable salt, solvate, stereoisomer, isotopic variant, or N-oxide thereof.

Embodiment #4: The compound according to any of Embodiments #1-3 above, wherein Y is N; or a pharmaceutically acceptable salt, solvate, stereoisomer, isotopic variant, or N-oxide thereof.

Embodiment #5: The compound according to any of Embodiments #1-3 above, wherein Y is CH; or a pharmaceutically acceptable salt, solvate, stereoisomer, isotopic variant, or N-oxide thereof.

Embodiment #6: The compound according to any of Embodiments #1-5 above, wherein $R^1$ is $C_{1-4}$alkyl; $C_{1-4}$alkyl substituted with OH, or $OCH_3$; $C_{2-4}$alkenyl; $C_{1-4}$haloalkyl; $C_{1-4}$haloalkyl substituted with OH, or $OCH_3$; $C_{2-4}$haloalkenyl; $N(CH_3)_2$; cyclopropyl; cyclopropyl substituted with $C_{1-4}$alkyl; or phenyl; or a pharmaceutically acceptable salt, solvate, stereoisomer, isotopic variant, or N-oxide thereof.

Embodiment #7: The compound according to any of Embodiments #1-5 above, wherein $R^1$ is $CH_3$, $CH_2CH_3$,

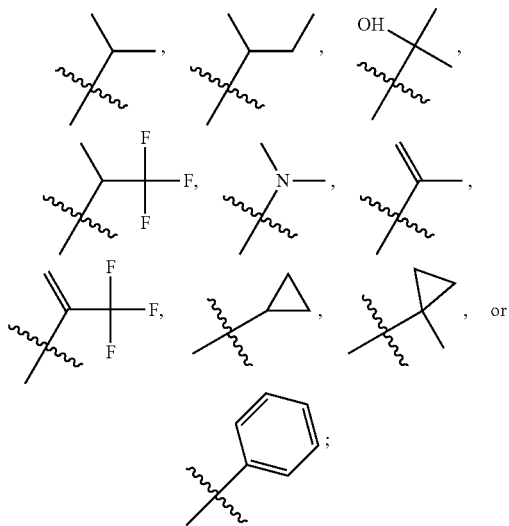

or a pharmaceutically acceptable salt, solvate, stereoisomer, isotopic variant, or N-oxide thereof.

Embodiment #8: The compound according to any of Embodiments #1-5 above, wherein $R^1$ is

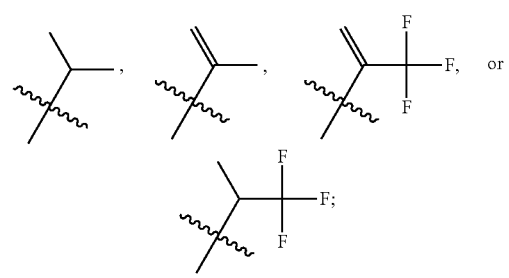

or a pharmaceutically acceptable salt, solvate, stereoisomer, isotopic variant, or N-oxide thereof.

Embodiment #9: The compound according to any of Embodiments #1-8 above, wherein $R^2$ is

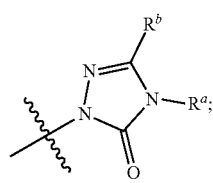

wherein
$R^b$ is $C_{1-4}$alkyl substituted with OH, halo, CN, $OC_{1-4}$alkyl, $OC_1$-4haloalkyl or $OC_{3-6}$cycloalkyl; and $R^a$ is $C_{1-4}$alkyl, $C_{1-4}$haloalkyl, or $C_{3-6}$cycloalkyl;
or a pharmaceutically acceptable salt, solvate, stereoisomer, isotopic variant, or N-oxide thereof.

Embodiment #10: The compound according to any of Embodiments #1-8 above, wherein $R^2$ is

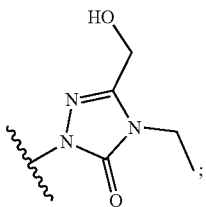 [SMILES: *n1nc(CO)n(CC)c1=O]

or a pharmaceutically acceptable salt, solvate, stereoisomer, isotopic variant, or N-oxide thereof.

Embodiment #11: The compound according to any of Embodiments #1-10 above, wherein $R^3$ is H; or a pharmaceutically acceptable salt, solvate, stereoisomer, isotopic variant, or N-oxide thereof.

Embodiment #12: The compound according to any of Embodiments #1-10 above, wherein $R^3$ is F; or a pharmaceutically acceptable salt, solvate, stereoisomer, isotopic variant, or N-oxide thereof.

Embodiment #13: The compound according to any of Embodiments #1-10 above, wherein $R^3$ is $CH_3$; or a pharmaceutically acceptable salt, solvate, stereoisomer, isotopic variant, or N-oxide thereof.

Embodiment #14: The compound according to any of Embodiments #1-10 above, wherein $R^3$ is $OCH_3$; or a pharmaceutically acceptable salt, solvate, stereoisomer, isotopic variant, or N-oxide thereof.

Embodiment #15: The compound according to any of Embodiments #1-14 above, wherein $R^4$ is

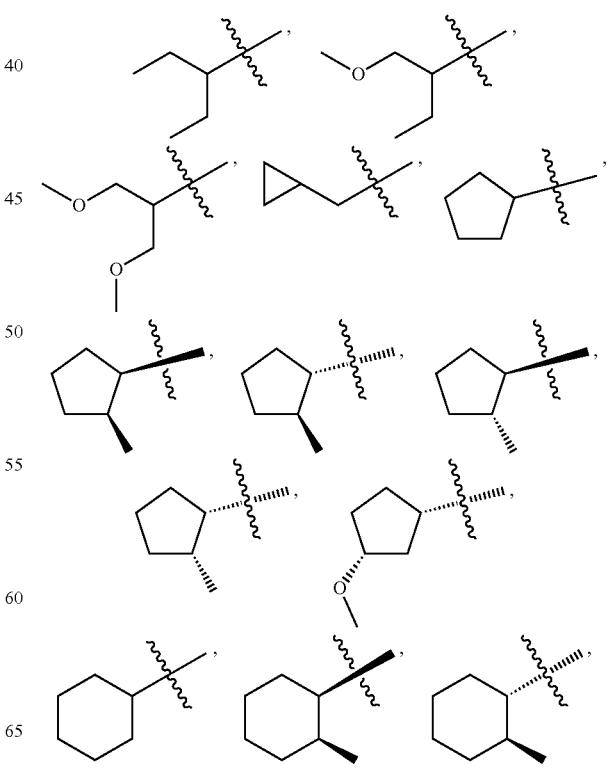

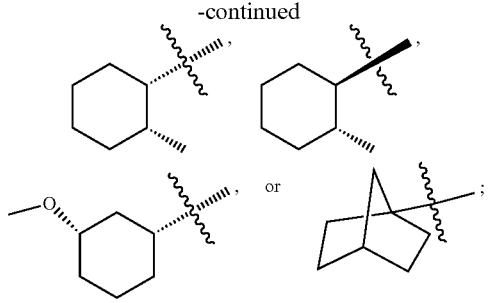

or a pharmaceutically acceptable salt, solvate, stereoisomer, isotopic variant, or N-oxide thereof.

Embodiment #16: The compound according to any of Embodiments #1-14, wherein $R^4$ is

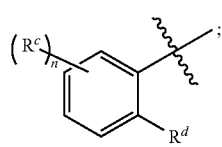

wherein
- each $R^c$ is independently selected from the group consisting of: H, halo, $C_{1-4}$alkyl, $C_{1-4}$haloalkyl, $NO_2$, O—$CH_2CH_2OH$, and $OC_{1-4}$alkyl;
- $R^d$ is selected from the group consisting of: H, halo, $C_{1-4}$alkyl, CN, and $OC_{1-6}$alkyl; and
- n is 1, or 2;

or a pharmaceutically acceptable salt, solvate, stereoisomer, isotopic variant, or N-oxide thereof.

Embodiment #17: The compound according to any of Embodiments #1-14 above, wherein $R^4$ is

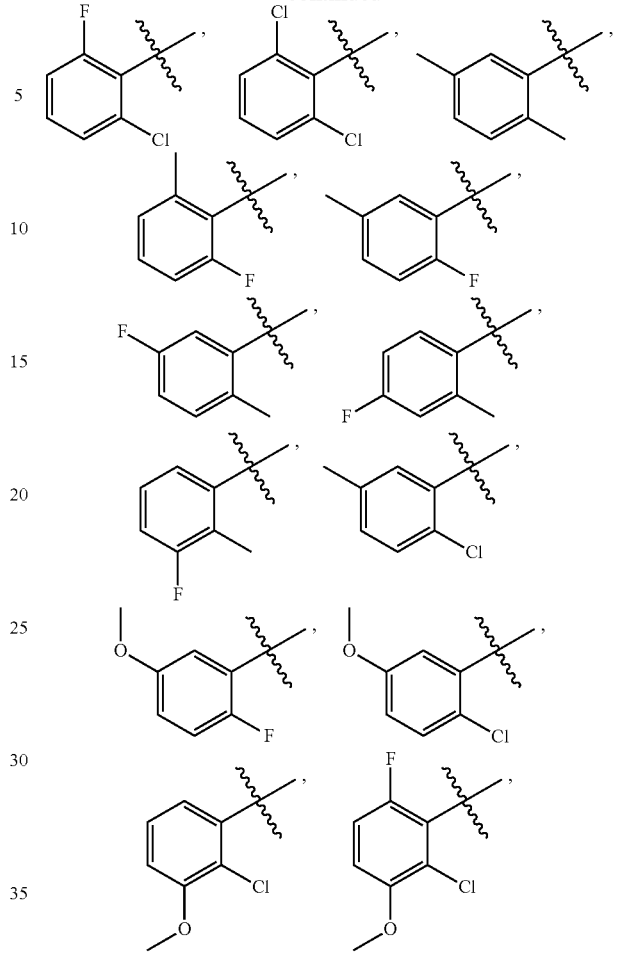

or a pharmaceutically acceptable salt, solvate, stereoisomer, isotopic variant, or N-oxide thereof.

Embodiment #18: The compound according to any of Embodiments #1-14 above, wherein $R^4$ is

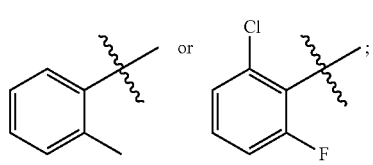

or a pharmaceutically acceptable salt, solvate, stereoisomer, isotopic variant, or N-oxide thereof.

Embodiment #19: The compound according to any of Embodiments #1-14 above, wherein $R^4$ is

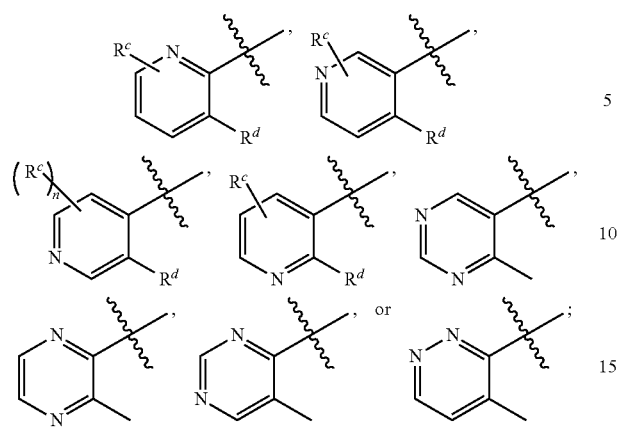

wherein
- each $R^c$ is independently selected from the group consisting of: H, halo, $C_{1-4}$alkyl, $C_{1-4}$haloalkyl, $OC_{1-4}$alkyl, and OH;
- $R^d$ is selected from the group consisting of: halo, $C_{1-4}$alkyl, and $OC_{1-4}$alkyl; and
- n is 1, or 2;

or a pharmaceutically acceptable salt, solvate, stereoisomer, isotopic variant, or N-oxide thereof.

Embodiment #20: The compound according to any of Embodiments #1-14 above, wherein $R^4$ is

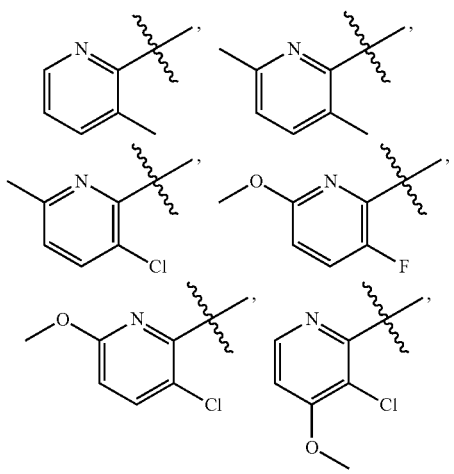

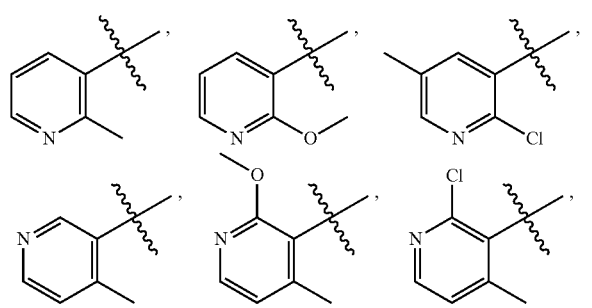

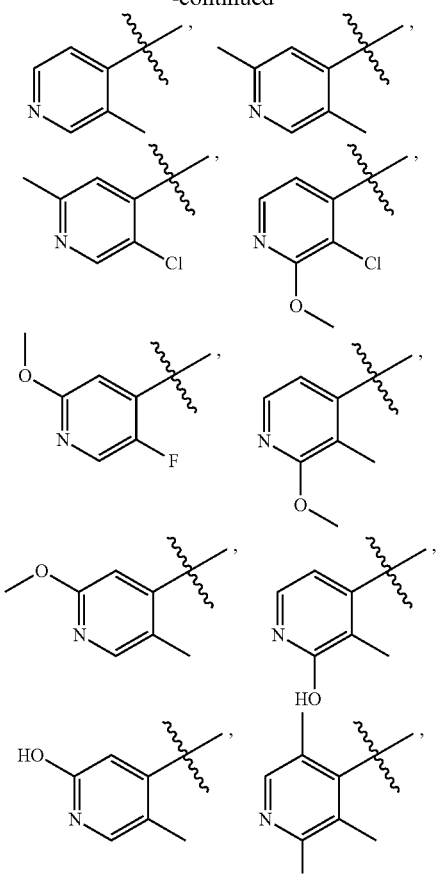

or a pharmaceutically acceptable salt, solvate, stereoisomer, isotopic variant, or N-oxide thereof.

Embodiment #21: The compound according to any of Embodiments #1-14 above, wherein $R^4$ is

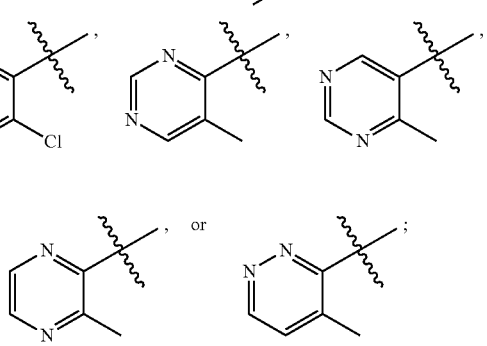

or a pharmaceutically acceptable salt, solvate, stereoisomer, isotopic variant, or N-oxide thereof.

Embodiment #22: The compound according to any of Embodiments #1-14 above, wherein $R^4$ is

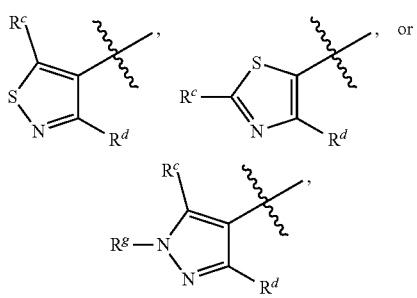

wherein

R$^c$ is H or halo;

R$^d$ is C$_{1-4}$alkyl; and

R$^g$ is H;

or a pharmaceutically acceptable salt, solvate, stereoisomer, isotopic variant, or N-oxide thereof.

Embodiment #23: The compound according to any of Embodiments #1-14 above, wherein R$^4$ is:

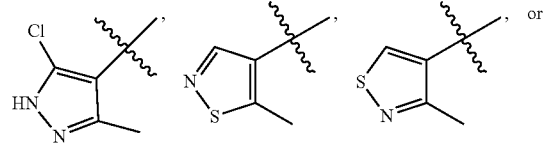

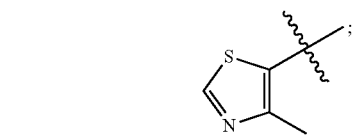

or a pharmaceutically acceptable salt, solvate, stereoisomer, isotopic variant, or N-oxide thereof.

Embodiment #24: The compound according to Embodiment #1 above, having the structure of Formula (IA):

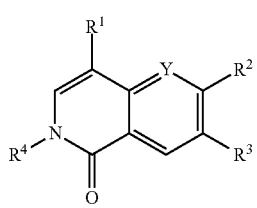

(IA)

wherein

Y is CH or N;

R$^1$ is selected from the group consisting of: C$_{1-6}$alkyl; C$_{1-6}$alkyl substituted with OH, or OCH$_3$; C$_{2-6}$alkenyl; C$_{1-6}$haloalkyl; C$_{1-6}$haloalkyl substituted with OH, or OCH$_3$; C$_{2-6}$haloalkenyl;

N(CH$_3$)$_2$; C$_{3-6}$cycloalkyl; C$_{3-6}$cycloalkyl substituted with C$_{1-6}$alkyl; and phenyl;

R$^2$ is

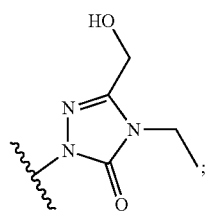 [SMILES: *n1nc(CO)n(CC)c1=O]

R$^3$ is selected from the group consisting of: H, halo, CH$_3$ and OCH$_3$;

R$^4$ is selected from the group consisting of:

(a) C$_{1-6}$alkyl; C$_{1-6}$alkyl substituted with one or two OCH$_3$; C$_{3-6}$cycloalkyl; C$_{3-6}$cycloalkyl substituted with CH$_3$, or OCH$_3$; CH$_2$—C$_{3-6}$cycloalkyl; and (b) 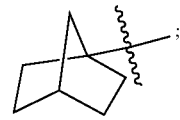

(c) 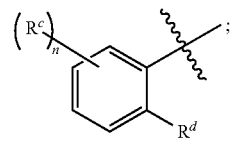

(d) 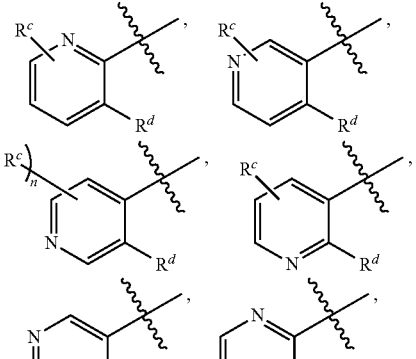

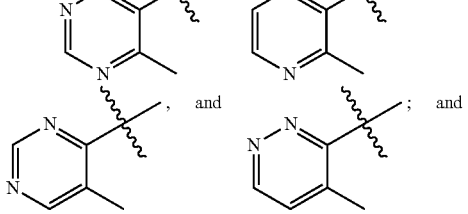

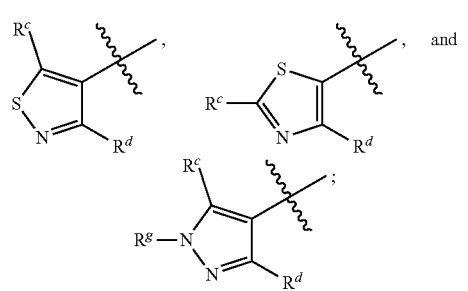

wherein each R$^c$ is independently selected from the group consisting of: H; halo; C$_{1-6}$alkyl; C$_{1-6}$alkyl substituted with a member selected from the group consisting of: OH, OCH₃, SCH₃, and OCF₃; C$_{1-6}$haloalkyl; C$_{1-6}$haloalkyl substituted with a member selected from the group consisting of: OH, and OCH₃; NO₂; OH; O—CH₂CH₂OH; and OC$_{1-6}$alkyl;

R$^d$ is selected from the group consisting of: H; halo; C$_{1-6}$alkyl; C$_{1-6}$alkyl substituted with a member selected from the group consisting of: OH, OCH₃, SCH₃, and OCF₃; C$_{1-6}$haloalkyl; C$_{1-6}$haloalkyl substituted with a member selected from the group consisting of: OH, and OCH₃; CN; and OC$_{1-6}$alkyl;

R$^g$ is selected from the group consisting of: H; C$_{1-6}$alkyl; C$_{1-6}$alkyl substituted with a member selected from the group consisting of: OH, OCH₃, SCH₃, and OCF₃; C$_1$-6haloalkyl; and C$_1$-6haloalkyl substituted with a member selected from the group consisting of: OH, and OCH₃; and n is 1, or 2;

or a pharmaceutically acceptable salt, solvate, stereoisomer, isotopic variant, or N-oxide thereof.

Embodiment #25: The compound according to Embodiment #1 above, having the structure of Formula (IB):

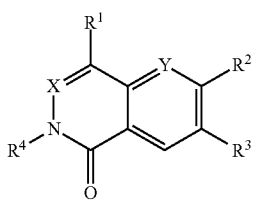

(IB)

wherein
Y is CH or N:
R$^1$ is selected from the group consisting of: C$_1$-6alkyl, C$_1$-6haloalkyl and C$_{2-6}$alkenyl;
R$^2$ is

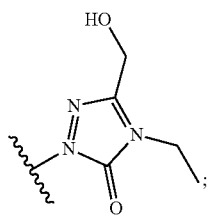

R$^3$ is selected from the group consisting of: H, halo and OCH₃;
R$^4$ is selected from the group consisting of:

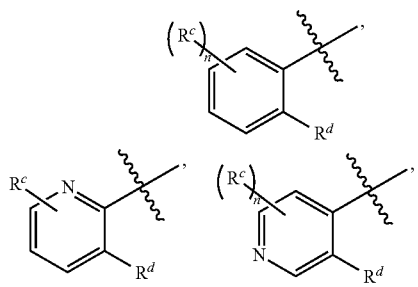

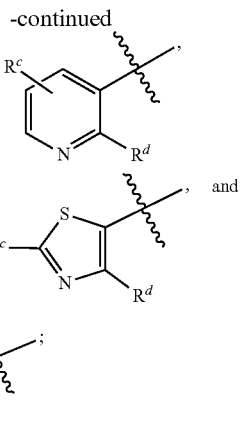

wherein
R$^c$ is selected from the group consisting of: H; halo; C$_1$-6alkyl; C$_1$-6alkyl substituted with a member selected from the group consisting of: OH, OCH₃, SCH₃, and OCF₃;
C$_{1-6}$haloalkyl; C$_{1-6}$haloalkyl substituted with a member selected from the group consisting of: OH, and OCH₃; and NO₂;

R$^d$ is selected from the group consisting of: H; halo; C$_{1-6}$alkyl; C$_{1-6}$alkyl substituted with a member selected from the group consisting of: OH, OCH₃, SCH₃, and OCF₃; C$_{1-6}$haloalkyl; C$_{1-6}$haloalkyl substituted with a member selected from the group consisting of: OH, and OCH₃; CN; and OC$_{1-6}$alkyl;

R$^g$ is selected from the group consisting of: H; C$_{1-6}$alkyl; C$_{1-6}$alkyl substituted with a member selected from the group consisting of: OH, OCH₃, SCH₃, and OCF₃; C$_{1-6}$ haloalkyl; and C$_{1-6}$haloalkyl substituted with a member selected from the group consisting of: OH, and OCH₃; and n is 1;

or a pharmaceutically acceptable salt, solvate, stereoisomer, isotopic variant, or N-oxide thereof.

Embodiment #26: A compound selected from the group consisting of Compounds 1-142 (as shown in Table 1); or a pharmaceutically acceptable salt, solvate, stereoisomer, isotopic variant, or N-oxide thereof.

Embodiment #27A: A compound selected from the group consisting of:

2-(2-Chloro-6-fluorophenyl)-6-(4-ethyl-3-(hydroxymethyl)-5-oxo-4,5-dihydro-1H-1,2,4-triazol-1-yl)-7-fluoro-4-isopropylisoquinolin-1(2H)-one;

6-(4-Ethyl-3-(hydroxymethyl)-5-oxo-4,5-dihydro-1H-1,2,4-triazol-1-yl)-7-fluoro-4-isopropyl-2-(o-tolyl)isoquinolin-1(2H)-one;

2-(2-Chloro-4-methylpyridin-3-yl)-6-(4-ethyl-3-(hydroxymethyl)-5-oxo-4,5-dihydro-1H-1,2,4-triazol-1-yl)-7-fluoro-4-isopropylisoquinolin-1(2H)-one;

2-(2-Chloro-6-fluorophenyl)-6-(4-ethyl-3-(hydroxymethyl)-5-oxo-4,5-dihydro-1H-1,2,4-triazol-1-yl)-4-(1-methylcyclopropyl)isoquinolin-1(2H)-one;

2-(2-Chloro-6-fluorophenyl)-6-(4-ethyl-3-(hydroxymethyl)-5-oxo-4,5-dihydro-1H-1,2,4-triazol-1-yl)-7-fluoro-4-(prop-1-en-2-yl)phthalazin-1(2H)-one;

2-(4-Ethyl-3-(hydroxymethyl)-5-oxo-4,5-dihydro-1H-1,2,4-triazol-1-yl)-3-fluoro-8-isopropyl-6-(o-tolyl)-1,6-naphthyridin-5(6H)-one;

6-(4-Ethyl-3-(hydroxymethyl)-5-oxo-4,5-dihydro-1H-1,2,4-triazol-1-yl)-7-fluoro-4-isopropyl-2-(o-tolyl)phthalazin-1(2H)-one;

2-(2-Chloro-6-fluorophenyl)-6-(4-ethyl-3-(hydroxymethyl)-5-oxo-4,5-dihydro-1H-1,2,4-triazol-1-yl)-7-fluoro-4-isopropylphthalazin-1(2H)-one;

6-(4-Ethyl-3-(hydroxymethyl)-5-oxo-4,5-dihydro-1H-1,2,4-triazol-1-yl)-7-fluoro-4-isopropyl-2-(2-(methyl-d3)phenyl)isoquinolin-1(2H)-one;

(R)-6-(4-Ethyl-3-(hydroxymethyl)-5-oxo-4,5-dihydro-1H-1,2,4-triazol-1-yl)-7-fluoro-2-(0-tolyl)-4-(1,1,1-trifluoropropan-2-yl)isoquinolin-1(2H)-one;

6-(4-Ethyl-3-(hydroxymethyl)-5-oxo-4,5-dihydro-1H-1,2,4-triazol-1-yl)-7-fluoro-4-isopropyl-2-(2-(trifluoromethyl)phenyl)isoquinolin-1(2H)-one; and 2-(2-(Difluoromethyl)phenyl)-6-(4-ethyl-3-(hydroxymethyl)-5-oxo-4,5-dihydro-1H-1,2,4-triazol-1-yl)-7-fluoro-4-isopropylisoquinolin-1(2H)-one;

or a pharmaceutically acceptable salt, solvate, stereoisomer, isotopic variant, or N-oxide thereof.

Embodiment #27B: A compound selected from compounds 82, 52, 51, 11, 22 (e.g., which demonstrated an $IC_{50}$ (nM) value of 0.4 or less (or from 0.1 to 0.4) according to the DHODH Enzymatic Assay, and an $IC_{50}$ (nM) value of 0.2 or less (or from 0.01 to 0.2) according to the MOLM-13 Cellular Assay); and, optionally, one or more of pharmaceutically acceptable salts, isotopes, N-oxides, solvates, and stereoisomers thereof.

Embodiment #28: A pharmaceutical composition comprising: (A) a compound according to any of Embodiments #1-27, or a pharmaceutically acceptable salt, solvate, stereoisomer, isotopic variant, or N-oxide thereof; and (B) at least one pharmaceutically acceptable excipient.

Embodiment #29A: A pharmaceutical composition comprising an effective amount of a compound selected from Compounds 1-142 (as shown in Table 1); or a pharmaceutically acceptable salt, solvate, stereoisomer, isotopic variant, or N-oxide thereof; and at least one pharmaceutically acceptable excipient.

Embodiment #29B: A pharmaceutical composition comprising an effective amount of a compound listed in Embodiment #27A or #27B above; or a pharmaceutically acceptable salt, solvate, stereoisomer, isotopic variant, or N-oxide thereof; and at least one pharmaceutically acceptable excipient.

Embodiment #30: A method of treating a subject suffering from or diagnosed with a disease, disorder, or medical condition comprising inhibiting or altering dihydroorotate oxygenase enzyme activity in the subject by administering to the subject an effective amount of at least one compound according to any of Embodiments #1-27 above, or a pharmaceutically acceptable salt, solvate, stereoisomer, isotopic variant, or N-oxide thereof.

Embodiment #31: The method according to Embodiment #30 above, wherein the disorder, disease or medical condition is selected from the group consisting of: inflammatory disorders and autoimmune disorders.

Embodiment #32: The method according to Embodiment #30 above, wherein the disorder, disease or medical condition is cancer.

Embodiment #33: The method according to Embodiment #30 above, wherein the disorder, disease or medical condition is selected from the group consisting of: lymphomas, leukemias, carcinomas, and sarcomas.

Embodiment #34: The method according to Embodiment #30 above, wherein the disorder, disease or medical condition is selected from the group consisting of: acute lymphoblastic leukemia, acute myeloid leukemia, (acute) T-cell leukemia, acute lymphoblastic leukemia, acute lymphocytic leukemia, acute monocytic leukemia, acute promyelocytic leukemia, bisphenotypic B myelomonocytic leukemia, chronic lymphocytic leukemia, chronic myelogenous leukemia, chronic myeloid leukemia, chronic myelomonocytic leukemia, large granular lymphocytic leukemia, plasma cell leukemia, and also myelodysplastic syndrome, which can develop into an acute myeloid leukemia.

Embodiment #35: The method according to Embodiment #30 above, wherein the disorder, disease or medical condition is acute myeloid leukemia.

Embodiment #36A: The method according to any of Embodiments #30-35 above, wherein the at least one compound is selected from Compounds 1-142 (as shown in Table 1), or a pharmaceutically acceptable salt, solvate, stereoisomer, isotopic variant, or N-oxide thereof.

Embodiment #36B: The method according to any of Embodiments #30-35 above, wherein the at least one compound is selected from those listed in Embodiment #27A or #27B above, or a pharmaceutically acceptable salt, solvate, stereoisomer, isotopic variant, or N-oxide thereof.

An additional embodiment of the present invention provides a method of inhibiting DHODH activity in cancer cells (in particular, a method of inhibiting DHODH activity in leukemia cells, and more particularly, a method of inhibiting DHODH activity in acute myeloid leukemia cells) comprising contacting the cells with, or otherwise exposing the cells to, a compound selected from any of the compounds described herein, e.g., a compound of Formula (I), or a compound of Formula IA or IB, or a compound selected from Compounds 1-142 in Table 1, or a compound selected from those listed in Embodiment #27A or #27B above; or a pharmaceutically acceptable salt, solvate, stereoisomer, isotopic variant, or N-oxide thereof (see, e.g., the biological assays described in the examples herein).

Embodiments of this invention also include compounds of Formula (I),

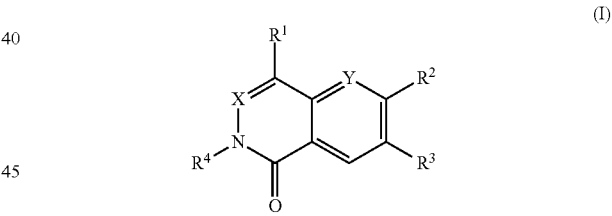

(I)

wherein
X is CH;
Y is CH;
$R^1$ is selected from the group consisting of: $C_{1-6}$alkyl; $C_{1-6}$alkyl substituted with OH, or $OCH_3$; $C_{2-6}$alkenyl; $C_{1-6}$haloalkyl; $C_{1-6}$haloalkyl substituted with OH, or $OCH_3$; $C_{2-6}$haloalkenyl; $N(CH_3)_2$; $C_{3-6}$cycloalkyl; $C_{3-6}$cycloalkyl substituted with $C_{1-6}$alkyl; and phenyl;
$R^2$ is

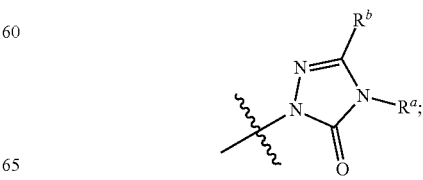

wherein
R$^a$ is selected from the group consisting of: C$_{1-6}$alkyl, C$_{1-6}$haloalkyl, and C$_{3-6}$cycloalkyl;
R$^b$ is C$_{1-6}$alkyl or C$_{1-6}$alkyl substituted with a member selected from the group consisting of: OH, halo, CN, OC$_{1-6}$alkyl, OC$_{1-6}$haloalkyl and OC$_{3-6}$cycloalkyl;
R$^3$ is selected from the group consisting of: H, halo, CH$_3$, and OCH$_3$;
R$^4$ is

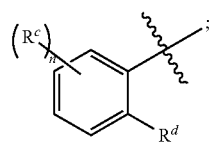

wherein
each R$^c$ is independently selected from the group consisting of: H; halo; C$_{1-6}$alkyl; C$_{1-6}$alkyl substituted with a member selected from the group consisting of: OH, OCH$_3$, SCH$_3$, and OCF$_3$; C$_{1-6}$haloalkyl; C$_{1-6}$haloalkyl substituted with a member selected from the group consisting of: OH, and OCH$_3$; NO$_2$; OH; O—CH$_2$CH$_2$OH; and OC$_{1-6}$alkyl;
R$^d$ is selected from the group consisting of: H; halo; C$_{1-6}$alkyl; C$_{1-6}$alkyl substituted with a member selected from the group consisting of: OH, OCH$_3$, SCH$_3$, and OCF$_3$; C$_{1-6}$haloalkyl; C$_{1-6}$haloalkyl substituted with a member selected from the group consisting of: OH, and OCH$_3$; CN; and OC$_{1-6}$alkyl; and
n is 1, or 2;
or a pharmaceutically acceptable salt, isotope, N-oxide, solvate, or stereoisomer thereof.

Embodiments of this invention also include compounds of Formula (I),

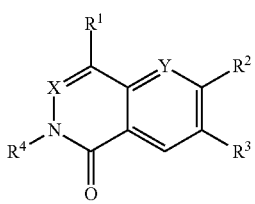

(I)

wherein
X is CH;
Y is CH;
R$^1$ is C$_{1-6}$alkyl;
R$^2$ is

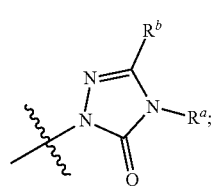

wherein
R$^a$ is selected from the group consisting of: C$_{1-6}$alkyl, C$_{1-6}$haloalkyl, and C$_{3-6}$cycloalkyl;
R$^b$ is C$_{1-6}$alkyl or C$_{1-6}$alkyl substituted with a member selected from the group consisting of: OH, halo, CN, OC$_{1-6}$alkyl, OC$_{1-6}$haloalkyl and OC$_{3-6}$cycloalkyl;
R$^3$ is selected from the group consisting of: H, halo, CH$_3$, and OCH$_3$;
R$^4$ is

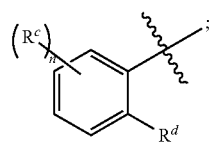

wherein
R$^c$ is H;
R$^d$ is selected from the group consisting of: H; halo; C$_{1-6}$alkyl; C$_{1-6}$alkyl substituted with a member selected from the group consisting of: OH, OCH$_3$, SCH$_3$, and OCF$_3$; C$_{1-6}$haloalkyl; C$_{1-6}$haloalkyl substituted with a member selected from the group consisting of: OH, and OCH$_3$; CN; and OC$_{1-6}$alkyl; and
n is 1;
or a pharmaceutically acceptable salt, isotope, N-oxide, solvate, or stereoisomer thereof.

Embodiments of this invention also include compounds of Formula (I),

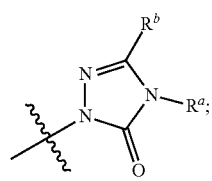

(I)

wherein
X is CH;
Y is CH;
R$^1$ is C$_{1-6}$alkyl;
R$^2$ is

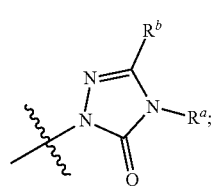

wherein
R$^a$ is C$_{1-6}$alkyl; R$^b$ is C$_{1-6}$alkyl or C$_{1-6}$alkyl substituted with OH; R$^3$ is halo; R$^4$ is

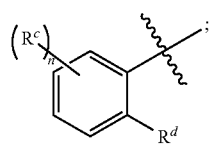

wherein
R$^c$ is H; R$^d$ is C$_{1-6}$alkyl; and n is 1;
or a pharmaceutically acceptable salt, isotope, N-oxide, solvate, or stereoisomer thereof.

An additional embodiment of the invention is a compound of Formula (I) wherein X is CH; and wherein Y is CH.

According to an embodiment, any of the above-described embodiments of the compounds of Formula (I) may be in free base form. According to another embodiment, any of the above-described embodiments of the compounds of Formula (I) may be a pharmaceutically acceptable salt thereof.

In an additional embodiment, the present invention relates to a subgroup of Formula (I) as defined in the preparative examples.

In an additional embodiment the compound of Formula (I) is selected from the group consisting of any of the exemplified compounds, pharmaceutically acceptable salts, isotopes, N-oxides, solvates, and stereoisomers thereof.

In an additional embodiment the compound of Formula (I) is selected from the group consisting of any of the exemplified compounds in free base form.

All possible combinations of the above indicated embodiments are considered to be embraced within the scope of the invention.

Additionally, the invention relates to a compound of Formula (I), or a pharmaceutically acceptable salt, isotope, N-oxide, solvate, or stereoisomer thereof, for use as a medicament.

Additionally, the invention relates to a compound of Formula (I), or a pharmaceutically acceptable salt, isotope, N-oxide, solvate, or stereoisomer thereof, for use in the treatment or in the prevention of a disease, disorder, or medical conditions where there is an advantage in inhibiting DHODH, in particular any disease, disorder, or medical conditions listed herein.

Additionally, the invention relates to a compound of Formula (I), or a pharmaceutically acceptable salt, isotope, N-oxide, solvate, or stereoisomer thereof, for use in the treatment or in the prevention of cancer, in particular any type of cancer as listed herein.

Additionally, the invention relates to a compound of Formula (I), or a pharmaceutically acceptable salt, isotope, N-oxide, solvate, or stereoisomer thereof, for use in the treatment or in the prevention of immunological diseases, in particular any type of immunological disease as listed herein.

Additionally, the invention relates to a compound of Formula (I), or a pharmaceutically acceptable salt, isotope, N-oxide, solvate, or stereoisomer thereof, for use in the treatment or prevention of any one of the diseases mentioned herein.

Additionally, the invention relates to a compound of Formula (I), or a pharmaceutically acceptable salt, isotope, N-oxide, solvate, or stereoisomer thereof, for use in treating or preventing any one of the diseases mentioned herein.

Additionally, the invention relates to a compound of Formula (I), or a pharmaceutically acceptable salt, isotope, N-oxide, solvate, or stereoisomer thereof, for the manufacture of a medicament for the treatment or prevention of any one of the disease, disorder, or medical condition mentioned herein.

Additionally, the invention relates to a compound of Formula (I), or a pharmaceutically acceptable salt, isotope, N-oxide, solvate, or stereoisomer thereof, for the manufacture of a medicament for the treatment of any one of the disease, disorder, or medical condition mentioned herein.

What is claimed is:

1. A compound having the structure:

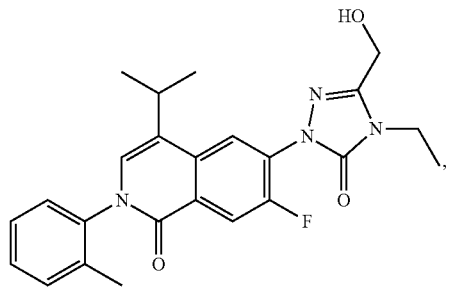 [SMILES: CCn1c(CO)nn(-c2cc3c(C(C)C)cn(-c4ccccc4C)c(=O)c3cc2F)c1=O]

or a pharmaceutically acceptable salt thereof.

2. A compound having the structure:

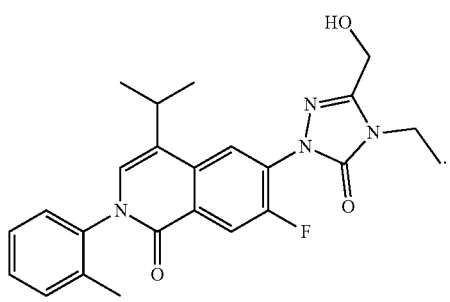 [SMILES: CCn1c(CO)nn(-c2cc3c(C(C)C)cn(-c4ccccc4C)c(=O)c3cc2F)c1=O]

3. A pharmaceutical composition comprising the compound according to claim 2, or a pharmaceutically acceptable salt thereof, and at least one pharmaceutically acceptable excipient.

4. A pharmaceutical composition comprising the compound according to claim 2; and at least one pharmaceutically acceptable excipient.

5. A method of treating cancer comprising administering to a subject in need thereof a therapeutically effective amount of the compound of claim 2, wherein the cancer is selected from a leukemia or myelodysplastic syndrome (MDS).

6. The method of claim 5, wherein the leukemia is selected from acute lymphoblastic leukemia (ALL), acute myeloid leukemia (AML), (acute) T-cell leukemia, acute monocytic leukemia, acute promyelocytic leukemia (APL) bisphenotypic B myelomonocytic leukemia, chronic myeloid leukemia (CML), chronic myelomonocytic leukemia (CMML), large granular lymphocytic leukemia, and plasma cell leukemia.

7. The method of claim 6, wherein the leukemia is acute myeloid leukemia.

8. The method of claim 5, wherein the cancer is myelodysplastic syndrome.

* * * * *